US011548931B2

(12) United States Patent
Dong et al.

(10) Patent No.: US 11,548,931 B2
(45) Date of Patent: Jan. 10, 2023

(54) PASYLATED VEGFR/PDGFR FUSION PROTEINS AND THEIR USE IN THERAPY

(71) Applicant: XL-PROTEIN GMBH, Freising (DE)

(72) Inventors: Qing Dong, Boonton, NJ (US); Michaela Gebauer, Leipzig (DE)

(73) Assignee: XL-PROTEIN GMBH, Freising (DE)

( * ) Notice: Subject to any disclaimer, the term of this patent is extended or adjusted under 35 U.S.C. 154(b) by 0 days.

(21) Appl. No.: 16/764,541

(22) PCT Filed: Nov. 15, 2018

(86) PCT No.: PCT/CN2018/115733
§ 371 (c)(1),
(2) Date: May 15, 2020

(87) PCT Pub. No.: WO2019/096226
PCT Pub. Date: May 23, 2019

(65) Prior Publication Data

US 2021/0139559 A1 May 13, 2021

(30) Foreign Application Priority Data

Nov. 16, 2017 (CN) ........................ 201711136582.6
Dec. 1, 2017 (EP) .................................... 17204968

(51) Int. Cl.
*C07K 14/71* (2006.01)
*C07K 19/00* (2006.01)
*C07K 14/14* (2006.01)

(52) U.S. Cl.
CPC .......... *C07K 14/71* (2013.01); *C07K 2319/02* (2013.01)

(58) Field of Classification Search
CPC ................ A61K 38/00; C07K 2319/00; C07K 2319/02; C07K 2319/21; C07K 2319/50
See application file for complete search history.

(56) References Cited

U.S. PATENT DOCUMENTS 5,952,199 A 9/1999 Davis-Smyth et al.

FOREIGN PATENT DOCUMENTS

| | | | |
|---|---|---|---|
| CN | 102311502 A | * | 1/2012 |
| CN | 102311502 B | | 12/2013 |
| CN | 107298714 A | | 10/2017 |
| EP | 2 119 716 A1 | | 11/2009 |
| WO | WO-95/21820 A1 | | 8/1995 |
| WO | WO-2004/048373 A1 | | 6/2004 |
| WO | WO-2005/067537 A2 | | 7/2005 |
| WO | WO-2006/005057 A2 | | 1/2006 |
| WO | WO-2007/089871 A2 | | 8/2007 |
| WO | WO-2007/146959 A2 | | 12/2007 |
| WO | WO-2009/126920 A2 | | 10/2009 |
| WO | WO-2010/059315 A1 | | 5/2010 |
| WO | WO-2011/001413 A1 | | 1/2011 |
| WO | WO-2014/160507 A1 | | 10/2014 |
| WO | WO-2015/132004 A1 | | 9/2015 |
| WO | WO-2016/082677 A1 | | 6/2016 |
| WO | WO-2016/145189 A1 | | 9/2016 |
| WO | WO-2017/109087 A1 | | 6/2017 |

OTHER PUBLICATIONS

CN 102311502A englich translation 2012, 01/11/ pp. 1-78.*
Gramer et al., "Expression of VEGFR and PDGFR-αl-β in 187 canine nasal carcinomas", Veterinary and Comparative Oncology, Dec. 2016, pp. 1-10, vol. 15, No. 3, John Wiley & Sons Ltd.
Rossi et al., "The Potential Role of Nintedanib in Treating Colorectal Cancer", Expert Opinion on Pharmacotherapy, Jul. 6, 2017, pp. 1-35, vol. 18, No. 11.
Taeger et al., "Targeting FGFR/PDGFR/VEGFR Impairs Tumor Growth, Angiogenesis, and Metastasis by Effects on Tumor Cells, Endothelial Cells, and Pericytes in Pancreatic Cancer", Molecular Cancer Therapeutics, 211, pp. 2157-2167, vol. 10, No. 11, American Association for Cancer Research.
Zhao et al., "Targeting Angiogenesis in Cancer Therapy: Moving Beyond Vascular Endothelial Growth Factor", The Oncologist, 2015, pp. 1-14, vol. 20, AlphaMed Press 2015.
International Search Report and Written Opinion of the International Searching Authority issued International Application No. PCT/CN2018/115733, dated Feb. 19, 2019.
Aiello et al., "Hypoxic Regulation of Vascular Endothelial Growth Factor in Retinal Cells", Archives of Ophthalmology, Dec. 1995, pp. 1538-1544, vol. 113.
Akiyama et al., "Intraocular Injection of an Aptamer that Binds PDGF-B: A Potential Treatment for Proliferative Retinopathies", Journal of Cellular Physiology, 2006, pp. 407-412, vol. 207, 2006 Wiley-Liss, Inc.
Altschul et al., "Basic Local Alignment Search Tool", Journal of Molecular Biology, 1990, pp. 403-410, vol. 215, 1990 Academic Press Limited.
Altschul et al., "Gapped BLAST and PSI-BLAST: a new generation of protein database search programs", Nucleic Acids Research, 1997, pp. 3389-3402, vol. 25, No. 17, 1997 Oxford University Press.
Altschul, "A Protein Alignment Scoring System Sensitive at All Evolutionary Distances", Journal of Molecular Evolution, 1993, pp. 290-300, vol. 36, Springer-Verlag New York Inc. 1993.
Anderson, "Human Gene Therapy", Science, May 8, 1992, pp. 808-813, vol. 256.
Andrae et al., "Role of platelet-derived growth factors in physiology and medicine", Genes & Development, 2008, pp. 1276-1312, vol. 22, 2008 by Cold Spring Harbor Laboratory Press.

(Continued)

*Primary Examiner* — Bao Q Li
(74) *Attorney, Agent, or Firm* — Foley & Lardner LLP

(57) ABSTRACT

A protein comprising (i) a domain of the Platelet-Derived Growth Factor receptor (PDGFR) and (ii) a domain of the Vascular Endothelial Growth Factor receptor (VEGFR) is provided. In a preferred embodiment, said domain of PDGFR and said domain of VEGFR are attached by a linker consisting of proline, alanine and serine. The domain of PDGFR and said domain of VEGFR can also be attached by a linker consisting of proline and alanine. Compositions comprising the proteins, as well as therapeutic uses thereof are also provided.

31 Claims, 27 Drawing Sheets

Specification includes a Sequence Listing.

(56) References Cited

OTHER PUBLICATIONS

Benjamin et al., "A plasticity window for blood vessel remodelling is defined by pericyte coverage of the preformed endothelial network and is regulated by PDGF-B and VEGF", Development, 1998, pp. 1591-1598, vol. 125, The Company of Biologists Limited 1998.
Berger et al., "The MultiBac Protein Complex Production Platform at the EMBL", Journal of Visualized Experiments, Jul. 2013, pp. 1-8, vol. 77, e50159, 2013 Journal of Visualized Experiments.
Bergers et al., "Benefits of targeting both pericytes and endothelial cells in the tumor vasculature with kinase inhibitors", The Journal of Clinical Investigation, May 2003, pp. 1287-1295, vol. 111, No. 9.
Boyer et al., "Combined inhibition of platelet derived (PDGF) and vascular endothelial (VEGF) growth factors for the treatment of neovascular age-related macular degeneration (NV-AMD)—results of a phase 1 study", Investigative Ophthalmology & Visual Science, Apr. 2009, vol. 50, Abstract Only.
Brizzard et al., "Epitope Tagging of Recombinant Proteins", Current Protocols in Neuroscience, 1997, pp. 5.8.1-5.8.10, 1997 by John Wiley & Sons, Inc.
Browne et al., "Selection methods for high-producing mammalian cell lines", Trends in Biotechnology, 2007, pp. 425-432, vol. 25, No. 9.
Brutlag et al., "Improved sensitivity of biological sequence database searches", Computer Applications in the Biosciences, 1990, pp. 237-245, vol. 6, No. 3, Oxford University Press.
Budisa, "Prolegomena to Future Experimental Efforts on Genetic Code Engineering by Expanding Its Amino Acid Repertoire", Angewandte Chemie, 2004, pp. 6426-6463, vol. 43, 2004 Wiley-VCH Verlag GMBH & Co.
Cao et al., "Angiogenesis stimulated by PDGF-CC, a novel member in the PDGF family, involves activation of PDGFR-αα and αβ-receptors", The FASB Journal, Oct. 2002, pp. 1575-1583, vol. 16.
Capella, "Study of Intravitreal REGN2176-3 in Patients With Neovascular ("Wet") Age-Related Macular Degeneration (AMD)", ClinicalTrials.gov Identifier: NCT02418754, 4 pages.
Carmeliet, "Mechanisms of angiogenesis and arteriogenesis", Nature Medicine, Mar. 2000, pp. 389-395, vol. 6, No. 3, 2000 Nature America Inc.
Cole-Strauss et al., "Correction of the Mutation Responsible for Sickle Cell Anemia by an RNA-DNA Oligonucleotide", Science, Sep. 6, 1996, pp. 1386-1389, vol. 273.
Creighton, "Proteins—Structures and Molecular Properties", 2nd ed., 1993, Chapter 5, pp. 171-199, W. H. Freeman and Company, New York.
Darland et al., "Pericyte production of cell-associated VEGF is differentiation-dependent and is associated with endothelial survival", Developmental Biology, 2003, pp. 275-288, vol. 264, 2003 Elsevier Inc.
Day et al., "Ocular complications after anti-vascular endothelial growth factor therapy in Medicare patients with age-related macular degeneration", Author Manuscript of American Journal of Ophthalmology, Aug. 2011, pp. 1-12, vol. 152, No. 2.
Diago et al., "Ranibizumab Combined With Low-Dose Sorafenib for Exudative Age-Related Macular Degeneration", Author Manuscript of Mayo Clinic Proceedings, Feb. 2008, pp. 1-6, vol. 83, No. 2.
Dugel, "Anti-PDGF Combination Therapy in Neovascular Age-related Macular Degeneration: Results of a Phase 2b Study", Retina Today, Mar. 2013, pp. 65-71.
Eppstein et al., "Biological activity of liposome-encapsulated murine interferon γ is mediated by a cell membrane receptor", Proceedings of the National Academy of Sciences of the United States of America, Jun. 1985, pp. 3688-3692, vol. 82.
Erber et al., "Combined inhibition of VEGF- and PDGF-signaling enforces tumor vessel regression by interfering with pericytemediated endothelial cell survival mechanisms", The FASEB Journal, 2004, pp. 1-25, vol. 18, No. 2, Epub Dec. 4, 2003.
Ferrara et al., "Development of Ranibizumab, an Anti-Vascular Endothelial Growth Factor Antigen Binding Fragment, as Therapy for Neovascular Age-Related Macular Degeneration", Retina, The Journal of Retinal and Vitreous Diseases, 2006, pp. 859-870, vol. 26, No. 8, Ophthalmic Communications Society, Inc.
Ferrara et al., "Discovery and Development of Bevacizumab, an Anti-VEGF Antibody for Treating Cancer", Nature Reviews | Drug Discovery, May 2004, pp. 391-400, vol. 3.
Fitzgerald et al., "Protein complex expression by using multigene baculoviral vectors", Nature Methods, Dec. 2006, pp. 1021-1032, vol. 3, No. 12, 2006 Nature Publishing Group.
Fritze et al., "Epitope Tagging: General Method for Tracking Recombinant Proteins", Methods in Enzymology, 2000, pp. 3-16, vol. 327, 2000 by Academic Press.
Fuh et al., "Requirements for Binding and Signaling of the Kinase Domain Receptor for Vascular Endothelial Growth Factor", The Journal of Biological Chemistry, 1998, pp. 11197-11204, vol. 272, No. 18, 1998 by The American Society for Biochemistry and Molecular Biology, Inc.
Gebauer et al., "Anticalins: Small Engineered Binding Proteins Based on the Lipocalin Scaffold", Methods in Enzymology, 2012, pp. 157-188, vol. 503, 2012 Elsevier Inc.
Geisse et al., "Therapeutic Proteins Methods and Protocols", Methods in Molecular Biology 899, Second Edition, Springer Protocols, Chapter 13 Transient Expression Technologies: Past, Present, and Future, pp. 203-219, Humana Press.
Giordano et al., "Intracoronary gene transfer of fibroblast growth factor-5 increases blood flow and contractile function in an ischemic region of the heart", Nature Medicine, May 1996, pp. 534-539, vol. 2, No. 5, 1996 Nature Publishing Group.
Giuliano et al., "Mechanisms of resistance to anti-angiogenesis therapies", Biochimie, 2013, pp. 1110-1119, vol. 95, 2013 Elsevier Masson SAS.
Gragoudas et al., "Pegaptanib for Neovascular Age-Related Macular Degeneration", The New England Journal of Medicine, Dec. 30, 2004, pp. 2805-2816, vol. 351, No. 27, 2004 Massachusetts Medical Society.
Grothey et al., "Targeting angiogenesis: progress with anti-VEGF treatment with large molecules", Nature Reviews | Clinical Oncology, Sep. 2009, pp. 507-518, vol. 6, 2009 Macmillan Publishers Limited.
Hacker et al., "Polyethyleneimine-based transient gene expression processes for suspension-adapted HEK-293E and CHO-DG44 cells", Protein Expression and Purification, 2013, pp. 67-76, vol. 92, 2013 Elsevier Inc.
Heier et al., "Intravitreal Aflibercept (VEGF Trap-Eye) in Wet Age-related Macular Degeneration", Ophthalmology, Dec. 2012, pp. 2537-2548, vol. 119, No. 12, Elsevier Inc.
Henikoff et al., "Amino acid substitution matrices from protein blocks", Proceedings of the National Academy of Sciences of the United States of America, Nov. 1992, p. 10915-10919, vol. 89.
Hoch et al., "Roles of PDGF in animal development", Development, 2003, pp. 4769-4784, vol. 130, No. 20, 2003 The Company of Biologist Ltd.
Holosh et al., "VEGF-Trap: A VEGF blocker with potent antitumor effects", Proceedings of the National Academy of Sciences of the United States of America, Aug. 20, 2002, pp. 11393-11398, vol. 99, No. 17.
Hou et al., "PDGF-CC blockade inhibits pathological angiogenesis by acting on multiple cellular and molecular targets", Proceedings of the National Academy of Sciences of the United States of America, Jul. 6, 2010, pp. 12216-12221, vol. 107, No. 27.
Hwang et al., "Hepatic uptake and degradation of unilamellar sphingomyelin/cholesterol liposomes: A kinetic study", Proceedings of the National Academy of Sciences of the United States of America, Jul. 1980, pp. 4030-4034, vol. 77, Number 7.
Isner et al., "Clinical evidence of angiogenesis after arterial gene transfer of $phVEGF_{165}$ in patient with ischaemic limb", The Lancet, Aug. 10, 1996, pp. 370-374, vol. 348.
Jaffe et al., "Dual Antagonism of PDGF and VEGF in Neovascular Age-Related Macular Degeneration", Opthalmology, Feb. 2017, pp. 224-234, vol. 124, No. 2, Elsevier Inc.

(56) References Cited

OTHER PUBLICATIONS

Klinke et al., “Physiologie”, 4th Edition, 2005, pp. 874-876, Georg Thieme Verlag, Stuttgart.
Langer et al., “Biocompatibility of polymeric delivery systems for macromolecules”, Journal of Biomedical Materials Research, 1981, pp. 267-277, vol. 15, John Wiley & Sons, Inc.
Langer, “Controlled release of macromolecules”, Chemtech, 1982, pp. 98-105, vol. 12.
Leppanen et al., “Structural and mechanistic insights into VEGF receptor 3 ligand binding and activation”, Proceedings of the National Academy of Sciences of the United States of America, Aug. 6, 2013, pp. 12960-12965, vol. 110, No. 32.
Liu et al., “Adding New Chemistries to the Genetic Code”, Annual Review of Biochemistry, 2010, pp. 413-444, vol. 79, 2010 by Annual Reviews.
Mahadevan et al., “Structural Role of Extracellular Domain 1 of α-Platelet-derived Growth Factor (PDGF) Receptor for PDGF-AA and PDGF-BB Binding”, The Journal of Biological Chemistry, 1995, pp. 27595-27600, vol. 270, No. 46, Issue of Nov. 17, 1995.
Matasci et al., “Recombinant therapeutic protein production in cultivated mammalian cells: current status and future prospects”, Drug Discovery Today: Technologies | Protein Therapeutics, 2008, pp. e37-e42, vol. 5, Nos. 2-3, 2009 Elsevier Ltd.
McDonald et al., “A Structural Superfamily of Growth Factors Containing a Cystine Knot Motif”, Cell, May 7, 1993, pp. 421-424, vol. 73, 1993 by Cell Press.
Mühlhauser et al., “$VEGF_{165}$ Expressed by a Replication-Deficient Recombinant Adenovirus Vector Induces Angiogenesis In Vivo”, Circulation Research, Dec. 1995, pp. 1-10, vol. 77, Issue 6, 1995 American Heart Association, Inc.
Murinello et al., “Fcγ Receptor Upregulation is Associated With Immune Complex Inflammation in the Mouse Retina and Early Age-Related Macular Degeneration”, Investigative Ophthalmology & Visual Science, Jan. 2014, pp. 247-258, vol. 55, No. 1, 2014 The Association for Research in Vision and Ophthalmology, Inc.
Nabel et al., “In Vivo Gene Transfer: A Biological Tool”, Annals New York Academy of Sciences, Dec. 2006, pp. 289-292, vol. 811.
Nagy et al., “Derivation of completely cell culture-derived mice from early-passage embryonic stem cells”, Proceedings of the National Academy of Sciences of the United States of America, Sep. 1993, pp. 8424-8428, vol. 90.
Onodera et al., “Successful Peripheral T-Lymphocyte-Directed Gene Transfer for a Patient With Severe Combined Immune Deficiency Caused by Adenosine Deaminase Deficiency”, Blood, Jan. 1, 1998, pp. 30-36, vol. 91, No. 1, 1998 by The American Society of Hematology.
Pachydaki et al., “Surgical management and ultrastructural study of choroidal neovascularization in punctate inner choroidopathy after bevacizumab”, The Journal of Ophthalmic Inflammation and Infection, 20102, pp. 29-37, vol. 2.
Papadopoulos et al., “Binding and neutralization of vascular endothelial growth factor (VEGF) and related ligands by VEGF Trap, ranibizumab and bevacizumab”, Angiogenesis, 2012, pp. 171-185, vol. 15.
Park et al., “Intraocular Pharmacokinetics of Intravitreal Aflibercept (Eylea) in a Rabbit Model”, Physiology and Pharmacology, 2016, pp. 2612-2617, vol. 57, No. 6.
Pavlakovic et al., “Soluble VEGFR-2: an Anti-lymphangiogenic Variant of VEGF Receptors”, Author Manuscript of Annals of the New York Academy of Sciences, Oct. 2010, pp. 1-14, vol. 1207.
Pham et al., “Large-Scale Transfection of Mammalian Cells for the Fast Production of Recombinant Protein”, Molecular Biotechnology, 2006, pp. 225-237, vol. 34, 2006 Humana Press Inc.
Powner et al., “Expression of Neonatal Fc Receptor in the Eye”, Physiology and Pharmacology, Investigative Ophthalmology & Visual Science, Mar. 2014, pp. 1607-1615, vol. 55, No. 3, 2014 The Association for Research in Vision and Ophthalmology, Inc.
Reinmuth et al., “Induction of VEGF in perivascular cells defines a potential paracrine mechanism for endothelial cell survival”, The FASEB Journal, 2001, pp. 1-19, vol. 15, No. 7.
Robbins et al., “Platelet-Derived Growth Factor Ligands and Receptors Immunolocalized in Proliferative Retinal Diseases”, Investigative Ophthalmology & Visual Science, Sep. 1994, pp. 3649-3663, vol. 35, No. 10, Association for Research in Vision and Opthalmology.
Rofagha et al., “Seven-Year Outcomes in Ranibizumab-Treated Patients in ANCHOR, MARINA, and HORIZON”, Ophthalmology, Nov. 2013, pp. 2292-2299, vol. 120, No. 11, Elsevier Inc.
Rosenfeld et al., “Characteristics of Patients Losing Vision after 2 Years of Monthly Dosing in the Phase III Ranibizumab Clinical Trials”, Ophthalmology, Mar. 2011, pp. 523-530, vol. 118, No. 3, Elsevier Inc.
Rosenfeld et al., “Ranibizumab for Neovascular Age-Related Macular Degeneration”, The New England Journal of Medicine, Oct. 5, 2006, pp. 1419-1431, vol. 355, No. 14, 2006 Massachusetts Medical Society.
Sampat et al., “Complications of intravitreal injections”, Current Opinion in Ophthalmology, 2010, pp. 178-183, vol. 21, 2010 Wolters Kluwer Health.
Schaper et al., “Molecular Mechanisms of Coronary Collateral Vessel Growth”, Circulation Research, Nov. 1, 1996, pp. 1-21, vol. 79, Issue 5, 1996 American Heart Association, Inc.
Schaper et al., “Therapeutic targets in cardiovascular disorders”, Current Opinion in Biotechnology, 1996, pp. 635-640, vol. 7, Current Biology Ltd.
Schlapschy et al., “PASylation: a biological alternative to PEGylation for extending the plasma half-life of pharmaceutically active proteins”, Protein Engineering, Design & Selection, 2013, pp. 489-501, vol. 26, No. 8, Oxford University Press.
Schlessinger, “Cell Signaling by Receptor Tyrosine Kinases,” Cell, Oct. 13, 2000, pp. 211-225, vol. 103, 2000 by Cell Press.
Sepah et al., “Twenty-four-Month Outcomes of the Ranibizumab for Edema of the Macula in Diabetes—Protocol 3 with High Dose(READ-3) Study”, Ophthalmology, Dec. 2016, pp. 2581-2587, vol. 123, No. 12, Elsevier Inc.
Shibuya et al., “Structure and Function of Vascular Endothelial Growth Factor Receptor-1 and -2”, Current Topics in Microbiology and Immunology, 1999, pp. 59-83, vol. 237.
Shim et al., “Structures of a platelet-derived growth factor/propeptide complex and a platelet-derived growth factor/receptor complex”, Proceedings of the National Academy of Sciences of the United States of America, Jun. 22, 2010, pp. 11307-11312, vol. 107, No. 25.
Sidman et al., “Controlled Release of Macromolecules and Pharmaceuticals from Synthetic Polypeptides Based on Glutamic Acid”, Biopolymers, 1983, pp. 547-556, vol. 22, John Wiley & Sons, Inc.
Smith et al., “The concept of a random coil Residual structure in peptides and denatured proteins”, Folding & Design, Oct. 1, 1996, pp. R95-R106, vol. 1, No. 5, Current Biology Ltd.
Souied et al., “Severe Ocular Inflammation Following Ranibizumab or Aflibercept Injections for Age-Related Macular Degeneration: A Retrospective Claims Database Analysis”, Ophthalmic Epidemiology, 2016, pp. 71-79, vol. 23, No. 2.
Stewart, “A Review of Ranibizumab for the Treatment of Diabetic Retinopathy”, Ophthalmology and Therapy, 2017, pp. 33-47, vol. 6.
Stuttfeld et al., “Structure and Function of VEGF Receptors”, International Union of Biochemistry and Molecular Biology Life, Sep. 2009, pp. 915-922, vol. 61, No. 9.
Terpe, “Overview of tag protein fusions: from molecular and biochemical fundamentals to commercial systems”, Applied Microbiology and Biotechnology, 2003, pp. 523-533, vol. 60, Springer-Verlag 2002.
Thompson et al., “Clustal W: improving the sensitivity of progressive multiple sequence alignment through sequence weighting, position-specific gap penalties and weight matrix choice”, Nucleic Acids Research, 1994, pp. 4673-4680, vol. 22, No. 22, 1994 Oxford University Press.
Uemura et al., “Recombinant angiopoietin-1 restores higher-order architecture of growing blood vessels in mice in the absence of mural cells”, The Journal of Clinical Investigation, Dec. 2002, pp. 1619-1628, vol. 110, No. 11.

(56) References Cited

OTHER PUBLICATIONS

Verma et al., "Gene therapy-promises, problems and prospects", Nature, Sep. 18, 1997, pp. 239-242, vol. 389, Macmillan Publishers Ltd 1997.
Verma et al., "Gene transfer into human umbilical cord blood-derived $CD34^+$ cells by particle-mediated gene transfer", Gene Therapy, 1998, pp. 692-699, vol. 5, 1998 Stockton Press.
Verzeletti et al., "Herpes Simplex Virus Thymidine Kinase Gene Transfer for Controlled Graft-versus-Host Disease and Graft-versus-Leukemia: Clinical Follow-up and Improved New Vectors", Human Gene Therapy, Oct. 10, 1998, pp. 2243-2251, vol. 9, Mary Ann Liebert, Inc.
Wagner et al., "New Naturally Occurring Amino Acids", Angewandte Chemie International Edition in English, 1983, pp. 816-828, vol. 22, Verlag Chemie GmbH.
Walsh, "Post-translational modifications of protein biopharmaceuticals", Drug Discovery Today, Sep. 2010, pp. 773-780, vol. 15, Nos. 17/18, 2010 Elsevier Ltd.
Wang et al., "Second-generation adenovirus vectors", Nature Medicine, Jun. 1996, pp. 714-716, vol. 2, No. 6, 1996 Nature Publishing Group.
Winkler et al., "Kinetics of vascular normalization by VEGFR2 blockade governs brain tumor response to radiation: Role of oxygenation, angiopoietin-1, and matrix metalloproteinases", Cancer Cell, Dec. 2004, pp. 553-563, vol. 6, 2004 Cell Press.
Wurm, "Production of recombinant protein therapeutics in cultivated mammalian cells", Nature Biotechnology, Nov. 2004, pp. 1393-1398, vol. 22, No. 11, 2004 Nature Publishing Group.
Ying et al., "Sustained Visual Acuity Loss in the Comparison of Age-Related Macular Degeneration Treatments Trials", Author Manuscript of JAMA Ophthalmology, Aug. 2014, pp. 1-14, vol. 132, No. 8.
Young et al., "Beyond the Canonical 20 Amino Acids: Expanding the Genetic Lexicon", The Journal of Biological Chemistry, Apr. 9, 2010, pp. 11039-11044, vol. 285, No. 15, The American Society for Biochemistry and Molecular Biology, Inc.
Yujing et al., "Progression and challenge of therapeutic strategies in neovascular age-related macular degeneration", Chinese Journal of Ocular Fundus Diseases, Jan. 2016, pp. 3-7, vol. 32, No. 1, English Abstract.
Zehetner et al., "Systemic Upregulation of PDGF-B in Patients With Neovascular AMD", Investigative Ophthalmology & Visual Science, Jan. 2014, pp. 337-344, vol. 55, No. 1, 2014 The Association for Research in Vision and Opthalmology, Inc.

* cited by examiner

A.

B.

A

B

A

B

A

B

A

B

A

B

A

B

A

B

A

B

A

B

A

B

PASYLATED VEGFR/PDGFR FUSION PROTEINS AND THEIR USE IN THERAPY

RELATED APPLICATIONS

The present application claims priority under 37 U.S.C. § 371 to International Patent Application No. PCT/CN2018/115733, filed Nov. 15, 2018, which claims priority to and the benefit of European Patent Application No. 17204968.6, filed on Dec. 1, 2017, and Chinese Patent Application No. 201711136582.6, filed on Nov. 16, 2017. The contents of these applications are hereby incorporated by reference in their entireties.

SEQUENCE LISTING

The instant application contains a Sequence Listing which has been submitted in ASCII format via EFS-Web and is hereby incorporated by reference in its entirety. Said ASCII copy, is named 028622-0317_SL_v3.txt and is 306 kb in size.

FIELD OF THE INVENTION

The present invention relates to a protein comprising (i) a domain of the Platelet-Derived Growth Factor receptor (PDGFR) and (ii) a domain of the Vascular Endothelial Growth Factor receptor (VEGFR). In a preferred embodiment, said domain of PDGFR and said domain of VEGFR are attached by a linker consisting of proline, alanine and serine. The domain of PDGFR and said domain of VEGFR can also be attached by a linker consisting of proline and alanine. The present invention also provides compositions comprising the proteins, as well as therapeutic uses thereof.

BACKGROUND OF THE INVENTION

Current state-of-the-art anti-angiogenic therapies target the VEGF pathway, which is the main essential signaling pathway for angiogenesis, including pathological angiogenesis in cancer and eye diseases. However, the long-term outcomes of anti-VEGF monotherapy in patients with eye diseases are somewhat disappointing (Dugel, 2013) since chronic anti-VEGF treatment seems to induce disease-resistance in some patient populations, which is often associated with a substantial loss of vision (Rofagha et al., 2013; Ying et al., 2014; Rosenfeld et al., 2011). As the VEGF level varies in the vitreous of patients, it was proposed that those poor responders of anti-VEGF therapy may need much higher doses of anti-VEGF drugs due to higher levels of VEGF. However, 1-year results from the Clinical Study READ-3 showed no additional benefit of using 4 times higher dose than the regular regimen (Nguyen et al., 2014; Bai et al, 2016). Such observations suggest that multiple pathways are involved in retinal and choroidal neovascularization in eye diseases. In fact, growing clinical and laboratory evidence indicates that, in addition to VEGF, which is a key player in neovascular (or wet) age-related macular degeneration (AMD; Rosenfeld et al., 2006; Heier et al., 2012), PDGF may also play a crucial role in the pathogenesis of this disease. In fact, dual inhibition of VEGF and PDGF may be more effective than targeting VEGF alone (Robins et al., 1994; Benjamin et al., 1998; Zehetner et al., 2014; Bergers et al., 2003; Erber et al., 2004; Pachydaki et al., 2012).

The pathological condition AMD occurs when unstable and highly permeable blood vessels grow and invade from the choroid into the retina, where leakage and bleeding results in a rapid loss of sight (during a period of a few weeks to months). In this setting, VEGF is one of the most potent inducers of vascular permeability known (Carmeliet, 2000), even though the precise mechanisms by which VEGF increases vascular permeability are not entirely clear.

Studies examining postnatal remodeling of the retina provided initial clues as to the importance of VEGF and PDGF in wet AMD (Benjamin et al., 1998) while work on cancer models gave the final push to pursue anti-VEGF/PDGF combination therapies for the treatment of wet AMD (Bergers et al., 2003; Erber et al., 2004). Patients under anti-VEGF monotherapy typically gain an initial improvement in visual acuity (i.e., clarity of vision) in the first 3 or 4 months of treatment, which is followed by a plateau that persists throughout the study (Dugel, 2013). In these first months of treatment, Anti-VEGF monotherapy acts primarily on fenestrated endothelial cells that form the inner lining of the vessel wall, causing a decrease in edema and, consequently, initial improvement in visual acuity. Thereafter, however, the remainder of the neovascular complex seems to be protected by pericyte cells that coat and stabilize the endothelial tube. In this situation, pericytes are thought to render the survival of blood vessels resistant to VEGF inhibition, which may account for the plateau that is usually observed after initial anti-VEGF treatment (Dugel, 2013). Notably, anti-VEGF therapy may not only lead to endothelial cell apoptosis but also enhance pericyte recruitment, thereby potentially reversing the effect of VEGF inhibition (Winkler et al., 2004; Pachydaki et al., 2012).

The arsenal of clinically useful VEGF blockers has evolved over time, with newer generations offering potentially improved anti-angiogenic activity by increasing the affinity towards VEGF-A and/or a number of VEGF isoforms as well as family members they inhibit. In principle, these blockers fall into two categories: (i) monoclonal antibodies, alternative binding proteins (scaffolds) or engineered soluble receptor fragments and (ii) small molecule inhibitors of the kinase domains of VEGFR and related receptors.

One of the first anti-VEGF therapies approved by the FDA for AMD was pegaptanib (Macugen), an RNA aptamer that binds and neutralizes VEGF-A165 (Gragoudas et al., 2004). The first protein-based therapy employing a VEGF-neutralizing strategy was bevacizumab (Avastin, Genentech), a recombinant humanized anti-VEGF antibody designed to block all VEGF isoforms via antigen recognition by its variable region. Bevacizumab was initially approved for the treatment of metastatic colorectal cancer, non-small-cell lung cancer and glioblastoma multiforme (Grothey et al., 2009; Ferrara et al., 2004).

Concomitantly with the development of such cancer therapies, VEGF was found to also play a pivotal role in neovascular AMD and diabetic retinopathy. Starting from this notion, ranibizumab (Lucentis, Genentech) was developed based on bevacizumab as an affinity-matured antigen-binding fragment (Fab) specifically for intravitreal administration to treat vascular eye diseases, especially the wet or neovascular form of AMD (Ferrara et al., 2006) and, recently, also for diabetic retinopathy (Stewart, 2017). The smaller size of the Fab compared with a full size antibody was thought to enhance its diffusion from the vitreous into the retina as well as choroid (Ferrara et al., 2006).

VEGF-Trap (aflibercept; Regeneron Pharmaceuticals) is an engineered soluble decoy receptor that binds VEGF-A based on the molecular interaction of the growth factor with its cognate cellular receptors VEGFR-1 and VEGFR-2.

VEGF-Trap consists of a fully human amino-acid sequence comprising the second Ig domain of human VEGFR-1 and the third Ig domain of human VEGFR-2 fused in-line with the constant region (Fc) of human IgG1 (Holash et al., 2002). Therefore, VEGF-Trap has a broader specificity than an antibody, recognizing not only multiple isoforms of VEGF-A but also the related VEGF-B, P1GF (placental growth factor), and PIGF2 (Papadopoulos et al., 2012), which all are physiological ligands of the two tyrosine kinase (TK) receptors VEGFR-1 and VEGFR-2.

SUMMARY OF THE INVENTION

Despite proven efficacy and availability of the reagents described so far, additional and more efficacious anti-VEGF therapies are needed in order to improve VEGF targeting and/or to overcome resistance to existing anti-VEGF therapies. Currently, chronic suppression with serial intravitreal injections of VEGF antagonists is often required for maintaining disease control, while none of the available medications causes complete regression of the choroidal neovascular membrane. In line with this, not all patients respond to treatment, with some developing into non-responders. Ideally, new approaches would address these limitations of current (mono)therapy.

One of the key factors responsible for resistance to VEGF blockage, either intrinsically or adapted during treatment, is the redundancy in the VEGF signalling system (Giuliano & Pages, 2013). An increase in the expression of other proangiogenic factors may possibly fuel alternate signaling pathways for angiogenesis, which could trigger VEGF-independent neovascularization and cause resistance to mono anti-VEGF drugs. The amalgamation of drugs that specifically address more than one pathologenic pathway could potentially enhance the efficacy of therapy by targeting key pathways in a characteristically synergistic or an additive manner.

Apart from the VEGF axis, PDGFs and PDGFRs are validated therapeutic targets in a variety of diseases, especially cancer and vascular disorders (Andrae et al., 2008). PDGFs are hetero- or homodimers of A and B polypeptide chains or homodimers of C or D chains that interact with their cognate PDGF receptors: all PDGF versions except for PDGF-DD bind the PDGFR-α receptor whereas only PDGF-BB and PDGF-DD bind the PDGF-β receptor (Hoch et al., 2003). Thus, compared to PDGFR-β, PDGFR-α possesses broader ligand-binding activity and, furthermore, higher affinity for both PDGF-AA and PDGF-BB as well as, in particular, PDGF-CC.

To date, the basis for such distinct specificities remains unclear. PDGF-CC has been shown to be relevant in both choroidal and retinal neovascularization (Hou et al., 2010; Cao et al., 2002). A pathogenic role for PDGF-BB was implicated in ischemic retinopathies such as proliferative diabetic retinopathy, proliferative vitreoretinopathy, and choroidal neovascularization. Notably, during the processes of angiogenesis and vessel maturation the recruitment of pericytes to the growing endothelial tube is regulated by platelet-derived growth factor-B (PDGF-BB) via signalling through the PDGF receptor β (PDGFR-β). In a pre-clinical rabbit model of proliferative retinopathy, intraocular injection of PDGF-BB-inhibiting aptamers was shown to protect the eye against retinal detachment (Akiyama et al. 2006).

Notably, preliminary results from clinical trials using intravitreal injection of PDGF-blocking agents in conjunction with intravitreal anti-VEGF therapy have demonstrated the potential of combining both strategies also for the treatment of AMD (Diago et al., 2008; Boyer et al., 2009).

However, addressing both types of growth factors at once in a clinical setting still faces technical difficulties. Recently, clinical phase II and phase III studies of Fovista (E10030; Ophthotech), an anti-PDGF-BB pegylated aptamer, were evaluated as an adjunct to ranibizumab. Although the first results from these trials partially demonstrated a benefit of co-administration of E10030 with ranibizumab to patients suffering from wet AMD (Jaffe et al., 2016), ocular adverse events were more frequently reported in the combination therapy group receiving both drugs by separate intravitreal injections.

In another phase II clinical trail on wet AMD, the co-formulation of the two antibody-like molecules aflibercept (VEGF trap) and rinucumab (anti-PDGFR-β antibody, known as REGN2176-3), being administered via single injection was related to more adverse events compared to the aflibercept monotherapy. Patients receiving the combination suffered from increase in conjunctival haemorrhage, eye irritation and eye pain: 23.5% and 20% for the two combination groups versus 16% for aflibercept alone. (CAPELLA; ClinicalTrials.gov Identifier: NCT02418754).

Of note, both drugs, aflibercept and rinucumab, contain crystallizable fragments (Fc) of IgG while it is not known if the Fc component, also known as immunological effector domain, affects physiological mechanisms in the eye. Normally, a physical barrier, the retina-blood-barrier, prevents the free entry of immunoglobulins (Igs) and other large macromolecules into and out of the eye, thus establishing an immune-priviliged microenvironment which makes this organ immunologically unique. Although the fate of high concentrations of therapeutic Ig-based drugs after intravitreal injection is not well understood, evidence exists that the Fc component interacts with retinal Fc receptors and therefore may contribute to an intraretinal inflammatory response in AMD (Souid et al., 2016; Powner et al., 2014; Murinello et al., 2014).

Ideally, protein-based drugs intended for chronical ocular disease treatment should offer extended intraocular half-life to allow less frequent dosing, as each injection procedure constitutes a significant burden for patients and entails a risk of complications (Day et al., 2011). For such a protein drug one way of gaining half-life extension is genetic fusion with a polypeptide that provides a desirable pharmacokinetic profile but is otherwise (physiologically and biochemically) inert. This approach further allows the design of stable second-generation protein drugs with two or more fusion partners, each comprising a unique targeting modality.

Thus, the technical problem underlying the present invention is the provision of means and methods for a therapy targeting both VEGF and ligands of PDGFR.

The technical problem is solved by provision of the embodiments characterized in the claims.

Accordingly, the present invention relates to a protein comprising (i) a domain of the Platelet-Derived Growth Factor receptor (PDGFR); and (ii) a domain of the Vascular Endothelial Growth Factor receptor (VEGFR).

In a preferred aspect, a protein is provided herein, the protein comprising (i) an extracellular domain of the human Platelet-Derived Growth Factor receptor (PDGFR); and (ii) an extracellular domain of the human Vascular Endothelial Growth Factor receptor (VEGFR).

In a preferred embodiment, said domain of PDGFR and said domain of VEGFR are attached by a linker consisting of proline, alanine and serine.

As explained herein below, the synergistic effect of VEGF and PDGF signaling inhibition can be mediated by one therapeutic protein. As illustrated in the examples, single-chain proteins were designed that are capable of binding to VEGF and PDGF ligands at the same time. This type of fusion protein functions as a molecular trap for VEGFs, PDGFs and related ligands and is therefore beneficial in pathological processes where these ligands act synergistically, including AMD or cancer.

As shown in the examples, these types of proteins were designed as fusion between the N-terminal ectodomains of VEGF receptors 1 and 2 as well as PDGF receptor α (PDGFR-α), which are involved in ligand-binding of VEGF or PDGF, respectively. Both classes of receptors (VEGFR-1/2 and PDGFR-α) encompass a very broad ligand-binding activity, which is thought to be beneficial in a disease state where angiogenesis is the dominating process. Like all protein-tyrosine kinase receptors, VEGFR-1, VEGFR-2 and PDGFR-α (and also PDGFR-β) consist of an extracellular region of five to seven Ig-like domains (D1-D7), a single transmembrane segment and an intracellular split catalytic tyrosine kinase domain (Shibuya et al., 1999; Stuttfeld et al., 2009). Binding of the dimeric VEGF/PDGF ligands to these receptors generally occurs at the second and third Ig-like domains (D2, D3), where it promotes homo- or heterodimerization of the receptor and, consequently, signal transduction. The proximal domains 4-7 (D4-7) of the extracellular region seem to be important for stabilizing the ligand-receptor complex, whereas the domain closest to the cell membrane, D7, is crucial for ligand-induced tyrosine phosphorylation and cell signaling.

Thus, for the construction of an effective decoy receptor fragment it is, as shown herein, adequate to utilize predominantly domains from the N-terminal extracellular region which are directly involved in binding of the ligands.

In the examples, the extracellular moiety of VEGFR was placed at the C-terminal end of the fusion protein and has the same composition as the high affinity ligand-binding region of the engineered hybrid VEGFR1-D2/VEGFR2-D3 ectodomains described in U.S. Pat. No. 5,952,199. The PDGFR-α moiety, comprising the first three ectodomains D1-3 of the receptor, was arranged at the N-terminal end of the fusion protein, thus preserving the natural N-terminus of PDGFR-α, including its signal peptide which gets processed upon secretion.

Although not much is known about the molecular structure of PDGFR-α, structures of the related PDGFR-13 and VEGFR receptors (Schlessinger, 2000; Shim et al., 2010) provide information about the central part of the corresponding ligand/receptor recognition complexes, which is perceived to be generally similar since PDGFs and VEGFs are of common evolutionary origin (McDonald and Hendrickson, 1993). From these structures it is known that the D1 domains of PDGFR-β and VEGFRs are not directly involved in ligand binding but, because of a hydrophobic interface between D1 and D2, serve as a cap for the ligand-binding D2 domains (Hye-Ryong et al., 2010; Leppanen et al., 2013). Therefore, inclusion of the first domain D1 in the decoy version of PDGFR-α was considered herein beneficial for the therapeutic fusion protein as provided herein in the examples. In fact, the presence of D1 in PDGFR-α seems to have also a small differential effect on ligand binding to PDGF-AA, as learnt from deletion analysis within the ectodomain of PDGF-α (Mahadewan et al., 1995).

In a preferred aspect, a fusion protein is provided, wherein the extracellular parts D1-3 of PDGFR-α and D2/D3 of VEGFR1/2 are linked by a PAS-polypeptide sequence or, alternatively, a Ser-free P/A sequence. Such PAS/PA sequences are for example disclosed in WO2008/155134 A1 and WO2011/144756 A1. The PAS/PA spacer provides structural flexibility to the individual ectodomains, thus allowing access of both VEGF and PDGF ligands. In addition, these random coil sequences greatly increase the hydrodynamic volume of the fusion protein, which slows down clearance of the fused ectodomains in vivo and, thus, prolongs and/or enhances the pharmacological effect (Schlapschy et al., 2013). In addition, PAS/PA polypeptides are hydrophilic homo-polymers of the small natural L-amino acids proline, alanine and serine (or proline and alanine, respectively), which provides biocompatibility and facilitates metabolization.

The random coil nature of the PAS linker/spacer sequence (Schlapschy et al., 2013) provides the individual VEGFR and PDGFR ectodomains with high flexibility such that, in the presence of ligands, each arm of the decoy receptor fusion is able to bind to the dimeric ligand (growth factor), eventually forming a functional decoy dimer (see FIG. 2). Once formed via complex formation with the first ligand, either VEGF or PDGF, such a dimerized fusion protein further gains functional affinity for the second ligand via the avidity effect. Hence, the affinities of PDGFR and VEGFR ectodomains should synergistically sum up by way of multiple binding interactions, especially in a disease condition where both ligands are abundant.

This is highly advantageous, as in the dimerized ectodomain receptor fusion, if the first ligand is present, ideally VEGF, the relatively moderate affinity of natural PDGFR ectodomains for their homo/heterodimeric PDGF ligands can be boosted by the high affinity ligand-binding site of the hybrid VEGFR1-D2/VEGFR2-D3 domains towards VEGF-A (Holash et al., 2002). The decoy receptor as provided and disclosed herein should be comparable with the corresponding membrane-bound natural receptors in terms of affinity and specificity on the one hand, but it should be incapable of triggering signaling, or presenting the agonist to signaling receptor complexes, on the other hand.

In accordance with the above, the examples demonstrate that exemplary proteins provided herein

- Inhibit $VEGF_{165}$-induced HUVEC cell proliferation (Example 20);
- Inhibit the intersegmental vessels (ISVs) development in zebrafish embryos (Example 21);
- Inhibit the tumor neovascularization induced by human VEGFA (Example 22);
- Show an increased half-life (T½) in SD rats (Example 23);
- Inhibit laser-induced Choroidal Neovascularization (CNV) in cynomolgus monkeys (Examples 24);
- Show an increased half-life (T½) in New Zealand rabbits (Example 25);
- Show complex formation with target compounds in native PAGE and electromobility gel shift assay (Example 26);
- Inhibit $VEGF_{165}$-induced HUVEC cell proliferation (Example 27).

In view of the herein demonstrated properties of the proteins, they can be advantageously used in a therapeutic setting as disclosed herein.

The present invention relates to the following items:

1. Protein comprising
   (i) an extracellular domain of the human Platelet-Derived Growth Factor receptor (PDGFR); and
   (ii) an extracellular domain of the human Vascular Endothelial Growth Factor receptor (VEGFR).
2. The protein of item 1, wherein said domain of PDGFR and said domain of VEGFR are attached by a linker consisting of proline, alanine and serine.
3. The protein of item 2, wherein said proline residues constitute more than 4% and less than 40% of said linker.
4. The protein of item 2 or 3, wherein said linker has an amino acid sequence as follows: (ASPAAPAPASPAAPAPSAPA (SEQ ID NO: 71)) n, wherein n is an integer of 10-100.
5. The protein of item 4, wherein said linker comprising an amino acid sequence as follows: (ASPAAPAPASPAAPAPSAPA (SEQ ID NO: 71)) n, wherein n is an integer of 10-60.
6. The protein of item 5, wherein said linker comprising an amino acid sequence as follows: CASPAAPAPASPAAPAPSAPA (SEQ ID NO: 71)) n, wherein n is an integer of 10-40.
7. The protein of item 6, wherein said linker comprising an amino acid sequence as follows: (ASPAAPAPASPAAPAPSAPA (SEQ ID NO: 71)) n, wherein n is an integer of 10-30.
8. The protein of item 7, wherein said linker comprising an amino acid sequence as follows: (ASPAAPAPASPAAPAPSAPA (SEQ ID NO: 71)) n, wherein n is 10, 20 or 30.
9. The protein of item 4, wherein said linker has an amino acid sequence as shown in SEQ ID No. 2 or wherein said linker is a polypeptide encoded by a nucleic acid molecule having a nucleotide sequence as shown in SEQ ID No. 1.
10. The protein of item 1, wherein said domain of PDGFR and said domain of VEGFR are attached by a linker consisting of proline and alanine.
11. The protein of item 10, wherein said proline residues constitute more than about 10% and less than about 75% of said linker.
12. The protein of item 10 or 11, wherein said linker has an amino acid sequence as follows: (AAPAAPAPAAPAAPAAPA (SEQ ID NO: 72)) n, wherein n is an integer of 10-100.
13. The protein of item 12, wherein said linker has an amino acid sequence as shown in SEQ ID No. 70 or wherein said linker is a polypeptide encoded by a nucleic acid molecule having a nucleotide sequence as shown in SEQ ID No. 69.
14. The protein of any one of items 2 to 10, wherein said linker has an amino acid sequence consisting of about 50 to about 3000 amino acid residues.
15. The protein of any one of item 14, wherein said domain of PDGFR comprises one or more of Ig domains 1 to 5 of PDGFR.
16. The protein of any one of item 15, wherein said domain of PDGFR comprises one or more of Ig domains 1 to 3 of PDGFR.
17. The protein of any one of items 1 to 16, wherein said domain of PDGFR comprises Ig domains 1 to 3 of PDGFR.
18. The protein of any one of items 1 to 17, wherein said domain of PDGFR is capable of binding to Platelet-Derived Growth Factor (PDGF).
19. The protein of item 18, wherein said PDGF is a PDGF dimer.
20. The protein of items 19, wherein said PDGF dimer is a PDGF homodimer or a PDGF heterodimer.
21. The protein of any one of items 1 to 20, wherein said PDGFR is human PDGFRα.
22. The protein of any one of items 1 to 21, wherein said domain of PDGFR comprises:
   (a) a protein having an amino acid sequence as shown in SEQ ID No. 4 or SEQ ID No. 20;
   (b) a protein as defined in (a) wherein 1 to 10 amino acids are deleted, inserted, added or substituted;
   (c) a polypeptide encoded by a nucleic acid molecule having a nucleotide sequence as shown in SEQ ID No. 3 or SEQ ID No. 19;
   (d) a polypeptide having an amino acid sequence encoded by a nucleic acid hybridizing under stringent conditions to the complementary strand of nucleic acid molecules as defined in (c);
   (e) a polypeptide having at least 70% identity to the polypeptide of any one of (a) to (d); and
   (f) a polypeptide having an amino acid sequence encoded by a nucleic acid being degenerate as a result of the genetic code to the nucleotide sequence of a nucleic acid as defined in (c) or (d).
23. The protein of item 21 or 22, wherein said domain of PDGFR is capable of binding to Platelet-Derived Growth Factor (PDGF), wherein said PDGF is a PDGF homodimer, and wherein said PDGF homodimer is a PDGFA homodimer, a PDGFB homodimer, or a PDGFC homodimer.
24. The protein of item 21 or 22, wherein said domain of PDGFR is capable of binding to Platelet-Derived Growth Factor (PDGF), wherein said PDGF preferably is a PDGF heterodimer, and wherein said PDGF heterodimer preferably is a heterodimer of PDGFAB.
25. The protein of any one of items 1 to 20, wherein said PDGFR is human PDGFRβ3.
26. The protein of any one of items 1 to 20 and 25, wherein said domain of PDGFR comprises:
   (a) a protein having an amino acid sequence as shown in SEQ ID No.6;
   (b) a protein as defined in (a) wherein 1 to 10 amino acids are deleted, inserted, added or substituted;
   (c) a polypeptide encoded by a nucleic acid molecule having a nucleotide sequence as shown in SEQ ID No. 5;
   (d) a polypeptide having an amino acid sequence encoded by a nucleic acid hybridizing under stringent conditions to the complementary strand of nucleic acid molecules as defined in (c);
   (e) a polypeptide having at least 70% identity to the polypeptide of any one of (a) to (d); and
   (f) a polypeptide having an amino acid sequence encoded by a nucleic acid being degenerate as a result of the genetic code to the nucleotide sequence of a nucleic acid as defined in (c) or (d).
27. The protein of item 25 or 26, wherein said domain of PDGFR is capable of binding to Platelet-Derived Growth Factor (PDGF), wherein said PDGF preferably is a PDGF homodimer, and wherein said PDGF homodimer preferably is a PDGFB homodimer.
28. The protein of any one of items 18 to 27, wherein said Platelet-Derived Growth Factor (PDGF) is human PDGF.
29. The protein of any one of items 1 to 28, wherein said domain of VEGFR comprises one or more of Ig domains 1 to 7 of VEGFR.

30. The protein of any one of items 1 to 29, wherein said domain of VEGFR comprises Ig domain 2 and/or Ig domain 3 of VEGFR.
31. The protein of any one of items 1 to 30, wherein said domain of VEGFR comprises Ig domain 2 and Ig domain 3 of VEGFR.
32. The protein of any one of items 1 to 31, wherein said VEGFR is human VEGFR-1 or human VEGFR-2.
33. The protein of any one of items 1 to 32, wherein said domain of VEGFR comprises Ig domain 2 of VEGFR-1 and Ig domain 3 of VEGFR-2.
34. The protein of any one of items 1 to 33, wherein said domain of VEGFR comprises
   (a) a protein having an amino acid sequence as shown in SEQ ID No. 8;
   (b) a protein as defined in (a) wherein 1 to 10 amino acids are deleted, inserted, added or substituted;
   (c) a polypeptide encoded by a nucleic acid molecule having a nucleotide sequence as shown in SEQ ID No. 7;
   (d) a polypeptide having an amino acid sequence encoded by a nucleic acid hybridizing under stringent conditions to the complementary strand of nucleic acid molecules as defined in (c);
   (e) a polypeptide having at least 70% identity to the polypeptide of any one of (a) to (d); and
   (f) a polypeptide having an amino acid sequence encoded by a nucleic acid being degenerate as a result of the genetic code to the nucleotide sequence of a nucleic acid as defined in (c) or (d).
35. The protein of any one of items 1 to 34, wherein said domain of VEGFR is capable of binding to Vascular Endothelial Growth Factor (VEGF).
36. The protein of item 35, wherein said Vascular Endothelial Growth Factor (VEGF) is a VEGF dimer.
37. The protein of item 36, wherein said VEGF dimer is a VEGF homodimer.
38. The protein of item 37, wherein said VEGF homodimer is a VEGFA homodimer.
39. The protein of any one of items 35 to 38, wherein said Vascular Endothelial Growth Factor (VEGF) is human VEGF.
40. The protein of any one of items 1 to 39, wherein said protein is a fusion protein.
41. The protein of any one of items 1 to 40, wherein said protein comprises:
   (a) a protein having an amino acid sequence as shown in SEQ ID No. 16, SEQ ID No. 46, SEQ ID No. 48, SEQ ID No. 50, SEQ ID No. 52, SEQ ID No. 54, SEQ ID No. 56, SEQ ID No. 58, SEQ ID No. 60, SEQ ID No. 62, SEQ ID No. 64, SEQ ID No. 66 or SEQ ID No. 68;
   (b) a protein as defined in (a) wherein 1 to 10 amino acids are deleted, inserted, added or substituted;
   (c) a polypeptide encoded by a nucleic acid molecule having a nucleotide sequence as shown in SEQ ID No. 15, SEQ ID No. 45, SEQ ID No. 47, SEQ ID No. 49, SEQ ID No. 51, SEQ ID No. 53, SEQ ID No. 55, SEQ ID No. 57, SEQ ID No. 59, SEQ ID No. 61, SEQ ID No. 63, SEQ ID No. 65 or SEQ ID No. 67;
   (d) a polypeptide having an amino acid sequence encoded by a nucleic acid hybridizing under stringent conditions to the complementary strand of nucleic acid molecules as defined in (c);
   (e) a polypeptide having at least 70% identity to the polypeptide of any one of (a) to (d); and
   (f) a polypeptide having an amino acid sequence encoded by a nucleic acid being degenerate as a result of the genetic code to the nucleotide sequence of a nucleic acid as defined in (c) or (d).
42. The protein of any one of items 1 to 41, wherein said protein comprises an N-terminal signal polypeptide sequence.
43. The protein of item 42, wherein said N-terminal signal polypeptide sequence is the N-terminal signal polypeptide sequence of PDGFR.
44. The protein of item 43, wherein said N-terminal signal polypeptide sequence is the N-terminal signal polypeptide sequence of human PDGFRα.
45. The protein of any one of items 42 to 44, wherein said N-terminal signal polypeptide sequence has an amino acid sequence as shown in SEQ ID No. 10 or wherein said N-terminal signal polypeptide sequence is a polypeptide encoded by a nucleic acid molecule having a nucleotide sequence as shown in SEQ ID No. 9.
46. The protein of any one of items 1 to 45, wherein said protein further comprises a purification tag.
47. The protein of item 46, wherein said purification tag is a His-tag.
48. The protein of item 46 or 47, wherein said purification tag has an amino acid sequence as shown in SEQ ID No. 12 or wherein said purification tag is a polypeptide encoded by a nucleic acid molecule having a nucleotide sequence as shown in SEQ ID No. 11.
49. The protein of any one of items 1 to 48, wherein the protein is arranged from N-terminus to C-terminus in the order:
   (optional signal sequence)-one or more domains of PDGFR-(optional linker)-one or more domains of VEGFR-(optional purification tag) or
   (optional signal sequence)-one or more domains of VEGFR-(optional linker)-one or more domains of PDGFR-(optional purification tag) or
   (optional signal sequence)-(optional linker)-one or more domains of VEGFR-one or more domains of PDGFR-(optional purification tag) or
   (optional signal sequence)-(optional linker)-one or more domains of PDGFR-one or more domains of VEGFR-(optional purification tag) or
   (optional signal sequence)-(optional linker)-one or more domains of PDGFR-(optional linker)-one or more domains of VEGFR-(optional linker)-(optional purification tag).
50. The protein of any one of items 1 to 49, wherein the protein is arranged from N-terminus to C-terminus in the order:
   (optional signal sequence)-one or more domains of PDGFR-(PAS/PA)-one or more domains of VEGFR-(optional purification tag) or
   (optional signal sequence)-one or more domains of VEGFR-(PAS/PA)-one or more domains of PDGFR-(optional purification tag) or
   (optional signal sequence)-(PAS/PA)-one or more domains of VEGFR-one or more domains of PDGFR-(optional purification tag) or
   (optional signal sequence)-(PAS/PA)-one or more domains of PDGFR-one or more domains of VEGFR-(optional purification tag) or
   (optional signal sequence)-(PAS/PA)-one or more domains of PDGFR-(PAS/PA)-one or more domains of VEGFR-(PAS/PA)-(optional purification tag).
51. The protein of any one of items 1 to 50, wherein the protein is arranged from N-terminus to C-terminus in the order:

(optional signal sequence)-one or more domains of PDGFR-(GGGGS (SEQ ID NO: 73))n-(PAS/PA) -(GGGGS (SEQ ID NO: 73))n-one or more domains of VEGFR-(optional purification tag) or (optional signal sequence)-one or more domains of VEGFR-(GGGGS (SEQ ID NO: 73))n-(PAS/PA) -(GGGGS (SEQ ID NO: 73))n-one or more domains of PDGFR-(optional purification tag);

wherein, n=0-5.

52. The protein of any one of items 1 to 51, wherein said protein comprises
   (a) a protein having an amino acid sequence as shown in SEQ ID No. 14, SEQ ID No. 22, SEQ ID No. 24, SEQ ID No. 26, SEQ ID No. 28, SEQ ID No. 30, SEQ ID No. 32, SEQ ID No. 34, SEQ ID No. 36, SEQ ID No. 38, SEQ ID No. 40, SEQ ID No. 42 or SEQ ID No. 44;
   (b) a protein as defined in (a) wherein 1 to 10 amino acids are deleted, inserted, added or substituted;
   (c) a polypeptide encoded by a nucleic acid molecule having a nucleotide sequence as shown in SEQ ID No. 13, SEQ ID No. 15, SEQ ID No. 21, SEQ ID No. 23, SEQ ID No. 25, SEQ ID No. 27, SEQ ID No. 29, SEQ ID No. 31, SEQ ID No. 33, SEQ ID No. 35, SEQ ID No. 37, SEQ ID No. 39, SEQ ID No. 41 or SEQ ID No. 43,
   (d) a polypeptide having an amino acid sequence encoded by a nucleic acid hybridizing under stringent conditions to the complementary strand of nucleic acid molecules as defined in (c);
   (e) a polypeptide having at least 70% identity to the polypeptide of any one of (a) to (d); and
   (f) a polypeptide having an amino acid sequence encoded by a nucleic acid being degenerate as a result of the genetic code to the nucleotide sequence of a nucleic acid as defined in (c) or (d).
53. A nucleic acid molecule encoding the protein of any one of items 1 to 52.
54. A vector comprising the nucleic acid of item 53.
55. A host cell comprising the nucleic acid of items 53 or the vector of item 54.
56. The host cell according to item 55, wherein said host cell is a eukaryotic host cell or a prokaryotic host cell.
57. The host cell according to item 56, wherein said prokaryotic host cell is *E. coli.*
58. The host cell according to item 56, wherein said eukaryotic host cell is a fungal or animal cell.
59. The host cell according to item 58, wherein said animal cell is a HEK cell or a CHO cell.
60. A method for the preparation of a protein of any one of items 1 to 52.
61. The method of item 60, comprising culturing the host cell according to any one of items 55 to 59 and isolating said protein from the culture or from said cell.
62. A composition comprising the protein of any one of items 1 to 52, the protein prepared by the method of item 60 or 61, the nucleic acid of item 53, the vector of item 54, or the cell of any one of items 55 to 58.
63. The composition according to item 62 which is a pharmaceutical composition, optionally further comprising (a) pharmaceutical acceptable carrier(s).
64. The protein of any one of items 1 to 52, the protein prepared by the method of item 60 or 61, the nucleic acid of item 53, the vector of item 54, the cell of any one of items 55 to 58, or the composition of item 62 or 63, for use as a medicament.
65. The protein of any one of items 1 to 52, the protein prepared by the method of item 60 or 61, the nucleic acid of item 53, the vector of item 54, the cell of any one of items 55 to 58, or the composition of item 62 or 63, for use in the treatment of ophthalmic diseases, cancer, renal fibrosis, cirrhosis, arthosclerosis, portal hypertension or systemic sclerosis.
66. The protein for use of item 65, the nucleic acid for use of item 65, the vector for use of item 65, the cell for use of item 65, or the composition for use of item 65, wherein said cancer is a solid cancer.
67. The protein for use of item 66, the nucleic acid for use of item 66, the vector for use of item 66, the cell for use of item 66, or the composition for use of item 66, wherein said solid cancer is colon cancer, hepatocellular carcinoma, non-small cell lung cancer, soft tissue sarcoma, prostate cancer, breast cancer, ovarian cancer, glioma, dermatofibrosarcoma protuberans, oral squamous cell carcinoma, pancreatic cancer.
68. The protein for use of item 65, the nucleic acid for use of item 65, the vector for use of item 65, the cell for use of item 65, or the composition for use of item 65, wherein said cancer is a non-solid cancer.
69. The protein for use of item 68, the nucleic acid for use of item 68, the vector for use of item 68, the cell for use of item 68, or the composition for use of item 68, wherein said non-solid cancer is leukemia or non-Hodgkin's lymphoma.
70. The protein for use of item 65, the nucleic acid for use of claim 65, the vector for use of claim 65, the cell for use of claim 65, or the composition for use of claim 65, wherein said ophthalmic diseases is age-related macular degeneration (AMD), Diabetic retinopathy (DR), Diabetic macular edema (DME), Choroidal neovascularization (CNV), Retinal vein occlusion (RVO), Central retinal vein occlusion (CRVO), Branch retinal vein occlusion (BRVO), or pathologic myopia (PM).
71. The protein for use of item 65, the nucleic acid for use of claim 65, the vector for use of claim 65, the cell for use of claim 65, or the composition for use of claim 65, wherein said ophthalmic diseases is age-related macular degeneration (AMID).

In certain aspects, the following items are provided herein:

As mentioned above, a protein is provided herein, the protein comprising
   (i) an extracellular domain of the human Platelet-Derived Growth Factor receptor (PDGFR); and
   (ii) an extracellular domain of the human Vascular Endothelial Growth Factor receptor (VEGFR).

As indicated above, said domain of PDGFR and said domain of VEGFR are, in a preferred embodiment, attached by a linker consisting of proline, alanine and serine.

The Platelet-Derived Growth Factor (PDGF) family consists of disulphide-bonded homodimers of A-, B-, C- and D-polypeptide chains, and the heterodimer PDGF-AB. PDGF isoforms are reported to exert their cellular effects by binding to their respective receptors (PDGF receptors (PDGFR)). The terms "Platelet-Derived Growth Factor", "PDGF", "Platelet-Derived Growth Factor protein" and "PDGF protein" are used interchangeably herein. The terms "Platelet-Derived Growth Factor receptor", "PDGF receptor", "PDGFR", "Platelet-Derived Growth Factor receptor protein", "PDGF receptor protein" and "PDGFR protein" are used interchangeably herein.

Vascular Endothelial Growth Factor (VEGF) and their receptors (VEGFR) are reported to regulate both vasculogenesis (the development of blood vessels from precursor cells during early embroygenesis) and angiogenesis (the formation of blood vessels from pre-existing vessels at a later stage). The VEGF family of genes contains at least 7 members, whereas the VEGFR family of genes has 3 to 4 members depending on the vertebrate species. The terms "Vascular Endothelial Growth Factor", "VEGF", "Vascular Endothelial Growth Factor protein" and "VEGF protein" are used interchangeably herein. The terms "Vascular Endothelial Growth Factor receptor", "VEGF receptor", "VEGFR", "Vascular Endothelial Growth Factor receptor protein", "VEGF receptor protein" and "VEGFR protein" are used interchangeably herein.

The meaning of the term "domain" or "protein domain" is well known in the art and the terms are used accordingly herein. The terms "domain" and "protein domain" are used interchangeably herein. A protein domain can be viewed as the basic structural unit of a protein structure. The core of each domain is usually largely composed of a set of interconnected β sheets or α helices or both. Domains are usually constructed from a section of a polypeptide chain that contains normally between 50 to 350 amino acids.

It is envisaged that the proteins provided herein can act as a "decoy" receptor, i.e. that they can bind to the ligand PDGF and/or VEGF.

In a preferred aspect, the domain of PDGFR is capable of binding to Platelet-Derived Growth Factor (PDGF). The PDGF can be a monomer, but is preferably a PDGF dimer. The PDGF dimer can be a PDGF homodimer or a PDGF heterodimer.

In a preferred aspect, the domain of VEGFR is capable of binding to Vascular Endothelial Growth Factor (VEGF). The VEGF can be a monomer, but is preferably a PDGF dimer. The VEGF dimer can be a VEGF homodimer, like a VEGFA homodimer.

More preferably, both the domain of PDGFR is capable of binding to Platelet-Derived Growth Factor (PDGF) and the domain of VEGFR is capable of binding to Vascular Endothelial Growth Factor (VEGF).

The terms "capable of binding", "binding capacity" and the like are used herein in accordance with the common meaning in the art. In context of ligand-receptor-interactions, "binding capacity" refers to the capacity of a ligand (here PDGF and VEGF respectively) to bind to its receptor (here the domain of PDGFR and domain of VEGFR, respectively).

Ligand binding can be characterized by the $IC_{50}$ (the concentration of a ligand at which half of the receptor binding sites are occupied).

Binding affinity can be determined using a radio labeled (tagged) ligand, known as a tagged ligand. Non-labelled methods include surface plasmon resonance, dual polarization interferometry, Multi-Parametric Surface Plasmon Resonance (MP-SPR) and Microscal thermophoresis.

PDGF binds normally to the extracellular domain of its receptor PDGFR.

It is preferred herein that the domain of PDGFR comprises or consists of the extracellular domain of PDGFR. The extracellular domain of PDGFR contains 5 Ig-like domains. The term "Ig-like domain" and "Ig domain" are used interchangeably herein. Ligand binding is thought to occur preferentially through Ig domains 2 and 3.

In accordance with the above, the domain of PDGFR can comprise or consist of one or more of Ig domains 1 to 5 of PDGFR, i.e. one or more of Ig domain 1 of PDGFR, Ig domain 2 of PDGFR, Ig domain 3 of PDGFR, Ig domain 4 of PDGFR, Ig domain 5 of PDGFR. Any combinations thereof, as well as the use of fragments or derivatives of one or more of Ig domains 1 to 5 of PDGFR (and any combinations of one or more Ig domains 1 to 5 of PDGFR and of any fragments or derivatives of one or more of Ig domains 1 to 5 of PDGFR is encompassed herein).

The domain of PDGFR to be used herein can for example comprise or consist of one or more of Ig domains 1 to 3 of PDGFR, i.e. one or more of Ig domain 1 of PDGFR, Ig domain 2 of PDGFR and Ig domain 3 of PDGFR. Any combinations thereof, as well as the use of fragments or derivatives of one or more of Ig domains 1 to 3 of PDGFR (and any combinations of one or more g domains 1 to 3 of PDGFR and of any fragments or derivatives of one or more of Ig domains 1 to 3 of PDGFR is encompassed herein).

As shown in the appended example, a protein comprising Ig domains 1 to 3 of PDGFR is indeed capable of binding to PDGF.

In a preferred aspect, the domain of PDGFR comprises or consists of Ig domains 1 to 3 of PDGFR, particularly preferably of Ig domains 1 to 3 of human PDGFRα.

The use of animal PDGFR (i.e. of animal origin), for example an extracellular domain of PDGFR and/or one or more of Ig domains 1 to 5 of PDGFR) is envisaged herein, for example mammalian PDGFR, e.g. rat, mouse, pig, guinea pig, ape PDGFR and the like. It is preferred herein that the PDGFR is human PDGFR (i.e. of human origin), for example an extracellular domain of human PDGFR and/or one or more of Ig domains 1 to 5 of human PDGFR). The amino acid sequence and nucleotide sequence of human PDGFR is well known in the prior art, see e.g. NCBI Reference Sequence: NP_001334758.1, NP_001334756.1, NP_001334757.1, NP_001341945.1, NP_002600.1

It is envisaged herein that the PDGFR domain herein can be composed of portions/fragments of various PDGFR proteins (or PDGFR isoforms), e.g. portions/fragments of PDGFR proteins (and/or PDGFR isoforms) of different origin, e.g. origin of different animals and/or of human origin. For example, the PDGFR domain herein can be composed of a portion/fragment of a PDGFR protein (including various PDGFR isoforms) of human origin and a portion/fragment of a PDGFR protein (including various PDGFR isoforms) of animal origin, e.g. of rat, mouse, pig, guinea pig, or ape PDGFR protein (including various PDGFR isoforms). It is envisaged herein that the PDGFR domain herein can be composed of portions/fragments of various PDGFR isoforms (e.g. various PDGFR isoforms of human and/or animal origin). For example, the PDGFR domain herein can be composed of portions of various human PDGFR isoforms (e.g. various PDGFR isoforms of human origin), e.g. portions of human PDGFRα and/or human PDGFRβ.

For example, the domain of PDGFR can comprise or consist of e.g. one or more of Ig domains 1 to 5 of PDGFR of e.g. origin of different animals and/or of human origin. For example, the domain of PDGFR can comprise or consist of Ig domain 1 and/or 2 of PDGFR of animal origin and Ig domain 3 of PDGFR of human origin (or vice versa). For example, the domain of PDGFR can comprise or consist of e.g. one or more of Ig domains 1 to 5 of various (human) PDGFR isoforms e.g. human PDGFRα and/or human PDGFRβ. For example, the domain of PDGFR can comprise or consist of Ig domain 1 and/or 2 of human PDGFRα and Ig domain 3 of human PDGFRβ (or vice versa). For example, the domain of PDGFR can comprise or consist of Ig domain 1 of human PDGFRα and Ig domains 2 and/or 3 of human PDGFRβ (or vice versa).

For example, compositions are envisaged herein that comprise e.g. proteins comprising a PDGFR domain of different origin, e.g. origin of different animals and/or of human origin. For example, compositions are envisaged that comprise e.g. proteins comprising a PDGFR domain of human origin and proteins comprising a PDGFR domain of animal origin, e.g. of rat, mouse, pig, guinea pig, or ape PDGFR. For example, compositions are envisaged that comprise e.g. proteins comprising a PDGFR domain of various PDGFR isoforms (e.g. various human PDGFR isoforms), like a composition comprising e.g. a protein comprising a PDGFR domain of human PDGFRα and comprising a protein comprising a VEGFR domain of human PDGFRβ.

In a herein preferred aspect, the PDGFR is human PDGFRα.

The domain of PDGFR can comprise or consist of:

(a) a protein having an amino acid sequence as shown in SEQ ID No. 4 or SEQ ID No. 20;
(b) a protein as defined in (a) wherein 1 to 10 amino acids are deleted, inserted, added or substituted;
(c) a polypeptide encoded by a nucleic acid molecule having a nucleotide sequence as shown in SEQ ID No. 3 or SEQ ID No. 19;
(d) a polypeptide having an amino acid sequence encoded by a nucleic acid hybridizing under stringent conditions to the complementary strand of nucleic acid molecules as defined in (c);
(e) a polypeptide having at least 70% identity to the polypeptide of any one of (a) to (d); and
(f) a polypeptide having an amino acid sequence encoded by a nucleic acid being degenerate as a result of the genetic code to the nucleotide sequence of a nucleic acid as defined in (c) or (d).

The protein having an amino acid sequence as shown in SEQ ID No. 4 corresponds to Ig domains 1 to 3 of human PDGFRα. A corresponding nucleic acid molecule encoding such a protein is shown in SEQ ID No. 3.

The protein having an amino acid sequence as shown in SEQ ID No. 20 corresponds to Ig domains 1 to 3 of human PDGFRα. A corresponding nucleic acid molecule encoding such a protein is shown in SEQ ID No. 19.

In a preferred embodiment, the domain of PDGFR can comprise or consist of:

(a) a protein having an amino acid sequence as shown in SEQ ID No. 4 or SEQ ID No. 20; or
(c) a polypeptide encoded by a nucleic acid molecule having a nucleotide sequence as shown in SEQ ID No. 3 or SEQ ID No. 19.

Particularly if the PDGFR is human PDGFRα (or if the PDGFR domain is the PDGFR domain of human PDGFRα), and if the domain of PDGFR is capable of binding to Platelet-Derived Growth Factor (PDGF), said PDGF can be a PDGF homodimer, for example a PDGFA homodimer, a PDGFB homodimer, or a PDGFC homodimer.

Particularly if the PDGFR is human PDGFRα (or if the PDGFR domain is the PDGFR domain of human PDGFRα), and if the domain of PDGFR is capable of binding to Platelet-Derived Growth Factor (PDGF), said PDGF can be a PDGF heterodimer, for example a heterodimer of PDGF-AB.

It is envisaged herein that the PDGFR herein can be human PDGFRβ (or that the PDGFR domain can be the PDGFR domain of human PDGFRβ).

The domain of PDGFR can comprise or consist of:

(a) a protein having an amino acid sequence as shown in SEQ ID No. 6;
(b) a protein as defined in (a) wherein 1 to 10 amino acids are deleted, inserted, added or substituted;
(c) a polypeptide encoded by a nucleic acid molecule having a nucleotide sequence as shown in SEQ ID No. 5;
(d) a polypeptide having an amino acid sequence encoded by a nucleic acid hybridizing under stringent conditions to the complementary strand of nucleic acid molecules as defined in (c);
(e) a polypeptide having at least 70% identity to the polypeptide of any one of (a) to (d); and
(f) a polypeptide having an amino acid sequence encoded by a nucleic acid being degenerate as a result of the genetic code to the nucleotide sequence of a nucleic acid as defined in (c) or (d).

The protein having an amino acid sequence as shown in SEQ ID No. 6 corresponds to Ig domains 1 to 3 of human PDGFRβ. A corresponding nucleic acid molecule encoding such a protein is shown in SEQ ID No. 5.

In a preferred aspect, the domain of PDGFR can comprise or consist of:

(a) a protein having an amino acid sequence as shown in SEQ ID No. 6;

or (c) a polypeptide encoded by a nucleic acid molecule having a nucleotide sequence as shown in SEQ ID No. 5.

Particularly if the PDGFR is human PDGFRβ (or if the PDGFR domain is the PDGFR domain of human PDGFRβ), and if the domain of PDGFR is capable of binding to Platelet-Derived Growth Factor (PDGF), said PDGF can be a PDGF homodimer, for example, a PDGF-B homodimer.

The use of animal PDGF (i.e. of animal origin) is envisaged herein, for example mammalian PDGF, e.g. rat, mouse, pig, guinea pig, ape PDGF and the like. It is preferred herein that the PDGF is human PDGF (i.e. of human origin). Also the amino acid sequence and nucleotide sequence of PDGF, such as human PDGF, is well known in the prior art, see e.g. NCBI Reference Sequences NP_002598.4, NP_148983.1, NP_002599, NP_148937 or NP_057289.1.

The protein provided herein comprises a domain of VEGFR.

VEGF binds normally to the extracellular domain of its receptor VEGFR.

It is preferred herein that the domain of VEGFR comprises or consists of the extracellular domain of VEGFR. The extracellular domain of VEGFR contains 7 Ig-like domains. The term "Ig-like domain" and "Ig domain" are used interchangeably herein. Ligand binding is thought to occur preferentially to Ig domains 2 and 3.

In accordance with the above, the domain of VEGFR can comprise or consist of one or more of Ig domains 1 to 7 of VEGFR, i.e. one or more of Ig domain 1 of VEGFR, Ig domain 2 of VEGFR, Ig domain 3 of VEGFR, Ig domain 4 of VEGFR, Ig domain 5 of VEGFR, Ig domain 6 of VEGFR and Ig domain 7 of VEGFR. Any combinations thereof, as well as the use of fragments or derivatives of one or more of Ig domains 1 to 7 of VEGFR (and any combinations of one or more Ig domains 1 to 7 of VEGFR and of any fragments or derivatives of one or more of Ig domains 1 to 7 of VEGFR is encompassed herein).

The domain of VEGFR to be used herein can for example comprise or consist of Ig domains 2 and/or 3 of VEGFR, i.e. Ig domain 2 and/or Ig domain 3 of VEGFR. Any combinations thereof, as well as the use of fragments or derivatives of Ig domain 2 and/or Ig domain 3 of VEGFR (and any combinations of Ig domain 2 and/or Ig domain 3 of VEGFR and of any fragments or derivatives of Ig domain 2 and/or Ig domain 3 of VEGFR of VEGFR) is encompassed herein.

As shown in the appended example, a protein comprising Ig domains 2 and 3 of VEGFR is indeed capable of binding to VEGF.

In a preferred aspect, the domain of VEGFR comprises or consists of Ig domains 2 and 3 of VEGFR.

The use of animal VEGFR (i.e. of animal origin), for example an extracellular domain of VEGFR and/or one or more of Ig domains 1 to 7 of VEGFR) is envisaged herein, for example mammalian VEGFR, e.g. rat, mouse, pig, guinea pig, or ape VEGFR and the like. It is preferred herein that the VEGFR is human VEGFR (i.e. of human origin), for example an extracellular domain of human VEGFR and/or one or more of Ig domains 1 to 7 of human VEGFR). The amino acid sequence and nucleotide sequence of human VEGFR is well known in the prior art, see e.g. NCBI Reference Sequences: NP_002010.2, NP_001153392.1, NP_001153502.1, NP_001153503.1 or NP_002244.1. It is preferred herein that the VEGFR is human VEGFR-1 and/or human VEGFR-2.

It is envisaged herein that the VEGFR domain herein can be composed of portions/fragments of various VEGFR proteins (or VEGFR isoforms), e.g. portions/fragments of VEGFR proteins (and/or VEGFR isoforms) of different origin, e.g. origin of different animals and/or of human origin. For example, the VEGFR domain herein can be composed of (a) portion(s)/fragment(s) of a VEGFR protein (including various VEGFR isoforms) of human origin and (a) portion(s)/fragment(s) of a VEGFR protein (including various VEGFR isoforms) of animal origin, e.g. of rat, mouse, pig, guinea pig, or ape VEGFR protein (VEGFR isoforms). It is also envisaged herein that the VEGFR domain herein can be composed of portions/fragments of various VEGFR isoforms (e.g. various VEGFR isoforms of human and/or animal origin). For example, the VEGFR domain herein can be composed of portions/fragments of various human VEGFR isoforms (e.g. various VEGFR isoforms of human origin), e.g. portions/fragments of human VEGFR-1 or human VEGFR-2.

For example, the domain of VEGFR can comprise or consist of e.g. one or more of Ig domains 1 to 7 of VEGFR of e.g. origin of different animals and/or of human origin. For example, the domain of VEGFR can comprise or consist of Ig domain 2 of VEGFR of animal origin and Ig domain 3 of VEGFR of human origin (or vice versa). For example, the domain of VEGFR can comprise or consist of e.g. one or more of Ig domains 1 to 7, 1 to 5, 1 to 4, 1 to 3, 1 to 2, or 2 to 3, of various (human) VEGFR isoforms e.g. of human VEGFR-1 and/or human VEGFR-2. For example, the domain of VEGFR can comprise or consist of Ig domain 1 and/or 2 of human VEGFR-1 and Ig domain 3 of human VEGFR-2 (or vice versa). For example, the domain of VEGFR can comprise or consist of Ig domain 1 of human VEGFR-1 and Ig domains 2 and/or 3 of human VEGFR-2 (or vice versa).

In a preferred aspect, the domain of VEGFR comprises or consists of Ig domain 2 of VEGFR-1 and Ig domain 3 of VEGFR-2. In a particularly preferred aspect, the domain of VEGFR comprises or consists of Ig domain 2 of human VEGFR-1 and Ig domain 3 of human VEGFR-2.

For example, compositions are envisaged herein that comprise e.g. proteins comprising a VEGFR domain of different origin, e.g. origin of different animals and/or of human origin. For example, compositions are envisaged that comprise e.g. proteins comprising a VEGFR domain of human origin and proteins comprising a VEGFR domain of animal origin, e.g. of rat, mouse, pig, guinea pig, or ape VEGFR. For example, compositions are envisaged that comprise e.g. proteins comprising a VEGFR domain of various VEGFR isoforms (e.g. various human VEGFR isoforms), like a composition comprising e.g. a protein comprising a VEGFR domain of human VEGFR-1 and comprising a protein comprising a VEGFR domain of human VEGFR-2.

The domain of VEGFR can comprise or consist of:

(a) a protein having an amino acid sequence as shown in SEQ ID No. 8;
(b) a protein as defined in (a) wherein 1 to 10 amino acids are deleted, inserted, added or substituted;
(c) a polypeptide encoded by a nucleic acid molecule having a nucleotide sequence as shown in SEQ ID No. 7;
(d) a polypeptide having an amino acid sequence encoded by a nucleic acid hybridizing under stringent conditions to the complementary strand of nucleic acid molecules as defined in (c);
(e) a polypeptide having at least 70% identity to the polypeptide of any one of (a) to (d); and
(f) a polypeptide having an amino acid sequence encoded by a nucleic acid being degenerate as a result of the genetic code to the nucleotide sequence of a nucleic acid as defined in (c) or (d).

The protein having an amino acid sequence as shown in SEQ ID No. 8 corresponds to Ig domain 2 of human VEGFR-1 and Ig domain 3 of human VEGFR-2. A corresponding nucleic acid molecule encoding such a protein is shown in SEQ ID No. 7.

In a preferred embodiment, the domain of VEGFR can comprise or consist of (a) a protein having an amino acid sequence as shown in SEQ ID No. 8; or
(c) a polypeptide encoded by a nucleic acid molecule having a nucleotide sequence as shown in SEQ ID No. 7.

As mentioned, preferably the domain of VEGFR is capable of binding to Vascular Endothelial Growth Factor (VEGF).

Particularly if the VEGFR is human VEGFR (or if the VEGFR domain is the VEGFR domain of human VEGFR), and if the domain of VEGFR is capable of binding to VEGF, said VEGF can be a VEGF dimer, particularly a VEGF homodimer, and preferably a VEGFA homodimer.

The use of animal VEGF (i.e. of animal origin) is envisaged herein, for example mammalian VEGF, e.g. rat, mouse, pig, guinea pig, ape VEGF and the like. It is preferred herein that the VEGF is human VEGF (i.e. of human origin). Also the amino acid sequence and nucleotide sequence of VEGF, such as human VEGF, is well known in the prior art, see e.g. NCBI Reference Sequences: NP_001020537.2, NP_001020538.2, NP_001020539.2, NP_001020540.2, NP_001020541.2, NP_001028928.1, NP_001165093.1, NP_001165094.1, NP_001165095.1, NP_001165096.1, NP_001165097.1, NP_001165098.1, NP_001165099.1, NP_001165100.1, NP_001165101.1, NP_001191313.1, NP_001191314.1, NP_001273973.1, NP_001303939.1 or NP_003367.4.

The domain of PDGFR and the domain of VEGFR can be attached by a linker, like a peptide or polypeptide linker. The linker to be used herein primarily serves the purpose to provide the VEGFR and PDGFR domains with high flexibility so that each domain (each arm of the decoy receptor) is able to bind to the (dimeric) ligand (VEGF and PDGF, respectively). Consequently, a protein dimer can form in the presence of ligands, i.e. a functional decoy dimer can form. Thus, the linker/linker sequences does not necessarily contribute to the biological activity, in particular ligand binding (i.e. binding of VEGF and PDGF, respectively), of the herein provided proteins. The linker is preferably a flexible linker. The peptide or polypeptide linker(s) can be composed of flexible residues, like glycine and/or serine.

The linker can have an amino acid sequence consisting of about 50 to about 3000 amino acid residues, e.g. about 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500 2600, 2700, 2800, 2900 or 3000 amino acid residues. In a preferred aspect, the linker has an amino acid sequence consisting of 200 amino acid residues.

In a preferred aspect, said domain of PDGFR and said domain of VEGFR are attached by a linker consisting of proline, alanine and serine. In this aspect, the proline residues can constitute more than 4% and less than 40% of said linker.

Preferably, said linker comprising an amino acid sequence as follows: (ASPAAPAPASPAAPAPSAPA (SEQ ID NO: 71)) n, wherein n=10-100; further preferably, n=10-60; more preferably, n=10-40; further preferably, n=10-30; more preferably, n=10, 20 or 30; particularly preferably, the linker can have an amino acid sequence as shown in SEQ ID NO: 2 or said linker can be a polypeptide encoded by a nucleic acid molecule having a nucleotide sequence as shown in SEQ ID No. 1. The linker can have an amino acid sequence consisting of about 50 to about 3000 amino acid residues.

The domain of PDGFR and the domain of VEGFR can be attached by a linker consisting of proline and alanine. In this aspect, the proline residues can constitute more than about 10% and less than about 75% of said linker. Preferably, said linker has an amino acid sequence as follows: (AAPAAPAPAAPAAPAAPA (SEQ ID NO: 72)) n, wherein n is an integer of 10-100; further preferably, said linker has an amino acid sequence as shown in SEQ ID No. 70 or wherein said linker is a polypeptide encoded by a nucleic acid molecule having a nucleotide sequence as shown in SEQ ID No. 69. The linker can have an amino acid sequence consisting of about 50 to about 3000 amino acid residues.

In a preferred aspect, a protein is provided herein, wherein said protein comprises:

(a) a protein having an amino acid sequence as shown in SEQ ID No. 16, SEQ ID No. 46, SEQ ID No. 48, SEQ ID No. 50, SEQ ID No. 52, SEQ ID No. 54, SEQ ID No. 56, SEQ ID No. 58, SEQ ID No. 60, SEQ ID No. 62, SEQ ID No. 64, SEQ ID No. 66 or SEQ ID No. 68;

(b) a protein as defined in (a) wherein 1 to 10 amino acids are deleted, inserted, added or substituted;

(c) a polypeptide encoded by a nucleic acid molecule having a nucleotide sequence as shown in SEQ ID No. 15, SEQ ID No. 45, SEQ ID No. 47, SEQ ID No. 49, SEQ ID No. 51, SEQ ID No. 53, SEQ ID No. 55, SEQ ID No. 57, SEQ ID No. 59, SEQ ID No. 61, SEQ ID No. 63, SEQ ID No. 65 or SEQ ID No. 67;

(d) a polypeptide having an amino acid sequence encoded by a nucleic acid hybridizing under stringent conditions to the complementary strand of nucleic acid molecules as defined in (c);

(e) a polypeptide having at least 70% identity to the polypeptide of any one of (a) to (d); and (f) a polypeptide having an amino acid sequence encoded by a nucleic acid being degenerate as a result of the genetic code to the nucleotide sequence of a nucleic acid as defined in (c) or (d).

Preferred herein are proteins termed herein EPS1104P, EPS1107P, EPS1108P and EPS1115P. Their sequences are shown among others in the following table:

| SEQ ID No. | Trivial Name | Construct |
|---|---|---|
| SEQ ID No. 14 | EPS1108P | PDGFR$_{\alpha D123}$-PAS(200)-VEGFR1$_{D}$2/R2$_{D3}$ |
| SEQ ID No. 22 | EPS1103P | PDGFRα$_{D123}$-PAS(300)-VEGFR1$_{D2}$/R2$_{D3}$ |
| SEQ ID No. 24 | EPS1104P | PDGFRα$_{D123}$-PAS(400)-VEGFR1$_{D2}$/R2$_{D3}$ |
| SEQ ID No. 26 | EPS1105P | VEGFR1$_{D2}$/R2$_{D3}$-PAS(200)- PDGFRα$_{D123}$ |
| SEQ ID No. 28 | EPS1106P | PDGFRα$_{D123}$-(GGGGS)$_3$-PAS(200)-(GGGGS)$_3$-VEGFR1$_{D2}$/R2$_{D3}$ |
| SEQ ID No. 30 | EPS1107P | VEGFR1$_{D2}$/R2$_{D3}$-(GGGGS)$_3$-PAS(200)-(GGGGS)$_3$-PDGFRα$_{D123}$ |
| SEQ ID No. 32 | EPS1109P | PAS(200)-VEGFR1$_{D2}$/R2$_{D3}$-PDGFRα$_{D123}$ |
| SEQ ID No. 34 | EPS1110P | PAS(200)-PDGFRα$_{D123}$-VEGFR1$_{D2}$/R2$_{D3}$ |
| SEQ ID No. 36 | EPS1111P | PDGFRβ$_{D123}$-PAS(200)-VEGFR1$_{D2}$/R2$_{D3}$ |
| SEQ ID No. 38 | EPS1113P | PDGFRα$_{D123}$-PAS(600)-VEGFR1$_{D2}$/R2$_{D3}$ |
| SEQ ID No. 40 | EPS1114P | PDGFRα$_{D123}$-(GGGGS)$_3$-PAS(600)-(GGGGS)$_3$-VEGFR1$_{D2}$/R2$_{D3}$ |
| SEQ ID No. 42 | EPS1115P | VEGFR1$_{D2}$/R2$_{D3}$-(GGGGS)$_3$-PAS(600)-(GGGGS)$_3$-PDGFRα$_{D123}$ |
| SEQ ID No. 44 | EPS1116P | mutantPDGFRα$_{D123}$-PAS(200)-VEGFR1$_{D2}$/R2$_{D3}$ |

The following further defines the linker consisting of proline, alanine and serine/the linker consisting of proline and alanine. It is envisaged herein that the linker forms a random coil.

As used herein, the term "random coil" relates to any conformation of a polymeric molecule, including amino acid polymers, in particular polypeptides made of L-amino acids, in which the individual monomeric elements that form said polymeric structure are essentially randomly oriented towards the adjacent monomeric element or elements while still being chemically linked. In particular, the encoded polypeptide or amino acid polymer adopting/having/forming "random coil conformation" substantially lacks a defined secondary and tertiary structure. The nature of the encoded polypeptide random coils and their methods of experimental identification are known to the person skilled in the art and have been described in the scientific literature (Cantor (1980) Biophysical Chemistry, 2nd ed., W. H. Freeman and Company, New York; Creighton (1993) Proteins—Structures and Molecular Properties, 2nd ed., W. H. Freeman and Company, New York; Smith (1996) Fold. Des. 1:R95-R106) and patent literature, e.g., WO2011/144756 and WO2008/155134.

The linker as comprised in the herein provided protein can adopt/form a random coil conformation, for example, in aqueous solution and/or at physiological conditions. The term "physiological conditions" is known in the art and relates to those conditions in which proteins usually adopt their native, folded conformation. More specifically, the term "physiological conditions" relates to the environmental biophysical parameters as they are typically valid for higher forms of life and, particularly, for mammals, most preferably human beings. The term "physiological conditions" may relate to the biochemical and biophysical parameters as they are normally found in the body, in particular in body fluids, of mammals and in particular in humans. Said "physiological conditions" may relate to the corresponding parameters found in the healthy body as well as the parameters found under disease conditions or in human patients. For example, a sick mammal or human patient may have a higher, yet "physiological" body temperature (i.e., temperature condition) when said mammal or said human suffers from fever. With respect to "physiological conditions" at which proteins adopt their native conformation/state, the most important parameters are temperature (37° C. for the healthy human body), pH (7.35-7.45 for human blood), osmolarity (280-300 mmol/kg $H_2O$), and, if necessary, general protein content (66-85 g/l serum).

Yet, the person skilled in the art is aware that at physiological conditions these parameters may vary, e.g. the temperature, pH, osmolarity, and protein content may be different in given body or tissue fluids such as blood, liquor cerebrospinalis, peritoneal fluid and lymph (Klinke (2005) Physiologie, 4th edition, Georg Thieme Verlag, Stuttgart). For example, in the liquor cerebrospinalis the osmolarity may be around 290 mmol/kg $H_2O$ and the protein concentration may be between 0.15 g/l and 0.45 g/l while in the lymph the pH may be around 7.4 and the protein content may be between 3 g/l and 5 g/l. When determining whether a polypeptide linker forms/adopts random coil conformation under experimental conditions, the biophysical parameters such as temperature, pH, osmolarity and protein content may be different from the physiological conditions normally found in vivo. Temperatures between 1° C. and 42° C. or preferably 4° C. to 25° C. may be considered useful to test and/or verify the biophysical properties and biological activity of a polypeptide linker (as comprised in the herein provide protein) under physiological conditions in vitro.

Several buffers, which may include solvents and/or excipients for pharmaceutical compositions, are considered to represent "physiological solutions"/"physiological conditions" in vitro, in particular, in experimental settings, for example in the context of CD measurements or other methods that allow the person skilled in the art to determine the structural properties of a protein/amino acid sequence. Examples of such buffers are, e.g., phosphate-buffered saline (PBS, e.g.: 115 mM NaCl, 4 mM $KH_2PO_4$, 16 mM $Na_2HPO_4$ pH 7.4), Tris buffers, acetate buffers, citrate buffers or similar buffers. Generally, the pH of a buffer representing "physiological solution conditions" should lie in a range from 6.5 to 8.5, preferably in a range from 7.0 to 8.0, most preferably in a range from 7.2 to 7.7, and the osmolarity should lie in a range from 10 to 1000 mmol/kg $H_2O$, more preferably in a range from 50 to 500 mmol/kg $H_2O$ and most preferably in a range from 200 to 350 mmol/kg $H_2O$. Optionally, the protein content of a physiological solution may lie in a range from 0 to 100 g/l, neglecting the investigated protein adopting random coil conformation itself; furthermore, typical stabilizing proteins may be present, for example human or bovine serum albumin.

The polypeptide linkers provided herein not only form random coil conformation under physiological conditions but, more generally, in aqueous solution; e.g., c.f. WO2011/144756. The term "aqueous solution" is well known in the art. An "aqueous solution" may be a solution with a water ($H_2O$) content of at least about 20%, of at least about 30%, of at least about 40%, of at least about 50%, of at least about 60%, of at least about 70%, of at least about 80% or of at least about 90% $H_2O$ (weight/weight). Accordingly, the encoded polypeptides provided in the present invention may form random coil conformation in aqueous solution, possibly containing other miscible solvents, or in aqueous dispersions with a wider range of temperatures, pH values, osmolarities or protein content.

It is envisaged herein that the random coil conformation of the polypeptide linker is maintained in pharmaceutical compositions like liquid pharmaceuticals/biologicals or lyophilized pharmaceutical compositions. Preferably, "physiological conditions" are to be used in corresponding buffer systems, solvents and/or excipients. Yet, for example, in lyophilized or dried compositions (like, e.g., pharmaceutical compositions), it is envisaged that the random coil conformation of the herein provided random coil polypeptide linker may transiently not be present and/or cannot be detected. However, said random coil polypeptide/linker will adopt/form its random coil again after reconstitution in corresponding buffers/solutions/excipients/solvents or after administration to the body of a patient or of an animal.

In certain aspects of the present invention, the linker consists of proline, alanine and, optionally, serine, wherein no more than 9 consecutive amino acid residues are identical. The linker adopting random coil conformation may comprise a plurality of amino acid repeats, wherein said "amino acid repeats" mainly or exclusively consist of proline, alanine and, optionally, serine amino acid residues, wherein no more than 9 consecutive amino acid residues are identical. The linker adopting random coil conformation may comprise a plurality of amino acid repeats, wherein said "amino acid repeats" mainly or exclusively consist of proline, alanine and serine amino acid residues, wherein no more than 9 consecutive amino acid residues are identical. The linker adopting random coil conformation may comprise a plurality of amino acid repeats, wherein said "amino acid repeats" mainly or exclusively consist of proline and alanine amino acid residues, wherein no more than 9 consecutive amino acid residues are identical.

In certain aspects, the linker comprises a plurality of amino acid repeats, wherein no more than 8 consecutive amino acid residues are identical and wherein said linker forms a random coil, wherein no more than 7 consecutive amino acid residues are identical and wherein said linker forms a random coil, or wherein no more than 6 consecutive amino acid residues are identical and wherein said linker forms a random coil. Particularly preferably, the linker comprises a plurality of amino acid repeats, wherein no more than 5 consecutive amino acid residues are identical and wherein said linker forms a random coil. More particularly preferably, the linker comprises a plurality of amino acid repeats, wherein no more than 4 consecutive amino acid residues are identical and wherein said linker forms a random coil. Most preferably, the linker comprises a plurality of amino acid repeats, wherein no more than 3 consecutive amino acid residues are identical and wherein said linker forms a random coil.

A non-limiting example of an amino acid repeat consisting exclusively of proline, alanine and serine residues is provided herein below: SEQ ID No. 2.

The linker can consist mainly or exclusively of the three amino acid residues proline (Pro, P), alanine (Ala, A) and, optionally, serine (Ser, S). The term "optionally" as used herein means that the linker either consists mainly or exclusively of proline, alanine and serine or consists mainly or exclusively of proline and alanine. The linker consisting mainly or exclusively of the three amino acid residues proline, alanine and serine is referred to herein as "PAS" linker. The linker consisting mainly or exclusively of the two amino acid residues proline and alanine is referred to herein as "PA" linker. A non-limiting example of linker consisting of proline, alanine and serine is given in SEQ ID No. 2. The term "mainly" as used herein means that preferably at least about 90% or at least about 95% of the encoded amino acids are proline, alanine and, optionally, serine, whereby proline, alanine and serine in sum constitute the majority but may not be the only amino acid residues; therefore, the amino acid sequence of the linker is not necessarily 100% proline, alanine and, optionally, serine. Hence, the linker may also comprise other amino acids than proline, alanine and, optionally, serine as minor constituents as long as the linker forms/adopts/has the random coil conformation. Such a random coil conformation can be easily determined by means and methods described herein. Accordingly, the linker that preferably forms random coil can consist mainly of proline, alanine and, optionally, serine.

In case the linker consists of proline and alanine, said proline residues constitute more than about 10% and less than about 75% of said linker. Accordingly, the linker can consist mainly of proline and alanine, wherein the proline residues constitute more than about 10% and less than 75% of the amino acid sequence. The alanine residues comprise the remaining at least 25% to 90% of the amino acid sequence.

Preferably, the amino acid sequence of the linker (the linker) comprises more than about 10%, preferably more than about 12%, more preferably more than about 14%, 18%, 20%, more preferably more than about 22%, 23%, 24%, or 25%, more preferably more than about 27%, 29%, or 30%, more preferably more than about 32%, 33%, or 34% and most preferably more than about 35% proline residues. The amino acid sequence of the linker (the linker) preferably comprises less than about 75%, more preferably less than 70%, more preferably less than 65%, more preferably less than 60%, more preferably less than 55%, more preferably less than 50% proline residues, wherein the lower values are preferred. Even more preferably, the amino acid sequence of the linker (the linker) comprises less than about 48%, 46%, 44%, 42% proline residues. More preferred are amino acid sequences of the linker (the linker) comprising less than about 41%, 40%, 39% 38%, 37% or 36% proline residues, whereby lower values are preferred. More preferred are amino acid sequences of the linker (the linker) comprising less than about 34%, 32%, or 30%. More preferred are amino acid sequences of the linker (the linker) comprising less than about 28%, 26% or 25%. Most preferably, the amino acid sequences of the linker (the linker) comprise less than about 35% proline residues.

Vice versa, the amino acid sequence of the linker (the linker) preferably comprises less than about 90%, more preferably less than 88%, 86%, 84%, 82% or 80% alanine residues, wherein the lower values are preferred. More preferably, the amino acid sequence of the linker (the linker) comprises less than about 79%, 78%, 77%, 76% alanine residues, whereby lower values are preferred. More preferably, the amino acid sequence of the linker (the linker) comprises less than about 74%, 72%, or 70% alanine residues, whereby lower values are preferred. More preferably, the amino acid sequence of the linker (the linker) comprises less than about 69%, 67%, or 65% alanine residues, whereby lower values are preferred. Most preferably, the amino acid sequence of the linker (the linker) comprises less than about 75% alanine residues. Also preferred herein is an amino acid sequence of the linker (the linker) comprising more than about 25%, preferably more than about 30%, more preferably more than about 35%, more preferably more than about 40%, more preferably more than about 45%, more preferably more than about 50%, more preferably more than about 52%, 54%, 56%, 58% or 59% alanine residues, wherein the higher values are preferred. Even more preferably, the amino acid sequence of the linker (the linker) comprises more than about 60%, 61%, 62%, 63% or 64% alanine residues. More preferably, the amino acid sequence of the linker (the linker) comprises more than about 66%, 67%, 69%, or 70% alanine residues. More preferably, the amino acid sequence of the linker (the linker) comprises more than about 72%, 74%, or 75%, alanine residues. Most preferably the amino acid sequence of the linker (the linker) comprises more than about 65% alanine residues.

Accordingly, the linker may comprise an amino acid sequence consisting of about 25% or 30% proline residues and about 75% or 70%, respectively, alanine residues. Alternatively, the linker may comprise an amino acid sequence consisting of about 35% proline residues and about 65% alanine residues. The term "about X %" as used herein above is not limited to the concise number of the percentage, but also comprises values of 10% to 20% additional or 10% to 20% less residues. For example, the term 10% may also relate to 11% or 12% and to 9% or 8%, respectively.

In case the linker consists of proline, alanine and serine, said proline residues can constitute more than about 4% and less than about 40% of said of the amino acid sequence of the linker (the linker). The alanine and the serine residues constitute the remaining amount of said amino acid sequence of the linker (the linker).

Preferably, the amino acid sequence of the linker (the linker) comprises more than about 4%, preferably more than about 6%, more preferably more than about 10%, more preferably more than about 15%, more preferably more than about 20%, more preferably more than about 22%, 23% or 24%, more preferably more than about 26%, 29%, or 30%, more preferably more than about 31%, 32%, 33%, 34% or 35% and most preferably more than about 25% proline residues. The amino acid sequence of the linker (the linker) preferably comprises less than about 40%, more preferably less than 38%, 35%, 30%, 26% proline residues, wherein the lower values are preferred.

The amino acid sequence of the linker (the linker) preferably comprises less than about 95%, more preferably less than 90%, 86%, 84%, 82% or 80% alanine residues, wherein the lower values are preferred. More preferably, the amino acid sequence of the linker (the linker) comprises less than about 79%, 78%, 77%, 76% alanine residues, whereby lower values are preferred. More preferably, the amino acid sequence of the linker (the linker) comprises less than about 75%, 73%, 71%, or 70% alanine residues, whereby lower values are preferred. More preferably, the amino acid sequence of the linker (the linker) comprises less than about 69%, 67%, 66%, or 65% alanine residues, whereby lower values are preferred. More preferably, the amino acid sequence of the linker (the linker) comprises less than about 64%, 63%, 62%, or 60% alanine residues, whereby lower values are preferred. More preferably, the amino acid sequence of the linker (the linker) comprises less than about 59%, 57%, 56%, or 55% alanine residues, whereby lower values are preferred. More preferably, the amino acid sequence of the linker (the linker) comprises less than about 54%, 53%, or 51%, alanine residues, whereby lower values are preferred. Most preferably, the amino acid sequence of the linker (the linker) comprises less than about 50% alanine residues.

Also preferred herein is an amino acid sequence of the linker (the linker) comprising more than about 10%, preferably more than about 15%, 17%, 19%, or 20%, more preferably more than about 22%, 24%, or 25%, more preferably more than about 27%, 29%, or 30%, more preferably more than about 32%, 34% or 35%, more preferably more than about 37%, 39%, or 40%, more preferably more than about 42%, 44% or 45%, more preferably more than about 46%, 47% or 49% alanine residues, wherein the higher values are preferred. Most preferably, the amino acid sequence comprises more than about 50 alanine residues. As mentioned above, the serine residues comprise the remaining amount of said amino acid sequence. Accordingly, the of the linker (the linker) may comprise an amino acid sequence consisting of about 35% proline residues, about 50% alanine and 15% serine residues. The term "about X %" as used herein above is not limited to the concise number of the percentage, but also comprises values of 10% to 20% additional or 10% to 20% less residues. For example, the term 10% may also relate to 11% or 12% or to 9% and 8%, respectively.

However, as mentioned above and further detailed herein below the amino acid sequence of the linker (the linker) may also comprise additional amino acids differing from proline, alanine and, optionally, serine as minor constituents. As already discussed herein above, said minor constituent(s), i.e. amino acid(s) different from proline, alanine or, optionally, serine, may comprise less than about 10% or less than about 5% of the of the linker.

The skilled person is aware that the linker may also form random coil conformation when other residues than proline, alanine and, optionally, serine are comprised as a minor constituent in said amino acid sequence of the linker (the linker). The term "minor constituent" as used herein means that maximally 5% or maximally 10% amino acid residues are different from proline, alanine or serine in the linker. This means that maximally 10 of 100 amino acids may be different from proline, alanine and, optionally, serine, preferably maximally 8%, i.e. maximally 8 of 100 amino acids may be different from proline, alanine and, optionally, serine, more preferably maximally 6%, i.e. maximally 6 of 100 amino acids may be different from proline, alanine and, optionally, serine, even more preferably maximally 5%, i.e. maximally 5 of 100 amino acids may be different from proline, alanine and, optionally, serine, particularly preferably maximally 4%, i.e. maximally 4 of 100 amino acids may be different from proline, alanine and, optionally, serine, more particularly preferably maximally 3%, i.e. maximally 3 of 100 amino acids may be different from proline, alanine and, optionally, serine, even more particularly preferably maximally 2%, i.e. maximally 2 of 100 amino acids may be different from proline, alanine and, optionally, serine and most preferably maximally 1%, i.e. maximally 1 of 100 of the amino acids that are comprised in the random coil polypeptide may be different from proline, alanine and, optionally, serine. Said amino acids different from proline, alanine and, optionally, serine may be selected from the group consisting of Arg, Asn, Asp, Cys, Gln, Glu, Gly, His, Ile, Leu, Lys, Met, Phe, Thr, Trp, Tyr, and Val, including posttranslationally modified amino acids or non-natural amino acids (see, e.g., Budisa (2004) Angew Chem Int Ed Engl 43:6426-6463; Young (2010) J Biol Chem 285:11039-11044; Liu (2010) Annu Rev Biochem 79:413-444; Wagner (1983) AngewChem Int Ed Engl 22:816-828; Walsh (2010) Drug Discov Today 15: 773-780. In certain cases PA-rich sequences can also comprise Ser as a minor constituent. For example, in case the linker consists of proline and alanine, serine can also be considered as minor constituent.

Generally, it is preferred herein that these "minor" amino acids (other than proline, alanine and, optionally, serine) are not present in the linker as described herein. In accordance with the above, the amino acid sequence of the linker (the linker) may, in particular, consist exclusively of proline, alanine and, optionally, serine residues (i.e. no other amino acid residues are present in the amino acid sequence of the linker (the linker)).

The herein provided protein can comprise an N-terminal signal polypeptide sequence, for example, the N-terminal signal polypeptide sequence of PDGFR, particularly of human PDGFRα. The N-terminal signal polypeptide sequence can have an amino acid sequence as shown in SEQ ID No. 10 or said N-terminal signal polypeptide sequence can be a polypeptide encoded by a nucleic acid molecule having a nucleotide sequence as shown in SEQ ID No. 9.

The protein can further comprise a tag, e.g. a purification tag, such as a His-tag. Herein also other established tags can be used, like HA-tag, Flag-tag, c-myc-tag, V5-tag or C9-tag. These tags can be used in the place of an His-tag or in addition thereto. The tags can be used in the purification and detection of the herein provided protein. By using antibodies specifically binding to the tag (e.g. via ELISA assays, like chemiluminescence ELISA (CLIA) and AlphaLISA), e.g. the level of protein can be reliably and rapidly assessed and/or purification be facilitated.

The purification tag can have an amino acid sequence as shown in SEQ ID No. 12 or it can be a polypeptide encoded by a nucleic acid molecule having a nucleotide sequence as shown in SEQ ID No. 11.

Primarily, the term "tag" refers to a "protein tag". The terms "tag" and "protein tag" are known in the art; see, inter alia, Fritze C E, Anderson T R. "Epitope tagging: general method for tracking recombinant proteins". Methods Enzymol. 2000; 327: 3-16; Brizzard B, Chubet R. Epitope tagging of recombinant proteins. Curr Protoc Neurosci. 2001 May; Chapter 5: Unit 5.8; and/or Terpe K. Overview of tag protein fusions: from molecular and biochemical fundamentals to commercial systems. Appl Microbiol Biotechnol. 2003 January; 60(5):523-33.

Typically, the tag to be used herein is a protein tag that is fused to the protein. For example, a nucleic acid encoding the tag can be fused to a nucleic acid encoding a protein comrpsing a PDGFR domain and a VEGFR domain, so that a fusion protein comprising both the tag and the PDGFR domain and a VEGFR domain is expressed. The tag(s) can be fused to the 5'-end of the nucleic acid encoding PDGFR domain and a VEGFR domain, inserted within the nucleic acid and/or fused to the 3'-end of the nucleic acid encoding PDGFR domain and a VEGFR domain. Thus, the resulting fusion protein can comprise (a) tag(s) at the N-terminus, internally (i.e. within the PDGFR domain and VEGFR domain), and/or at the C-terminus.

Various tags are known in the art and can be used in accordance with the present invention. Usually, a tag to be used herein has a low molecular weight of about 1-3 kDa, preferably of about 1 kDa. Exemplary, non-limiting low molecular weight tags are HA-tag, His-tag, Flag-tag, c-myc-tag, V5-tag or C9-tag. The Flag-tag to be used herein can be 1×Flag-tag or 3×Flag-tag. The low molecular weight is reflected in the length of the tag, i.e. the number of amino acid residues of which the tag consists. For example, His-tag (6 amino acids), HA-tag (9 amino acids), FLAG-tag (8 amino acids), or 3×FLAG-tag (22 amino acids) can be used herein.

The domains can be arranged in any order from N-terminus to C-terminus. Preferably, the protein is arranged from N-terminus to C-terminus in the order:

(optional signal sequence)-one or more domains of PDGFR-(optional linker)-one or more domains of VEGFR-(optional purification tag);

(optional signal sequence)-one or more domains of VEGFR-(optional linker)-one or more domains of PDGFR-(optional purification tag);

(optional signal sequence)-(optional linker)-one or more domains of VEGFR-one or more domains of PDGFR-(optional purification tag);

(optional signal sequence)-(optional linker)-one or more domains of PDGFR-one or more domains of VEGFR-(optional purification tag);

(optional signal sequence)-(optional linker)-one or more domains of PDGFR-(optional linker)-one or more domains of VEGFR-(optional linker)-(optional purification tag).

The domains can be arranged in any order from N-terminus to C-terminus. More preferably, the protein is arranged from N-terminus to C-terminus in the order:

(optional signal sequence)-one or more domains of PDGFR-(PAS/PA)-one or more domains of VEGFR-(optional purification tag);

(optional signal sequence)-one or more domains of VEGFR-(PAS/PA)-one or more domains of PDGFR-(optional purification tag);

(optional signal sequence)-(PAS/PA)-one or more domains of VEGFR-one or more domains of PDGFR-(optional purification tag);

(optional signal sequence)-(PAS/PA)-one or more domains of PDGFR-one or more domains of VEGFR-(optional purification tag);

(optional signal sequence)-(PAS/PA)-one or more domains of PDGFR-(PAS/PA)-one or more domains of VEGFR-(PAS/PA)-(optional purification tag).

The domains can be arranged in any order from N-terminus to C-terminus. Further preferably, the protein is arranged from N-terminus to C-terminus in the order:

(optional signal sequence)-one or more domains of PDGFR-(GGGGS (SEQ ID NO: 73))n-(PAS/PA) -(GGGGS (SEQ ID NO: 73))n-one or more domains of VEGFR-(optional purification tag), wherein, n=0-5, e.g. 1, 2, 3, 4 or 5 and preferably 3;

(optional signal sequence)-one or more domains of VEGFR-(GGGGS (SEQ ID NO: 73))n-(PAS/PA) -(GGGGS (SEQ ID NO: 73))n-one or more domains of PDGFR-(optional purification tag);

wherein, n=0-5, e.g. 1, 2, 3, 4 or 5 and preferably 3.

In a preferred embodiment, a protein is provided herein, wherein said protein comprises (a) a protein having an amino acid sequence as shown in SEQ ID No. 14, SEQ ID No. 22, SEQ ID No. 24, SEQ ID No. 26, SEQ ID No. 28, SEQ ID No. 30, SEQ ID No. 32, SEQ ID No. 34, SEQ ID No. 36, SEQ ID No. 38, SEQ ID No. 40, SEQ ID No. 42 or SEQ ID No. 44;

(b) a protein as defined in (a) wherein 1 to 10 amino acids are deleted, inserted, added or substituted;

(c) a polypeptide encoded by a nucleic acid molecule having a nucleotide sequence as shown in SEQ ID No. 13, SEQ ID No. 21, SEQ ID No. 23, SEQ ID No. 25, SEQ ID No. 27, SEQ ID No. 29, SEQ ID No. 31, SEQ ID No. 33, SEQ ID No. 35, SEQ ID No. 37, SEQ ID No. 39, SEQ ID No. 41 or SEQ ID No. 43;

(d) a polypeptide having an amino acid sequence encoded by a nucleic acid hybridizing under stringent conditions to the complementary strand of nucleic acid molecules as defined in (c);

(e) a polypeptide having at least 70% identity to the polypeptide of any one of (a) to (d); and (f) a polypeptide having an amino acid sequence encoded by a nucleic acid being degenerate as a result of the genetic code to the nucleotide sequence of a nucleic acid as defined in (c) or (d).

The following relates to proteins (or a functional fragment or derivative thereof) to be used in accordance with the present invention.

The meaning of the term "protein" and "nucleic acid sequence(s)/molecule(s)" are well known in the art and are used accordingly in context of the present invention.

For example, the term "protein" as used herein refers to a biomolecule consisting of one or more chains of amino acid residues. The terms "polypeptide" and "chain of amino acid residues" can be used interchangeably herein. A single linear chain of amino acid residues is usually called a polypeptide. The term protein usually refers to a biological molecule in a stable conformation (i.e. implies that a three-dimensional structure has formed). Normally, a protein contains more than 20-30 amino acid residues, particularly more than 50 amino acid residues. A protein can contain up to 3000 amino acid residues, e.g. up to 1500 amino acid residues. Yet, even larger proteins are envisaged herein.

The individual amino acid residues are bonded together by peptide bonds. In general, the genetic code specifies 20 standard amino acids; however, also the use of non-standard amino acids like selenocysteine is envisaged herein. Also chemical modification e.g. post-translational modification is envisaged herein.

Short proteins can also be synthesized chemically by a family of methods known as peptide synthesis, which rely on organic synthesis techniques such as chemical ligation.

As described herein, a method for the preparation of the herein disclosed protein is provided. The method can comprise culturing the host cell as provided herein and isolating said protein from the culture or from the (host) cell(s). As described herein, a fusion protein as provided herein can be prepared by expressing the nucleic acid molecule as provided herein, and optionally, by isolating the expressed fusion protein.

Alternatively, the protein can be prepared by culturing/raising the host comprising the nucleotide sequence encoding the linker, particularly the linker consisting of proline, alanine and, optionally serine. Thus, the linker can be expressed in the host and/or optionally, isolated. The linker consisting of proline, alanine and, optionally, serine can then be conjugated to the PDGFR and/or VEGFR domain, e.g., via a peptide bond or a non-peptide bond. In particular, the PDGFR or VEGFR domain can be site-specifically conjugated, e.g., in the presence of an activating agent such as N-(3-dimethylaminopropyl)-N'-ethylcarbodiimide (EDC) or as an N-hydroxysuccinimide (NHS) ester (Hermanson (1996) Bioconjugate Techniques, 1st edition, Academic Press, San Diego, Calif.) to the N-terminus of the linker, particularly the linker consisting of proline, alanine and, optionally, serine. Alternatively, the PDGFR or VEGFR domain can be site-specifically conjugated to the C-terminus of the linker, particularly the linker consisting of proline, alanine and, optionally, serine, e.g., in the presence of an activating agent such as EDC or after activation as an NHS ester.

It is preferred herein that the protein is a fusion protein.

In order to prepare a fusion protein, a nucleotide sequence encoding the PDGFR domain, can be operably linked in the same reading frame to the VEGFR domain. If the fusion protein comprises a linker (particularly a linker consisting of proline, alanine and, optionally, serine), the fusion protein can, for example, be prepared in that a nucleotide sequence encoding the PDGFR domain, is operably linked in the same reading frame to a nucleotide sequence encoding the linker, and the nucleotide sequence encoding the linker is operably linked in the same reading frame to a nucleotide sequence encoding the VEGFR domain.

Thus, a nucleic acid molecule provided herein can encode a fusion protein/heterologous drug conjugate comprising a PDGFR domain, a linker consisting of proline, alanine and, optionally, serine, and a VEGFR domain.

As used herein, the term "operably linked" refers to a juxtaposition, wherein the components in question are in a relationship permitting them to both function in their intended manner.

The nucleotide sequence encoding the linker, particularly the linker consisting of proline, alanine and, optionally, serine can be conjugated to the nucleotide sequence encoding the PDGFR domain and/or VEGFR domain seamlessly, i.e., no further spacers intersperse these sequences. Spacers can cause an immune response in the subject receiving the fusion protein that carries such a spacer. Therefore, the nucleotide sequence encoding the linker can be conjugated to the nucleotide sequence encoding the PDGFR domain and/or VEGFR domain seamlessly. As used herein, "seamless" means that the nucleotide sequence encoding the linker is directly conjugated to the nucleotide sequence encoding the PDGFR domain and/or VEGFR domain. Thus, no additional nucleotides are introduced that encode amino acid residues other than proline, alanine and, optionally, serine.

Alternatively, a spacer structure can be comprised between the linker and the PDGFR domain and/or VEGFR domain. Thus, in certain aspects of the invention, a nucleotide sequence encoding an amino acid spacer is inserted between the nucleotide sequence encoding the linker and the nucleotide sequence encoding PDGFR domain and/or VEGFR domain. An exemplary spacer can be a protease sensitive cleavage site, a serine/glycine-linker, an affinity tag such as the His6-tag or the Strep-tag II, a signal peptide, retention peptide, a targeting peptide like a membrane translocation peptide or additional effector domains, e.g., antibody fragments for tumour targeting associated with an anti-tumour toxin or an enzyme for prodrug activation etc. The protein comprising a spacer can have a plasma protease cleavage site that allows the controlled release of said protein. Spacers of different types or lengths may be identified without undue burden to obtain/preserve optimal biological activity of the proteins. An exemplary serine/glycine-linker can have the sequence (GGGGS (SEQ ID NO: 73))n, wherein, n=0-5, e.g. 1, 2, 3, 4 or 5. Preferably, n=3. If n=0 the serine/glycine-linker is absent. For example, the serine/glycine-linker may be arranged in the protein in the following order:

(optional signal sequence)-one or more domains of PDGFR-(GGGGS (SEQ ID NO: 73))n-(PAS/PA) -(GGGGS (SEQ ID NO: 73))n-one or more domains of VEGFR-(optional purification tag), wherein, n=0-5, e.g. 1, 2, 3, 4 or 5 and preferably 3; or (optional signal sequence)-one or more domains of VEGFR-(GGGGS (SEQ ID NO: 73))n-(PAS/PA) -(GGGGS (SEQ ID NO: 73))n-one or more domains of PDGFR-(optional purification tag);

wherein, n=0-5, e.g. 1, 2, 3, 4 or 5 and preferably 3.

Nucleic acid sequences with a certain level of identity to the herein provided sequences can be identified by the skilled person using methods known in the art, e.g. by using hybridization assays or by using alignments, either manually or by using computer programs such as those mentioned herein below in connection with the definition of the term "hybridization" and degrees of homology.

The nucleic acid sequence may be at least 70% identical to the nucleic acid sequence as shown in any one of SEQ ID No. 3, 5, 7, 13, 15, 19, 21, 23, 25, 27, 29, 31, 33, 35, 37, 39, 41, 43, 45, 47, 49, 51, 53, 55, 57, 59, 61, 63, 65 or 67.

More preferably, the nucleic acid sequence is at least 90%, 91%, 92%, 93%, 94%, 95%, 96%, 97% or 98% identical to the nucleic acid sequence as shown in any one of SEQ ID No. 3, 5, 7, 13, 15, 19, 21, 23, 25, 27, 29, 31, 33, 35, 37, 39, 41, 43, 45, 47, 49, 51, 53, 55, 57, 59, 61, 63, 65 or 67, wherein the higher values are preferred. Most preferably, the nucleic acid sequence is at least 99% identical to the nucleic acid sequence as shown in any one of SEQ ID No. 3, 5, 7, 13, 15, 19, 21, 23, 25, 27, 29, 31, 33, 35, 37, 39, 41, 43, 45, 47, 49, 51, 53, 55, 57, 59, 61, 63, 65 or 67.

Hybridization assays for the characterization of nucleic acids with a certain level of identity to the nucleic acid sequences as provided herein are well known in the art; see e.g. Sambrook, Russell "Molecular Cloning, A Laboratory Manual", Cold Spring Harbor Laboratory, N.Y. (2001); Ausubel, "Current Protocols in Molecular Biology", Green Publishing Associates and Wiley Interscience, N.Y. (1989). The term "hybridization" or "hybridizes" as used herein may relate to hybridizations under stringent or non-stringent conditions. If not further specified, the conditions are preferably non-stringent. Said hybridization conditions may be established according to conventional protocols described, e.g., in Sambrook (2001) loc. cit.; Ausubel (1989) loc. cit., or Higgins and Hames (Eds.) "Nucleic acid hybridization, a practical approach" IRL Press Oxford, Washington D.C., (1985). The setting of conditions is well within the skill of the artisan and can be determined according to protocols described in the art. Thus, the detection of only specifically hybridizing sequences will usually require stringent hybridization and washing conditions such as, for example, the highly stringent hybridization conditions of 0.1×SSC, 0.1% SDS at 65° C. or 2×SSC, 60° C., 0.1% SDS. Low stringent hybridization conditions for the detection of homologous or not exactly complementary sequences may, for example, be set at 6×SSC, 1% SDS at 65° C. As is well known, the length of the probe and the composition of the nucleic acid to be determined constitute further parameters of the hybridization conditions. It is envisaged herein that a nucleic acid can be a primer or probe, for example, a nucleic acid hybridizing under stringent conditions to the complementary strand of the nucleic acid of the herein provide protein (or of a fragment thereof as defined herein) the like as defined and provided herein above. Primers and probes are often in the range of 10-30 nucleotides. Thus, herein provided is a nucleic acid (like a primer or probe) hybridizing under stringent conditions to the complementary strand of the protein as defined and provided herein above, wherein said hybridizing nucleic acid is smaller than 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, or 20 nucleotides and is larger than 5, 6, 7, 8, 9, 10, 11, 12, 13, 14, or 15 nucleotides. Preferably, the nucleic acid has a length of 10 to 35 nucleotides, more preferably 15 to 25 nucleotides, particularly preferred a length of 18 to 21, e.g. 18, 19, 20 or 21 nucleotides.

In accordance with the present invention, the terms "homology" or "percent homology" or "identical" or "percent identity" or "percentage identity" or "sequence identity" in the context of two or more nucleic acid sequences refers to two or more sequences or subsequences that are the same, or that have a specified percentage of nucleotides that are the same (at least 70%, 75%, 80%, 85%, most preferably at least 90%, 91%, 92%, 93%, 94%, 95%, 96%, 97% or 98% identity, most preferably at least 99% identity), when compared and aligned for maximum correspondence over a window of comparison (preferably over the full length), or over a designated region as measured using a sequence comparison algorithm as known in the art, or by manual alignment and visual inspection. Sequences having, for example, 75% to 90% or greater sequence identity may be considered to be substantially identical. Such a definition also applies to the complement of a test sequence. Preferably the described identity exists over a region that is at least about 15 to 25 nucleotides in length, more preferably, over a region that is at least about 50 to 100 nucleotides in length and most preferably over the full length. Those having skill in the art will know how to determine percent identity between/among sequences using, for example, algorithms such as those based on CLUSTALW computer program (Thompson Nucl. Acids Res. 2 (1994), 4673-4680) or FASTDB (Brutlag Comp. App. Biosci. 6 (1990), 237-245), as known in the art.

Although the FASTDB algorithm typically does not consider internal non-matching deletions or additions in sequences, i.e., gaps, in its calculation, this can be corrected manually to avoid an overestimation of the % identity. CLUSTALW, however, does take sequence gaps into account in its identity calculations. Also available to those having skill in this art are the BLAST and BLAST 2.0 algorithms (Altschul, (1997) Nucl. Acids Res. 25:3389-3402; Altschul (1993) J. Mol. Evol. 36:290-300; Altschul (1990) J. Mol. Biol. 215:403-410). The BLASTN program for nucleic acid sequences uses as defaults a word length (W) of 11, an expectation (E) of 10, M=5, N=4, and a comparison of both strands. The BLOSUM62 scoring matrix (Henikoff (1989) PNAS 89:10915) uses alignments (B) of 50, expectation (E) of 10, M=5, N=4, and a comparison of both strands.

In order to determine whether a nucleotide residue in a nucleic acid sequence corresponds to a certain position in the nucleotide sequence of e.g. SEQ ID No. 3, 5, 7, 13 or 15, 19, 21, 23, 25, 27, 29, 31, 33, 35, 37, 39, 41, 43, 45, 47, 49, 51, 53, 55, 57, 59, 61, 63, 65 or 67, respectively, the skilled person can use means and methods well-known in the art, e.g., alignments, either manually or by using computer programs such as those mentioned herein. For example, BLAST 2.0, which stands for Basic Local Alignment Search Tool BLAST (Altschul (1997), loc. cit.; Altschul (1993), loc. cit.; Altschul (1990), loc. cit.), can be used to search for local sequence alignments. BLAST, as discussed above, produces alignments of nucleotide sequences to determine sequence similarity. Because of the local nature of the alignments, BLAST is especially useful in determining exact matches or in identifying similar sequences. The fundamental unit of BLAST algorithm output is the High-scoring Segment Pair (HSP). An HSP consists of two sequence fragments of arbitrary but equal lengths whose alignment is locally maximal and for which the alignment score meets or exceeds a threshold or cut-off score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

Analogous computer techniques using BLAST (Altschul (1997), loc. cit.; Altschul (1993), loc. cit.; Altschul (1990), loc. cit.) are used to search for identical or related molecules in nucleotide databases such as GenBank or EMBL. This analysis is much faster than multiple membrane-based hybridizations. In addition, the sensitivity of the computer search can be modified to determine whether any particular match is categorized as exact or similar. The basis of the search is the product score, which is defined as:

$$\frac{\%\ \text{sequence identity} \times \%\ \text{maximum BLAST score}}{100}$$

and it takes into account both the degree of similarity between two sequences and the length of the sequence match. For example, with a product score of 40, the match will be exact within a 1-2% error; and at 70, the match will be exact. Similar molecules are usually identified by selecting those, which show product scores between 15 and 40, although lower scores may identify related molecules. Another example for a program capable of generating sequence alignments is the CLUSTALW computer program (Thompson (1994) Nucl. Acids Res. 2:4673-4680) or FASTDB (Brutlag (1990) Comp. App. Biosci. 6:237-245), as known in the art.

The explanations and definitions given herein above in respect of "homology/identity of nucleic acid sequences" apply, mutatis mutandis, to "amino acid sequences" of the herein provided proteins as depicted in any one of SEQ ID No.s: 4, 6, 8, 14, 16, 20, 22, 24, 26, 28, 30, 32, 34, 36, 38, 40, 42, 44, 46, 48, 50, 52, 54, 56, 58, 60, 62, 64, 66 or 68, respectively, as explained below.

The proteins to be used in accordance with the present invention may have at least 70% identity/similarity to the proteins having the amino acid sequence as shown in any one of SEQ ID No.s: 4, 6, 8, 14, 16, 20, 22, 24, 26, 28, 30, 32, 34, 36, 38, 40, 42, 44, 46, 48, 50, 52, 54, 56, 58, 60, 62, 64, 66 or 68, respectively. More preferably, the proteins has at least 90%, 91%, 92%, 93%, 94%, 95%, 96%, 97% or 98% identity/similarity to the proteins having the amino acid sequence as shown in any one of SEQ ID No.s: 4, 6, 8, 14 and 16, respectively, wherein the higher values are preferred. Most preferably, the proteins have at least 99% identity/similarity to the proteins having the amino acid sequence as shown in any one of SEQ ID No.s: 4, 6, 8, 14, 16, 20, 22, 24, 26, 28, 30, 32, 34, 36, 38, 40, 42, 44, 46, 48, 50, 52, 54, 56, 58, 60, 62, 64, 66 or 68, respectively.

Also (a) (functional) fragment(s) or (a) (functional) derivative(s) of the herein provided proteins can be used, for example, (functional) fragment(s) or (functional) derivative(s) of the proteins having the amino acid sequence as shown in any one of SEQ ID No.s: 4, 6, 8, 14 and 16, respectively.

Thus, a (functional) fragment of the protein(s) provided herein and to be used in accordance with the present invention can be any of the above specific proteins as shown in any one of SEQ ID No.s: 4, 6, 8, 14, 16, 20, 22, 24, 26, 28, 30, 32, 34, 36, 38, 40, 42, 44, 46, 48, 50, 52, 54, 56, 58, 60, 62, 64, 66 or 68, respectively, wherein one or more amino acids are deleted.

The term "one or more amino acids" refers for example to "1, 2, 3, 4, 5, 6, 7, 8, 9 or 10" amino acids.

A (functional) derivative(s) of the protein(s) provided herein and to be used in accordance with the present invention can be any of the above specific proteins as shown in any one of SEQ ID No.s: 4, 6, 8, 14, 16, 20, 22, 24, 26, 28, 30, 32, 34, 36, 38, 40, 42, 44, 46, 48, 50, 52, 54, 56, 58, 60, 62, 64, 66 or 68, respectively, wherein one or more amino acids are inserted, added or substituted.

A (functional) fragment of the proteins provided herein and to be used in accordance with the present invention can consist of at least 100, 120, 140, 160, or 180 contiguous amino acids of the amino acid sequence as shown in any one of SEQ ID No.s: 4, 6, 8, 14, 16, 20, 22, 24, 26, 28, 30, 32, 34, 36, 38, 40, 42, 44, 46, 48, 50, 52, 54, 56, 58, 60, 62, 64, 66 or 68.

The fragment or derivative preferably has the same (or essentially the same) biological activity as the full length protein from which it is derived, the full length polypeptide having the amino acid sequence as shown in as shown in any one of SEQ ID No.s: 4, 6, 8, 14, 16, 20, 22, 24, 26, 28, 30, 32, 34, 36, 38, 40, 42, 44, 46, 48, 50, 52, 54, 56, 58, 60, 62, 64, 66 or 68, respectively. In this sense, the fragment or derivative is a "functional" fragment or derivative to be used herein.

The herein provided protein (having the amino acid sequence as shown in as shown in any one of SEQ ID No.s: 4, 6, 8, 14, 16, 20, 22, 24, 26, 28, 30, 32, 34, 36, 38, 40, 42, 44, 46, 48, 50, 52, 54, 56, 58, 60, 62, 64, 66 or 68, may have one or more amino acids deleted, inserted, added and/or substituted provided that the polypeptide maintains essentially the biological activity which is characteristic of the polypeptides from which it is derived.

Preferably, any such deletions, insertions, additions and/or substitutions (in this context particularly substitutions) are conservative, i.e. amino acids are substituted by amino acids having the same or similar characteristics. For example, a hydrophobic amino acid will preferably be substituted by another hydrophobic amino acid and so on.

The "biological activity" characteristic of the herein provided proteins can, for example, be considered as capacity to bind the ligand (PDGF and VEGF, respectively) as defined herein. As regards the linker, particularly the linker consisting of proline, alanine and, optionally, serine, the "biological activity" can particularly be considered as capacity to form random conformation.

Herein provided is a nucleic acid molecule encoding the herein provided protein.

For example, "nucleic acid sequence(s)/molecule(s)" as used herein refer(s) to all forms of naturally occurring or recombinantly generated types of nucleic acids and/or nucleic acid sequences/molecules as well as to chemically synthesized nucleic acid sequences/molecules. This term also encompasses nucleic acid analogs and nucleic acid derivatives such as e.g. locked DNA, PNA, oligonucleotide thiophosphates and substituted ribo-oligonucleotides. Furthermore, the term "nucleic acid sequence(s)/molecules(s)" also refers to any molecule that comprises nucleotides or nucleotide analogs. The terms "nucleic acid" and "nucleic acid molecule" are used interchangeably herein.

Preferably, the term "nucleic acid sequence(s)/molecule(s)" refers to deoxyribonucleic acid (DNA) and ribonucleic acid (RNA). The "nucleic acid sequence(s)/molecule(s)" may be made by synthetic chemical methodology known to one of ordinary skill in the art, or by the use of recombinant technology, or may be isolated from natural sources, or by a combination thereof. The DNA and RNA may optionally comprise unnatural nucleotides and may be single or double stranded. "Nucleic acid sequence(s)/molecule(s)" also refers to sense and anti-sense DNA and RNA, that is, a nucleotide sequence which is complementary to a specific sequence of nucleotides in DNA and/or RNA.

Furthermore, the term "nucleic acid sequence(s)/molecule(s)" may refer to DNA or RNA or hybrids thereof or any modification thereof that is known in the state of the art (see, e.g., U.S. Pat. Nos. 5,525,711, 4,711,955, 5,792,608 or EP 302175 for examples of modifications). The nucleic acid molecule(s) may be single- or double-stranded, linear or circular, natural or synthetic, and without any size limitation. For instance, the nucleic acid molecule(s) may be genomic DNA, cDNA, mRNA, antisense RNA, ribozymal or a DNA encoding such RNAs or chimeroplasts (Colestrauss, Science (1996), 1386-1389). Said nucleic acid molecule(s) may be in the form of a plasmid or of viral DNA or RNA. "Nucleic acid sequence(s)/molecule(s)" may also refer to (an) oligonucleotide(s), wherein any of the state of the art modifications such as phosphothioates or peptide nucleic acids (PNA) are included.

Further, a vector comprising the nucleic acid is provided.

Many suitable vectors are known to those skilled in molecular biology. The choice of a suitable vector depends on the function desired, including plasmids, cosmids, viruses, bacteriophages and other vectors used conventionally in genetic engineering.

Preferably, the vector is a plasmid, more preferably a plasmid based on the generic *E. coli* expression vector pASK37, pASK75 or pXL2.

Methods which are well known to those skilled in the art can be used to construct various plasmids; see, for example, the techniques described in Sambrook (2001) loc cit. and Ausubel (1989) loc. cit. Typical plasmid vectors include, e.g., pQE-12, the pUCseries of plasmids, pBluescript (Stratagene), the pET series of expression vectors (Novagen) or pCRTOPO (Invitrogen), lambda gt11, pJOE, the pBBR1-MCS series, pJB861, pBSMuL, pBC2, pUCPKS, pTACT1. Typical vectors compatible with expression in mammalian cells inlcude E-027 pCAG Kosak-Cherry (L45a) vector system, pREP (Invitrogen), pCEP4 (Invitrogen), pMC1neo (Stratagene), pXT1 (Stratagene), pSG5 (Stratagene), EBO-pSV2neo, pBPV-1, pdBPVMMTneo, pRSVgpt, pRSVneo, pSV2-dhfr, pIZD35, Okayama-Berg cDNA expression vector pcDV1 (Pharmacia), pRc/CMV, pcDNA1, pcDNA3 (Invitrogen), pcDNA3.1, pSPORT1 (GIBCO BRL), pGEMHE (Promega), pLXIN, pSIR (Clontech), pIRES-EGFP (Clontech), pEAK-10 (Edge Biosystems) pTriEx-Hygro (Novagen) and pCINeo (Promega). Non-limiting examples for plasmid vectors suitable for *Pichia pastoris* comprise e.g. the plasmids pAO815, pPIC9K and pPIC3.5K (all Invitrogen).

Generally, vectors can contain one or more origins of replication (ori) and inheritance systems for cloning or expression, one or more markers for selection in the host, e.g., antibiotic resistance, and one or more expression cassettes. Examples of suitable origins of replication include, for example, the full length ColE1, its truncated versions such as those present on the pUC plasmids, the SV40 viral and the M13 phage origins of replication. Non-limiting examples of selectable markers include ampicillin, chloramphenicol, tetracycline, kanamycin, dhfr, gpt, neomycin, hygromycin, blasticidin or geneticin.

Further, said vector comprises a regulatory sequence that is operably linked to said nucleotide sequence or the nucleic acid molecule defined herein.

The coding sequence(s), e.g., said nucleotide sequence encoding the herein provided protein comprising a PDGFR domain and a VEGFR domain, and preferably, a linker consisting of PAS or PA, comprised in the vector can be linked to (a) transcriptional regulatory element(s) and/or to other amino acid encoding sequences using established methods. Such regulatory sequences are well known to those skilled in the art and include, without being limiting, regulatory sequences ensuring the initiation of transcription, internal ribosomal entry sites (IRES) and, optionally, regulatory elements ensuring termination of transcription and stabilization of the transcript. Non-limiting examples for such regulatory sequences ensuring the initiation of transcription comprise promoters, a translation initiation codon, enhancers, insulators and/or regulatory elements ensuring transcription termination. Further examples include Kozak sequences and intervening sequences flanked by donor and acceptor sites for RNA splicing, nucleic acid sequences encoding secretion signals or, depending on the expression system used, signal polypeptide sequences capable of directing the expressed protein to a cellular compartment or to the culture medium.

Examples of suitable promoters include, without being limiting, the cytomegalovirus (CMV) promoter, SV40 promoter, RSV (Rous sarcome virus) promoter, the lacZ promoter, chicken β-actin promoter, CAG promoter (a combination of chicken β-actin promoter and cytomegalovirus immediate-early enhancer), human elongation factor 1a promoter, AOX1 promoter, GAL1 promoter, CaM-kinase promoter, the lac, trp or tac promoter, the lacUV5 promoter, the T7 or T5 promoter, the *Autographa californica* multiple nuclear polyhedrosis virus (AcMNPV) polyhedral promoter or a globin intron in mammalian and other animal cells. One example of an enhancer is, e.g., the SV40 enhancer. Non-limiting additional examples for regulatory elements/sequences ensuring transcription termination include the SV40 poly-A site, the tk poly-A site or the AcMNPV polyhedral polyadenylation signals.

Furthermore, depending on the expression system, leader sequences capable of directing the polypeptide to a cellular compartment or secreting it into the medium may be added to the coding sequence of the nucleic acid molecule provided herein. The leader sequence(s) is (are) assembled in frame with translation, initiation and termination sequences, and preferably, a leader sequence is capable of directing secretion of translated protein, or a portion thereof, into the periplasmic space or into the extracellular medium. Suitable leader sequences are, for example, the signal polypeptide sequences of BAP (bacterial alkaline phosphatase), CTB (cholera toxin subunit B), DsbA, ENX, OmpA, PhoA, stII, OmpT, PelB, Tat (Twin-arginine translocation) in *E. coli*, and the signal polypeptide sequences of bovine growth hormone, human chymotrypsinogen, human factor VIII, human ig-kappa, human insulin, human interleukin-2, luciferase from Metrida or Vargula, human trypsinogen-2, inulinase from *Kluyveromyces marxianus*, mating factor alpha-1 from *Saccharomyces cerevisiae*, mellitin, human azurocidin and the like in eukaryotic cells.

The vectors may also contain an additional expressible nucleic acid sequence coding for one or more chaperones to facilitate correct protein folding.

The vector present in the host of the described herein can either be an expression vector, or the vector can mediate the stable integration of the nucleic acid molecule as provided herein into the genome of the host cell in such a manner that expression of the protein is ensured. Means and methods for selecting a host cell in which the nucleic acid molecule as provided herein has been successfully introduced such that expression of the protein is ensured are well known in the art and have been described (Browne (2007) Trends Biotechnol. 25:425-432; Matasci (2008) Drug Discov. Today: Technol. 5:e37-e42; Wurm (2004) Nat. Biotechnol. 22:1393-1398).

Preferably, the vector to be used herein is an expression vector. An expression vector to be used herein is capable of directing the replication and the expression of the nucleic acid molecule provided herein, e.g., the nucleic acid molecule comprising the nucleotide sequence encoding the protein provided herein.

Herein disclosed is (a) host cell (s) comprising the herein provided nucleic acid or the herein provided vector. The host cell can be a eukaryotic host cell or a prokaryotic host cell. A preferred prokaryotic host cell is *E. coli*. The eukaryotic host cell can be a fungal or animal cell. Preferred animal cell(s) is(are) (a) HEK cell(s) or (a) CHO cell(s).

The present disclosure also relates to (a) host cell(s) or a non-human host transformed with a vector or the nucleic acid molecule as provided herein. It will be appreciated that the term "host cell or a non-human host transformed with the vector", in accordance with the present disclosure, relates to a host cell or a non-human host that comprises the vector or the nucleic acid molecule as provided herein.

Host cells for the expression of polypeptides are well known in the art and comprise prokaryotic cells as well as eukaryotic cells. Thus, the host/host cell can be selected from the group consisting of a bacterium, a mammalian cell, an algal cell, a ciliate, yeast and a plant cell.

Suitable bacterial expression hosts comprise, e.g., strains derived from *Escherichia coli* JM83, W3110, KS272, TG1, BL21 (such as BL21(DE3), BL21(DE3)PlysS, BL21(DE3) RIL, BL21(DE3)PRARE), Origami (K-12), Origami B or Rosetta. For vector modification, PCR amplification and ligation techniques, see methods described in Sambrook (2001) loc. cit.

Additionally, baculoviral systems can also be used as a vector in order to express the nucleic acid molecules of the invention in eukaryotic expression systems. In these aspects, the pFBDM vector can be used as an expression vector. The insertion into the MultiBac baculoviral DNA is mediated via the Tn7 transposition sequence upon transformation of DH10 MultiBac *E. coli* cells (Berger (2013) J. Vis. Exp. 77:50159, Fitzgerald (2006) Nat. Methods. 2006 3:1021-1032.). Virus amplification and expression can be performed in Sf21 (*Spodoptera frugiperda*) or High Five (*Trichoplusia ni*) cells.

The nucleic acid molecules and/or vectors as described herein above may be designed for introduction into cells by, e.g., non-chemical methods (electroporation, sonoporation, optical transfection, gene electrotransfer, hydrodynamic delivery or naturally occurring transformation upon contacting cells with the nucleic acid molecule of the invention), chemical-based methods (calcium phosphate, DMSO, PEG, liposomes, DEAE-dextrane, polyethylenimine, nucleofection etc.), particle-based methods (gene gun, magnetofection, impalefection), phage or phagemid vector-based methods and viral methods. For example, expression vectors derived from viruses such as retroviruses, vaccinia virus, adeno-associated virus, herpes viruses, Semliki Forest Virus or bovine papilloma virus, may be used for delivery of the nucleic acid molecules into a targeted cell population.

Preferably, the nucleic acid molecules and/or vectors provided herein are designed for transformation of electrocompetent *E. coli* by electroporation or for stable transfection of CHO cells by calcium phosphate, polyethylenimine or lipofectaminetransfection (Pham (2006) Mol. Biotechnol. 34:225-237; Geisse (2012) Methods Mol. Biol. 899:203-219; Hacker (2013) Protein Expr. Purif. 92:67-76).

Typical bacteria include *Escherichia, Corynebacterium* (*glutamicum*), *Pseudomonas* (*fluorescens*), *Lactobacillus, Streptomyces, Salmonella Bacillus* (such as *Bacillus megaterium* or *Bacillus subtilis*), or *Corynebacterium* (like *Corynebacterium glutamicum*). The most preferred bacterium host herein is *E. coli*. An exemplary ciliate to be used herein is Tetrahymena, e.g. Tetrahymena *thermophila.*

Typical mammalian cells include, Hela, HEK293, HEK293T, H9, Per.C6 and Jurkat cells, mouse NIH3T3, NS0 and C127 cells, COS 1, COS 7 and CV1, quail QC1-3 cells, mouse L cells, mouse sarcoma cells, Bowes melanoma cells and Chinese hamster ovary (CHO) cells. Most preferred mammalian host cells in accordance with the present invention are CHO cells. An exemplary host to be used herein is *Cricetulus*, e.g. *Cricetulus griseus* (Chinese hamster). Also, human embryonic kidney (HEK) cells are preferred.

Other suitable eukaryotic host cells are e.g. yeasts such as *Pichia pastoris, Kluyveromyces lactis, Saccharomyces cerevisiae* and *Schizosaccharomyces pombe* or chicken cells, such as e.g. DT40 cells. Insect cells suitable for expression are e.g. *Drosophila* S2, *Drosophila* Kc, *Spodoptera* Sf9 and Sf21 or *Trichoplusia* Hi5 cells. Preferable algal cells are *Chlamydomonas reinhardtii* or *Synechococcus elongatus* cells and the like. An exemplary plant is *Physcomitrella*, for example *Physcomitrella patens*. An exemplary plant cell is a *Physcomitrella* plant cell, e.g. a *Physcomitrella patens* plant cell.

Also within the scope of the present invention are primary mammalian cells or cell lines. Primary cells are cells which are directly obtained from an organism. Suitable primary cells are, for example, mouse embryonic fibroblasts (MEF), mouse primary hepatocytes, cardiomyocytes and neuronal cells as well as mouse muscle stem cells (satellite cells), human dermal and pulmonary fibroblasts, human epithelial cells (nasal, tracheal, renal, placental, intestinal, bronchial epithelial cells), human secretory cells (from salivary, sebaceous and sweat glands), human endocrine cells (thyroid cells), human adipose cells, human smooth muscle cells, human skeletal muscle cells, human leucocytes such as B-cells, T-cells, NK-cells or dendritic cells and stable, immortalized cell lines derived thereof (for example hTERT or oncogene immortalized cells). Appropriate culture media and conditions for the above described host cells are known in the art.

The host cells may e.g. be employed to produce large amounts of the nucleic acid molecule provided herein, and/or the protein as provided herein. Accordingly, herein provided is a method for preparing the nucleic acid molecule or the vector provided herein, the method comprising culturing the host or host cell of the invention under suitable conditions and optionally isolating the produced nucleic acid molecule and/or vector. Furthermore, herein provided is to a method for preparing the protein as described and provided herein, the method comprising culturing the host or host cell as provided herein under suitable conditions and optionally isolating the produced protein. Particularly in this aspect, it is envisaged that the protein is a fusion protein.

Alternatively, the method can also comprise culturing the host or host cell as provided herein (i.e. a host or host cell comprising a nucleic acid encoding a linker, particularly a linker consisting of proline, alanine and, optionally, serine, as provided herein) and/or culturing the host or host cell comprising a nucleic acid encoding the PDGFR domain and/or VEGFR domain as defined herein, and optionally isolating the produced linker and/or isolating the produced PDGFR domain and/or VEGFR domain, and further optionally conjugating the linker and the PDGFR domain and/or VEGFR domain (e.g. by chemical coupling) to produce the protein.

"Culturing the host or host cell" includes in this context expression of the linker as defined herein and/or of the PDGFR domain and/or of the VEGFR domain in the host or host cell.

Suitable conditions for culturing prokaryotic or eukaryotic host cells are well known to the person skilled in the art. For example, bacteria such as e.g. *E. coli* can be cultured under aeration in Luria Bertani (LB) medium, typically at a temperature from 4 to about 37° C. To increase the yield and the solubility of the expression product, the medium can be buffered or supplemented with suitable additives known to enhance or facilitate both. In those cases where an inducible promoter controls the nucleic acid molecule of the invention in the vector present in the host cell, expression of the polypeptide can be induced by addition of an appropriate inducing agent, such as, e.g., isopropyl-β-D-thiogalactopyranoside (IPTG) or anhydrotetracycline (aTc) as employed in the appended examples. Suitable expression protocols and strategies have been described in the art, e.g. in Sambrook (2001) loc. cit., (Gebauer (2012) Meth. Enzymol. 503:157-188) and can be adapted to the needs of the specific host cells and the requirements of the protein to be expressed, if required.

Depending on the cell type and its specific requirements, mammalian cell culture can, e.g., be carried out in RPMI, Williams' E or medium DMEM containing 10% (v/v) FCS, 2 mM L-glutamine and 100 U/ml penicillin/streptomycin. The cells can be kept, e.g., at 37° C., or at 41° C. for DT40 chicken cells, in a 5% CO2, water-saturated atmosphere. A suitable medium for insect cell culture is, e.g., TNM+10% FCS, SF900 or HyClone SFX-Insect medium. Insect cells are usually grown at 27° C. as adhesion or suspension cultures. Suitable expression protocols for eukaryotic or vertebrate cells are well known to the skilled person and can be retrieved, e.g., from Sambrook (2001) (loc. cit).

Preferably, the method for preparing the protein, nucleic acid molecule, the vector as described herein is carried out using either bacterial cells, such as, e.g., *E. coli* cells, or mammalian cells, such as, e.g., CHO cells. More preferably, the method is carried out using *E. coli* cells or CHO cells and most preferably, the method is carried out using *E. coli* cells.

Methods for the isolation of the encoded polypeptides produced comprise, without limitation, purification steps such as affinity chromatography (preferably using a fusion tag such as the Strep-tag II or the His6-tag), gel filtration (size exclusion chromatography), anion exchange chromatography, cation exchange chromatography, hydrophobic interaction chromatography, high pressure liquid chromatography (HPLC), reversed phase HPLC, ammonium sulfate precipitation or immunoprecipitation. These methods are well known in the art and have been generally described, e.g., in Sambrook (2001) loc. cit. Such methods provide substantially pure polypeptides. Said pure polypeptides have a homogeneity of, preferably, at least about 90 to 95% (on the protein level), more preferably, at least about 98 to 99%. Most preferably, these pure polypeptides are suitable for pharmaceutical use/applications. Depending upon the host cell/organism employed in the production procedure, the proteins provided herein of the present invention may be glycosylated or may be non-glycosylated. Preferably, the linker consisting of proline, alanine and, optionally, serine provided herein is not post-translationally modified, particularly not glycosylated. Most preferably, the linker consisting of proline, alanine and, optionally, serine provided herein is not posttranslationally modified in its side chains such as, for example, by proline hydroxylation.

In the linker that can consist of alanine, proline and, optionally, serine residues, the amino acid residues threonine or asparagine (or serine, if applicable), which is/are required for 0- or N-glycosylation, can be absent. Thus, the linker would be (essentially) devoid of post-translational modifications within the Pro/Ala/Ser or Pro/Ala sequence. This is an advantage for recombinant protein production in eukaryotic cells, like chinese hamster ovarian cells (CHO), HEK cells, or yeast, which are often chosen for the biosynthesis of complex proteins.

Herein disclosed is a composition comprising the protein as provided herein or as prepared by the method as disclosed herein above, the nucleic acid as provided herein, the vector as provided herein, or the (host) cell as provided herein.

The composition can be a pharmaceutical composition, optionally further comprising (a) pharmaceutical acceptable carrier(s).

In one aspect, the protein as provided herein or as prepared by the method as disclosed herein above, the nucleic acid as provided herein, the vector as provided herein, the cell as provided herein, or the composition as provided herein, is for use as a medicament.

In one aspect, the protein as provided herein or as prepared by the method as disclosed herein above, the nucleic acid as provided herein, the vector as provided herein, the cell as provided herein, or the composition as provided herein, is for use in therapy.

In one aspect, use of the protein as provided herein or as prepared by the method as disclosed herein above, use of the nucleic acid as provided herein, use of the vector as provided herein, use of the cell as provided herein, or use of the composition as provided herein, is disclosed for the preparation of a pharmaceutical composition for use in therapy.

In one aspect, the protein as provided herein or as prepared by the method as disclosed herein above, the nucleic acid as provided herein, the vector as provided herein, the cell as provided herein, or the composition as provided herein, can inhibit angiogenesis effectively, and is for use in the treatment of diseases associated with angiogenesis, including but not limited to all types of tumor, all types of ophthalmic disease (for example, Diabetic retinopathy (DR), Diabetic macular edema (DME), Choroidal neovascularization (CNV), Retinal vein occlusion (RVO), Central retinal vein occlusion (CRVO), Branch retinal vein occlusion (BRVO), or pathologic myopia (PM); preferably age-related macular degeneration (AMD)), cancer, renal fibrosis, cirrhosis, arthosclerosis, portal hypertension or systemic sclerosis.

Specifically, in one aspect, the protein as provided herein or as prepared by the method as disclosed herein above, the nucleic acid as provided herein, the vector as provided herein, the cell as provided herein, or the composition as provided herein, is for use in the treatment of ophthalmic disease (for example, Diabetic retinopathy (DR), Diabetic macular edema (DME), Choroidal neovascularization (CNV), Retinal vein occlusion (RVO), Central retinal vein occlusion (CRVO), Branch retinal vein occlusion (BRVO), or pathologic myopia (PM); preferably, age-related macular degeneration (AMD)), cancer, renal fibrosis, cirrhosis, arthosclerosis, portal hypertension or systemic sclerosis. In one aspect, the protein as provided herein or as prepared by the method as disclosed herein above, the nucleic acid as provided herein, the vector as provided herein, the cell as provided herein, or the composition as provided herein, is for use in inhibiting angiogenesis (particularly in a diseased patient).

Age-related macular degeneration (AMD) is the preferred ophthalmic disease to be treated herein.

In one aspect, use of the protein as provided herein or as prepared by the method as disclosed herein above, use of the nucleic acid as provided herein, use of the vector as provided herein, use of the cell as provided herein, or use of the composition as provided herein, is disclosed for the preparation of a pharmaceutical composition for the treatment of ophthalmic disease (for example, Diabetic retinopathy (DR), Diabetic macular edema (DME), Choroidal neovascularization (CNV), Retinal vein occlusion (RVO), Central retinal vein occlusion (CRVO), Branch retinal vein occlusion (BRVO), or pathologic myopia (PM); preferably age-related macular degeneration (AMD)), cancer, renal fibrosis, cirrhosis, arthosclerosis, portal hypertension or systemic sclerosis.

In one aspect, a method for treating ophthalmic disease (for example, Diabetic retinopathy (DR), Diabetic macular edema (DME), Choroidal neovascularization (CNV), Retinal vein occlusion (RVO), Central retinal vein occlusion (CRVO), Branch retinal vein occlusion (BRVO), or pathologic myopia (PM); preferably age-related macular degeneration (AMD)), cancer, renal fibrosis, cirrhosis, arthosclerosis, portal hypertension or systemic sclerosis is disclosed, the method comprising the administration of (an effective amount of) the protein as provided herein or as prepared by the method as disclosed herein above, the nucleic acid as provided herein, the vector as provided herein, the cell as provided herein, or the composition as provided herein, to a subject (in need of the treatment).

The cancer can be a solid cancer. The solid cancer can be colon cancer, hepatocellular carcinoma, non-small cell lung cancer, soft tissue sarcoma, prostate cancer, breast cancer, ovarian cancer, glioma, dermatofibrosarcoma protuberans, oral squamous cell carcinoma, or pancreatic cancer. The cancer can be a non-solid cancer, such as leukemia or non-Hodgkin's lymphoma.

The terms "treatment", "treating" and the like are used herein to generally mean obtaining a desired pharmacological and/or physiological effect. The effect may be prophylactic in terms of completely or partially preventing a disease or symptom thereof and/or may be therapeutic in terms of partially or completely curing a disease and/or adverse effect attributed to the disease. The term "treatment" as used herein covers any treatment of a disease in a subject and includes: (a) preventing a disease related in a subject which may be predisposed to the disease; (b) inhibiting the disease, i.e. arresting its development; or (c) relieving the disease, i.e. causing regression of the disease.

An "individual", "patient" or "subject" for the purposes of the present invention includes both humans and other animals, particularly mammals, and other organisms. Thus, the methods are applicable to both human therapy and veterinary applications. Preferably, the "individual", "patient" or "subject" is a mammal, and most preferably the "individual", "patient" or "subject" is human.

The protein provided herein may be administered as a single agent (i.e. in form of a monotherapy) or in form of a combination therapy, for example, conventional therapies of retinopathies like diabetic retinopathy, retinitis pigmentosa, dry/wet age related macular degeneration or glaucoma. Examples of cancers which may be treated by the present invention include those intra-axial brain cancers, ovarian cancers, colon cancers, prostate cancers, lung cancers, Kaposi's sarcoma and skin cancers, which have inappropriate PDGF-R activity. Examples of blood vessel proliferation disorders include, restenosis and atherosclerosis.

The pharmaceutical composition will be formulated and dosed in a fashion consistent with good medical practice, taking into account the clinical condition of the individual patient, the site of delivery of the pharmaceutical composition, the method of administration, the scheduling of administration, and other factors known to practitioners. The "effective amount" of the pharmaceutical composition for purposes herein is thus determined by such considerations.

The skilled person knows that the effective amount of pharmaceutical composition administered to an individual will, inter alia, depend on the nature of the compound. The administration of the herein provided compositions may, inter alia, comprise an administration twice daily, every day, every other day, every third day, every forth day, every fifth day, once a week, once every second week, once every third week, once every month, etc.

Pharmaceutical compositions of the invention preferably comprise a pharmaceutically acceptable carrier. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The pharmaceutical composition is also suitably administered by sustained release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman, U. et al., Biopolymers 22:547-556 (1983)), poly (2-hydroxyethyl methacrylate) (R. Langer et al., J. Biomed. Mater. Res. 15:167-277 (1981), and R. Langer, Chem. Tech. 12:98-105 (1982)), ethylene vinyl acetate (R. Langer et al., Id.) or poly-D-(−)-3-hydroxybutyric acid (EP 133,988). Sustained release pharmaceutical composition also include liposomally entrapped compound. Liposomes containing the pharmaceutical composition are prepared by methods known per se: DE 3,218,121; Epstein et al., Proc. Natl. Acad. Sci. (USA) 82:3688-3692 (1985); Hwang et al., Proc. Natl. Acad. Sci. (USA) 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal therapy.

Generally, the formulations are prepared by contacting the components of the pharmaceutical composition uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non aqueous vehicles such as fixed oils and ethyl oleate are also useful herein, as well as liposomes. The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) (poly)peptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The components of the pharmaceutical composition to be used for therapeutic administration must be sterile. Sterility is readily accomplished by filtration through sterile filtration membranes (e.g., 0.2 micron membranes). Therapeutic components of the pharmaceutical composition generally are placed into a container having a sterile access port, for example, an intravenous solution bag or vial having a stopper pierceable by a hypodermic injection needle.

The components of the pharmaceutical composition ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous solution, and the resulting mixture is lyophilized. The infusion solution is prepared by reconstituting the lyophilized compound(s) using bacteriostatic Water-for-Injection.

The nucleic acid molecule provided herein can also be employed alone or as part of a vector for gene therapy purposes. Gene therapy, which is based on introducing therapeutic genes into cells by ex vivo or in vivo techniques, is one of the most important applications of gene transfer. Suitable vectors, methods or gene delivery systems for in vivo gene therapy are described in the literature and are known to the person skilled in the art; see, e.g., Giordano (1996) Nat. Med. 2:534-539; Schaper (1996) Circ. Res. 79:911-919; Anderson (1992) Science 256:808-813; Verma (1997) Nature 389:239-249; Isner (1996) Lancet 348:370-374; Muhlhauser (1995) Circ. Res. 77:1077-1086; Onodera (1998) Blood 91:30-36; Verma (1998) Gene Ther. 5:692-699; Nabel (1997) Ann. N.Y. Acad. Sci. 811:289-292; Verzeletti (1998) Hum. Gene Ther. 9:2243-2251; Wang (1996) Nat. Med. 2:714-716; WO 94/29469; WO 97/00957, U.S. Pat. Nos. 5,580,859; 5,589,466; or Schaper (1996) Curr. Opin. Biotechnol. 7:635-640.

The nucleic acid molecules and vectors provided herein may be designed for direct introduction or for introduction via liposomes or viral vectors (e.g., adenoviral, retroviral) into the cell. For example, the vector can be an adeno-associated-virus (AAV) vector, in particular, an AAV8 vector. AAV vectors are attractive for gene therapy. The AAV system has several advantages including long-term gene expression, the inability to autonomously replicate without a helper virus, transduction of dividing and nondividing cells, and the lack of pathogenicity from wild-type infections. Preferably, said cell in which the nucleic acid molecule or vector is introduced is a germ line cell, embryonic cell or egg cell or derived therefrom, most preferably said cell is a stem cell. An example for an embryonic stem cell can be, inter alia, a stem cell as described in Nagy (1993) Proc. Natl. Acad. Sci. USA 90:8424-8428.

As used herein, the terms "comprising" or "including" or grammatical variants thereof are to be taken as specifying the stated features, integers, steps or components but do not preclude the addition of one or more additional features, integers, steps, components or groups thereof. The terms "comprising"/"including" encompass the terms "consisting of" and "consisting essentially of". Thus, whenever the terms "comprising"/"including" are used herein, they can be replaced by "consisting essentially of" or, preferably, by "consisting of".

The terms "comprising"/"including" mean that any further component (or likewise features, integers, steps and the like) can be present.

The term "consisting of" means that no further component (or likewise features, integers, steps and the like) can be present.

The term "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed product, composition, device or method and the like.

Thus, the term "consisting essentially of" means that specific further components (or likewise features, integers, steps and the like) can be present, namely those not materially affecting the essential characteristics of the product, composition, device or method. In other words, the term "consisting essentially of" (which can be interchangeably used herein with the term "comprising substantially"), allows the presence of other components in the product, composition, device or method in addition to the mandatory components (or likewise features, integers, steps and the like), provided that the essential characteristics of the product, composition, device or method are not materially affected by the presence of other components.

The term "method" refers to manners, means, techniques and procedures for accomplishing a given task including, but not limited to, those manners, means, techniques and procedures either known to, or readily developed from known manners, means, techniques and procedures by practitioners of the chemical, biological and biophysical arts.

If not otherwise indicated, the term "about" as used herein refers to ±10%.

BRIEF DESCRIPTION OF THE FIGURES

The present invention is further described by reference to the following non-limiting figures and examples.

The Figures show.

Figure 1:
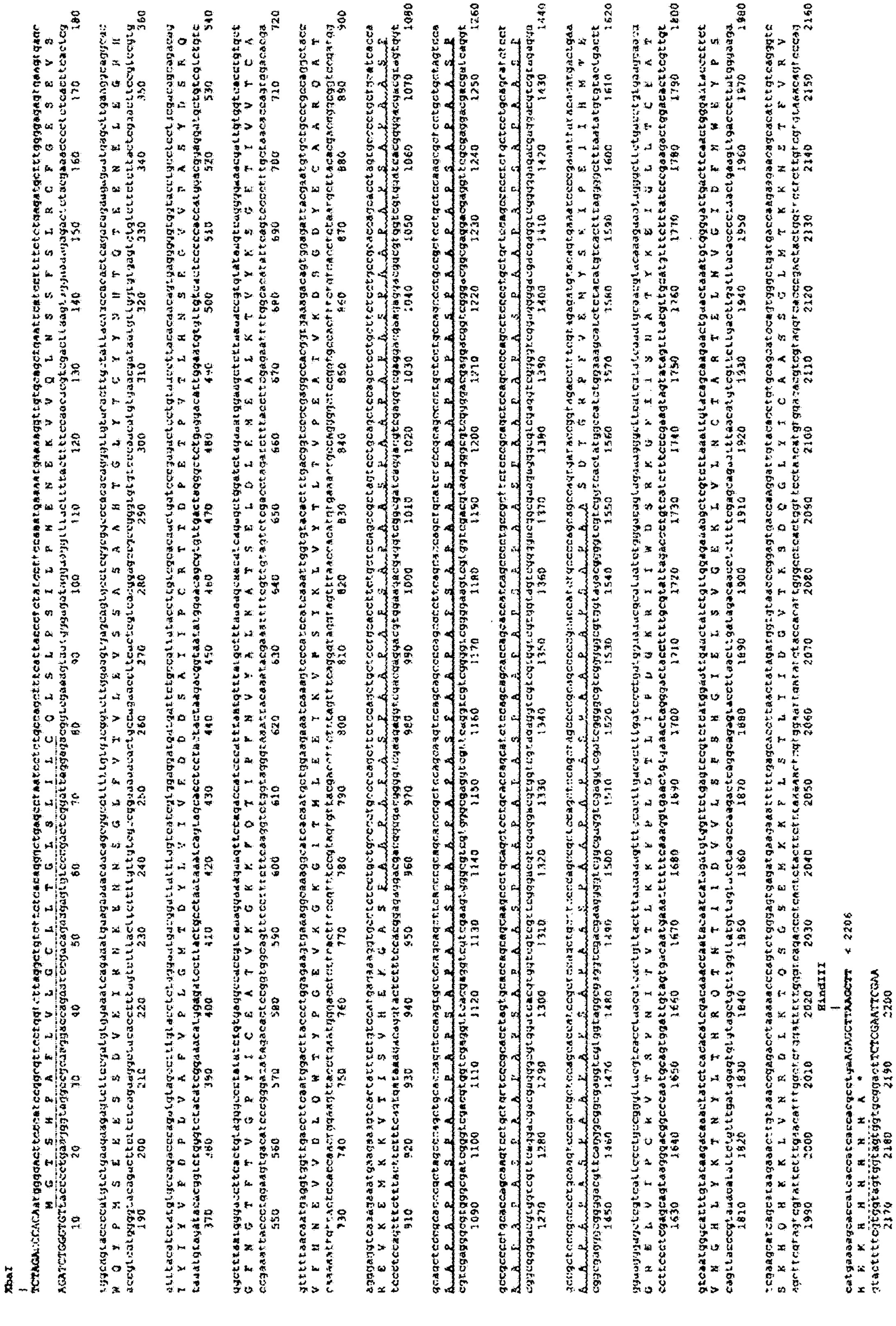
FIG. 1.

Nucleotide and amino acid sequence of the $PDGFR_{\alpha D123}$-PAS(200)-$VEGFR1_{D2}/R2_{D3}$ fusion protein referred to herein as EPS1108P encoded on pDSG33-PDGFR-PAS200-VEGFR (flanked by XbaI and HindIII restriction sites). Underlined: signal polypeptide sequence of PDGFR-α, which is cleaved off during secretion. Waved underlined: PAS polypeptide sequence. Broken underlined: His6 tag for affinity purification and detection.

FIG. 2.

3D model of the fully ligand-bound complex of $PDGFR\alpha_{D123}$-PAS(200)-$VEGFR1_{D2}/R2_{D3}$ with both ligands, VEGF and PDGF, in its homo-dimeric state. For modelling the crystal structures of PDGFR-β in complex with PDGF-BB (PDB entry 3MJG) and VEGFR2 in complex with VEGF-C (PDB entry 2X1W) were used. The flexible PAS polypeptide spacer in a random coil conformation is depicted over-simplified as ribbon. (N or C=N- or C-terminal ending)

FIG. 3.

Purification and SDS-PAGE analysis of the $PDGFR_{\alpha D12}$3-PAS(200)-$VEGFR1_{D2}/R2_{D3}$ fusion protein referred to herein as EPS1108P. (A) SDS-PAGE analysis of the different purification steps for $PDGFR\alpha_{D123}$-PAS(200)-$VEGFR1_{D}2/R2_{D3}$ transiently expressed in MEXi-293E cells after 7 days of transfection. (1) $NH_4SO_4$ precipitate from conditioned medium supernatant. (2) Protein after Resource Q (anion exchange) chromatography. (3) Protein after Resource S (cation exchange) chromatography. (4) Protein after size exclusion chromatography. Samples were analyzed on a 4-20% Gradient Bis-Tris Gel and visualized using InstantBlue colloidal Coomassie blue protein stain. Protein molecular weight marker: PageRuler Plus Prestained Protein Ladder (250, 130, 100, 70, 55, 35, 25, 15, 10 kDa). (B) SDS-PAGE analysis of $PDGFR\alpha_{D123}$-PAS(200)-$VEGFR1_{D2}/R2_{D3}$ purified from MEXi-293E conditioned medium under (1) reduced and (2) unreduced conditions (+/−5 mM DTT). (C) Western blot analysis of purified $PDGFR_{\alpha D123}$-PAS(200)-$VEGFR1_{D2}/R2_{D3}$ via the C-terminal His6-tag using an anti-polyHis antibody. Protein molecular weight marker: PageRuler Plus Prestained Protein Ladder (250, 130, 100, 70, 55, 35, 25, 15, 10 kDa).

FIG. 4.

Size exclusion chromatography (SEC) analysis of $PDGFR_{\alpha D123}$-PAS (200)-$VEGFR1_{D2}/R2_{D3}$ referred to herein as EPS1108P on Superdex 200 10/30 GL (running buffer: 10 mM Hepes/NaOH, 150 mM NaCl pH 7.4; void volume $V_0$=7.1 ml; column volume: 23.6 ml; sample volume: 0.5 ml). (A) $PDGFR_{\alpha D123}$-PAS(200)-$VEGFR1_{D2}/R2_{D3}$ purified from conditioned MEXi-293E medium elutes at 9.6 ml as a sharp peak. (B) The calibration line used to estimate the native molecular weight based on the retention volumes of various globular size standard proteins during analytical gel filtration on the same Superdex 200 10/30 GL column. Calculated from the semi-logarithmic fit, the PASylated fusion protein reveals an apparent molecular weight of approximately 530 kDa, which is 7-fold larger than the calculated molecular mass based on amino acid sequence (75 kDa) of $PDGFR_{\alpha D123}$-PAS(200)-$VEGFR1_{D2}/R2_{D3}$, thus illustrating the expanded molecular volume due to the random coil behavior of the PAS spacer.

FIG. 5.

Electromobility gel shift assay via native PAGE of $PDGFR_{\alpha D123}$-PAS(200)-$VEGFR1_{D2}/R2_{D3}$ referred to herein as EPS1108P in the presence of equimolar amounts of either PDGF-AA or VEGF-A165 or both. (1) The $PDGFR_{\alpha D123}$-PAS(200)-$VEGFR1_{D2}/R2_{D3}$ fusion protein purified from conditioned MEXi-293E medium is glycosylated and runs as a broad band according to a calculated mass of 72.3 kDa based on the amino acid sequence (without glycosylation). Binding of 38.4 kDa homodimeric VEGF-A165 (3), 28.6 kDa homodimeric PDGF-AA (4) or both protein ligands, VEGF-A165 and PDGF-AA (2), considerably changes the electrophoretic migration behavior of $PDGFR_{\alpha D123}$-PAS(200)-$VEGFR1_{D2}/R2_{D3}$ and also leads to a more focused and defined protein band, which is indicative of the complexes formed.

FIG. 6.

Figure 6:
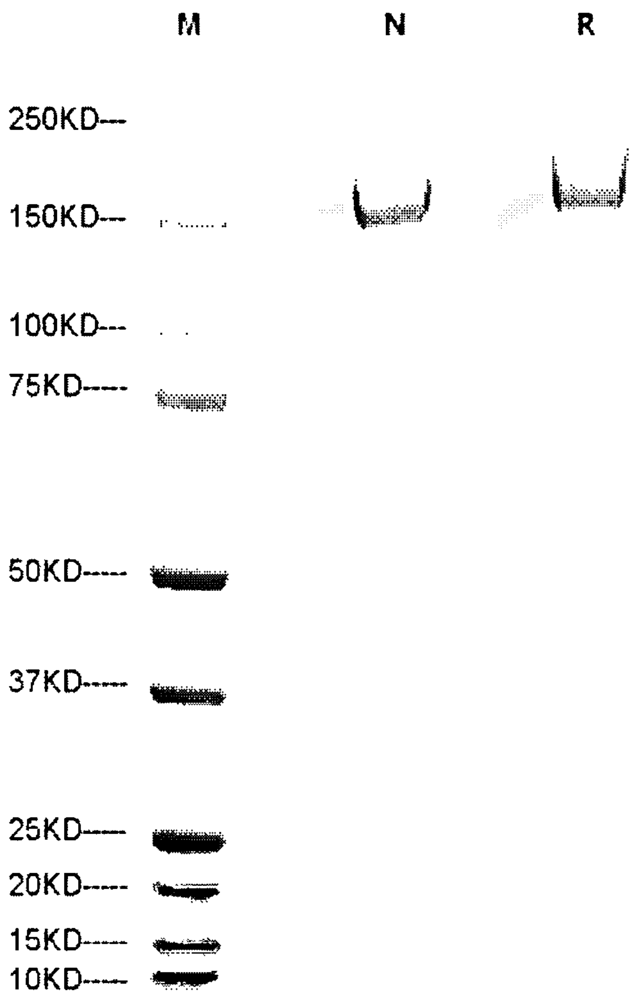
Figure 6:
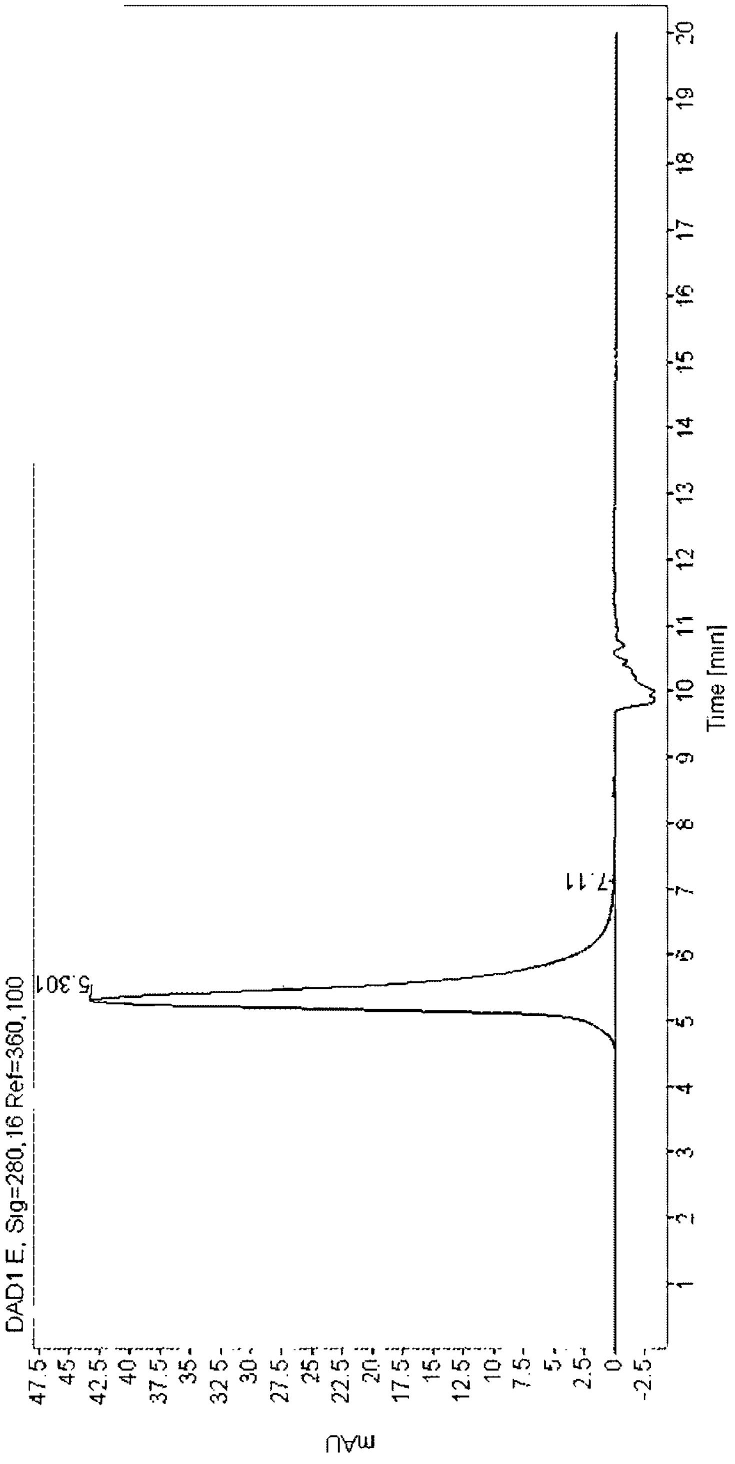

SDS-PAGE analysis result of purified $PDGFR\alpha_{D123}$-PAS (300)-$VEGFR1_{D2}/R2_{D3}$, referred to herein as EPS1103P, was shown in FIG. 6A. SEC analysis of purified EPS1103P protein was shown in FIG. 6B, which showed a purity of 98.88%.

FIG. 7.

Figure 7:
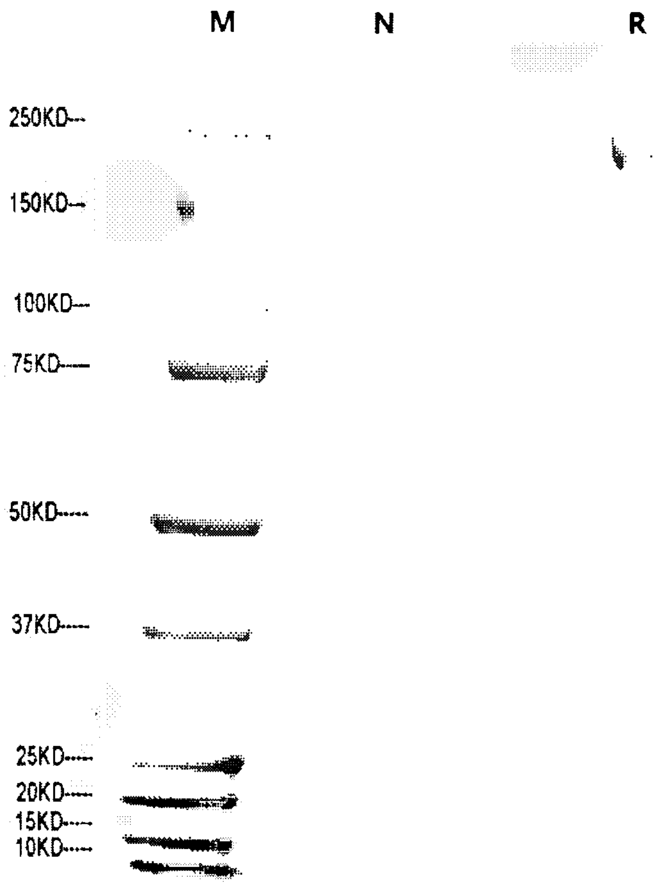
Figure 7:
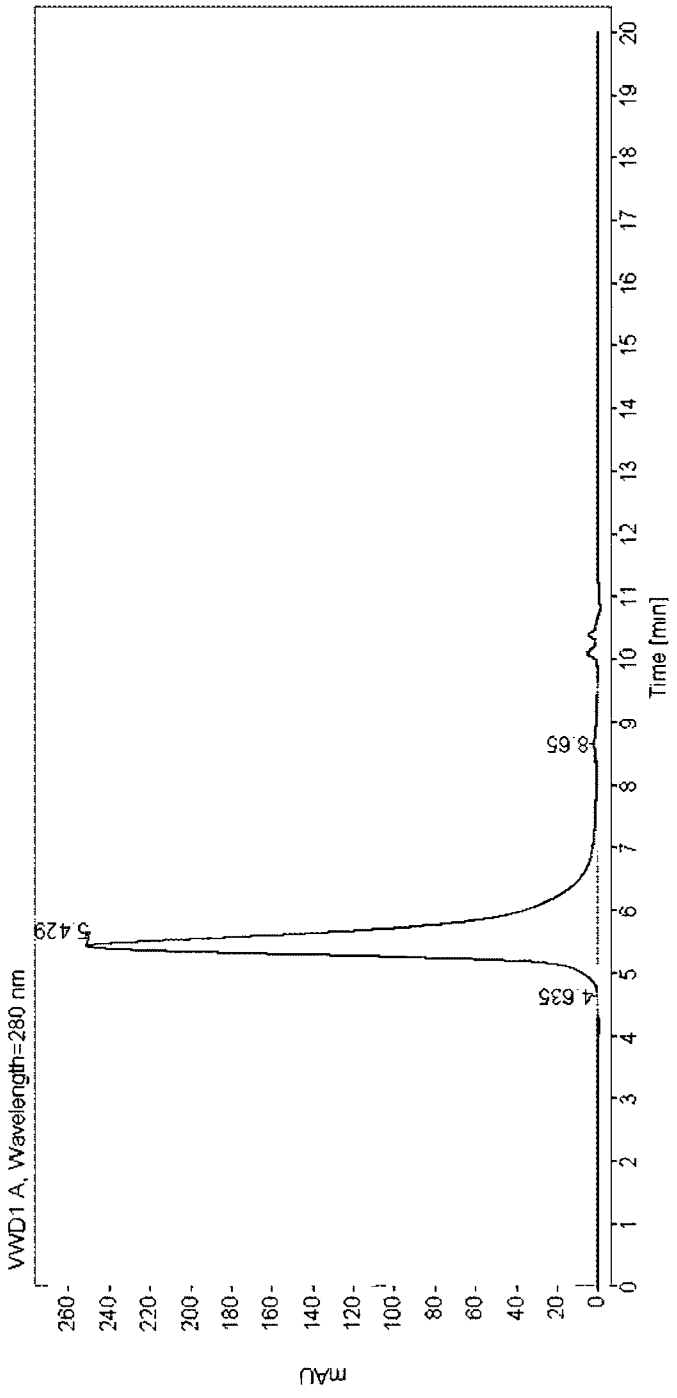

SDS-PAGE analysis result of purified $PDGFR\alpha_{D123}$-PAS (400)-$VEGFR1_{D2}/R2_{D3}$, referred to herein as EPS1104P, was shown in FIG. 7A. SEC analysis of purified EPS1104P protein was shown in FIG. 7B, which showed a purity of 98.97%.

FIG. 8.

Figure 8:
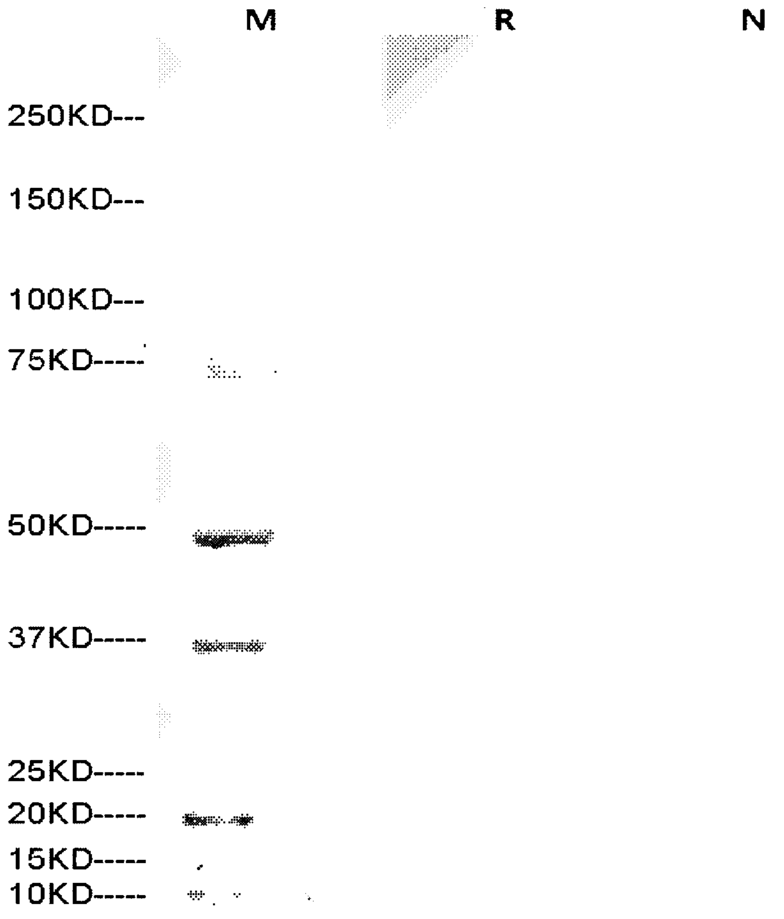
Figure 8:
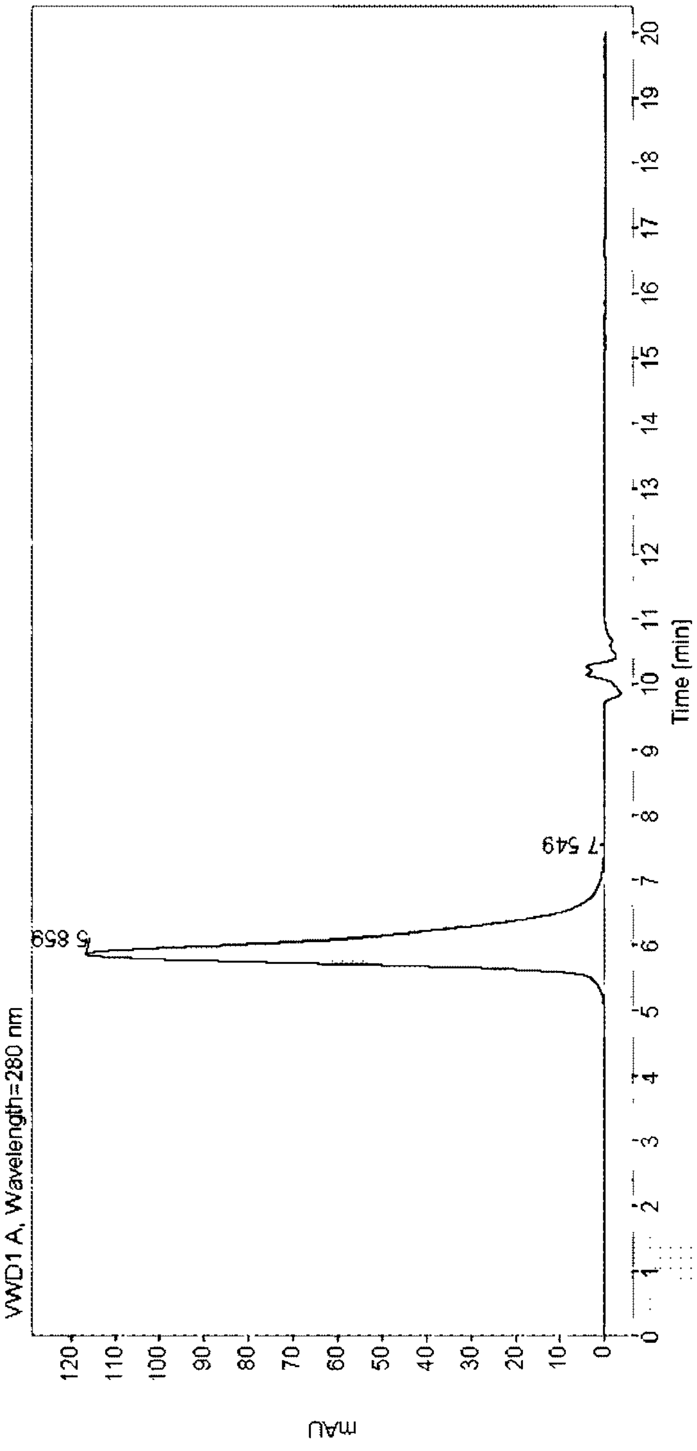

SDS-PAGE analysis result of purified $VEGFR1_{D2}/R2_{D3}$-PAS(200)-$PDGFR\alpha_{D123}$, referred to herein as EPS1105P, was shown in FIG. 8A. SEC analysis result of purified EPS1105P protein was done, the result was shown in FIG. 8B, which showed a purity of 99.82%.

FIG. 9.

Figure 9:
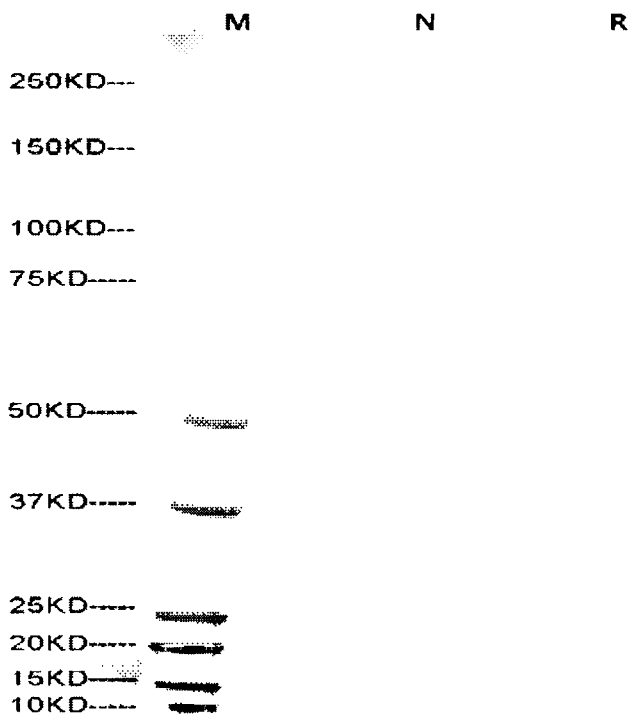
Figure 9:
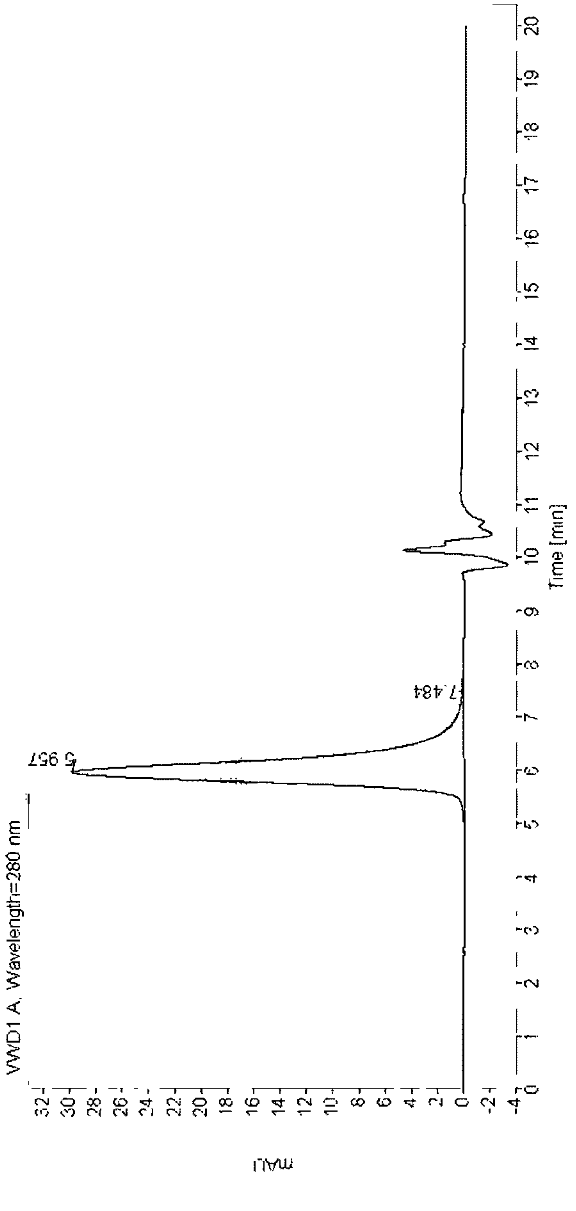

SDS-PAGE analysis result of purified $PDGFR\alpha_{D123}$-(GGGGS (SEQ ID NO: 73))$_3$-PAS(200)-(GGGGS (SEQ ID NO: 73))$_3$-VEGFR1*D*2/R2*D*3 referred to herein as EPS1106P, was shown in FIG. 9A. SEC analysis of purified EPS1106P protein was done, the result was shown in FIG. 9B, which showed a purity of 99.79%.

FIG. 10.

Figure 10:
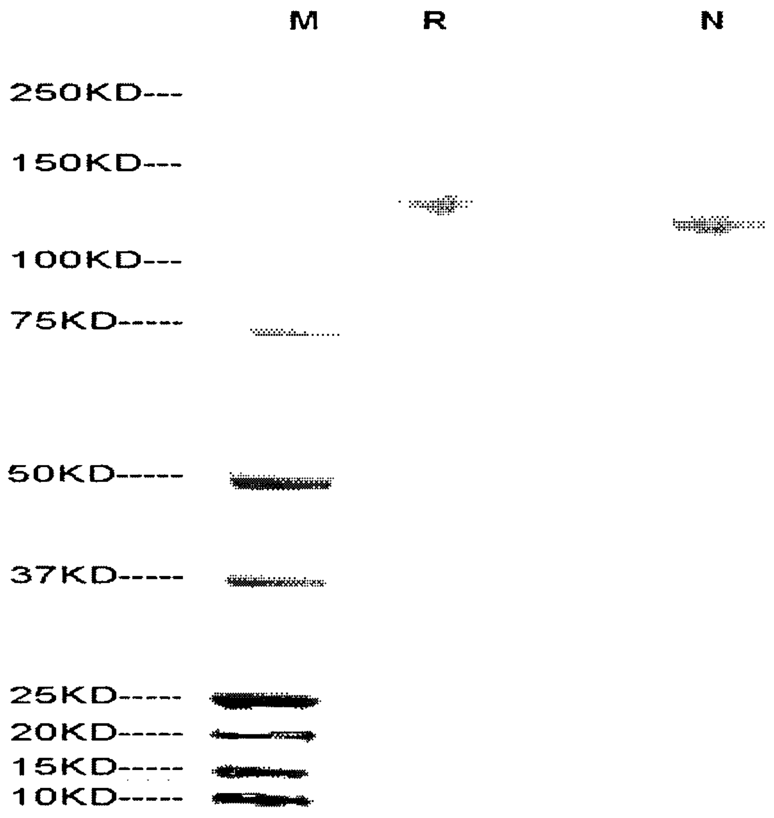
Figure 10:
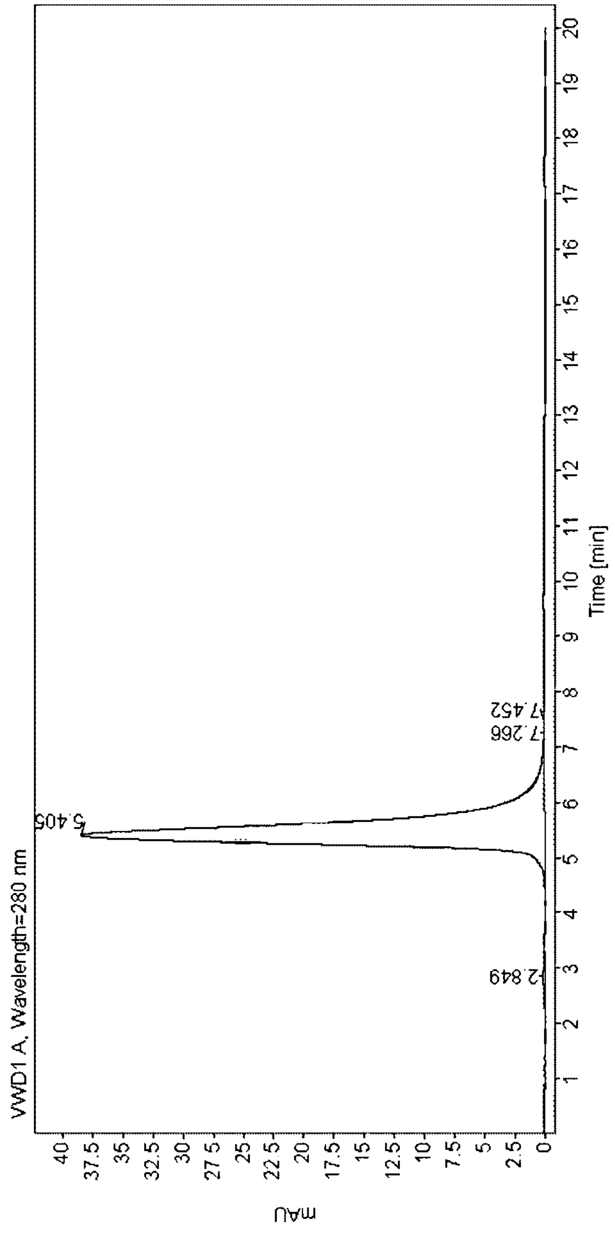

SDS-PAGE analysis result of purified VEGFR$1_{D2}$/R$2_{D3}$-(GGGGS (SEQ ID NO: 73))$_3$-PAS(200)-(GGGGS (SEQ ID NO: 73))$_3$-PDGFRα*D*123 referred to herein as EPS1107P, was shown in FIG. 10A SEC analysis of purified EPS1107P protein was done, the result was shown in FIG. 10B, which showed a purity of 99.43%.

FIG. 11.

Figure 11:
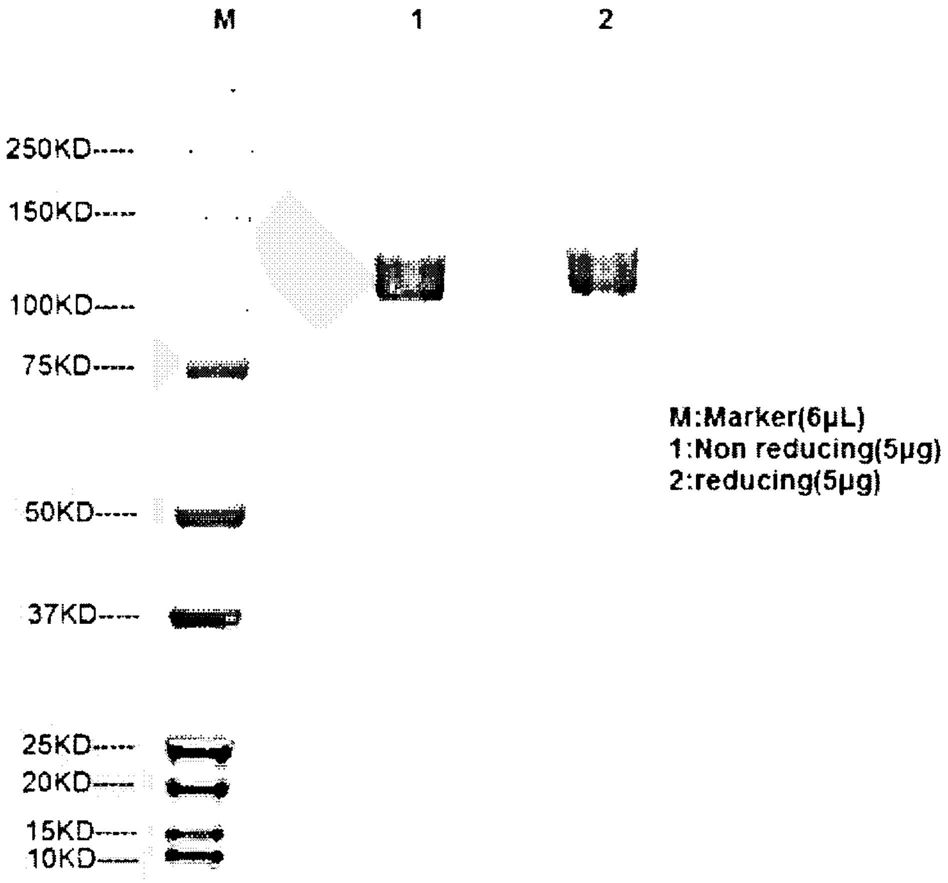
Figure 11:
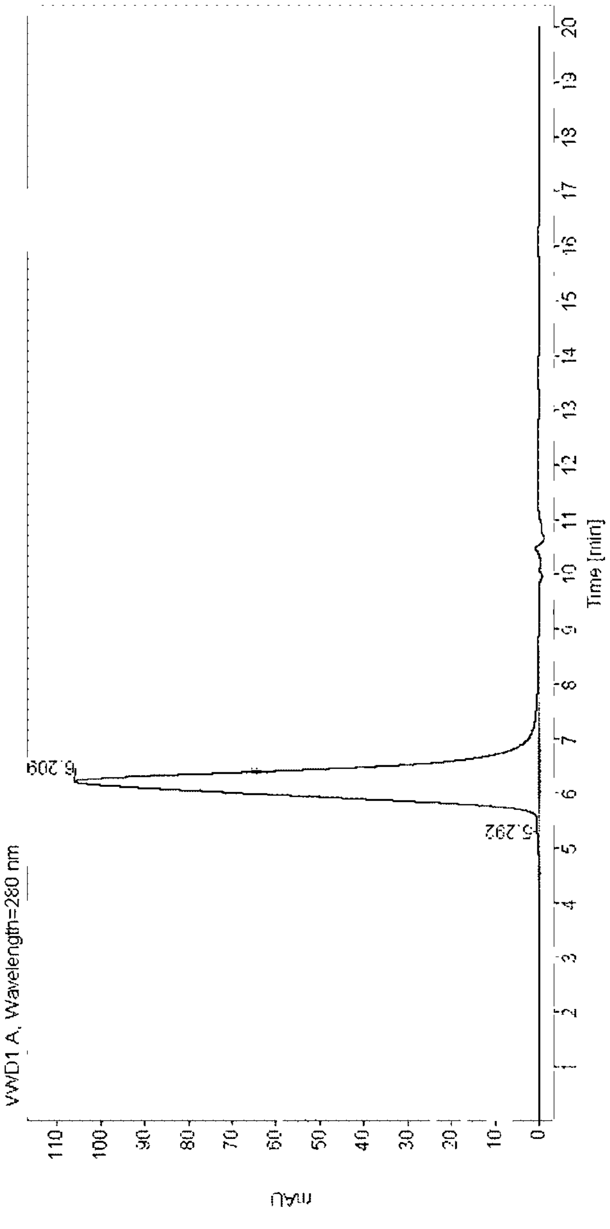

SDS-PAGE analysis result of purified PAS(200)-VEGFR$1_{D2}$/R$2_{D3}$-PDGFR$\alpha_{D123}$ referred to herein as EPS1109P, was shown in FIG. 11A. SEC analysis of purified EPS1109P protein was done, the result was shown in FIG. 11B, which showed a purity of 99.62%.

FIG. 12.

Figure 12:
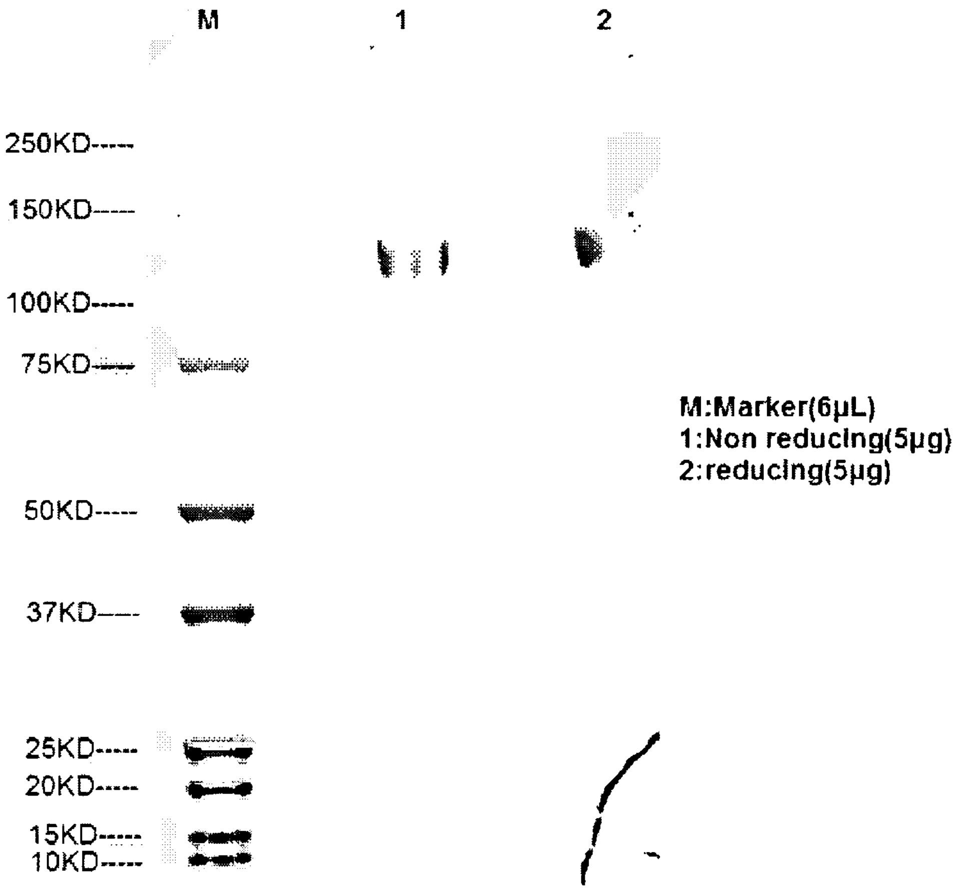
Figure 12:
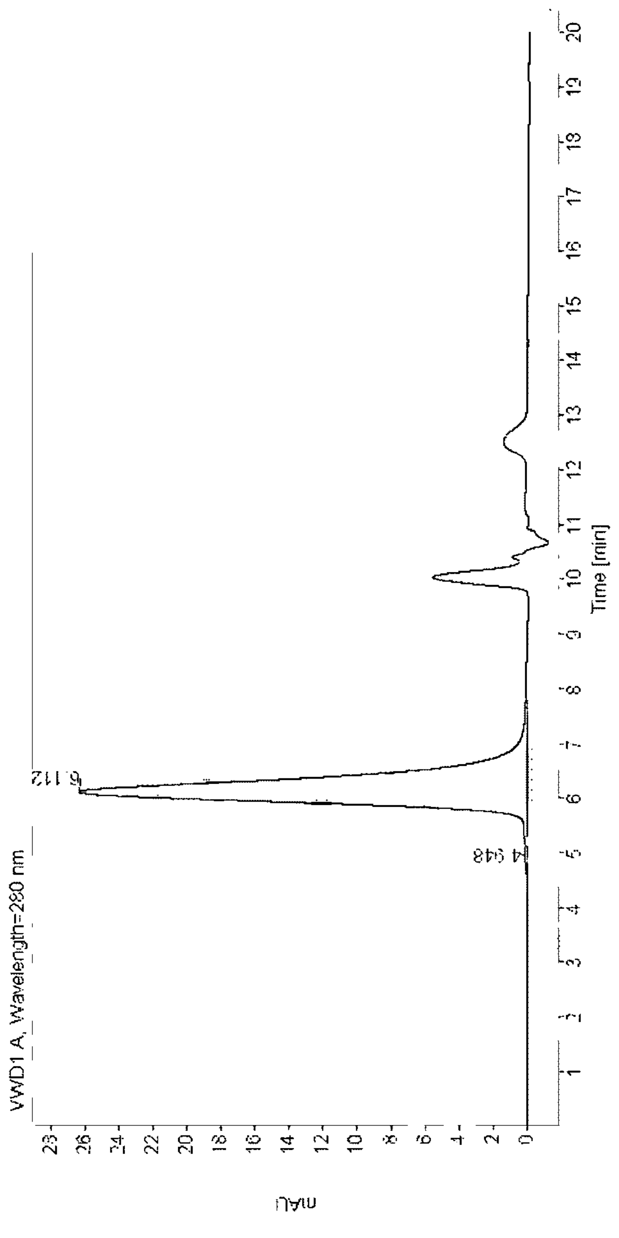

SDS-PAGE analysis result of purified PAS(200)-PDGFR$\alpha_{D123}$-VEGFR$1_{D2}$/R$2_{D3}$, referred to herein as EPS1110P, was shown in FIG. 12A. SEC analysis of purified EPS1110P protein was done, the result was shown in FIG. 12B, which showed a purity of 99.52%.

FIG. 13.

Figure 13:
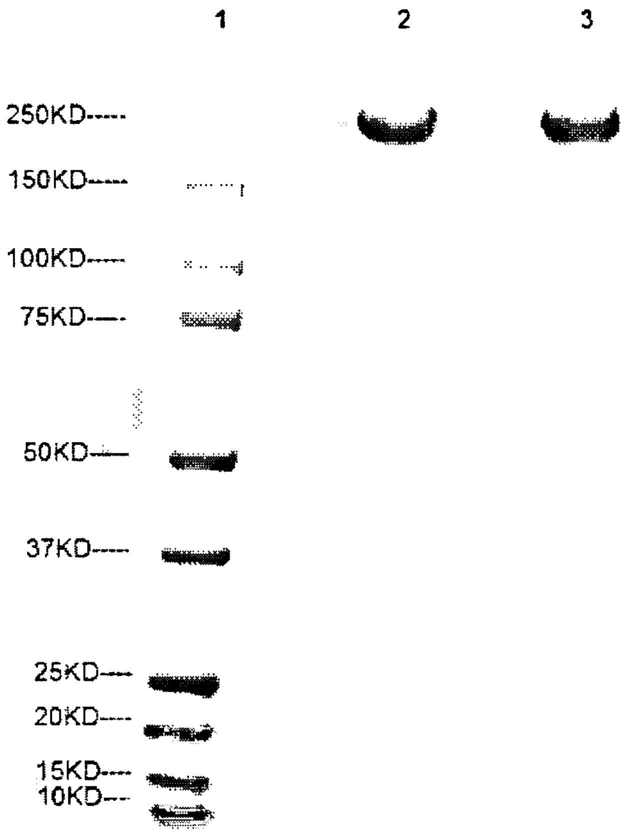
Figure 13:
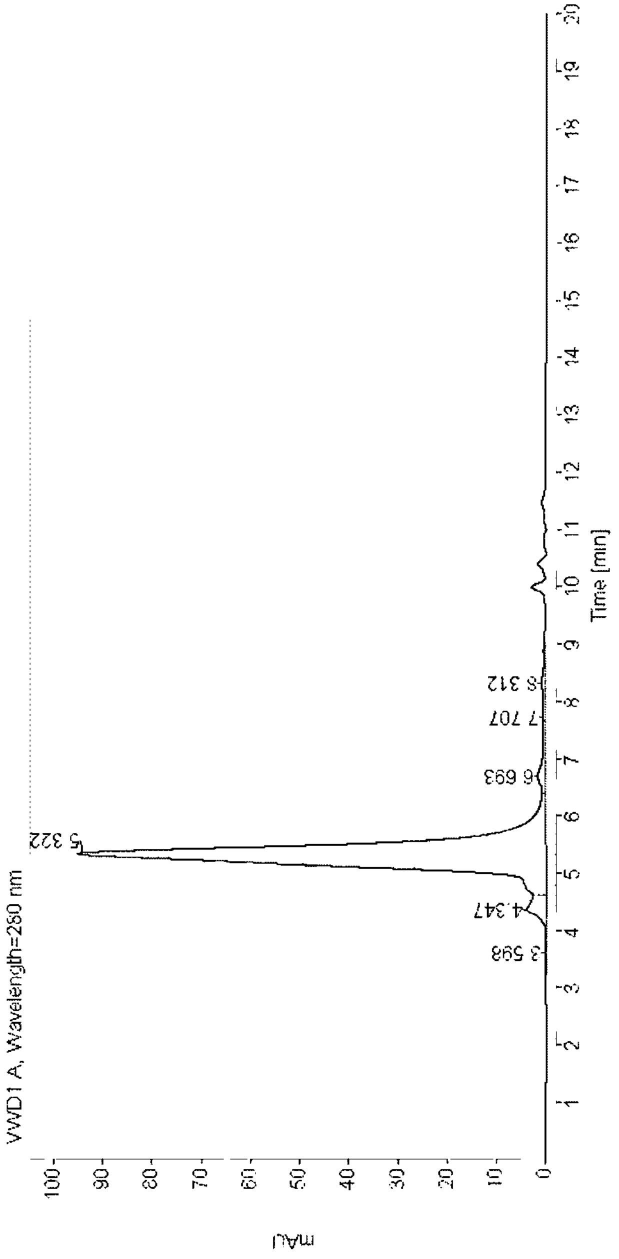

SDS-PAGE analysis result of purified PDGFRα$D_{123}$-PAS (600)-VEGFR$1_{D2}$/R$2_{D3}$, referred to herein as EPS1113P, was shown in FIG. 13A. SEC analysis of purified EPS1113P protein was done, the result was shown in FIG. 13B, which showed a purity of 92.28%.

FIG. 14.

Figure 14:
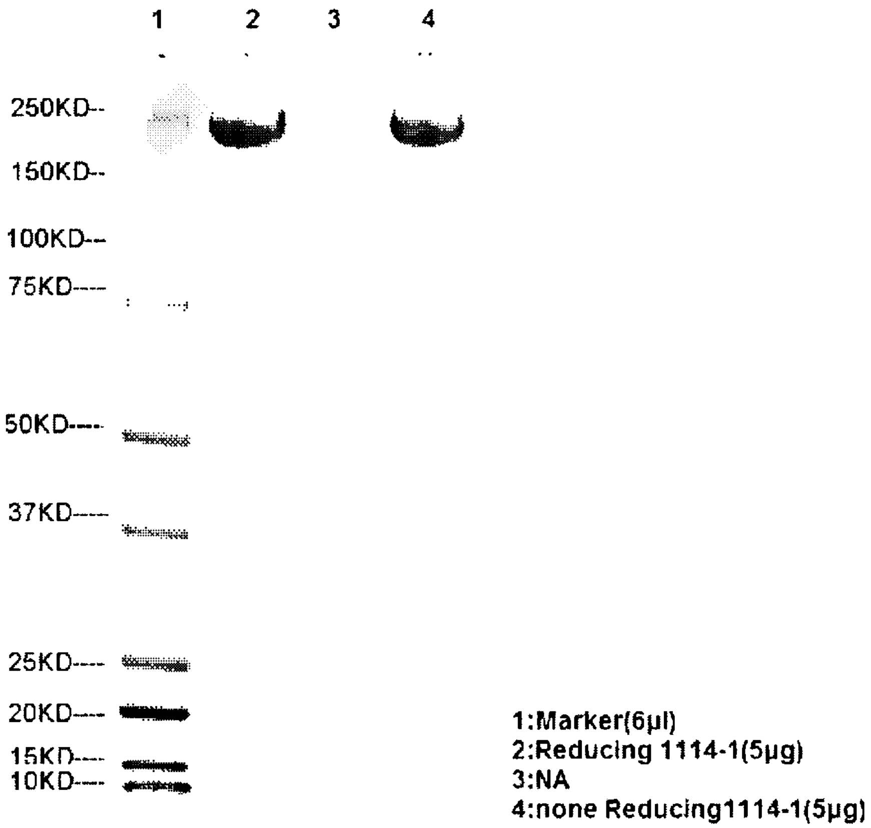
Figure 14:
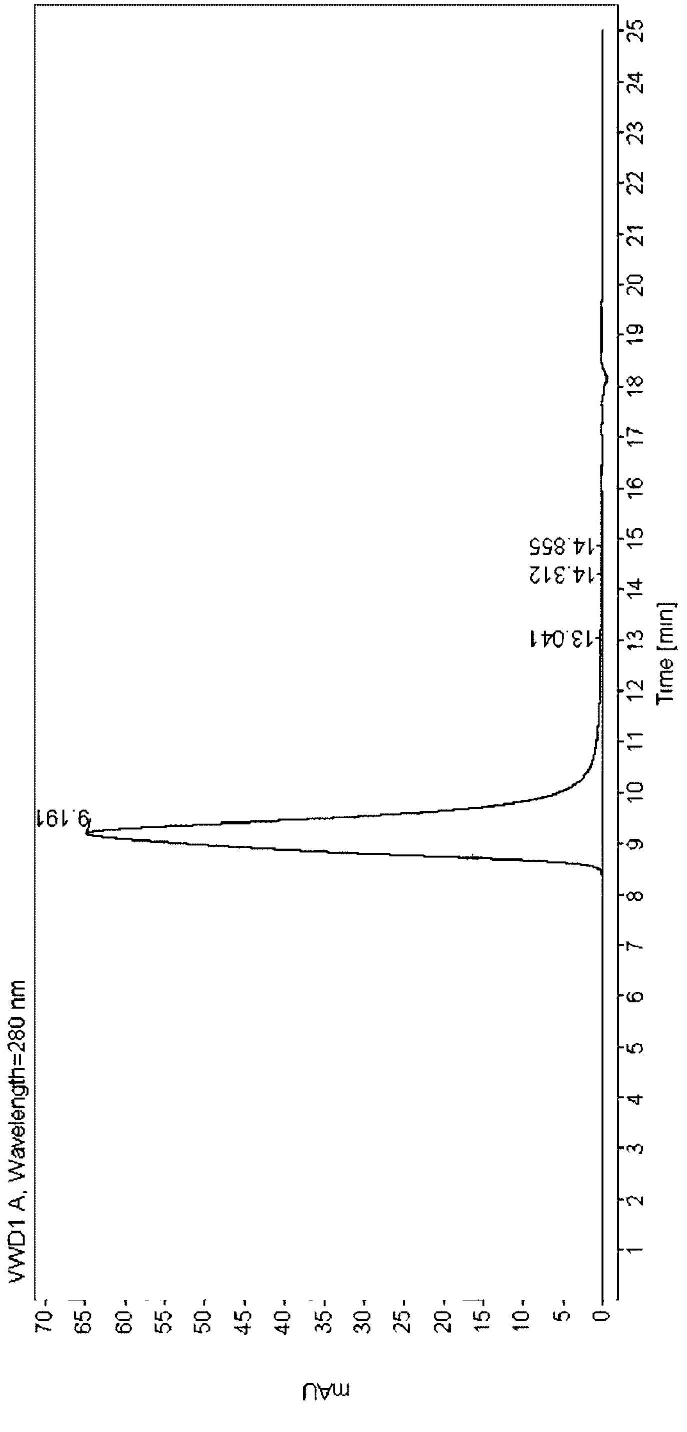

SDS-PAGE analysis result of purified PDGFR$\alpha_{D123}$-(GGGGS)$_3$-PAS(600)-(GGGGS)$_3$-VEGFR$1_{D2}$/R$2_{D3}$, referred to herein as EPS1114P, was shown in FIG. 14A. SEC analysis of purified EPS1114P protein was done, the result was shown in FIG. 14B, which showed a purity of 98.77%.

FIG. 15.

Figure 15:
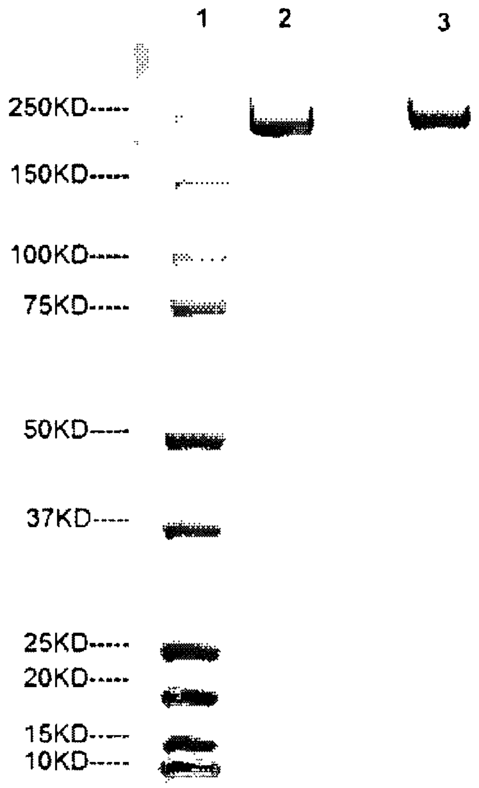
Figure 15:
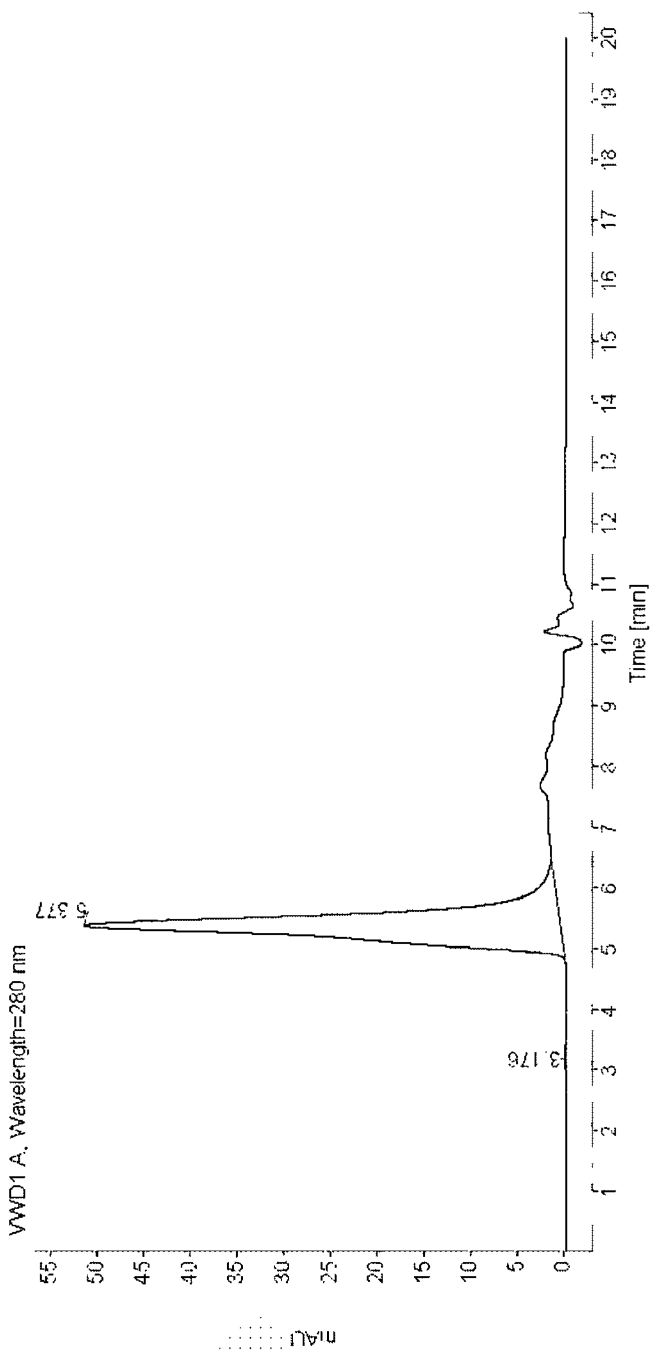

SDS-PAGE analysis result of purified PDGFRα*D*123-(GGGGS (SEQ ID NO: 73))$_3$-PAS(600)-(GGGGS (SEQ ID NO: 73))$_3$-VEGFR$1_{D2}$/R$2_{D3}$, referred to herein as EPS1114P, was shown in FIG. 15A. SEC analysis of purified EPS1114P protein was done, the result was shown in FIG. 15B, which showed a purity of 98.77%.

FIG. 16.

SDS-PAGE analysis result of purified VEGFR$1_{D2}$/R$2_{D3}$-(GGGGS (SEQ ID NO: 73))$_3$-PAS(600)-(GGGGS (SEQ ID NO: 73))$_3$-PDGFR$\alpha_{D123}$, referred to herein as EPS1115P, was shown in FIG. 16A. SEC analysis of purified EPS1115P protein was done, the result was shown in FIG. 16B, which showed a purity of 99.58%.

The Examples illustrate the invention.

Example 1: Cloning of PDGFR$\alpha_{D123}$-PAS(200)-VEGFR$1_{D2}$/R$2_{D3}$

PDGFR$\alpha_{D123}$-PAS(200)-VEGFR$1_{D2}$/R$2_{D3}$ is referred to herein as EPS1108P.

The DNA sequence encoding the fusion protein PDGFR$\alpha_{\alpha123}$-PAS(200)-VEGFR$1_{D2}$/R$2_{D3}$ was constructed in two steps. First, the coding region for the two receptor ectodomains was obtained by gene synthesis from Geneart (Regensburg, Germany; SEQ ID No. 17). In this construct, (i) the DNA sequence coding for the PDGFR-α leader signal polypeptide sequence (69 bp, including the start Met) is followed by (ii) the 876 bp nucleotide sequence for the PDGF-receptor a domains D1-D3, (iii) the 615 bp sequence for VEGFR$1_{D2}$/VEGFR$2_{D3}$, (iv) a His$_6$-tag and, finally, a stop-codon. Restriction sites for SapI were introduced between the coding regions for PDGFR-$\alpha_{D123}$ and VEGFR$1_{D2}$/VEGFR$2_{D3}$ to allow subsequent in-frame cloning of a PAS or P/A sequence serving as flexible linker/spacer. In addition, restriction sites for XbaI and HindIII were introduced at the flanking regions of the entire synthetic gene to simplify cloning onto expression vectors with compatible restriction endonuclease sites. Note that a naturally occurring restriction site for XbaI within the gene of PDGFR-α is sensitive to dam methylation and is blocked for restriction digest with XbaI when using plasmid DNA prepared from a $dam^+$ host bacterium such as *E. coli* strain XL1Blue. Nucleotide sequences for the receptor ectodomains were taken from Genbank entry NM006206.4 for PDGFR-$\alpha_{D123}$ and from U.S. Pat. No. 5,952,199 for VEGFR$1_{D2}$/R$2_{D3}$ (Aflibercept). The full length synthetic gene (990 bp) was cloned via the XbaI/HindIII sites on pDSG33, a derivative of pDSG-IBA33 (IBA, Göttingen, Germany), designed for high-level stable and non-replicative transient expression in mammalian host cells. In the second step, a gene fragment encoding a PAS sequence of 200 residues was excised from the plasmid pXL1-PAS(200) via double cut with the restriction enzyme SapI and inserted into the pDSG33 vector with the cloned synthetic gene, which had been linearized with SapI. After analytical restriction digest and confirmation of the correct insert via DNA sequencing (MWG, Ebersberg, Germany) the resulting expression plasmid encoding the PDGFR$\alpha_{D123}$-PAS(200)-VEGFR$1_{D2}$/R$2_{D3}$ fusion protein (SEQ ID No. 18; SEQ ID No. 14; FIG. 1) was designated as pDSG33-PDGFR-PAS200-VEGFR (SEQ ID No. 13).

Example 2: Expression of PDGFR$\alpha_{D123}$-PAS(200)-VEGFR$1_{D2}$/R$2_{D3}$ For production of milligram quantities of the fusion protein (FIG. 1) plasmid DNA of pDSG33-PDGFR-PAS200-VEGFR (SEQ ID No. 13) was prepared using the QIAGEN Plasmid Midi Kit (Qiagen, Hilden, Germany) and then used to transfect 200 ml of exponentially growing MEXi-293E suspension cells (IBA, Gottingen, Germany) in MEXi-TM Transfection medium (IBA; supplemented with 8 mM L-Alanyl-L-Glutamin). Transfection was accomplished according to the manufacturer's instructions using polyethylenimine (PEI; Polyscienences, Warrington Pa., USA) and plasmid DNA at a mass ratio of 4 to 1 and applying 1 μg DNA per one million cells at a density of $1\times10^6$ cells/ml. Four hours after transfection, cells were diluted in fresh MEXi-CM cultivation medium (IBA; supplemented with 50 mg/l G-418 and 8 mM L-Alanyl-L-Glutamin) to a final culture volume of 400 ml. The transfected cells were incubated for 7 days under mild agitation, at 120 rpm, at 37° C. in a humified $CO_2$—Incubator. After that, cells were removed by centrifugation at 4500 g for 20 min and the cleared conditioned medium containing the PDGFR$\alpha_{D123}$-PAS(200)-VEGFR$1_{D2}$/R$2_{D3}$ fusion protein, referred to herein as EPS1108P was collected and sterile filtered (0.2 μm).

Example 3: Protein Purification of PDGFR$\alpha_{D123}$-PAS(200)-VEGFR$1_{D2}$/R$2_{D3}$ PDGFR$\alpha_{D123}$-PAS(200)-VEGFR$1_{D2}$/R$2_{D3}$ (FIG. 1), referred to herein as EPS1108P was precipitated from the cleared culture medium obtained above by adding 150 g of ammonium sulphate to 400 ml of the conditioned medium. The mixture was incubated over night at 4° C. under gentle stirring, then the precipitate was collected by centrifugation at 15.000 g for 40 min. The pellet was recovered and dissolved in 100 ml 40 mM Hepes/NaOH, pH 7.4 containing 1 M NaCl and dialyzed against the same buffer over night at 4° C. For immobilized metal ion affinity chromatography (IMAC), a 6 ml HisTrap HP column (GE Healthcare, Uppsala, Sweden) was equilibrated with 100 ml 40 mM Hepes/NaOH, pH 7.4, 1 M NaCl (running buffer) and approximately 100 ml of the sterile-filtered protein solution was loaded. The column was washed with the same buffer until absorbance at 280 nm ($A_{280}$) reached baseline and PDGFR$\alpha_{D123}$-PAS(200)-VEGFR$1_{D2}$/R$2_{D3}$ was eluted using a linear gradient of 0 to 210 mM imidazole/HCl in running buffer over 8 column volumes. For subsequent anion exchange chromatography, the elution fraction containing PDGFR$\alpha_{D123}$-PA S(200)-VEGFR$1_{D2}$/R$2_{D3}$ was dialyzed against chromatography buffer (20 mM MES/NaOH, pH 5.9) over night at 4°, sterile-filtered and then loaded on a pre-equilibrated Resource Q column (GE Healthcare, Uppsala, Sweden) with a bed volume of 85 ml. The column was washed with chromatography buffer to $A_{280}$ baseline before the fusion protein was eluted in one step by buffer change to chromatography buffer supplemented with 225 mM NaCl. In the eluted fraction the fusion protein was about 85% pure. As a final polishing step, this protein solution was dialysed against 20 mM MES/NaOH, pH 5.9 overnight and loaded on a Resource S column (GE Healthcare) with 85 ml bed volume and equilibrated with the same buffer. Elution was achieved by applying a step-wise concentration gradient, in the same buffer, starting with 150 mM NaCl followed by 225 mM NaCl, and 300 NaCl, finally yielding the fusion protein. The purity of the PDGFR$\alpha_{D123}$-PAS(200)-VEGFR$1_{D2}$/R$2_{D3}$ was analysed by SDS-PAGE (FIG. 3) using 4-20% Bis-Tris gradient gels (Genscript, Piscataway N.J., USA) in MOPS running buffer according to the manufacturer's instructions, followed by staining with InstantBlue colloidal Coomassie blue protein stain (Expedeon, Cambridge, UK). The gels were documented by digital imaging. Note: the apparently higher molecular weight of the decoy receptor fusion seen in SDS-PAGE (FIG. 3) results from PASylation, which has already been observed for other PASylated proteins in Schlapschy et al., 2013.

Figure 3:
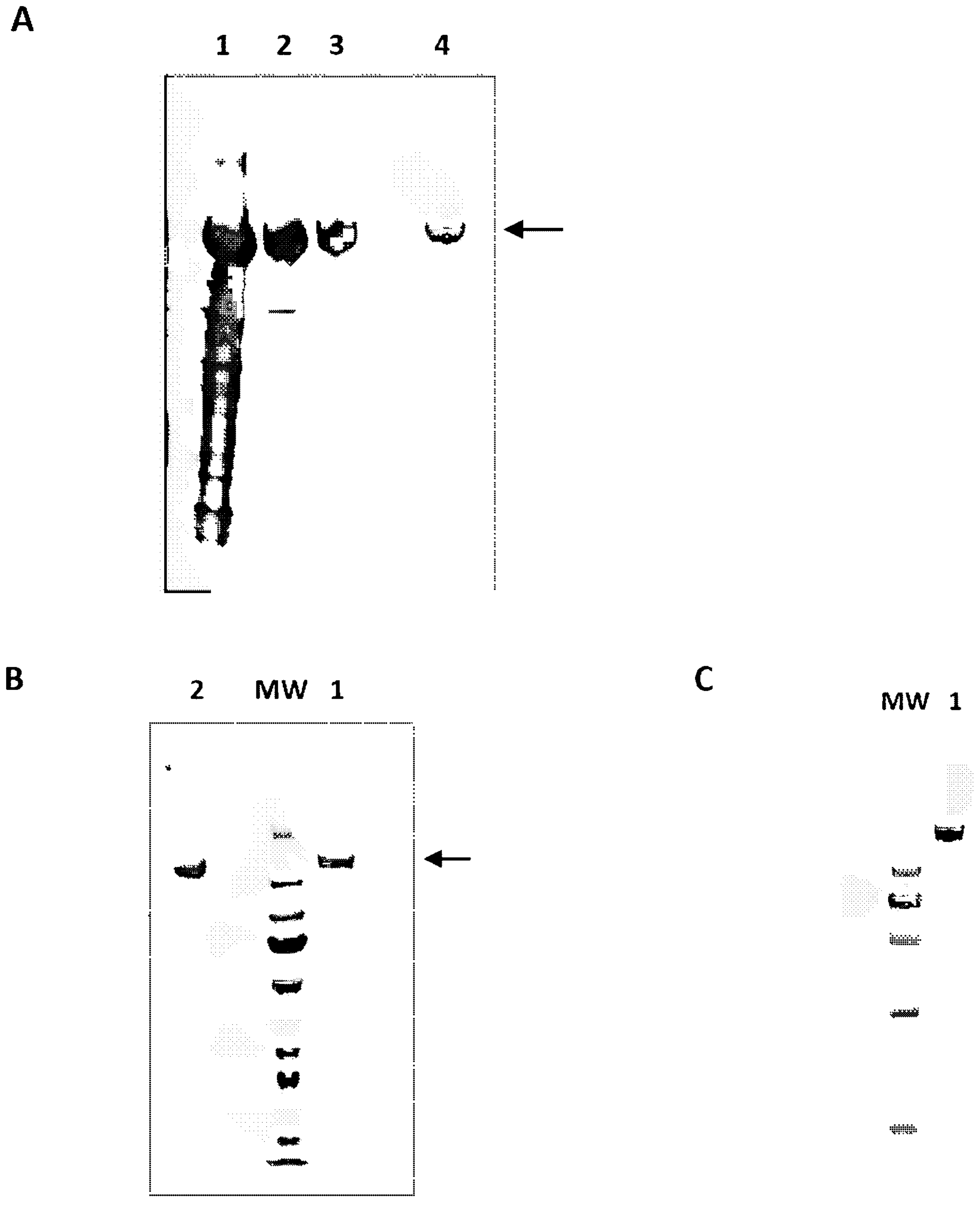

Example 4: Western Blot Analysis of PDGFR$\alpha_{D123}$-PAS(200)-VEGFR$1_{D2}$/R$2_{D3}$ Purified PDGFR$\alpha_{D123}$-PAS(200)-VEGFR$1_{D2}$/R$2_{D3}$, referred to herein as EPS1108P, carrying a C-terminal $His_6$-tag, was separated on a 4-20% SDS Bis-Tris gradient gel (Genscript) in MOPS running buffer according to the manufacturer's instructions and blotted onto an Immobilion-P PVDF membrane (Merck, Darmstadt, Germany) using a semi-dry transfer apparatus. The membrane was washed twice with phosphate-buffered saline (PBS; 4 mM $KH_2PO_4$, 16 mM $Na_2HPO_4$, 115 mM NaCl pH 7.4) supplemented with 0.1% Tween-20 (PBST) and then blocked for unspecific binding with a solution of 3% (w/v) BSA in PBST for 1 h at room temperature (RT). Next, the blocked membrane was incubated in a solution of Monoclonal Anti-polyHistidine-Peroxidase clone HIS-1 antibody conjugate (A7058; Sigma Aldrich, St. Louis, Mo., USA), diluted to 1:2000 in 0.1% (w/v) BSA, PBST for 1 h at RT. The membrane was washed twice with PBST and then the horseradish peroxidase substrate 3,3'-diaminobenzidine (Sigma Aldrich) was added. At the size of PDGFRαD$_{123}$-PAS(200)-VEGFR$1_{D2}$/R$2_{D3}$ a brownish precipitate was detected on the membrane, which was documented by digital imaging (FIG. 3).

Figure 4:
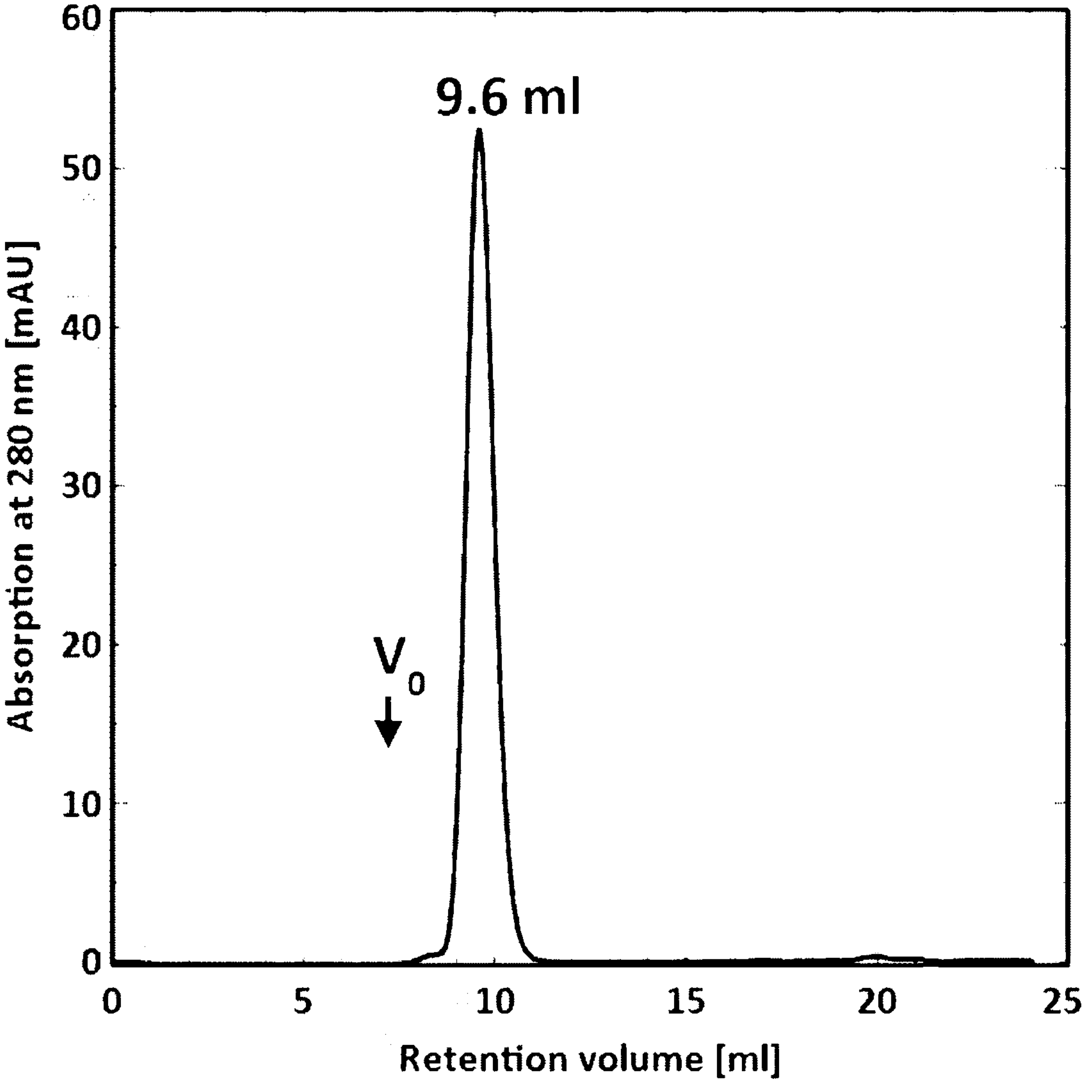
Figure 4:
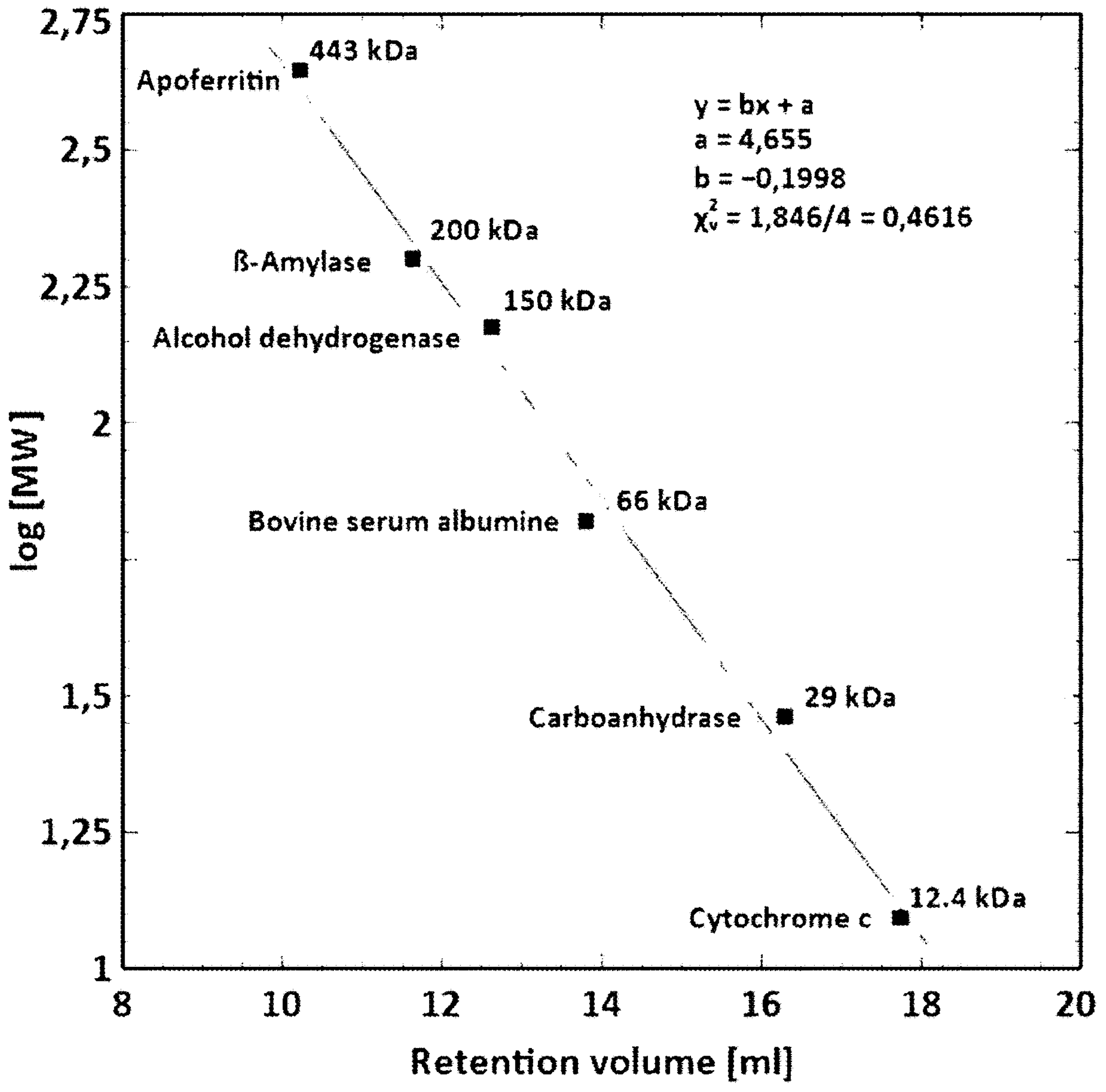

Example 5: Size Exclusion Chromatography of PDGFR$\alpha_{D123}$-PAS(200)-VEGFR$1_{D2}$/R$2_{D3}$ For analyzing the integrity and apparent size of the purified PDGFR$\alpha_{D123}$-PAS(200)-VEGFR$1_{D2}$/R$2_{D3}$, referred to herein as EPS1108P, 500 µl of a 0.43 mg/ml protein sample (3 nmol) in 20 mM MES/NaOH, pH 5.9, 300 mM NaCl was loaded on a Superdex 200 10/30 GL column (GE Healthcare) that was pre-equilibrated with 10 mM Hepes/NaOH, pH 7.4, 150 mM NaCl. Purified PDGFR$\alpha_{D123}$-PAS(200)-VEGFR$1_{D2}$/R$2_{D3}$ from conditioned MEXi-293E medium as described above elutes at 9.6 ml as a sharp peak (FIG. 4, A), which corresponds to an average molecular weight of 530 kDa, as calculated from the calibration curve (FIG. 4, B).

Example 6: Native PAGE and Electromobility Gel Shift Assay

Figure 2:
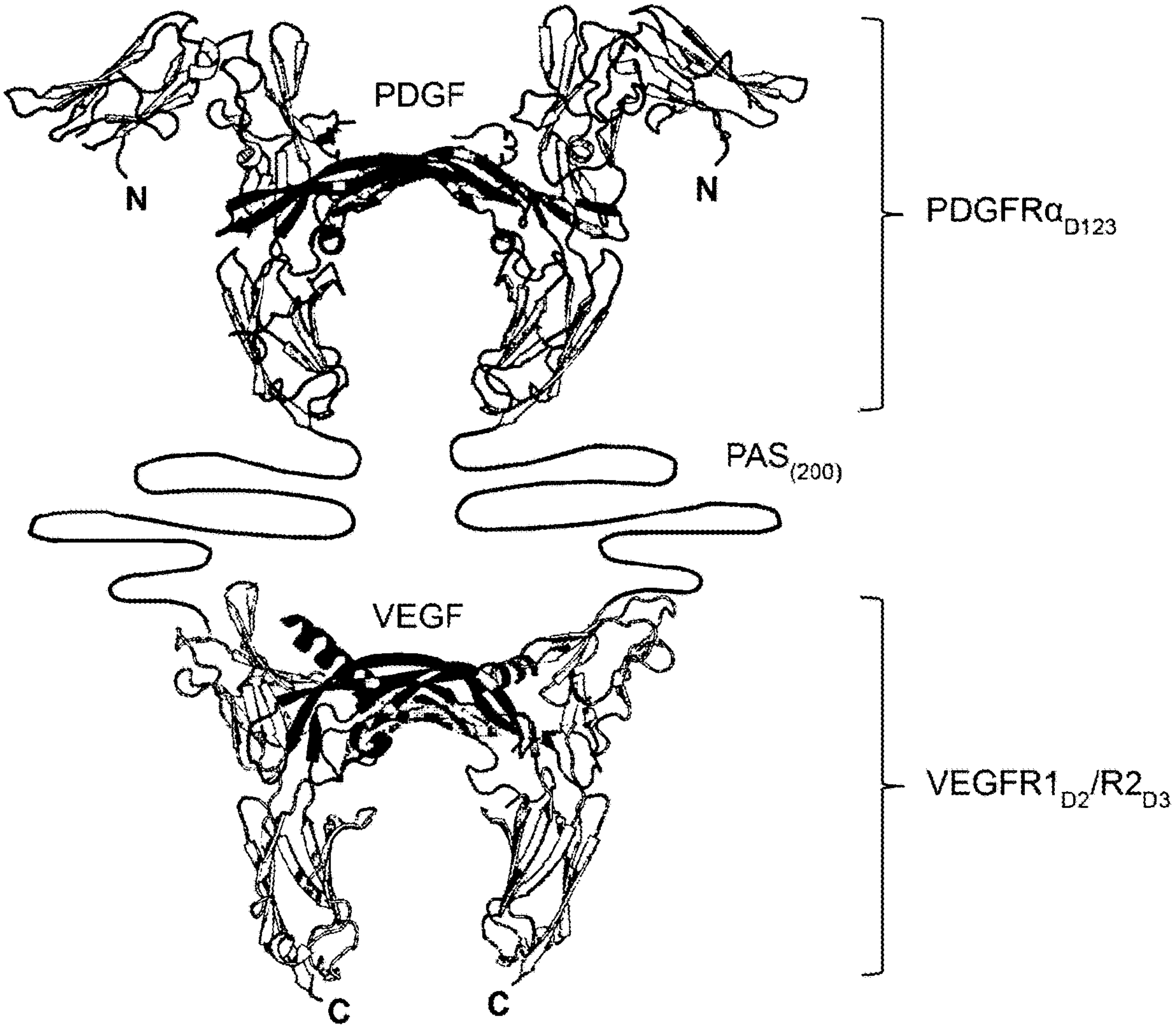
Figure 5:
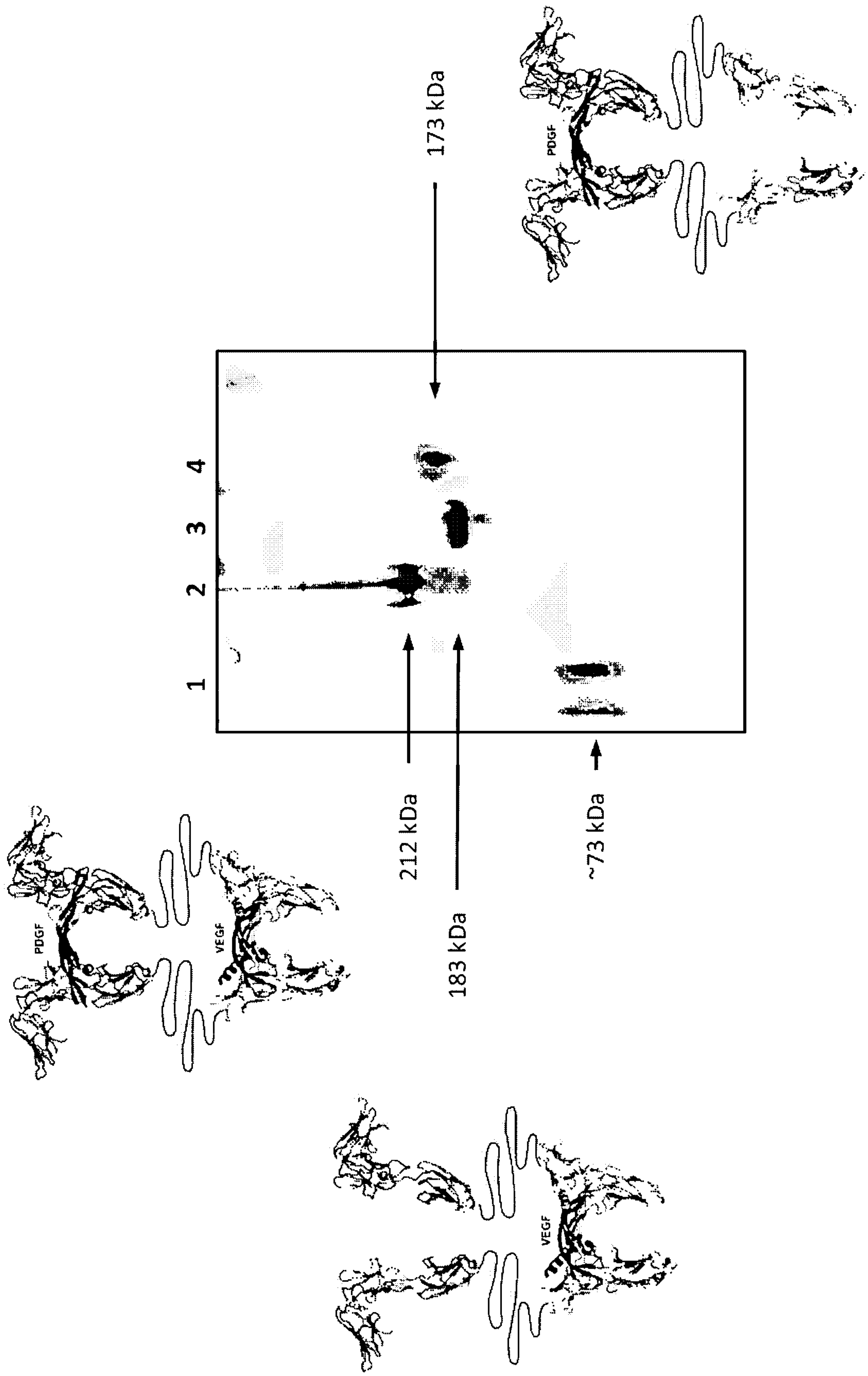

Purified PDGFR$\alpha_{D123}$-PAS(200)-VEGFR$1_{D2}$/R$2_{D3}$, referred to herein as EPS1108P (25 pmol) was incubated with either 25 pmol VEGF-$A_{165}$ (#8065-LF; Cell Signaling Technology, Danvers Mass., USA) or 25 pmol PDGF-AA (#8913-LF; Cell Signaling Technology) or both ligands (each 25 pmol), as indicated in FIG. 5, in 25 µl reactions in the presence of 20 mM HEPES/NaOH, pH 7.4, 100 mM NaCl for 30 min on ice. The solutions were then mixed with 10× native sample buffer (60 mM Tris base, 480 mM glycine, pH 8.3; 50% (v/v) glycerol, 0.01% (w/v) bromophenol blue) and immediately loaded onto a 3-8% Tris-acetate polyacrylamide gel (without SDS; Invitrogen, Carlsbad, Calif., USA). The gel was run at 90 V in Tris-glycine native running buffer, pH 8.3 (Invitrogen) at RT until the bromophenol blue marker reached the bottom of the gel. The gel was shortly rinsed in water and then stained using InstantBlue colloidal Coomassie blue protein stain (Expedeon, Cambridge, UK). The gel was documented by digital imaging. Under native conditions used for PAGE, both ligands, VEGF-A165 and PDGF-AA, bind to PDGFRαD123-PAS(200)-VEGFR1D2/R2D3 and result in stable complexes (ref. FIG. 2), that can be detected: (I) Simultaneous binding of both ligands, when both ligands are present or (II) binding of either PDGF-AA or VEGF-A165, in the absence of the other ligand (FIG. 5).

Example 7

Cloning, Expression and Purification of PDGFR$\alpha_{D123}$-PAS (300)-VEGFR$1_{D2}$/R$2_{D3}$ PDGFR$\alpha_{pin}$-PAS (300)-VEGFR$1_{D2}$/R$2_{D3}$ is referred to herein as EPS1103P.

Cloning of EPS1103P:

PCR primer and the sequencing primer of EPS1103P were designed, and the gene was synthesized de novo. The gene was amplified based on the PCR primer and then ligated into vector pUC57. The vectors were transfected into *E. coli* competent cells, which were incubated at 37° C. overnight; the positive clones were identified by colony PCR screening; and the plasmids from the positive clones were extracted for verification of the correct insert. The extracted plasmids and the target vector (pcDNA3.4) were digested by restriction enzyme; the digested products were recovered by electrophoresis, and then ligated by ligase in buffer; the buffer solution was incubated at 37° C. overnight; the positive clones were identified by colony PCR screening; and the plasmids from the positive clones were extracted for verification of the correct insert.

An aliquot of the above plasmids were digested by enzyme in a thermostatic water bath, and then the mixture was verified by agarose gel electrophoresis; the verified plasmids were transfected into *E. coli*; an aliquot of the bacteria culture were spread on solid LB plate with resistance for screening; then the bacteria clones were amplified in medium overnight in an incubator; the plasmids were extracted from the positive clones.

Expression of EPS1103P:

CHO-3E7 cells were grown in serum-free FreeStyle™ CHO Expression Medium (Life Technologies, Carlsbad, Calif., USA). The cells were maintained in Erlenmeyer Flasks (Corning Inc., Acton, Mass.) at 37° C. with 5% $CO_2$ on an orbital shaker (VWR Scientific, Chester, P A). Two days before the transfection, the cells were seeded at an appropriate density. On the day of transfection, the plasmid and transfection reagent were mixed at an optimal ratio and then added into the flask with cells. The cell culture supernatants collected on day 6 were used for purification.

Purification of EPS1103P:

The above cell culture broth was centrifuged and followed by filtration. The filtered supernatants were diluted with 25 mM Tris-HCl buffer, pH8.0, then loaded onto a Hitrap Q HPColumn (GE, Cat. No. 17115401) at 1.0 ml/min, after washing and elution with appropriate buffer, the eluted fractions were pooled and purified by Ni column (GenScript, Cat. No. L00465). The target protein was further purified via HiLoad Superdex 200 26/600 pg column (GE Healthcare, Uppsala, Sweden) to remove HMW aggregation and other impurities. The purified proteins were analyzed by SDS-PAGE and SEC-HPLC by using standard protocols for molecular weight and purity measurements as shown in FIG. 6A and FIG. 6B; the result of SEC-HPLC showed a purity of 98.88%.

Example 8: Cloning, Expression and Purification of PDGFRα$_{D123}$-PAS (400)-VEGFR1$_{D2}$/R2 D$_3$ PDGFRα$_{D123}$-PAS(400)-VEGFR1$_{D2}$/R2$_{D3}$ is referred to herein as EPS1104P. The Cloning, Expression and Purification procedures of EPS1104P were referred to Example 7. SDS-PAGE analysis result of purified EPS1104P protein was shown in FIG. 7A, and the SEC analysis of purified EPS1104P protein was done, the result was shown in FIG. 7B, which showed a purity of 98.97%.

Example 9: Cloning, Expression and Purification of VEGFR1$_{D2}$/R2$_{D3}$-PAS(200)-PDGFRα$_{D123}$ VEGFR1$_{D2}$/R2$_{D3}$-PAS(200)-PDGFRα$_{D123}$ is referred to herein as EPS1105P. The Cloning, Expression and Purification procedures of EPS1105P were referred to Example 7. SDS-PAGE analysis result of purified EPS1105P protein was shown in FIG. 8A, and SEC analysis of purified EPS1105P protein was done, the result was shown in FIG. 8B, which showed a purity of 99.82%.

Example 10: Cloning, Expression and Purification of PDGFRα$_{D123}$-(GGGGS)$_3$-PAS(200)-(GGGGS)$_3$-VEGFR1$_{D2}$/R2$_{D3}$ PDGFRα$_{D123}$-(GGGGS)$_3$-PAS(200)-(GGGGS)$_3$-VEGFR1$_{D2}$/R2$_{D3}$ is referred to herein as EPS1106P. The Cloning, Expression and Purification procedures of EPS1106P were referred to Example 7. SDS-PAGE result analysis of purified EPS1106P protein was shown in FIG. 9A, and SEC analysis of purified EPS1106P protein was done, the result was shown in FIG. 9B, which showed a purity of 99.79%.

Example 11: Cloning, Expression and Purification of VEGFR1$_{D2}$/R2$_{D3}$-(GGGGS)$_3$-PAS(200)-(GGGGS)$_3$-PDGFRα$_{D123}$ VEGFR1$_{D2}$/R2$_{D3}$-(GGGGS)$_3$-PAS(200)-(GGGGS)$_3$-PDGFRα$_{D123}$ is referred to herein as EPS1107P. The Cloning, Expression and Purification procedures of EPS1107P were referred to Example 7. SDS-PAGE analysis result of purified EPS1107P protein was shown in FIG. 10A, and SEC analysis of purified EPS1107P protein was done, the result was shown in FIG. 10B, which showed a purity of 99.43%.

Example 12: Cloning, Expression and Purification of PAS(200)-VEGFR1$_{D2}$/R2$_{D3}$-PDGFRα$_{D123}$ PAS(200)-VEGFR1$_{D2}$/R2$_{D3}$-PDGFRα$_{D123}$ is referred to herein as EPS1109P. The Cloning, Expression and Purification procedures of EPS1109P were referred to Example 7, respectively. SDS-PAGE analysis of result purified EPS1109P protein was shown in FIG. 11A, and SEC analysis of purified EPS1109P protein was done, the result was shown in FIG. 11B, which showed a purity of 99.62%.

Example 13: Cloning, Expression and Purification of PAS(200)-PDGFRα$_{D123}$-VEGFR1$_{D2}$/R2$_{D3}$ PAS(200)-PDGFRα$_{D123}$-VEGFR1$_{D2}$/R2$_{D3}$ is referred to herein as EPS1110P. The Cloning, Expression and Purification procedures of EPS1110P were referred to Example 7. SDS-PAGE analysis result of purified EPS1110P protein was shown in FIG. 12A, and SEC analysis of purified EPS1110P protein was done, the result was shown in FIG. 12B, which showed a purity of 99.52%.

Example 14: Cloning, Expression and Purification of PDGFRβ$_{D123}$-PAS(200)-VEGFR1$_{D2}$/R2$_{D3}$ PDGFRβ$_{D123}$-PAS(200)-VEGFR1$_{D2}$/R2$_{D3}$, is named herein as EPS1111P. Its Cloning, Expression and Purification procedures refer to the described method of Example 7.

Example 15: Cloning, Expression and Purification of PDGFRαD$_{123}$-PAS(600)-VEGFR1$_{D2}$/R2$_{D3}$ PDGFRαD$_{123}$-PAS(600)-VEGFR1$_{D2}$/R2$_{D3}$ is referred to herein as EPS1113P. The Cloning, Expression and Purification procedures of EPS1113P were referred to Example 7. SDS-PAGE analysis result of purified EPS1113P protein was shown in FIG. 13A, and SEC analysis of purified EPS1113P protein was done, the result was shown in FIG. 13B, which showed a purity of 92.28%.

Example 16: Cloning, Expression and Purification of PDGFRα$_{D123}$-(GGGGS)$_3$-PAS(600)-(GGGGS)$_3$-VEGFR1$_{D2}$/R2$_{D3}$ PDGFRα$_{D123}$-(GGGGS)$_3$-PAS(600)-(GGGGS)$_3$-VEGFR1$_{D2}$/R2$_{D3}$ is referred to herein as EPS1114P. The Cloning, Expression and Purification procedures of EPS1114P were referred to Example 7. SDS-PAGE analysis result of purified EPS1114P protein was shown in FIG. 14A, and SEC analysis of purified EPS1114P protein was done the result was shown in FIG. 14B, which showed a purity of 98.77%.

Example 17: Cloning, Expression and Purification of VEGFR1$_{D2}$/R2$_{D3}$-(GGGGS)$_3$-PAS(600)-(GGGGS)$_3$-PDGFRα$_{D123}$ VEGFR1$_{D2}$/R2$_{D3}$-(GGGGS)$_3$-PAS(600)-(GGGGS)$_3$-PDGFRα$_{D123}$ is referred to herein as EPS1115P. The Cloning, Expression and Purification procedures of EPS1115P were referred to Example 7. SDS-PAGE analysis result of purified EPS1115P protein was shown in FIG. 15A, and SEC analysis of purified EPS1115P protein was done, the result was shown in FIG. 15B, which showed a purity of 99.58%.

Example 18: Cloning, Expression and Purification of Mutant PDGFRα$_{D123}$-PAS(200)-VEGFR1$_{D2}$/R2$_{D3}$ Mutant PDGFRα$_{D123}$-PAS(200)-VEGFR1$_{D2}$/R2$_{D3}$, is named herein as EPS1116P. Its Cloning, Expression and Purification procedures refers to the described method of Example 7.

Example 19: Binding Affinity with VEGF$_{165}$/PDGF-BB Ligands

1. Assay Method

To detect the affinity with VEGF, the test fusion proteins and the reference were serially diluted with reagent dilution solution respectively, mixed with human VEGF$_{165}$ ligand (final concentration was 50 μM), and incubated for 1 hour at room temperature on a shaker set at 300 RPM. The amount of unbound VEGF$_{165}$ was then measured by a human VEGF-specific ELISA (Human VEGF DuoSet ELISA kit, R&D Systems, CAT. No. DY293B-05).

To detect the affinity with PDGF-BB, the test fusion proteins and the reference were serially diluted with reagent dilution solution respectively, mixed with human PDGF-BB ligand (final concentration was 1 ng/ml), and incubated for 1 hour at room temperature on a shaker set at 300 RPM. The amount of unbound PDGF-BB was then measured by a human PDGF-BB-specific ELISA (Human PDGF-BB DuoSet ELISA kit, R&D Systems, CAT. No. DY220).

2. Assay Procedure 2.1 Reagents Preparation 2.1.1 Coating Buffer

PBS: 137 mM NaCl, 2.7 mM KCl, 8.1 mM $Na_2HPO_4$, 1.5 mM $KH_2PO_4$, pH 7.2-7.4, filtered through a 0.2 μm filter.

2.1.2 Washing Buffer

Dissolved 9.55 g PBS power into Milli-Q water, and brought to the total volume up to 1 L that contained 0.05% Tween 20 (v/v), and adjusted pH to 7.4.

2.1.3 Blocking Buffer 3 g of Bovine Serum Albumin (BSA) was added into 100 mL of PBS.

2.1.4 Reagent Dilution Solution 1 g of Bovine Serum Albumin (BSA) was added into 100 mL of PBS.

2.1.5 Stop Solution 81.4 mL of 36-38% hydrochloric acid was added to Mill-Q water, and brought the total volume up to 1 L.

2.2. Procedure 2.2.1 Plate Coating

Diluted the captured antibody using PBS to the working concentration (400 ng/mL), which was transferred into a 96-well microplate with 100 μL per well immediately. Sealed the plate and incubated at room temperature overnight.

2.2.2 Washing

Aspirated each well and washed with washing buffer (300 μL), repeating this process twice.

2.2.3 Blocking

Blocked the plates by adding 300 μL blocking buffer to each well, incubated at room temperature for 1 hour.

2.2.4 Sample Preparation and Pre-Incubation

To prepare affinity samples, the test fusion proteins (EPS1103P, EPS1104P, EPS1105P, EPS1106P, EPS1107P, EPS1108P, EPS1109P, EPS1110P, EPS1111P, EPS1113P, EPS1114P, EPS1115P or EPS1116P) or Reference (Affibercept) were serially diluted with reagent dilution solution respectively, mixed with human VEGF$_{165}$ ligand (final concentration was 50 pM) or human PDGFBB ligand (final concentration was 1 ng/ml), incubated for 1 hour at room temperature on a shaker set at 300 RPM.

To prepare the standard samples, PDGF-BB or VEGF$_{165}$ was diluted using 2-fold serial dilutions with reagent dilution solution (2000, 1000, 500, 250, 125, 62.5 and 31.25 pg/ml), respectively.

2.2.5 Sample Incubation

100 μL of the sample solution per well was transferred into the coated assay plate, all samples were duplicated. The assay plates were covered with acetate plate sealers, and the plates were incubated for 2 hour at room temperature on the shaker set at 500 rpm, washing the plate three times.

2.2.6 Incubation with Detection Antibody

100 μL of the diluted detection antibody was added into each well of the plate, which was then covered with a new adhesive strip and incubated for 1 hour at RT on the shaker set at 500 rpm; washing the plate three times.

2.2.7 Incubation with Streptavidin-HRP

100 μL of the pre-prepared Streptavidin-HRP solution was added into each well, which was then covered with a new adhesive strip and incubated for 30 minutes at room temperature; washing the plates three times.

2.2.8 Incubation with Substrate Solution (TMB)

100 μL of substrate solution was added into each well, incubated for 10 minutes at room temperature.

2.2.9 Adding Stop Solution (1N HCl)

After incubation with TMB for 10 minutes, 100 μL of stop solution (1 N HCL) was added to each well, the plate was gently tapped to ensure thoroughly mix.

2.2.10 Plate Reading

The optical density of each well was determined immediately, using Molecular Devices M2E plate reader with SoftMax Pro 6.5.1 GxP set at 450 nm and 570 nm; readings at 570 nm were subtracted from the readings at 450 nm to give the optical density of each well.

2.2.11 Data Analysis

Unbound human VEGF$_{165}$ or PDGF-BB was calculated using 4 parameters curve with the absorbance value. And the $IC_{50}$ of the tested fusion proteins and the reference was calculated using 4 parameters curve with unbound human VEGF$_{165}$ or PDGF-BB.

3. Result

TAB 1

Binding affinity with VEGF$_{165}$/PDGFBB ligands ($IC_{50}$)

| Analyte | Human VEGF$_{165}$ (M) | Human PDGFBB (M) |
|---|---|---|
| Aflibercept | 9.82E−12 | —* |
| EPS1108P | 3.20E−10 | 6.63E−8 |
| EPS1103P | 8.69E−10 | TBD |
| EPS1104P | 4.95E−10 | TBD |
| EPS1105P | 5.46E−10 | TBD |

TAB 1-continued

| Binding affinity with $VEGF_{165}$/PDGFBB ligands ($IC_{50}$) | | |
|---|---|---|
| Analyte | Human $VEGF_{165}$ (M) | Human PDGFBB (M) |
| EPS1106P | 5.55E−10 | TBD |
| EPS1107P | 3.04E−10 | TBD |
| EPS1109P | 2.18E−10 | TBD |
| EPS1110P | 3.31E−10 | TBD |
| EPS1111P | TBD | TBD |
| EPS1113P | 6.46E−10 | TBD |
| EPS1114P | 5.06E−10 | TBD |
| EPS1115P | 4.40E−10 | TBD |
| EPS1116P | TBD | TBD |

*No binding affinity was detected.

4. Conclusion

High binding affinity with human $VEGF_{165}$ ligand was observed for both the tested fusion proteins and the reference; while only the fusion proteins could bind with human PDGFBB, and the affinity is strong.

Example 20: Inhibition of VEGF-induced HUVEC Proliferation

1. Assay Methods 1.1 Three groups were designed, they are including Blank control, Model control (VEGF control) and Test articles (TAs) groups. Samples were tested in triplicate, and repeated the tests three times.

1.2 HUVEC cells growing in an exponential growth phase were harvested and prepared for single cell suspension.

1.3 The cells were counted and adjusted to the concentration of $5\times10^4$ cells/mL with basal Medium. 100 μL of the cell suspension was seeded into the 96 well plate, or 100 μL of PBS was added (Blank control). Incubated at 37° C., 5% $CO_2$ overnight (without feed).

1.4 TAs were serially diluted to working concentration with assay medium (mixed by Complete Medium and Basal Medium) containing $VEGF_{165}$, working concentration was determined by pre-experiment, and the final concentration of $VEGF_{165}$ was 25 ng/ml. 100 μL of diluted TAs were added into the 96 well plate, incubated for 72 h at 37° C., 5% $CO_2$.

1.5 After incubation, 20 μL of Cell Counting Kit-8 was added into each well of the 96 well plate, then incubated in incubator for 4-6 h.

1.6 Absorbance (OD value) was measured at 450 nm with a microplate reader.

1.7 The $IC_{50}$ in each group was calculated with graphpad prism 5 software (GraphPad Software, Inc).

2. Results

TAB 2

| Inhibition of HUVEC cells proliferation in each group | |
|---|---|
| Samples | $IC_{50}$(nM) |
| EPS1108P | 28.49 |
| EPS1105P | 28.45 |
| EPS1106P | 39.67 |
| EPS1107P | 53.11 |

3. Conclusion

High inhibition potency to $VEGF_{165}$-induced HUVEC cell proliferation were observed for all TAs (EPS1108P, EPS1105P, EPS1106P and EPS1107P).

Example 21: Inhibition of Intersegmental Vessels (ISVs) Development in Zebrafish 1. Methods Angiogenesis leads to formation of the intersegmental vessels (ISVs) of zebrafish embryo trunk, thus it has been utilitized as a human disease model to investigate the effect of testing compounds.

Procedure:

Collected Tg(Flka-GFP) transgenic zebrafish embryos at 28 hpf and removed the chorion with Proteinase E of *Streptomyces griseus* (Biology Institute of Shandong Academy of Sciences). Chose normal embryos under a stereomicroscope, anesthetized the embryos in a fresh prepared fish water containing 200 μg/mL tricaine, and then 10 nanoliters of the tested fusion proteins (500, 250, 25 or 2.5 μg/ml, respectively) were injected into the yolk sac of the zebrafish embryos by using an electronically regulated airpressure microinjector; then the zebrafish embryos were transferred into a 24 well plate, 8-10 embryos per well; three paralleled wells for each testing sample group. The plate were covered and incubated at 28° C. in an illuminating incubator. Anesthetized embryos were observed and photographed under a fluorescence stereomicroscope at 48 hpf, vessel length of ISVs was measured, meanwhile observing the mortality and abnormality of the embryos.

2. Result

No mortality and abnormality were observed in any group, and the everage vessel length of ISVs in each group was listed in the table below (table 3):

TABLE 3

| Inhibition of intersegmental vessels (ISVs) development in zebrafish | | |
|---|---|---|
| Fusion protein | Concentration (μg/mL) | vessel length of ISVs (μm) |
| Vehicle Control | — | 3299.05 ± 204.81 |
| EPS1108P | 250 | 2314.25 ± 85.37** |
| EPS1104P | 250 | 2493.25 ± 141.37** |
| EPS1107P | 250 | 2514.25 ± 125.47** |
| EPS1113P | 250 | 2719.59 ± 238.38* |
| | 500 | 2446.46 ± 368.47** |
| EPS1114P | 250 | 2696.03 ± 179.86* |
| | 500 | 2426.69 ± 324.37** |
| EPS1115P | 500 | 2511.79 ± 418.55** |

*Compared with Vehicle Control group, the difference is significant ($p < 0.05$);
**Compared with Vehicle Control group, the difference is significant ($p < 0.01$).

3. Conclusion

Compared with the Tg(Flk1-GFP) transgenic zebrafish embryos of vehicle control group, a significant decrease of vessel length was observed ($p<0.01$) in EPS1104P, EPS1107P, EPS1108P, EPS1113P, EPS1114P and EPS1115P groups, the results indicated that the tested fusion proteins (EPS1104P, EPS1107P, EPS1108P, EPS1113P, EPS1114P and EPS1115P) can significantly inhibit the intersegmental vessels (ISVs) development in zebrafish embryos.

Example 22: Inhibition of Tumor Neovascularization in Zebrafish

1. Methods

In the present study, a novel xenograft tumor model in Tg(Flk1:EGFP) transgenic zebrafish was established, in which individual green endothelial cells can be clearly distinguished from red tumor cells. This model can be used to investigate the inhibition effect of antiangiogenic compounds on tumor neovascularization.

Procedure:

1.1 Establishment of Xenograft Tumor Model in Zebrafish

B16-F10-mCherry tumor cells were transfected with pcDNA3.1 plasmids or pcDNA3.1 plasmids encoding human VEGFA, the cells were cultured and harvested at 48 h, and 10 nanoliters suspension containing about 200 cells were implanted into each Tg(Flk1-GFP) transgenic zebrafish embryo (State Key Laboratory of Biotherapy, Sichuan University, China) through the perivitelline space by using an electronically regulated air-pressure microinjector.

1.2 Group Assignment and Administration Dose

Zebrafish were randomly assigned into 5 groups, the assignment was shown in the table below (table 4):

TABLE 4

Summary of group assignment

| Group | Treatment |
| --- | --- |
| Blank control (BC) | B16-F10-mCherry cells were implanted into zebrafish embryos |
| Vector control (VC) | B16-F10-mCherry cells transfected with pcDNA3.1 plasmids were implanted into zebrafish embryos |
| Model control (VEC) | B16-F10-mCherry cells transfected with pcDNA3.1 plasmids encoding human VEGFA were implanted into zebrafish embryos |
| EPS1108P-250 μg/ml<br>EPS1108P-1250 μg/ml | B16-F10-mCherry cells transfected with pcDNA3.1 plasmids encoding human VEGFA were implanted into zebrafish embryos; and the zebrafish embryos were treated with EPS1108P |

10 nanoliters of EPS1108P solution (250, 1250 μg/ml) were injected into the yolk sac of zebrafish embryos by using an electronically regulated air-pressure microinjector at 12 h after tumor cells implanted. Tumor growth and neovascularization in zebrafish embryos were observed and recorded under a laser scanning confocal microscope (Lieca SP5 II) at 12 h after EPS1108P administrated. the areas of tumor vessel and tumor were determined by Image J software, and the ratio of areas (tumor vessel/tumor) were calculated.

1.3 Data Analysis

Data are presented as mean±SD and analyzed by SPSS19.0 software (IBM Corporation). Difference among groups was determined with one-way analysis of variance (ANOVA). Comparison is considered to be statistically significant if p<0.05. When a significant difference is determined, the Least Significant Difference test was performed for further analysis.

2. Result

The ratio of areas (tumor vessel/tumor) in each group is listed in the table below (table 5):

TABLE 5

The ratio of areas (tumor vessel/tumor) in each group

| Group | ratio of areas (tumor vessel/tumor) % |
| --- | --- |
| Blank control (BC) | 28.54 ± 6.61 |
| Vector control (VC) | 25.91 ± 5.61 |
| Model control (VEC) | $78.79 \pm 9.37^{a,b}$ |
| EPS1108P-250 μg/ml | $54.12 \pm 1.48^{c}$ |
| EPS1108P-1250 μg/ml | $46.38 \pm 2.28^{c}$ |

[a]Compared with blank control (BC) group, the difference is significant (p < 0.05);

[b]Compared with Vector control (VC) group, the difference is significant (p < 0.05).

[c]Compared with Model control (VEC) group, the difference is significant (p < 0.05);

3. Conclusion

Compared with blank control (BC) and vector control (VC), The ratio of areas (tumor vessel/tumor) in model control group (VEC) group was significantly increased (p<0.05), the results indicated that hVEGFA significantly induced tumor neovascularization, the zebrafish xenograft tumor model in zebrafish was established successfully.

Compared with model control (VEC), the ratio of areas (tumor vessel/tumor) in EPS1108P-250 μg/ml and EPS1108P-1250 μg/ml group was significantly decreased (p<0.05), the results indicated that EPS1108P could significantly inhibit the tumor neovascularization induced by human VEGFA.

Example 23: Serum Half-Life ($T_{1/2}$) In Vivo

1. Experimental Methods and Procedures 1.1 Animal Study

SD rats (Sichuan Dashuo Biotech Inc. SCXK [Sichuan] 2015-030), weight 200-250 g, were randomly assigned into 4 groups, the group assignment and dose information were listed in table below (table 6):

TABLE 6

The group assignment and dose information

| group | animal | number | pathway | dose | Volume |
| --- | --- | --- | --- | --- | --- |
| EPS1108P | SD rats, Male | 3 | i.v | 1 mg/kg | 4 ml/kg |
| EPS1104P | SD rats, Male | 3 | i.v | 1 mg/kg | 4 ml/kg |
| EPS1113P | SD rats, Male | 3 | i.v | 1 mg/kg | 4 ml/kg |
| Aflibercept | SD rats, Male | 3 | i.v | 1 mg/kg | 4 ml/kg |

All test fusion proteins were diluted to 0.25 mg/ml with saline under sterile conditions. A single dose was administrated by i.v. injection (lmg/kg); 300 μL blood were collected from each rat at 5 min, 1 h, 6 h, 24 h, 48 h, 96 h and 144 h post injection via jugular vein. The blood samples were clotted for 1 h at room temperature, then the blood was centrifuged at 1000 g for 15 minutes, serum samples were separated, collected and stored at −80° C. The serum samples were analyzed by ELISA assay.

1.2 Sample Analysis 1.2.1 $VEGF_{165}$ ligand (0.5 μg/ml, R&D Systems, Cat. No. 293-VE) was coated in a 96 well plate, incubated overnight at room temperature;

1.2.2 Washed the plate 3 times with PBST, Blocked plates by adding 300 μL PBS containing 3% BSA, then incubated for 2 h at 37° C.

1.2.3 Washed the plate 3 times with PBST, then added 100 μL of serially diluted standard samples and the serum samples into the wells, and then incubated for 2 h at 37° C.

1.2.4 Washed the plate 3 times with PBST, then added 100 μL of the diluted detection antibody solution (450 ng/ml), then incubated for 2 h at 37° C.

1.2.5 Washed the plate 3 times with PBST, then added 100 μL of the pre-prepared Streptavidin-Horseradish Peroxidase solution, then incubated for 20 min at room temperature.

1.2.6 Washed the plate 3 times with PBST, than added 100 μL of the TMB solution, then incubated for 20 min at room temperature.

1.2.7 Added 504, of the stop solution, gently tap the plate to ensure thorough mixing.

1.2.8 Determined the optical density (OD valume) of each well immediately, using a microplate reader set to 450 nm.

1.2.9 Serum concentration of the test samples were calculated by using the four-parameter fit of the standard curve.

2. Results

The pharmacokinetic parameters ($T_{1/2}$) were calculated by using the non-compartmental model in DAS3.0 software (Drug and Statistics, Wannan Medical College, Wuhu, China).

TABLE 7

$T_{1/2}$ in each group after single rat i.v injection

| Fusion protein | $T_{1/2}$ $\overline{X}$ ± SD, h |
|---|---|
| EPS1108P | 4.95 ± 0.43 |
| EPS1104P | 17.76 ± 3.76 |
| EPS1113P | TBD |
| Aflibercept | 42.00 ± 6.45 |

3. Conclusion

The tested fusion proteins of the invention comprised domain of PDGFR and domain of VEGFR which are attached by a linker consisting of proline, alanine and serine, the length (the number of amino acid residues) of the linkers in EPS1108P, EPS1104P and EPS1113P were 200, 400 and 600, respectively. The result indicated that the half-life (T½) of the proteins in rat became longer with increasing length of the amino acid residues. The T½ of EPS1113P was obviously extended.

Example 24: Efficacy of EPS1108P on Inhibition of Laser-Induced Choroidal Neovascularization (CNV) in Cynomolgus Monkeys 1. Establishment of Laser-Induced CNV Model 1.1 CNV Model Induction Laser photocoagulation was performed on screened animals and laser treatment day was recorded as Day 1 (D1).

Modeling method: Choroidal neovascularization was induced by binocular laser photocoagulations with 6-8 spots in each eye.

Procedure:

1) Mydriasis: Both eyes of an animal were instilled with 1-2 drops of 0.5% Compound Tropicamide Eye Drops.

2) Anesthesia: The animals were anesthetized with Zoletil® intramuscular injection, the absence of corneal reflection, loose in limbs and abdominal muscle and steady breath indicated a moderate anesthesia.

3) Laser photocoagulation: Carbomer Eye Drops (0.2%) were delivered to the eyes before laser photocoagulation, then placed the laser lens appropriately onto the eye to observe the fundus clearly, laser photocoagulation was conducted in the perimacular region which are about 1.5-2PD disk diameter from the foveal center. Care was taken to avoid any visible vessels. The laser parameters were as following: wavelength, 532 nm; power, 400-500 mW; spot size, 50 μm; and exposure time, 100 ms.

4) Animal care: The eyes of animals were smeared with ofloxacin eye ointment after laser photocoagulation. The animals were put on the blanket to keep warm, and put back to the cages after they were conscious.

1.2 Assessment of Success CNV

On Day 14, fluorescein leakage of the laser spots were tested to grade the CNV lesion by fundus fluorescein angiography. Four grades were assigned according to the degree of fluorescein leakage as follow: Grade 1, no hyperfluorescence; Grade 2, hyperfluorescence without leakage; Grade 3, early hyperfluorescence and late mild leakage within the border of fluorescence burn area; Grade 4, early hyperfluorescence and late severe dye leakage beyond the border of the burn area. Meanwhile, the leakage area of Grade 4 lesions will be measured for randomization.

2. Group Assignment

On Day 15, animals with Grade 4 fluorescein leakage lesions were selected for randomization, the average leakage area and rate of Grade 4 lesions were taken into account for group assignment to make sure there was no significance among groups. The specific group assignment is shown in the table below (table 8):

TABLE 8

The Group Assignment

| group | Dose (μg/eye) | Concentration (mg/mL) | Dose volume (μL) | Eye number (N) |
|---|---|---|---|---|
| Vehicle Control | — | — | — | 4 |
| Aflibercept-500 μg/Eye | 500 | 10 | 50 | 4 |
| EPS1108P-250 μg/Eye | 250 | 5 | 50 | 4 |
| EPS1108P-500 μg/Eye | 500 | 10 | 50 | 4 |

3. Dose Procedure

Dose Route: Intravitreal injection

Dose Frequency and Duration: Single dose on Day 15.

Dose Volume: 50 μL/eye, both eyes

Dosing Method: Both eyes of each animal were instilled with 1-2 drops of 0.5% Tropicamide Eye Drops, then anesthesia were conducted as described in CNV Model Induction. Following anesthesia, the animals were laid on an operating table, limbus pal pebralis, eyelash, skin and hair around the eyes were disinfected with povidone iodine. The eyeball was fully exposed, the intravitreal injection was performed at 2-3 mm behind the superior temporal or nasal limbus carefully, toavoid damage to posterior lens capsule and other parts of retina, kept the pinhead in vitreous chamber for 2-5 seconds after injection, then withdrew the needle slowly. After the needle was pulled out, pressed the injection point immediately for about 10 seconds with povidone iodine swabs, ofloxacin eye ointment were applied twice daily for the first three days. The animals were put on the blanket to keep them warm before they get consciousness and put back after they were conscious.

4. Ocular Examination

Before ocular examination, the animals' both eyes were instilled with 1-2 drops of 0.5% Tropicamide Eye Drops, then anesthesia was conducted as described in CNV Model Induction.

4.1 General Ocular Examination

A general ocular examination was conducted. The observation contents of general ocular examinations include eyelid, conjunctiva, cornea, iris, sclera, pupil, lens, vitreous and fundus.

4.2 Fundus Photography and Fluorescein Angiography (FP & FFA)

Fundus photography and fluorescein angiography were conducted on all the animals prior to model induction, and on D14, D22, D29, D36 and D43. Animals were given Fluorescein Sodium Injection (10 mg/kg, 100 mg/mL) by intravenous injection before fluorescein angiography.

Observation: Compared the early and late phase FFA images to detect and measure the evidence and extent of leakage of CNV. If CNV is present, hyperfluorescence develops around the laser spot, which progresses to late diffuse leakage with dye pooling in the serous detachment surrounding the burn area. The leakage was graded on a standardized scale of 1 to 4; grading scores were defined in Section Assessment of Successful CNV. Grade 4 lesions was defined as clinically significant fluorescence leakage of classic experimental CNV model, the area of leakage was measured. Meanwhile, the rate of Grade 4 lesions in each group was calculated by following formulas:

Rate of Grade 4 lesions (%)=number of Grade 4 lesions/number of the laser spots*100%

5. Statistical Analysis

Data are presented as mean±SD and analyzed by SPSS13.0 software (IBM Corporation). Difference among mean of the groups is determined with ANOVA. Comparison is considered to be statistically significant if $p<0.05$. When a significant difference is determined, the Least Significant Difference test was performed for further analysis. In the case of heterogeneity of variance at $p<0.05$, a Kruskal-Wallis test was performed.

6. Result

No abnormalities were found on the fundus photography or FFA in any eye of these animals before the CNV induction. After Laser induction, Fundus photography and FFA were performed on D14, D22, D29, D36 and D43; no evidence of fundus abnormalities except laser photocoagulation lesions was found on the fundus photography.

6.1.1 The Rate of Grade 4 Lesion Occurrence

Summary of Grade 4 lesion rate is shown in the table below (Table 9):

TABLE 9

Summary of Grade 4 lesion rate in each group pre/post dosing

| Group | | Grade 4 lesion rate (%) | | | | |
|---|---|---|---|---|---|---|
| | | D14 (pre-dose) | D22 (7 d post-dose) | D29 (14 d post-dose) | D36 (21 d post-dose) | D43 (28 d post-dose) |
| Vehicle Control | Mean ± SD | 75.4 ± 14.2 | 64.7 ± 19.1 | 60.7 ± 31.7 | 64.3 ± 27.3 | 64.3 ± 27.3 |
| | n | 4 | 4 | 4 | 4 | 4 |
| Aflibercept- | Mean ± SD | 75.0 ± 41.0 | 10.7 ± 21.5 [a] | 3.6 ± 7.2 [a] | 7.2 ± 14.3 [a] | 14.3 ± 28.6 [a] |
| 500 μg/Eye | n | 4 | 4 | 4 | 4 | 4 |
| EPS1108P- | Mean ± SD | 75.0 ± 24.4 | 53.6 ± 17.9 [b] | 25.0 ± 18.0 | 17.9 ± 18.0 [a] | 17.9 ± 18.0 [a] |
| 250 μg/Eye | n | 4 | 4 | 4 | 4 | 4 |
| EPS1108P- | Mean ± SD | 74.4 ± 31.4 | 38.1 ± 27.5 | 18.5 ± 26.9 [a] | 14.9 ± 20.3 [a] | 18.5 ± 26.9 [a] |
| 500 μg/Eye | n | 4 | 4 | 4 | 4 | 4 |

n: the number of Eyes;
[a] Compared with Vehicle Control group, the difference is significant ( $p<0.05$);
[b] Compared with Aflibercept-500 μg/Eye group, the difference is significant ($p<0.05$).

6.1.2 The Average Area of Leakage

Summary of the average area of fluorescein leakage is shown in the table below (Table 10):

TABLE 10

The average area of fluorescein leakage in each group pre/post dosing

| Group | | Average area of fluorescein leakage ($mm^2$) | | | | |
|---|---|---|---|---|---|---|
| | | D14 (pre-dose) | D22 (7 d post-dose) | D29 (14 d post-dose) | D36 (21 d post-dose) | D43 (28 d post-dose) |
| Vehicle Control | Mean ± SD | 1.56 ± 0.61 | 1.57 ± 0.73 | 1.77 ± 1.07 | 1.86 ± 1.01 | 1.92 ± 1.05 |
| | n | 4 | 4 | 4 | 4 | 4 |
| Aflibercept- | Mean ± SD | 1.51 ± 0.61 | 0.61 ± 0.30 [a] | 0.52 ± 0.33 [a] | 0.54 ± 0.45 [a] | 0.64 ± 0.38 |
| 500 μg/Eye | n | 4 | 4 | 4 | 4 | 4 |
| EPS1108P- | Mean ± SD | 1.54 ± 0.46 | 0.94 ± 0.50 | 0.88 ± 0.49 | 1.06 ± 1.02 | 1.04 ± 0.97 |
| 250 μg/Eye | n | 4 | 4 | 4 | 4 | 4 |
| EPS1108P- | Mean ± SD | 1.52 ± 0.47 | 0.75 ± 0.16 [a] | 0.68 ± 0.35 [a] | 0.71 ± 0.39 [a] | 0.77 ± 0.30 |
| 500 μg/Eye | n | 4 | 4 | 4 | 4 | 4 |

n: the number of Eyes;
[a] Compared with Vehicle Control group, the difference is significant ( $p<0.05$);
[b] Compared with Aflibercept-500 μg/Eye group, the difference is significant ($p<0.05$).

7. Conclusion

The Fundus photography and fluorescein angiography (FP & FFA) results indicated that the animal eyelaser-induced CNV Model was successfully established. When the animals were treated with EPS1108P (250 and 500 μg/Eye) by single Intravitreal injection (IVT), the Grade 4 lesion rate and the average area of fluorescein leakage were significantly decreased, and the inhibition effect was dose dependent, which showed that EPS1108P is effective drug in treating CNV in the cynomolgus monkey model.

Compared with the positive control, the inhibitory effects of EPS1108P were comparable to that of aflibercept at D36 (21 d post-dose) and D43 (28 d post-dose); the positive control immediately improved the Grade 4 lesion rate and the average area of fluorescein leakage, while EPS1108P was more gentle, and sustainably inhibited to the same level as the positive control.

Example 25: Pharmacokinetic Study of Single Intravitreal Injection in New Zealand Rabbits 1. Experimental Methods and Procedures 1.1 Animal Study New Zealand rabbit, 2-2.5 kg, male or female, purchased from Chengdu Dashuo Experimental Animal Co., Ltd. (license No. SCXK [Sichuan] 2015-030). All rabbits were randomly divided into 3 groups; the group and dose information are listed in the table below (Table 11):

TABLE 11

The group and dose information

| group | number | pathway | dose | volume |
|---|---|---|---|---|
| EPS1108P | 3 | intravitreal injection | 250 μg/eye | 50 μL/eye |
| EPS1104P | 3 | intravitreal injection | 500 μg/eye | 50 μL/eye |
| Aflibercept | 3 | intravitreal injection | 500 μg/eye | 50 μL/eye |

All test fusion proteins were diluted with saline under sterile conditions.

All animals were allowed to acclimatize for at least 7 days prior to experiments. Before administration, 2 drops of oxybuprocaine hydrochloride eye drops (#B2030, Santen Pharmaceutical CO., Ltd.) were dripped into the rabbit eyes and wiped with 5% povidone iodine on the periocular region and the conjunctiva of the eyes. A single dose of the different test fusion proteins was administrated by intravitreal injection (50 μL/eye) after eye local anesthesia. The eyes of rabbits were excised at each of the following time points: Day 1, 4, 8, 12, 16 and 21 days after injection. The vitreous was collected and immediately frozen at −80° C. The vitreous samples were analyzed by ELISA assay.

2. Results

The pharmacokinetic parameters ($T_{1/2}$) were calculated by using the non-compartmental model in Phoenix.

TABLE 12

The estimated half-life ($T_{1/2}$) of each group

| Fusion protein | $T_{1/2}$ (Day) |
|---|---|
| EPS1108P | 5.77 |
| EPS1104P | 8.72 |
| Aflibercept | 4.26 |

3. Conclusion

The tested fusion proteins of the invention comprised domains of PDGFR and domains of VEGFR which were attached by a linker consisting of proline, alanine and serine, wherein the length (i.e., the number of amino acid residues) of the linkers in EPS1108P and EPS1104P were 200 and 400, respectively.

The result indicated that the half-life (T½) of the proteins in New Zealand rabbits became longer with increasing length of the linker. Compared with Aflibercept, whose reported half life was 3.9 days (Park S J, Choi Y, Na Y M, et al. Intraocular pharmacokinetics of intravitreal aflibercept (eylea) in a rabbit model. Invest Ophthalmol Vis Sci. 2016; 57:2612-2617.), the $T_{1/2}$ of both EPS1108P and EPS1104P was significantly longer. A significantly longer half-life means the potential to be a longer-acting drug, which can significantly reduce the frequency of administration of ophthalmic patients, reduce the risk of eye infections, and reduce the pain and financial burden of patients.

Example 26: Native PAGE and Electromobility Gel Shift Assay

Figure 16:

EPS1104P was mixed with $VEGF_{165}$ (#C083, Novoprotein, Shanghai, China), PDGF-BB (#C199, Novoprotein, Shanghai, China) and VEGF+PDGF-BB, and incubated in an ice bath for 30 min. 40 μL of the above three incubation mixtures and EPS1104P were added to 10 μl of 5× Loading buffer (#ES005, Wanshenghaotian, Shanghai, China), respectively, and the four samples were loaded on a native PAGE gel (#NGSH2001-8T, Wanshenghaotian, Shanghai, China). The electrophoresis was run at 70 V for 6 hours. The gel was stained with Coomassie blue and then bleached. The gel electropherogram is shown in FIG. 16. The electropherogram reveals that the molecular weights of lanes 2 (EPS1104P+PDGF-BB), 3 (EPS1104P+$VEGF_{165}$), and 4 (EPS1104P+$VEGF_{165}$+PDGF-BB) are larger than those of lane 1 (EPS1104P), indicating that EPS1104P can be combined with $VEGF_{165}$ or PDGF-BB alone to each form a stable complex. It is also possible to combine EPS1104P with both VEGF165 and PDGF-BB to form a stable complex.

Example 27: Inhibition of $VEGF_{165}$-Induced HUVEC Proliferation

1. Assay Methods 1.1 A blank control group, a VEGF control group, and a test sample group (EPS1104P) were established in the experiment. Three parallel wells were set in each group, and the experiment was repeated three times.

1.2 HUVEC cells growing in an exponential growth phase were harvested and prepared for single cell suspension.

1.3 The cells were counted and adjusted to a density of $5\times10^4$ cells/mL with basal Medium (#1001-b, Sciencell). 100 μL of the cell suspension was seeded into a 96 well plate. Incubated at 37° C., 5% $CO_2$ overnight (without feed).

1.4 The dilution medium was mixed with a complete medium (#1001, Sciencell) and a basal medium. 100 μl of dilution medium without $VEGF_{165}$ was added to the well of the blank control group. 100 μl of dilution medium containing 25 ng/ml of $VEGF_{165}$ was added to the well of the VEGF control group. EPS1104P was serially diluted to working concentrations (200 nM, 50 nM, 12.5 nM, 3.125 nM, 0.781 nM, 0.195 nM, 0.049 nM and 0.012 nM) with dilution medium containing 25 ng/ml of $VEGF_{165}$0.100 μL of the diluted EPS1104P was added to the well of the test sample group. The 96 well plate of the three groups was incubated for 72 h at 37° C., 5% $CO_2$.

1.5 After incubation, 20 μL of Cell Counting Kit-8 (#CK04, Dojindo, Shanghai, China) was added into each well, then incubated in incubator for 2-3 h.

1.6 Absorbance (OD value) was measured at 450 nm by using a microplate reader (Thermofisher).

1.7 The $IC_{50}$ in each group was calculated with Origin.

2. Results

TABLE 13

| Inhibition of HUVEC cells proliferation | |
|---|---|
| Sample | $IC_{50}$ (nM) |
| EPS1104P | 1.43 |

3. Conclusion

EPS1104P showed significant inhibition in the $VEGF_{165}$-induced HUVEC cell proliferation test.

The present disclosure refers to the following nucleotide and amino acid sequences.

Some of the sequences provided herein are, inter alia, available in the NCBI database and can be retrieved from www.ncbi.nlm.nih.gov/sites/entrez?db=gene; Theses sequences also relate to annotated and modified sequences. Techniques and methods are provided herein wherein homologous sequences, and variants of the concise sequences provided herein are used. Preferably, such "variants" are genetic variants.

```
SEQ ID No. 1:
Nucleotide sequence encoding PAS linker
Gcctctcctgctgcccctgccccagcttctccagctgctcctgcaccttctgctccagccgctagtcctgcagctccagctcc

tgcttctcctgccgcaccagcacctagtgcccctgctgcatcaccagcagctcccgcacccgctagcccagctgcaccagctc

caagtgctccagcagcttcacccgcagcacccgctccagcaagtccagcagccccagccccttcagcaccagctgcatctccc

gcagcccctgctcctgccagccctgccgctcctgctccaagcgctcctgctgctagtccagccgcccctgcaccagcaagtcc

tgctgctcccgcacctagtgcaccagcagcaagccctgcagctcctgcaccagcatctccagcagcaccagcaccatcagccc

ctgccgcttctcccgcagctccagccccagcctcccctgctgctccagccccctctgctcctgcagcatctcctgccgctccc

gcccctgcaagtcccgccgctccagcaccatccgctccagctgcttccccagccgctccagctccagctagccccgcagcccc

cgcaccatctgccccagca

SEQ ID No. 2:
Amino acid sequence of PAS linker
ASPAAPAPASPAAPAPSAPAASPAAPAPASPAAPAPSAPAASPAAPAPASPAAPAPSAPAASPAAPAPASPAAPAPSAPAASP

AAPAPASPAAPAPSAPAASPAAPAPASPAAPAPSAPAASPAAPAPASPAAPAPSAPAASPAAPAPASPAAPAPSAPAASPAAP

APASPAAPAPSAPAASPAAPAPASPAAPAPSAPA

SEQ ID No. 3:
Nucleotide sequence encoding Ig domains 1 to 3 of PDGFRα
cagctgagcctgccctccatcctgcctaacgagaatgagaaggtggtgcagctgaactccagcttctccctgagatgctttgg

cgagtctgaggtgtcctggcagtacccaatgagcgaggaggagtcttccgacgtggagatccgcaatgaggagaacaattctg

gcctgttcgtgaccgtgctggaggtgagctctgcctccgccgctcacaccggcctgtacacatgttactataaccatacccag

acagaggagaatgagctggagggcagacacatctacatctatgtgcccgatcctgacgtggcctttgtgccactgggcatgac

cgattacctggtcatcgtggaggacgatgacagcgccatcatcccctgcaggaccacagaccccgagacacctgtgacactgc

ataactctgagggcgtggtgccagccagctacgattctcggcagggcttcaatggcacctttacagtgggcccctatatctgt

gaggccaccgtgaagggcaagaagttccagacaatcccttttaacgtgtacgccctgaaggctaccagcgagctggacctgga

gatggaggccctgaagacagtgtataagtctggcgagacaatcgtggtgacatgcgccgtgttcaacaatgaggtggtggatc

tgcagtggacctaccccggcgaggtgaagggcaagggcatcacaatgctggaggagatcaaggtgccttctatcaagctggtg

tacaccctgacagtgccagaggccaccgtgaaggattccggcgactatgagtgtgccgctaggcaggctacccgggaggtgaa

ggagatgaagaaggtgacaatctctgtgcacgagaaggga

SEQ ID No. 4:
Amino acid sequence of Ig domains 1 to 3 of PDGFRα
QLSLPSILPNENEKVVQLNSSFSLRCFGESEVSWQYPMSEEESSDVEIRNEENNSGLFVTVLEVSSASAAHTGLYTCYYNHTQ

TEENELEGRHIYIYVPDPDVAFVPLGMTDYLVIVEDDDSAIIPCRTTDPETPVTLHNSEGVVPASYDSRQGFNGTFTVGPYIC

EATVKGKKFQTIPFNVYALKATSELDLEMEALKTVYKSGETIVVTCAVFNNEVVDLQWTYPGEVKGKGITMLEEIKVPSIKLV

YTLTVPEATVKDSGDYECAARQATREVKEMKKVTISVHEKG
```

-continued

SEQ ID No. 5:
Nucleotide sequence encoding Ig domains 1 to 3 of PDGFRβ
aacgatgccgaggaactgttcatcttcctgaccgagattaccgagatcacaatcccctgccgcgtgacagatcctcagctggt ggttaccctgcatgagaagaaaggcgacgtggccctgcctgtgccttacgatcatcagagaggcttctccggcatcttcgagg accggtcttacatctgcaagaccaccatcggcgacagagaggtggactccgacgcctactacgtgtacagactccaggtgtcc tccatcaacgtgtccgtgaatgccgtgcagacagttgtgcggcagggcgagaatatcaccctgatgtgcatcgtgatcggcaa cgaggtggtcaacttcgagtggacctatcctcggaaagaatctggccggctggtggaacctgtgaccgacttcctgctggaca tgccctaccacatccggtctatcctgcacatcccttccgccgagctggaagattccggcacctacacctgtaacgtgaccgag tccgtgaacgaccaccaggacgagaaggccatcaatatcaccgtggtggaatccggctacgtgcggctgttgggagaagtggg cacactgcagtttgctgagctg SEQ ID No. 6:
Amino acid sequence of Ig domains 1 to 3 of PDGFRβ
NDAEELFIFLTEITEITIPCRVTDPQLVVTLHEKKGDVALPVPYDHQRGFSGIFEDRSYICKTTIGDREVDSDAYYVYRLQVS SINVSVNAVQTVVRQGENITLMCIVIGNEVVNFEWTYPRKESGRLVEPVTDFLLDMPYHIRSILHIPSAELEDSGTYTCNVTE

SVNDHQDEKAINITVVESGYVRLLGEVGTLQFAEL

SEQ ID No. 7:
Nucleotide sequence encoding Ig domain 2 of VEGFR-1 and Ig domain 3 of VEGFR-2
agtgataccggtagacctttcgtagagatgtacagtgaaatccccgaaattatacacatgactgaaggaagggagctcgtcat tccctgccgggttacgtcacctaacatcactgttactttaaaaaagtttccacttgacactttgatccctgatggaaaacgca taatctgggacagtagaaagggcttcatcatatcaaatgcaacgtacaaagaaatagggcttctgacctgtgaagcaacagtc aatgggcatttgtataagacaaactatctcacacatcgacaaaccaatacaatcatagatgtggttctgagtccgtctcatgg aattgaactatctgttggagaaaagctcgtcttaaattgtacagcaagaactgaactaaatgtggggattgacttcaactggg aatacccttcttcgaagcatcagcataagaaacttgtaaaccgagacctaaaaacccagtctgggagtgagatgaagaaattt ttgagcaccttaactatagatggtgtaacccggagtgaccaaggattgtacacctgtgcagcatccagtgggctgatgaccaa gaagaacagcacatttgtcagggtccatgaaaag SEQ ID No. 8:
Amino acid sequence of Ig domain 2 of VEGFR-1 and Ig domain 3 of VEGFR-2
SDTGRPFVEMYSEIPEIIHMTEGRELVIPCRVTSPNITVTLKKFPLDTLIPDGKRIIWDSRKGFIISNATYKEIGLLTCEATV NGHLYKTNYLTHRQTNTIIDVVLSPSHGIELSVGEKLVLNCTARTELNVGIDFNWEYPSSKHQHKKLVNRDLKTQSGSEMKKF

LSTLTIDGVTRSDQGLYTCAASSGLMTKKNSTFVRVHEK

SEQ ID No. 9:
Nucleotide sequence encoding N-terminal signal polypeptide sequence
atggggacttcccatccggcgttcctggtcttaggctgtcttctcacagggctgagcctaatcctctgc SEQ ID No. 10:
Amino acid sequence of N-terminal signal polypeptide sequence
MGTSHPAFLVLGCLLTGLSLILC SEQ ID No. 11:
Nucleotide sequence encoding purification tag
caccatcaccatcaccacgcc SEQ ID No. 12:
Amino acid sequence of purification tag
HHHHHHA SEQ ID No. 13:
Nuleotide sequence of vector pDSG33-PDGFR-PAS200-VEGFR (7190 bp)
acccacaatggggacttcccatccggcgttcctggtcttaggctgtcttctcacagggctgagcctaatcctctgccagc tttcattaccctctatccttccaaatgaaaatgaaaaggttgtgcagctgaattcatccttttctctgagatgctttggg gagagtgaagtgagctggcagtaccccatgtctgaagaagagtcttccgatgtggaaatcagaaatgaagaaaacaacag cggcctttttgtgacggtcttggaagtgagcagtgcctcggcggcccacacagggttgtacacttgctattacaaccaca ctcagacagaagagaatgagcttgaaggcaggcacatttacatctatgtgccagacccagatgtagcctttgtacctcta -continued ggaatgacggattatttagtcatcgtggaggatgatgattctgccattataccttgtcgcacaactgatcccgagactcc tgtaaccttacacaacagtgagggggtggtacctgcctcctacgacagcagacagggctttaatgggaccttcactgtag ggccctatatctgtgaggccaccgtcaaaggaaagaagttccagaccatcccatttaatgtttatgctttaaaagcaaca tcagagctggatctagaaatggaagctcttaaaaccgtgtataagtcaggggaaacgattgtggtcacctgtgctgtttt taacaatgaggtggttgaccttcaatggacttaccctggagaagtgaaaggcaaaggcatcacaatgctggaagaaatca aagtcccatccatcaaattggtgtacactttgacggtccccgaggccacggtgaaagacagtggagattacgaatgtgct gcccgccaggctaccagggaggtcaaagaaatgaagaaagtcactatttctgtccatgagaaaggtgcctctcctgctgc ccctgccccagcttctccagctgctcctgcaccttctgctccagccgctagtcctgcagctccagctcctgcttctcctg ccgcaccagcacctagtgcccctgctgcatcaccagcagctcccgcacccgctagcccagctgcaccagctccaagtgct ccagcagcttcacccgcagcacccgctccagcaagtccagcagccccagccccttcagcaccagctgcatctcccgcagc ccctgctcctgccagccctgccgctcctgctccaagcgctcctgctgctagtccagccgcccctgcaccagcaagtcctg ctgctcccgcacctagtgcaccagcagcaagccctgcagctcctgcaccagcatctccagcagcaccagcaccatcagcc cctgccgcttctcccgcagctccagccccagcctcccctgctgctccagcccccctctgctcctgcagcatctcctgccgc tcccgcccctgcaagtcccgccgctccagcaccatccgctccagctgcttccccagccgctccagctccagctagccccg cagcccccgcaccatctgccccagcagccagtgataccggtagacctttcgtagagatgtacagtgaaatccccgaaatt atacacatgactgaaggaagggagctcgtcattccctgccgggttacgtcacctaacatcactgttactttaaaaaagtt tccacttgacactttgatccctgatggaaaacgcataatctgggacagtagaaagggcttcatcatatcaaatgcaacgt acaaagaaatagggcttctgacctgtgaagcaacagtcaatgggcatttgtataagacaaactatctcacacatcgacaa accaatacaatcatagatgtggttctgagtccgtctcatggaattgaactatctgttggagaaaagctcgtcttaaattg tacagcaagaactgaactaaatgtggggattgacttcaactgggaatacccttcttcgaagcatcagcataagaaacttg taaaccgagacctaaaaacccagtctgggagtgagatgaagaaatttttgagcaccttaactatagatggtgtaacccgg agtgaccaaggattgtacacctgtgcagcatccagtgggctgatgaccaagaagaacagcacatttgtcagggtccatga aaagcaccatcaccatcaccacgcctgaagagcttaagcttgcggccgcagatctagcttaagtttaaaccgctgatcag cctcgactgtgccttctagttgccagccatctgttgtttgcccctcccccgtgccttccttgaccctggaaggtgccact cccactgtcctttcctaataaaatgaggaaattgcatcgcattgtctgagtaggtgtcattctattctggggggtggggt ggggcaggacagcaagggggaggattgggaagacaatagcaggcatgctggggatgcggtgggctctatggagcttggcc gcgttgctggcgtttttccataggctccgcccccctgacgagcatcacaaaaatcgacgctcaagtcagaggtggcgaaa cccgacaggactataaagataccaggcgtttccccctggaagctccctcgtgcgctctcctgttccgaccctgccgctta ccggatacctgtccgcctttctcccttcgggaagcgtggcgctttctcatagctcacgctgtaggtatctcagttcggtg taggtcgttcgctccaagctgggctgtgtgcacgaaccccccgttcagcccgaccgctgcgccttatccggtaactatcg tcttgagtccaacccggtaagacacgacttatcgccactggcagcagccactggtaacaggattagcagagcgaggtatg taggcggtgctacagagttcttgaagtggtggcctaactacggctacactagaagaacagtatttggtatctgcgctctg ctgaagccagttaccttcggaaaaagagttggtagctcttgatccggcaaacaaaccaccgctggtagcggtggtttttt tgtttgcaagcagcagattacgcgcagaaaaaaaggatctcaagaagatcctttgatcttttctacggggtctgacgctc agtggaacgaaaactcacgttaagggattttggtcatgagattatcaaaaaggatcttcacctagatccttttaaattaa aaatgaagttttaaatcaatctaaagtatatatgagtaaacttggtctgacagttaccaatgcttaatcagtgaggcacc tatctcagcgatctgtctatttcgttcatccatagttgcctgactccccgtcgtgtagataactacgatacgggagggct taccatctggccccagtgctgcaatgataccgcgagacccacgctcaccggctccagatttatcagcaataaaccagcca gccggaagggccgagcgcagaagtggtcctgcaactttatccgcctccatccagtctattaattgttgccgggaagctag agtaagtagttcgccagttaatagtttgcgcaacgttgttgccattgctacaggcatcgtggtgtcacgctcgtcgtttg gtatggcttcattcagctccggttcccaacgatcaaggcgagttacatgatcccccatgttgtgcaaaaaagcggttagc -continued tccttcggtcctccgatcgttgtcagaagtaagttggccgcagtgttatcactcatggttatggcagcactgcataattc tcttactgtcatgccatccgtaagatgcttttctgtgactggtgagtactcaaccaagtcattctgagaatagtgtatgc ggcgaccgagttgctcttgcccggcgtcaatacgggataataccgcgccacatagcagaactttaaaagtgctcatcatt ggaaaacgttcttcggggcgaaaactctcaaggatcttaccgctgttgagatccagttcgatgtaacccactcgtgcacc caactgatcttcagcatcttttactttcaccagcgtttctgggtgagcaaaaacaggaaggcaaaatgccgcaaaaaagg gaataagggcgacacggaaatgttgaatactcatactcttcctttttcaatattattgaagcatttatcagggttattgt ctcatgagcggatacatatttgaatgtatttagaaaaataaacaaataggggttccgcgcacatttccccgaaaagtgcc acctgacgtctaggttcacctaagaatgggagcaaccagcaggaaaaggacaagcagcgaaaattcacgcccccttggga ggtggcggcatatgcaaaggatagcactcccactctactactgggtatcatatgctgactgtatatgcatgaggatagca tatgctacccggatacagattaggatagcatatactacccagatatagattaggatagcatatgctacccagatatagat taggatagcctatgctacccagatataaattaggatagcatatactacccagatatagattaggatagcatatgctaccc agatatagattaggatagcctatgctacccagatatagattaggatagcatatgctacccagatatagattaggatagca tatgctatccagatatttgggtagtatatgctacccagatataaattaggatagcatatactaccctaatctctattagg atagcatatgctacccggatacagattaggatagcatatactacccagatatagattaggatagcatatgctacccagat atagattaggatagcctatgctacccagatataaattaggatagcatatactacccagatatagattaggatagcatatg ctacccagatatagattaggatagcctatgctacccagatatagattaggatagcatatgctatccagatatttgggtag tatatgctacccatggcaacattagcccaccgtgctctcagcgacctcgtgaatatgaggaccaacaaccctgtgcttgg cgctcaggcgcaagtgtgtgtaatttgtcctccagatcgcagcaatcgcgcccctatcttggcccgcccacctacttatg caggtattccccggggtgccattagtggttttgtgggcaagtggtttgaccgcagtggttagcggggttacaatcagcca agttattacacccttattttacagtccaaaaccgcagggcggcgtgtgggggctgacgcgtgcccccactccacaatttc aaaaaaaagagtggccacttgtctttgtttatgggccccattggcgtggagccccgtttaattttcgggggtgttagaga caaccagtggagtccgctgctgtcggcgtccactctctttccccttgttacaaatagagtgtaacaacatggttcacctg tcttggtccctgcctgggacacatcttaataaccccagtatcatattgcactaggattatgtgttgcccatagccataaa ttcgtgtgagatggacatccagtctttacggcttgtccccaccccatggatttctattgttaaagatattcagaatgttt cattcctacactagtatttattgcccaaggggtttgtgagggttatattggtgtcatagcacaatgccaccactgaaccc cccgtccaaattttattctgggggcgtcacctgaaaccttgttttcgagcacctcacatacaccttactgttcacaactc agcagttattctattagctaaacgaaggagaatgaagaagcaggcgaagattcaggagagttcactgcccgctccttgat cttcagccactgcccttgtgactaaaatggttcactaccctcgtggaatcctgaccccatgtaaataaaaccgtgacagc tcatggggtgggagatatcgctgttccttaggacccttttactaaccctaattcgatagcatatgcttcccgttgggtaa catatgctattgaattagggttagtctggatagtatatactactacccgggaagcatatgctacccgtttagggttaaca agggggccttataaacactattgctaatgccctcttgagggtccgcttatcggtagctacacaggcccctctgattgacg ttggtgtagcctcccgtagtcttcctgggcccctgggaggtacatgtcccccagcattggtgtaagagcttcagccaaga gttacacataaaggcaatgttgtgttgcagtccacagactgcaaagtctgctccaggatgaaagccactcagtgttggca aatgtgcacatccatttataaggatgtcaactacagtcagagaacccctttgtgtttggtcccccccccgtgtcacatgtg gaacagggcccagttggcaagttgtaccaaccaactgaagggattacatgcactgccccgcattaattgcatgaagaatc tgcttagggttaggcgttttgcgctgcttcgcgatgtacgggccagatatacgcgttgacattgattattgactagttat taatagtaatcaattacggggtcattagttcatagcccatatatggagttccgcgttacataacttacggtaaatggccc gcctggctgaccgcccaacgacccccgcccattgacgtcaataatgacgtatgttcccatagtaacgccaatagggactt tccattgacgtcaatgggtggagtatttacggtaaactgcccacttggcagtacatcaagtgtatcatatgccaagtacg ccccctattgacgtcaatgacggtaaatggcccgcctggcattatgcccagtacatgaccttatgggactttcctacttg -continued gcagtacatctacgtattagtcatcgctattaccatggtgatgcggttttggcagtacatcaatgggcgtggatagcggt ttgactcacggggatttccaagtctccaccccattgacgtcaatgggagtttgttttggcaccaaaatcaacgggacttt ccaaaatgtcgtaacaactccgccccattgacgcaaatgggcggtaggcgtgtacggtgggaggtctatataagcagagc tctctggctaactagagaacccactgcttactggcttatcgaaattaatacgactcactatagggtctag SEQ ID No. 14:
Translation of pDSG33-PDGFR-PAS200-VEGFR nucleotides 8-2188 coding for protein sequence PDGFR$_{\alpha D123}$-PAS(200)-VEGFR1$_{D}$2/R2$_{D3}$ (726 amino acids; includes signal sequence and purification tag)

MGTSHPAFLVLGCLLTGLSLILCQLSLPSILPNENEKVVQLNSSFSLRCFGESEVSWQYPMSEEESSDVEIRNEENNSGL

FVTVLEVSSASAAHTGLYTCYYNHTQTEENELEGRHIYIYVPDPDVAFVPLGMTDYLVIVEDDDSAIIPCRTTDPETPVT

LHNSEGVVPASYDSRQGFNGTFTVGPYICEATVKGKKFQTIPFNVYALKATSELDLEMEALKTVYKSGETIVVTCAVFNN

EVVDLQWTYPGEVKGKGITMLEEIKVPSIKLVYTLTVPEATVKDSGDYECAARQATREVKEMKKVTISVHEKGASPAAPA

PASPAAPAPSAPAASPAAPAPASPAAPAPSAPAASPAAPAPASPAAPAPSAPAASPAAPAPASPAAPAPSAPAASPAAPA

PASPAAPAPSAPAASPAAPAPASPAAPAPSAPAASPAAPAPASPAAPAPSAPAASPAAPAPASPAAPAPSAPAASPAAPA

PASPAAPAPSAPAASPAAPAPASPAAPAPSAPAASDTGRPFVEMYSEIPEIIHMTEGRELVIPCRVTSPNITVTLKKFPL

DTLIPDGKRIIWDSRKGFIISNATYKEIGLLTCEATVNGHLYKTNYLTHRQTNTIIDVVLSPSHGIELSVGEKLVLNCTA

RTELNVGIDFNWEYPSSKHQHKKLVNRDLKTQSGSEMKKFLSTLTIDGVTRSDQGLYTCAASSGLMTKKNSTFVRVHEKH

HHHHHA

SEQ ID No. 15:
Nucleotide sequence encoding EPS1108P excluding signal polypeptide sequence and purification-tag cagctttcattaccctctatccttccaaatgaaaatgaaaaggttgtgcagctgaattcatccttttctctgagatgctttgg ggagagtgaagtgagctggcagtaccccatgtctgaagaagagtcttccgatgtggaaatcagaaatgaagaaaacaacagcg gcctttttgtgacggtcttggaagtgagcagtgcctcggcggcccacacagggttgtacacttgctattacaaccacactcag acagaagagaatgagcttgaaggcaggcacatttacatctatgtgccagacccagatgtagcctttgtacctctaggaatgac ggattatttagtcatcgtggaggatgatgattctgccattataccttgtcgcacaactgatcccgagactcctgtaaccttac acaacagtgagggggtggtacctgcctcctacgacagcagacagggctttaatgggaccttcactgtagggccctatatctgt gaggccaccgtcaaaggaaagaagttccagaccatcccatttaatgtttatgctttaaaagcaacatcagagctggatctaga aatggaagctcttaaaaccgtgtataagtcaggggaaacgattgtggtcacctgtgctgtttttaacaatgaggtggttgacc ttcaatggacttaccctggagaagtgaaaggcaaaggcatcacaatgctggaagaaatcaaagtcccatccatcaaattggtg tacactttgacggtccccgaggccacggtgaaagacagtggagattacgaatgtgctgcccgccaggctaccagggaggtcaa agaaatgaagaaagtcactatttctgtccatgagaaaggtgcctctcctgctgcccctgccccagcttctccagctgctcctg caccttctgctccagccgctagtcctgcagctccagctcctgcttctcctgccgcaccagcacctagtgcccctgctgcatca ccagcagctcccgcacccgctagcccagctgcaccagctccaagtgctccagcagcttcacccgcagcacccgctccagcaag tccagcagccccagccccttcagcaccagctgcatctcccgcagcccctgctcctgccagccctgccgctcctgctccaagcg ctcctgctgctagtccagccgcccctgcaccagcaagtcctgctgctcccgcacctagtgcaccagcagcaagccctgcagct cctgcaccagcatctccagcagcaccagcaccatcagcccctgccgcttctcccgcagctccagccccagcctcccctgctgc tccagccccctctgctcctgcagcatctcctgccgctcccgcccctgcaagtcccgccgctccagcaccatccgctccagctg cttccccagccgctccagctccagctagccccgcagcccccgcaccatctgccccagcagccagtgataccggtagacctttc gtagagatgtacagtgaaatccccgaaattatacacatgactgaaggaagggagctcgtcattccctgccgggttacgtcacc taacatcactgttactttaaaaaagtttccacttgacactttgatccctgatggaaaacgcataatctgggacagtagaaagg gcttcatcatatcaaatgcaacgtacaaagaaatagggcttctgacctgtgaagcaacagtcaatgggcatttgtataagaca aactatctcacacatcgacaaaccaatacaatcatagatgtggttctgagtccgtctcatggaattgaactatctgttggaga aaagctcgtcttaaattgtacagcaagaactgaactaaatgtggggattgacttcaactgggaatacccttcttcgaagcatc -continued agcataagaaacttgtaaaccgagacctaaaaacccagtctgggagtgagatgaagaaatttttgagcaccttaactatagat ggtgtaacccggagtgaccaaggattgtacacctgtgcagcatccagtgggctgatgaccaagaagaacagcacatttgtcag ggtccatgaaaag SEQ ID No. 16:
Amino acid sequence of EPS1108P excluding signal polypeptide sequence and purification-tag
QLSLPSILPNENEKVVQLNSSFSLRCFGESEVSWQYPMSEEESSDVEIRNEENNSGLFVTVLEVSSASAAHTGLYTCYYNHTQ TEENELEGRHIYIYVPDPDVAFVPLGMTDYLVIVEDDDSAIIPCRTTDPETPVTLHNSEGVVPASYDSRQGFNGTFTVGPYIC EATVKGKKFQTIPFNVYALKATSELDLEMEALKTVYKSGETIVVTCAVFNNEVVDLQWTYPGEVKGKGITMLEEIKVPSIKLV YTLTVPEATVKDSGDYECAARQATREVKEMKKVTISVHEKGASPAAPAPASPAAPAPSAPAASPAAPAPASPAAPAPSAPAAS PAAPAPASPAAPAPSAPAASPAAPAPASPAAPAPSAPAASPAAPAPASPAAPAPSAPAASPAAPAPASPAAPAPSAPAASPAA PAPASPAAPAPSAPAASPAAPAPASPAAPAPSAPAASPAAPAPASPAAPAPSAPAASPAAPAPASPAAPAPSAPAASDTGRPF VEMYSEIPEIIHMTEGRELVIPCRVTSPNITVTLKKFPLDTLIPDGKRIIWDSRKGFIISNATYKEIGLLTCEATVNGHLYKT NYLTHRQTNTIIDVVLSPSHGIELSVGEKLVLNCTARTELNVGIDFNWEYPSSKHQHKKLVNRDLKTQSGSEMKKFLSTLTID

GVTRSDQGLYTCAASSGLMTKKNSTFVRVHEK

SEQ ID No. 17:
DNA-Sequence of PDGFR$_{\alpha D123}$-cloning site-VEGFR1$_D$2/R2$_{D3}$ for cloning into pDSG33-PDGFR-PAS200-VEGFR (sequence flanked by restriction sites for XbaI and HindIII; underlined)
<u>tctaga</u>cccacaatggggacttcccatccggcgttcctggtcttaggctgtcttctcacagggctgagcctaatcctctg ccagctttcattaccctctatccttccaaatgaaaatgaaaaggttgtgcagctgaattcatcctttttctctgagatgct ttggggagagtgaagtgagctggcagtaccccatgtctgaagaagagtcttccgatgtggaaatcagaaatgaagaaaac aacagcggcctttttgtgacggtcttggaagtgagcagtgcctcggcggcccacacagggttgtacacttgctattacaa ccacactcagacagaagagaatgagcttgaaggcaggcacatttacatctatgtgccagacccagatgtagcctttgtac ctctaggaatgacggattatttagtcatcgtggaggatgatgattctgccattataccttgtcgcacaactgatcccgag actcctgtaaccttacacaacagtgagggggtggtacctgcctcctacgacagcagacagggctttaatgggaccttcac tgtagggccctatatctgtgaggccaccgtcaaaggaaagaagttccagaccatcccatttaatgtttatgctttaaaag caacatcagagctggatctagaaatggaagctcttaaaaccgtgtataagtcaggggaaacgattgtggtcacctgtgct gtttttaacaatgaggtggttgaccttcaatggacttaccctggagaagtgaaaggcaaaggcatcacaatgctggaaga aatcaaagtcccatccatcaaattggtgtacactttgacggtccccgaggccacggtgaaagacagtggagattacgaat gtgctgcccgccaggctaccagggaggtcaaagaaatgaagaaagtcactatttctgtccatgagaaaggtgccagaaga gcagatctgggctcttctgcccaccatcaccatcaccattaagcttgcggctcttctgccagtgataccggtagaccttt cgtagagatgtacagtgaaatccccgaaattatacacatgactgaaggaagggagctct<u>aagctt</u>

SEQ ID No. 18:
DNA-Sequence of PDGFR$_{\alpha D123}$-PAS(200)-VEGFR1$_D$2/R2$_{D3}$ in pDSG33-PDGFR-PAS200-VEGFR (sequence flanked by restriction sites for XbaI and HindIII; underlined)
<u>tctaga</u>cccacaatggggacttcccatccggcgttcctggtcttaggctgtcttctcacagggctgagcctaatcctctg ccagctttcattaccctctatccttccaaatgaaaatgaaaaggttgtgcagctgaattcatcctttttctctgagatgct ttggggagagtgaagtgagctggcagtaccccatgtctgaagaagagtcttccgatgtggaaatcagaaatgaagaaaac aacagcggcctttttgtgacggtcttggaagtgagcagtgcctcggcggcccacacagggttgtacacttgctattacaa ccacactcagacagaagagaatgagcttgaaggcaggcacatttacatctatgtgccagacccagatgtagcctttgtac ctctaggaatgacggattatttagtcatcgtggaggatgatgattctgccattataccttgtcgcacaactgatcccgag actcctgtaaccttacacaacagtgagggggtggtacctgcctcctacgacagcagacagggctttaatgggaccttcac tgtagggccctatatctgtgaggccaccgtcaaaggaaagaagttccagaccatcccatttaatgtttatgctttaaaag caacatcagagctggatctagaaatggaagctcttaaaaccgtgtataagtcaggggaaacgattgtggtcacctgtgct gtttttaacaatgaggtggttgaccttcaatggacttaccctggagaagtgaaaggcaaaggcatcacaatgctggaaga -continued aatcaaagtcccatccatcaaattggtgtacactttgacggtccccgaggccacggtgaaagacagtggagattacgaat gtgctgcccgccaggctaccagggaggtcaaagaaatgaagaaagtcactatttctgtccatgagaaaggtgcctctcct gctgcccctgccccagcttctccagctgctcctgcaccttctgctccagccgctagtcctgcagctccagctcctgcttc tcctgccgcaccagcacctagtgcccctgctgcatcaccagcagctcccgcacccgctagcccagctgcaccagctccaa gtgctccagcagcttcacccgcagcacccgctccagcaagtccagcagccccagccccttcagcaccagctgcatctccc gcagcccctgctcctgccagccctgccgctcctgctccaagcgctcctgctgctagtccagccgcccctgcaccagcaag tcctgctgctcccgcacctagtgcaccagcagcaagccctgcagctcctgcaccagcatctccagcagcaccagcaccat cagcccctgccgcttctcccgcagctccagccccagcctcccctgctgctccagccccctctgctcctgcagcatctcct gccgctcccgcccctgcaagtcccgccgctccagcaccatccgctccagctgcttccccagccgctccagctccagctag ccccgcagcccccgcaccatctgccccagcagccagtgataccggtagacctttcgtagagatgtacagtgaaatccccg aaattatacacatgactgaaggaagggagctcgtcattccctgccgggttacgtcacctaacatcactgttactttaaaa aagtttccacttgacactttgatccctgatggaaaacgcataatctgggacagtagaaagggcttcatcatatcaaatgc aacgtacaaagaaatagggcttctgacctgtgaagcaacagtcaatgggcatttgtataagacaaactatctcacacatc gacaaaccaatacaatcatagatgtggttctgagtccgtctcatggaattgaactatctgttggagaaaagctcgtctta aattgtacagcaagaactgaactaaatgtggggattgacttcaactgggaataccctttcttcgaagcatcagcataagaa acttgtaaaccgagacctaaaaacccagtctgggagtgagatgaagaaatttttgagcaccttaactatagatggtgtaa cccggagtgaccaaggattgtacacctgtgcagcatccagtgggctgatgaccaagaagaacagcacatttgtcagggtc catgaaaagcaccatcaccatcaccacgcctgaagagctt<u>aagctt</u>

SEQ ID No. 19:
Nucleotide sequence encoding Ig domains 1 to 3 of mutantPDGFR α
cagctgagcctgccaagcatcctgcctaacgaaaatgagaaggtggtccagctgaacagctccttcagtctgagatgctttgg cgaatcagaggtgagctggcagtacccaatgtcagaggaagagtctagtgacgtggaaattaggaatgaagagaacaattcag gactgttcgtgaccgtcctggaggtgtcaagcgccagcgccgctcacaccggactgtacacatgttactataaccatactcag accgaagagaatgaactggaggggaggcacatctccatccacgtgcccgatcctgacgtggcctttgccccactgggaatgac agattacctggtcatcgtcgaggacgatgactctgccatcattccctgccgcacctcagactccgaaactcctgtgaccctgc ataacagtgagggcgtggtccccgcctcctacgattctcgacagggattcaatggcaccttcaccgtcggaccctatatctgt gaggccactgtgaagggcaagaaattccagaccattccttttaacgtgtacgcactgaaagccacatccgaactggacctgga aatggaggccctgaagactgtctataaatctggagagactatcgtggtcacctgcgccgtgttcaacaatgaagtggtcgatg cgcagtggacttaccccggcgaggtcaagggcaaagggattaccatggacgaagagatcaaggtgcctagccagaagctggtg tacaccctgacagtcccagaagccaccgtgaaggattccggggactatgagtgtgcagcccggcaggcctccagagaagtgaa ggagatgaagaaagtgacaatcagtgtccacgagaaagga SEQ ID No. 20:
Amino acid sequence of Ig domains 1 to 3 of mutantPDGFRα
QLSLPSILPNENEKVVQLNSSFSLRCFGESEVSWQYPMSEEESSDVEIRNEENNSGLFVTVLEVSSASAAHTGLYTCYYNHTQ TEENELEGRHISIHVPDPDVAFAPLGMTDYLVIVEDDDSAIIPCRTSDSETPVTLHNSEGVVPASYDSRQGFNGTFTVGPYIC EATVKGKKFQTIPFNVYALKATSELDLEMEALKTVYKSGETIVVTCAVFNNEVVDAQWTYPGEVKGKGITMDEEIKVPSQKLV

YTLTVPEATVKDSGDYECAARQASREVKEMKKVTISVHEKG

SEQ ID No. 21:
Nucleotide sequence encoding EPS1103P
atgggtacaagccatcccgccttcctggtcctgggttgcctgctgactggtctgtctctgatcctgtgccagctg agcctgccttcaatcctgcccaacgagaatgagaaggtggtgcagctgaactccagcttcagcctgagatgcttt ggcgagtctgaggtgtcctggcagtaccctatgtctgaggaggagtcttccgacgtggagatccgcaatgaggag aacaattccggcctgttcgtgaccgtgctggaggtgagctctgccagcgccgctcacaccggcctgtacacatgt -continued tactataaccatacccagacagaggagaatgagctggagggcagacacatctacatctatgtgcccgatcctgac gtggcctttgtgccactgggcatgaccgattacctggtcatcgtggaggacgatgactctgccatcatcccctgc aggaccacagacccagagacacccgtgacactgcataactccgagggagtggtgccagctagctacgattctcgg cagggcttcaatggcacctttacagtgggcccctatatctgtgaggccaccgtgaagggcaagaagttccagaca atcccttttaacgtgtacgccctgaaggctacctctgagctggacctggagatggaggccctgaagacagtgtat aagtccggcgagacaatcgtggtgacatgcgccgtgttcaacaatgaggtggtggatctgcagtggacctaccct ggcgaggtgaagggcaagggcatcacaatgctggaggagatcaaggtgccttccatcaagctggtgtacaccctg acagtgccagaggccaccgtgaaggatagcggcgactatgagtgtgctgctaggcaggctaccagggaggtgaag gagatgaagaaggtgacaatctccgtgcacgagaagggagctagcccagctgctccagctccagctagccccgcc gctcctgctccatctgctcctgctgcttccccagctgctcccgcccctgcttctcctgctgctccagctccatcc gccccagctgcttctcctgccgctcctgccccagcttccccagccgctcccgccccttccgctccagccgcctct cccgccgcccctgctccagctagcccagcagccccagccccttctgctccagccgcctctccagccgcccctgct cccgcatcccccgccgcccccgccccttccgcccctgccgcctccccagctgccccagctcctgcctctcctgct gcccctgctccatccgctccagccgccagtcccgccgcccccgctccagctagcccagccgcaccagccccttct gctcccgccgcctctcccgccgcacctgctccagcatcccccgccgccccagccccttccgcccctgcagcctcc ccagctgcccccgctcctgcctctcctgcagcccctgctccttccgctccagccgcatctcccgccgccccagcc ccagctagcccagcagcaccagccccctctgctccagccgccagccctgccgcccctgctcccgcttcccccgcc gccccagcaccttccgcccctgccgcatccccagcagcccccgctcctgccagccctgctgcccctgcaccttcc gctccagccgcttctcccgccgccccagcacccgctagcccagctgcccctgccccttctgctccagcagcctct cctgccgcccctgctcctgcatcccccgccgcacccgccccttccgcccccgccgcctccccagctgcaccagct ccagcctctccagctgctccagctccttccgccccagctagcgataccggccgcccttttgtggagatgtacagc gagatccccgagatcatccacatgaccgagggcagggagctggtcatcccatgccgggtgacatctcccaacatc accgtgacactgaagaagttccctctggataccctgatcccagacggcaagagaatcatctgggactctcgcaag ggctttatcatctccaatgccacatataaggagatcggcctgctgacctgcgaggctacagtgaacggccacctg tacaagaccaattatctgacacataggcagaccaacacaatcatcgatgtggtgctgagcccatctcatggcatc gagctgagcgtgggcgagaagctggtgctgaattgtaccgcccggacagagctgaacgtgggcatcgacttcaat tgggagtacccttccagcaagcaccagcataagaagctggtgaacagagatctgaagacccagtccggcagcgag atgaagaagtttctgagcaccctgacaatcgatggcgtgacccgctctgaccagggcctgtatacatgtgccgct tcttccggcctgatgactaagaaaaactccacctttgtgcgggtccacgaaaaacaccaccaccaccaccat SEQ ID No. 22:
Amino acid sequence of EPS1103P
MGTSHPAFLVLGCLLTGLSLILCQLSLPSILPNENEKVVQLNSSFSLRCFGESEVSWQYPMSEEESSDVEIRNEENNSGLFVT VLEVSSASAAHTGLYTCYYNHTQTEENELEGRHIYIYVPDPDVAFVPLGMTDYLVIVEDDDSAIIPCRTTDPETPVTLHNSEG VVPASYDSRQGFNGTFTVGPYICEATVKGKKFQTIPFNVYAIKATSELDLEMEALKTVYKSGETIVVTCAVFNNEVVDLQWTY PGEVKGKGITMLEEIKVPSIKLVYTLTVPEATVKDSGDYECAARQATREVKEMKKVTISVHEKGASPAAPAPASPAAPAPSAP AASPAAPAPASPAAPAPSAPAASPAAPAPASPAAPAPSAPAASPAAPAPASPAAPAPSAPAASPAAPAPASPAAPAPSAPAAS PAAPAPASPAAPAPSAPAASPAAPAPASPAAPAPSAPAASPAAPAPASPAAPAPSAPAASPAAPAPASPAAPAPSAPAASPAA PAPASPAAPAPSAPAASPAAPAPASPAAPAPSAPAASPAAPAPASPAAPAPSAPAASPAAPAPASPAAPAPSAPAASPAAPAP ASPAAPAPSAPAASPAAPAPASPAAPAPSAPASDTGRPFVEMYSEIPEIIHMTEGRELVIPCRVTSPNITVTLKKFPLDTLIP DGKRIIWDSRKGFIISNATYKEIGLLTCEATVNGHLYKTNYLTHRQTNTIIDVVLSPSHGIELSVGEKLVLNCTARTELNVGI

DFNWEYPSSKHQHKKLVNRDLKTQSGSEMKKFLSTLTIDGVTRSDQGLYTCAASSGLMTKKNSTFVRVHEKHHHHHH

-continued

SEQ ID No. 23:
Nucleotide sequence encoding EPS1104P atgggtacttcacatcctgcttttctggtoctgggttgtctgctgactggtctgagcctgatcctgtgccagctg agcctgccctccatcctgcctaacgagaatgagaaggtggtgcagctgaactccagcttctccctgagatgcttt ggcgagtctgaggtgtcctggcagtacccaatgagcgaggaggagtcttccgacgtggagatccgcaatgaggag aacaattctggcctgttcgtgaccgtgctggaggtgagctctgcctccgccgctcacaccggcctgtacacatgt tactataaccatacccagacagaggagaatgagctggagggcagacacatctacatctatgtgcccgatcctgac gtggcctttgtgccactgggcatgaccgattacctggtcatcgtggaggacgatgacagcgccatcatcccctgc aggaccacagaccccgagacacctgtgacactgcataactctgagggcgtggtgccagccagctacgattctcgg cagggcttcaatggcacctttacagtgggcccctatatctgtgaggccaccgtgaagggcaagaagttccagaca atcccttttaacgtgtacgccctgaaggctaccagcgagctggacctggagatggaggccctgaagacagtgtat aagtctggcgagacaatcgtggtgacatgcgccgtgttcaacaatgaggtggtggatctgcagtggacctacccc ggcgaggtgaagggcaagggcatcacaatgctggaggagatcaaggtgccttctatcaagctggtgtacaccctg acagtgccagaggccaccgtgaaggattccggcgactatgagtgtgccgctaggcaggctacccgggaggtgaag gagatgaagaaggtgacaatctctgtgcacgagaagggagcttccccagctgctccagctccagcttcccccgcc gctcctgccccatctgctccagctgcctctccagctgctccagctcctgctagccctgccgctccagcccccctcc gcccctgccgcttctccagccgctcctgccccagctagccctgctgctccagctccttccgctccagccgcctct ccagccgctccagcccccgcctctcctgctgccccagctccttctgctccagctgccagccccgccgcccctgcc cccgcctctcccgctgcccctgctccttccgccccagctgcctcccctgctgctcctgccccagcttcacctgcc gcccctgccccttccgctccagccgcatctcccgccgctccagcccccgcaagccctgcagccccagctccctct gctccagctgcctcacccgccgcccctgcccctgcctctcccgctgcccccgctccttccgccccagcagcctcc cctgcagctcctgccccagcttctccagccgctcccgccccttccgctcccgccgcctctcctgctgcaccagcc cccgcttccccagctgctectgctccatccgccccagctgcttccccagctgctccagctccagcttcccccgcc gctcctgccccatctgctccagctgcctctccagctgctccagctcctgctagccctgccgctccagcccccctcc gcccctgccgcttctccagccgctcctgccccagctagccctgctgctccagctccttccgctccagccgcctct ccagccgctccagcccccgcctctcctgctgccccagctccttctgctccagctgccagccccgccgcccctgcc cccgcctctcccgctgcccctgctccttccgccccagctgcctcccctgctgctcctgccccagcttcacctgcc gcccctgccccttccgctccagccgcatctcccgccgctccagcccccgcaagccctgcagccccagctccctct gctccagctgcctcacccgccgcccctgcccctgcctctcccgctgcccccgctccttccgccccagcagcctcc cctgcagctcctgccccagcttctccagccgctcccgccccttccgctcccgccgcctctcctgctgcaccagcc cccgcttccccagctgctcctgctccatccgccccagctagcgataccggccgcccttttgtggagatgtacagc gagatccctgagatcatccacatgaccgagggcagggagctggtcatcccatgccgggtgacatctcccaacatc accgtgacactgaagaagttccctctggataccctgatcccagacggcaagagaatcatctgggacagccgcaag ggctttatcatctctaatgccacatataaggagatcggcctgctgacctgcgaggctacagtgaacggccacctg tacaagaccaattatctgacacataggcagaccaacacaatcatcgatgtggtgctgagcccctctcatggcatc gagctgtccgtgggcgagaagctggtgctgaattgtaccgcccggacagagctgaacgtgggcatcgacttcaat tgggagtacccttccagcaagcaccagcataagaagctggtgaacagagatctgaagacccagtccggcagcgag atgaagaagtttctgtccaccctgacaatcgatggagtgacccgcagcgaccagggcctgtatacatgtgccgct tcttccggcctgatgactaagaaaaatagcacctttgtgagggtccacgaaaaacaccaccaccaccaccat -continued SEQ ID No. 24:
Amino acid sequence of EPS1104P
MGTSHPAFLVLGCLLTGLSLILCQLSLPSILPNENEKVVQLNSSFSLRCFGESEVSWQYPMSEEESSDVEIRNEENNSGLFVT VLEVSSASAAHTGLYTCYYNHTQTEENELEGRHIYIYVPDPDVAFVPLGMTDYLVIVEDDDSAIIPCRTTDPETPVTLHNSEG VVPASYDSRQGFNGTFTVGPYICEATVKGKKFQTIPFNVYALKATSELDLEMEALKTVYKSGETIVVTCAVFNNEVVDLQWTY PGEVKGKGITMLEEIKVPSIKLVYTLTVPEATVKDSGDYECAARQATREVKEMKKVTISVHEKGASPAAPAPASPAAPAPSAP AASPAAPAPASPAAPAPSAPAASPAAPAPASPAAPAPSAPAASPAAPAPASPAAPAPSAPAASPAAPAPASPAAPAPSAPAAS PAAPAPASPAAPAPSAPAASPAAPAPASPAAPAPSAPAASPAAPAPASPAAPAPSAPAASPAAPAPASPAAPAPSAPAASPAA PAPASPAAPAPSAPAASPAAPAPASPAAPAPSAPAASPAAPAPASPAAPAPSAPAASPAAPAPASPAAPAPSAPAASPAAPAP ASPAAPAPSAPAASPAAPAPASPAAPAPSAPAASPAAPAPASPAAPAPSAPAASPAAPAPASPAAPAPSAPAASPAAPAPASP AAPAPSAPAASPAAPAPASPAAPAPSAPAASPAAPAPASPAAPAPSAPASDTGRPFVEMYSEIPEIIHMTEGRELVIPCRVTS PNITVTLKKFPLDTLIPDGKRIIWDSRKGFIISNATYKEIGLLTCEATVNGHLYKTNYLTHRQTNTIIDVVLSPSHGIELSVG EKLVLNCTARTELNVGIDFNWEYPSSKHQHKKLVNRDLKTQSGSEMKKFLSTLTIDGVTRSDQGLYTCAASSGLMTKKNSTFV

RVHEKHHHHHH

SEQ ID No. 25:
Nucleotide sequence encoding EPS1105P
atggtctcttattgggacactggggtgctgctgtgcgccctgctgagttgcctgctgctgactggttcttcttcc gggagcgataccggccgccccttcgtggagatgtacagcgagatccctgagatcatccacatgaccgagggcagg gagctggtcatcccttgccgggtgacatctccaaacatcaccgtgacactgaagaagttcccccctggataccctg atccctgacggcaagagaatcatctgggactctcgcaagggctttatcatctccaatgccacctataaggagatc ggcctgctgacctgcgaggctacagtgaacggccacctgtacaagaccaattatctgacacatcggcagaccaac acaatcatcgatgtggtgctgagcccttctcatggcatcgagctgtccgtgggcgagaagctggtgctgaattgt accgccagaacagagctgaacgtgggcatcgatttcaattgggagtacccatccagcaagcaccagcataagaag ctggtgaacagggacctgaagacccagtccggcagcgagatgaagaagtttctgtctaccctgacaatcgatgga gtgacccgctccgaccagggcctgtatacatgtgccgcttcttccggcctgatgaccaagaagaatagcacattt gtgagggtgcacgagaaggcctccccagctgctccagctcctgctagcccagccgctccagcccccctctgctcca gccgcttcccccgccgctcctgccccagcttctccagccgctcccgccccttccgcccctgccgcttctcctgct gctccagcccctgcctctcctgccgctcctgccccatccgctcccgccgctagccctgccgctcccgcccctgct agccctgctgcccctgctccttctgctcctgctgcctctccagctgccccagctcctgcctcccctgctgcccct gcaccatccgccccagccgcttctcctgcagctccagcccctgccagccctgctgccccagctccttccgctcct gctgccagtccagctgcccctgctcctgctagccctgctgcacctgctccttctgctcccgctgcctctccagct gcaccagctcctgcctcccccgctgcccctgctccatccgcccccgccgcttctcctgccgccccagcccctgcc tctccagctgctccagctccctccgctcctgctgccagcccagctgcccctgcacctgctagccctgctgctcct gccccctctgccccagctcagctgtctctgccatccatcctgcccaacgagaatgagaaggtggtgcagctgaac agctctttctctctgcggtgctttggcgagagcgaggtgtcttggcagtaccccatgtccgaggaggagtccagc gacgtggagatcagaaatgaggagaacaatagcggcctgttcgtgaccgtgctggaggtgtcttccgcctctgcc gctcacaccggcctgtacacatgttactataaccatacccagacagaggagaatgagctggagggccggcacatc tacatctatgtgcctgatccagacgtggcctttgtgcccctgggcatgaccgattacctggtcatcgtggaggac gatgactccgccatcatcccttgccgcaccacagaccccgagacacctgtgacactgcataacagcgagggagtg gtgccagcttcctacgatagcaggcagggcttcaatggcacctttacagtgggcccttatatctgtgaggccacc gtgaagggcaagaagttccagacaatccccttcaacgtgtacgccctgaaggctacctccgagctggacctggag atggaggccctgaagacagtgtataagagcggcgagacaatcgtggtgacatgcgccgtgttcaacaatgaggtg -continued gtggatctgcagtggacctaccctggcgaggtgaagggcaagggcatcacaatgctggaggagatcaaggtgcca agcatcaagctggtgtacaccctgacagtgcccgaggccaccgtgaaggattctggcgactatgagtgtgccgct aggcaggctacacgggaggtgaaagaaatgaagaaggtcacaatcagcgtccacgaaaaggggcatcaccaccac caccat SEQ ID No. 26:
Amino acid sequence of EPS1105P
MVSYWDTGVLLCALLSCLLLTGSSSGSDTGRPFVEMYSEIPEIIHMTEGRELVIPCRVTSPNITVTLKKFPLDTLIPDGKRII WDSRKGFIISNATYKEIGLLTCEATVNGHLYKTNYLTHRQTNTIIDVVLSPSHGIELSVGEKLVLNCTARTELNVGIDFNWEY PSSKHQHKKLVNRDLKTQSGSEMKKFLSTLTIDGVTRSDQGLYTCAASSGLMTKKNSTFVRVHEKASPAAPAPASPAAPAPSA PAASPAAPAPASPAAPAPSAPAASPAAPAPASPAAPAPSAPAASPAAPAPASPAAPAPSAPAASPAAPAPASPAAPAPSAPAA SPAAPAPASPAAPAPSAPAASPAAPAPASPAAPAPSAPAASPAAPAPASPAAPAPSAPAASPAAPAPASPAAPAPSAPAASPA APAPASPAAPAPSAPAQLSLPSILPNENEKVVQLNSSFSLRCFGESEVSWQYPMSEEESSDVEIRNEENNSGLFVTVLEVSSA SAAHTGLYTCYYNHTQTEENELEGRHIYIYVPDPDVAFVPLGMTDYLVIVEDDDSAIIPCRTTDPETPVTLHNSEGVVPASYD SRQGFNGTFTVGPYICEATVKGKKFQTIPFNVYALKATSELDLEMEALKTVYKSGETIVVTCAVFNNEVVDLQWTYPGEVKGK

GITMLEEIKVPSIKLVYTLTVPEATVKDSGDYECAARQATREVKEMKKVTISVHEKGHHHHHH

SEQ ID No. 27:
Nucleotide sequence encoding EPS1106P
atgggcaccagccatcctgcttttctggtgctgggatgcctgctgaccggcctgtctctgattctgtgccagctgtccctgcc ttccatcctgcctaacgagaacgagaaggtggtgcagctgaactcctccttctctctgcggtgcttcggcgagtccgaagtgt cttggcagtaccccatgtccgaagaggaatcctccgacgtggaaatccggaacgaggaaaacaactccggcctgttcgtgacc gtgctggaagtgtcctctgcctctgctgctcacaccggactgtacacctgttactacaatcacacccagaccgaagagaacga gctggaaggccggcacatctacatctacgtgcccgatcctgacgtggcctttgtgcctctgggcatgaccgactacctggtca tcgtggaagatgacgactccgctatcatcccctgccggaccacagatcctgagacacctgtgacactgcacaactccgaaggc gtggtgcctgcctcctacgattctagacagggcttcaacggcaccttcaccgtgggaccttacatctgcgaggctaccgtgaa gggcaagaagttccagacaatccccttcaacgtgtacgccctgaaggccacctctgagctggacctggaaatggaagccctga aaaccgtgtacaagagcggcgagacaatcgtcgtgacctgcgccgtgttcaacaacgaggtggtggacctgcagtggacctat cctggcgaagtgaaaggcaagggcatcaccatgctggaagagatcaaggtgccctccatcaagctggtgtataccctgaccgt gcctgaggccacagtgaaggactctggcgactacgagtgtgccgctagacaggccaccagagaagtcaaagagatgaagaaag tcaccatctccgtgcacgagaaaggcggcggaggcggaagcggtggcggaggaagcggaggcggcggatctgcttctcctgct gctccagctccagcttctccagcagctcctgcaccttctgcaccagctgcaagtcctgcagcacccgcaccagctagtcctgc cgctcctgctcctagtgctcctgccgcaagtccagctgctcccgctcctgcatcaccagccgcaccagcaccaagtgctccag ctgcctctccagcagcaccagctccagcaagccctgctgcaccagcaccttcagctccagcagcatcacccgctgcacccgct ccagcatctcccgctgctccagcaccaagcgcacccgctgctagcccagccgctccagctcctgccagtcctgctgctcctgc accatctgctcccgcagcttcaccagctgctcccgcaccagctagcccagcagcaccagcaccatctgcacccgccgcatctc ccgccgcaccagctccagctagtcccgcagctcccgctccatctgctccagccgctagtcccgctgctcctgctccagctagt cctgctgcacccgctcctagcgcaccagctgcttcacccgcagctccagctccagcttcacccgctgcaccagctccatctgc tccagctggtggcggaggatctggcggaggcggatctggcggcggtggttcttctgataccggcagacccttcgtggaaatgt acagcgagatccccgagatcatccacatgaccgagggcagagagctggtcatcccttgcagagtgacctctcctaacatcaca gtgaccctgaagaagtttcccctggacacactgatccccgacggcaagagaatcatctgggactcccggaagggcttcatcat ctccaacgccacctacaaagagatcggactgctgacctgcgaagccactgtgaacggccacctgtacaagaccaactatctga cccacagacagaccaacaccatcatcgacgtggtgctgagcccctctcatggcatcgagctgtccgtgggagagaaactggtg ctgaactgcaccgccagaaccgagctgaacgtgggcatcgacttcaactgggagtaccccagctccaaacaccagcacaagaa gctggtcaaccgggatctgaaaacccagtccggctccgaaatgaagaaattcctgagcaccctgaccatcgacggcgtgacca -continued gatctgaccagggcctgtatacctgtgccgcctcttctggcctgatgaccaagaaaaactccaccttcgtgcgggtccacgag aagcaccatcaccaccatcat SEQ ID No. 28:
Amino acid sequence of EPS1106P
MGTSHPAFLVLGCLLTGLSLILCQLSLPSILPNENEKVVQLNSSFSLRCFGESEVSWQYPMSEEESSDVEIRNEENNSGLFVT VLEVSSASAAHTGLYTCYYNHTQTEENELEGRHIYIYVPDPDVAFVPLGMTDYLVIVEDDDSAIIPCRTTDPETPVTLHNSEG VVPASYDSRQGFNGTFTVGPYICEATVKGKKFQTIPFNVYALKATSELDLEMEALKTVYKSGETIVVTCAVFNNEVVDLQWTY PGEVKGKGITMLEEIKVPSIKLVYTLTVPEATVKDSGDYECAARQATREVKEMKKVTISVHEKGGGGGSGGGGSGGGGSASPA APAPASPAAPAPSAPAASPAAPAPASPAAPAPSAPAASPAAPAPASPAAPAPSAPAASPAAPAPASPAAPAPSAPAASPAAPA PASPAAPAPSAPAASPAAPAPASPAAPAPSAPAASPAAPAPASPAAPAPSAPAASPAAPAPASPAAPAPSAPAASPAAPAPAS PAAPAPSAPAASPAAPAPASPAAPAPSAPAGGGGSGGGGSGGGGSSDTGRPFVEMYSEIPEIIHMTEGRELVIPCRVTSPNIT VTLKKFPLDTLIPDGKRIIWDSRKGFIISNATYKEIGLLTCEATVNGHLYKTNYLTHRQTNTIIDVVLSPSHGIELSVGEKLV LNCTARTELNVGIDFNWEYPSSKHQHKKLVNRDLKTQSGSEMKKFLSTLTIDGVTRSDQGLYTCAASSGLMTKKNSTFVRVHE

KHHHHHH

SEQ ID No. 29:
Nucleotide sequence encoding EPS1107P
atggtgtcctactgggatacaggcgtgctgctgtgtgccctgctgtcttgtctgctgctgaccggctcctcttctggctctga taccggcagacccttcgtggaaatgtacagcgagatccccgagatcatccacatgaccgagggcagagagctggtcatcccct gcagagtgacctctcctaacatcaccgtgactctgaagaagttccctctggacacactgatccccgacggcaagagaatcatc tgggactcccggaagggcttcatcatctccaacgccacctacaaagagatcggcctgctgacctgcgaggccaccgttaatgg ccacctgtacaagaccaactatctgacccacagacagaccaacaccatcatcgacgtggtgctgagcccctctcatggcatcg agctgtccgtgggagaaaagctggtgctgaactgcaccgccagaaccgagctgaacgtgggcatcgacttcaactgggagtac ccctccagcaagcaccagcacaagaagctggtcaaccgggacctgaaaacccagtccggctccgagatgaagaaattcctgag caccctgaccatcgacggcgtgaccagatctgaccagggcctgtatacctgcgccgcttcctctggcctgatgaccaagaaaa actccaccttcgtgcgggtgcacgagaaaggtggcggaggatctggcggaggcggctctggcggcggtggatctgcttctcct gctgctccagctccagcttctccagcagctcctgcaccttctgcaccagctgcaagtcctgcagcacccgcaccagctagtcc tgccgctcctgctcctagtgctcctgccgcaagtccagctgctcccgctcctgcaagcccagctgcaccagcaccaagtgctc cagctgcctcaccagccgcaccagctccagcaagccctgcagctcccgctccttcagctcctgctgcttctcccgcagcaccc gctccagcatcaccagccgctccagcaccatcagctccagcagcatctcctgcagctccagctcctgctagtcccgctgctcc cgcacctagtgcaccagccgcttctcccgccgctcctgctcctgcatctcctgctgcacccgctccatctgctcccgccgcat cacccgcagctcccgcaccagcctctccagctgcaccagctcctagcgcaccagcagctagcccagctgctcctgcaccagct agccccgcagctccagctccaagcgctcctgctgcatccccagctgctccagctcctgcctcaccagctgctccagcaccttc tgctcccgctggcggtggcggaagcggaggtggtggtagtggcggcggaggttctcagctgtccctgccttctatcctgccta acgagaacgagaaggtggtccagctgaactcctccttctctctgcggtgcttcggcgagtccgaagtgtcttggcagtacccc atgtccgaagaggaatcctccgacgtggaaatccggaacgaggaaaacaactccggcctgttcgtgaccgtgctggaagtgtc ctctgcctctgctgctcacaccggcctgtacacatgctactacaatcacacccagaccgaagagaacgagctggaaggccggc acatctacatctacgtgcccgatcctgacgtggcctttgtgcctctgggcatgaccgactacctggtcatcgtggaagatgac gactccgctatcatcccttgccggaccaccgatccagagacacctgtgacactgcacaactccgaaggcgtggtgcctgcctc ctacgattctagacagggcttcaacggcaccttcaccgtgggaccttacatctgcgaggctacagtgaagggcaagaagtttc agacaatccccttcaacgtgtacgccctgaaggccacctctgagctggacctggaaatggaagctctgaaaaccgtgtacaag tccggcgagacaatcgtcgtgacctgtgccgtgttcaacaacgaagtggtggacctgcagtggacctatcctggcgaagtgaa aggcaagggcatcaccatgctggaagagatcaaggtgccctccatcaagctggtgtataccctgaccgtgcctgaggccactg -continued tgaaggactctggcgactacgagtgtgccgctagacaggccaccagagaagtcaaagaaatgaagaaagtgaccatctccgtc cacgagaagggccaccaccaccatcaccat SEQ ID No. 30:
Amino acid sequence of EPS1107P MVSYWDTGVLLCALLSCLLLTGSSSGSDTGRPFVEMYSEIPEIIHMTEGRELVIPCRVTSPNITVTLKKFPLDTLIPDGKRII WDSRKGFIISNATYKEIGLLTCEATVNGHLYKTNYLTHRQTNTIIDVVLSPSHGIELSVGEKLVLNCTARTELNVGIDFNWEY PSSKHQHKKLVNRDLKTQSGSEMKKFLSTLTIDGVTRSDQGLYTCAASSGLMTKKNSTFVRVHEKGGGGSGGGGSGGGGSASP AAPAPASPAAPAPSAPAASPAAPAPASPAAPAPSAPAASPAAPAPASPAAPAPSAPAASPAAPAPASPAAPAPSAPAASPAAP APASPAAPAPSAPAASPAAPAPASPAAPAPSAPAASPAAPAPASPAAPAPSAPAASPAAPAPASPAAPAPSAPAASPAAPAPA SPAAPAPSAPAASPAAPAPASPAAPAPSAPAGGGGSGGGGSGGGGSQLSLPSILPNENEKVVQLNSSFSLRCFGESEVSWQYP MSEEESSDVEIRNEENNSGLFVTVLEVSSASAAHTGLYTCYYNHTQTEENELEGRHIYIYVPDPDVAFVPLGMTDYLVIVEDD DSAIIPCRTTDPETPVTLHNSEGVVPASYDSRQGFNGTFTVGPYICEATVKGKKFQTIPFNVYALKATSELDLEMEALKTVYK SGETIVVTCAVFNNEVVDLQWTYPGEVKGKGITMLEEIKVPSIKLVYTLTVPEATVKDSGDYECAARQATREVKEMKKVTISV

HEKGHHHHHH

SEQ ID No. 31:
Nucleotide sequence encoding EPS1109P atgggctggtcctgcatcatcctgtttctggtggctaccgctaccggcgtgcactctcaccaccatcaccatcacgcttctcc agccgctccagctcctgcttctcctgctgcaccagcaccatctgctccagctgcaagtccagctgctcccgcaccagcaagtc ctgcagcacccgctcctagtgctccagcagcatctcccgcagcaccagctccagcttcaccagcagctcccgctccatcagca ccagccgcatcacccgctgctccagcaccagcttctcccgccgctcctgcaccttctgcacccgcagctagccctgctgctcc tgctccagcatctccagctgcacccgctccaagcgcacccgctgctagtccagcagcaccagcaccagctagtcccgctgctc cagctccttctgctccagcagcttcaccagccgctccagcaccagctagcccagccgcaccagcacctagtgctcccgccgct agtcctgcagctccagctcctgctagcccagctgctcccgctcctagcgctcctgccgcttcaccagctgcaccagctccagc aagtccagccgctcctgctccaagtgcaccagctgcctctccagctgctcctgctcctgcaagtcccgcagctccagcaccta gcgcaccagcatctgataccggcagacccttcgtggaaatgtacagcgagatccccgagatcatccacatgaccgagggcaga gagctggtcatcccctgcagagtgacctctcctaacatcaccgtgactctgaagaagttccctctggacacactgatccccga cggcaagagaatcatctgggactcccggaagggcttcatcatctccaacgccacctacaaagagatcggcctgctgacctgcg aggccaccgttaatggccacctgtacaagaccaactatctgacccacagacagaccaacaccatcatcgacgtggtgctgagc cccctctcatggcatcgagctgtccgtgggagaaaagctcgtgctgaactgcaccgccagaaccgagctgaacgtgggcatcga cttcaactgggagtaccccagctccaaacaccagcacaagaaactggtcaaccgggacctgaaaacccagtccggctccgaga tgaagaaattcctgagcaccctgaccatcgacggcgtgaccagatctgaccagggcctgtatacctgcgccgcttcttctggc ctgatgaccaagaaaaactccaccttcgtgcgcgtgcacgagaagcagctgtccctgccttctatcctgcctaacgagaacga gaaggtggtccagctgaactcctccttctctctgcggtgcttcggcgagtccgaagtgtcttggcagtaccccatgtccgaag aggaatcctccgacgtggaaatccggaacgaggaaaacaactccggcctgttcgtgaccgtgctggaagtgtcctctgcctct gctgctcacaccggcctgtacacatgctactacaatcacacccagaccgaagagaacgagctggaaggccggcacatctacat ctacgtgcccgatcctgacgtggcctttgtgcctctgggcatgaccgactacctggtcatcgtggaagatgacgactccgcta tcatcccttgccggaccaccgatccagagacacctgtgacactgcacaactccgaaggcgtggtgcctgcctcctacgattct agacagggcttcaacggcaccttcaccgtgggaccttacatctgcgaggctacagtgaagggcaagaagtttcagacaatccc cttcaacgtgtacgccctgaaggccacctctgagctggacctggaaatggaagctctgaaaaccgtgtacaagtccggcgaga caatcgtcgtgacctgtgccgtgttcaacaacgaggtggtggacctgcagtggacctatcctggcgaagtgaaaggcaagggc atcaccatgctggaagagatcaaggtgccctccatcaagctggtgtataccctgaccgtgcctgaggccactgtgaaggactc tggcgactacgagtgtgccgctagacaggccaccagagaagtcaaagaaatgaagaaagtgaccatctccgtccacgagaagg gc -continued SEQ ID No. 32:
Amino acid sequence of EPS1109P
MGWSCIILFLVATATGVHSHHHHHHASPAAPAPASPAAPAPSAPAASPAAPAPASPAAPAPSAPAASPAAPAPASPAAPAPSA PAASPAAPAPASPAAPAPSAPAASPAAPAPASPAAPAPSAPAASPAAPAPASPAAPAPSAPAASPAAPAPASPAAPAPSAPAA SPAAPAPASPAAPAPSAPAASPAAPAPASPAAPAPSAPAASPAAPAPASPAAPAPSAPASDTGRPFVEMYSEIPEIIHMTEGR ELVIPCRVTSPNITVTLKKFPLDTLIPDGKRIIWDSRKGFIISNATYKEIGLLTCEATVNGHLYKTNYLTHRQTNTIIDVVLS PSHGIELSVGEKLVLNCTARTELNVGIDFNWEYPSSKHQHKKLVNRDLKTQSGSEMKKFLSTLTIDGVTRSDQGLYTCAASSG LMTKKNSTFVRVHEKQLSLPSILPNENEKVVQLNSSFSLRCFGESEVSWQYPMSEEESSDVEIRNEENNSGLFVTVLEVSSAS AAHTGLYTCYYNHTQTEENELEGRHIYIYVPDPDVAFVPLGMTDYLVIVEDDDSAIIPCRTTDPETPVTLHNSEGVVPASYDS RQGFNGTFTVGPYICEATVKGKKFQTIPFNVYALKATSELDLEMEALKTVYKSGETIVVTCAVFNNEVVDLQWTYPGEVKGKG

ITMLEEIKVPSIKLVYTLTVPEATVKDSGDYECAARQATREVKEMKKVTISVHEKG

SEQ ID No. 33:
Nucleotide sequence encoding EPS1110P
atgggctggtcctgcatcatcctgtttctggtggctaccgctaccggcgtgcactctcaccaccatcaccatcacgcttctcc agccgctccagctcctgcttctcctgctgcaccagcaccatctgctccagctgcaagtccagctgctcccgcaccagcaagtc ctgcagcacccgctcctagtgctccagcagcatctcccgcagcaccagctccagcttcaccagcagctcccgctccatcagca ccagccgcatcacccgctgctccagcaccagcttctcccgccgctcctgcaccttctgcacccgcagctagccctgctgctcc tgctccagcatctccagctgcacccgctccaagcgcacccgctgctagtccagcagcaccagcaccagctagtcccgctgctc cagctccttctgctccagcagcttcaccagccgctccagcaccagctagcccagccgcaccagcacctagtgctcccgccgct agtcctgcagctccagctectgctagcccagctgctcccgctcctagcgctcctgccgcttcaccagctgcaccagctccagc aagtccagccgctcctgctccaagtgcaccagctgcctctccagctgctcctgctcctgcaagtcccgcagctccagcaccta gcgcaccagctcaactgtccctgccttccatcctgcctaacgagaacgagaaggtggtccagctgaactcctccttctctctg cggtgcttcggcgagtccgaagtgtcttggcagtaccccatgtccgaagaggaatcctccgacgtggaaatccggaacgagga aaacaactccggcctgttcgtgaccgtgctggaagtgtcctctgcctctgctgctcacaccggcctgtacacctgttactaca atcacacccagaccgaagagaacgagctggaaggccggcacatctacatctacgtgcccgatcctgacgtggcctttgtgcct ctgggcatgaccgactacctggtcatcgtggaagatgacgactccgctatcatcccctgccggaccacagatcctgagacacc tgtgacactgcacaactccgaaggcgtggtgcctgcctcctacgattctagacagggcttcaacggcaccttcaccgtgggac cttacatctgcgaggctaccgtgaagggcaagaagttccagacaatccccttcaacgtgtacgccctgaaggccacctctgag ctggacctggaaatggaagccctgaaaaccgtgtacaagtccggcgagacaatcgtcgtgacctgcgccgtgttcaacaacga ggtggtggacctgcagtggacctatcctggcgaagtgaaaggcaagggcatcaccatgctggaagagatcaaggtgccctcca tcaagctggtgtataccctgaccgtgcctgaggccacagtgaaggactctggcgactacgagtgtgccgctagacaggccacc agagaagtcaaagagatgaagaaagtcaccatctccgtgcacgagaagggctccgataccggcagacccttcgtggaaatgta cagcgagatccccgagatcatccacatgaccgagggcagagagctggtcatcccttgcagagtgacctctcctaacatcacag tgaccctgaagaagtttcccctggacacactgatccccgacggcaagagaatcatctgggactcccggaagggcttcatcatc tccaacgccacctacaaagagatcggcctgctgacctgtgaagccaccgtgaatggccacctgtacaagaccaactatctgac ccacagacagaccaacaccatcatcgacgtggtgctgtccccaagccatggcatcgagctgtccgtgggagaaaagctcgtgc tgaactgcaccgccagaaccgagctgaacgtgggcatcgacttcaactgggagtaccccagctccaaacaccagcacaagaaa ctggtcaaccgggacctcaagacccagtccggctccgaaatgaagaaattcctgagcaccctgaccatcgacggcgtgaccag atctgaccagggactgtatacctgtgccgcctcctctggcctgatgaccaagaaaaactccaccttcgtgcgggtccacgaga ag -continued SEQ ID No. 34:
Amino acid sequence of EPS1110P
MGWSCIILFLVATATGVHSHHHHHHASPAAPAPASPAAPAPSAPAASPAAPAPASPAAPAPSAPAASPAAPAPASPAAPAPSA PAASPAAPAPASPAAPAPSAPAASPAAPAPASPAAPAPSAPAASPAAPAPASPAAPAPSAPAASPAAPAPASPAAPAPSAPAA SPAAPAPASPAAPAPSAPAASPAAPAPASPAAPAPSAPAASPAAPAPASPAAPAPSAPAQLSLPSILPNENEKVVQLNSSFSL RCFGESEVSWQYPMSEEESSDVEIRNEENNSGLFVTVLEVSSASAAHTGLYTCYYNHTQTEENELEGRHIYIYVPDPDVAFVP LGMTDYLVIVEDDDSAIIPCRTTDPETPVTLHNSEGVVPASYDSRQGFNGTFTVGPYICEATVKGKKFQTIPFNVYALKATSE LDLEMEALKTVYKSGETIVVTCAVFNNEVVDLQWTYPGEVKGKGITMLEEIKVPSIKLVYTLTVPEATVKDSGDYECAARQAT REVKEMKKVTISVHEKGSDTGRPFVEMYSEIPEIIHMTEGRELVIPCRVTSPNITVTLKKFPLDTLIPDGKRIIWDSRKGFII SNATYKEIGLLTCEATVNGHLYKTNYLTHRQTNTIIDVVLSPSHGIELSVGEKLVLNCTARTELNVGIDFNWEYPSSKHQHKK

LVNRDLKTQSGSEMKKFLSTLTIDGVTRSDQGLYTCAASSGLMTKKNSTFVRVHEK

SEQ ID No. 35:
Nucleotide sequence encoding EPS1111P
atgggctggtcctgcatcatcctgtttctggtggctaccgctaccggcgtgcactctcaccaccatcaccatcacgcttctcc agccgctccagctcctgcttctcctgctgcaccagcaccatctgctccagctgcaagtccagctgctcccgcaccagcaagtc ctgcagcacccgctcctagtgctccagcagcatctcccgcagcaccagctccagcttcaccagcagctcccgctccatcagca ccagccgcatcacccgctgctccagcaccagcttctcccgccgctcctgcaccttctgcacccgcagctagccctgctgctcc tgctccagcatctccagctgcacccgctccaagcgcacccgctgctagtccagcagcaccagcaccagctagtcccgctgctc cagctccttctgctccagcagcttcaccagccgctccagcaccagctagcccagccgcaccagcacctagtgctcccgccgct agtcctgcagctccagctcctgctagcccagctgctcccgctcctagcgctcctgccgcttcaccagctgcaccagctccagc aagtccagccgctcctgctccaagtgcaccagctgcctctccagctgctcctgctcctgcaagtcccgcagctccagcaccta gcgcaccagcatctgataccggcagacccttcgtggaaatgtacagcgagatccccgagatcatccacatgaccgagggcaga gagctggtcatcccctgcagagtgacctctcctaacatcaccgtgactctgaagaagttccctctggacacactgatccccga cggcaagagaatcatctgggactcccggaagggcttcatcatctccaacgccacctacaaagagatcggcctgctgacctgcg aggccaccgttaatggccacctgtacaagaccaactatctgacccacagacagaccaacaccatcatcgacgtggtgctgagc cctctcatggcatcgagctgtccgtgggagaaaagctcgtgctgaactgcaccgccagaaccgagctgaacgtgggcatcga cttcaactgggagtaccccagctccaaacaccagcacaagaaactggtcaaccgggacctgaaaacccagtccggctccgaga tgaagaaattcctgagcaccctgaccatcgacggcgtgaccagatctgaccagggcctgtatacctgcgccgcttcttctggc ctgatgaccaagaaaaactccaccttcgtgcgcgtgcacgagaagaacgatgccgaggaactgttcatcttcctgaccgagat taccgagatcacaatcccctgccgcgtgacagatcctcagctggtggttaccctgcatgagaagaaaggcgacgtggccctgc ctgtgccttacgatcatcagagaggcttctccggcatcttcgaggaccggtcttacatctgcaagaccaccatcggcgacaga gaggtggactccgacgcctactacgtgtacagactccaggtgtcctccatcaacgtgtccgtgaatgccgtgcagacagttgt gcggcagggcgagaatatcaccctgatgtgcatcgtgatcggcaacgaggtggtcaacttcgagtggacctatcctcggaaag aatctggccggctggtggaacctgtgaccgacttcctgctggacatgccctaccacatccggtctatcctgcacatcccttcc gccgagctggaagattccggcacctacacctgtaacgtgaccgagtccgtgaacgaccaccaggacgagaaggccatcaatat caccgtggtggaatccggctacgtgcggctgttgggagaagtgggcacactgcagtttgctgagctg SEQ ID No. 36:
Amino acid sequence of EPS1111P
MGWSCIILFLVATATGVHS HHHHHHASPAAPAPASPAAPAPSAPAASPAAPAPASPAAPAPSAPAASPAAPAPASPAAPAPSAPAASPAAPAPASPAAPAPS APAASPAAPAPASPAAPAPSAPAASPAAPAPASPAAPAPSAPAASPAAPAPASPAAPAPSAPAASPAAPAPASPAAPAPSAPA ASPAAPAPASPAAPAPSAPAASPAAPAPASPAAPAPSAPASDTGRPFVEMYSEIPEIIHMTEGRELVIPCRVTSPNITVTLKK FPLDTLIPDGKRIIWDSRKGFIISNATYKEIGLLTCEATVNGHLYKTNYLTHRQTNTIIDVVLSPSHGIELSVGEKLVLNCTA -continued RTELNVGIDFNWEYPSSKHQHKKLVNRDLKTQSGSEMKKFLSTLTIDGVTRSDQGLYTCAASSGLMTKKNSTFVRVHEKNDAE ELFIFLTEITEITIPCRVTDPQLVVTLHEKKGDVALPVPYDHQRGFSGIFEDRSYICKTTIGDREVDSDAYYVYRLQVSSINV SVNAVQTVVRQGENITLMCIVIGNEVVNFEWTYPRKESGRLVEPVTDFLLDMPYHIRSILHIPSAELEDSGTYTCNVTESVND

HQDEKAINITVVESGYVRLLGEVGTLQFAEL

SEQ ID No. 37:
Nucleotide sequence encoding EPS1113P
atgggtacaagccatcccgccttcctggtcctgggttgcctgctgactggtctgtctctgatcctgtgc cagctgtccctgccttctatcctgcctaacgagaacgagaaggtggtgcagctgaactcctccttctctctgcggtgcttcgg cgagtccgaagtgtcttggcagtaccccatgtccgaagaggaatcctccgacgtggaaatccggaacgaggaaaacaactccg gcctgttcgtgaccgtgctggaagtgtcctctgcctctgctgctcacaccggcctgtacacctgttactacaatcacacccag accgaagagaacgagctggaaggccggcacatctacatctacgtgcccgatcctgacgtggcctttgtgcctctgggcatgac cgactacctggtcatcgtggaagatgacgactccgctatcatcccctgccggaccacagatcctgagacacctgtgacactgc acaactccgaaggcgtggtgcctgcctcctacgattctagacagggcttcaacggcaccttcaccgtgggaccttacatctgc gaggctaccgtgaagggcaagaagttccagacaatccccttcaacgtgtacgccctgaaggccacctctgagctggacctgga aatggaagccctgaaaaccgtgtacaagtccggcgagacaatcgtcgtgacctgcgccgtgttcaacaacgaggtggtggacc tgcagtggacctatcctggcgaagtgaaaggcaagggcatcaccatgctggaagagatcaaggtgccctccatcaagctggtg tataccctgaccgtgcctgaggccacagtgaaggactctggcgactacgagtgtgccgctagacaggccaccagagaagtcaa agagatgaagaaagtcaccatctccgtgcacgagaagggcgcctctccagctgctcctgctccagctagtcctgcagctccag ctccatctgcaccagctgcttctccagcagcacccgcaccagcttctcccgccgctcctgcacctagtgcaccagcagctagc cctgctgcaccagcaccagcaagtccagccgcaccagctcctagtgctccagctgcatcccctgctgctcccgctcctgcttc accagccgctccagcaccatcagctcccgcagcatctccagcagctccagctcctgcttctcctgctgcacccgctccatctg ctcccgctgcaagtcctgctgctcctgcaccagcatcacccgcagctcccgcaccaagcgctccagccgcttcacccgcagca ccagctccagcctcaccagcagcaccagcaccttccgctccagctgctagtccagccgctcctgctcctgcaagccccgctgc tccagctcctagcgcacccgctgctagccccgcagctcccgctccagcaagcccagcagctcctgctccttctgctccagcag catctcctgccgcaccagctccagctagcccagctgctcccgcaccatccgcaccagcagcaagtcccgcagctccagcacca gctagtcccgcagcacccgcaccttcagcaccagccgcatcaccagctgctccagctccagcatctcccgctgcaccagcacc aagtgctcccgctgcttctcctgcagctcctgctccagcctctccagctgctcccgcaccttctgctccagctgcctctccag ctgctccagcaccagcttcaccagctgctcccgctcctagtgctcctgccgctagtccagcagctcccgcaccagctagccct gccgctcctgctccaagtgctccagccgcaagtcccgctgcacccgctccagcttctccagcagctcccgctccaagcgcacc cgcagcttctcccgctgctcccgcaccagcaagtcctgctgctccagctccttcagctcctgccgcttctcctgctgctccag ctcctgcaagtccagctgctccagcaccaagtgcaccagcagcaagtccagctgctcctgctcctgcctctccagcagcacca gctcctagcgcaccagccgccagtcctgcagcaccagctccagcttctcccgctgctcctgctccttcagcaccagctgctag tcctgctgctcctgctccagcttctcctgccgctccagcaccaagcgctccagctgcatctcccgcagctcccgctccagcat ctcctgcagcacccgcaccatcagctccagctgcttccccagccgctcctgcaccagctagcccagcagctcctgcacctagc gctcccgctgcttcaccagcagctccagcaccagccagtccagctgctcctgcaccatctgcacccgctgctagtcccgctgc tccagctcctgctagccctgcagcaccagctccaagtgcacccgccgcatcacccgccgcaccagcaccagcaagccctgcag cacccgctccaagcgctccagctgctagcccagcagcaccagcaccagcatcaccagccgctccagcaccttctgcaccagca gcttcacccgctgcacccgctccagcatcacccgccgctccagctcctagcgctcctgcagcctctcctgcagctccagcacc agcaagccccgctgcaccagcaccatctgctccagcagctagccctgcagctcccgctcctgcatctcccgccgcaccagctc catctgcacccgcagcatctgataccggcagacccttcgtggaaatgtacagcgagatccccgagatcatccacatgaccgag ggcagagagctggtcatcccttgcagagtgacctctcctaacatcacagtgaccctgaagaagtttcccctggacacactgat ccccgacggcaagagaatcatctgggactoccggaagggcttcatcatctccaacgccacctacaaagagatcggcctgctga -continued cctgtgaagccaccgtgaatggccacctgtacaagaccaactatctgacccacagacagaccaacaccatcatcgacgtggtg ctgagcccctctcatggcatcgagctgtccgtgggagagaagctcgtgctgaactgtaccgccagaaccgagctgaacgtggg catcgacttcaactgggagtaccctagctccaaacaccagcacaagaaactggtcaaccgggacctcaagacccagtccggct ccgaaatgaagaaattcctgtccacactgaccatcgacggcgtgaccagatctgaccagggactgtatacctgtgccgcctcc tctggcctgatgaccaagaaaaactccaccttcgtgcgggtccacgagaagcaccaccaccatcatcat SEQ ID No. 38:
Amino acid sequence of EPS1113P
MGTSHPAFLVLGCLLTGLSLILCQLSLPSILPNENEKVVQLNSSFSLRCFGESEVSWQYPMSEEESSDVEIRNEENNSGLFVT VLEVSSASAAHTGLYTCYYNHTQTEENELEGRHIYIYVPDPDVAFVPLGMTDYLVIVEDDDSAIIPCRTTDPETPVTLHNSEG VVPASYDSRQGFNGTFTVGPYICEATVKGKKFQTIPFNVYALKATSELDLEMEALKTVYKSGETIVVTCAVFNNEVVDLQWTY PGEVKGKGITMLEEIKVPSIKLVYTLTVPEATVKDSGDYECAARQATREVKEMKKVTISVHEKGASPAAPAPASPAAPAPSAP AASPAAPAPASPAAPAPSAPAASPAAPAPASPAAPAPSAPAASPAAPAPASPAAPAPSAPAASPAAPAPASPAAPAPSAPAAS PAAPAPASPAAPAPSAPAASPAAPAPASPAAPAPSAPAASPAAPAPASPAAPAPSAPAASPAAPAPASPAAPAPSAPAASPAA PAPASPAAPAPSAPAASPAAPAPASPAAPAPSAPAASPAAPAPASPAAPAPSAPAASPAAPAPASPAAPAPSAPAASPAAPAP ASPAAPAPSAPAASPAAPAPASPAAPAPSAPAASPAAPAPASPAAPAPSAPAASPAAPAPASPAAPAPSAPAASPAAPAPASP AAPAPSAPAASPAAPAPASPAAPAPSAPAASPAAPAPASPAAPAPSAPAASPAAPAPASPAAPAPSAPAASPAAPAPASPAAP APSAPAASPAAPAPASPAAPAPSAPAASPAAPAPASPAAPAPSAPAASPAAPAPASPAAPAPSAPAASPAAPAPASPAAPAPS APAASPAAPAPASPAAPAPSAPAASPAAPAPASPAAPAPSAPAASPAAPAPASPAAPAPSAPAASPAAPAPASPAAPAPSAPA ASDTGRPFVEMYSEIPEIIHMTEGRELVIPCRVTSPNITVTLKKFPLDTLIPDGKRIIWDSRKGFIISNATYKEIGLLTCEAT VNGHLYKTNYLTHRQTNTIIDVVLSPSHGIELSVGEKLVLNCTARTELNVGIDFNWEYPSSKHQHKKLVNRDLKTQSGSEMKK

FLSTLTIDGVTRSDQGLYTCAASSGLMTKKNSTFVRVHEKHHHHHH

SEQ ID No. 39:
Nucleotide sequence encoding EPS1114P
atgggcaccagccatcctgcttttctggtgctgggatgcctgctgaccggcctgtctctgattctgtgccagctgtccctgcc ttccatcctgcctaacgagaacgagaaggtggtgcagctgaactcctccttctctctgcggtgcttcggcgagtccgaagtgt cttggcagtaccccatgtccgaagaggaatcctccgacgtggaaatccggaacgaggaaaacaactccggcctgttcgtgacc gtgctggaagtgtcctctgcctctgctgctcacaccggactgtacacctgttactacaatcacacccagaccgaagagaacga gctggaaggccggcacatctacatctacgtgcccgatcctgacgtggcctttgtgcctctgggcatgaccgactacctggtca tcgtggaagatgacgactccgctatcatcccctgccggaccacagatcctgagacacctgtgacactgcacaactccgaaggc gtggtgcctgcctcctacgattctagacagggcttcaacggcaccttcaccgtgggaccttacatctgcgaggctaccgtgaa gggcaagaagttccagacaatccccttcaacgtgtacgccctgaaggccacctctgagctggacctggaaatggaagccctga aaaccgtgtacaagagcggcgagacaatcgtcgtgacctgcgccgtgttcaacaacgaggtggtggacctgcagtggacctat cctggcgaagtgaaaggcaagggcatcaccatgctggaagagatcaaggtgccctccatcaagctggtgtataccctgaccgt gcctgaggccacagtgaaggactctggcgactacgagtgtgccgctagacaggccaccagagaagtcaaagagatgaagaaag tcaccatctccgtgcacgagaaaggcggcggaggcggaagcggtggcggaggaagcggaggcggcggatctgcttctcctgct gctcctgctccagctagtcctgctgcaccagcaccttcagctccagctgcttctccagcagcacccgcaccagcatcaccagc cgctccagcaccaagtgcaccagctgctagcccagctgctcccgctcctgcatctcctgcagcaccagctccatctgcaccag cagcaagtccagcagctccagctcctgcttcacccgctgctcccgcaccatctgctccagccgcatcacccgctgcaccagct ccagcttctcccgccgctccagctccttctgctcctgcagcatctcctgctgctccagcaccagcaagcccagccgctcctgc tccatcagcacccgctgcctctccagctgctcctgcaccagcctctccagctgcacccgctcctagtgctccagctgcaagtc ccgccgcaccagcaccagctagtcctgcagctcctgcaccaagcgctccagcagcttcccctgcagctcctgctcctgcctct cctgccgctcctgctcctagtgcaccagccgcatctcccgcagctcccgctcctgctagtccagcagctcccgcaccttctgc -continued accagcagcttccccagccgcaccagctccagcaagccccgctgctccagcacctagtgctcccgctgcctcaccagcagctc ccgctccagcaagccctgctgcacccgctccaagcgcaccagcagcatcaccagctgcacccgcaccagctagcccagcagca ccagctcctagcgctcccgcagctagccctgctgctcccgcaccagcttcacccgcagcacccgctcoatcagctcccgccgc tagtcccgctgctcctgctcctgcaagccctgctgctcctgctccttctgctccagctgctagtcctgccgctcctgctccag cttctccagcagctcctgcacctagcgcacccgccgctagtccagcagcaccagcaccagcttctccagctgcaccagcacca tcagcacccgcagcttcaccagcagctccagcaccagcatctcccgcagctccagcaccatcagctccagcagcaagcccagc tgcaccagctccagcatcaccagctgctcccgctccaagcgctcctgctgcttctcctgccgcaccagctccagccagtccag cagcacccgctccaagtgcacccgccgcttctccagctgctccagctcctgctagccccgcagctccagctccaagtgctcca gccgccagtcctgcagctcccgcaccagctagccccgctgctcctgcaccatccgcaccagctgctagtcccgcagcaccagc tccagctagcccagccgcaccagcaccatctgctcccgctgctagccctgcagcacccgctccagccagtcctgctgctccag ctcoatctgctcccgccgcttctcctgcagctcctgcaccagcttctcccgctgctcctgctcctagcgctccagcagcctct ccagcagcaccagctccagcaagtcctgcagcaccagcacctagtgcaccagcagcttcacccgctgctcccgctccagcatc tccagctgctccagcaccttctgctccagctgcaagccccgcagctcctgcaccagcaagtcctgccgctccagctcctagcg ctcctgctgcaagtccagctgctcccgctccagcttcaccagccgcaccagcaccttccgcaccagcagctagtccagctgct cctgctccagctagcccagctgctccagctccttcagcaccagcagccggtggcggaggatctggcggaggcggatctggcgg cggtggttcttctgataccggcagacccttcgtggaaatgtacagcgagat ccccgagatcatccacatgaccgagggcagagagctggtcatcccttgcagagtgacctctcctaacatcacagtgaccctga agaagtttcccctggacacactgatccccgacggcaagagaatcatctgggactcccggaagggcttcatcatctccaacgcc acctacaaagagatcggactgctgacctgcgaagccactgtgaacggccacctgtacaagaccaactatctgacccacagaca gaccaacaccatcatcgacgtggtgctgagcccctctcatggcatcgagctgtccgt gggagagaaactggtgctgaactgcaccgccagaaccgagctgaacgtgggcatcgacttcaactgggagtaccccagctcca aacaccagcacaagaagctggtcaaccgggatctgaaaacccagtccggctccgaaatgaagaaattcctgagcaccctgacc atcgacggcgtgaccagatctgaccagggcctgtatacctgtgccgcctcttctggcctgatgaccaagaaaaactccacctt cgtgcgggtccacgagaagcaccatcaccaccatcat SEQ ID No. 40:
Amino acid sequence of EPS1114P
MGTSHPAFLVLGCLLTGLSLILCQLSLPSILPNENEKVVQLNSSFSLRCFGESEVSWQYPMSEEESSDVEIRNEENNSGLFVT VLEVSSASAAHTGLYTCYYNHTQTEENELEGRHIYIYVPDPDVAFVPLGMTDYLVIVEDDDSAIIPCRTTDPETPVTLHNSEG VVPASYDSRQGFNGTFTVGPYICEATVKGKKFQTIPFNVYALKATSELDLEMEALKTVYKSGETIVVTCAVFNNEVVDLQWTY PGEVKGKGITMLEEIKVPSIKLVYTLTVPEATVKDSGDYECAARQATREVKEMKKVTISVHEKGGGGGSGGGGSGGGGSASPA APAPASPAAPAPSAPAASPAAPAPASPAAPAPSAPAASPAAPAPASPAAPAPSAPAASPAAPAPASPAAPAPSAPAASPAAPA PASPAAPAPSAPAASPAAPAPASPAAPAPSAPAASPAAPAPASPAAPAPSAPAASPAAPAPASPAAPAPSAPAASPAAPAPAS PAAPAPSAPAASPAAPAPASPAAPAPSAPAASPAAPAPASPAAPAPSAPAASPAAPAPASPAAPAPSAPAASPAAPAPASPAA PAPSAPAASPAAPAPASPAAPAPSAPAASPAAPAPASPAAPAPSAPAASPAAPAPASPAAPAPSAPAASPAAPAPASPAAPAP SAPAASPAAPAPASPAAPAPSAPAASPAAPAPASPAAPAPSAPAASPAAPAPASPAAPAPSAPAASPAAPAPASPAAPAPSAP AASPAAPAPASPAAPAPSAPAASPAAPAPASPAAPAPSAPAASPAAPAPASPAAPAPSAPAASPAAPAPASPAAPAPSAPAAS PAAPAPASPAAPAPSAPAASPAAPAPASPAAPAPSAPAASPAAPAPASPAAPAPSAPAASPAAPAPASPAAPAPSAPAASPAA PAPASPAAPAPSAPAAGGGGSGGGGSGGGGSSDTGRPFVEMYSEIPEIIHMTEGRELVIPCRVTSPNITVTLKKFPLDTLIPD GKRIIWDSRKGFIISNATYKEIGLLTCEATVNGHLYKTNYLTHRQTNTIIDVVLSPSHGIELSVGEKLVLNCTARTELNVGID

FNWEYPSSKHQHKKLVNRDLKTQSGSEMKKFLSTLTIDGVTRSDQGLYTCAASSGLMTKKNSTFVRVHEKHHHHHH

-continued

SEQ ID No. 41:
Nucleotide sequence encoding EPS1115P atggtgtcctactgggatacaggcgtgctgctgtgtgccctgctgtcttgtctgctgctgaccggctcctcttctggctctga taccggcagacccttcgtggaaatgtacagcgagatccccgagatcatccacatgaccgagggcagagagctggtcatcccct gcagagtgacctctcctaacatcaccgtgactctgaagaagttccctctggacacactgatccccgacggcaagagaatcatc tgggactcccggaagggcttcatcatctccaacgccacctacaaagagatcggcctgctgacctgcgaggccaccgttaatgg ccacctgtacaagaccaactatctgacccacagacagaccaacaccatcatcgacgtggtgctgagcccctctcatggcatcg agctgtccgtgggagaaaagctggtgctgaactgcaccgccagaaccgagctgaacgtgggcatcgacttcaactgggagtac ccctccagcaagcaccagcacaagaagctggtcaaccgggacctgaaaacccagtccggctccgagatgaagaaattcctgag caccctgaccatcgacggcgtgaccagatctgaccagggcctgtatacctgcgccgcttcctctggcctgatgaccaagaaaa actccaccttcgtgcgggtgcacgagaaaggtggcggaggatctggcggaggcggctctggcggcggtggatctgcttctcct gctgctccagctccagcttctccagcagctcctgcaccttctgcaccagctgcaagtcctgcagcacccgcaccagctagtcc tgccgctcctgctcctagtgctcctgccgcaagtccagctgctcccgctcctgcaagcccagctgcaccagcaccaagtgctc cagctgcctcaccagccgcaccagctccagcaagccctgcagctcccgctecttcagctcctgctgcttctcccgcagcaccc gctccagcatcaccagccgctccagcaccatcagctccagcagcatctcctgcagctccagctcctgctagtcccgctgctcc cgcacctagtgcaccagccgcttctcccgccgctcctgctcctgcatctcctgctgcacccgctccatctgctcccgccgcat cacccgcagctcccgcaccagcctctccagctgcaccagctcctagcgcaccagcagctagcccagctgctcctgcaccagct agccccgcagctccagctccaagcgctcctgctgcatccccagctgctccagctcctgcctcaccagctgctccagcaccttc tgctcccgccgcttctcctgccgcaccagctccagctagtccagccgcaccagcaccatctgcacccgctgctagccctgctg caccagctccagcatcacccgctgcaccagctccatccgcaccagctgcttcaccagcagctcccgctccagcttcacccgct gctcccgctcctagcgctcccgcagcttcaccagctgcacccgctccagccagtccagctgctcccgcaccatccgcaccagc agcaagtcccgccgctccagctccagctagcccagctgctccagctccatctgcaccagccgcatctccagctgctccagctc cagctagtcctgctgcacccgctcctagcgctccagctgcaagtcctgccgctcctgctccagcctctcctgccgctccagca cctagcgctcccgctgccagtccagcagctccagctcctgcatctcccgccgcaccagcaccaagcgcacccgcagcatctcc cgctgctcccgctccagcaagccctgccgctcctgcaccaagtgcaccagcagcatccccagcagctcccgctccagcatctc cagcagctccagctccaagtgctccagcagctagtcctgctgctccagctcctgctagccctgcagctcctgcaccatctgct cccgcagccagtcctgcagctcctgcaccagcaagtccagctgctcctgcacctagcgctccagctgcatctcccgctgcacc agctccagcaagtcccgctgctcctgctccttctgctccagcagcttcccctgctgctcctgctcctgcttcacccgccgctc cagctccatctgctcccgctgcctctccagccgctcctgcaccagcatcaccagctgctcccgcaccaagcgcacccgctgca agcccagccgctcctgctcctgctagtccagccgctcctgcaccttcagcacccgcagcttccccagctgctccagctccagc aagtccagcagctccagctccttccgctccagctgcaagccccgcagctccagctcctgcttctcctgctgctcctgcaccat cagctccagctgctagtccagcagctcctgcaccagccagtcctgccgcaccagcaccttcagctccagctgcttcacccgct gctcccgcaccagctagtccagccgctccagcaccaagtgctcccgccgctggtggtggtggatctggtggtggcggaagcgg aggtggtggttctcagctgtccctgccttccatcctgcctaacgagaacgagaaggtggtccagctgaactcctccttctctc tgcggtgcttcggcgagtccgaagtgtcttggcagtaccccatgtccgaagaggaatcctccgacgtggaaatccggaacgag gaaaacaactccggcctgttcgtgaccgtgctggaagtgtcctctgcctctgctgctcacaccggcctgtacacatgctacta caatcacacccagaccgaagagaacgagctggaaggccggcacatctacatctacgtgcccgatcctgacgtggcctttgtgc ctctgggcatgaccgactacctggtcatcgtggaagatgacgactccgctatcatcccttgccggaccaccgatccagagaca cctgtgacactgcacaactccgaaggcgtggtgcctgcctcctacgattctagacagggcttcaacggcaccttcaccgtggg accttacatctgcgaggctacagtgaagggcaagaagtttcagacaatccccttcaacgtgtacgccctgaaggccacctctg agctggacctggaaatggaagctctgaaaaccgtgtacaagtccggcgagacaatcgtcgtgacctgtgccgtgttcaacaac -continued gaagtggtggacctgcagtggacctatcctggcgaagtgaaaggcaagggcatcacaatgctggaagagatcaaggtgccctc catcaagctggtgtataccctgaccgtgcctgaggccactgtgaaggactctggcgactacgagtgtgccgctagacaggcca ccagagaagtcaaagaaatgaagaaagtgaccatctccgtccacgagaagggccaccatcatcaccaccat SEQ ID No. 42:
Amino acid sequence of EPS1115P
MVSYWDTGVLLCALLSCLLLTGSSSG SDTGRPFVEMYSEIPEIIHMTEGRELVIPCRVTSPNITVTLKKFPLDTLIPDGKRIIWDSRKGFIISNATYKEIGLLTCEATV NGHLYKTNYLTHRQTNTIIDVVLSPSHGIELSVGEKLVLNCTARTELNVGIDFNWEYPSSKHQHKKLVNRDLKTQSGSEMKKF LSTLTIDGVTRSDQGLYTCAASSGLMTKKNSTFVRVHEKGGGGSGGGGSGGGGSASPAAPAPASPAAPAPSAPAASPAAPAPA SPAAPAPSAPAASPAAPAPASPAAPAPSAPAASPAAPAPASPAAPAPSAPAASPAAPAPASPAAPAPSAPAASPAAPAPASPA APAPSAPAASPAAPAPASPAAPAPSAPAASPAAPAPASPAAPAPSAPAASPAAPAPASPAAPAPSAPAASPAAPAPASPAAPA PSAPAASPAAPAPASPAAPAPSAPAASPAAPAPASPAAPAPSAPAASPAAPAPASPAAPAPSAPAASPAAPAPASPAAPAPSA PAASPAAPAPASPAAPAPSAPAASPAAPAPASPAAPAPSAPAASPAAPAPASPAAPAPSAPAASPAAPAPASPAAPAPSAPAA SPAAPAPASPAAPAPSAPAASPAAPAPASPAAPAPSAPAASPAAPAPASPAAPAPSAPAASPAAPAPASPAAPAPSAPAASPA APAPASPAAPAPSAPAASPAAPAPASPAAPAPSAPAASPAAPAPASPAAPAPSAPAASPAAPAPASPAAPAPSAPAASPAAPA PASPAAPAPSAPAASPAAPAPASPAAPAPSAPAASPAAPAPASPAAPAPSAPAASPAAPAPASPAAPAPSAPAAGGGGSGGGG SGGGGSQLSLPSILPNENEKVVQLNSSFSLRCFGESEVSWQYPMSEEESSDVEIRNEENNSGLFVTVLEVSSASAAHTGLYTC YYNHTQTEENELEGRHIYIYVPDPDVAFVPLGMTDYLVIVEDDDSAIIPCRTTDPETPVTLHNSEGVVPASYDSRQGFNGTFT VGPYICEATVKGKKFQTIPFNVYALKATSELDLEMEALKTVYKSGETIVVTCAVFNNEVVDLQWTYPGEVKGKGITMLEEIKV

PSIKLVYTLTVPEATVKDSGDYECAARQATREVKEMKKVTISVHEKGHHHHHH

SEQ ID No. 43:
Nucleotide sequence encoding EPS1116P
atggggacctctcatcctgccttcctggtgctggggtgcctgctgaccggcctgtctctgattctgtgccagctgagcctgcc aagcatcctgcctaacgaaaatgagaaggtggtccagctgaacagctccttcagtctgagatgctttggcgaatcagaggtga gctggcagtacccaatgtcagaggaagagtctagtgacgtggaaattaggaatgaagagaacaattcaggactgttcgtgacc gtcctggaggtgtcaagcgccagcgccgctcacaccggactgtacacatgttactataaccatactcagaccgaagagaatga actggaggggaggcacatctccatccacgtgcccgatcctgacgtggcctttgccccactgggaatgacagattacctggtca tcgtcgaggacgatgactctgccatcattccctgccgcacctcagactccgaaactcctgtgaccctgcataacagtgagggc gtggtccccgcctcctacgattctcgacagggattcaatggcaccttcaccgtcggaccctatatctgtgaggccactgtgaa gggcaagaaattccagaccattccttttaacgtgtacgcactgaaagccacatccgaactggacctggaaatggaggccctga agactgtctataaatctggagagactatcgtggtcacctgcgccgtgttcaacaatgaagtggtcgatgcgcagtggacttac cccggcgaggtcaagggcaaagggattaccatggacgaagagatcaaggtgcctagccagaagctggtgtacaccctgacagt cccagaagccaccgtgaaggattccggggactatgagtgtgcagcccggcaggcctccagagaagtgaaggagatgaagaaag tgacaatcagtgtccacgagaaaggagcaagccccgccgctccagcccccgcaagcccagccgcaccagcaccttccgcacca gccgcctccccagcagcacccgcacccgcttcccctgccgcccccgcccctagcgcccccgccgcctcccctgccgccccagc ccccgcctctccagccgcccctgccccatctgccccagccgccagcccagccgcccccgcccctgccagccccgccgccccag ccccctccgcccctgctgcttcccctgccgcccctgccccagccagcccagctgctcctgctccaagcgcccctgctgcaagc ccagctgctccagcccccgcctctcccgctgctccagctccttctgcccctgctgcttccccagctgctcccgcccctgcctc tcctgctgctcctgctccctccgcccctgctgcatcccccgctgctcctgccccagcttccccagctgcacctgctccaagcg ccccagctgcaagcccagctgcacctgcacctgcttcccccgctgcccctgccccaagcgcccccgccgcatcccccgccgca ccagcccccgcctcacccgcagcaccagccccatcagcaccagccgcctcaccagccgcccccgcacccgcaagtccagcagc acccgcaccatccgcccccgccgcaagcccagccgcccccgctccagcatcccctgccgcccccgcccccagcgcccccgccg cctcccctgccgccccagcccccgcctctccagccgcccctgccccatctgccccagccgccagccccgccgcccccgcccct -continued gccagccccgccgccccagcccccctccgcccctgctgcttcccccgccgcccctgccccagccagcccagctgctcccgctcc aagcgcccccgctgcaagcccagctgctccagcccccgcctctcccgctgctccagctccttctgcccctgctgcttcccccg ctgctcccgcccccgcctctcctgctgctcccgctccctccgcccctgctgcatcccccgctgctcctgccccagcttcccca gctgcacctgctcccagcgccccagctgcaagccccgctgcacctgcacctgcttcccccgctgccccctgccccaagcgcccc cgccgcctcacccgcagcccccgctccagccagccccgcagcaccagcaccctcagccccagcctcagataccggccggcctt ttgtggagatgtactccgaaatccccgagatcattcacatgaccgaagggcgagagctggtcatcccatgccgggtgacaagc cccaacattactgtgaccctgaagaaattccctctggatactctgatcccagacgggaagaggatcatttgggacagccgcaa aggcttcatcatttccaatgccacatataaggaaattggcctgctgacatgcgaggccactgtgaacgggcacctgtacaaaa ccaattatctgacacatcggcagacaaacactatcattgatgtggtcctgagcccttcccatgggatcgaactgagcgtcgga gagaagctggtgctgaattgtacagccagaactgaactgaacgtgggcattgacttcaattgggagtacccctcctctaagca ccagcataagaaactggtgaatagggatctgaaaacccagtctgggagtgagatgaagaaatttctgtctaccctgacaatcg atggcgtgacacgcagtgaccaggggctgtatacttgtgcagccagttcaggcctgatgaccaagaagaacagcacatttgtc cgagtccacgaaaagcaccaccaccaccatcac SEQ ID No. 44:
Amino acid sequence of EPS1116P
MGTSHPAFLVLGCLLTGLSLILCQLSLPSILPNENEKVVQLNSSFSLRCFGESEVSWQYPMSEEESSDVEIRNEENNSGLFVT VLEVSSASAAHTGLYTCYYNHTQTEENELEGRHISIHVPDPDVAFAPLGMTDYLVIVEDDDSAIIPCRTSDSETPVTLHNSEG VVPASYDSRQGFNGTFTVGPYICEATVKGKKFQTIPFNVYALKATSELDLEMEALKTVYKSGETIVVTCAVFNNEVVDAQWTY PGEVKGKGITMDEEIKVPSQKLVYTLTVPEATVKDSGDYECAARQASREVKEMKKVTISVHEKGASPAAPAPASPAAPAPSAP AASPAAPAPASPAAPAPSAPAASPAAPAPASPAAPAPSAPAASPAAPAPASPAAPAPSAPAASPAAPAPASPAAPAPSAPAAS PAAPAPASPAAPAPSAPAASPAAPAPASPAAPAPSAPAASPAAPAPASPAAPAPSAPAASPAAPAPASPAAPAPSAPAASPAA PAPASPAAPAPSAPAASPAAPAPASPAAPAPSAPAASPAAPAPASPAAPAPSAPAASPAAPAPASPAAPAPSAPAASPAAPAP ASPAAPAPSAPAASPAAPAPASPAAPAPSAPAASPAAPAPASPAAPAPSAPAASPAAPAPASPAAPAPSAPAASPAAPAPASP AAPAPSAPAASPAAPAPASPAAPAPSAPAASPAAPAPASPAAPAPSAPASDTGRPFVEMYSEIPEIIHMTEGRELVIPCRVTS PNITVTLKKFPLDTLIPDGKRIIWDSRKGFIISNATYKEIGLLTCEATVNGHLYKTNYLTHRQTNTIIDVVLSPSHGIELSVG EKLVLNCTARTELNVGIDFNWEYPSSKHQHKKLVNRDLKTQSGSEMKKFLSTLTIDGVTRSDQGLYTCAASSGLMTKKNSTFV

RVHEKHHHHHH

SEQ ID No. 45:
Nucleotide sequence encoding EPS1103P, excluding signal polypeptide sequence and purification-tag
cagctgagcctgccttcaatcctgcccaacgagaatgagaaggtggtgcagctgaactccagcttcagcctgagatgcttt ggcgagtctgaggtgtcctggcagtaccctatgtctgaggaggagtcttccgacgtggagatccgcaatgaggag aacaattccggcctgttcgtgaccgtgctggaggtgagctctgccagcgccgctcacaccggcctgtacacatgt tactataaccatacccagacagaggagaatgagctggagggcagacacatctacatctatgtgcccgatcctgac gtggcctttgtgccactgggcatgaccgattacctggtcatcgtggaggacgatgactctgccatcatcccctgc aggaccacagacccagagacacccgtgacactgcataactccgagggagtggtgccagctagctacgattctcgg cagggcttcaatggcacctttacagtgggcccctatatctgtgaggccaccgtgaagggcaagaagttccagaca atcccttttaacgtgtacgccctgaaggctacctctgagctggacctggagatggaggccctgaagacagtgtat aagtccggcgagacaatcgtggtgacatgcgccgtgttcaacaatgaggtggtggatctgcagtggacctaccct ggcgaggtgaagggcaagggcatcacaatgctggaggagatcaaggtgccttccatcaagctggtgtacaccctg acagtgccagaggccaccgtgaaggatagcggcgactatgagtgtgctgctaggcaggctaccagggaggtgaag gagatgaagaaggtgacaatctccgtgcacgagaagggagctagcccagctgctccagctccagctagccccgcc gctcctgctccatctgctcctgctgcttccccagctgctcccgcccctgcttctcctgctgctccagctccatcc -continued gccccagctgcttctcctgccgctcctgccccagcttccccagccgctcccgccccttccgctccagccgcctct cccgccgcccctgctccagctagcccagcagccccagccccttctgctccagccgcctctccagccgcccctgct cccgcatcccccgccgcccccgccccttccgcccctgccgcctccccagctgccccagctcctgcctctcctgct gcccctgctccatccgctccagccgccagtcccgccgcccccgctccagctagcccagccgcaccagccccttct gctcccgccgcctctcccgccgcacctgctccagcatcccccgccgccccagccccttccgcccctgcagcctcc ccagctgcccccgctcctgcctctcctgcagcccctgctccttccgctccagccgcatctcccgccgccccagcc ccagctagcccagcagcaccagcccccctctgctccagccgccagccctgccgcccctgctcccgcttcccccgcc gccccagcaccttccgcccctgccgcatccccagcagcccccgctcctgccagccctgctgcccctgcaccttcc gctccagccgcttctcccgccgccccagcacccgctagcccagctgcccctgccccttctgctccagcagcctct cctgccgcccctgctcctgcatcccccgccgcacccgccccttccgcccccgccgcctccccagctgcaccagct ccagcctctccagctgctccagctccttccgccccagctagcgataccggccgcccttttgtggagatgtacagc gagatccccgagatcatccacatgaccgagggcagggagctggtcatcccatgccgggtgacatctcccaacatc accgtgacactgaagaagttccctctggataccctgatcccagacggcaagagaatcatctgggactctcgcaag ggctttatcatctccaatgccacatataaggagatcggcctgctgacctgcgaggctacagtgaacggccacctg tacaagaccaattatctgacacataggcagaccaacacaatcatcgatgtggtgctgagcccatctcatggcatc gagctgagcgtgggcgagaagctggtgctgaattgtaccgcccggacagagctgaacgtgggcatcgacttcaat tgggagtacccttccagcaagcaccagcataagaagctggtgaacagagatctgaagacccagtccggcagcgag atgaagaagtttctgagcaccctgacaatcgatggcgtgacccgctctgaccagggcctgtatacatgtgccgct tcttccggcctgatgactaagaaaaactccacctttgtgcgggtccacgaaaaa SEQ ID No. 46:
Amino acid sequence of EPS1103P, excluding signal polypeptide sequence and purification-tag
QLSLPSILPNENEKVVQLNSSFSLRCFGESEVSWQYPMSEEESSDVEIRNEENNSGLFVTVLEVSSASAAHTGLYTCYYNHTQ TEENELEGRHIYIYVPDPDVAFVPLGMTDYLVIVEDDDSAIIPCRTTDPETPVTLHNSEGVVPASYDSRQGFNGTFTVGPYIC EATVKGKKFQTIPFNVYALKATSELDLEMEALKTVYKSGETIVVTCAVFNNEVVDLQWTYPGEVKGKGITMLEEIKVPSIKLV YTLTVPEATVKDSGDYECAARQATREVKEMKKVTISVHEKGASPAAPAPASPAAPAPSAPAASPAAPAPASPAAPAPSAPAAS PAAPAPASPAAPAPSAPAASPAAPAPASPAAPAPSAPAASPAAPAPASPAAPAPSAPAASPAAPAPASPAAPAPSAPAASPAA PAPASPAAPAPSAPAASPAAPAPASPAAPAPSAPAASPAAPAPASPAAPAPSAPAASPAAPAPASPAAPAPSAPAASPAAPAP ASPAAPAPSAPAASPAAPAPASPAAPAPSAPAASPAAPAPASPAAPAPSAPAASPAAPAPASPAAPAPSAPAASPAAPAPASP AAPAPSAPASDTGRPFVEMYSEIPEIIHMTEGRELVIPCRVTSPNITVTLKKFPLDTLIPDGKRIIWDSRKGFIISNATYKEI GLLTCEATVNGHLYKTNYLTHRQTNTIIDVVLSPSHGIELSVGEKLVLNCTARTELNVGIDFNWEYPSSKHQHKKLVNRDLKT

QSGSEMKKFLSTLTIDGVTRSDQGLYTCAASSGLMTKKNSTFVRVHEK

SEQ ID No. 47:
Nucleotide sequence encoding EPS1104P, excluding signal polypeptide sequence and purification-tag
cagctgagcctgccctccatcctgcctaacgagaatgagaaggtggtgcagctgaactccagcttctccctgagatgcttt ggcgagtctgaggtgtcctggcagtacccaatgagcgaggaggagtcttccgacgtggagatccgcaatgaggag aacaattctggcctgttcgtgaccgtgctggaggtgagctctgcctccgccgctcacaccggcctgtacacatgt tactataaccatacccagacagaggagaatgagctggagggcagacacatctacatctatgtgcccgatcctgac gtggcctttgtgccactgggcatgaccgattacctggtcatcgtggaggacgatgacagcgccatcatcccctgc aggaccacagaccccgagacacctgtgacactgcataactctgagggcgtggtgccagccagctacgattctcgg cagggcttcaatggcacctttacagtgggcccctatatctgtgaggccaccgtgaagggcaagaagttccagaca atcccttttaacgtgtacgccctgaaggctaccagcgagctggacctggagatggaggccctgaagacagtgtat -continued aagtctggcgagacaatcgtggtgacatgcgccgtgttcaacaatgaggtggtggatctgcagtggacctacccc ggcgaggtgaagggcaagggcatcacaatgctggaggagatcaaggtgccttctatcaagctggtgtacaccctg acagtgccagaggccaccgtgaaggattccggcgactatgagtgtgccgctaggcaggctacccgggaggtgaag gagatgaagaaggtgacaatctctgtgcacgagaagggagcttccccagctgctccagctccagcttcccccgcc gctcctgccccatctgctccagctgcctctccagctgctccagctcctgctagccctgccgctccagccccctcc gcccctgccgcttctccagccgctcctgccccagctagccctgctgctccagctccttccgctccagccgcctct ccagccgctccagcccccgcctctcctgctgccccagctccttctgctccagctgccagccccgccgcccctgcc cccgcctctcccgctgcccctgctccttccgccccagctgcctcccctgctgctcctgccccagcttcacctgcc gcccctgccccttccgctccagccgcatctcccgccgctccagcccccgcaagccctgcagccccagctccctct gctccagctgcctcacccgccgcccctgcccctgcctctcccgctgcccccgctccttccgccccagcagcctcc cctgcagctcctgccccagcttctccagccgctcccgccccttccgctcccgccgcctctcctgctgcaccagcc cccgcttccccagctgctcctgctccatccgccccagctgcttccccagctgctccagctccagcttcccccgcc gctcctgccccatctgctccagctgcctctccagctgctccagctcctgctagccctgccgctccagccccctcc gcccctgccgcttctccagccgctcctgccccagctagccctgctgctccagctccttccgctccagccgcctct ccagccgctccagcccccgcctctcctgctgccccagctccttctgctccagctgccagccccgccgcccctgcc cccgcctctcccgctgcccctgctccttccgccccagctgcctcccctgctgctcctgccccagcttcacctgcc gcccctgccccttccgctccagccgcatctcccgccgctccagcccccgcaagccctgcagccccagctccctct gctccagctgcctcacccgccgcccctgcccctgcctctcccgctgcccccgctccttccgccccagcagcctcc cctgcagctcctgccccagcttctccagccgctcccgccccttccgctcccgccgcctctcctgctgcaccagcc cccgcttccccagctgctcctgctccatccgccccagctagcgataccggccgcccttttgtggagatgtacagc gagatccctgagatcatccacatgaccgagggcagggagctggtcatcccatgccgggtgacatctcccaacatc accgtgacactgaagaagttccctctggataccctgatcccagacggcaagagaatcatctgggacagccgcaag ggctttatcatctctaatgccacatataaggagatcggcctgctgacctgcgaggctacagtgaacggccacctg tacaagaccaattatctgacacataggcagaccaacacaatcatcgatgtggtgctgagcccctctcatggcatc gagctgtccgtgggcgagaagctggtgctgaattgtaccgcccggacagagctgaacgtgggcatcgacttcaat tgggagtacccttccagcaagcaccagcataagaagctggtgaacagagatctgaagacccagtccggcagcgag atgaagaagtttctgtccaccctgacaatcgatggagtgacccgcagcgaccagggcctgtatacatgtgccgct tcttccggcctgatgactaagaaaaatagcacctttgtgagggtccacgaaaaa SEQ ID No. 48:
Amino acid sequence of EPS1104P, excluding signal polypeptide sequence and purification-tag
QLSLPSILPNENEKVVQLNSSFSLRCFGESEVSWQYPMSEEESSDVEIRNEENNSGLFVTVLEVSSASAAHTGLYTCYYNHTQ TEENELEGRHIYIYVPDPDVAFVPLGMTDYLVIVEDDDSAIIPCRTTDPETPVTLHNSEGVVPASYDSRQGFNGTFTVGPYIC EATVKGKKFQTIPFNVYALKATSELDLEMEALKTVYKSGETIVVTCAVFNNEVVDLQWTYPGEVKGKGITMLEEIKVPSIKLV YTLTVPEATVKDSGDYECAARQATREVKEMKKVTISVHEKGASPAAPAPASPAAPAPSAPAASPAAPAPASPAAPAPSAPAAS PAAPAPASPAAPAPSAPAASPAAPAPASPAAPAPSAPAASPAAPAPASPAAPAPSAPAASPAAPAPASPAAPAPSAPAASPAA PAPASPAAPAPSAPAASPAAPAPASPAAPAPSAPAASPAAPAPASPAAPAPSAPAASPAAPAPASPAAPAPSAPAASPAAPAP ASPAAPAPSAPAASPAAPAPASPAAPAPSAPAASPAAPAPASPAAPAPSAPAASPAAPAPASPAAPAPSAPAASPAAPAPASP AAPAPSAPAASPAAPAPASPAAPAPSAPAASPAAPAPASPAAPAPSAPAASPAAPAPASPAAPAPSAPAASPAAPAPASPAAP APSAPAASPAAPAPASPAAPAPSAPASDTGRPFVEMYSEIPEIIHMTEGRELVIPCRVTSPNITVTLKKFPLDTLIPDGKRII WDSRKGFIISNATYKEIGLLTCEATVNGHLYKTNYLTHRQTNTIIDVVLSPSHGIELSVGEKLVLNCTARTELNVGIDFNWEY

PSSKHQHKKLVNRDLKTQSGSEMKKFLSTLTIDGVTRSDQGLYTCAASSGLMTKKNSTFVRVHEK

-continued

SEQ ID No. 49:
Nucleotide sequence encoding EPS1105P, excluding signal polypeptide sequence and purification-tag agcgataccggccgccccttcgtggagatgtacagcgagatccctgagatcatccacatgaccgagggcagg gagctggtcatcccttgccgggtgacatctccaaacatcaccgtgacactgaagaagttcccctggataccctg atccctgacggcaagagaatcatctgggactctcgcaagggctttatcatctccaatgccacctataaggagatc ggcctgctgacctgcgaggctacagtgaacggccacctgtacaagaccaattatctgacacatcggcagaccaac acaatcatcgatgtggtgctgagcccttctcatggcatcgagctgtccgtgggcgagaagctggtgctgaattgt accgccagaacagagctgaacgtgggcatcgatttcaattgggagtacccatccagcaagcaccagcataagaag ctggtgaacagggacctgaagacccagtccggcagcgagatgaagaagtttctgtctaccctgacaatcgatgga gtgacccgctccgaccagggcctgtatacatgtgccgcttcttccggcctgatgaccaagaagaatagcacattt gtgagggtgcacgagaaggcctccccagctgctccagctcctgctagcccagccgctccagccccctctgctcca gccgcttcccccgccgctcctgccccagcttctccagccgctcccgccccttccgcccctgccgcttctcctgct gctccagcccctgcctctcctgccgctcctgccccatccgctcccgccgctagccctgccgctcccgcccctgct agccctgctgcccctgctccttctgctcctgctgcctctccagctgccccagctcctgcctcccctgctgcccct gcaccatccgccccagccgcttctcctgcagctccagcccctgccagccctgctgccccagctccttccgctcct gctgccagtccagctgcccctgctcctgctagccctgctgcacctgctccttctgctcccgctgcctctccagct gcaccagctcctgcctcccccgctgcccctgctccatccgcccccgccgcttctcctgccgccccagcccctgcc tctccagctgctccagctccctccgctcctgctgccagcccagctgcccctgcacctgctagccctgctgctcct gcccccctctgccccagctcagctgtctctgccatccatcctgcccaacgagaatgagaaggtggtgcagctgaac agctctttctctctgcggtgctttggcgagagcgaggtgtcttggcagtaccccatgtccgaggaggagtccagc gacgtggagatcagaaatgaggagaacaatagcggcctgttcgtgaccgtgctggaggtgtcttccgcctctgcc gctcacaccggcctgtacacatgttactataaccatacccagacagaggagaatgagctggagggccggcacatc tacatctatgtgcctgatccagacgtggcctttgtgcccctgggcatgaccgattacctggtcatcgtggaggac gatgactccgccatcatcccttgccgcaccacagaccccgagacacctgtgacactgcataacagcgagggagtg gtgccagcttcctacgatagcaggcagggcttcaatggcacctttacagtgggcccttatatctgtgaggccacc gtgaagggcaagaagttccagacaatccccttcaacgtgtacgccctgaaggctacctccgagctggacctggag atggaggccctgaagacagtgtataagagcggcgagacaatcgtggtgacatgcgccgtgttcaacaatgaggtg gtggatctgcagtggacctaccctggcgaggtgaagggcaagggcatcacaatgctggaggagatcaaggtgcca agcatcaagctggtgtacaccctgacagtgcccgaggccaccgtgaaggattctggcgactatgagtgtgccgct aggcaggctacacgggaggtgaaagaaatgaagaaggtcacaatcagcgtccacgaaaagggg SEQ ID No. 50:
Amino acid sequence of EPS1105P, excluding signal polypeptide sequence and purification-tag SDTGRPFVEMYSEIPEIIHMTEGRELVIPCRVTSPNITVTLKKFPLDTLIPDGKRIIWDSRKGFIISNATYKEIGLLTCEATV NGHLYKTNYLTHRQTNTIIDVVLSPSHGIELSVGEKLVLNCTARTELNVGIDFNWEYPSSKHQHKKLVNRDLKTQSGSEMKKF LSTLTIDGVTRSDQGLYTCAASSGLMTKKNSTFVRVHEKASPAAPAPASPAAPAPSAPAASPAAPAPASPAAPAPSAPAASPA APAPASPAAPAPSAPAASPAAPAPASPAAPAPSAPAASPAAPAPASPAAPAPSAPAASPAAPAPASPAAPAPSAPAASPAAPA PASPAAPAPSAPAASPAAPAPASPAAPAPSAPAASPAAPAPASPAAPAPSAPAASPAAPAPASPAAPAPSAPAQLSLPSILPN ENEKVVQLNSSFSLRCFGESEVSWQYPMSEEESSDVEIRNEENNSGLFVTVLEVSSASAAHTGLYTCYYNHTQTEENELEGRH IYIYVPDPDVAFVPLGMTDYLVIVEDDDSAIIPCRTTDPETPVTLHNSEGVVPASYDSRQGFNGTFTVGPYICEATVKGKKFQ TIPFNVYALKATSELDLEMEALKTVYKSGETIVVTCAVFNNEVVDLQWTYPGEVKGKGITMLEEIKVPSIKLVYTLTVPEATV

KDSGDYECAARQATREVKEMKKVTISVHEKG

-continued

SEQ ID No. 51:
Nucleotide sequence encoding EPS1106P, excluding signal polypeptide sequence and purification-tag cagctgtccctgccttccatcctgcctaacgagaacgagaaggtggtgcagctgaactcctccttctctctgcggtgcttcgg
cgagtccgaagtgtcttggcagtaccccatgtccgaagaggaatcctccgacgtggaaatccggaacgaggaaaacaactccg
gcctgttcgtgaccgtgctggaagtgtcctctgcctctgctgctcacaccggactgtacacctgttactacaatcacacccag
accgaagagaacgagctggaaggccggcacatctacatctacgtgcccgatcctgacgtggcctttgtgcctctgggcatgac
cgactacctggtcatcgtggaagatgacgactccgctatcatcccctgccggaccacagatcctgagacacctgtgacactgc
acaactccgaaggcgtggtgcctgcctcctacgattctagacagggcttcaacggcaccttcaccgtgggaccttacatctgc
gaggctaccgtgaagggcaagaagttccagacaatccccttcaacgtgtacgccctgaaggccacctctgagctggacctgga
aatggaagccctgaaaaccgtgtacaagagcggcgagacaatcgtcgtgacctgcgccgtgttcaacaacgaggtggtggacc
tgcagtggacctatcctggcgaagtgaaaggcaagggcatcaccatgctggaagagatcaaggtgccctccatcaagctggtg
tataccctgaccgtgcctgaggccacagtgaaggactctggcgactacgagtgtgccgctagacaggccaccagagaagtcaa
agagatgaagaaagtcaccatctccgtgcacgagaaaggcggcggaggcggaagcggtggcggaggaagcggaggcggcggat
ctgcttctcctgctgctccagctccagcttctccagcagctcctgcaccttctgcaccagctgcaagtcctgcagcacccgca
ccagctagtcctgccgctcctgctcctagtgctcctgccgcaagtccagctgctcccgctcctgcatcaccagccgcaccagc
accaagtgctccagctgcctctccagcagcaccagctccagcaagccctgctgcaccagcaccttcagctccagcagcatcac
ccgctgcacccgctccagcatctcccgctgctccagcaccaagcgcacccgctgctagcccagccgctccagctcctgccagt
cctgctgctcctgcaccatctgctcccgcagcttcaccagctgctcccgcaccagctagcccagcagcaccagcaccatctgc
acccgccgcatctcccgccgcaccagctccagctagtcccgcagctcccgctccatctgctccagccgctagtcccgctgctc
ctgctccagctagtcctgctgcacccgctcctagcgcaccagctgcttcacccgcagctccagctccagcttcacccgctgca
ccagctccatctgctccagctggtggcggaggatctggcggaggcggatctggcggcggtggttcttctgataccggcagacc
cttcgtggaaatgtacagcgagatccccgagatcatccacatgaccgagggcagagagctggtcatcccttgcagagtgacct
ctcctaacatcacagtgaccctgaagaagtttcccctggacacactgatccccgacggcaagagaatcatctgggactcccgg
aagggcttcatcatctccaacgccacctacaaagagatcggactgctgacctgcgaagccactgtgaacggccacctgtacaa
gaccaactatctgacccacagacagaccaacaccatcatcgacgtggtgctgagcccctctcatggcatcgagctgtccgtgg
gagagaaactggtgctgaactgcaccgccagaaccgagctgaacgtgggcatcgacttcaactgggagtaccccagctccaaa
caccagcacaagaagctggtcaaccgggatctgaaaacccagtccggctccgaaatgaagaaattcctgagcaccctgaccat
cgacggcgtgaccagatctgaccagggcctgtatacctgtgccgcctcttctggcctgatgaccaagaaaaactccaccttcg
tgcgggtccacgagaag SEQ ID No. 52:
Amino acid sequence of EPS1106P, excluding signal polypeptide sequence and purification-tag QLSLPSILPNENEKVVQLNSSFSLRCFGESEVSWQYPMSEEESSDVEIRNEENNSGLFVTVLEVSSASAAHTGLYTCYYNHTQ
TEENELEGRHIYIYVPDPDVAFVPLGMTDYLVIVEDDDSAIIPCRTTDPETPVTLHNSEGVVPASYDSRQGFNGTFTVGPYIC
EATVKGKKFQTIPFNVYALKATSELDLEMEALKTVYKSGETIVVTCAVFNNEVVDLQWTYPGEVKGKGITMLEEIKVPSIKLV
YTLTVPEATVKDSGDYECAARQATREVKEMKKVTISVHEKGGGGGSGGGGSGGGGSASPAAPAPASPAAPAPSAPAASPAAPA
PASPAAPAPSAPAASPAAPAPASPAAPAPSAPAASPAAPAPASPAAPAPSAPAASPAAPAPASPAAPAPSAPAASPAAPAPAS
PAAPAPSAPAASPAAPAPASPAAPAPSAPAASPAAPAPASPAAPAPSAPAASPAAPAPASPAAPAPSAPAASPAAPAPASPAA
PAPSAPAGGGGSGGGGSGGGGSSDTGRPFVEMYSEIPEIIHMTEGRELVIPCRVTSPNITVTLKKFPLDTLIPDGKRIIWDSR
KGFIISNATYKEIGLLTCEATVNGHLYKTNYLTHRQTNTIIDVVLSPSHGIELSVGEKLVLNCTARTELNVGIDFNWEYPSSK
HQHKKLVNRDLKTQSGSEMKKFLSTLTIDGVTRSDQGLYTCAASSGLMTKKNSTFVRVHEK -continued SEQ ID No. 53:
Nucleotide sequence encoding EPS1107P, excluding signal polypeptide sequence and purification-tag tctgataccggcagacccttcgtggaaatgtacagcgagatccccgagatcatccacatgaccgagggcagagagctggtcat cccctgcagagtgacctctcctaacatcaccgtgactctgaagaagttccctctggacacactgatccccgacggcaagagaa tcatctgggactcccggaagggcttcatcatctccaacgccacctacaaagagatcggcctgctgacctgcgaggccaccgtt aatggccacctgtacaagaccaactatctgacccacagacagaccaacaccatcatcgacgtggtgctgagcccctctcatgg catcgagctgtccgtgggagaaaagctggtgctgaactgcaccgccagaaccgagctgaacgtgggcatcgacttcaactggg agtacccctccagcaagcaccagcacaagaagctggtcaaccgggacctgaaaacccagtccggctccgagatgaagaaattc ctgagcaccctgaccatcgacggcgtgaccagatctgaccagggcctgtatacctgcgccgcttcctctggcctgatgaccaa gaaaaactccaccttcgtgcgggtgcacgagaaaggtggcggaggatctggcggaggcggctctggcggcggtggatctgctt ctcctgctgctccagctccagcttctccagcagctcctgcaccttctgcaccagctgcaagtcctgcagcacccgcaccagct agtcctgccgctcctgctcctagtgctcctgccgcaagtccagctgctcccgctcctgcaagcccagctgcaccagcaccaag tgctccagctgcctcaccagccgcaccagctccagcaagccctgcagctcccgctccttcagctcctgctgcttctcccgcag cacccgctccagcatcaccagccgctccagcaccatcagctccagcagcatctcctgcagctccagctcctgctagtcccgct gctcccgcacctagtgcaccagccgcttctcccgccgctcctgctcctgcatctcctgctgcacccgctccatctgctcccgc cgcatcacccgcagctcccgcaccagcctctccagctgcaccagctcctagcgcaccagcagctagcccagctgctcctgcac cagctagccccgcagctccagctccaagcgctcctgctgcatccccagctgctccagctcctgcctcaccagctgctccagca ccttctgctcccgctggcggtggcggaagcggaggtggtggtagtggcggcggaggttctcagctgtccctgccttctatcct gcctaacgagaacgagaaggtggtccagctgaactcctccttctctctgcggtgcttcggcgagtccgaagtgtcttggcagt accccatgtccgaagaggaatcctccgacgtggaaatccggaacgaggaaaacaactccggcctgttcgtgaccgtgctggaa gtgtcctctgcctctgctgctcacaccggcctgtacacatgctactacaatcacacccagaccgaagagaacgagctggaagg ccggcacatctacatctacgtgcccgatcctgacgtggcctttgtgcctctgggcatgaccgactacctggtcatcgtggaag atgacgactccgctatcatcccttgccggaccaccgatccagagacacctgtgacactgcacaactccgaaggcgtggtgcct gcctcctacgattctagacagggcttcaacggcaccttcaccgtgggaccttacatctgcgaggctacagtgaagggcaagaa gtttcagacaatccccttcaacgtgtacgccctgaaggccacctctgagctggacctggaaatggaagctctgaaaaccgtgt acaagtccggcgagacaatcgtcgtgacctgtgccgtgttcaacaacgaagtggtggacctgcagtggacctatcctggcgaa gtgaaaggcaagggcatcaccatgctggaagagatcaaggtgccctccatcaagctggtgtataccctgaccgtgcctgaggc cactgtgaaggactctggcgactacgagtgtgccgctagacaggccaccagagaagtcaaagaaatgaagaaagtgaccatct ccgtccacgagaagggc SEQ ID No. 54:
Amino acid sequence of EPS1107P, excluding signal polypeptide sequence and purification-tag SDTGRPFVEMYSEIPEIIHMTEGRELVIPCRVTSPNITVTLKKFPLDTLIPDGKRIIWDSRKGFIISNATYKEIGLLTCEATV NGHLYKTNYLTHRQTNTIIDVVLSPSHGIELSVGEKLVLNCTARTELNVGIDFNWEYPSSKHQHKKLVNRDLKTQSGSEMKKF LSTLTIDGVTRSDQGLYTCAASSGLMTKKNSTFVRVHEKGGGGSGGGGSGGGGSASPAAPAPASPAAPAPSAPAASPAAPAPA SPAAPAPSAPAASPAAPAPASPAAPAPSAPAASPAAPAPASPAAPAPSAPAASPAAPAPASPAAPAPSAPAASPAAPAPASPA APAPSAPAASPAAPAPASPAAPAPSAPAASPAAPAPASPAAPAPSAPAASPAAPAPASPAAPAPSAPAASPAAPAPASPAAPA PSAPAGGGGSGGGGSGGGGSQLSLPSILPNENEKVVQLNSSFSLRCFGESEVSWQYPMSEEESSDVEIRNEENNSGLFVTVLE VSSASAAHTGLYTCYYNHTQTEENELEGRHIYIYVPDPDVAFVPLGMTDYLVIVEDDDSAIIPCRTTDPETPVTLHNSEGVVP ASYDSRQGFNGTFTVGPYICEATVKGKKFQTIPFNVYALKATSELDLEMEALKTVYKSGETIVVTCAVFNNEVVDLQWTYPGE

VKGKGITMLEEIKVPSIKLVYTLTVPEATVKDSGDYECAARQATREVKEMKKVTISVHEKG

-continued

SEQ ID No. 55:
Nucleotide sequence encoding EPS1109P, excluding signal polypeptide sequence and purification-tag gcttctccagccgctccagctcctgcttctcctgctgcaccagcaccatctgctccagctgcaagtccagctgctcccgcacc agcaagtcctgcagcacccgctcctagtgctccagcagcatctcccgcagcaccagctccagcttcaccagcagctcccgctc catcagcaccagccgcatcacccgctgctccagcaccagcttctcccgccgctcctgcaccttctgcacccgcagctagccct gctgctcctgctccagcatctccagctgcacccgctccaagcgcacccgctgctagtccagcagcaccagcaccagctagtcc cgctgctccagctccttctgctccagcagcttcaccagccgctccagcaccagctagcccagccgcaccagcacctagtgctc ccgccgctagtcctgcagctccagctcctgctagcccagctgctcccgctcctagcgctcctgccgcttcaccagctgcacca gctccagcaagtccagccgctcctgctccaagtgcaccagctgcctctccagctgctcctgctcctgcaagtcccgcagctcc agcacctagcgcaccagcatctgataccggcagacccttcgtggaaatgtacagcgagatccccgagatcatccacatgaccg agggcagagagctggtcatcccctgcagagtgacctctcctaacatcaccgtgactctgaagaagttccctctggacacactg atccccgacggcaagagaatcatctgggactcccggaagggcttcatcatctccaacgccacctacaaagagatcggcctgct gacctgcgaggccaccgttaatggccacctgtacaagaccaactatctgacccacagacagaccaacaccatcatcgacgtgg tgctgagcccctctcatggcatcgagctgtccgtgggagaaaagctcgtgctgaactgcaccgccagaaccgagctgaacgtg ggcatcgacttcaactgggagtaccccagctccaaacaccagcacaagaaactggtcaaccgggacctgaaaacccagtccgg ctccgagatgaagaaattcctgagcaccctgaccatcgacggcgtgaccagatctgaccagggcctgtatacctgcgccgctt cttctggcctgatgaccaagaaaaactccaccttcgtgcgcgtgcacgagaagcagctgtccctgccttctatcctgcctaac gagaacgagaaggtggtccagctgaactcctccttctctctgcggtgcttcggcgagtccgaagtgtcttggcagtaccccat gtccgaagaggaatcctccgacgtggaaatccggaacgaggaaaacaactccggcctgttcgtgaccgtgctggaagtgtcct ctgcctctgctgctcacaccggcctgtacacatgctactacaatcacacccagaccgaagagaacgagctggaaggccggcac atctacatctacgtgcccgatcctgacgtggcctttgtgcctctgggcatgaccgactacctggtcatcgtggaagatgacga ctccgctatcatcccttgccggaccaccgatccagagacacctgtgacactgcacaactccgaaggcgtggtgcctgcctcct acgattctagacagggcttcaacggcaccttcaccgtgggaccttacatctgcgaggctacagtgaagggcaagaagtttcag acaatccccttcaacgtgtacgccctgaaggccacctctgagctggacctggaaatggaagctctgaaaaccgtgtacaagtc cggcgagacaatcgtcgtgacctgtgccgtgttcaacaacgaggtggtggacctgcagtggacctatcctggcgaagtgaaag gcaagggcatcaccatgctggaagagatcaaggtgccctccatcaagctggtgtataccctgaccgtgcctgaggccactgtg aaggactctggcgactacgagtgtgccgctagacaggccaccagagaagtcaaagaaatgaagaaagtgaccatctccgtcca cgagaagggc SEQ ID No. 56:
Amino acid sequence of EPS1109P, excluding signal polypeptide sequence and purification-tag ASPAAPAPASPAAPAPSAPAASPAAPAPASPAAPAPSAPAASPAAPAPASPAAPAPSAPAASPAAPAPASPAAPAPSAPAASP AAPAPASPAAPAPSAPAASPAAPAPASPAAPAPSAPAASPAAPAPASPAAPAPSAPAASPAAPAPASPAAPAPSAPAASPAAP APASPAAPAPSAPAASPAAPAPASPAAPAPSAPASDTGRPFVEMYSEIPEIIHMTEGRELVIPCRVTSPNITVTLKKFPLDTL IPDGKRIIWDSRKGFIISNATYKEIGLLTCEATVNGHLYKTNYLTHRQTNTIIDVVLSPSHGIELSVGEKLVLNCTARTELNV GIDFNWEYPSSKHQHKKLVNRDLKTQSGSEMKKFLSTLTIDGVTRSDQGLYTCAASSGLMTKKNSTFVRVHEKQLSLPSILPN ENEKVVQLNSSFSLRCFGESEVSWQYPMSEEESSDVEIRNEENNSGLFVTVLEVSSASAAHTGLYTCYYNHTQTEENELEGRH IYIYVPDPDVAFVPLGMTDYLVIVEDDDSAIIPCRTTDPETPVTLHNSEGVVPASYDSRQGFNGTFTVGPYICEATVKGKKFQ TIPFNVYALKATSELDLEMEALKTVYKSGETIVVTCAVFNNEVVDLQWTYPGEVKGKGITMLEEIKVPSIKLVYTLTVPEATV

KDSGDYECAARQATREVKEMKKVTISVHEKG

-continued

SEQ ID No. 57:
Nucleotide sequence encoding EPS1110P, excluding signal polypeptide sequence and purification-tag gcttctccagccgctccagctcctgcttctcctgctgcaccagcaccatctgctccagctgcaagtccagctgctcccgcacc agcaagtcctgcagcacccgctcctagtgctccagcagcatctcccgcagcaccagctccagcttcaccagcagctcccgctc catcagcaccagccgcatcacccgctgctccagcaccagcttctcccgccgctcctgcaccttctgcacccgcagctagccct gctgctcctgctccagcatctccagctgcacccgctccaagcgcacccgctgctagtccagcagcaccagcaccagctagtcc cgctgctccagctccttctgctccagcagcttcaccagccgctccagcaccagctagcccagccgcaccagcacctagtgctc ccgccgctagtcctgcagctccagctcctgctagcccagctgctcccgctcctagcgctcctgccgcttcaccagctgcacca gctccagcaagtccagccgctcctgctccaagtgcaccagctgcctctccagctgctcctgctcctgcaagtcccgcagctcc agcacctagcgcaccagctcaactgtccctgccttccatcctgcctaacgagaacgagaaggtggtccagctgaactcctcct tctctctgcggtgcttcggcgagtccgaagtgtcttggcagtaccccatgtccgaagaggaatcctccgacgtggaaatccgg aacgaggaaaacaactccggcctgttcgtgaccgtgctggaagtgtcctctgcctctgctgctcacaccggcctgtacacctg ttactacaatcacacccagaccgaagagaacgagctggaaggccggcacatctacatctacgtgcccgatcctgacgtggcct ttgtgcctctgggcatgaccgactacctggtcatcgtggaagatgacgactccgctatcatcccctgccggaccacagatcct gagacacctgtgacactgcacaactccgaaggcgtggtgcctgcctcctacgattctagacagggcttcaacggcaccttcac cgtgggaccttacatctgcgaggctaccgtgaagggcaagaagttccagacaatccccttcaacgtgtacgccctgaaggcca cctctgagctggacctggaaatggaagccctgaaaaccgtgtacaagtccggcgagacaatcgtcgtgacctgcgccgtgttc aacaacgaggtggtggacctgcagtggacctatcctggcgaagtgaaaggcaagggcatcaccatgctggaagagatcaaggt gccctccatcaagctggtgtataccctgaccgtgcctgaggccacagtgaaggactctggcgactacgagtgtgccgctagac aggccaccagagaagtcaaagagatgaagaaagtcaccatctccgtgcacgagaagggctccgataccggcagacccttcgtg gaaatgtacagcgagatccccgagatcatccacatgaccgagggcagagagctggtcatcccttgcagagtgacctctcctaa catcacagtgaccctgaagaagtttcccctggacacactgatccccgacggcaagagaatcatctgggactcccggaagggct tcatcatctccaacgccacctacaaagagatcggcctgctgacctgtgaagccaccgtgaatggccacctgtacaagaccaac tatctgacccacagacagaccaacaccatcatcgacgtggtgctgtccccaagccatggcatcgagctgtccgtgggagaaaa gctcgtgctgaactgcaccgccagaaccgagctgaacgtgggcatcgacttcaactgggagtaccccagctccaaacaccagc acaagaaactggtcaaccgggacctcaagacccagtccggctccgaaatgaagaaattcctgagcaccctgaccatcgacggc gtgaccagatctgaccagggactgtatacctgtgccgcctcctctggcctgatgaccaagaaaaactccaccttcgtgcgggt ccacgagaag SEQ ID No. 58:
Amino acid sequence of EPS1110P, excluding signal polypeptide sequence and purification-tag ASPAAPAPASPAAPAPSAPAASPAAPAPASPAAPAPSAPAASPAAPAPASPAAPAPSAPAASPAAPAPASPAAPAPSAPAASP AAPAPASPAAPAPSAPAASPAAPAPASPAAPAPSAPAASPAAPAPASPAAPAPSAPAASPAAPAPASPAAPAPSAPAASPAAP APASPAAPAPSAPAASPAAPAPASPAAPAPSAPAQLSLPSILPNENEKVVQLNSSFSLRCFGESEVSWQYPMSEEESSDVEIR NEENNSGLFVTVLEVSSASAAHTGLYTCYYNHTQTEENELEGRHIYIYVPDPDVAFVPLGMTDYLVIVEDDDSAIIPCRTTDP ETPVTLHNSEGVVPASYDSRQGFNGTFTVGPYICEATVKGKKFQTIPFNVYALKATSELDLEMEALKTVYKSGETIVVTCAVF NNEVVDLQWTYPGEVKGKGITMLEEIKVPSIKLVYTLTVPEATVKDSGDYECAARQATREVKEMKKVTISVHEKGSDTGRPFV EMYSEIPEIIHMTEGRELVIPCRVTSPNITVTLKKFPLDTLIPDGKRIIWDSRKGFIISNATYKEIGLLTCEATVNGHLYKTN YLTHRQTNTIIDVVLSPSHGIELSVGEKLVLNCTARTELNVGIDFNWEYPSSKHQHKKLVNRDLKTQSGSEMKKFLSTLTIDG

VTRSDQGLYTCAASSGLMTKKNSTFVRVHEK

-continued

SEQ ID No. 59:
Nucleotide sequence encoding EPS1111P, excluding signal polypeptide sequence and purification-tag
gcttctccagccgctccagctcctgcttctcctgctgcaccagcaccatctgctccagctgcaagtccagctgctcccgcacc agcaagtcctgcagcacccgctcctagtgctccagcagcatctcccgcagcaccagctccagcttcaccagcagctcccgctc catcagcaccagccgcatcacccgctgctccagcaccagcttctcccgccgctcctgcaccttctgcacccgcagctagccct gctgctcctgctccagcatctccagctgcacccgctccaagcgcacccgctgctagtccagcagcaccagcaccagctagtcc cgctgctccagctccttctgctccagcagcttcaccagccgctccagcaccagctagcccagccgcaccagcacctagtgctc ccgccgctagtcctgcagctccagctcctgctagcccagctgctcccgctcctagcgctcctgccgcttcaccagctgcacca gctccagcaagtccagccgctcctgctccaagtgcaccagctgcctctccagctgctcctgctcctgcaagtcccgcagctcc agcacctagcgcaccagcatctgataccggcagacccttcgtggaaatgtacagcgagatccccgagatcatccacatgaccg agggcagagagctggtcatcccctgcagagtgacctctcctaacatcaccgtgactctgaagaagttccctctggacacactg atccccgacggcaagagaatcatctgggactcccggaagggcttcatcatctccaacgccacctacaaagagatcggcctgct gacctgcgaggccaccgttaatggccacctgtacaagaccaactatctgacccacagacagaccaacaccatcatcgacgtgg tgctgagcccctctcatggcatcgagctgtccgtgggagaaaagctcgtgctgaactgcaccgccagaaccgagctgaacgtg ggcatcgacttcaactgggagtaccccagctccaaacaccagcacaagaaactggtcaaccgggacctgaaaacccagtccgg ctccgagatgaagaaattcctgagcaccctgaccatcgacggcgtgaccagatctgaccagggcctgtatacctgcgccgctt cttctggcctgatgaccaagaaaaactccaccttcgtgcgcgtgcacgagaagaacgatgccgaggaactgttcatcttcctg accgagattaccgagatcacaatcccctgccgcgtgacagatcctcagctggtggttaccctgcatgagaagaaaggcgacgt ggccctgcctgtgccttacgatcatcagagaggcttctccggcatcttcgaggaccggtcttacatctgcaagaccaccatcg gcgacagagaggtggactccgacgcctactacgtgtacagactccaggtgtcctccatcaacgtgtccgtgaatgccgtgcag acagttgtgcggcagggcgagaatatcaccctgatgtgcatcgtgatcggcaacgaggtggtcaacttcgagtggacctatcc tcggaaagaatctggccggctggtggaacctgtgaccgacttcctgctggacatgccctaccacatccggtctatcctgcaca tcccttccgccgagctggaagattccggcacctacacctgtaacgtgaccgagtccgtgaacgaccaccaggacgagaaggcc atcaatatcaccgtggtggaatccggctacgtgcggctgttgggagaagtgggcacactgcagtttgctgagctg SEQ ID No. 60:
Amino acid sequence of EPS1111P, excluding signal polypeptide sequence and purification-tag
ASPAAPAPASPAAPAPSAPAASPAAPAPASPAAPAPSAPAASPAAPAPASPAAPAPSAPAASPAAPAPASPAAPAPSAPAASP AAPAPASPAAPAPSAPAASPAAPAPASPAAPAPSAPAASPAAPAPASPAAPAPSAPAASPAAPAPASPAAPAPSAPAASPAAP APASPAAPAPSAPAASPAAPAPASPAAPAPSAPASDTGRPFVEMYSEIPEIIHMTEGRELVIPCRVTSPNITVTLKKFPLDTL IPDGKRIIWDSRKGFIISNATYKEIGLLTCEATVNGHLYKTNYLTHRQTNTIIDVVLSPSHGIELSVGEKLVLNCTARTELNV GIDFNWEYPSSKHQHKKLVNRDLKTQSGSEMKKFLSTLTIDGVTRSDQGLYTCAASSGLMTKKNSTFVRVHEKNDAEELFIFL TEITEITIPCRVTDPQLVVTLHEKKGDVALPVPYDHQRGFSGIFEDRSYICKTTIGDREVDSDAYYVYRLQVSSINVSVNAVQ TVVRQGENITLMCIVIGNEVVNFEWTYPRKESGRLVEPVTDFLLDMPYHIRSILHIPSAELEDSGTYTCNVTESVNDHQDEKA

INITVVESGYVRLLGEVGTLQFAEL

SEQ ID No. 61:
Nucleotide sequence encoding EPS1113P, excluding signal polypeptide sequence and purification-tag
cagctgtccctgccttctatcctgcctaacgagaacgagaaggtggtgcagctgaactcctccttctctctgcggtgcttcgg cgagtccgaagtgtcttggcagtaccccatgtccgaagaggaatcctccgacgtggaaatccggaacgaggaaaacaactccg gcctgttcgtgaccgtgctggaagtgtcctctgcctctgctgctcacaccggcctgtacacctgttactacaatcacacccag accgaagagaacgagctggaaggccggcacatctacatctacgtgcccgatcctgacgtggcctttgtgcctctgggcatgac cgactacctggtcatcgtggaagatgacgactccgctatcatcccctgccggaccacagatcctgagacacctgtgacactgc acaactccgaaggcgtggtgcctgcctcctacgattctagacagggcttcaacggcaccttcaccgtgggaccttacatctgc -continued gaggctaccgtgaagggcaagaagttccagacaatccccttcaacgtgtacgccctgaaggccacctctgagctggacctgga aatggaagccctgaaaaccgtgtacaagtccggcgagacaatcgtcgtgacctgcgccgtgttcaacaacgaggtggtggacc tgcagtggacctatcctggcgaagtgaaaggcaagggcatcaccatgctggaagagatcaaggtgccctccatcaagctggtg tataccctgaccgtgcctgaggccacagtgaaggactctggcgactacgagtgtgccgctagacaggccaccagagaagtcaa agagatgaagaaagtcaccatctccgtgcacgagaagggcgcctctccagctgctcctgctccagctagtcctgcagctccag ctccatctgcaccagctgcttctccagcagcacccgcaccagcttctcccgccgctcctgcacctagtgcaccagcagctagc cctgctgcaccagcaccagcaagtccagccgcaccagctcctagtgctccagctgcatcccctgctgctcccgctcctgcttc accagccgctccagcaccatcagctcccgcagcatctccagcagctccagctcctgcttctcctgctgcacccgctccatctg ctcccgctgcaagtcctgctgctcctgcaccagcatcacccgcagctcccgcaccaagcgctccagccgcttcacccgcagca ccagctccagcctcaccagcagcaccagcaccttccgctccagctgctagtccagccgctcctgctcctgcaagccccgctgc tccagctcctagcgcacccgctgctagccccgcagctcccgctccagcaagcccagcagctcctgctccttctgctccagcag catctcctgccgcaccagctccagctagcccagctgctcccgcaccatccgcaccagcagcaagtcccgcagctccagcacca gctagtcccgcagcacccgcaccttcagcaccagccgcatcaccagctgctccagctccagcatctcccgctgcaccagcacc aagtgctcccgctgcttctcctgcagctcctgctccagcctctccagctgctcccgcaccttctgctccagctgcctctccag ctgctccagcaccagcttcaccagctgctcccgctcctagtgctcctgccgctagtccagcagctcccgcaccagctagccct gccgctcctgctccaagtgctccagccgcaagtcccgctgcacccgctccagcttctccagcagctcccgctccaagcgcacc cgcagcttctcccgctgctcccgcaccagcaagtcctgctgctccagctccttcagctcctgccgcttctcctgctgctccag ctcctgcaagtccagctgctccagcaccaagtgcaccagcagcaagtccagctgctcctgctcctgcctctccagcagcacca gctcctagcgcaccagccgccagtcctgcagcaccagctccagcttctcccgctgctcctgctccttcagcaccagctgctag tcctgctgctcctgctccagcttctcctgccgctccagcaccaagcgctccagctgcatctcccgcagctcccgctccagcat ctcctgcagcacccgcaccatcagctccagctgcttccccagccgctcctgcaccagctagcccagcagctcctgcacctagc gctcccgctgcttcaccagcagctccagcaccagccagtccagctgctcctgcaccatctgcacccgctgctagtcccgctgc tccagctcctgctagccctgcagcaccagctccaagtgcacccgccgcatcacccgccgcaccagcaccagcaagccctgcag cacccgctccaagcgctccagctgctagcccagcagcaccagcaccagcatcaccagccgctccagcaccttctgcaccagca gcttcacccgctgcacccgctccagcatcacccgccgctccagctcctagcgctcctgcagcctctcctgcagctccagcacc agcaagccccgctgcaccagcaccatctgctccagcagctagccctgcagctcccgctcctgcatctcccgccgcaccagctc catctgcacccgcagcatctgataccggcagacccttcgtggaaatgtacagcgagatccccgagatcatccacatgaccgag ggcagagagctggtcatcccttgcagagtgacctctcctaacatcacagtgaccctgaagaagtttcccctggacacactgat ccccgacggcaagagaatcatctgggactcccggaagggcttcatcatctccaacgccacctacaaagagatcggcctgctga cctgtgaagccaccgtgaatggccacctgtacaagaccaactatctgacccacagacagaccaacaccatcatcgacgtggtg ctgagcccctctcatggcatcgagctgtccgtgggagagaagctcgtgctgaactgtaccgccagaaccgagctgaacgtggg catcgacttcaactgggagtaccctagctccaaacaccagcacaagaaactggtcaaccgggacctcaagacccagtccggct ccgaaatgaagaaattcctgtccacactgaccatcgacggcgtgaccagatctgaccagggactgtatacctgtgccgcctcc tctggcctgatgaccaagaaaaactccaccttcgtgcgggtccacgagaag SEQ ID No. 62:
Amino acid sequence of EPS1113P, excluding signal polypeptide sequence and purification-tag
QLSLPSILPNENEKVVQLNSSFSLRCFGESEVSWQYPMSEEESSDVEIRNEENNSGLFVTVLEVSSASAAHTGLYTCYYNHTQ TEENELEGRHIYIYVPDPDVAFVPLGMTDYLVIVEDDDSAIIPCRTTDPETPVTLHNSEGVVPASYDSRQGFNGTFTVGPYIC EATVKGKKFQTIPFNVYALKATSELDLEMEALKTVYKSGETIVVTCAVFNNEVVDLQWTYPGEVKGKGITMLEEIKVPSIKLV YTLTVPEATVKDSGDYECAARQATREVKEMKKVTISVHEKGASPAAPAPASPAAPAPSAPAASPAAPAPASPAAPAPSAPAAS PAAPAPASPAAPAPSAPAASPAAPAPASPAAPAPSAPAASPAAPAPASPAAPAPSAPAASPAAPAPASPAAPAPSAPAASPAA -continued PAPASPAAPAPSAPAASPAAPAPASPAAPAPSAPAASPAAPAPASPAAPAPSAPAASPAAPAPASPAAPAPSAPAASPAAPAP ASPAAPAPSAPAASPAAPAPASPAAPAPSAPAASPAAPAPASPAAPAPSAPAASPAAPAPASPAAPAPSAPAASPAAPAPASP AAPAPSAPAASPAAPAPASPAAPAPSAPAASPAAPAPASPAAPAPSAPAASPAAPAPASPAAPAPSAPAASPAAPAPASPAAP APSAPAASPAAPAPASPAAPAPSAPAASPAAPAPASPAAPAPSAPAASPAAPAPASPAAPAPSAPAASPAAPAPASPAAPAPS APAASPAAPAPASPAAPAPSAPAASPAAPAPASPAAPAPSAPAASPAAPAPASPAAPAPSAPAASPAAPAPASPAAPAPSAPA ASPAAPAPASPAAPAPSAPAASPAAPAPASPAAPAPSAPAASPAAPAPASPAAPAPSAPAASDTGRPFVEMYSEIPEIIHMTE GRELVIPCRVTSPNITVTLKKFPLDTLIPDGKRIIWDSRKGFIISNATYKEIGLLTCEATVNGHLYKTNYLTHRQTNTIIDVV LSPSHGIELSVGEKLVLNCTARTELNVGIDFNWEYPSSKHQHKKLVNRDLKTQSGSEMKKFLSTLTIDGVTRSDQGLYTCAAS

SGLMTKKNSTFVRVHEK

SEQ ID No. 63:
Nucleotide sequence encoding EPS1114P, excluding signal polypeptide sequence and purification-tag
cagctgtccctgccttccatcctgcctaacgagaacgagaaggtggtgcagctgaactcctccttctctctgcggtgcttcgg cgagtccgaagtgtcttggcagtaccccatgtccgaagaggaatcctccgacgtggaaatccggaacgaggaaaacaactccg gcctgttcgtgaccgtgctggaagtgtcctctgcctctgctgctcacaccggactgtacacctgttactacaatcacacccag accgaagagaacgagctggaaggccggcacatctacatctacgtgcccgatcctgacgtggcctttgtgcctctgggcatgac cgactacctggtcatcgtggaagatgacgactccgctatcatcccctgccggaccacagatcctgagacacctgtgacactgc acaactccgaaggcgtggtgcctgcctcctacgattctagacagggcttcaacggcaccttcaccgtgggaccttacatctgc gaggctaccgtgaagggcaagaagttccagacaatccccttcaacgtgtacgccctgaaggccacctctgagctggacctgga aatggaagccctgaaaaccgtgtacaagagcggcgagacaatcgtcgtgacctgcgccgtgttcaacaacgaggtggtggacc tgcagtggacctatcctggcgaagtgaaaggcaagggcatcaccatgctggaagagatcaaggtgccctccatcaagctggtg tataccctgaccgtgcctgaggccacagtgaaggactctggcgactacgagtgtgccgctagacaggccaccagagaagtcaa agagatgaagaaagtcaccatctccgtgcacgagaaaggcggcggaggcggaagcggtggcggaggaagcggaggcggcggat ctgcttctcctgctgctcctgctccagctagtcctgctgcaccagcaccttcagctccagctgcttctccagcagcacccgca ccagcatcaccagccgctccagcaccaagtgcaccagctgctagcccagctgctcccgctcctgcatctcctgcagcaccagc tccatctgcaccagcagcaagtccagcagctccagctcctgcttcacccgctgctcccgcaccatctgctccagccgcatcac ccgctgcaccagctccagcttctcccgccgctccagctccttctgctcctgcagcatctcctgctgctccagcaccagcaagc ccagccgctcctgctccatcagcacccgctgcctctccagctgctcctgcaccagcctctccagctgcacccgctcctagtgc tccagctgcaagtcccgccgcaccagcaccagctagtcctgcagctcctgcaccaagcgctccagcagcttcccctgcagctc ctgctcctgcctctcctgccgctcctgctcctagtgcaccagccgcatctcccgcagctcccgctcctgctagtccagcagct cccgcaccttctgcaccagcagcttccccagccgcaccagctccagcaagccccgctgctccagcacctagtgctcccgctgc ctcaccagcagctcccgctccagcaagccctgctgcacccgctccaagcgcaccagcagcatcaccagctgcacccgcaccag ctagcccagcagcaccagctcctagcgctcccgcagctagccctgctgctcccgcaccagcttcacccgcagcacccgctcca tcagctcccgccgctagtcccgctgctcctgctcctgcaagccctgctgctcctgctccttctgctccagctgctagtcctgc cgctcctgctccagcttctccagcagctcctgcacctagcgcacccgccgctagtccagcagcaccagcaccagcttctccag ctgcaccagcaccatcagcacccgcagcttcaccagcagctccagcaccagcatctcccgcagctccagcaccatcagctcca gcagcaagcccagctgcaccagctccagcatcaccagctgctcccgctccaagcgctcctgctgcttctcctgccgcaccagc tccagccagtccagcagcacccgctccaagtgcacccgccgcttctccagctgctccagctcctgctagccccgcagctccag ctccaagtgctccagccgccagtcctgcagctcccgcaccagctagccccgctgctcctgcaccatccgcaccagctgctagt cccgcagcaccagctccagctagcccagccgcaccagcaccatctgctcccgctgctagccctgcagcacccgctccagccag tcctgctgctccagctccatctgctcccgccgcttctcctgcagctcctgcaccagcttctcccgctgctcctgctcctagcg ctccagcagcctctccagcagcaccagctccagcaagtcctgcagcaccagcacctagtgcaccagcagcttcacccgctgct -continued cccgctccagcatctccagctgctccagcaccttctgctccagctgcaagccccgcagctcctgcaccagcaagtcctgccgc tccagctcctagcgctcctgctgcaagtccagctgctcccgctccagcttcaccagccgcaccagcaccttccgcaccagcag ctagtccagctgctcctgctccagctagcccagctgctccagctccttcagcaccagcagccggtggcggaggatctggcgga ggcggatctggcggcggtggttcttctgataccggcagacccttcgtggaaatgtacagcgagat ccccgagatcatccacatgaccgagggcagagagctggtcatcccttgcagagtgacctctcctaacatcacagtgaccctga agaagtttcccctggacacactgatccccgacggcaagagaatcatctgggactcccggaagggcttcatcatctccaacgcc acctacaaagagatcggactgctgacctgcgaagccactgtgaacggccacctgtacaagaccaactatctgacccacagaca gaccaacaccatcatcgacgtggtgctgagcccctctcatggcatcgagctgtccgt gggagagaaactggtgctgaactgcaccgccagaaccgagctgaacgtgggcatcgacttcaactgggagtaccccagctcca aacaccagcacaagaagctggtcaaccgggatctgaaaacccagtccggctccgaaatgaagaaattcctgagcaccctgacc atcgacggcgtgaccagatctgaccagggcctgtatacctgtgccgcctcttctggcctgatgaccaagaaaaactccacctt cgtgcgggtccacgagaag SEQ ID No. 64:
Amino acid sequence of EPS1114P, excluding signal polypeptide sequence and purification-tag
QLSLPSILPNENEKVVQLNSSFSLRCFGESEVSWQYPMSEEESSDVEIRNEENNSGLFVTVLEVSSASAAHTGLYTCYYNHTQ TEENELEGRHIYIYVPDPDVAFVPLGMTDYLVIVEDDDSAIIPCRTTDPETPVTLHNSEGVVPASYDSRQGFNGTFTVGPYIC EATVKGKKFQTIPFNVYALKATSELDLEMEALKTVYKSGETIVVTCAVFNNEVVDLQWTYPGEVKGKGITMLEEIKVPSIKLV YTLTVPEATVKDSGDYECAARQATREVKEMKKVTISVHEKGGGGGSGGGGSGGGGSASPAAPAPASPAAPAPSAPAASPAAPA PASPAAPAPSAPAASPAAPAPASPAAPAPSAPAASPAAPAPASPAAPAPSAPAASPAAPAPASPAAPAPSAPAASPAAPAPAS PAAPAPSAPAASPAAPAPASPAAPAPSAPAASPAAPAPASPAAPAPSAPAASPAAPAPASPAAPAPSAPAASPAAPAPASPAA PAPSAPAASPAAPAPASPAAPAPSAPAASPAAPAPASPAAPAPSAPAASPAAPAPASPAAPAPSAPAASPAAPAPASPAAPAP SAPAASPAAPAPASPAAPAPSAPAASPAAPAPASPAAPAPSAPAASPAAPAPASPAAPAPSAPAASPAAPAPASPAAPAPSAP AASPAAPAPASPAAPAPSAPAASPAAPAPASPAAPAPSAPAASPAAPAPASPAAPAPSAPAASPAAPAPASPAAPAPSAPAAS PAAPAPASPAAPAPSAPAASPAAPAPASPAAPAPSAPAASPAAPAPASPAAPAPSAPAASPAAPAPASPAAPAPSAPAASPAA PAPASPAAPAPSAPAASPAAPAPASPAAPAPSAPAASPAAPAPASPAAPAPSAPAASPAAPAPASPAAPAPSAPAAGGGGSGG GGSGGGGSSDTGRPFVEMYSEIPEIIHMTEGRELVIPCRVTSPNITVTLKKFPLDTLIPDGKRIIWDSRKGFIISNATYKEIG LLTCEATVNGHLYKTNYLTHRQTNTIIDVVLSPSHGIELSVGEKLVLNCTARTELNVGIDFNWEYPSSKHQHKKLVNRDLKTQ

SGSEMKKFLSTLTIDGVTRSDQGLYTCAASSGLMTKKNSTFVRVHEK

SEQ ID No. 65:
Nucleotide sequence encoding EPS1115P, excluding signal polypeptide sequence and purification-tag
tctgataccggcagacccttcgtggaaatgtacagcgagatccccgagatcatccacatgaccgagggcagagagctggtcat cccctgcagagtgacctctcctaacatcaccgtgactctgaagaagttccctctggacacactgatccccgacggcaagagaa tcatctgggactcccggaagggcttcatcatctccaacgccacctacaaagagatcggcctgctgacctgcgaggccaccgtt aatggccacctgtacaagaccaactatctgacccacagacagaccaacaccatcatcgacgtggtgctgagcccctctcatgg catcgagctgtccgtgggagaaaagctggtgctgaactgcaccgccagaaccgagctgaacgtgggcatcgacttcaactggg agtacccctccagcaagcaccagcacaagaagctggtcaaccgggacctgaaaacccagtccggctccgagatgaagaaattc ctgagcaccctgaccatcgacggcgtgaccagatctgaccagggcctgtatacctgcgccgcttcctctggcctgatgaccaa gaaaaactccaccttcgtgcgggtgcacgagaaaggtggcggaggatctggcggaggcggctctggcggcggtggatctgctt ctcctgctgctccagctccagcttctccagcagctcctgcaccttctgcaccagctgcaagtcctgcagcacccgcaccagct agtcctgccgctcctgctcctagtgctcctgccgcaagtccagctgctcccgctcctgcaagcccagctgcaccagcaccaag tgctccagctgcctcaccagccgcaccagctccagcaagccctgcagctcccgctccttcagctcctgctgcttctcccgcag -continued cacccgctccagcatcaccagccgctccagcaccatcagctccagcagcatctcctgcagctccagctcctgctagtcccgct gctcccgcacctagtgcaccagccgcttctcccgccgctcctgctcctgcatctcctgctgcacccgctccatctgctcccgc cgcatcacccgcagctcccgcaccagcctctccagctgcaccagctcctagcgcaccagcagctagcccagctgctcctgcac cagctagccccgcagctccagctccaagcgctcctgctgcatccccagctgctccagctcctgcctcaccagctgctccagca ccttctgctcccgccgcttctcctgccgcaccagctccagctagtccagccgcaccagcaccatctgcacccgctgctagccc tgctgcaccagctccagcatcacccgctgcaccagctccatccgcaccagctgcttcaccagcagctcccgctccagcttcac ccgctgctcccgctcctagcgctcccgcagcttcaccagctgcacccgctccagccagtccagctgctcccgcaccatccgca ccagcagcaagtcccgccgctccagctccagctagcccagctgctccagctccatctgcaccagccgcatctccagctgctcc agctccagctagtcctgctgcacccgctcctagcgctccagctgcaagtcctgccgctcctgctccagcctctcctgccgctc cagcacctagcgctcccgctgccagtccagcagctccagctcctgcatctcccgccgcaccagcaccaagcgcacccgcagca tctcccgctgctcccgctccagcaagccctgccgctcctgcaccaagtgcaccagcagcatccccagcagctcccgctccagc atctccagcagctccagctccaagtgctccagcagctagtcctgctgctccagctcctgctagccctgcagctcctgcaccat ctgctcccgcagccagtcctgcagctcctgcaccagcaagtccagctgctcctgcacctagcgctccagctgcatctcccgct gcaccagctccagcaagtcccgctgctcctgctccttctgctccagcagcttcccctgctgctcctgctcctgcttcacccgc cgctccagctccatctgctcccgctgcctctccagccgctcctgcaccagcatcaccagctgctcccgcaccaagcgcacccg ctgcaagcccagccgctcctgctcctgctagtccagccgctcctgcaccttcagcacccgcagcttccccagctgctccagct ccagcaagtccagcagctccagctccttccgctccagctgcaagccccgcagctccagctcctgcttctcctgctgctcctgc accatcagctccagctgctagtccagcagctcctgcaccagccagtcctgccgcaccagcaccttcagctccagctgcttcac ccgctgctcccgcaccagctagtccagccgctccagcaccaagtgctcccgccgctggtggtggtggatctggtggtggcgga agcggaggtggtggttctcagctgtccctgccttccatcctgcctaacgagaacgagaaggtggtccagctgaactcctcctt ctctctgcggtgcttcggcgagtccgaagtgtcttggcagtaccccatgtccgaagaggaatcctccgacgtggaaatccgga acgaggaaaacaactccggcctgttcgtgaccgtgctggaagtgtcctctgcctctgctgctcacaccggcctgtacacatgc tactacaatcacacccagaccgaagagaacgagctggaaggccggcacatctacatctacgtgcccgatcctgacgtggcctt tgtgcctctgggcatgaccgactacctggtcatcgtggaagatgacgactccgctatcatcccttgccggaccaccgatccag agacacctgtgacactgcacaactccgaaggcgtggtgcctgcctcctacgattctagacagggcttcaacggcaccttcacc gtgggaccttacatctgcgaggctacagtgaagggcaagaagtttcagacaatccccttcaacgtgtacgccctgaaggccac ctctgagctggacctggaaatggaagctctgaaaaccgtgtacaagtccggcgagacaatcgtcgtgacctgtgccgtgttca acaacgaagtggtggacctgcagtggacctatcctggcgaagtgaaaggcaagggcatcacaatgctggaagagatcaaggtg ccctccatcaagctggtgtataccctgaccgtgcctgaggccactgtgaaggactctggcgactacgagtgtgccgctagaca ggccaccagagaagtcaaagaaatgaagaaagtgaccatctccgtccacgagaagggc SEQ ID No. 66:
Amino acid sequence of EPS1115P, excluding signal polypeptide sequence and purification-tag SDTGRPFVEMYSEIPEIIHMTEGRELVIPCRVTSPNITVTLKKFPLDTLIPDGKRIIWDSRKGFIISNATYKEIGLLTCEATV NGHLYKTNYLTHRQTNTIIDVVLSPSHGIELSVGEKLVLNCTARTELNVGIDFNWEYPSSKHQHKKLVNRDLKTQSGSEMKKF LSTLTIDGVTRSDQGLYTCAASSGLMTKKNSTFVRVHEKGGGGSGGGGSGGGGSASPAAPAPASPAAPAPSAPAASPAAPAPA SPAAPAPSAPAASPAAPAPASPAAPAPSAPAASPAAPAPASPAAPAPSAPAASPAAPAPASPAAPAPSAPAASPAAPAPASPA APAPSAPAASPAAPAPASPAAPAPSAPAASPAAPAPASPAAPAPSAPAASPAAPAPASPAAPAPSAPAASPAAPAPASPAAPA PSAPAASPAAPAPASPAAPAPSAPAASPAAPAPASPAAPAPSAPAASPAAPAPASPAAPAPSAPAASPAAPAPASPAAPAPSA PAASPAAPAPASPAAPAPSAPAASPAAPAPASPAAPAPSAPAASPAAPAPASPAAPAPSAPAASPAAPAPASPAAPAPSAPAA SPAAPAPASPAAPAPSAPAASPAAPAPASPAAPAPSAPAASPAAPAPASPAAPAPSAPAASPAAPAPASPAAPAPSAPAASPA APAPASPAAPAPSAPAASPAAPAPASPAAPAPSAPAASPAAPAPASPAAPAPSAPAASPAAPAPASPAAPAPSAPAASPAAPA -continued PASPAAPAPSAPAASPAAPAPASPAAPAPSAPAASPAAPAPASPAAPAPSAPAASPAAPAPASPAAPAPSAPAAGGGGSGGGG SGGGGSQLSLPSILPNENEKVVQLNSSFSLRCFGESEVSWQYPMSEEESSDVEIRNEENNSGLFVTVLEVSSASAAHTGLYTC YYNHTQTEENELEGRHIYIYVPDPDVAFVPLGMTDYLVIVEDDDSAIIPCRTTDPETPVTLHNSEGVVPASYDSRQGFNGTFT VGPYICEATVKGKKFQTIPFNVYALKATSELDLEMEALKTVYKSGETIVVTCAVFNNEVVDLQWTYPGEVKGKGITMLEEIKV

PSIKLVYTLTVPEATVKDSGDYECAARQATREVKEMKKVTISVHEKG

SEQ ID No. 67:
Nucleotide sequence encoding EPS1116P, excluding signal polypeptide sequence and purification-tag cagctgagcctgccaagcatcctgcctaacgaaaatgagaaggtggtccagctgaacagctccttcagtctgagatgctttgg cgaatcagaggtgagctggcagtacccaatgtcagaggaagagtctagtgacgtggaaattaggaatgaagagaacaattcag gactgttcgtgaccgtcctggaggtgtcaagcgccagcgccgctcacaccggactgtacacatgttactataaccatactcag accgaagagaatgaactggaggggaggcacatctccatccacgtgcccgatcctgacgtggcctttgccccactgggaatgac agattacctggtcatcgtcgaggacgatgactctgccatcattccctgccgcacctcagactccgaaactcctgtgaccctgc ataacagtgagggcgtggtccccgcctcctacgattctcgacagggattcaatggcaccttcaccgtcggaccctatatctgt gaggccactgtgaagggcaagaaattccagaccattccttttaacgtgtacgcactgaaagccacatccgaactggacctgga aatggaggccctgaagactgtctataaatctggagagactatcgtggtcacctgcgccgtgttcaacaatgaagtggtcgatg cgcagtggacttaccccggcgaggtcaagggcaaagggattaccatggacgaagagatcaaggtgcctagccagaagctggtg tacaccctgacagtcccagaagccaccgtgaaggattccggggactatgagtgtgcagcccggcaggcctccagagaagtgaa ggagatgaagaaagtgacaatcagtgtccacgagaaaggagcaagccccgccgctccagcccccgcaagcccagccgcaccag caccttccgcaccagccgcctccccagcagcacccgcacccgcttcccctgccgcccccgcccctagcgcccccgccgcctcc cctgccgccccagcccccgcctctccagccgcccctgccccatctgccccagccgccagcccagccgcccccgcccctgccag ccccgccgccccagccccctccgcccctgctgcttcccctgccgcccctgccccagccagcccagctgctcctgctccaagcg cccctgctgcaagcccagctgctccagcccccgcctctcccgctgctccagctccttctgcccctgctgcttccccagctgct cccgcccctgcctctcctgctgctcctgctccctccgcccctgctgcatcccccgctgctcctgccccagcttccccagctgc acctgctccaagcgccccagctgcaagcccagctgcacctgcacctgcttcccccgctgcccctgccccaagcgcccccgccg catcccccgccgcaccagcccccgcctcacccgcagcaccagccccatcagcaccagccgcctcaccagccgcccccgcaccc gcaagtccagcagcacccgcaccatccgcccccgccgcaagcccagccgcccccgctccagcatcccctgccgcccccgcccc cagcgcccccgccgcctcccctgccgccccagcccccgcctctccagccgcccctgccccatctgccccagccgccagccccg ccgcccccgcccctgccagccccgccgccccagcccccctccgcccctgctgcttcccccgccgcccctgccccagccagccca gctgctcccgctccaagcgcccccgctgcaagcccagctgctccagcccccgcctctcccgctgctccagctccttctgcccc tgctgcttcccccgctgctcccgcccccgcctctcctgctgctcccgctccctccgcccctgctgcatcccccgctgctcctg ccccagcttccccagctgcacctgctcccagcgccccagctgcaagccccgctgcacctgcacctgcttcccccgctgcccct gccccaagcgcccccgccgcctcacccgcagcccccgctccagccagccccgcagcaccagcaccctcagccccagcctcaga taccggccggccttttgtggagatgtactccgaaatccccgagatcattcacatgaccgaagggcgagagctggtcatcccat gccgggtgacaagccccaacattactgtgaccctgaagaaattccctctggatactctgatcccagacgggaagaggatcatt tgggacagccgcaaaggcttcatcatttccaatgccacatataaggaaattggcctgctgacatgcgaggccactgtgaacgg gcacctgtacaaaaccaattatctgacacatcggcagacaaacactatcattgatgtggtcctgagcccttcccatgggatcg aactgagcgtcggagagaagctggtgctgaattgtacagccagaactgaactgaacgtgggcattgacttcaattgggagtac ccctcctctaagcaccagcataagaaactggtgaatagggatctgaaaacccagtctgggagtgagatgaagaaatttctgtc taccctgacaatcgatggcgtgacacgcagtgaccaggggctgtatacttgtgcagccagttcaggcctgatgaccaagaaga acagcacatttgtccgagtccacgaaaag -continued

```
SEQ ID No. 68:
Amino acid sequence of EPS1116P, excluding signal polypeptide sequence and
purification-tag
QLSLPSILPNENEKVVQLNSSFSLRCFGESEVSWQYPMSEEESSDVEIRNEENNSGLFVTVLEVSSASAAHTGLYTCYYNHTQ

TEENELEGRHISIHVPDPDVAFAPLGMTDYLVIVEDDDSAIIPCRTSDSETPVTLHNSEGVVPASYDSRQGFNGTFTVGPYIC

EATVKGKKFQTIPFNVYALKATSELDLEMEALKTVYKSGETIVVTCAVFNNEVVDAQWTYPGEVKGKGITMDEEIKVPSQKLV

YTLTVPEATVKDSGDYECAARQASREVKEMKKVTISVHEKGASPAAPAPASPAAPAPSAPAASPAAPAPASPAAPAPSAPAAS

PAAPAPASPAAPAPSAPAASPAAPAPASPAAPAPSAPAASPAAPAPASPAAPAPSAPAASPAAPAPASPAAPAPSAPAASPAA

PAPASPAAPAPSAPAASPAAPAPASPAAPAPSAPAASPAAPAPASPAAPAPSAPAASPAAPAPASPAAPAPSAPAASPAAPAP

ASPAAPAPSAPAASPAAPAPASPAAPAPSAPAASPAAPAPASPAAPAPSAPAASPAAPAPASPAAPAPSAPAASPAAPAPASP

AAPAPSAPAASPAAPAPASPAAPAPSAPAASPAAPAPASPAAPAPSAPAASPAAPAPASPAAPAPSAPAASPAAPAPASPAAP

APSAPAASPAAPAPASPAAPAPSAPASDTGRPFVEMYSEIPEIIHMTEGRELVIPCRVTSPNITVTLKKFPLDTLIPDGKRII

WDSRKGFIISNATYKEIGLLTCEATVNGHLYKTNYLTHRQTNTIIDVVLSPSHGIELSVGEKLVLNCTARTELNVGIDFNWEY

PSSKHQHKKLVNRDLKTQSGSEMKKFLSTLTIDGVTRSDQGLYTCAASSGLMTKKNSTFVRVHEK

SEQ ID No. 69:
Nucleotide sequence encoding PA linker
gccgctcctg ctgctccagc tcctgctgcc ccagcagccc ctgccccagc tgctcctgca

gcagctcccg cagccccagc acccgccgca ccagcagctc cagcccctgc agcaccagct

gctgcccctg ccgcccctgc tccagccgca cccgctgcac ccgcaccagc tgccccagcc

gccgcacccg cagctccagc tcccgctgct cctgctgcac cagcccctgc cgctccagca

gccgcaccag cagcaccagc cccagctgct cccgctgctc cagcacccgc agcccccgca

gcagcaccag ccgctcctgc tcctgccgcc ccagcagctc ctgctccagc agcccctgct

gctgctccag cagcaccagc accagctgct ccagctgccc cagctcctgc agcacccgcc

gctgctcccg cagctcctgc ccctgctgca cccgcagcac ccgctccagc agcacctgca

gctgcaccag ctgctcccgc acctgccgct cccgcagctc ccgctcctgc agctccagcc

gcagctcctg ctgctcctgc accagcagct cccgccgcac cagctccagc tgcccctgct

SEQ ID No. 70:
Amino acid sequence of PA linker
AAPAAPAPAAPAAPAPAAPAAAPAAPAPAAPAAPAPAAPAAAPAAPAPAAPAAPAPAAPA

AAPAAPAPAAPAAPAPAAPAAAPAAPAPAAPAAPAPAAPAAAPAAPAPAAPAAPAPAAPA

AAPAAPAPAAPAAPAPAAPAAAPAAPAPAAPAAPAPAAPAAAPAAPAPAAPAAPAPAAPA

AAPAAPAPAAPAAPAPAAPA
```

LIST OF REFERENCES

Andrae, Johanna, Radiosa Gallini, and Christer Betsholtz. "Role of Platelet-Derived Growth Factors in Physiology and Medicine." Genes & Development 2008; 1276-1312.

Akiyama H., Kachi S., Silva R. L., Umeda N., Hackett S. F., McCauley D., McCauley T., Zoltoski A., Epstein D. M., Campochiaro P. A. Intraocular injection of an aptamer that binds PDGF-B: A potential treatment for proliferative retinopathies. J. Cell. Physiol. 2006; 207:407-412

Aiello L P, Northrup J M, Keyt B A, et al. Hypoxic regulation of vascular endothelial growth factor in retinal cells. Arch Ophthalmol 1995; 113:1538-1544.

Benjamin L E, Hemo I, Keshet E. A plasticity window for blood vessel remodelling is defined by pericyte coverage of the preformed endothelial network and is regulated by PDGF-B and VEGF. Development. May 1998; 125(9): 1591-1598.

Bai Yujing, Li Xiaoxin. Progression and challenge of therapeutic strategies in neovascular age-related macular degeneration. Chin J Ocul Fundus Dis, 2016; 32 (1):3-7.

Boyer D S; Ophthotech Anti-PDGF in AMD Study Group. Combined inhibition of platelet derived (PDGF) and vascular endothelial (VEGF) growth factors for the treatment of neovascular age-related macular degeneration (NV-AMD)—results of a phase 1 study [ARVO abstract]. Invest Ophthalmol Vis Sci. 2009; 50:1260.

Carmeliet P, Mechanisms of angiogenesis and arteriogenesis. Nat Med. 2000 April; 6(4):389-95.

Darland D C, Massingham L J, Smith S R, Piek E, Saint-Geniez M, D'Amore P A. Pericyte production of cell-associated VEGF is differentiation-dependent and is associated with endothelial survival. Dev Biol. 2003; 264: 275-288

Day S, Acquah K, Mruthyunjaya P, Grossman D S, Lee P P, Sloan F A. Ocular complications after anti-vascular endothelial growth factor therapy in Medicare patients with age-related macular degeneration. American journal of ophthalmology. 2011; 152(2):266-272.

Diago T, Pulido J S, Molina J R, Collett L C, Link T P, Ryan E H. Jr. Ranibizumab combined with low-dose sorafenib for exudative age-related macular degeneration. Mayo Clin. Proc. 2008; 83(2); 231-234

Dugel P U. Anti-PDGF combination therapy in neovascular age-related macular degeneration: results of a phase 2b study 2013; (March).

Erber R, Thurnher A, Katsen A D et al. Combined inhibition of VEGF and PDGF signaling enforces tumor vessel regression by interfering with pericyte-mediated endothelial cell survival mechanisms. FASEBJ. 2004 February; 18(2): 338-340

Ferrara N, Hillan K J, Gerber H P, Novotny W. Discovery and development of bevacizumab, an anti-VEGF antibody for treating cancer. Nat Rev Drug Discov. 2004; 3:391-400

Ferrara N, Damico L, Shams N, Lowman H, Kim R. Development of ranibizumab, an anti-vascular endothelial growth factor antigen binding fragment, as therapy for neovascular age-related macular degeneration. Retina. 2006; 26:859-870

Fuh G, Li B, Crowley C, Cunningham B, Wells J A. Requirements for binding and signaling of the kinase domain receptor for vascular endothelial growth factor. J Biol Chem 1998; 273: 11197-11204.

Grothey Al, Galanis E. Targeting angiogenesis: progress with anti-VEGF treatment with large molecules. Nat Rev Clin Oncol. 2009 September; 6(9):507-18.

Sandy Giuliano, Gilles Pages, Mechanisms of resistance to anti-angiogenesis therapies. Biochimie 2013; 95(6): 1110-1119.

E. S. Gragoudas, A. P. Adamis, E. T. Cunningham Jr, M. Feinsod, D. R. Guyer, VEGF Inhibition Study in Ocular Neovascularization Clinical Trial Group Pegaptanib for neovascular age-related macular degeneration. N Engl J Med, 2004, 351:2805-2816

Heier J S, Brown D M, Chong V, Korobelnik J F, Kaiser P K, Nguyen Q D, Kirchhof B, Ho A, Ogura Y, Yancopoulos G D, Stahl N, Vitti R, Berliner A J, Soo Y, Anderesi M, Groetzbach G, Sommerauer B, Sandbrink R, Simader C, Schmidt-Erfurth U, VIEW 1 and VIEW 2 Study Groups. Intravitreal aflibercept (VEGF trap-eye) in wet age-related macular degeneration. Ophthalmology. 2012 December; 119(12):2537-48.

Holash J, Davis S, Papadopoulos N, Croll S D, Ho L, Russell M, Boland P, Leidich R, Hylton D, Burova E, Ioffe E, Huang T, Radziejewski C, Bailey K, Fandl J P, Daly T, Wiegand S J, Yancopoulos G D, Rudge J S. VEGF-Trap: a VEGF blocker with potent antitumor effects. Proc Natl Acad Sci USA. 2002; 99:11393-11398.

Hoch R V, Soriano P. Roles of PDGF in animal development. Development 2003; 130(20):4769-4784. Jaffe G J, Ciulla T A, Ciardella A P, Devin F, Dugel P U, Eandi C M, Masonson H, Monés J, Pearlman J A, Quaranta-El Maftouhi M, Ricci F, Westby K, Patel S C. Dual Antagonism of PDGF and VEGF in Neovascular Age-Related Macular Degeneration. Ophthalmology 2017 February; 124(2):224-234.

Leppänen V-M, Tvorogov D, Kisko K, et al. Structural and mechanistic insights into VEGF receptor 3 ligand binding and activation. Proceedings of the National Academy of Sciences of the United States of America. 2013; 110(32): 12960-12965.

Mahadevan D., Yu J.-C., Saldanha J. W., Thanki N., McPhie P., Uren A., LaRochelle W. J., Heidaran M. A. J. Biol. Chem. 1995; 270:27595-27600. McDonald N Q, Hendrickson W A. A structural superfamily of growth factors containing a cystine knot motif. Cell. 1993; 73:421-424

Murinello S, Mullins R F, Lotery A J, Perry V H, Teeling J L. Fey Receptor Upregulation Is Associated With Immune Complex Inflammation in the Mouse Retina and Early Age-Related Macular Degeneration. Investigative Ophthalmology & Visual Science. 2014; 55(1):247-258.

Nguyen Q. High Dose Ranibizumab for Diabetic Macular Edema: Month 24 Outcomes of the READ-3 Study (Ranibizumab for Edema of the mAcula in Diabetes—Protocol 3). Abstract, American Society of Retina Specialists Meeting. 2014

Papadopoulos N, Martin J, Ruan Q, et al. Binding and neutralization of vascular endothelial growth factor (VEGF) and related ligands by VEGF Trap, ranibizumab and bevacizumab. Angiogenesis. 2012; 15:171-185

Pachydaki S I, Jakobiec F A, Bhat P, et al. Surgical management and ultrastructural study of choroidal neovascularization in punctate inner choroidopathy after bevacizumab. J Ophthalmic Inflamm Infect. 2012; 2(1):29-37.

Pavlakovic H, Becker J, Albuquerque R, Wilting J, Ambati J. Soluble VEGFR-2: an Anti-lymphangiogenic Variant of VEGF Receptors. Annals of the New York Academy of Sciences. 2010; 1207 (Suppl 1):E7-15.

Powner M B, McKenzie J A G, Christianson G J, Roopenian D C, Fruttiger M; Expression of Neonatal Fc Receptor in the Eye. Invest. Ophthalmol. Vis. Sci. 2014; 55(3):1607-1615.

Reinmuth N, Liu W, Jung Y D, et al. Induction of VEGF in perivascular cells defines a potential paracrine mechanism for endothelial cell survival. FASEB J. 2001; 15(7):1239-1241.

Robbins S G, Mixon R N, Wilson D J, et al. Platelet-derived growth factor ligands and receptors immunolocalized in proliferative retinal diseases. Invest Ophthalmol Vis Sci. September 1994; 35(10):3649-3663.

Rofagha, Soraya et al. Seven-Year Outcomes in Ranibizumab-Treated Patients in ANCHOR, MARINA, and HORIZON. Ophthalmology, 2013; 120(11):2292-2299.

Rosenfeld P J, Brown D M, Heier J S, Boyer D S, Kaiser P K, Chung C Y, Kim R Y, MARINA Study Group. Ranibizumab for neovascular age-related macular degeneration. N Engl J Med. 2006; 355(14):1419-31.

Rosenfeld, Philip J. et al. Characteristics of Patients Losing Vision after 2 Years of Monthly Dosing in the Phase III Ranibizumab Clinical Trials. Ophthalmology, 2011; 118 (3):523-530

Sampat K M Garg S J Complications of intravitreal injections. Curr Opin Ophthalmol. 2010; 21: 178-1 83.

Schlessinger J. Cell signaling by receptor tyrosine kinases. Cell. 2000; 103:211-225.

Schlapschy M., Binder U., Borger C., Theobald I., Wachinger K., Kisling S., Haller D., Skerra A. PASylation: a biological alternative to PEGylation for extending the plasma half-life of pharmaceutically active proteins. Protein Eng. Des. Sel. 2013; 26:489-501.

Shibuya M, Ito N, Claesson-Welsh L. Structure and function of vascular endothelial growth factor receptor-1 and -2. Curr Top Microbiol Immunol. 1999; 237:59-83.

Hye-Ryong Shim, Ann et al. "Structures of a Platelet-Derived Growth Factor/propeptide Complex and a Platelet-Derived Growth Factor/receptor Complex." Proceedings of the National Academy of Sciences of the United States of America 2010:11307-11312.

Stewart M W. A Review of Ranibizumab for the Treatment of Diabetic Retinopathy. Ophthalmology and Therapy. 2017; 6(1):33-47.

Stuttfeld E, Ballmer-Hofer K. Structure and function of VEGF receptors. IUBMB Life. 2009; 61:915-922.

Souied E H, Dugel P U, Ferreira A, Hashmonay R, Lu J, Kelly S P. Severe Ocular Inflammation Following Ranibizumab or Aflibercept Injections for Age-Related Macular Degeneration: A Retrospective Claims Database Analysis. Ophthalmic Epidemiology. 2016; 23(2):71-79.

Uemura A, Ogawa M, Hirashima M, Fujiwara T, Koyama S, Takagi H, Honda Y, Wiegand S J, Yancopoulos G D, Nishikawa S Recombinant angiopoietin-1 restores higher-order architecture of growing blood vessels in mice in the absence of mural cells. J Clin Invest. 2002; 110(11):1619-28.

Winkler F, Kozin S V, Tong R T, Chae S S, Booth M F, Garkavtsev I, Xu L, Hicklin D J, Fukumura D, di Tomaso E, Munn L L, Jain R K. Kinetics of vascular normalization by VEGFR2 blockade governs brain tumor response to radiation: role of oxygenation, angiopoietin-1, and matrix metalloproteinases. Cancer Cell. 2004; 6(6):553-63.

Ying G, Kim B J, Maguire M G, Huang J, Daniel E, Jaffe G J, Grunwald J E, Blinder K J, Flaxel C J, Rahhal F, Regillo C, Martin D F, for the CATT Research Group. Sustained Visual Acuity Loss in the Comparison of Age-Related Macular Degeneration Treatments Trials. JAMA Ophthalmol. 2014; 132(8): 915-921.

Zehetner C1, Kirchmair R, Neururer S B, Kralinger M T, Bechrakis N E, Kieselbach G F. Systemic upregulation of PDGF-B in patients with neovascular AMD. Investigative Ophthalmology & Visual Science 2014; 55:337-344.

All references cited herein are fully incorporated by reference. Having now fully described the invention, it will be understood by a person skilled in the art that the invention may be practiced within a wide and equivalent range of conditions, parameters and the like, without affecting the spirit or scope of the invention or any embodiment thereof.

The invention claimed is:

1. A protein consisting essentially of:

(i) an extracellular domain of the human Platelet-Derived Growth Factor receptor (PDGFR);

(ii) an extracellular domain of the human Vascular Endothelial Growth Factor receptor (VEGFR); and (iii) a linker attaching said domain of PDGFR and said domain of VEGFR, wherein the linker (a) consists of proline, alanine, and serine, or (b) consists of proline and alanine.

2. The protein of claim 1, wherein when the linker consists of proline, alanine, and serine, said proline residues constitute more than 4% and less than 40% of said linker.

3. The protein of claim 2, wherein said linker comprises an amino acid sequence as follows: (ASPAAPA-PASPAAPAPSAPA (SEQ ID NO: 71))n, wherein n is an integer of 10-100, 10-60, 10-40, or 10-30, or wherein n is 10, 20, or 30.

4. The protein of claim 2, wherein said linker has an amino acid sequence as shown in SEQ ID No. 2 or wherein said linker is a polypeptide encoded by a nucleic acid molecule having a nucleotide sequence as shown in SEQ ID No. 1.

5. The protein of claim 1, wherein when the linker consists of proline and alanine, said proline residues constitute more than about 10% and less than about 75% of said linker.

6. The protein of claim 5, wherein said linker has an amino acid sequence as follows: (AAPAAPA-PAAPAAPAAPA (SEQ ID NO: 72))n, wherein n is an integer of 10-100.

7. The protein of claim 5, wherein said linker has an amino acid sequence as shown in SEQ ID No. 70 or wherein said linker is a polypeptide encoded by a nucleic acid molecule having a nucleotide sequence as shown in SEQ ID No. 69.

8. The protein of claim 2, wherein said linker has an amino acid sequence consisting of about 50 to about 3000 amino acid residues.

9. The protein of claim 1, wherein said domain of PDGFR comprises one or more of Ig domains 1 to 5 of PDGFR, one or more of Ig domains 1 to 3 of PDGFR, or wherein said domain of PDGFR comprises Ig domains 1 to 3 of PDGFR.

10. The protein of claim 1, wherein said domain of PDGFR is capable of binding to human Platelet-Derived Growth Factor (PDGF), optionally wherein said PDGF is a PDGF dimer, wherein said PDGF dimer is a PDGF homodimer or a PDGF heterodimer.

11. The protein of claim 1, wherein said PDGFR is human PDGFR-α.

12. The protein of claim 1, wherein said domain of PDGFR comprises:
- (a) a protein having an amino acid sequence as shown in SEQ ID No. 4 or SEQ ID No. 20;
- (b) a polypeptide encoded by a nucleic acid molecule having a nucleotide sequence as shown in SEQ ID No. 3 or SEQ ID No. 19;
- (c) a polypeptide having an amino acid sequence encoded by a nucleic acid hybridizing under stringent conditions to the complementary strand of nucleic acid molecules as defined in (b); and
- (d) a polypeptide having an amino acid sequence encoded by a nucleic acid being degenerate as a result of the genetic code to the nucleotide sequence of a nucleic acid as defined in (b) or (c).

13. The protein of claim 11, wherein said domain of PDGFR is capable of binding to Platelet-Derived Growth Factor (PDGF), wherein said PDGF is a PDGF homodimer, and wherein said PDGF homodimer is a PDGF-A homodimer, a PDGF-B homodimer, or a PDGF-C homodimer; or wherein said domain of PDGFR is capable of binding to Platelet-Derived Growth Factor (PDGF), wherein said PDGF preferably is a PDGF heterodimer, and wherein said PDGF heterodimer preferably is a heterodimer of PDGF-AB.

14. The protein of claim 1, wherein said PDGFR is human PDGFR-β.

15. The protein of claim 1, wherein said domain of PDGFR comprises:
- (a) a protein having an amino acid sequence as shown in SEQ ID No. 6;
- (b) a polypeptide encoded by a nucleic acid molecule having a nucleotide sequence as shown in SEQ ID No. 5;
- (c) a polypeptide having an amino acid sequence encoded by a nucleic acid hybridizing under stringent conditions to the complementary strand of nucleic acid molecules as defined in (b); and
- (d) a polypeptide having an amino acid sequence encoded by a nucleic acid being degenerate as a result of the genetic code to the nucleotide sequence of a nucleic acid as defined in (b) or (c).

16. The protein of claim 14, wherein said domain of PDGFR is capable of binding to Platelet-Derived Growth Factor (PDGF), wherein said PDGF preferably is a PDGF homodimer, and wherein said PDGF homodimer preferably is a PDGF-B homodimer.

17. The protein of claim 1, wherein said domain of VEGFR comprises one or more of Ig domains 1 to 7 of VEGFR, wherein said domain of VEGFR comprises Ig domain 2 and/or Ig domain 3 of VEGFR, or wherein said domain of VEGFR comprises Ig domain 2 and Ig domain 3 of VEGFR.

18. The protein of claim 1, wherein said VEGFR is human VEGFR-1 or human VEGFR-2, wherein said domain of VEGFR comprises Ig domain 2 of VEGFR-1 and Ig domain 3 of VEGFR-2.

19. The protein of claim 1, wherein said domain of VEGFR comprises:
- (a) a protein having an amino acid sequence as shown in SEQ ID No. 8;
- (b) a polypeptide encoded by a nucleic acid molecule having a nucleotide sequence as shown in SEQ ID No. 7;
- (c) a polypeptide having an amino acid sequence encoded by a nucleic acid hybridizing under stringent conditions to the complementary strand of nucleic acid molecules as defined in (b); and
- (d) a polypeptide having an amino acid sequence encoded by a nucleic acid being degenerate as a result of the genetic code to the nucleotide sequence of a nucleic acid as defined in (b) or (c).

20. The protein of claim 1, wherein said domain of VEGFR is capable of binding to human Vascular Endothelial Growth Factor (VEGF), optionally wherein said Vascular Endothelial Growth Factor (VEGF) is a VEGF dimer, such as a VEGF homodimer or a VEGF-A homodimer.

21. The protein of claim 1, wherein said protein is a fusion protein.

22. The protein of claim 1, wherein said protein comprises:
- (a) a protein having an amino acid sequence as shown in SEQ ID No. 16, SEQ ID NO: 46, SEQ ID No. 48, SEQ ID No. 50, EQ ID No. 52, SEQ ID No.54, SEQ ID No. 56, SEQ ID No. 58, SEQ ID No. 60, SEQ ID No. 62, SEQ ID No. 64, SEQ ID No. 66 or SEQ ID No. 68;
- (b) a polypeptide encoded by a nucleic acid molecule having a nucleotide sequence as shown in SEQ ID No. 15, SEQ ID No. 45, SEQ ID No. 47, SEQ ID No. 49, SEQ ID No. 51, SEQ ID No. 53, SEQ ID No. 55, SEQ ID No. 57, SEQ ID No. 59, SEQ ID No. 61, SEQ ID No. 63, SEQ ID No. 65 or SEQ ID No. 67;
- (c) a polypeptide having an amino acid sequence encoded by a nucleic acid hybridizing under stringent conditions to the complementary strand of nucleic acid molecules as defined in (b); and
- (d) a polypeptide having an amino acid sequence encoded by a nucleic acid being degenerate as a result of the genetic code to the nucleotide sequence of a nucleic acid as defined in (b) or (c).

23. The protein of claim 1, wherein said protein comprises an N-terminal signal sequence, wherein said N-terminal signal sequence is the N-terminal signal sequence of PDGFR, such as the N-terminal signal sequence of human PDGFRα.

24. The protein of claim 23, wherein said N-terminal signal sequence has an amino acid sequence as shown in SEQ ID No. 10 or wherein said N-terminal signal sequence is a polypeptide encoded by a nucleic acid molecule having a nucleotide sequence as shown in SEQ ID No. 9.

25. The protein of any claim 1, wherein the protein is arranged from N-terminus to C-terminus in the order:
- (optional signal sequence)-one or more domains of PDGFR-(PAS/PA)-one or more domains of VEGFR-(optional purification tag) or
- (optional signal sequence)-one or more domains of VEGFR-(PAS/PA)-one or more domains of PDGFR-(optional purification tag) or
- (optional signal sequence)-(PAS/PA)-one or more domains of VEGFR-one or more domains of PDGFR-(optional purification tag) or
- (optional signal sequence)-(PAS/PA)-one or more domains of PDGFR-one or more domains of VEGFR-(optional purification tag) or (optional signal sequence)-(PAS/PA)-one or more domains of PDGFR-(PAS/PA)-one or more domains of VEGFR-(PAS/PA)-(optional purification tag); or wherein the protein is arranged from N-terminus to C-terminus in the order:

(optional signal sequence)-one or more domains of PDGFR-(GGGGS (SEQ ID NO: 73))n-(PAS/PA)-(GGGGS (SEQ ID NO: 73))n-one or more domains of VEGFR-(optional purification tag) or (optional signal sequence)-one or more domains of VEGFR-(GGGGS (SEQ ID NO: 73))n-(PAS/PA)-(GGGGS (SEQ ID NO: 73))n-one or more domains of PDGFR-(optional purification tag);

wherein, n=0-5.

26. The protein of claim 1, wherein said protein comprises:

(a) a protein having an amino acid sequence as shown in SEQ ID No. 14, SEQ ID No. 22, SEQ ID No. 24, SEQ ID No. 26, SEQ ID No.28, SEQ ID No.30, SEQ ID No. 32, SEQ ID No. 34, SEQ ID No. 36, SEQ ID No. 38, SEQ ID No. 40, SEQ ID No. 42 or SEQ ID No. 44;

(b) a polypeptide encoded by a nucleic acid molecule having a nucleotide sequence as shown in SEQ ID No. 13, SEQ ID No.21, SEQ ID No.23, SEQ ID No.25, SEQ ID No. 27, SEQ ID No. 29, EQ ID No. 31, SEQ ID No. 33, SEQ ID No. 35, SEQ ID No. 37, SEQ ID No. 39, SEQ ID No. 41 or SEQ ID No. 43;

(c) a polypeptide having an amino acid sequence encoded by a nucleic acid hybridizing under stringent conditions to the complementary strand of nucleic acid molecules as defined in (b); and (d) a polypeptide having an amino acid sequence encoded by a nucleic acid being degenerate as a result of the genetic code to the nucleotide sequence of a nucleic acid as defined in (b) or (c).

27. A nucleic acid molecule encoding the protein of claim 1.

28. A vector comprising the nucleic acid of claim 27.

29. A host cell comprising the nucleic acid of claim 27.

30. A pharmaceutical composition comprising the protein of claim 1, optionally further comprising (a) pharmaceutical acceptable carrier(s).

31. A method for treating ophthalmic diseases, cancer, renal fibrosis, cirrhosis, arthosclerosis, portal hypertension or systemic sclerosis comprising administering the protein of claim 1 wherein said cancer is a solid cancer or non-solid cancer, optionally wherein said solid cancer is colon cancer, hepatocellular carcinoma, non-small cell lung cancer, soft tissue sarcoma, prostate cancer, breast cancer, ovarian cancer, glioma, dermatofibrosarcoma protuberans, oral squamous cell carcinoma or pancreatic cancer, optionally wherein said non-solid cancer is leukemia or non-Hodgkin's lymphoma, optionally, wherein said ophthalmic diseases is age-related macular degeneration (AMD), Diabetic retinopathy (DR), Diabetic macular edema (DME), Choroidal neovascularization (CNV), Retinal vein occlusion (RVO), Central retinal vein occlusion (CRVO), Branch retinal vein occlusion (BRVO), pathologic myopia (PM).

* * * * *

SEQUENCE LISTING

```
<160> NUMBER OF SEQ ID NOS: 73

<210> SEQ ID NO 1
<211> LENGTH: 600
<212> TYPE: DNA
<213> ORGANISM: Artificial Sequence
<220> FEATURE:
<223> OTHER INFORMATION: sequence encoding PAS polypeptide/linker

<400> SEQUENCE: 1

gcctctcctg ctgcccctgc cccagcttct ccagctgctc ctgcaccttc tgctccagcc     60

gctagtcctg cagctccagc tcctgcttct cctgccgcac cagcacctag tgcccctgct    120

gcatcaccag cagctcccgc acccgctagc ccagctgcac cagctccaag tgctccagca    180

gcttcacccg cagcacccgc tccagcaagt ccagcagccc cagccccttc agcaccagct    240

gcatctcccg cagcccctgc tcctgccagc cctgccgctc ctgctccaag cgctcctgct    300

gctagtccag ccgcccctgc accagcaagt cctgctgctc ccgcacctag tgcaccagca    360

gcaagccctg cagctcctgc accagcatct ccagcagcac cagcaccatc agcccctgcc    420

gcttctcccg cagctccagc cccagcctcc cctgctgctc cagccccctc tgctcctgca    480

gcatctcctg ccgctcccgc ccctgcaagt cccgccgctc cagcaccatc cgctccagct    540

gcttccccag ccgctccagc tccagctagc cccgcagccc ccgcaccatc tgccccagca    600


<210> SEQ ID NO 2
<211> LENGTH: 200
<212> TYPE: PRT
<213> ORGANISM: Artificial Sequence
<220> FEATURE:
<223> OTHER INFORMATION: sequence of PAS polypeptide/linker

<400> SEQUENCE: 2

Ala Ser Pro Ala Ala Pro Ala Pro Ala Ser Pro Ala Ala Pro Ala Pro
1               5                   10                  15

Ser Ala Pro Ala Ala Ser Pro Ala Ala Pro Ala Pro Ala Ser Pro Ala
            20                  25                  30

Ala Pro Ala Pro Ser Ala Pro Ala Ala Ser Pro Ala Ala Pro Ala Pro
        35                  40                  45

Ala Ser Pro Ala Ala Pro Ala Pro Ser Ala Pro Ala Ala Ser Pro Ala
    50                  55                  60
```

-continued

```
Ala Pro Ala Pro Ala Ser Pro Ala Ala Pro Ala Pro Ser Ala Pro Ala
65                  70                  75                  80

Ala Ser Pro Ala Ala Pro Ala Pro Ala Ser Pro Ala Ala Pro Ala Pro
                85                  90                  95

Ser Ala Pro Ala Ala Ser Pro Ala Ala Pro Ala Pro Ala Ser Pro Ala
            100                 105                 110

Ala Pro Ala Pro Ser Ala Pro Ala Ala Ser Pro Ala Ala Pro Ala Pro
        115                 120                 125

Ala Ser Pro Ala Ala Pro Ala Pro Ser Ala Pro Ala Ala Ser Pro Ala
    130                 135                 140

Ala Pro Ala Pro Ala Ser Pro Ala Ala Pro Ala Pro Ser Ala Pro Ala
145                 150                 155                 160

Ala Ser Pro Ala Ala Pro Ala Pro Ala Ser Pro Ala Ala Pro Ala Pro
                165                 170                 175

Ser Ala Pro Ala Ala Ser Pro Ala Ala Pro Ala Pro Ala Ser Pro Ala
            180                 185                 190

Ala Pro Ala Pro Ser Ala Pro Ala
        195                 200


<210> SEQ ID NO 3
<211> LENGTH: 870
<212> TYPE: DNA
<213> ORGANISM: Artificial Sequence
<220> FEATURE:
<223> OTHER INFORMATION: sequence encoding Ig-like domains 1 to 3 of
      PDGFRalpha

<400> SEQUENCE: 3

cagctgagcc tgccctccat cctgcctaac gagaatgaga aggtggtgca gctgaactcc     60

agcttctccc tgagatgctt tggcgagtct gaggtgtcct ggcagtaccc aatgagcgag    120

gaggagtctt ccgacgtgga gatccgcaat gaggagaaca attctggcct gttcgtgacc    180

gtgctggagg tgagctctgc ctccgccgct cacaccggcc tgtacacatg ttactataac    240

catacccaga cagaggagaa tgagctggag ggcagacaca tctacatcta tgtgcccgat    300

cctgacgtgg cctttgtgcc actgggcatg accgattacc tggtcatcgt ggaggacgat    360

gacagcgcca tcatcccctg caggaccaca gaccccgaga cacctgtgac actgcataac    420

tctgagggcg tggtgccagc cagctacgat tctcggcagg gcttcaatgg cacctttaca    480

gtgggcccct atatctgtga ggccaccgtg aagggcaaga agttccagac aatccctttt    540

aacgtgtacg ccctgaaggc taccagcgag ctggacctgg agatggaggc cctgaagaca    600

gtgtataagt ctggcgagac aatcgtggtg acatgcgccg tgttcaacaa tgaggtggtg    660

gatctgcagt ggacctaccc cggcgaggtg aagggcaagg gcatcacaat gctggaggag    720

atcaaggtgc cttctatcaa gctggtgtac accctgacag tgccagaggc caccgtgaag    780

gattccggcg actatgagtg tgccgctagg caggctaccc gggaggtgaa ggagatgaag    840

aaggtgacaa tctctgtgca cgagaaggga                                     870


<210> SEQ ID NO 4
<211> LENGTH: 290
<212> TYPE: PRT
<213> ORGANISM: Artificial Sequence
<220> FEATURE:
<223> OTHER INFORMATION: sequence of Ig-like domains 1 to 3 of
      PDGFRalpha

<400> SEQUENCE: 4
```

-continued

```
Gln Leu Ser Leu Pro Ser Ile Leu Pro Asn Glu Asn Glu Lys Val Val
1               5                   10                  15

Gln Leu Asn Ser Ser Phe Ser Leu Arg Cys Phe Gly Glu Ser Glu Val
            20                  25                  30

Ser Trp Gln Tyr Pro Met Ser Glu Glu Glu Ser Ser Asp Val Glu Ile
        35                  40                  45

Arg Asn Glu Glu Asn Asn Ser Gly Leu Phe Val Thr Val Leu Glu Val
    50                  55                  60

Ser Ser Ala Ser Ala Ala His Thr Gly Leu Tyr Thr Cys Tyr Tyr Asn
65                  70                  75                  80

His Thr Gln Thr Glu Glu Asn Glu Leu Glu Gly Arg His Ile Tyr Ile
                85                  90                  95

Tyr Val Pro Asp Pro Asp Val Ala Phe Val Pro Leu Gly Met Thr Asp
            100                 105                 110

Tyr Leu Val Ile Val Glu Asp Asp Asp Ser Ala Ile Ile Pro Cys Arg
        115                 120                 125

Thr Thr Asp Pro Glu Thr Pro Val Thr Leu His Asn Ser Glu Gly Val
    130                 135                 140

Val Pro Ala Ser Tyr Asp Ser Arg Gln Gly Phe Asn Gly Thr Phe Thr
145                 150                 155                 160

Val Gly Pro Tyr Ile Cys Glu Ala Thr Val Lys Gly Lys Lys Phe Gln
                165                 170                 175

Thr Ile Pro Phe Asn Val Tyr Ala Leu Lys Ala Thr Ser Glu Leu Asp
            180                 185                 190

Leu Glu Met Glu Ala Leu Lys Thr Val Tyr Lys Ser Gly Glu Thr Ile
        195                 200                 205

Val Val Thr Cys Ala Val Phe Asn Asn Glu Val Val Asp Leu Gln Trp
    210                 215                 220

Thr Tyr Pro Gly Glu Val Lys Gly Lys Gly Ile Thr Met Leu Glu Glu
225                 230                 235                 240

Ile Lys Val Pro Ser Ile Lys Leu Val Tyr Thr Leu Thr Val Pro Glu
                245                 250                 255

Ala Thr Val Lys Asp Ser Gly Asp Tyr Glu Cys Ala Ala Arg Gln Ala
            260                 265                 270

Thr Arg Glu Val Lys Glu Met Lys Lys Val Thr Ile Ser Val His Glu
        275                 280                 285

Lys Gly
    290
```

<210> SEQ ID NO 5
<211> LENGTH: 603
<212> TYPE: DNA
<213> ORGANISM: Artificial Sequence
<220> FEATURE:
<223> OTHER INFORMATION: sequence encoding Ig-like domains 1 to 3 of PDGFRbeta

<400> SEQUENCE: 5

```
aacgatgccg aggaactgtt catcttcctg accgagatta ccgagatcac aatcccctgc     60

cgcgtgacag atcctcagct ggtggttacc ctgcatgaga agaaaggcga cgtggccctg    120

cctgtgcctt acgatcatca gagaggcttc tccggcatct tcgaggaccg gtcttacatc    180

tgcaagacca ccatcggcga cagagaggtg gactccgacg cctactacgt gtacagactc    240

caggtgtcct ccatcaacgt gtccgtgaat gccgtgcaga cagttgtgcg gcagggcgag    300

aatatcaccc tgatgtgcat cgtgatcggc aacgaggtgg tcaacttcga gtggacctat    360
```

```
cctcggaaag aatctggccg gctggtggaa cctgtgaccg acttcctgct ggacatgccc    420

taccacatcc ggtctatcct gcacatccct tccgccgagc tggaagattc cggcacctac    480

acctgtaacg tgaccgagtc cgtgaacgac caccaggacg agaaggccat caatatcacc    540

gtggtggaat ccggctacgt gcggctgttg ggagaagtgg gcacactgca gtttgctgag    600

ctg                                                                  603
```

```
<210> SEQ ID NO 6
<211> LENGTH: 201
<212> TYPE: PRT
<213> ORGANISM: Artificial Sequence
<220> FEATURE:
<223> OTHER INFORMATION: Sequence of Ig-like domains 1 to 3 of PDGFRbeta

<400> SEQUENCE: 6

Asn Asp Ala Glu Glu Leu Phe Ile Phe Leu Thr Glu Ile Thr Glu Ile
1               5                   10                  15

Thr Ile Pro Cys Arg Val Thr Asp Pro Gln Leu Val Val Thr Leu His
            20                  25                  30

Glu Lys Lys Gly Asp Val Ala Leu Pro Val Pro Tyr Asp His Gln Arg
        35                  40                  45

Gly Phe Ser Gly Ile Phe Glu Asp Arg Ser Tyr Ile Cys Lys Thr Thr
    50                  55                  60

Ile Gly Asp Arg Glu Val Asp Ser Asp Ala Tyr Tyr Val Tyr Arg Leu
65                  70                  75                  80

Gln Val Ser Ser Ile Asn Val Ser Val Asn Ala Val Gln Thr Val Val
                85                  90                  95

Arg Gln Gly Glu Asn Ile Thr Leu Met Cys Ile Val Ile Gly Asn Glu
            100                 105                 110

Val Val Asn Phe Glu Trp Thr Tyr Pro Arg Lys Glu Ser Gly Arg Leu
        115                 120                 125

Val Glu Pro Val Thr Asp Phe Leu Leu Asp Met Pro Tyr His Ile Arg
    130                 135                 140

Ser Ile Leu His Ile Pro Ser Ala Glu Leu Glu Asp Ser Gly Thr Tyr
145                 150                 155                 160

Thr Cys Asn Val Thr Glu Ser Val Asn Asp His Gln Asp Glu Lys Ala
                165                 170                 175

Ile Asn Ile Thr Val Val Glu Ser Gly Tyr Val Arg Leu Leu Gly Glu
            180                 185                 190

Val Gly Thr Leu Gln Phe Ala Glu Leu
        195                 200


<210> SEQ ID NO 7
<211> LENGTH: 615
<212> TYPE: DNA
<213> ORGANISM: Artificial Sequence
<220> FEATURE:
<223> OTHER INFORMATION: Sequence encoding Ig-like domain 2 of VEGFR-1
      and Ig-like domain 3 of VEGFR-2

<400> SEQUENCE: 7

agtgataccg gtagaccttt cgtagagatg tacagtgaaa tccccgaaat tatacacatg     60

actgaaggaa gggagctcgt cattccctgc cgggttacgt cacctaacat cactgttact    120

ttaaaaaagt ttccacttga cactttgatc cctgatggaa aacgcataat ctgggacagt    180

agaaagggct tcatcatatc aaatgcaacg tacaaagaaa tagggcttct gacctgtgaa    240
```

-continued

```
gcaacagtca atgggcattt gtataagaca aactatctca cacatcgaca aaccaataca    300

atcatagatg tggttctgag tccgtctcat ggaattgaac tatctgttgg agaaaagctc    360

gtcttaaatt gtacagcaag aactgaacta aatgtgggga ttgacttcaa ctgggaatac    420

ccttcttcga agcatcagca taagaaactt gtaaaccgag acctaaaaac ccagtctggg    480

agtgagatga agaaattttt gagcacctta actatagatg gtgtaacccg gagtgaccaa    540

ggattgtaca cctgtgcagc atccagtggg ctgatgacca agaagaacag cacatttgtc    600

agggtccatg aaaag                                                      615
```

<210> SEQ ID NO 8
<211> LENGTH: 205
<212> TYPE: PRT
<213> ORGANISM: Artificial Sequence
<220> FEATURE:
<223> OTHER INFORMATION: Sequence of Ig-like domain 2 of VEGFR-1 and Ig-like domain 3 of VEGFR-2

<400> SEQUENCE: 8

```
Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys
        195                 200                 205
```

<210> SEQ ID NO 9
<211> LENGTH: 69
<212> TYPE: DNA
<213> ORGANISM: Artificial Sequence
<220> FEATURE:
<223> OTHER INFORMATION: Sequence encoding N-terminal signal peptide

<400> SEQUENCE: 9

```
atggggactt cccatccggc gttcctggtc ttaggctgtc ttctcacagg gctgagccta     60

atcctctgc                                                              69
```

<210> SEQ ID NO 10
<211> LENGTH: 23
<212> TYPE: PRT
<213> ORGANISM: Artificial Sequence
<220> FEATURE:
<223> OTHER INFORMATION: Sequence of N-terminal signal peptide

<400> SEQUENCE: 10

```
Met Gly Thr Ser His Pro Ala Phe Leu Val Leu Gly Cys Leu Leu Thr
1               5                   10                  15

Gly Leu Ser Leu Ile Leu Cys
            20
```

<210> SEQ ID NO 11
<211> LENGTH: 21
<212> TYPE: DNA
<213> ORGANISM: Artificial Sequence
<220> FEATURE:
<223> OTHER INFORMATION: Sequence encoding purification tag

<400> SEQUENCE: 11

```
caccatcacc atcaccacgc c                                              21
```

<210> SEQ ID NO 12
<211> LENGTH: 7
<212> TYPE: PRT
<213> ORGANISM: Artificial Sequence
<220> FEATURE:
<223> OTHER INFORMATION: Sequence of purification tag

<400> SEQUENCE: 12

```
His His His His His His Ala
1               5
```

<210> SEQ ID NO 13
<211> LENGTH: 7190
<212> TYPE: DNA
<213> ORGANISM: Artificial Sequence
<220> FEATURE:
<223> OTHER INFORMATION: Sequence of vector pDSG33-PDGFR-PAS200-VEGFR

<400> SEQUENCE: 13

```
acccacaatg gggacttccc atccggcgtt cctggtctta ggctgtcttc tcacagggct     60

gagcctaatc ctctgccagc tttcattacc ctctatcctt ccaaatgaaa atgaaaaggt    120

tgtgcagctg aattcatcct tttctctgag atgctttggg gagagtgaag tgagctggca    180

gtaccccatg tctgaagaag agtcttccga tgtggaaatc agaaatgaag aaaacaacag    240

cggccttttt gtgacggtct tggaagtgag cagtgcctcg gcggcccaca cagggttgta    300

cacttgctat tacaaccaca ctcagacaga agagaatgag cttgaaggca ggcacattta    360

catctatgtg ccagacccag atgtagcctt tgtacctcta ggaatgacgg attatttagt    420

catcgtggag gatgatgatt ctgccattat accttgtcgc acaactgatc ccgagactcc    480

tgtaacctta cacaacagtg agggggtggt acctgcctcc tacgacagca gacagggctt    540

taatgggacc ttcactgtag ggccctatat ctgtgaggcc accgtcaaag gaaagaagtt    600

ccagaccatc ccatttaatg tttatgcttt aaaagcaaca tcagagctgg atctagaaat    660

ggaagctctt aaaaccgtgt ataagtcagg ggaaacgatt gtggtcacct gtgctgtttt    720

taacaatgag gtggttgacc ttcaatggac ttaccctgga gaagtgaaag gcaaaggcat    780

cacaatgctg gaagaaatca aagtcccatc catcaaattg gtgtacactt tgacggtccc    840

cgaggccacg gtgaaagaca gtggagatta cgaatgtgct gcccgccagg ctaccaggga    900
```

-continued

```
ggtcaaagaa atgaagaaag tcactatttc tgtccatgag aaaggtgcct ctcctgctgc    960
ccctgcccca gcttctccag ctgctcctgc accttctgct ccagccgcta gtcctgcagc   1020
tccagctcct gcttctcctg ccgcaccagc acctagtgcc cctgctgcat caccagcagc   1080
tcccgcaccc gctagcccag ctgcaccagc tccaagtgct ccagcagctt cacccgcagc   1140
acccgctcca gcaagtccag cagccccagc cccttcagca ccagctgcat ctcccgcagc   1200
ccctgctcct gccagccctg ccgctcctgc tccaagcgct cctgctgcta gtccagccgc   1260
ccctgcacca gcaagtcctg ctgctcccgc acctagtgca ccagcagcaa gccctgcagc   1320
tcctgcacca gcatctccag cagcaccagc accatcagcc cctgccgctt ctcccgcagc   1380
tccagcccca gcctcccctg ctgctccagc cccctctgct cctgcagcat ctcctgccgc   1440
tcccgcccct gcaagtcccg ccgctccagc accatccgct ccagctgctt ccccagccgc   1500
tccagctcca gctagccccg cagcccccgc accatctgcc ccagcagcca gtgataccgg   1560
tagacctttc gtagagatgt acagtgaaat ccccgaaatt atacacatga ctgaaggaag   1620
ggagctcgtc attccctgcc gggttacgtc acctaacatc actgttactt taaaaaagtt   1680
tccacttgac actttgatcc ctgatggaaa acgcataatc tgggacagta gaaagggctt   1740
catcatatca aatgcaacgt acaaagaaat agggcttctg acctgtgaag caacagtcaa   1800
tgggcatttg tataagacaa actatctcac acatcgacaa accaatacaa tcatagatgt   1860
ggttctgagt ccgtctcatg gaattgaact atctgttgga gaaaagctcg tcttaaattg   1920
tacagcaaga actgaactaa atgtggggat tgacttcaac tgggaatacc cttcttcgaa   1980
gcatcagcat aagaaacttg taaaccgaga cctaaaaacc cagtctggga gtgagatgaa   2040
gaaatttttg agcaccttaa ctatagatgg tgtaacccgg agtgaccaag gattgtacac   2100
ctgtgcagca tccagtgggc tgatgaccaa gaagaacagc acatttgtca gggtccatga   2160
aaagcaccat caccatcacc acgcctgaag agcttaagct tgcggccgca gatctagctt   2220
aagtttaaac cgctgatcag cctcgactgt gccttctagt tgccagccat ctgttgtttg   2280
cccctccccc gtgccttcct tgaccctgga aggtgccact cccactgtcc tttcctaata   2340
aaatgaggaa attgcatcgc attgtctgag taggtgtcat tctattctgg ggggtggggt   2400
ggggcaggac agcaaggggg aggattggga agacaatagc aggcatgctg gggatgcggt   2460
gggctctatg gagcttggcc gcgttgctgg cgtttttcca taggctccgc ccccctgacg   2520
agcatcacaa aaatcgacgc tcaagtcaga ggtggcgaaa cccgacagga ctataaagat   2580
accaggcgtt tccccctgga agctccctcg tgcgctctcc tgttccgacc ctgccgctta   2640
ccggatacct gtccgccttt ctcccttcgg gaagcgtggc gctttctcat agctcacgct   2700
gtaggtatct cagttcggtg taggtcgttc gctccaagct gggctgtgtg cacgaacccc   2760
ccgttcagcc cgaccgctgc gccttatccg gtaactatcg tcttgagtcc aacccggtaa   2820
gacacgactt atcgccactg gcagcagcca ctggtaacag gattagcaga gcgaggtatg   2880
taggcggtgc tacagagttc ttgaagtggt ggcctaacta cggctacact agaagaacag   2940
tatttggtat ctgcgctctg ctgaagccag ttaccttcgg aaaaagagtt ggtagctctt   3000
gatccggcaa acaaaccacc gctggtagcg gtggtttttt tgtttgcaag cagcagatta   3060
cgcgcagaaa aaaaggatct caagaagatc ctttgatctt ttctacgggg tctgacgctc   3120
agtggaacga aaactcacgt taagggattt tggtcatgag attatcaaaa aggatcttca   3180
cctagatcct tttaaattaa aaatgaagtt ttaaatcaat ctaaagtata tatgagtaaa   3240
```

```
cttggtctga cagttaccaa tgcttaatca gtgaggcacc tatctcagcg atctgtctat   3300
ttcgttcatc catagttgcc tgactccccg tcgtgtagat aactacgata cgggagggct   3360
taccatctgg ccccagtgct gcaatgatac cgcgagaccc acgctcaccg gctccagatt   3420
tatcagcaat aaaccagcca gccggaaggg ccgagcgcag aagtggtcct gcaactttat   3480
ccgcctccat ccagtctatt aattgttgcc gggaagctag agtaagtagt tcgccagtta   3540
atagtttgcg caacgttgtt gccattgcta caggcatcgt ggtgtcacgc tcgtcgtttg   3600
gtatggcttc attcagctcc ggttcccaac gatcaaggcg agttacatga tcccccatgt   3660
tgtgcaaaaa agcggttagc tccttcggtc ctccgatcgt tgtcagaagt aagttggccg   3720
cagtgttatc actcatggtt atggcagcac tgcataattc tcttactgtc atgccatccg   3780
taagatgctt ttctgtgact ggtgagtact caaccaagtc attctgagaa tagtgtatgc   3840
ggcgaccgag ttgctcttgc ccggcgtcaa tacgggataa taccgcgcca catagcagaa   3900
ctttaaaagt gctcatcatt ggaaaacgtt cttcggggcg aaaactctca aggatcttac   3960
cgctgttgag atccagttcg atgtaaccca ctcgtgcacc caactgatct tcagcatctt   4020
ttactttcac cagcgtttct gggtgagcaa aaacaggaag gcaaaatgcc gcaaaaaagg   4080
gaataagggc gacacggaaa tgttgaatac tcatactctt cctttttcaa tattattgaa   4140
gcatttatca gggttattgt ctcatgagcg gatacatatt tgaatgtatt tagaaaaata   4200
aacaaatagg ggttccgcgc acatttcccc gaaaagtgcc acctgacgtc taggttcacc   4260
taagaatggg agcaaccagc aggaaaagga caagcagcga aaattcacgc cccctggga   4320
ggtggcggca tatgcaaagg atagcactcc cactctacta ctgggtatca tatgctgact   4380
gtatatgcat gaggatagca tatgctaccc ggatacagat taggatagca tatactaccc   4440
agatatagat taggatagca tatgctaccc agatatagat taggatagcc tatgctaccc   4500
agatataaat taggatagca tatactaccc agatatagat taggatagca tatgctaccc   4560
agatatagat taggatagcc tatgctaccc agatatagat taggatagca tatgctaccc   4620
agatatagat taggatagca tatgctatcc agatatttgg gtagtatatg ctacccagat   4680
ataaattagg atagcatata ctaccctaat ctctattagg atagcatatg ctacccggat   4740
acagattagg atagcatata ctacccagat atagattagg atagcatatg ctacccagat   4800
atagattagg atagcctatg ctacccagat ataaattagg atagcatata ctacccagat   4860
atagattagg atagcatatg ctacccagat atagattagg atagcctatg ctacccagat   4920
atagattagg atagcatatg ctatccagat atttgggtag tatatgctac ccatggcaac   4980
attagcccac cgtgctctca gcgacctcgt gaatatgagg accaacaacc ctgtgcttgg   5040
cgctcaggcg caagtgtgtg taatttgtcc tccagatcgc agcaatcgcg cccctatctt   5100
ggcccgccca cctacttatg caggtattcc ccggggtgcc attagtggtt ttgtgggcaa   5160
gtggtttgac cgcagtggtt agcggggtta caatcagcca agttattaca cccttatttt   5220
acagtccaaa accgcagggc ggcgtgtggg ggctgacgcg tgcccccact ccacaatttc   5280
aaaaaaaaga gtggccactt gtctttgttt atgggcccca ttggcgtgga gccccgttta   5340
attttcgggg gtgttagaga caaccagtgg agtccgctgc tgtcggcgtc cactctcttt   5400
ccccttgtta caaatagagt gtaacaacat ggttcacctg tcttggtccc tgcctgggac   5460
acatcttaat aaccccagta tcatattgca ctaggattat gtgttgccca tagccataaa   5520
ttcgtgtgag atggacatcc agtctttacg gcttgtcccc accccatgga tttctattgt   5580
taaagatatt cagaatgttt cattcctaca ctagtattta ttgcccaagg ggtttgtgag   5640
```

```
ggttatattg gtgtcatagc acaatgccac cactgaaccc cccgtccaaa ttttattctg   5700

ggggcgtcac ctgaaacctt gttttcgagc acctcacata caccttactg ttcacaactc   5760

agcagttatt ctattagcta aacgaaggag aatgaagaag caggcgaaga ttcaggagag   5820

ttcactgccc gctccttgat cttcagccac tgcccttgtg actaaaatgg ttcactaccc   5880

tcgtggaatc ctgaccccat gtaaataaaa ccgtgacagc tcatggggtg ggagatatcg   5940

ctgttcctta ggaccctttt actaacccta attcgatagc atatgcttcc cgttgggtaa   6000

catatgctat tgaattaggg ttagtctgga tagtatatac tactacccgg gaagcatatg   6060

ctacccgttt agggttaaca agggggcctt ataaacacta ttgctaatgc cctcttgagg   6120

gtccgcttat cggtagctac acaggcccct ctgattgacg ttggtgtagc ctcccgtagt   6180

cttcctgggc ccctgggagg tacatgtccc ccagcattgg tgtaagagct tcagccaaga   6240

gttacacata aaggcaatgt tgtgttgcag tccacagact gcaaagtctg ctccaggatg   6300

aaagccactc agtgttggca aatgtgcaca tccatttata aggatgtcaa ctacagtcag   6360

agaacccctt tgtgtttggt ccccccccgt gtcacatgtg gaacagggcc cagttggcaa   6420

gttgtaccaa ccaactgaag ggattacatg cactgccccg cattaattgc atgaagaatc   6480

tgcttagggt taggcgtttt gcgctgcttc gcgatgtacg ggccagatat acgcgttgac   6540

attgattatt gactagttat taatagtaat caattacggg gtcattagtt catagcccat   6600

atatggagtt ccgcgttaca taacttacgg taaatggccc gcctggctga ccgcccaacg   6660

acccccgccc attgacgtca ataatgacgt atgttcccat agtaacgcca atagggactt   6720

tccattgacg tcaatgggtg gagtatttac ggtaaactgc ccacttggca gtacatcaag   6780

tgtatcatat gccaagtacg ccccctattg acgtcaatga cggtaaatgg cccgcctggc   6840

attatgccca gtacatgacc ttatgggact ttcctacttg gcagtacatc tacgtattag   6900

tcatcgctat taccatggtg atgcggtttt ggcagtacat caatgggcgt ggatagcggt   6960

ttgactcacg gggatttcca agtctccacc ccattgacgt caatgggagt ttgttttggc   7020

accaaaatca acgggacttt ccaaaatgtc gtaacaactc cgccccattg acgcaaatgg   7080

gcggtaggcg tgtacggtgg gaggtctata taagcagagc tctctggcta actagagaac   7140

ccactgctta ctggcttatc gaaattaata cgactcacta tagggtctag              7190
```

<210> SEQ ID NO 14
<211> LENGTH: 726
<212> TYPE: PRT
<213> ORGANISM: Artificial Sequence
<220> FEATURE:
<223> OTHER INFORMATION: sequence of PDGFRalphaD123-PAS(200)-
      VEGFR1D2/R2D3 fusion protein

<400> SEQUENCE: 14

```
Met Gly Thr Ser His Pro Ala Phe Leu Val Leu Gly Cys Leu Leu Thr
1               5                   10                  15

Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45

Cys Phe Gly Glu Ser Glu Val Ser Trp Gln Tyr Pro Met Ser Glu Glu
    50                  55                  60

Glu Ser Ser Asp Val Glu Ile Arg Asn Glu Glu Asn Asn Ser Gly Leu
65                  70                  75                  80
```

-continued

```
Phe Val Thr Val Leu Glu Val Ser Ser Ala Ser Ala Ala His Thr Gly
                85                  90                  95

Leu Tyr Thr Cys Tyr Tyr Asn His Thr Gln Thr Glu Glu Asn Glu Leu
            100                 105                 110

Glu Gly Arg His Ile Tyr Ile Tyr Val Pro Asp Pro Asp Val Ala Phe
        115                 120                 125

Val Pro Leu Gly Met Thr Asp Tyr Leu Val Ile Val Glu Asp Asp Asp
    130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
            180                 185                 190

Val Lys Gly Lys Lys Phe Gln Thr Ile Pro Phe Asn Val Tyr Ala Leu
        195                 200                 205

Lys Ala Thr Ser Glu Leu Asp Leu Glu Met Glu Ala Leu Lys Thr Val
    210                 215                 220

Tyr Lys Ser Gly Glu Thr Ile Val Val Thr Cys Ala Val Phe Asn Asn
225                 230                 235                 240

Glu Val Val Asp Leu Gln Trp Thr Tyr Pro Gly Glu Val Lys Gly Lys
                245                 250                 255

Gly Ile Thr Met Leu Glu Glu Ile Lys Val Pro Ser Ile Lys Leu Val
            260                 265                 270

Tyr Thr Leu Thr Val Pro Glu Ala Thr Val Lys Asp Ser Gly Asp Tyr
        275                 280                 285

Glu Cys Ala Ala Arg Gln Ala Thr Arg Glu Val Lys Glu Met Lys Lys
    290                 295                 300

Val Thr Ile Ser Val His Glu Lys Gly Ala Ser Pro Ala Ala Pro Ala
305                 310                 315                 320

Pro Ala Ser Pro Ala Ala Pro Ala Pro Ser Ala Pro Ala Ala Ser Pro
                325                 330                 335

Ala Ala Pro Ala Pro Ala Ser Pro Ala Ala Pro Ala Pro Ser Ala Pro
            340                 345                 350

Ala Ala Ser Pro Ala Ala Pro Ala Pro Ala Ser Pro Ala Ala Pro Ala
        355                 360                 365

Pro Ser Ala Pro Ala Ala Ser Pro Ala Ala Pro Ala Pro Ala Ser Pro
    370                 375                 380

Ala Ala Pro Ala Pro Ser Ala Pro Ala Ala Ser Pro Ala Ala Pro Ala
385                 390                 395                 400

Pro Ala Ser Pro Ala Ala Pro Ala Pro Ser Ala Pro Ala Ala Ser Pro
                405                 410                 415

Ala Ala Pro Ala Pro Ala Ser Pro Ala Ala Pro Ala Pro Ser Ala Pro
            420                 425                 430

Ala Ala Ser Pro Ala Ala Pro Ala Pro Ala Ser Pro Ala Ala Pro Ala
        435                 440                 445

Pro Ser Ala Pro Ala Ala Ser Pro Ala Ala Pro Ala Pro Ala Ser Pro
    450                 455                 460

Ala Ala Pro Ala Pro Ser Ala Pro Ala Ala Ser Pro Ala Ala Pro Ala
465                 470                 475                 480

Pro Ala Ser Pro Ala Ala Pro Ala Pro Ser Ala Pro Ala Ala Ser Pro
                485                 490                 495

Ala Ala Pro Ala Pro Ala Ser Pro Ala Ala Pro Ala Pro Ser Ala Pro
```

500 505 510

Ala Ala Ser Asp Thr Gly Arg Pro Phe Val Glu Met Tyr Ser Glu Ile
515 520 525

Pro Glu Ile Ile His Met Thr Glu Gly Arg Glu Leu Val Ile Pro Cys
530 535 540

Arg Val Thr Ser Pro Asn Ile Thr Val Thr Leu Lys Lys Phe Pro Leu
545 550 555 560

Asp Thr Leu Ile Pro Asp Gly Lys Arg Ile Ile Trp Asp Ser Arg Lys
565 570 575

Gly Phe Ile Ile Ser Asn Ala Thr Tyr Lys Glu Ile Gly Leu Leu Thr
580 585 590

Cys Glu Ala Thr Val Asn Gly His Leu Tyr Lys Thr Asn Tyr Leu Thr
595 600 605

His Arg Gln Thr Asn Thr Ile Ile Asp Val Val Leu Ser Pro Ser His
610 615 620

Gly Ile Glu Leu Ser Val Gly Glu Lys Leu Val Leu Asn Cys Thr Ala
625 630 635 640

Arg Thr Glu Leu Asn Val Gly Ile Asp Phe Asn Trp Glu Tyr Pro Ser
645 650 655

Ser Lys His Gln His Lys Lys Leu Val Asn Arg Asp Leu Lys Thr Gln
660 665 670

Ser Gly Ser Glu Met Lys Lys Phe Leu Ser Thr Leu Thr Ile Asp Gly
675 680 685

Val Thr Arg Ser Asp Gln Gly Leu Tyr Thr Cys Ala Ala Ser Ser Gly
690 695 700

Leu Met Thr Lys Lys Asn Ser Thr Phe Val Arg Val His Glu Lys His
705 710 715 720

His His His His His Ala
725

<210> SEQ ID NO 15
<211> LENGTH: 2088
<212> TYPE: DNA
<213> ORGANISM: Artificial Sequence
<220> FEATURE:
<223> OTHER INFORMATION: Sequence encoding EPS1108P excluding signal peptide and purification tag

<400> SEQUENCE: 15
cagctttcat taccctctat ccttccaaat gaaaatgaaa aggttgtgca gctgaattca 60
tccttttctc tgagatgctt tggggagagt gaagtgagct ggcagtaccc catgtctgaa 120
gaagagtctt ccgatgtgga aatcagaaat gaagaaaaca acagcggcct tttgtgacg 180 gtcttggaag tgagcagtgc ctcggcggcc cacacagggt tgtacacttg ctattacaac 240
cacactcaga cagaagagaa tgagcttgaa ggcaggcaca tttacatcta tgtgccagac 300
ccagatgtag cctttgtacc tctaggaatg acggattatt tagtcatcgt ggaggatgat 360
gattctgcca ttataccttg tcgcacaact gatcccgaga ctcctgtaac cttacacaac 420
agtgaggggg tggtacctgc ctcctacgac agcagacagg gctttaatgg gaccttcact 480
gtagggccct atatctgtga ggccaccgtc aaaggaaaga agttccagac catcccattt 540
aatgtttatg ctttaaaagc aacatcagag ctggatctag aaatggaagc tcttaaaacc 600
gtgtataagt caggggaaac gattgtggtc acctgtgctg tttttaacaa tgaggtggtt 660
gaccttcaat ggacttaccc tggagaagtg aaaggcaaag gcatcacaat gctggaagaa 720

```
atcaaagtcc catccatcaa attggtgtac actttgacgg tccccgaggc cacggtgaaa    780

gacagtggag attacgaatg tgctgcccgc caggctacca gggaggtcaa agaaatgaag    840

aaagtcacta tttctgtcca tgagaaaggt gcctctcctg ctgcccctgc cccagcttct    900

ccagctgctc ctgcaccttc tgctccagcc gctagtcctg cagctccagc tcctgcttct    960

cctgccgcac cagcacctag tgcccctgct gcatcaccag cagctcccgc acccgctagc   1020

ccagctgcac cagctccaag tgctccagca gcttcacccg cagcacccgc tccagcaagt   1080

ccagcagccc cagccccttc agcaccagct gcatctcccg cagcccctgc tcctgccagc   1140

cctgccgctc ctgctccaag cgctcctgct gctagtccag ccgcccctgc accagcaagt   1200

cctgctgctc ccgcacctag tgcaccagca gcaagccctg cagctcctgc accagcatct   1260

ccagcagcac cagcaccatc agcccctgcc gcttctcccg cagctccagc cccagcctcc   1320

cctgctgctc cagccccctc tgctcctgca gcatctcctg ccgctcccgc ccctgcaagt   1380

cccgccgctc cagcaccatc cgctccagct gcttccccag ccgctccagc tccagctagc   1440

cccgcagccc ccgcaccatc tgccccagca gccagtgata ccggtagacc tttcgtagag   1500

atgtacagtg aaatccccga aattatacac atgactgaag gaagggagct cgtcattccc   1560

tgccgggtta cgtcacctaa catcactgtt actttaaaaa agtttccact tgacactttg   1620

atccctgatg gaaaacgcat aatctgggac agtagaaagg gcttcatcat atcaaatgca   1680

acgtacaaag aaatagggct tctgacctgt gaagcaacag tcaatgggca tttgtataag   1740

acaaactatc tcacacatcg acaaaccaat acaatcatag atgtggttct gagtccgtct   1800

catggaattg aactatctgt tggagaaaag ctcgtcttaa attgtacagc aagaactgaa   1860

ctaaatgtgg ggattgactt caactgggaa tacccttctt cgaagcatca gcataagaaa   1920

cttgtaaacc gagacctaaa aacccagtct gggagtgaga tgaagaaatt tttgagcacc   1980

ttaactatag atggtgtaac ccggagtgac caaggattgt acacctgtgc agcatccagt   2040

gggctgatga ccaagaagaa cagcacattt gtcagggtcc atgaaaag                2088
```

```
<210> SEQ ID NO 16
<211> LENGTH: 696
<212> TYPE: PRT
<213> ORGANISM: Artificial Sequence
<220> FEATURE:
<223> OTHER INFORMATION: Sequence of EPS1108P excluding signal peptide
      and purification tag

<400> SEQUENCE: 16

Gln Leu Ser Leu Pro Ser Ile Leu Pro Asn Glu Asn Glu Lys Val Val
1               5                   10                  15

Gln Leu Asn Ser Ser Phe Ser Leu Arg Cys Phe Gly Glu Ser Glu Val
            20                  25                  30

Ser Trp Gln Tyr Pro Met Ser Glu Glu Glu Ser Ser Asp Val Glu Ile
        35                  40                  45

Arg Asn Glu Glu Asn Asn Ser Gly Leu Phe Val Thr Val Leu Glu Val
    50                  55                  60

Ser Ser Ala Ser Ala Ala His Thr Gly Leu Tyr Thr Cys Tyr Tyr Asn
65                  70                  75                  80

His Thr Gln Thr Glu Glu Asn Glu Leu Glu Gly Arg His Ile Tyr Ile
                85                  90                  95

Tyr Val Pro Asp Pro Asp Val Ala Phe Val Pro Leu Gly Met Thr Asp
            100                 105                 110

Tyr Leu Val Ile Val Glu Asp Asp Asp Ser Ala Ile Ile Pro Cys Arg
```

-continued

```
        115                 120                 125

Thr Thr Asp Pro Glu Thr Pro Val Thr Leu His Asn Ser Glu Gly Val
    130                 135                 140

Val Pro Ala Ser Tyr Asp Ser Arg Gln Gly Phe Asn Gly Thr Phe Thr
145                 150                 155                 160

Val Gly Pro Tyr Ile Cys Glu Ala Thr Val Lys Gly Lys Lys Phe Gln
                165                 170                 175

Thr Ile Pro Phe Asn Val Tyr Ala Leu Lys Ala Thr Ser Glu Leu Asp
            180                 185                 190

Leu Glu Met Glu Ala Leu Lys Thr Val Tyr Lys Ser Gly Glu Thr Ile
        195                 200                 205

Val Val Thr Cys Ala Val Phe Asn Asn Glu Val Val Asp Leu Gln Trp
    210                 215                 220

Thr Tyr Pro Gly Glu Val Lys Gly Lys Gly Ile Thr Met Leu Glu Glu
225                 230                 235                 240

Ile Lys Val Pro Ser Ile Lys Leu Val Tyr Thr Leu Thr Val Pro Glu
                245                 250                 255

Ala Thr Val Lys Asp Ser Gly Asp Tyr Glu Cys Ala Ala Arg Gln Ala
            260                 265                 270

Thr Arg Glu Val Lys Glu Met Lys Lys Val Thr Ile Ser Val His Glu
        275                 280                 285

Lys Gly Ala Ser Pro Ala Ala Pro Ala Pro Ala Ser Pro Ala Ala Pro
    290                 295                 300

Ala Pro Ser Ala Pro Ala Ala Ser Pro Ala Ala Pro Ala Pro Ala Ser
305                 310                 315                 320

Pro Ala Ala Pro Ala Pro Ser Ala Pro Ala Ala Ser Pro Ala Ala Pro
                325                 330                 335

Ala Pro Ala Ser Pro Ala Ala Pro Ala Pro Ser Ala Pro Ala Ala Ser
            340                 345                 350

Pro Ala Ala Pro Ala Pro Ala Ser Pro Ala Ala Pro Ala Pro Ser Ala
        355                 360                 365

Pro Ala Ala Ser Pro Ala Ala Pro Ala Pro Ala Ser Pro Ala Ala Pro
    370                 375                 380

Ala Pro Ser Ala Pro Ala Ala Ser Pro Ala Ala Pro Ala Pro Ala Ser
385                 390                 395                 400

Pro Ala Ala Pro Ala Pro Ser Ala Pro Ala Ala Ser Pro Ala Ala Pro
                405                 410                 415

Ala Pro Ala Ser Pro Ala Ala Pro Ala Pro Ser Ala Pro Ala Ala Ser
            420                 425                 430

Pro Ala Ala Pro Ala Pro Ala Ser Pro Ala Ala Pro Ala Pro Ser Ala
        435                 440                 445

Pro Ala Ala Ser Pro Ala Ala Pro Ala Pro Ala Ser Pro Ala Ala Pro
    450                 455                 460

Ala Pro Ser Ala Pro Ala Ala Ser Pro Ala Ala Pro Ala Pro Ala Ser
465                 470                 475                 480

Pro Ala Ala Pro Ala Pro Ser Ala Pro Ala Ala Ser Asp Thr Gly Arg
                485                 490                 495

Pro Phe Val Glu Met Tyr Ser Glu Ile Pro Glu Ile Ile His Met Thr
            500                 505                 510

Glu Gly Arg Glu Leu Val Ile Pro Cys Arg Val Thr Ser Pro Asn Ile
        515                 520                 525

Thr Val Thr Leu Lys Lys Phe Pro Leu Asp Thr Leu Ile Pro Asp Gly
    530                 535                 540
```

-continued

```
Lys Arg Ile Ile Trp Asp Ser Arg Lys Gly Phe Ile Ile Ser Asn Ala
545                 550                 555                 560

Thr Tyr Lys Glu Ile Gly Leu Leu Thr Cys Glu Ala Thr Val Asn Gly
                565                 570                 575

His Leu Tyr Lys Thr Asn Tyr Leu Thr His Arg Gln Thr Asn Thr Ile
            580                 585                 590

Ile Asp Val Val Leu Ser Pro Ser His Gly Ile Glu Leu Ser Val Gly
        595                 600                 605

Glu Lys Leu Val Leu Asn Cys Thr Ala Arg Thr Glu Leu Asn Val Gly
    610                 615                 620

Ile Asp Phe Asn Trp Glu Tyr Pro Ser Ser Lys His Gln His Lys Lys
625                 630                 635                 640

Leu Val Asn Arg Asp Leu Lys Thr Gln Ser Gly Ser Glu Met Lys Lys
                645                 650                 655

Phe Leu Ser Thr Leu Thr Ile Asp Gly Val Thr Arg Ser Asp Gln Gly
            660                 665                 670

Leu Tyr Thr Cys Ala Ala Ser Ser Gly Leu Met Thr Lys Lys Asn Ser
        675                 680                 685

Thr Phe Val Arg Val His Glu Lys
    690                 695
```

<210> SEQ ID NO 17
<211> LENGTH: 1105
<212> TYPE: DNA
<213> ORGANISM: Artificial Sequence
<220> FEATURE:
<223> OTHER INFORMATION: Sequence of synthesized DNA-fragment PDGFRalphaD123-cloning site-VEGFR1D2/R2D3 for cloning on vector pDSG33

<400> SEQUENCE: 17

```
tctagaccca caatggggac ttcccatccg gcgttcctgg tcttaggctg tcttctcaca      60

gggctgagcc taatcctctg ccagctttca ttaccctcta tccttccaaa tgaaaatgaa     120

aaggttgtgc agctgaattc atccttttct ctgagatgct ttggggagag tgaagtgagc     180

tggcagtacc ccatgtctga agaagagtct tccgatgtgg aaatcagaaa tgaagaaaac     240

aacagcggcc tttttgtgac ggtcttggaa gtgagcagtg cctcggcggc ccacacaggg     300

ttgtacactt gctattacaa ccacactcag acagaagaga atgagcttga aggcaggcac     360

atttacatct atgtgccaga cccagatgta gcctttgtac ctctaggaat gacggattat     420

ttagtcatcg tggaggatga tgattctgcc attatacctt gtcgcacaac tgatcccgag     480

actcctgtaa ccttacacaa cagtgagggg gtggtacctg cctcctacga cagcagacag     540

ggctttaatg ggaccttcac tgtagggccc tatatctgtg aggccaccgt caaaggaaag     600

aagttccaga ccatcccatt taatgtttat gctttaaaag caacatcaga gctggatcta     660

gaaatggaag ctcttaaaac cgtgtataag tcaggggaaa cgattgtggt cacctgtgct     720

gtttttaaca atgaggtggt tgaccttcaa tggacttacc ctggagaagt gaaaggcaaa     780

ggcatcacaa tgctggaaga aatcaaagtc ccatccatca aattggtgta cactttgacg     840

gtccccgagg ccacggtgaa agacagtgga gattacgaat gtgctgcccg ccaggctacc     900

agggaggtca aagaaatgaa gaaagtcact atttctgtcc atgagaaagg tgccagaaga     960

gcagatctgg gctcttctgc ccaccatcac catcaccatt aagcttgcgg ctcttctgcc    1020

agtgataccg gtagaccttt cgtagagatg tacagtgaaa tccccgaaat tatacacatg    1080
```

actgaaggaa gggagctcta agctt 1105

<210> SEQ ID NO 18
<211> LENGTH: 2206
<212> TYPE: DNA
<213> ORGANISM: Artificial Sequence
<220> FEATURE:
<223> OTHER INFORMATION: Sequence of PDGFRalphaD123-PAS(200)-VEGFR1D2/R2D3 in pDSG33-PDGFR-PAS200-VEGFR

<400> SEQUENCE: 18
tctagaccca caatggggac ttcccatccg gcgttcctgg tcttaggctg tcttctcaca 60
gggctgagcc taatcctctg ccagctttca ttaccctcta tccttccaaa tgaaaatgaa 120
aaggttgtgc agctgaattc atccttttct ctgagatgct ttggggagag tgaagtgagc 180
tggcagtacc ccatgtctga agaagagtct tccgatgtgg aaatcagaaa tgaagaaaac 240
aacagcggcc tttttgtgac ggtcttggaa gtgagcagtg cctcggcggc ccacacaggg 300
ttgtacactt gctattacaa ccacactcag acagaagaga atgagcttga aggcaggcac 360
atttacatct atgtgccaga cccagatgta gcctttgtac ctctaggaat gacggattat 420
ttagtcatcg tggaggatga tgattctgcc attatacctt gtcgcacaac tgatcccgag 480
actcctgtaa ccttacacaa cagtgagggg gtggtacctg cctcctacga cagcagacag 540
ggctttaatg ggaccttcac tgtagggccc tatatctgtg aggccaccgt caaaggaaag 600
aagttccaga ccatcccatt taatgtttat gctttaaaag caacatcaga gctggatcta 660
gaaatggaag ctcttaaaac cgtgtataag tcaggggaaa cgattgtggt cacctgtgct 720
gtttttaaca atgaggtggt tgaccttcaa tggacttacc ctggagaagt gaaaggcaaa 780
ggcatcacaa tgctggaaga aatcaaagtc ccatccatca aattggtgta cactttgacg 840
gtccccgagg ccacggtgaa agacagtgga gattacgaat gtgctgcccg ccaggctacc 900
agggaggtca aagaaatgaa gaaagtcact atttctgtcc atgagaaagg tgcctctcct 960
gctgcccctg ccccagcttc tccagctgct cctgcacctt ctgctccagc cgctagtcct 1020
gcagctccag ctcctgcttc tcctgccgca ccagcaccta gtgcccctgc tgcatcacca 1080
gcagctcccg cacccgctag cccagctgca ccagctccaa gtgctccagc agcttcaccc 1140
gcagcacccg ctccagcaag tccagcagcc ccagcccctt cagcaccagc tgcatctccc 1200
gcagcccctg ctcctgccag ccctgccgct cctgctccaa gcgctcctgc tgctagtcca 1260
gccgcccctg caccagcaag tcctgctgct cccgcaccta gtgcaccagc agcaagccct 1320
gcagctcctg caccagcatc tccagcagca ccagcaccat cagcccctgc cgcttctccc 1380
gcagctccag ccccagcctc ccctgctgct ccagccccct ctgctcctgc agcatctcct 1440
gccgctcccg cccctgcaag tcccgccgct ccagcaccat ccgctccagc tgcttcccca 1500
gccgctccag ctccagctag ccccgcagcc cccgcaccat ctgccccagc agccagtgat 1560
accggtagac ctttcgtaga gatgtacagt gaaatccccg aaattataca catgactgaa 1620
ggaagggagc tcgtcattcc ctgccgggtt acgtcaccta acatcactgt tactttaaaa 1680
aagtttccac ttgacacttt gatccctgat ggaaaacgca taatctggga cagtagaaag 1740
ggcttcatca tatcaaatgc aacgtacaaa gaaatagggc ttctgacctg tgaagcaaca 1800
gtcaatgggc atttgtataa gacaaactat ctcacacatc gacaaaccaa tacaatcata 1860
gatgtggttc tgagtccgtc tcatggaatt gaactatctg ttggagaaaa gctcgtctta 1920
aattgtacag caagaactga actaaatgtg gggattgact tcaactggga ataccttct 1980

```
tcgaagcatc agcataagaa acttgtaaac cgagacctaa aaacccagtc tgggagtgag   2040

atgaagaaat ttttgagcac cttaactata gatggtgtaa cccggagtga ccaaggattg   2100

tacacctgtg cagcatccag tgggctgatg accaagaaga acagcacatt tgtcagggtc   2160

catgaaaagc accatcacca tcaccacgcc tgaagagctt aagctt                  2206


<210> SEQ ID NO 19
<211> LENGTH: 870
<212> TYPE: DNA
<213> ORGANISM: Artificial Sequence
<220> FEATURE:
<223> OTHER INFORMATION: Sequence encoding Ig-like domains 1 to 3 of
      mutant PDGFRalpha

<400> SEQUENCE: 19

cagctgagcc tgccaagcat cctgcctaac gaaaatgaga aggtggtcca gctgaacagc     60

tccttcagtc tgagatgctt tggcgaatca gaggtgagct ggcagtaccc aatgtcagag    120

gaagagtcta gtgacgtgga aattaggaat gaagagaaca attcaggact gttcgtgacc    180

gtcctggagg tgtcaagcgc cagcgccgct cacaccggac tgtacacatg ttactataac    240

catactcaga ccgaagagaa tgaactggag gggaggcaca tctccatcca cgtgcccgat    300

cctgacgtgg cctttgcccc actgggaatg acagattacc tggtcatcgt cgaggacgat    360

gactctgcca tcattccctg ccgcacctca gactccgaaa ctcctgtgac cctgcataac    420

agtgagggcg tggtccccgc ctcctacgat tctcgacagg gattcaatgg caccttcacc    480

gtcggaccct atatctgtga ggccactgtg aagggcaaga aattccagac cattcctttt    540

aacgtgtacg cactgaaagc cacatccgaa ctggacctgg aaatggaggc cctgaagact    600

gtctataaat ctggagagac tatcgtggtc acctgcgccg tgttcaacaa tgaagtggtc    660

gatgcgcagt ggacttaccc cggcgaggtc aagggcaaag ggattaccat ggacgaagag    720

atcaaggtgc ctagccagaa gctggtgtac accctgacag tcccagaagc caccgtgaag    780

gattccgggg actatgagtg tgcagcccgg caggcctcca gagaagtgaa ggagatgaag    840

aaagtgacaa tcagtgtcca cgagaaagga                                     870


<210> SEQ ID NO 20
<211> LENGTH: 290
<212> TYPE: PRT
<213> ORGANISM: Artificial Sequence
<220> FEATURE:
<223> OTHER INFORMATION: Sequence of Ig-like domains 1 to 3 of mutant
      PDGFRalpha

<400> SEQUENCE: 20

Gln Leu Ser Leu Pro Ser Ile Leu Pro Asn Glu Asn Glu Lys Val Val
1               5                   10                  15

Gln Leu Asn Ser Ser Phe Ser Leu Arg Cys Phe Gly Glu Ser Glu Val
            20                  25                  30

Ser Trp Gln Tyr Pro Met Ser Glu Glu Glu Ser Ser Asp Val Glu Ile
        35                  40                  45

Arg Asn Glu Glu Asn Asn Ser Gly Leu Phe Val Thr Val Leu Glu Val
    50                  55                  60

Ser Ser Ala Ser Ala Ala His Thr Gly Leu Tyr Thr Cys Tyr Tyr Asn
65                  70                  75                  80

His Thr Gln Thr Glu Glu Asn Glu Leu Glu Gly Arg His Ile Ser Ile
                85                  90                  95

His Val Pro Asp Pro Asp Val Ala Phe Ala Pro Leu Gly Met Thr Asp
```

```
            100                 105                 110

Tyr Leu Val Ile Val Glu Asp Asp Asp Ser Ala Ile Ile Pro Cys Arg
        115                 120                 125

Thr Ser Asp Ser Glu Thr Pro Val Thr Leu His Asn Ser Glu Gly Val
    130                 135                 140

Val Pro Ala Ser Tyr Asp Ser Arg Gln Gly Phe Asn Gly Thr Phe Thr
145                 150                 155                 160

Val Gly Pro Tyr Ile Cys Glu Ala Thr Val Lys Gly Lys Lys Phe Gln
                165                 170                 175

Thr Ile Pro Phe Asn Val Tyr Ala Leu Lys Ala Thr Ser Glu Leu Asp
            180                 185                 190

Leu Glu Met Glu Ala Leu Lys Thr Val Tyr Lys Ser Gly Glu Thr Ile
        195                 200                 205

Val Val Thr Cys Ala Val Phe Asn Asn Glu Val Val Asp Ala Gln Trp
    210                 215                 220

Thr Tyr Pro Gly Glu Val Lys Gly Lys Gly Ile Thr Met Asp Glu Glu
225                 230                 235                 240

Ile Lys Val Pro Ser Gln Lys Leu Val Tyr Thr Leu Thr Val Pro Glu
                245                 250                 255

Ala Thr Val Lys Asp Ser Gly Asp Tyr Glu Cys Ala Ala Arg Gln Ala
            260                 265                 270

Ser Arg Glu Val Lys Glu Met Lys Lys Val Thr Ile Ser Val His Glu
        275                 280                 285

Lys Gly
    290
```

<210> SEQ ID NO 21
<211> LENGTH: 2472
<212> TYPE: DNA
<213> ORGANISM: Artificial Sequence
<220> FEATURE:
<223> OTHER INFORMATION: Sequence encoding EPS1103P

<400> SEQUENCE: 21

```
atgggtacaa gccatcccgc cttcctggtc ctgggttgcc tgctgactgg tctgtctctg      60

atcctgtgcc agctgagcct gccttcaatc ctgcccaacg agaatgagaa ggtggtgcag     120

ctgaactcca gcttcagcct gagatgcttt ggcgagtctg aggtgtcctg gcagtaccct     180

atgtctgagg aggagtcttc cgacgtggag atccgcaatg aggagaacaa ttccggcctg     240

ttcgtgaccg tgctggaggt gagctctgcc agcgccgctc acaccggcct gtacacatgt     300

tactataacc atacccagac agaggagaat gagctggagg gcagacacat ctacatctat     360

gtgcccgatc ctgacgtggc ctttgtgcca ctgggcatga ccgattacct ggtcatcgtg     420

gaggacgatg actctgccat catcccctgc aggaccacag acccagagac acccgtgaca     480

ctgcataact ccgagggagt ggtgccagct agctacgatt ctcggcaggg cttcaatggc     540

acctttacag tgggccccta tatctgtgag gccaccgtga agggcaagaa gttccagaca     600

atccctttta acgtgtacgc cctgaaggct acctctgagc tggacctgga gatggaggcc     660

ctgaagacag tgtataagtc cggcgagaca atcgtggtga catgcgccgt gttcaacaat     720

gaggtggtgg atctgcagtg gacctaccct ggcgaggtga agggcaaggg catcacaatg     780

ctggaggaga tcaaggtgcc ttccatcaag ctggtgtaca ccctgacagt gccagaggcc     840

accgtgaagg atagcggcga ctatgagtgt gctgctaggc aggctaccag ggaggtgaag     900

gagatgaaga aggtgacaat ctccgtgcac gagaagggag ctagcccagc tgctccagct     960
```

ccagctagcc ccgccgctcc tgctccatct gctcctgctg cttccccagc tgctcccgcc 1020
cctgcttctc ctgctgctcc agctccatcc gccccagctg cttctcctgc cgctcctgcc 1080
ccagcttccc cagccgctcc cgccccttcc gctccagccg cctctcccgc cgcccctgct 1140
ccagctagcc cagcagcccc agccccttct gctccagccg cctctccagc cgcccctgct 1200
cccgcatccc ccgccgcccc cgccccttcc gcccctgccg cctccccagc tgccccagct 1260
cctgcctctc ctgctgcccc tgctccatcc gctccagccg ccagtcccgc cgcccccgct 1320
ccagctagcc cagccgcacc agccccttct gctcccgccg cctctcccgc cgcacctgct 1380
ccagcatccc ccgccgcccc agccccttcc gcccctgcag cctccccagc tgcccccgct 1440
cctgcctctc ctgcagcccc tgctccttcc gctccagccg catctcccgc cgccccagcc 1500
ccagctagcc cagcagcacc agccccctct gctccagccg ccagccctgc cgcccctgct 1560
cccgcttccc ccgccgcccc agcaccttcc gcccctgccg catccccagc agcccccgct 1620
cctgccagcc ctgctgcccc tgcaccttcc gctccagccg cttctcccgc cgccccagca 1680
cccgctagcc cagctgcccc tgccccttct gctccagcag cctctcctgc cgcccctgct 1740
cctgcatccc ccgccgcacc cgccccttcc gcccccgccg cctccccagc tgcaccagct 1800
ccagcctctc cagctgctcc agctccttcc gccccagcta gcgataccgg ccgccctttt 1860
gtggagatgt acagcgagat ccccgagatc atccacatga ccgagggcag ggagctggtc 1920
atcccatgcc gggtgacatc tcccaacatc accgtgacac tgaagaagtt ccctctggat 1980
accctgatcc cagacggcaa gagaatcatc tgggactctc gcaagggctt tatcatctcc 2040
aatgccacat ataaggagat cggcctgctg acctgcgagg ctacagtgaa cggccacctg 2100
tacaagacca attatctgac acataggcag accaacacaa tcatcgatgt ggtgctgagc 2160
ccatctcatg gcatcgagct gagcgtgggc gagaagctgg tgctgaattg taccgcccgg 2220
acagagctga acgtgggcat cgacttcaat tgggagtacc cttccagcaa gcaccagcat 2280
aagaagctgg tgaacagaga tctgaagacc cagtccggca gcgagatgaa gaagtttctg 2340
agcaccctga caatcgatgg cgtgacccgc tctgaccagg gcctgtatac atgtgccgct 2400
tcttccggcc tgatgactaa gaaaaactcc acctttgtgc gggtccacga aaaacaccac 2460
caccaccacc at 2472

<210> SEQ ID NO 22
<211> LENGTH: 824
<212> TYPE: PRT
<213> ORGANISM: Artificial Sequence
<220> FEATURE:
<223> OTHER INFORMATION: Sequence of EPS1103P

<400> SEQUENCE: 22

Met Gly Thr Ser His Pro Ala Phe Leu Val Leu Gly Cys Leu Leu Thr
1 5 10 15

Gly Leu Ser Leu Ile Leu Cys Gln Leu Ser Leu Pro Ser Ile Leu Pro
20 25 30

Asn Glu Asn Glu Lys Val Val Gln Leu Asn Ser Ser Phe Ser Leu Arg
35 40 45

Cys Phe Gly Glu Ser Glu Val Ser Trp Gln Tyr Pro Met Ser Glu Glu
50 55 60

Glu Ser Ser Asp Val Glu Ile Arg Asn Glu Glu Asn Asn Ser Gly Leu
65 70 75 80

Phe Val Thr Val Leu Glu Val Ser Ser Ala Ser Ala Ala His Thr Gly

-continued

```
                85                  90                  95

Leu Tyr Thr Cys Tyr Tyr Asn His Thr Gln Thr Glu Glu Asn Glu Leu
            100                 105                 110

Glu Gly Arg His Ile Tyr Ile Tyr Val Pro Asp Pro Asp Val Ala Phe
        115                 120                 125

Val Pro Leu Gly Met Thr Asp Tyr Leu Val Ile Val Glu Asp Asp Asp
    130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
            180                 185                 190

Val Lys Gly Lys Lys Phe Gln Thr Ile Pro Phe Asn Val Tyr Ala Leu
        195                 200                 205

Lys Ala Thr Ser Glu Leu Asp Leu Glu Met Glu Ala Leu Lys Thr Val
    210                 215                 220

Tyr Lys Ser Gly Glu Thr Ile Val Val Thr Cys Ala Val Phe Asn Asn
225                 230                 235                 240

Glu Val Val Asp Leu Gln Trp Thr Tyr Pro Gly Glu Val Lys Gly Lys
                245                 250                 255

Gly Ile Thr Met Leu Glu Glu Ile Lys Val Pro Ser Ile Lys Leu Val
            260                 265                 270

Tyr Thr Leu Thr Val Pro Glu Ala Thr Val Lys Asp Ser Gly Asp Tyr
        275                 280                 285

Glu Cys Ala Ala Arg Gln Ala Thr Arg Glu Val Lys Glu Met Lys Lys
    290                 295                 300

Val Thr Ile Ser Val His Glu Lys Gly Ala Ser Pro Ala Ala Pro Ala
305                 310                 315                 320

Pro Ala Ser Pro Ala Ala Pro Ala Pro Ser Ala Pro Ala Ala Ser Pro
                325                 330                 335

Ala Ala Pro Ala Pro Ala Ser Pro Ala Ala Pro Ala Pro Ser Ala Pro
            340                 345                 350

Ala Ala Ser Pro Ala Ala Pro Ala Pro Ala Ser Pro Ala Ala Pro Ala
        355                 360                 365

Pro Ser Ala Pro Ala Ala Ser Pro Ala Ala Pro Ala Pro Ala Ser Pro
    370                 375                 380

Ala Ala Pro Ala Pro Ser Ala Pro Ala Ala Ser Pro Ala Ala Pro Ala
385                 390                 395                 400

Pro Ala Ser Pro Ala Ala Pro Ala Pro Ser Ala Pro Ala Ala Ser Pro
                405                 410                 415

Ala Ala Pro Ala Pro Ala Ser Pro Ala Ala Pro Ala Pro Ser Ala Pro
            420                 425                 430

Ala Ala Ser Pro Ala Ala Pro Ala Pro Ala Ser Pro Ala Ala Pro Ala
        435                 440                 445

Pro Ser Ala Pro Ala Ala Ser Pro Ala Ala Pro Ala Pro Ala Ser Pro
    450                 455                 460

Ala Ala Pro Ala Pro Ser Ala Pro Ala Ala Ser Pro Ala Ala Pro Ala
465                 470                 475                 480

Pro Ala Ser Pro Ala Ala Pro Ala Pro Ser Ala Pro Ala Ala Ser Pro
                485                 490                 495

Ala Ala Pro Ala Pro Ala Ser Pro Ala Ala Pro Ala Pro Ser Ala Pro
            500                 505                 510
```

```
Ala Ala Ser Pro Ala Ala Pro Ala Pro Ala Ser Pro Ala Ala Pro Ala
        515                 520                 525

Pro Ser Ala Pro Ala Ala Ser Pro Ala Ala Pro Ala Pro Ala Ser Pro
    530                 535                 540

Ala Ala Pro Ala Pro Ser Ala Pro Ala Ala Ser Pro Ala Ala Pro Ala
545                 550                 555                 560

Pro Ala Ser Pro Ala Ala Pro Ala Pro Ser Ala Pro Ala Ala Ser Pro
                565                 570                 575

Ala Ala Pro Ala Pro Ala Ser Pro Ala Ala Pro Ala Pro Ser Ala Pro
            580                 585                 590

Ala Ala Ser Pro Ala Ala Pro Ala Pro Ala Ser Pro Ala Ala Pro Ala
        595                 600                 605

Pro Ser Ala Pro Ala Ser Asp Thr Gly Arg Pro Phe Val Glu Met Tyr
    610                 615                 620

Ser Glu Ile Pro Glu Ile Ile His Met Thr Glu Gly Arg Glu Leu Val
625                 630                 635                 640

Ile Pro Cys Arg Val Thr Ser Pro Asn Ile Thr Val Thr Leu Lys Lys
                645                 650                 655

Phe Pro Leu Asp Thr Leu Ile Pro Asp Gly Lys Arg Ile Ile Trp Asp
            660                 665                 670

Ser Arg Lys Gly Phe Ile Ile Ser Asn Ala Thr Tyr Lys Glu Ile Gly
        675                 680                 685

Leu Leu Thr Cys Glu Ala Thr Val Asn Gly His Leu Tyr Lys Thr Asn
    690                 695                 700

Tyr Leu Thr His Arg Gln Thr Asn Thr Ile Ile Asp Val Val Leu Ser
705                 710                 715                 720

Pro Ser His Gly Ile Glu Leu Ser Val Gly Glu Lys Leu Val Leu Asn
                725                 730                 735

Cys Thr Ala Arg Thr Glu Leu Asn Val Gly Ile Asp Phe Asn Trp Glu
            740                 745                 750

Tyr Pro Ser Ser Lys His Gln His Lys Lys Leu Val Asn Arg Asp Leu
        755                 760                 765

Lys Thr Gln Ser Gly Ser Glu Met Lys Lys Phe Leu Ser Thr Leu Thr
    770                 775                 780

Ile Asp Gly Val Thr Arg Ser Asp Gln Gly Leu Tyr Thr Cys Ala Ala
785                 790                 795                 800

Ser Ser Gly Leu Met Thr Lys Lys Asn Ser Thr Phe Val Arg Val His
                805                 810                 815

Glu Lys His His His His His His
            820
```

<210> SEQ ID NO 23
<211> LENGTH: 2772
<212> TYPE: DNA
<213> ORGANISM: Artificial Sequence
<220> FEATURE:
<223> OTHER INFORMATION: Sequence encoding EPS1104P

<400> SEQUENCE: 23

```
atgggtactt cacatcctgc ttttctggtc ctgggttgtc tgctgactgg tctgagcctg     60

atcctgtgcc agctgagcct gccctccatc ctgcctaacg agaatgagaa ggtggtgcag    120

ctgaactcca gcttctccct gagatgcttt ggcgagtctg aggtgtcctg gcagtaccca    180

atgagcgagg aggagtcttc cgacgtggag atccgcaatg aggagaacaa ttctggcctg    240
```

-continued

```
ttcgtgaccg tgctggaggt gagctctgcc tccgccgctc acaccggcct gtacacatgt    300
tactataacc atacccagac agaggagaat gagctggagg gcagacacat ctacatctat    360
gtgcccgatc ctgacgtggc ctttgtgcca ctgggcatga ccgattacct ggtcatcgtg    420
gaggacgatg acagcgccat catcccctgc aggaccacag accccgagac acctgtgaca    480
ctgcataact ctgagggcgt ggtgccagcc agctacgatt ctcggcaggg cttcaatggc    540
acctttacag tgggccccta tatctgtgag gccaccgtga agggcaagaa gttccagaca    600
atccctttta acgtgtacgc cctgaaggct accagcgagc tggacctgga gatggaggcc    660
ctgaagacag tgtataagtc tggcgagaca atcgtggtga catgcgccgt gttcaacaat    720
gaggtggtgg atctgcagtg gacctacccc ggcgaggtga agggcaaggg catcacaatg    780
ctggaggaga tcaaggtgcc ttctatcaag ctggtgtaca ccctgacagt gccagaggcc    840
accgtgaagg attccggcga ctatgagtgt gccgctaggc aggctacccg ggaggtgaag    900
gagatgaaga aggtgacaat ctctgtgcac gagaagggag cttccccagc tgctccagct    960
ccagcttccc ccgccgctcc tgccccatct gctccagctg cctctccagc tgctccagct   1020
cctgctagcc ctgccgctcc agccccctcc gcccctgccg cttctccagc cgctcctgcc   1080
ccagctagcc ctgctgctcc agctccttcc gctccagccg cctctccagc cgctccagcc   1140
cccgcctctc ctgctgcccc agctccttct gctccagctg ccagccccgc cgcccctgcc   1200
cccgcctctc ccgctgcccc tgctccttcc gccccagctg cctcccctgc tgctcctgcc   1260
ccagcttcac ctgccgcccc tgccccttcc gctccagccg catctcccgc cgctccagcc   1320
cccgcaagcc ctgcagcccc agctccctct gctccagctg cctcacccgc cgcccctgcc   1380
cctgcctctc ccgctgcccc cgctccttcc gccccagcag cctcccctgc agctcctgcc   1440
ccagcttctc cagccgctcc cgccccttcc gctcccgccg cctctcctgc tgcaccagcc   1500
cccgcttccc cagctgctcc tgctccatcc gccccagctg cttccccagc tgctccagct   1560
ccagcttccc ccgccgctcc tgccccatct gctccagctg cctctccagc tgctccagct   1620
cctgctagcc ctgccgctcc agccccctcc gcccctgccg cttctccagc cgctcctgcc   1680
ccagctagcc ctgctgctcc agctccttcc gctccagccg cctctccagc cgctccagcc   1740
cccgcctctc ctgctgcccc agctccttct gctccagctg ccagccccgc cgcccctgcc   1800
cccgcctctc ccgctgcccc tgctccttcc gccccagctg cctcccctgc tgctcctgcc   1860
ccagcttcac ctgccgcccc tgccccttcc gctccagccg catctcccgc cgctccagcc   1920
cccgcaagcc ctgcagcccc agctccctct gctccagctg cctcacccgc cgcccctgcc   1980
cctgcctctc ccgctgcccc cgctccttcc gccccagcag cctcccctgc agctcctgcc   2040
ccagcttctc cagccgctcc cgccccttcc gctcccgccg cctctcctgc tgcaccagcc   2100
cccgcttccc cagctgctcc tgctccatcc gccccagcta gcgataccgg ccgccctttt   2160
gtggagatgt acagcgagat ccctgagatc atccacatga ccgagggcag ggagctggtc   2220
atcccatgcc gggtgacatc tcccaacatc accgtgacac tgaagaagtt ccctctggat   2280
accctgatcc cagacggcaa gagaatcatc tgggacagcc gcaagggctt tatcatctct   2340
aatgccacat ataaggagat cggcctgctg acctgcgagg ctacagtgaa cggccacctg   2400
tacaagacca attatctgac acataggcag accaacacaa tcatcgatgt ggtgctgagc   2460
ccctctcatg gcatcgagct gtccgtgggc gagaagctgg tgctgaattg taccgcccgg   2520
acagagctga acgtgggcat cgacttcaat tgggagtacc cttccagcaa gcaccagcat   2580
aagaagctgg tgaacagaga tctgaagacc cagtccggca gcgagatgaa gaagtttctg   2640
```

tccaccctga caatcgatgg agtgacccgc agcgaccagg gcctgtatac atgtgccgct 2700
tcttccggcc tgatgactaa gaaaaatagc acctttgtga gggtccacga aaaacaccac 2760
caccaccacc at 2772

<210> SEQ ID NO 24
<211> LENGTH: 924
<212> TYPE: PRT
<213> ORGANISM: Artificial Sequence
<220> FEATURE:
<223> OTHER INFORMATION: Sequence of EPS1104P

<400> SEQUENCE: 24

Met Gly Thr Ser His Pro Ala Phe Leu Val Leu Gly Cys Leu Leu Thr
1 5 10 15

Gly Leu Ser Leu Ile Leu Cys Gln Leu Ser Leu Pro Ser Ile Leu Pro
20 25 30

Asn Glu Asn Glu Lys Val Val Gln Leu Asn Ser Ser Phe Ser Leu Arg
35 40 45

Cys Phe Gly Glu Ser Glu Val Ser Trp Gln Tyr Pro Met Ser Glu Glu
50 55 60

Glu Ser Ser Asp Val Glu Ile Arg Asn Glu Glu Asn Asn Ser Gly Leu
65 70 75 80

Phe Val Thr Val Leu Glu Val Ser Ser Ala Ser Ala Ala His Thr Gly
85 90 95

Leu Tyr Thr Cys Tyr Tyr Asn His Thr Gln Thr Glu Glu Asn Glu Leu
100 105 110

Glu Gly Arg His Ile Tyr Ile Tyr Val Pro Asp Pro Asp Val Ala Phe
115 120 125

Val Pro Leu Gly Met Thr Asp Tyr Leu Val Ile Val Glu Asp Asp Asp
130 135 140

Ser Ala Ile Ile Pro Cys Arg Thr Thr Asp Pro Glu Thr Pro Val Thr
145 150 155 160

Leu His Asn Ser Glu Gly Val Val Pro Ala Ser Tyr Asp Ser Arg Gln
165 170 175

Gly Phe Asn Gly Thr Phe Thr Val Gly Pro Tyr Ile Cys Glu Ala Thr
180 185 190

Val Lys Gly Lys Lys Phe Gln Thr Ile Pro Phe Asn Val Tyr Ala Leu
195 200 205

Lys Ala Thr Ser Glu Leu Asp Leu Glu Met Glu Ala Leu Lys Thr Val
210 215 220

Tyr Lys Ser Gly Glu Thr Ile Val Val Thr Cys Ala Val Phe Asn Asn
225 230 235 240

Glu Val Val Asp Leu Gln Trp Thr Tyr Pro Gly Glu Val Lys Gly Lys
245 250 255

Gly Ile Thr Met Leu Glu Glu Ile Lys Val Pro Ser Ile Lys Leu Val
260 265 270

Tyr Thr Leu Thr Val Pro Glu Ala Thr Val Lys Asp Ser Gly Asp Tyr
275 280 285

Glu Cys Ala Ala Arg Gln Ala Thr Arg Glu Val Lys Glu Met Lys Lys
290 295 300

Val Thr Ile Ser Val His Glu Lys Gly Ala Ser Pro Ala Ala Pro Ala
305 310 315 320

Pro Ala Ser Pro Ala Ala Pro Ala Pro Ser Ala Pro Ala Ala Ser Pro
325 330 335

```
Ala Ala Pro Ala Pro Ala Ser Pro Ala Ala Pro Ala Pro Ser Ala Pro
            340                 345                 350

Ala Ala Ser Pro Ala Ala Pro Ala Pro Ala Ser Pro Ala Ala Pro Ala
        355                 360                 365

Pro Ser Ala Pro Ala Ala Ser Pro Ala Ala Pro Ala Pro Ala Ser Pro
    370                 375                 380

Ala Ala Pro Ala Pro Ser Ala Pro Ala Ala Ser Pro Ala Ala Pro Ala
385                 390                 395                 400

Pro Ala Ser Pro Ala Ala Pro Ala Pro Ser Ala Pro Ala Ala Ser Pro
                405                 410                 415

Ala Ala Pro Ala Pro Ala Ser Pro Ala Ala Pro Ala Pro Ser Ala Pro
            420                 425                 430

Ala Ala Ser Pro Ala Ala Pro Ala Pro Ala Ser Pro Ala Ala Pro Ala
        435                 440                 445

Pro Ser Ala Pro Ala Ala Ser Pro Ala Ala Pro Ala Pro Ala Ser Pro
    450                 455                 460

Ala Ala Pro Ala Pro Ser Ala Pro Ala Ala Ser Pro Ala Ala Pro Ala
465                 470                 475                 480

Pro Ala Ser Pro Ala Ala Pro Ala Pro Ser Ala Pro Ala Ala Ser Pro
                485                 490                 495

Ala Ala Pro Ala Pro Ala Ser Pro Ala Ala Pro Ala Pro Ser Ala Pro
            500                 505                 510

Ala Ala Ser Pro Ala Ala Pro Ala Pro Ala Ser Pro Ala Ala Pro Ala
        515                 520                 525

Pro Ser Ala Pro Ala Ala Ser Pro Ala Ala Pro Ala Pro Ala Ser Pro
    530                 535                 540

Ala Ala Pro Ala Pro Ser Ala Pro Ala Ala Ser Pro Ala Ala Pro Ala
545                 550                 555                 560

Pro Ala Ser Pro Ala Ala Pro Ala Pro Ser Ala Pro Ala Ala Ser Pro
                565                 570                 575

Ala Ala Pro Ala Pro Ala Ser Pro Ala Ala Pro Ala Pro Ser Ala Pro
            580                 585                 590

Ala Ala Ser Pro Ala Ala Pro Ala Pro Ala Ser Pro Ala Ala Pro Ala
        595                 600                 605

Pro Ser Ala Pro Ala Ala Ser Pro Ala Ala Pro Ala Pro Ala Ser Pro
    610                 615                 620

Ala Ala Pro Ala Pro Ser Ala Pro Ala Ala Ser Pro Ala Ala Pro Ala
625                 630                 635                 640

Pro Ala Ser Pro Ala Ala Pro Ala Pro Ser Ala Pro Ala Ala Ser Pro
                645                 650                 655

Ala Ala Pro Ala Pro Ala Ser Pro Ala Ala Pro Ala Pro Ser Ala Pro
            660                 665                 670

Ala Ala Ser Pro Ala Ala Pro Ala Pro Ala Ser Pro Ala Ala Pro Ala
        675                 680                 685

Pro Ser Ala Pro Ala Ala Ser Pro Ala Ala Pro Ala Pro Ala Ser Pro
    690                 695                 700

Ala Ala Pro Ala Pro Ser Ala Pro Ala Ser Asp Thr Gly Arg Pro Phe
705                 710                 715                 720

Val Glu Met Tyr Ser Glu Ile Pro Glu Ile Ile His Met Thr Glu Gly
                725                 730                 735

Arg Glu Leu Val Ile Pro Cys Arg Val Thr Ser Pro Asn Ile Thr Val
            740                 745                 750
```

-continued

```
Thr Leu Lys Lys Phe Pro Leu Asp Thr Leu Ile Pro Asp Gly Lys Arg
        755                 760                 765

Ile Ile Trp Asp Ser Arg Lys Gly Phe Ile Ile Ser Asn Ala Thr Tyr
    770                 775                 780

Lys Glu Ile Gly Leu Leu Thr Cys Glu Ala Thr Val Asn Gly His Leu
785                 790                 795                 800

Tyr Lys Thr Asn Tyr Leu Thr His Arg Gln Thr Asn Thr Ile Ile Asp
                805                 810                 815

Val Val Leu Ser Pro Ser His Gly Ile Glu Leu Ser Val Gly Glu Lys
            820                 825                 830

Leu Val Leu Asn Cys Thr Ala Arg Thr Glu Leu Asn Val Gly Ile Asp
        835                 840                 845

Phe Asn Trp Glu Tyr Pro Ser Ser Lys His Gln His Lys Lys Leu Val
    850                 855                 860

Asn Arg Asp Leu Lys Thr Gln Ser Gly Ser Glu Met Lys Lys Phe Leu
865                 870                 875                 880

Ser Thr Leu Thr Ile Asp Gly Val Thr Arg Ser Asp Gln Gly Leu Tyr
                885                 890                 895

Thr Cys Ala Ala Ser Ser Gly Leu Met Thr Lys Lys Asn Ser Thr Phe
            900                 905                 910

Val Arg Val His Glu Lys His His His His His His
        915                 920
```

<210> SEQ ID NO 25
<211> LENGTH: 2181
<212> TYPE: DNA
<213> ORGANISM: Artificial Sequence
<220> FEATURE:
<223> OTHER INFORMATION: Sequence encoding EPS1105P

<400> SEQUENCE: 25

```
atggtctctt attgggacac tggggtgctg ctgtgcgccc tgctgagttg cctgctgctg     60

actggttctt cttccgggag cgataccggc cgccccttcg tggagatgta cagcgagatc    120

cctgagatca tccacatgac cgagggcagg gagctggtca tcccttgccg ggtgacatct    180

ccaaacatca ccgtgacact gaagaagttc cccctggata ccctgatccc tgacggcaag    240

agaatcatct gggactctcg caagggcttt atcatctcca atgccaccta taaggagatc    300

ggcctgctga cctgcgaggc tacagtgaac ggccacctgt acaagaccaa ttatctgaca    360

catcggcaga ccaacacaat catcgatgtg gtgctgagcc cttctcatgg catcgagctg    420

tccgtgggcg agaagctggt gctgaattgt accgccagaa cagagctgaa cgtgggcatc    480

gatttcaatt gggagtaccc atccagcaag caccagcata agaagctggt gaacagggac    540

ctgaagaccc agtccggcag cgagatgaag aagtttctgt ctaccctgac aatcgatgga    600

gtgacccgct ccgaccaggg cctgtataca tgtgccgctt cttccggcct gatgaccaag    660

aagaatagca catttgtgag ggtgcacgag aaggcctccc cagctgctcc agctcctgct    720

agcccagccg ctccagcccc ctctgctcca gccgcttccc ccgccgctcc tgccccagct    780

tctccagccg ctcccgcccc ttccgcccct gccgcttctc ctgctgctcc agcccctgcc    840

tctcctgccg ctcctgcccc atccgctccc gccgctagcc ctgccgctcc cgcccctgct    900

agccctgctg cccctgctcc ttctgctcct gctgcctctc cagctgcccc agctcctgcc    960

tcccctgctg cccctgcacc atccgcccca gccgcttctc ctgcagctcc agcccctgcc   1020

agccctgctg ccccagctcc ttccgctcct gctgccagtc cagctgcccc tgctcctgct   1080
```

```
agccctgctg cacctgctcc ttctgctccc gctgcctctc cagctgcacc agctcctgcc   1140

tcccccgctg cccctgctcc atccgccccc gccgcttctc ctgccgcccc agcccctgcc   1200

tctccagctg ctccagctcc ctccgctcct gctgccagcc cagctgcccc tgcacctgct   1260

agccctgctg ctcctgcccc ctctgcccca gctcagctgt ctctgccatc catcctgccc   1320

aacgagaatg agaaggtggt gcagctgaac agctctttct ctctgcggtg ctttggcgag   1380

agcgaggtgt cttggcagta ccccatgtcc gaggaggagt ccagcgacgt ggagatcaga   1440

aatgaggaga acaatagcgg cctgttcgtg accgtgctgg aggtgtcttc cgcctctgcc   1500

gctcacaccg gcctgtacac atgttactat aaccataccc agacagagga gaatgagctg   1560

gagggccggc acatctacat ctatgtgcct gatccagacg tggcctttgt gcccctgggc   1620

atgaccgatt acctggtcat cgtggaggac gatgactccg ccatcatccc ttgccgcacc   1680

acagaccccg agacacctgt gacactgcat aacagcgagg gagtggtgcc agcttcctac   1740

gatagcaggc agggcttcaa tggcaccttt acagtgggcc cttatatctg tgaggccacc   1800

gtgaagggca agaagttcca gacaatcccc ttcaacgtgt acgccctgaa ggctacctcc   1860

gagctggacc tggagatgga ggccctgaag acagtgtata agagcggcga gacaatcgtg   1920

gtgacatgcg ccgtgttcaa caatgaggtg gtggatctgc agtggaccta ccctggcgag   1980

gtgaagggca agggcatcac aatgctggag gagatcaagg tgccaagcat caagctggtg   2040

tacaccctga cagtgcccga ggccaccgtg aaggattctg gcgactatga gtgtgccgct   2100

aggcaggcta cacgggaggt gaaagaaatg aagaaggtca caatcagcgt ccacgaaaag   2160

gggcatcacc accaccacca t                                             2181
```

```
<210> SEQ ID NO 26
<211> LENGTH: 727
<212> TYPE: PRT
<213> ORGANISM: Artificial Sequence
<220> FEATURE:
<223> OTHER INFORMATION: Sequence of EPS1105P

<400> SEQUENCE: 26

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Asp Thr Gly Arg Pro
            20                  25                  30

Phe Val Glu Met Tyr Ser Glu Ile Pro Glu Ile Ile His Met Thr Glu
        35                  40                  45

Gly Arg Glu Leu Val Ile Pro Cys Arg Val Thr Ser Pro Asn Ile Thr
    50                  55                  60

Val Thr Leu Lys Lys Phe Pro Leu Asp Thr Leu Ile Pro Asp Gly Lys
65                  70                  75                  80

Arg Ile Ile Trp Asp Ser Arg Lys Gly Phe Ile Ile Ser Asn Ala Thr
                85                  90                  95

Tyr Lys Glu Ile Gly Leu Leu Thr Cys Glu Ala Thr Val Asn Gly His
            100                 105                 110

Leu Tyr Lys Thr Asn Tyr Leu Thr His Arg Gln Thr Asn Thr Ile Ile
        115                 120                 125

Asp Val Val Leu Ser Pro Ser His Gly Ile Glu Leu Ser Val Gly Glu
    130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
```

-continued

```
                165                 170                 175

Val Asn Arg Asp Leu Lys Thr Gln Ser Gly Ser Glu Met Lys Lys Phe
            180                 185                 190

Leu Ser Thr Leu Thr Ile Asp Gly Val Thr Arg Ser Asp Gln Gly Leu
        195                 200                 205

Tyr Thr Cys Ala Ala Ser Ser Gly Leu Met Thr Lys Lys Asn Ser Thr
    210                 215                 220

Phe Val Arg Val His Glu Lys Ala Ser Pro Ala Ala Pro Ala Pro Ala
225                 230                 235                 240

Ser Pro Ala Ala Pro Ala Pro Ser Ala Pro Ala Ala Ser Pro Ala Ala
                245                 250                 255

Pro Ala Pro Ala Ser Pro Ala Ala Pro Ala Pro Ser Ala Pro Ala Ala
            260                 265                 270

Ser Pro Ala Ala Pro Ala Pro Ala Ser Pro Ala Ala Pro Ala Pro Ser
        275                 280                 285

Ala Pro Ala Ala Ser Pro Ala Ala Pro Ala Pro Ala Ser Pro Ala Ala
    290                 295                 300

Pro Ala Pro Ser Ala Pro Ala Ala Ser Pro Ala Ala Pro Ala Pro Ala
305                 310                 315                 320

Ser Pro Ala Ala Pro Ala Pro Ser Ala Pro Ala Ala Ser Pro Ala Ala
                325                 330                 335

Pro Ala Pro Ala Ser Pro Ala Ala Pro Ala Pro Ser Ala Pro Ala Ala
            340                 345                 350

Ser Pro Ala Ala Pro Ala Pro Ala Ser Pro Ala Ala Pro Ala Pro Ser
        355                 360                 365

Ala Pro Ala Ala Ser Pro Ala Ala Pro Ala Pro Ala Ser Pro Ala Ala
    370                 375                 380

Pro Ala Pro Ser Ala Pro Ala Ala Ser Pro Ala Ala Pro Ala Pro Ala
385                 390                 395                 400

Ser Pro Ala Ala Pro Ala Pro Ser Ala Pro Ala Ala Ser Pro Ala Ala
                405                 410                 415

Pro Ala Pro Ala Ser Pro Ala Ala Pro Ala Pro Ser Ala Pro Ala Gln
            420                 425                 430

Leu Ser Leu Pro Ser Ile Leu Pro Asn Glu Asn Glu Lys Val Val Gln
        435                 440                 445

Leu Asn Ser Ser Phe Ser Leu Arg Cys Phe Gly Glu Ser Glu Val Ser
    450                 455                 460

Trp Gln Tyr Pro Met Ser Glu Glu Glu Ser Ser Asp Val Glu Ile Arg
465                 470                 475                 480

Asn Glu Glu Asn Asn Ser Gly Leu Phe Val Thr Val Leu Glu Val Ser
                485                 490                 495

Ser Ala Ser Ala Ala His Thr Gly Leu Tyr Thr Cys Tyr Tyr Asn His
            500                 505                 510

Thr Gln Thr Glu Glu Asn Glu Leu Glu Gly Arg His Ile Tyr Ile Tyr
        515                 520                 525

Val Pro Asp Pro Asp Val Ala Phe Val Pro Leu Gly Met Thr Asp Tyr
    530                 535                 540

Leu Val Ile Val Glu Asp Asp Asp Ser Ala Ile Ile Pro Cys Arg Thr
545                 550                 555                 560

Thr Asp Pro Glu Thr Pro Val Thr Leu His Asn Ser Glu Gly Val Val
                565                 570                 575

Pro Ala Ser Tyr Asp Ser Arg Gln Gly Phe Asn Gly Thr Phe Thr Val
            580                 585                 590
```

```
Gly Pro Tyr Ile Cys Glu Ala Thr Val Lys Gly Lys Lys Phe Gln Thr
        595                 600                 605

Ile Pro Phe Asn Val Tyr Ala Leu Lys Ala Thr Ser Glu Leu Asp Leu
    610                 615                 620

Glu Met Glu Ala Leu Lys Thr Val Tyr Lys Ser Gly Glu Thr Ile Val
625                 630                 635                 640

Val Thr Cys Ala Val Phe Asn Asn Glu Val Val Asp Leu Gln Trp Thr
                645                 650                 655

Tyr Pro Gly Glu Val Lys Gly Lys Gly Ile Thr Met Leu Glu Glu Ile
            660                 665                 670

Lys Val Pro Ser Ile Lys Leu Val Tyr Thr Leu Thr Val Pro Glu Ala
        675                 680                 685

Thr Val Lys Asp Ser Gly Asp Tyr Glu Cys Ala Ala Arg Gln Ala Thr
    690                 695                 700

Arg Glu Val Lys Glu Met Lys Lys Val Thr Ile Ser Val His Glu Lys
705                 710                 715                 720

Gly His His His His His His
                725
```

<210> SEQ ID NO 27
<211> LENGTH: 2262
<212> TYPE: DNA
<213> ORGANISM: Artificial Sequence
<220> FEATURE:
<223> OTHER INFORMATION: Sequence encoding EPS1106P

<400> SEQUENCE: 27

```
atgggcacca gccatcctgc ttttctggtg ctgggatgcc tgctgaccgg cctgtctctg     60

attctgtgcc agctgtccct gccttccatc ctgcctaacg agaacgagaa ggtggtgcag    120

ctgaactcct ccttctctct gcggtgcttc ggcgagtccg aagtgtcttg gcagtacccc    180

atgtccgaag aggaatcctc cgacgtggaa atccggaacg aggaaaacaa ctccggcctg    240

ttcgtgaccg tgctggaagt gtcctctgcc tctgctgctc acaccggact gtacacctgt    300

tactacaatc acacccagac cgaagagaac gagctggaag gccggcacat ctacatctac    360

gtgcccgatc ctgacgtggc ctttgtgcct ctgggcatga ccgactacct ggtcatcgtg    420

gaagatgacg actccgctat catcccctgc cggaccacag atcctgagac acctgtgaca    480

ctgcacaact ccgaaggcgt ggtgcctgcc tcctacgatt ctagacaggg cttcaacggc    540

accttcaccg tgggacctta catctgcgag gctaccgtga agggcaagaa gttccagaca    600

atccccttca acgtgtacgc cctgaaggcc acctctgagc tggacctgga aatggaagcc    660

ctgaaaaccg tgtacaagag cggcgagaca atcgtcgtga cctgcgccgt gttcaacaac    720

gaggtggtgg acctgcagtg gacctatcct ggcgaagtga aaggcaaggg catcaccatg    780

ctggaagaga tcaaggtgcc ctccatcaag ctggtgtata ccctgaccgt gcctgaggcc    840

acagtgaagg actctggcga ctacgagtgt gccgctagac aggccaccag agaagtcaaa    900

gagatgaaga aagtcaccat ctccgtgcac gagaaaggcg gcggaggcgg aagcggtggc    960

ggaggaagcg gaggcggcgg atctgcttct cctgctgctc cagctccagc ttctccagca   1020

gctcctgcac cttctgcacc agctgcaagt cctgcagcac ccgcaccagc tagtcctgcc   1080

gctcctgctc ctagtgctcc tgccgcaagt ccagctgctc ccgctcctgc atcaccagcc   1140

gcaccagcac caagtgctcc agctgcctct ccagcagcac cagctccagc aagccctgct   1200

gcaccagcac cttcagctcc agcagcatca cccgctgcac ccgctccagc atctcccgct   1260
```

```
gctccagcac caagcgcacc cgctgctagc ccagccgctc cagctcctgc cagtcctgct   1320

gctcctgcac catctgctcc cgcagcttca ccagctgctc ccgcaccagc tagcccagca   1380

gcaccagcac catctgcacc cgccgcatct cccgccgcac cagctccagc tagtcccgca   1440

gctcccgctc catctgctcc agccgctagt cccgctgctc ctgctccagc tagtcctgct   1500

gcacccgctc ctagcgcacc agctgcttca cccgcagctc cagctccagc ttcacccgct   1560

gcaccagctc catctgctcc agctggtggc ggaggatctg gcggaggcgg atctggcggc   1620

ggtggttctt ctgataccgg cagacccttc gtggaaatgt acagcgagat ccccgagatc   1680

atccacatga ccgagggcag agagctggtc atcccttgca gagtgacctc tcctaacatc   1740

acagtgaccc tgaagaagtt tcccctggac acactgatcc ccgacggcaa gagaatcatc   1800

tgggactccc ggaagggctt catcatctcc aacgccacct acaaagagat cggactgctg   1860

acctgcgaag ccactgtgaa cggccacctg tacaagacca actatctgac ccacagacag   1920

accaacacca tcatcgacgt ggtgctgagc cctctcatgg gcatcgagct gtccgtggga   1980

gagaaactgg tgctgaactg caccgccaga accgagctga acgtgggcat cgacttcaac   2040

tgggagtacc ccagctccaa acaccagcac aagaagctgg tcaaccggga tctgaaaacc   2100

cagtccggct ccgaaatgaa gaaattcctg agcaccctga ccatcgacgg cgtgaccaga   2160

tctgaccagg gcctgtatac ctgtgccgcc tcttctggcc tgatgaccaa gaaaaactcc   2220

accttcgtgc gggtccacga gaagcaccat caccaccatc at                      2262
```

<210> SEQ ID NO 28
<211> LENGTH: 754
<212> TYPE: PRT
<213> ORGANISM: Artificial Sequence
<220> FEATURE:
<223> OTHER INFORMATION: Sequence of EPS1106P

<400> SEQUENCE: 28

```
Met Gly Thr Ser His Pro Ala Phe Leu Val Leu Gly Cys Leu Leu Thr
1               5                   10                  15

Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45

Cys Phe Gly Glu Ser Glu Val Ser Trp Gln Tyr Pro Met Ser Glu Glu
    50                  55                  60

Glu Ser Ser Asp Val Glu Ile Arg Asn Glu Glu Asn Asn Ser Gly Leu
65                  70                  75                  80

Phe Val Thr Val Leu Glu Val Ser Ser Ala Ser Ala Ala His Thr Gly
                85                  90                  95

Leu Tyr Thr Cys Tyr Tyr Asn His Thr Gln Thr Glu Glu Asn Glu Leu
            100                 105                 110

Glu Gly Arg His Ile Tyr Ile Tyr Val Pro Asp Pro Asp Val Ala Phe
        115                 120                 125

Val Pro Leu Gly Met Thr Asp Tyr Leu Val Ile Val Glu Asp Asp Asp
    130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
```

-continued

```
            180                 185                 190

Val Lys Gly Lys Lys Phe Gln Thr Ile Pro Phe Asn Val Tyr Ala Leu
        195                 200                 205

Lys Ala Thr Ser Glu Leu Asp Leu Glu Met Glu Ala Leu Lys Thr Val
    210                 215                 220

Tyr Lys Ser Gly Glu Thr Ile Val Val Thr Cys Ala Val Phe Asn Asn
225                 230                 235                 240

Glu Val Val Asp Leu Gln Trp Thr Tyr Pro Gly Glu Val Lys Gly Lys
                245                 250                 255

Gly Ile Thr Met Leu Glu Glu Ile Lys Val Pro Ser Ile Lys Leu Val
            260                 265                 270

Tyr Thr Leu Thr Val Pro Glu Ala Thr Val Lys Asp Ser Gly Asp Tyr
        275                 280                 285

Glu Cys Ala Ala Arg Gln Ala Thr Arg Glu Val Lys Glu Met Lys Lys
    290                 295                 300

Val Thr Ile Ser Val His Glu Lys Gly Gly Gly Gly Gly Ser Gly Gly
305                 310                 315                 320

Gly Gly Ser Gly Gly Gly Gly Ser Ala Ser Pro Ala Ala Pro Ala Pro
                325                 330                 335

Ala Ser Pro Ala Ala Pro Ala Pro Ser Ala Pro Ala Ala Ser Pro Ala
            340                 345                 350

Ala Pro Ala Pro Ala Ser Pro Ala Ala Pro Ala Pro Ser Ala Pro Ala
        355                 360                 365

Ala Ser Pro Ala Ala Pro Ala Pro Ala Ser Pro Ala Ala Pro Ala Pro
    370                 375                 380

Ser Ala Pro Ala Ala Ser Pro Ala Ala Pro Ala Pro Ala Ser Pro Ala
385                 390                 395                 400

Ala Pro Ala Pro Ser Ala Pro Ala Ala Ser Pro Ala Ala Pro Ala Pro
                405                 410                 415

Ala Ser Pro Ala Ala Pro Ala Pro Ser Ala Pro Ala Ala Ser Pro Ala
            420                 425                 430

Ala Pro Ala Pro Ala Ser Pro Ala Ala Pro Ala Pro Ser Ala Pro Ala
        435                 440                 445

Ala Ser Pro Ala Ala Pro Ala Pro Ala Ser Pro Ala Ala Pro Ala Pro
    450                 455                 460

Ser Ala Pro Ala Ala Ser Pro Ala Ala Pro Ala Pro Ala Ser Pro Ala
465                 470                 475                 480

Ala Pro Ala Pro Ser Ala Pro Ala Ala Ser Pro Ala Ala Pro Ala Pro
                485                 490                 495

Ala Ser Pro Ala Ala Pro Ala Pro Ser Ala Pro Ala Ala Ser Pro Ala
            500                 505                 510

Ala Pro Ala Pro Ala Ser Pro Ala Ala Pro Ala Pro Ser Ala Pro Ala
        515                 520                 525

Gly Gly Gly Gly Ser Gly Gly Gly Gly Ser Gly Gly Gly Gly Ser Ser
    530                 535                 540

Asp Thr Gly Arg Pro Phe Val Glu Met Tyr Ser Glu Ile Pro Glu Ile
545                 550                 555                 560

Ile His Met Thr Glu Gly Arg Glu Leu Val Ile Pro Cys Arg Val Thr
                565                 570                 575

Ser Pro Asn Ile Thr Val Thr Leu Lys Lys Phe Pro Leu Asp Thr Leu
            580                 585                 590

Ile Pro Asp Gly Lys Arg Ile Ile Trp Asp Ser Arg Lys Gly Phe Ile
        595                 600                 605
```

```
Ile Ser Asn Ala Thr Tyr Lys Glu Ile Gly Leu Leu Thr Cys Glu Ala
    610                 615                 620

Thr Val Asn Gly His Leu Tyr Lys Thr Asn Tyr Leu Thr His Arg Gln
625                 630                 635                 640

Thr Asn Thr Ile Ile Asp Val Val Leu Ser Pro Ser His Gly Ile Glu
                645                 650                 655

Leu Ser Val Gly Glu Lys Leu Val Leu Asn Cys Thr Ala Arg Thr Glu
            660                 665                 670

Leu Asn Val Gly Ile Asp Phe Asn Trp Glu Tyr Pro Ser Ser Lys His
        675                 680                 685

Gln His Lys Lys Leu Val Asn Arg Asp Leu Lys Thr Gln Ser Gly Ser
    690                 695                 700

Glu Met Lys Lys Phe Leu Ser Thr Leu Thr Ile Asp Gly Val Thr Arg
705                 710                 715                 720

Ser Asp Gln Gly Leu Tyr Thr Cys Ala Ala Ser Ser Gly Leu Met Thr
                725                 730                 735

Lys Lys Asn Ser Thr Phe Val Arg Val His Glu Lys His His His His
            740                 745                 750

His His
```

<210> SEQ ID NO 29
<211> LENGTH: 2271
<212> TYPE: DNA
<213> ORGANISM: Artificial Sequence
<220> FEATURE:
<223> OTHER INFORMATION: Sequence encoding EPS1107P

<400> SEQUENCE: 29

```
atggtgtcct actgggatac aggcgtgctg ctgtgtgccc tgctgtcttg tctgctgctg     60

accggctcct cttctggctc tgataccggc agacccttcg tggaaatgta cagcgagatc    120

cccgagatca tccacatgac cgagggcaga gagctggtca tcccctgcag agtgacctct    180

cctaacatca ccgtgactct gaagaagttc cctctggaca cactgatccc cgacggcaag    240

agaatcatct gggactcccg gaagggcttc atcatctcca acgccaccta caaagagatc    300

ggcctgctga cctgcgaggc caccgttaat ggccacctgt acaagaccaa ctatctgacc    360

cacagacaga ccaacaccat catcgacgtg gtgctgagcc cctctcatgg catcgagctg    420

tccgtgggag aaaagctggt gctgaactgc accgccagaa ccgagctgaa cgtgggcatc    480

gacttcaact gggagtaccc ctccagcaag caccagcaca agaagctggt caaccgggac    540

ctgaaaaccc agtccggctc cgagatgaag aaattcctga gcaccctgac catcgacggc    600

gtgaccagat ctgaccaggg cctgtatacc tgcgccgctt cctctggcct gatgaccaag    660

aaaaactcca ccttcgtgcg ggtgcacgag aaaggtggcg gaggatctgg cggaggcggc    720

tctggcggcg gtggatctgc ttctcctgct gctccagctc cagcttctcc agcagctcct    780

gcaccttctg caccagctgc aagtcctgca gcacccgcac cagctagtcc tgccgctcct    840

gctcctagtg ctcctgccgc aagtccagct gctcccgctc ctgcaagccc agctgcacca    900

gcaccaagtg ctccagctgc ctcaccagcc gcaccagctc cagcaagccc tgcagctccc    960

gctccttcag ctcctgctgc ttctcccgca gcacccgctc cagcatcacc agccgctcca   1020

gcaccatcag ctccagcagc atctcctgca gctccagctc ctgctagtcc cgctgctccc   1080

gcacctagtg caccagccgc ttctcccgcc gctcctgctc ctgcatctcc tgctgcaccc   1140

gctccatctg ctcccgccgc atcacccgca gctcccgcac cagcctctcc agctgcacca   1200
```

```
gctcctagcg caccagcagc tagcccagct gctcctgcac cagctagccc cgcagctcca   1260

gctccaagcg ctcctgctgc atccccagct gctccagctc ctgcctcacc agctgctcca   1320

gcaccttctg ctcccgctgg cggtggcgga agcggaggtg gtggtagtgg cggcggaggt   1380

tctcagctgt ccctgccttc tatcctgcct aacgagaacg agaaggtggt ccagctgaac   1440

tcctccttct ctctgcggtg cttcggcgag tccgaagtgt cttggcagta ccccatgtcc   1500

gaagaggaat cctccgacgt ggaaatccgg aacgaggaaa acaactccgg cctgttcgtg   1560

accgtgctgg aagtgtcctc tgcctctgct gctcacaccg gcctgtacac atgctactac   1620

aatcacaccc agaccgaaga gaacgagctg gaaggccggc acatctacat ctacgtgccc   1680

gatcctgacg tggcctttgt gcctctgggc atgaccgact acctggtcat cgtggaagat   1740

gacgactccg ctatcatccc ttgccggacc accgatccag agacacctgt gacactgcac   1800

aactccgaag gcgtggtgcc tgcctcctac gattctagac agggcttcaa cggcaccttc   1860

accgtgggac cttacatctg cgaggctaca gtgaagggca agaagtttca gacaatcccc   1920

ttcaacgtgt acgccctgaa ggccacctct gagctggacc tggaaatgga agctctgaaa   1980

accgtgtaca agtccggcga gacaatcgtc gtgacctgtg ccgtgttcaa caacgaagtg   2040

gtggacctgc agtggaccta tcctggcgaa gtgaaaggca agggcatcac catgctggaa   2100

gagatcaagg tgccctccat caagctggtg tataccctga ccgtgcctga ggccactgtg   2160

aaggactctg gcgactacga gtgtgccgct agacaggcca ccagagaagt caaagaaatg   2220

aagaaagtga ccatctccgt ccacgagaag ggccaccacc accatcacca t            2271
```

<210> SEQ ID NO 30
<211> LENGTH: 757
<212> TYPE: PRT
<213> ORGANISM: Artificial Sequence
<220> FEATURE:
<223> OTHER INFORMATION: Sequence of EPS1107P

<400> SEQUENCE: 30

```
Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Asp Thr Gly Arg Pro
            20                  25                  30

Phe Val Glu Met Tyr Ser Glu Ile Pro Glu Ile Ile His Met Thr Glu
        35                  40                  45

Gly Arg Glu Leu Val Ile Pro Cys Arg Val Thr Ser Pro Asn Ile Thr
    50                  55                  60

Val Thr Leu Lys Lys Phe Pro Leu Asp Thr Leu Ile Pro Asp Gly Lys
65                  70                  75                  80

Arg Ile Ile Trp Asp Ser Arg Lys Gly Phe Ile Ile Ser Asn Ala Thr
                85                  90                  95

Tyr Lys Glu Ile Gly Leu Leu Thr Cys Glu Ala Thr Val Asn Gly His
            100                 105                 110

Leu Tyr Lys Thr Asn Tyr Leu Thr His Arg Gln Thr Asn Thr Ile Ile
        115                 120                 125

Asp Val Val Leu Ser Pro Ser His Gly Ile Glu Leu Ser Val Gly Glu
    130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                165                 170                 175
```

-continued

```
Val Asn Arg Asp Leu Lys Thr Gln Ser Gly Ser Glu Met Lys Lys Phe
            180                 185                 190

Leu Ser Thr Leu Thr Ile Asp Gly Val Thr Arg Ser Asp Gln Gly Leu
        195                 200                 205

Tyr Thr Cys Ala Ala Ser Ser Gly Leu Met Thr Lys Lys Asn Ser Thr
    210                 215                 220

Phe Val Arg Val His Glu Lys Gly Gly Gly Gly Ser Gly Gly Gly Gly
225                 230                 235                 240

Ser Gly Gly Gly Gly Ser Ala Ser Pro Ala Ala Pro Ala Pro Ala Ser
                245                 250                 255

Pro Ala Ala Pro Ala Pro Ser Ala Pro Ala Ala Ser Pro Ala Ala Pro
            260                 265                 270

Ala Pro Ala Ser Pro Ala Ala Pro Ala Pro Ser Ala Pro Ala Ala Ser
        275                 280                 285

Pro Ala Ala Pro Ala Pro Ala Ser Pro Ala Ala Pro Ala Pro Ser Ala
    290                 295                 300

Pro Ala Ala Ser Pro Ala Ala Pro Ala Pro Ala Ser Pro Ala Ala Pro
305                 310                 315                 320

Ala Pro Ser Ala Pro Ala Ala Ser Pro Ala Ala Pro Ala Pro Ala Ser
                325                 330                 335

Pro Ala Ala Pro Ala Pro Ser Ala Pro Ala Ala Ser Pro Ala Ala Pro
            340                 345                 350

Ala Pro Ala Ser Pro Ala Ala Pro Ala Pro Ser Ala Pro Ala Ala Ser
        355                 360                 365

Pro Ala Ala Pro Ala Pro Ala Ser Pro Ala Ala Pro Ala Pro Ser Ala
    370                 375                 380

Pro Ala Ala Ser Pro Ala Ala Pro Ala Pro Ala Ser Pro Ala Ala Pro
385                 390                 395                 400

Ala Pro Ser Ala Pro Ala Ala Ser Pro Ala Ala Pro Ala Pro Ala Ser
                405                 410                 415

Pro Ala Ala Pro Ala Pro Ser Ala Pro Ala Ala Ser Pro Ala Ala Pro
            420                 425                 430

Ala Pro Ala Ser Pro Ala Ala Pro Ala Pro Ser Ala Pro Ala Gly Gly
        435                 440                 445

Gly Gly Ser Gly Gly Gly Gly Ser Gly Gly Gly Gly Ser Gln Leu Ser
    450                 455                 460

Leu Pro Ser Ile Leu Pro Asn Glu Asn Glu Lys Val Val Gln Leu Asn
465                 470                 475                 480

Ser Ser Phe Ser Leu Arg Cys Phe Gly Glu Ser Glu Val Ser Trp Gln
                485                 490                 495

Tyr Pro Met Ser Glu Glu Glu Ser Ser Asp Val Glu Ile Arg Asn Glu
            500                 505                 510

Glu Asn Asn Ser Gly Leu Phe Val Thr Val Leu Glu Val Ser Ser Ala
        515                 520                 525

Ser Ala Ala His Thr Gly Leu Tyr Thr Cys Tyr Tyr Asn His Thr Gln
    530                 535                 540

Thr Glu Glu Asn Glu Leu Glu Gly Arg His Ile Tyr Ile Tyr Val Pro
545                 550                 555                 560

Asp Pro Asp Val Ala Phe Val Pro Leu Gly Met Thr Asp Tyr Leu Val
                565                 570                 575

Ile Val Glu Asp Asp Asp Ser Ala Ile Ile Pro Cys Arg Thr Thr Asp
            580                 585                 590
```

-continued

```
Pro Glu Thr Pro Val Thr Leu His Asn Ser Glu Gly Val Val Pro Ala
        595                 600                 605

Ser Tyr Asp Ser Arg Gln Gly Phe Asn Gly Thr Phe Thr Val Gly Pro
    610                 615                 620

Tyr Ile Cys Glu Ala Thr Val Lys Gly Lys Lys Phe Gln Thr Ile Pro
625                 630                 635                 640

Phe Asn Val Tyr Ala Leu Lys Ala Thr Ser Glu Leu Asp Leu Glu Met
                645                 650                 655

Glu Ala Leu Lys Thr Val Tyr Lys Ser Gly Glu Thr Ile Val Val Thr
            660                 665                 670

Cys Ala Val Phe Asn Asn Glu Val Val Asp Leu Gln Trp Thr Tyr Pro
        675                 680                 685

Gly Glu Val Lys Gly Lys Gly Ile Thr Met Leu Glu Glu Ile Lys Val
    690                 695                 700

Pro Ser Ile Lys Leu Val Tyr Thr Leu Thr Val Pro Glu Ala Thr Val
705                 710                 715                 720

Lys Asp Ser Gly Asp Tyr Glu Cys Ala Ala Arg Gln Ala Thr Arg Glu
                725                 730                 735

Val Lys Glu Met Lys Lys Val Thr Ile Ser Val His Glu Lys Gly His
            740                 745                 750

His His His His His
        755
```

<210> SEQ ID NO 31
<211> LENGTH: 2160
<212> TYPE: DNA
<213> ORGANISM: Artificial Sequence
<220> FEATURE:
<223> OTHER INFORMATION: Sequence encoding EPS1109P

<400> SEQUENCE: 31

```
atgggctggt cctgcatcat cctgtttctg gtggctaccg ctaccggcgt gcactctcac     60
caccatcacc atcacgcttc tccagccgct ccagctcctg cttctcctgc tgcaccagca    120
ccatctgctc cagctgcaag tccagctgct cccgcaccag caagtcctgc agcacccgct    180
cctagtgctc cagcagcatc tcccgcagca ccagctccag cttcaccagc agctcccgct    240
ccatcagcac cagccgcatc acccgctgct ccagcaccag cttctcccgc cgctcctgca    300
ccttctgcac ccgcagctag ccctgctgct cctgctccag catctccagc tgcacccgct    360
ccaagcgcac ccgctgctag tccagcagca ccagcaccag ctagtcccgc tgctccagct    420
ccttctgctc cagcagcttc accagccgct ccagcaccag ctagcccagc cgcaccagca    480
cctagtgctc ccgccgctag tcctgcagct ccagctcctg ctagcccagc tgctcccgct    540
cctagcgctc ctgccgcttc accagctgca ccagctccag caagtccagc cgctcctgct    600
ccaagtgcac cagctgcctc tccagctgct cctgctcctg caagtcccgc agctccagca    660
cctagcgcac cagcatctga taccggcaga cccttcgtgg aaatgtacag cgagatcccc    720
gagatcatcc acatgaccga gggcagagag ctggtcatcc cctgcagagt gacctctcct    780
aacatcaccg tgactctgaa gaagttccct ctggacacac tgatccccga cggcaagaga    840
atcatctggg actcccggaa gggcttcatc atctccaacg ccacctacaa agagatcggc    900
ctgctgacct gcgaggccac cgttaatggc cacctgtaca agaccaacta tctgacccac    960
agacagacca acaccatcat cgacgtggtg ctgagcccct ctcatggcat cgagctgtcc   1020
gtgggagaaa agctcgtgct gaactgcacc gccagaaccg agctgaacgt gggcatcgac   1080
```

-continued

```
ttcaactggg agtaccccag ctccaaacac cagcacaaga aactggtcaa ccgggacctg   1140

aaaacccagt ccggctccga gatgaagaaa ttcctgagca ccctgaccat cgacggcgtg   1200

accagatctg accagggcct gtatacctgc gccgcttctt ctggcctgat gaccaagaaa   1260

aactccacct tcgtgcgcgt gcacgagaag cagctgtccc tgccttctat cctgcctaac   1320

gagaacgaga aggtggtcca gctgaactcc tccttctctc tgcggtgctt cggcgagtcc   1380

gaagtgtctt ggcagtaccc catgtccgaa gaggaatcct ccgacgtgga aatccggaac   1440

gaggaaaaca actccggcct gttcgtgacc gtgctggaag tgtcctctgc ctctgctgct   1500

cacaccggcc tgtacacatg ctactacaat cacacccaga ccgaagagaa cgagctggaa   1560

ggccggcaca tctacatcta cgtgcccgat cctgacgtgg cctttgtgcc tctgggcatg   1620

accgactacc tggtcatcgt ggaagatgac gactccgcta tcatcccttg ccggaccacc   1680

gatccagaga cacctgtgac actgcacaac tccgaaggcg tggtgcctgc ctcctacgat   1740

tctagacagg gcttcaacgg caccttcacc gtgggacctt acatctgcga ggctacagtg   1800

aagggcaaga agtttcagac aatccccttc aacgtgtacg ccctgaaggc cacctctgag   1860

ctggacctgg aaatggaagc tctgaaaacc gtgtacaagt ccggcgagac aatcgtcgtg   1920

acctgtgccg tgttcaacaa cgaggtggtg gacctgcagt ggacctatcc tggcgaagtg   1980

aaaggcaagg gcatcaccat gctggaagag atcaaggtgc cctccatcaa gctggtgtat   2040

accctgaccg tgcctgaggc cactgtgaag gactctggcg actacgagtg tgccgctaga   2100

caggccacca gagaagtcaa agaaatgaag aaagtgacca tctccgtcca cgagaagggc   2160
```

<210> SEQ ID NO 32
<211> LENGTH: 720
<212> TYPE: PRT
<213> ORGANISM: Artificial Sequence
<220> FEATURE:
<223> OTHER INFORMATION: Sequence of EPS1109P

<400> SEQUENCE: 32

```
Met Gly Trp Ser Cys Ile Ile Leu Phe Leu Val Ala Thr Ala Thr Gly
1               5                   10                  15

Val His Ser His His His His His His Ala Ser Pro Ala Ala Pro Ala
            20                  25                  30

Pro Ala Ser Pro Ala Ala Pro Ala Pro Ser Ala Pro Ala Ala Ser Pro
        35                  40                  45

Ala Ala Pro Ala Pro Ala Ser Pro Ala Ala Pro Ala Pro Ser Ala Pro
    50                  55                  60

Ala Ala Ser Pro Ala Ala Pro Ala Pro Ala Ser Pro Ala Ala Pro Ala
65                  70                  75                  80

Pro Ser Ala Pro Ala Ala Ser Pro Ala Ala Pro Ala Pro Ala Ser Pro
                85                  90                  95

Ala Ala Pro Ala Pro Ser Ala Pro Ala Ala Ser Pro Ala Ala Pro Ala
            100                 105                 110

Pro Ala Ser Pro Ala Ala Pro Ala Pro Ser Ala Pro Ala Ala Ser Pro
        115                 120                 125

Ala Ala Pro Ala Pro Ala Ser Pro Ala Ala Pro Ala Pro Ser Ala Pro
    130                 135                 140

Ala Ala Ser Pro Ala Ala Pro Ala Pro Ala Ser Pro Ala Ala Pro Ala
145                 150                 155                 160

Pro Ser Ala Pro Ala Ala Ser Pro Ala Ala Pro Ala Pro Ala Ser Pro
                165                 170                 175
```

-continued

```
Ala Ala Pro Ala Pro Ser Ala Pro Ala Ala Ser Pro Ala Ala Pro Ala
            180                 185                 190

Pro Ala Ser Pro Ala Ala Pro Ala Pro Ser Ala Pro Ala Ala Ser Pro
        195                 200                 205

Ala Ala Pro Ala Pro Ala Ser Pro Ala Ala Pro Ala Pro Ser Ala Pro
    210                 215                 220

Ala Ser Asp Thr Gly Arg Pro Phe Val Glu Met Tyr Ser Glu Ile Pro
225                 230                 235                 240

Glu Ile Ile His Met Thr Glu Gly Arg Glu Leu Val Ile Pro Cys Arg
                245                 250                 255

Val Thr Ser Pro Asn Ile Thr Val Thr Leu Lys Lys Phe Pro Leu Asp
            260                 265                 270

Thr Leu Ile Pro Asp Gly Lys Arg Ile Ile Trp Asp Ser Arg Lys Gly
        275                 280                 285

Phe Ile Ile Ser Asn Ala Thr Tyr Lys Glu Ile Gly Leu Leu Thr Cys
    290                 295                 300

Glu Ala Thr Val Asn Gly His Leu Tyr Lys Thr Asn Tyr Leu Thr His
305                 310                 315                 320

Arg Gln Thr Asn Thr Ile Ile Asp Val Val Leu Ser Pro Ser His Gly
                325                 330                 335

Ile Glu Leu Ser Val Gly Glu Lys Leu Val Leu Asn Cys Thr Ala Arg
            340                 345                 350

Thr Glu Leu Asn Val Gly Ile Asp Phe Asn Trp Glu Tyr Pro Ser Ser
        355                 360                 365

Lys His Gln His Lys Lys Leu Val Asn Arg Asp Leu Lys Thr Gln Ser
    370                 375                 380

Gly Ser Glu Met Lys Lys Phe Leu Ser Thr Leu Thr Ile Asp Gly Val
385                 390                 395                 400

Thr Arg Ser Asp Gln Gly Leu Tyr Thr Cys Ala Ala Ser Ser Gly Leu
                405                 410                 415

Met Thr Lys Lys Asn Ser Thr Phe Val Arg Val His Glu Lys Gln Leu
            420                 425                 430

Ser Leu Pro Ser Ile Leu Pro Asn Glu Asn Glu Lys Val Val Gln Leu
        435                 440                 445

Asn Ser Ser Phe Ser Leu Arg Cys Phe Gly Glu Ser Glu Val Ser Trp
    450                 455                 460

Gln Tyr Pro Met Ser Glu Glu Glu Ser Ser Asp Val Glu Ile Arg Asn
465                 470                 475                 480

Glu Glu Asn Asn Ser Gly Leu Phe Val Thr Val Leu Glu Val Ser Ser
                485                 490                 495

Ala Ser Ala Ala His Thr Gly Leu Tyr Thr Cys Tyr Tyr Asn His Thr
            500                 505                 510

Gln Thr Glu Glu Asn Glu Leu Glu Gly Arg His Ile Tyr Ile Tyr Val
        515                 520                 525

Pro Asp Pro Asp Val Ala Phe Val Pro Leu Gly Met Thr Asp Tyr Leu
    530                 535                 540

Val Ile Val Glu Asp Asp Asp Ser Ala Ile Ile Pro Cys Arg Thr Thr
545                 550                 555                 560

Asp Pro Glu Thr Pro Val Thr Leu His Asn Ser Glu Gly Val Val Pro
                565                 570                 575

Ala Ser Tyr Asp Ser Arg Gln Gly Phe Asn Gly Thr Phe Thr Val Gly
            580                 585                 590

Pro Tyr Ile Cys Glu Ala Thr Val Lys Gly Lys Lys Phe Gln Thr Ile
```

-continued

```
        595                 600                 605

Pro Phe Asn Val Tyr Ala Leu Lys Ala Thr Ser Glu Leu Asp Leu Glu
    610                 615                 620

Met Glu Ala Leu Lys Thr Val Tyr Lys Ser Gly Glu Thr Ile Val Val
625                 630                 635                 640

Thr Cys Ala Val Phe Asn Asn Glu Val Val Asp Leu Gln Trp Thr Tyr
                645                 650                 655

Pro Gly Glu Val Lys Gly Lys Gly Ile Thr Met Leu Glu Glu Ile Lys
            660                 665                 670

Val Pro Ser Ile Lys Leu Val Tyr Thr Leu Thr Val Pro Glu Ala Thr
        675                 680                 685

Val Lys Asp Ser Gly Asp Tyr Glu Cys Ala Ala Arg Gln Ala Thr Arg
    690                 695                 700

Glu Val Lys Glu Met Lys Lys Val Thr Ile Ser Val His Glu Lys Gly
705                 710                 715                 720


<210> SEQ ID NO 33
<211> LENGTH: 2160
<212> TYPE: DNA
<213> ORGANISM: Artificial Sequence
<220> FEATURE:
<223> OTHER INFORMATION: Sequence encoding EPS1110P

<400> SEQUENCE: 33

atgggctggt cctgcatcat cctgtttctg gtggctaccg ctaccggcgt gcactctcac     60

caccatcacc atcacgcttc tccagccgct ccagctcctg cttctcctgc tgcaccagca    120

ccatctgctc cagctgcaag tccagctgct cccgcaccag caagtcctgc agcacccgct    180

cctagtgctc cagcagcatc tcccgcagca ccagctccag cttcaccagc agctcccgct    240

ccatcagcac cagccgcatc acccgctgct ccagcaccag cttctcccgc cgctcctgca    300

ccttctgcac ccgcagctag ccctgctgct cctgctccag catctccagc tgcacccgct    360

ccaagcgcac ccgctgctag tccagcagca ccagcaccag ctagtcccgc tgctccagct    420

ccttctgctc cagcagcttc accagccgct ccagcaccag ctagcccagc cgcaccagca    480

cctagtgctc ccgccgctag tcctgcagct ccagctcctg ctagcccagc tgctcccgct    540

cctagcgctc ctgccgcttc accagctgca ccagctccag caagtccagc cgctcctgct    600

ccaagtgcac cagctgcctc tccagctgct cctgctcctg caagtcccgc agctccagca    660

cctagcgcac cagctcaact gtccctgcct tccatcctgc ctaacgagaa cgagaaggtg    720

gtccagctga actcctcctt ctctctgcgg tgcttcggcg agtccgaagt gtcttggcag    780

taccccatgt ccgaagagga atcctccgac gtggaaatcc ggaacgagga aaacaactcc    840

ggcctgttcg tgaccgtgct ggaagtgtcc tctgcctctg ctgctcacac cggcctgtac    900

acctgttact acaatcacac ccagaccgaa gagaacgagc tggaaggccg gcacatctac    960

atctacgtgc ccgatcctga cgtggccttt gtgcctctgg gcatgaccga ctacctggtc   1020

atcgtggaag atgacgactc cgctatcatc ccctgccgga ccacagatcc tgagacacct   1080

gtgacactgc acaactccga aggcgtggtg cctgcctcct acgattctag acagggcttc   1140

aacggcacct tcaccgtggg accttacatc tgcgaggcta ccgtgaaggg caagaagttc   1200

cagacaatcc ccttcaacgt gtacgccctg aaggccacct ctgagctgga cctggaaatg   1260

gaagccctga aaaccgtgta caagtccggc gagacaatcg tcgtgacctg cgccgtgttc   1320

aacaacgagg tggtggacct gcagtggacc tatcctggcg aagtgaaagg caagggcatc   1380
```

```
accatgctgg aagagatcaa ggtgccctcc atcaagctgg tgtataccct gaccgtgcct   1440

gaggccacag tgaaggactc tggcgactac gagtgtgccg ctagacaggc caccagagaa   1500

gtcaaagaga tgaagaaagt caccatctcc gtgcacgaga agggctccga taccggcaga   1560

cccttcgtgg aaatgtacag cgagatcccc gagatcatcc acatgaccga gggcagagag   1620

ctggtcatcc cttgcagagt gacctctcct aacatcacag tgaccctgaa gaagtttccc   1680

ctggacacac tgatccccga cggcaagaga atcatctggg actcccggaa gggcttcatc   1740

atctccaacg ccacctacaa agagatcggc ctgctgacct gtgaagccac cgtgaatggc   1800

cacctgtaca agaccaacta tctgacccac agacagacca acaccatcat cgacgtggtg   1860

ctgtccccaa gccatggcat cgagctgtcc gtgggagaaa agctcgtgct gaactgcacc   1920

gccagaaccg agctgaacgt gggcatcgac ttcaactggg agtaccccag ctccaaacac   1980

cagcacaaga aactggtcaa ccgggacctc aagacccagt ccggctccga aatgaagaaa   2040

ttcctgagca ccctgaccat cgacggcgtg accagatctg accagggact gtatacctgt   2100

gccgcctcct ctggcctgat gaccaagaaa aactccacct tcgtgcgggt ccacgagaag   2160
```

<210> SEQ ID NO 34
<211> LENGTH: 720
<212> TYPE: PRT
<213> ORGANISM: Artificial Sequence
<220> FEATURE:
<223> OTHER INFORMATION: Sequence of EPS1110P

<400> SEQUENCE: 34

```
Met Gly Trp Ser Cys Ile Ile Leu Phe Leu Val Ala Thr Ala Thr Gly
1               5                   10                  15

Val His Ser His His His His His His Ala Ser Pro Ala Ala Pro Ala
            20                  25                  30

Pro Ala Ser Pro Ala Ala Pro Ala Pro Ser Ala Pro Ala Ala Ser Pro
        35                  40                  45

Ala Ala Pro Ala Pro Ala Ser Pro Ala Ala Pro Ala Pro Ser Ala Pro
    50                  55                  60

Ala Ala Ser Pro Ala Ala Pro Ala Pro Ala Ser Pro Ala Ala Pro Ala
65                  70                  75                  80

Pro Ser Ala Pro Ala Ala Ser Pro Ala Ala Pro Ala Pro Ala Ser Pro
                85                  90                  95

Ala Ala Pro Ala Pro Ser Ala Pro Ala Ala Ser Pro Ala Ala Pro Ala
            100                 105                 110

Pro Ala Ser Pro Ala Ala Pro Ala Pro Ser Ala Pro Ala Ala Ser Pro
        115                 120                 125

Ala Ala Pro Ala Pro Ala Ser Pro Ala Ala Pro Ala Pro Ser Ala Pro
    130                 135                 140

Ala Ala Ser Pro Ala Ala Pro Ala Pro Ala Ser Pro Ala Ala Pro Ala
145                 150                 155                 160

Pro Ser Ala Pro Ala Ala Ser Pro Ala Ala Pro Ala Pro Ala Ser Pro
                165                 170                 175

Ala Ala Pro Ala Pro Ser Ala Pro Ala Ala Ser Pro Ala Ala Pro Ala
            180                 185                 190

Pro Ala Ser Pro Ala Ala Pro Ala Pro Ser Ala Pro Ala Ala Ser Pro
        195                 200                 205

Ala Ala Pro Ala Pro Ala Ser Pro Ala Ala Pro Ala Pro Ser Ala Pro
    210                 215                 220

Ala Gln Leu Ser Leu Pro Ser Ile Leu Pro Asn Glu Asn Glu Lys Val
```

```
225                 230                 235                 240

Val Gln Leu Asn Ser Ser Phe Ser Leu Arg Cys Phe Gly Glu Ser Glu
                245                 250                 255

Val Ser Trp Gln Tyr Pro Met Ser Glu Glu Glu Ser Ser Asp Val Glu
            260                 265                 270

Ile Arg Asn Glu Glu Asn Asn Ser Gly Leu Phe Val Thr Val Leu Glu
        275                 280                 285

Val Ser Ser Ala Ser Ala Ala His Thr Gly Leu Tyr Thr Cys Tyr Tyr
    290                 295                 300

Asn His Thr Gln Thr Glu Glu Asn Glu Leu Glu Gly Arg His Ile Tyr
305                 310                 315                 320

Ile Tyr Val Pro Asp Pro Asp Val Ala Phe Val Pro Leu Gly Met Thr
                325                 330                 335

Asp Tyr Leu Val Ile Val Glu Asp Asp Asp Ser Ala Ile Ile Pro Cys
            340                 345                 350

Arg Thr Thr Asp Pro Glu Thr Pro Val Thr Leu His Asn Ser Glu Gly
        355                 360                 365

Val Val Pro Ala Ser Tyr Asp Ser Arg Gln Gly Phe Asn Gly Thr Phe
    370                 375                 380

Thr Val Gly Pro Tyr Ile Cys Glu Ala Thr Val Lys Gly Lys Lys Phe
385                 390                 395                 400

Gln Thr Ile Pro Phe Asn Val Tyr Ala Leu Lys Ala Thr Ser Glu Leu
                405                 410                 415

Asp Leu Glu Met Glu Ala Leu Lys Thr Val Tyr Lys Ser Gly Glu Thr
            420                 425                 430

Ile Val Val Thr Cys Ala Val Phe Asn Asn Glu Val Val Asp Leu Gln
        435                 440                 445

Trp Thr Tyr Pro Gly Glu Val Lys Gly Lys Gly Ile Thr Met Leu Glu
    450                 455                 460

Glu Ile Lys Val Pro Ser Ile Lys Leu Val Tyr Thr Leu Thr Val Pro
465                 470                 475                 480

Glu Ala Thr Val Lys Asp Ser Gly Asp Tyr Glu Cys Ala Ala Arg Gln
                485                 490                 495

Ala Thr Arg Glu Val Lys Glu Met Lys Lys Val Thr Ile Ser Val His
            500                 505                 510

Glu Lys Gly Ser Asp Thr Gly Arg Pro Phe Val Glu Met Tyr Ser Glu
        515                 520                 525

Ile Pro Glu Ile Ile His Met Thr Glu Gly Arg Glu Leu Val Ile Pro
    530                 535                 540

Cys Arg Val Thr Ser Pro Asn Ile Thr Val Thr Leu Lys Lys Phe Pro
545                 550                 555                 560

Leu Asp Thr Leu Ile Pro Asp Gly Lys Arg Ile Ile Trp Asp Ser Arg
                565                 570                 575

Lys Gly Phe Ile Ile Ser Asn Ala Thr Tyr Lys Glu Ile Gly Leu Leu
            580                 585                 590

Thr Cys Glu Ala Thr Val Asn Gly His Leu Tyr Lys Thr Asn Tyr Leu
        595                 600                 605

Thr His Arg Gln Thr Asn Thr Ile Ile Asp Val Val Leu Ser Pro Ser
    610                 615                 620

His Gly Ile Glu Leu Ser Val Gly Glu Lys Leu Val Leu Asn Cys Thr
625                 630                 635                 640

Ala Arg Thr Glu Leu Asn Val Gly Ile Asp Phe Asn Trp Glu Tyr Pro
                645                 650                 655
```

```
Ser Ser Lys His Gln His Lys Lys Leu Val Asn Arg Asp Leu Lys Thr
            660                 665                 670

Gln Ser Gly Ser Glu Met Lys Lys Phe Leu Ser Thr Leu Thr Ile Asp
        675                 680                 685

Gly Val Thr Arg Ser Asp Gln Gly Leu Tyr Thr Cys Ala Ala Ser Ser
    690                 695                 700

Gly Leu Met Thr Lys Lys Asn Ser Thr Phe Val Arg Val His Glu Lys
705                 710                 715                 720


<210> SEQ ID NO 35
<211> LENGTH: 1893
<212> TYPE: DNA
<213> ORGANISM: Artificial Sequence
<220> FEATURE:
<223> OTHER INFORMATION: Sequence encoding EPS1111P

<400> SEQUENCE: 35

atgggctggt cctgcatcat cctgtttctg gtggctaccg ctaccggcgt gcactctcac     60

caccatcacc atcacgcttc tccagccgct ccagctcctg cttctcctgc tgcaccagca    120

ccatctgctc cagctgcaag tccagctgct cccgcaccag caagtcctgc agcacccgct    180

cctagtgctc cagcagcatc tcccgcagca ccagctccag cttcaccagc agctcccgct    240

ccatcagcac cagccgcatc acccgctgct ccagcaccag cttctcccgc cgctcctgca    300

ccttctgcac ccgcagctag ccctgctgct cctgctccag catctccagc tgcacccgct    360

ccaagcgcac ccgctgctag tccagcagca ccagcaccag ctagtcccgc tgctccagct    420

ccttctgctc cagcagcttc accagccgct ccagcaccag ctagcccagc cgcaccagca    480

cctagtgctc ccgccgctag tcctgcagct ccagctcctg ctagcccagc tgctcccgct    540

cctagcgctc ctgccgcttc accagctgca ccagctccag caagtccagc cgctcctgct    600

ccaagtgcac cagctgcctc tccagctgct cctgctcctg caagtcccgc agctccagca    660

cctagcgcac cagcatctga taccggcaga cccttcgtgg aaatgtacag cgagatcccc    720

gagatcatcc acatgaccga gggcagagag ctggtcatcc cctgcagagt gacctctcct    780

aacatcaccg tgactctgaa gaagttccct ctggacacac tgatccccga cggcaagaga    840

atcatctggg actcccggaa gggcttcatc atctccaacg ccacctacaa agagatcggc    900

ctgctgacct gcgaggccac cgttaatggc cacctgtaca agaccaacta tctgacccac    960

agacagacca acaccatcat cgacgtggtg ctgagcccct ctcatggcat cgagctgtcc   1020

gtgggagaaa agctcgtgct gaactgcacc gccagaaccg agctgaacgt gggcatcgac   1080

ttcaactggg agtaccccag ctccaaacac cagcacaaga aactggtcaa ccgggacctg   1140

aaaacccagt ccggctccga gatgaagaaa ttcctgagca ccctgaccat cgacggcgtg   1200

accagatctg accagggcct gtatacctgc gccgcttctt ctggcctgat gaccaagaaa   1260

aactccacct tcgtgcgcgt gcacgagaag aacgatgccg aggaactgtt catcttcctg   1320

accgagatta ccgagatcac aatcccctgc cgcgtgacag atcctcagct ggtggttacc   1380

ctgcatgaga agaaaggcga cgtggccctg cctgtgcctt acgatcatca gagaggcttc   1440

tccggcatct tcgaggaccg gtcttacatc tgcaagacca ccatcggcga cagagaggtg   1500

gactccgacg cctactacgt gtacagactc caggtgtcct ccatcaacgt gtccgtgaat   1560

gccgtgcaga cagttgtgcg gcagggcgag aatatcaccc tgatgtgcat cgtgatcggc   1620

aacgaggtgg tcaacttcga gtggacctat cctcggaaag aatctggccg gctggtggaa   1680
```

```
cctgtgaccg acttcctgct ggacatgccc taccacatcc ggtctatcct gcacatccct   1740

tccgccgagc tggaagattc cggcacctac acctgtaacg tgaccgagtc cgtgaacgac   1800

caccaggacg agaaggccat caatatcacc gtggtggaat ccggctacgt gcggctgttg   1860

ggagaagtgg gcacactgca gtttgctgag ctg                                1893


<210> SEQ ID NO 36
<211> LENGTH: 631
<212> TYPE: PRT
<213> ORGANISM: Artificial Sequence
<220> FEATURE:
<223> OTHER INFORMATION: Sequence of EPS1111P

<400> SEQUENCE: 36

Met Gly Trp Ser Cys Ile Ile Leu Phe Leu Val Ala Thr Ala Thr Gly
1               5                   10                  15

Val His Ser His His His His His His Ala Ser Pro Ala Ala Pro Ala
            20                  25                  30

Pro Ala Ser Pro Ala Ala Pro Ala Pro Ser Ala Pro Ala Ala Ser Pro
        35                  40                  45

Ala Ala Pro Ala Pro Ala Ser Pro Ala Ala Pro Ala Pro Ser Ala Pro
    50                  55                  60

Ala Ala Ser Pro Ala Ala Pro Ala Pro Ala Ser Pro Ala Ala Pro Ala
65                  70                  75                  80

Pro Ser Ala Pro Ala Ala Ser Pro Ala Ala Pro Ala Pro Ala Ser Pro
                85                  90                  95

Ala Ala Pro Ala Pro Ser Ala Pro Ala Ala Ser Pro Ala Ala Pro Ala
            100                 105                 110

Pro Ala Ser Pro Ala Ala Pro Ala Pro Ser Ala Pro Ala Ala Ser Pro
        115                 120                 125

Ala Ala Pro Ala Pro Ala Ser Pro Ala Ala Pro Ala Pro Ser Ala Pro
    130                 135                 140

Ala Ala Ser Pro Ala Ala Pro Ala Pro Ala Ser Pro Ala Ala Pro Ala
145                 150                 155                 160

Pro Ser Ala Pro Ala Ala Ser Pro Ala Ala Pro Ala Pro Ala Ser Pro
                165                 170                 175

Ala Ala Pro Ala Pro Ser Ala Pro Ala Ala Ser Pro Ala Ala Pro Ala
            180                 185                 190

Pro Ala Ser Pro Ala Ala Pro Ala Pro Ser Ala Pro Ala Ala Ser Pro
        195                 200                 205

Ala Ala Pro Ala Pro Ala Ser Pro Ala Ala Pro Ala Pro Ser Ala Pro
    210                 215                 220

Ala Ser Asp Thr Gly Arg Pro Phe Val Glu Met Tyr Ser Glu Ile Pro
225                 230                 235                 240

Glu Ile Ile His Met Thr Glu Gly Arg Glu Leu Val Ile Pro Cys Arg
                245                 250                 255

Val Thr Ser Pro Asn Ile Thr Val Thr Leu Lys Lys Phe Pro Leu Asp
            260                 265                 270

Thr Leu Ile Pro Asp Gly Lys Arg Ile Ile Trp Asp Ser Arg Lys Gly
        275                 280                 285

Phe Ile Ile Ser Asn Ala Thr Tyr Lys Glu Ile Gly Leu Leu Thr Cys
    290                 295                 300

Glu Ala Thr Val Asn Gly His Leu Tyr Lys Thr Asn Tyr Leu Thr His
305                 310                 315                 320

Arg Gln Thr Asn Thr Ile Ile Asp Val Val Leu Ser Pro Ser His Gly
```

-continued

```
                325                 330                 335

Ile Glu Leu Ser Val Gly Glu Lys Leu Val Leu Asn Cys Thr Ala Arg
            340                 345                 350

Thr Glu Leu Asn Val Gly Ile Asp Phe Asn Trp Glu Tyr Pro Ser Ser
        355                 360                 365

Lys His Gln His Lys Lys Leu Val Asn Arg Asp Leu Lys Thr Gln Ser
    370                 375                 380

Gly Ser Glu Met Lys Lys Phe Leu Ser Thr Leu Thr Ile Asp Gly Val
385                 390                 395                 400

Thr Arg Ser Asp Gln Gly Leu Tyr Thr Cys Ala Ala Ser Ser Gly Leu
                405                 410                 415

Met Thr Lys Lys Asn Ser Thr Phe Val Arg Val His Glu Lys Asn Asp
            420                 425                 430

Ala Glu Glu Leu Phe Ile Phe Leu Thr Glu Ile Thr Glu Ile Thr Ile
        435                 440                 445

Pro Cys Arg Val Thr Asp Pro Gln Leu Val Val Thr Leu His Glu Lys
    450                 455                 460

Lys Gly Asp Val Ala Leu Pro Val Pro Tyr Asp His Gln Arg Gly Phe
465                 470                 475                 480

Ser Gly Ile Phe Glu Asp Arg Ser Tyr Ile Cys Lys Thr Thr Ile Gly
                485                 490                 495

Asp Arg Glu Val Asp Ser Asp Ala Tyr Tyr Val Tyr Arg Leu Gln Val
            500                 505                 510

Ser Ser Ile Asn Val Ser Val Asn Ala Val Gln Thr Val Val Arg Gln
        515                 520                 525

Gly Glu Asn Ile Thr Leu Met Cys Ile Val Ile Gly Asn Glu Val Val
    530                 535                 540

Asn Phe Glu Trp Thr Tyr Pro Arg Lys Glu Ser Gly Arg Leu Val Glu
545                 550                 555                 560

Pro Val Thr Asp Phe Leu Leu Asp Met Pro Tyr His Ile Arg Ser Ile
                565                 570                 575

Leu His Ile Pro Ser Ala Glu Leu Glu Asp Ser Gly Thr Tyr Thr Cys
            580                 585                 590

Asn Val Thr Glu Ser Val Asn Asp His Gln Asp Glu Lys Ala Ile Asn
        595                 600                 605

Ile Thr Val Val Glu Ser Gly Tyr Val Arg Leu Leu Gly Glu Val Gly
    610                 615                 620

Thr Leu Gln Phe Ala Glu Leu
625                 630
```

<210> SEQ ID NO 37
<211> LENGTH: 3375
<212> TYPE: DNA
<213> ORGANISM: Artificial Sequence
<220> FEATURE:
<223> OTHER INFORMATION: Sequence encoding EPS1113P

<400> SEQUENCE: 37

```
atgggtacaa gccatcccgc cttcctggtc ctgggttgcc tgctgactgg tctgtctctg      60

atcctgtgcc agctgtccct gccttctatc ctgcctaacg agaacgagaa ggtggtgcag     120

ctgaactcct ccttctctct gcggtgcttc ggcgagtccg aagtgtcttg gcagtacccc     180

atgtccgaag aggaatcctc cgacgtggaa atccggaacg aggaaaacaa ctccggcctg     240

ttcgtgaccg tgctggaagt gtcctctgcc tctgctgctc acaccggcct gtacacctgt     300
```

-continued

```
tactacaatc acacccagac cgaagagaac gagctggaag gccggcacat ctacatctac    360
gtgcccgatc ctgacgtggc ctttgtgcct ctgggcatga ccgactacct ggtcatcgtg    420
gaagatgacg actccgctat catcccctgc cggaccacag atcctgagac acctgtgaca    480
ctgcacaact ccgaaggcgt ggtgcctgcc tcctacgatt ctagacaggg cttcaacggc    540
accttcaccg tgggacctta catctgcgag gctaccgtga agggcaagaa gttccagaca    600
atccccttca acgtgtacgc cctgaaggcc acctctgagc tggacctgga aatggaagcc    660
ctgaaaaccg tgtacaagtc cggcgagaca atcgtcgtga cctgcgccgt gttcaacaac    720
gaggtggtgg acctgcagtg gacctatcct ggcgaagtga aaggcaaggg catcaccatg    780
ctggaagaga tcaaggtgcc ctccatcaag ctggtgtata ccctgaccgt gcctgaggcc    840
acagtgaagg actctggcga ctacgagtgt gccgctagac aggccaccag agaagtcaaa    900
gagatgaaga aagtcaccat ctccgtgcac gagaagggcg cctctccagc tgctcctgct    960
ccagctagtc ctgcagctcc agctccatct gcaccagctg cttctccagc agcacccgca   1020
ccagcttctc ccgccgctcc tgcacctagt gcaccagcag ctagccctgc tgcaccagca   1080
ccagcaagtc cagccgcacc agctcctagt gctccagctg catcccctgc tgctcccgct   1140
cctgcttcac cagccgctcc agcaccatca gctcccgcag catctccagc agctccagct   1200
cctgcttctc ctgctgcacc cgctccatct gctcccgctg caagtcctgc tgctcctgca   1260
ccagcatcac ccgcagctcc cgcaccaagc gctccagccg cttcacccgc agcaccagct   1320
ccagcctcac cagcagcacc agcaccttcc gctccagctg ctagtccagc cgctcctgct   1380
cctgcaagcc ccgctgctcc agctcctagc gcacccgctg ctagccccgc agctcccgct   1440
ccagcaagcc cagcagctcc tgctccttct gctccagcag catctcctgc cgcaccagct   1500
ccagctagcc cagctgctcc cgcaccatcc gcaccagcag caagtcccgc agctccagca   1560
ccagctagtc ccgcagcacc cgcaccttca gcaccagccg catcaccagc tgctccagct   1620
ccagcatctc ccgctgcacc agcaccaagt gctcccgctg cttctcctgc agctcctgct   1680
ccagcctctc cagctgctcc cgcaccttct gctccagctg cctctccagc tgctccagca   1740
ccagcttcac cagctgctcc cgctcctagt gctcctgccg ctagtccagc agctcccgca   1800
ccagctagcc ctgccgctcc tgctccaagt gctccagccg caagtcccgc tgcacccgct   1860
ccagcttctc cagcagctcc cgctccaagc gcacccgcag cttctcccgc tgctcccgca   1920
ccagcaagtc ctgctgctcc agctccttca gctcctgccg cttctcctgc tgctccagct   1980
cctgcaagtc cagctgctcc agcaccaagt gcaccagcag caagtccagc tgctcctgct   2040
cctgcctctc cagcagcacc agctcctagc gcaccagccg ccagtcctgc agcaccagct   2100
ccagcttctc ccgctgctcc tgctccttca gcaccagctg ctagtcctgc tgctcctgct   2160
ccagcttctc ctgccgctcc agcaccaagc gctccagctg catctcccgc agctcccgct   2220
ccagcatctc ctgcagcacc cgcaccatca gctccagctg cttccccagc cgctcctgca   2280
ccagctagcc cagcagctcc tgcacctagc gctcccgctg cttcaccagc agctccagca   2340
ccagccagtc cagctgctcc tgcaccatct gcacccgctg ctagtcccgc tgctccagct   2400
cctgctagcc ctgcagcacc agctccaagt gcacccgccg catcacccgc cgcaccagca   2460
ccagcaagcc ctgcagcacc cgctccaagc gctccagctg ctagcccagc agcaccagca   2520
ccagcatcac cagccgctcc agcaccttct gcaccagcag cttcacccgc tgcacccgct   2580
ccagcatcac ccgccgctcc agctcctagc gctcctgcag cctctcctgc agctccagca   2640
ccagcaagcc ccgctgcacc agcaccatct gctccagcag ctagccctgc agctcccgct   2700
```

```
cctgcatctc ccgccgcacc agctccatct gcacccgcag catctgatac cggcagaccc   2760

ttcgtggaaa tgtacagcga gatccccgag atcatccaca tgaccgaggg cagagagctg   2820

gtcatccctt gcagagtgac ctctcctaac atcacagtga ccctgaagaa gtttcccctg   2880

gacacactga tccccgacgg caagagaatc atctgggact cccggaaggg cttcatcatc   2940

tccaacgcca cctacaaaga gatcggcctg ctgacctgtg aagccaccgt gaatggccac   3000

ctgtacaaga ccaactatct gacccacaga cagaccaaca ccatcatcga cgtggtgctg   3060

agcccctctc atggcatcga gctgtccgtg ggagagaagc tcgtgctgaa ctgtaccgcc   3120

agaaccgagc tgaacgtggg catcgacttc aactgggagt accctagctc caaacaccag   3180

cacaagaaac tggtcaaccg ggacctcaag acccagtccg gctccgaaat gaagaaattc   3240

ctgtccacac tgaccatcga cggcgtgacc agatctgacc agggactgta tacctgtgcc   3300

gcctcctctg gcctgatgac caagaaaaac tccaccttcg tgcgggtcca cgagaagcac   3360

caccaccatc atcat                                                    3375
```

<210> SEQ ID NO 38
<211> LENGTH: 1125
<212> TYPE: PRT
<213> ORGANISM: Artificial Sequence
<220> FEATURE:
<223> OTHER INFORMATION: Sequence of EPS1113P

<400> SEQUENCE: 38

```
Met Gly Thr Ser His Pro Ala Phe Leu Val Leu Gly Cys Leu Leu Thr
1               5                   10                  15

Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45

Cys Phe Gly Glu Ser Glu Val Ser Trp Gln Tyr Pro Met Ser Glu Glu
    50                  55                  60

Glu Ser Ser Asp Val Glu Ile Arg Asn Glu Glu Asn Asn Ser Gly Leu
65                  70                  75                  80

Phe Val Thr Val Leu Glu Val Ser Ser Ala Ser Ala Ala His Thr Gly
                85                  90                  95

Leu Tyr Thr Cys Tyr Tyr Asn His Thr Gln Thr Glu Glu Asn Glu Leu
            100                 105                 110

Glu Gly Arg His Ile Tyr Ile Tyr Val Pro Asp Pro Asp Val Ala Phe
        115                 120                 125

Val Pro Leu Gly Met Thr Asp Tyr Leu Val Ile Val Glu Asp Asp Asp
    130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
            180                 185                 190

Val Lys Gly Lys Lys Phe Gln Thr Ile Pro Phe Asn Val Tyr Ala Leu
        195                 200                 205

Lys Ala Thr Ser Glu Leu Asp Leu Glu Met Glu Ala Leu Lys Thr Val
    210                 215                 220

Tyr Lys Ser Gly Glu Thr Ile Val Val Thr Cys Ala Val Phe Asn Asn
225                 230                 235                 240
```

```
Glu Val Val Asp Leu Gln Trp Thr Tyr Pro Gly Glu Val Lys Gly Lys
                245                 250                 255

Gly Ile Thr Met Leu Glu Glu Ile Lys Val Pro Ser Ile Lys Leu Val
            260                 265                 270

Tyr Thr Leu Thr Val Pro Glu Ala Thr Val Lys Asp Ser Gly Asp Tyr
        275                 280                 285

Glu Cys Ala Ala Arg Gln Ala Thr Arg Glu Val Lys Glu Met Lys Lys
    290                 295                 300

Val Thr Ile Ser Val His Glu Lys Gly Ala Ser Pro Ala Ala Pro Ala
305                 310                 315                 320

Pro Ala Ser Pro Ala Ala Pro Ala Pro Ser Ala Pro Ala Ala Ser Pro
                325                 330                 335

Ala Ala Pro Ala Pro Ala Ser Pro Ala Ala Pro Ala Pro Ser Ala Pro
            340                 345                 350

Ala Ala Ser Pro Ala Ala Pro Ala Pro Ala Ser Pro Ala Ala Pro Ala
        355                 360                 365

Pro Ser Ala Pro Ala Ala Ser Pro Ala Ala Pro Ala Pro Ala Ser Pro
    370                 375                 380

Ala Ala Pro Ala Pro Ser Ala Pro Ala Ala Ser Pro Ala Ala Pro Ala
385                 390                 395                 400

Pro Ala Ser Pro Ala Ala Pro Ala Pro Ser Ala Pro Ala Ala Ser Pro
                405                 410                 415

Ala Ala Pro Ala Pro Ala Ser Pro Ala Ala Pro Ala Pro Ser Ala Pro
            420                 425                 430

Ala Ala Ser Pro Ala Ala Pro Ala Pro Ala Ser Pro Ala Ala Pro Ala
        435                 440                 445

Pro Ser Ala Pro Ala Ala Ser Pro Ala Ala Pro Ala Pro Ala Ser Pro
    450                 455                 460

Ala Ala Pro Ala Pro Ser Ala Pro Ala Ala Ser Pro Ala Ala Pro Ala
465                 470                 475                 480

Pro Ala Ser Pro Ala Ala Pro Ala Pro Ser Ala Pro Ala Ala Ser Pro
                485                 490                 495

Ala Ala Pro Ala Pro Ala Ser Pro Ala Ala Pro Ala Pro Ser Ala Pro
            500                 505                 510

Ala Ala Ser Pro Ala Ala Pro Ala Pro Ala Ser Pro Ala Ala Pro Ala
        515                 520                 525

Pro Ser Ala Pro Ala Ala Ser Pro Ala Ala Pro Ala Pro Ala Ser Pro
    530                 535                 540

Ala Ala Pro Ala Pro Ser Ala Pro Ala Ala Ser Pro Ala Ala Pro Ala
545                 550                 555                 560

Pro Ala Ser Pro Ala Ala Pro Ala Pro Ser Ala Pro Ala Ala Ser Pro
                565                 570                 575

Ala Ala Pro Ala Pro Ala Ser Pro Ala Ala Pro Ala Pro Ser Ala Pro
            580                 585                 590

Ala Ala Ser Pro Ala Ala Pro Ala Pro Ala Ser Pro Ala Ala Pro Ala
        595                 600                 605

Pro Ser Ala Pro Ala Ala Ser Pro Ala Ala Pro Ala Pro Ala Ser Pro
    610                 615                 620

Ala Ala Pro Ala Pro Ser Ala Pro Ala Ala Ser Pro Ala Ala Pro Ala
625                 630                 635                 640

Pro Ala Ser Pro Ala Ala Pro Ala Pro Ser Ala Pro Ala Ala Ser Pro
                645                 650                 655
```

-continued

```
Ala Ala Pro Ala Pro Ala Ser Pro Ala Ala Pro Ala Pro Ser Ala Pro
            660                 665                 670

Ala Ala Ser Pro Ala Ala Pro Ala Pro Ala Ser Pro Ala Ala Pro Ala
        675                 680                 685

Pro Ser Ala Pro Ala Ala Ser Pro Ala Ala Pro Ala Pro Ala Ser Pro
    690                 695                 700

Ala Ala Pro Ala Pro Ser Ala Pro Ala Ala Ser Pro Ala Ala Pro Ala
705                 710                 715                 720

Pro Ala Ser Pro Ala Ala Pro Ala Pro Ser Ala Pro Ala Ala Ser Pro
                725                 730                 735

Ala Ala Pro Ala Pro Ala Ser Pro Ala Ala Pro Ala Pro Ser Ala Pro
            740                 745                 750

Ala Ala Ser Pro Ala Ala Pro Ala Pro Ala Ser Pro Ala Ala Pro Ala
        755                 760                 765

Pro Ser Ala Pro Ala Ala Ser Pro Ala Ala Pro Ala Pro Ala Ser Pro
    770                 775                 780

Ala Ala Pro Ala Pro Ser Ala Pro Ala Ala Ser Pro Ala Ala Pro Ala
785                 790                 795                 800

Pro Ala Ser Pro Ala Ala Pro Ala Pro Ser Ala Pro Ala Ala Ser Pro
                805                 810                 815

Ala Ala Pro Ala Pro Ala Ser Pro Ala Ala Pro Ala Pro Ser Ala Pro
            820                 825                 830

Ala Ala Ser Pro Ala Ala Pro Ala Pro Ala Ser Pro Ala Ala Pro Ala
        835                 840                 845

Pro Ser Ala Pro Ala Ala Ser Pro Ala Ala Pro Ala Pro Ala Ser Pro
    850                 855                 860

Ala Ala Pro Ala Pro Ser Ala Pro Ala Ala Ser Pro Ala Ala Pro Ala
865                 870                 875                 880

Pro Ala Ser Pro Ala Ala Pro Ala Pro Ser Ala Pro Ala Ala Ser Pro
                885                 890                 895

Ala Ala Pro Ala Pro Ala Ser Pro Ala Ala Pro Ala Pro Ser Ala Pro
            900                 905                 910

Ala Ala Ser Asp Thr Gly Arg Pro Phe Val Glu Met Tyr Ser Glu Ile
        915                 920                 925

Pro Glu Ile Ile His Met Thr Glu Gly Arg Glu Leu Val Ile Pro Cys
    930                 935                 940

Arg Val Thr Ser Pro Asn Ile Thr Val Thr Leu Lys Lys Phe Pro Leu
945                 950                 955                 960

Asp Thr Leu Ile Pro Asp Gly Lys Arg Ile Ile Trp Asp Ser Arg Lys
                965                 970                 975

Gly Phe Ile Ile Ser Asn Ala Thr Tyr Lys Glu Ile Gly Leu Leu Thr
            980                 985                 990

Cys Glu Ala Thr Val Asn Gly His  Leu Tyr Lys Thr Asn  Tyr Leu Thr
        995                 1000                1005

His Arg  Gln Thr Asn Thr Ile  Ile Asp Val Val Leu  Ser Pro Ser
    1010                1015                1020

His Gly  Ile Glu Leu Ser Val  Gly Glu Lys Leu Val  Leu Asn Cys
    1025                1030                1035

Thr Ala  Arg Thr Glu Leu Asn  Val Gly Ile Asp Phe  Asn Trp Glu
    1040                1045                1050

Tyr Pro  Ser Ser Lys His Gln  His Lys Lys Leu Val  Asn Arg Asp
    1055                1060                1065

Leu Lys  Thr Gln Ser Gly Ser  Glu Met Lys Lys Phe  Leu Ser Thr
```

```
    1070                1075                1080

Leu Thr  Ile Asp Gly Val Thr  Arg Ser Asp Gln Gly  Leu Tyr Thr
    1085                1090                1095

Cys Ala  Ala Ser Ser Gly Leu  Met Thr Lys Lys Asn  Ser Thr Phe
    1100                1105                1110

Val Arg  Val His Glu Lys His  His His His His His
    1115                1120                1125

<210> SEQ ID NO 39
<211> LENGTH: 3465
<212> TYPE: DNA
<213> ORGANISM: Artificial Sequence
<220> FEATURE:
<223> OTHER INFORMATION: Sequence encoding EPS1114P

<400> SEQUENCE: 39

atgggcacca gccatcctgc ttttctggtg ctgggatgcc tgctgaccgg cctgtctctg     60

attctgtgcc agctgtccct gccttccatc ctgcctaacg agaacgagaa ggtggtgcag    120

ctgaactcct ccttctctct gcggtgcttc ggcgagtccg aagtgtcttg gcagtacccc    180

atgtccgaag aggaatcctc cgacgtggaa atccggaacg aggaaaacaa ctccggcctg    240

ttcgtgaccg tgctggaagt gtcctctgcc tctgctgctc acaccggact gtacacctgt    300

tactacaatc acacccagac cgaagagaac gagctggaag gccggcacat ctacatctac    360

gtgcccgatc ctgacgtggc ctttgtgcct ctgggcatga ccgactacct ggtcatcgtg    420

gaagatgacg actccgctat catcccctgc cggaccacag atcctgagac acctgtgaca    480

ctgcacaact ccgaaggcgt ggtgcctgcc tcctacgatt ctagacaggg cttcaacggc    540

accttcaccg tgggacctta catctgcgag gctaccgtga agggcaagaa gttccagaca    600

atccccttca acgtgtacgc cctgaaggcc acctctgagc tggacctgga aatggaagcc    660

ctgaaaaccg tgtacaagag cggcgagaca atcgtcgtga cctgcgccgt gttcaacaac    720

gaggtggtgg acctgcagtg gacctatcct ggcgaagtga aaggcaaggg catcaccatg    780

ctggaagaga tcaaggtgcc ctccatcaag ctggtgtata ccctgaccgt gcctgaggcc    840

acagtgaagg actctggcga ctacgagtgt gccgctagac aggccaccag agaagtcaaa    900

gagatgaaga aagtcaccat ctccgtgcac gagaaaggcg gcggaggcgg aagcggtggc    960

ggaggaagcg gaggcggcgg atctgcttct cctgctgctc ctgctccagc tagtcctgct   1020

gcaccagcac cttcagctcc agctgcttct ccagcagcac ccgcaccagc atcaccagcc   1080

gctccagcac caagtgcacc agctgctagc ccagctgctc ccgctcctgc atctcctgca   1140

gcaccagctc catctgcacc agcagcaagt ccagcagctc cagctcctgc ttcacccgct   1200

gctcccgcac catctgctcc agccgcatca cccgctgcac cagctccagc ttctcccgcc   1260

gctccagctc cttctgctcc tgcagcatct cctgctgctc cagcaccagc aagcccagcc   1320

gctcctgctc catcagcacc cgctgcctct ccagctgctc ctgcaccagc ctctccagct   1380

gcacccgctc ctagtgctcc agctgcaagt cccgccgcac cagcaccagc tagtcctgca   1440

gctcctgcac caagcgctcc agcagcttcc cctgcagctc ctgctcctgc ctctcctgcc   1500

gctcctgctc ctagtgcacc agccgcatct cccgcagctc ccgctcctgc tagtccagca   1560

gctcccgcac cttctgcacc agcagcttcc ccagccgcac cagctccagc aagcccccgct  1620

gctccagcac ctagtgctcc cgctgcctca ccagcagctc ccgctccagc aagccctgct   1680

gcacccgctc caagcgcacc agcagcatca ccagctgcac ccgcaccagc tagcccagca   1740
```

```
gcaccagctc ctagcgctcc cgcagctagc cctgctgctc ccgcaccagc ttcacccgca   1800

gcacccgctc catcagctcc cgccgctagt cccgctgctc ctgctcctgc aagccctgct   1860

gctcctgctc cttctgctcc agctgctagt cctgccgctc ctgctccagc ttctccagca   1920

gctcctgcac ctagcgcacc cgccgctagt ccagcagcac cagcaccagc ttctccagct   1980

gcaccagcac catcagcacc cgcagcttca ccagcagctc cagcaccagc atctcccgca   2040

gctccagcac catcagctcc agcagcaagc ccagctgcac cagctccagc atcaccagct   2100

gctcccgctc caagcgctcc tgctgcttct cctgccgcac cagctccagc cagtccagca   2160

gcacccgctc caagtgcacc cgccgcttct ccagctgctc cagctcctgc tagccccgca   2220

gctccagctc caagtgctcc agccgccagt cctgcagctc ccgcaccagc tagccccgct   2280

gctcctgcac catccgcacc agctgctagt cccgcagcac cagctccagc tagcccagcc   2340

gcaccagcac catctgctcc cgctgctagc cctgcagcac ccgctccagc cagtcctgct   2400

gctccagctc catctgctcc cgccgcttct cctgcagctc ctgcaccagc ttctcccgct   2460

gctcctgctc ctagcgctcc agcagcctct ccagcagcac cagctccagc aagtcctgca   2520

gcaccagcac ctagtgcacc agcagcttca cccgctgctc ccgctccagc atctccagct   2580

gctccagcac cttctgctcc agctgcaagc cccgcagctc ctgcaccagc aagtcctgcc   2640

gctccagctc ctagcgctcc tgctgcaagt ccagctgctc ccgctccagc ttcaccagcc   2700

gcaccagcac cttccgcacc agcagctagt ccagctgctc ctgctccagc tagcccagct   2760

gctccagctc cttcagcacc agcagccggt ggcggaggat ctggcggagg cggatctggc   2820

ggcggtggtt cttctgatac cggcagaccc ttcgtggaaa tgtacagcga gatccccgag   2880

atcatccaca tgaccgaggg cagagagctg gtcatccctt gcagagtgac ctctcctaac   2940

atcacagtga ccctgaagaa gtttcccctg gacacactga tccccgacgg caagagaatc   3000

atctgggact cccggaaggg cttcatcatc tccaacgcca cctacaaaga gatcggactg   3060

ctgacctgcg aagccactgt gaacggccac ctgtacaaga ccaactatct gacccacaga   3120

cagaccaaca ccatcatcga cgtggtgctg agcccctctc atggcatcga gctgtccgtg   3180

ggagagaaac tggtgctgaa ctgcaccgcc agaaccgagc tgaacgtggg catcgacttc   3240

aactgggagt accccagctc caaacaccag cacaagaagc tggtcaaccg ggatctgaaa   3300

acccagtccg gctccgaaat gaagaaattc ctgagcaccc tgaccatcga cggcgtgacc   3360

agatctgacc agggcctgta tacctgtgcc gcctcttctg gcctgatgac caagaaaaac   3420

tccaccttcg tgcgggtcca cgagaagcac catcaccacc atcat                   3465


<210> SEQ ID NO 40
<211> LENGTH: 1155
<212> TYPE: PRT
<213> ORGANISM: Artificial Sequence
<220> FEATURE:
<223> OTHER INFORMATION: Sequence of EPS1114P

<400> SEQUENCE: 40

Met Gly Thr Ser His Pro Ala Phe Leu Val Leu Gly Cys Leu Leu Thr
1               5                   10                  15

Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45

Cys Phe Gly Glu Ser Glu Val Ser Trp Gln Tyr Pro Met Ser Glu Glu
    50                  55                  60
```

```
Glu Ser Ser Asp Val Glu Ile Arg Asn Glu Glu Asn Asn Ser Gly Leu
65                  70                  75                  80

Phe Val Thr Val Leu Glu Val Ser Ser Ala Ser Ala Ala His Thr Gly
                85                  90                  95

Leu Tyr Thr Cys Tyr Tyr Asn His Thr Gln Thr Glu Glu Asn Glu Leu
            100                 105                 110

Glu Gly Arg His Ile Tyr Ile Tyr Val Pro Asp Pro Asp Val Ala Phe
        115                 120                 125

Val Pro Leu Gly Met Thr Asp Tyr Leu Val Ile Val Glu Asp Asp Asp
    130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
            180                 185                 190

Val Lys Gly Lys Lys Phe Gln Thr Ile Pro Phe Asn Val Tyr Ala Leu
        195                 200                 205

Lys Ala Thr Ser Glu Leu Asp Leu Glu Met Glu Ala Leu Lys Thr Val
    210                 215                 220

Tyr Lys Ser Gly Glu Thr Ile Val Val Thr Cys Ala Val Phe Asn Asn
225                 230                 235                 240

Glu Val Val Asp Leu Gln Trp Thr Tyr Pro Gly Glu Val Lys Gly Lys
                245                 250                 255

Gly Ile Thr Met Leu Glu Glu Ile Lys Val Pro Ser Ile Lys Leu Val
            260                 265                 270

Tyr Thr Leu Thr Val Pro Glu Ala Thr Val Lys Asp Ser Gly Asp Tyr
        275                 280                 285

Glu Cys Ala Ala Arg Gln Ala Thr Arg Glu Val Lys Glu Met Lys Lys
    290                 295                 300

Val Thr Ile Ser Val His Glu Lys Gly Gly Gly Gly Gly Ser Gly Gly
305                 310                 315                 320

Gly Gly Ser Gly Gly Gly Gly Ser Ala Ser Pro Ala Ala Pro Ala Pro
                325                 330                 335

Ala Ser Pro Ala Ala Pro Ala Pro Ser Ala Pro Ala Ala Ser Pro Ala
            340                 345                 350

Ala Pro Ala Pro Ala Ser Pro Ala Ala Pro Ala Pro Ser Ala Pro Ala
        355                 360                 365

Ala Ser Pro Ala Ala Pro Ala Pro Ala Ser Pro Ala Ala Pro Ala Pro
    370                 375                 380

Ser Ala Pro Ala Ala Ser Pro Ala Ala Pro Ala Pro Ala Ser Pro Ala
385                 390                 395                 400

Ala Pro Ala Pro Ser Ala Pro Ala Ala Ser Pro Ala Ala Pro Ala Pro
                405                 410                 415

Ala Ser Pro Ala Ala Pro Ala Pro Ser Ala Pro Ala Ala Ser Pro Ala
            420                 425                 430

Ala Pro Ala Pro Ala Ser Pro Ala Ala Pro Ala Pro Ser Ala Pro Ala
        435                 440                 445

Ala Ser Pro Ala Ala Pro Ala Pro Ala Ser Pro Ala Ala Pro Ala Pro
    450                 455                 460

Ser Ala Pro Ala Ala Ser Pro Ala Ala Pro Ala Pro Ala Ser Pro Ala
465                 470                 475                 480
```

-continued

```
Ala Pro Ala Pro Ser Ala Pro Ala Ala Ser Pro Ala Ala Pro Ala Pro
                485                 490                 495

Ala Ser Pro Ala Ala Pro Ala Pro Ser Ala Pro Ala Ala Ser Pro Ala
            500                 505                 510

Ala Pro Ala Pro Ala Ser Pro Ala Ala Pro Ala Pro Ser Ala Pro Ala
        515                 520                 525

Ala Ser Pro Ala Ala Pro Ala Pro Ala Ser Pro Ala Ala Pro Ala Pro
    530                 535                 540

Ser Ala Pro Ala Ala Ser Pro Ala Ala Pro Ala Pro Ala Ser Pro Ala
545                 550                 555                 560

Ala Pro Ala Pro Ser Ala Pro Ala Ala Ser Pro Ala Ala Pro Ala Pro
                565                 570                 575

Ala Ser Pro Ala Ala Pro Ala Pro Ser Ala Pro Ala Ala Ser Pro Ala
            580                 585                 590

Ala Pro Ala Pro Ala Ser Pro Ala Ala Pro Ala Pro Ser Ala Pro Ala
        595                 600                 605

Ala Ser Pro Ala Ala Pro Ala Pro Ala Ser Pro Ala Ala Pro Ala Pro
    610                 615                 620

Ser Ala Pro Ala Ala Ser Pro Ala Ala Pro Ala Pro Ala Ser Pro Ala
625                 630                 635                 640

Ala Pro Ala Pro Ser Ala Pro Ala Ala Ser Pro Ala Ala Pro Ala Pro
                645                 650                 655

Ala Ser Pro Ala Ala Pro Ala Pro Ser Ala Pro Ala Ala Ser Pro Ala
            660                 665                 670

Ala Pro Ala Pro Ala Ser Pro Ala Ala Pro Ala Pro Ser Ala Pro Ala
        675                 680                 685

Ala Ser Pro Ala Ala Pro Ala Pro Ala Ser Pro Ala Ala Pro Ala Pro
    690                 695                 700

Ser Ala Pro Ala Ala Ser Pro Ala Ala Pro Ala Pro Ala Ser Pro Ala
705                 710                 715                 720

Ala Pro Ala Pro Ser Ala Pro Ala Ala Ser Pro Ala Ala Pro Ala Pro
                725                 730                 735

Ala Ser Pro Ala Ala Pro Ala Pro Ser Ala Pro Ala Ala Ser Pro Ala
            740                 745                 750

Ala Pro Ala Pro Ala Ser Pro Ala Ala Pro Ala Pro Ser Ala Pro Ala
        755                 760                 765

Ala Ser Pro Ala Ala Pro Ala Pro Ala Ser Pro Ala Ala Pro Ala Pro
    770                 775                 780

Ser Ala Pro Ala Ala Ser Pro Ala Ala Pro Ala Pro Ala Ser Pro Ala
785                 790                 795                 800

Ala Pro Ala Pro Ser Ala Pro Ala Ala Ser Pro Ala Ala Pro Ala Pro
                805                 810                 815

Ala Ser Pro Ala Ala Pro Ala Pro Ser Ala Pro Ala Ala Ser Pro Ala
            820                 825                 830

Ala Pro Ala Pro Ala Ser Pro Ala Ala Pro Ala Pro Ser Ala Pro Ala
        835                 840                 845

Ala Ser Pro Ala Ala Pro Ala Pro Ala Ser Pro Ala Ala Pro Ala Pro
    850                 855                 860

Ser Ala Pro Ala Ala Ser Pro Ala Ala Pro Ala Pro Ala Ser Pro Ala
865                 870                 875                 880

Ala Pro Ala Pro Ser Ala Pro Ala Ala Ser Pro Ala Ala Pro Ala Pro
                885                 890                 895

Ala Ser Pro Ala Ala Pro Ala Pro Ser Ala Pro Ala Ala Ser Pro Ala
```

-continued

```
            900                 905                 910

Ala Pro Ala Pro Ala Ser Pro Ala Ala Pro Ala Pro Ser Ala Pro Ala
        915                 920                 925

Ala Gly Gly Gly Gly Ser Gly Gly Gly Gly Ser Gly Gly Gly Gly Ser
    930                 935                 940

Ser Asp Thr Gly Arg Pro Phe Val Glu Met Tyr Ser Glu Ile Pro Glu
945                 950                 955                 960

Ile Ile His Met Thr Glu Gly Arg Glu Leu Val Ile Pro Cys Arg Val
                965                 970                 975

Thr Ser Pro Asn Ile Thr Val Thr Leu Lys Lys Phe Pro Leu Asp Thr
            980                 985                 990

Leu Ile Pro Asp Gly Lys Arg Ile  Ile Trp Asp Ser Arg  Lys Gly Phe
        995                 1000                1005

Ile Ile  Ser Asn Ala Thr Tyr  Lys Glu Ile Gly Leu  Leu Thr Cys
    1010                 1015                 1020

Glu Ala  Thr Val Asn Gly His  Leu Tyr Lys Thr Asn  Tyr Leu Thr
    1025                 1030                 1035

His Arg  Gln Thr Asn Thr Ile  Ile Asp Val Val Leu  Ser Pro Ser
    1040                 1045                 1050

His Gly  Ile Glu Leu Ser Val  Gly Glu Lys Leu Val  Leu Asn Cys
    1055                 1060                 1065

Thr Ala  Arg Thr Glu Leu Asn  Val Gly Ile Asp Phe  Asn Trp Glu
    1070                 1075                 1080

Tyr Pro  Ser Ser Lys His Gln  His Lys Lys Leu Val  Asn Arg Asp
    1085                 1090                 1095

Leu Lys  Thr Gln Ser Gly Ser  Glu Met Lys Lys Phe  Leu Ser Thr
    1100                 1105                 1110

Leu Thr  Ile Asp Gly Val Thr  Arg Ser Asp Gln Gly  Leu Tyr Thr
    1115                 1120                 1125

Cys Ala  Ala Ser Ser Gly Leu  Met Thr Lys Lys Asn  Ser Thr Phe
    1130                 1135                 1140

Val Arg  Val His Glu Lys His  His His His His His
    1145                 1150                 1155
```

<210> SEQ ID NO 41
<211> LENGTH: 3474
<212> TYPE: DNA
<213> ORGANISM: Artificial Sequence
<220> FEATURE:
<223> OTHER INFORMATION: Sequence encoding EPS1115P

<400> SEQUENCE: 41

```
atggtgtcct actgggatac aggcgtgctg ctgtgtgccc tgctgtcttg tctgctgctg      60

accggctcct cttctggctc tgataccggc agacccttcg tggaaatgta cagcgagatc     120

cccgagatca tccacatgac cgagggcaga gagctggtca tcccctgcag agtgacctct     180

cctaacatca ccgtgactct gaagaagttc cctctggaca cactgatccc cgacggcaag     240

agaatcatct gggactcccg gaagggcttc atcatctcca acgccaccta caaagagatc     300

ggcctgctga cctgcgaggc caccgttaat ggccacctgt acaagaccaa ctatctgacc     360

cacagacaga ccaacaccat catcgacgtg gtgctgagcc cctctcatgg catcgagctg     420

tccgtgggag aaaagctggt gctgaactgc accgccagaa ccgagctgaa cgtgggcatc     480

gacttcaact gggagtaccc ctccagcaag caccagcaca agaagctggt caaccgggac     540

ctgaaaaccc agtccggctc cgagatgaag aaattcctga gcaccctgac catcgacggc     600
```

-continued

```
gtgaccagat ctgaccaggg cctgtatacc tgcgccgctt cctctggcct gatgaccaag    660
aaaaactcca ccttcgtgcg ggtgcacgag aaaggtggcg gaggatctgg cggaggcggc    720
tctggcggcg gtggatctgc ttctcctgct gctccagctc cagcttctcc agcagctcct    780
gcaccttctg caccagctgc aagtcctgca gcacccgcac cagctagtcc tgccgctcct    840
gctcctagtg ctcctgccgc aagtccagct gctcccgctc ctgcaagccc agctgcacca    900
gcaccaagtg ctccagctgc ctcaccagcc gcaccagctc cagcaagccc tgcagctccc    960
gctccttcag ctcctgctgc ttctcccgca gcacccgctc cagcatcacc agccgctcca   1020
gcaccatcag ctccagcagc atctcctgca gctccagctc ctgctagtcc cgctgctccc   1080
gcacctagtg caccagccgc ttctcccgcc gctcctgctc ctgcatctcc tgctgcaccc   1140
gctccatctg ctcccgccgc atcacccgca gctcccgcac cagcctctcc agctgcacca   1200
gctcctagcg caccagcagc tagcccagct gctcctgcac cagctagccc cgcagctcca   1260
gctccaagcg ctcctgctgc atccccagct gctccagctc ctgcctcacc agctgctcca   1320
gcaccttctg ctcccgccgc ttctcctgcc gcaccagctc cagctagtcc agccgcacca   1380
gcaccatctg cacccgctgc tagccctgct gcaccagctc cagcatcacc cgctgcacca   1440
gctccatccg caccagctgc ttcaccagca gctcccgctc cagcttcacc cgctgctccc   1500
gctcctagcg ctcccgcagc ttcaccagct gcacccgctc cagccagtcc agctgctccc   1560
gcaccatccg caccagcagc aagtcccgcc gctccagctc cagctagccc agctgctcca   1620
gctccatctg caccagccgc atctccagct gctccagctc cagctagtcc tgctgcaccc   1680
gctcctagcg ctccagctgc aagtcctgcc gctcctgctc cagcctctcc tgccgctcca   1740
gcacctagcg ctcccgctgc cagtccagca gctccagctc ctgcatctcc cgccgcacca   1800
gcaccaagcg cacccgcagc atctcccgct gctcccgctc cagcaagccc tgccgctcct   1860
gcaccaagtg caccagcagc atccccagca gctcccgctc cagcatctcc agcagctcca   1920
gctccaagtg ctccagcagc tagtcctgct gctccagctc ctgctagccc tgcagctcct   1980
gcaccatctg ctcccgcagc cagtcctgca gctcctgcac cagcaagtcc agctgctcct   2040
gcacctagcg ctccagctgc atctcccgct gcaccagctc cagcaagtcc cgctgctcct   2100
gctccttctg ctccagcagc ttcccctgct gctcctgctc ctgcttcacc cgccgctcca   2160
gctccatctg ctcccgctgc ctctccagcc gctcctgcac cagcatcacc agctgctccc   2220
gcaccaagcg cacccgctgc aagcccagcc gctcctgctc ctgctagtcc agccgctcct   2280
gcaccttcag cacccgcagc ttccccagct gctccagctc cagcaagtcc agcagctcca   2340
gctccttccg ctccagctgc aagccccgca gctccagctc ctgcttctcc tgctgctcct   2400
gcaccatcag ctccagctgc tagtccagca gctcctgcac cagccagtcc tgccgcacca   2460
gcaccttcag ctccagctgc ttcacccgct gctcccgcac cagctagtcc agccgctcca   2520
gcaccaagtg ctcccgccgc tggtggtggt ggatctggtg gtggcggaag cggaggtggt   2580
ggttctcagc tgtccctgcc ttccatcctg cctaacgaga acgagaaggt ggtccagctg   2640
aactcctcct tctctctgcg gtgcttcggc gagtccgaag tgtcttggca gtaccccatg   2700
tccgaagagg aatcctccga cgtggaaatc cggaacgagg aaaacaactc cggcctgttc   2760
gtgaccgtgc tggaagtgtc ctctgcctct gctgctcaca ccggcctgta cacatgctac   2820
tacaatcaca cccagaccga agagaacgag ctggaaggcc ggcacatcta catctacgtg   2880
cccgatcctg acgtggcctt tgtgcctctg ggcatgaccg actacctggt catcgtggaa   2940
```

```
gatgacgact ccgctatcat cccttgccgg accaccgatc cagagacacc tgtgacactg   3000

cacaactccg aaggcgtggt gcctgcctcc tacgattcta gacagggctt caacggcacc   3060

ttcaccgtgg gaccttacat ctgcgaggct acagtgaagg gcaagaagtt tcagacaatc   3120

cccttcaacg tgtacgccct gaaggccacc tctgagctgg acctggaaat ggaagctctg   3180

aaaaccgtgt acaagtccgg cgagacaatc gtcgtgacct gtgccgtgtt caacaacgaa   3240

gtggtggacc tgcagtggac ctatcctggc gaagtgaaag gcaagggcat cacaatgctg   3300

gaagagatca aggtgccctc catcaagctg gtgtataccc tgaccgtgcc tgaggccact   3360

gtgaaggact ctggcgacta cgagtgtgcc gctagacagg ccaccagaga agtcaaagaa   3420

atgaagaaag tgaccatctc cgtccacgag aagggccacc atcatcacca ccat         3474
```

<210> SEQ ID NO 42
<211> LENGTH: 1158
<212> TYPE: PRT
<213> ORGANISM: Artificial Sequence
<220> FEATURE:
<223> OTHER INFORMATION: Sequence of EPS1115P

<400> SEQUENCE: 42

```
Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Asp Thr Gly Arg Pro
            20                  25                  30

Phe Val Glu Met Tyr Ser Glu Ile Pro Glu Ile Ile His Met Thr Glu
        35                  40                  45

Gly Arg Glu Leu Val Ile Pro Cys Arg Val Thr Ser Pro Asn Ile Thr
    50                  55                  60

Val Thr Leu Lys Lys Phe Pro Leu Asp Thr Leu Ile Pro Asp Gly Lys
65                  70                  75                  80

Arg Ile Ile Trp Asp Ser Arg Lys Gly Phe Ile Ile Ser Asn Ala Thr
                85                  90                  95

Tyr Lys Glu Ile Gly Leu Leu Thr Cys Glu Ala Thr Val Asn Gly His
            100                 105                 110

Leu Tyr Lys Thr Asn Tyr Leu Thr His Arg Gln Thr Asn Thr Ile Ile
        115                 120                 125

Asp Val Val Leu Ser Pro Ser His Gly Ile Glu Leu Ser Val Gly Glu
    130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                165                 170                 175

Val Asn Arg Asp Leu Lys Thr Gln Ser Gly Ser Glu Met Lys Lys Phe
            180                 185                 190

Leu Ser Thr Leu Thr Ile Asp Gly Val Thr Arg Ser Asp Gln Gly Leu
        195                 200                 205

Tyr Thr Cys Ala Ala Ser Ser Gly Leu Met Thr Lys Lys Asn Ser Thr
    210                 215                 220

Phe Val Arg Val His Glu Lys Gly Gly Gly Gly Ser Gly Gly Gly Gly
225                 230                 235                 240

Ser Gly Gly Gly Gly Ser Ala Ser Pro Ala Ala Pro Ala Pro Ala Ser
                245                 250                 255

Pro Ala Ala Pro Ala Pro Ser Ala Pro Ala Ala Ser Pro Ala Ala Pro
            260                 265                 270
```

```
Ala Pro Ala Ser Pro Ala Ala Pro Ala Pro Ser Ala Pro Ala Ala Ser
        275                 280                 285

Pro Ala Ala Pro Ala Pro Ala Ser Pro Ala Ala Pro Ala Pro Ser Ala
    290                 295                 300

Pro Ala Ala Ser Pro Ala Ala Pro Ala Pro Ala Ser Pro Ala Ala Pro
305                 310                 315                 320

Ala Pro Ser Ala Pro Ala Ala Ser Pro Ala Ala Pro Ala Pro Ala Ser
                325                 330                 335

Pro Ala Ala Pro Ala Pro Ser Ala Pro Ala Ala Ser Pro Ala Ala Pro
            340                 345                 350

Ala Pro Ala Ser Pro Ala Ala Pro Ala Pro Ser Ala Pro Ala Ala Ser
        355                 360                 365

Pro Ala Ala Pro Ala Pro Ala Ser Pro Ala Ala Pro Ala Pro Ser Ala
    370                 375                 380

Pro Ala Ala Ser Pro Ala Ala Pro Ala Pro Ala Ser Pro Ala Ala Pro
385                 390                 395                 400

Ala Pro Ser Ala Pro Ala Ala Ser Pro Ala Ala Pro Ala Pro Ala Ser
                405                 410                 415

Pro Ala Ala Pro Ala Pro Ser Ala Pro Ala Ala Ser Pro Ala Ala Pro
            420                 425                 430

Ala Pro Ala Ser Pro Ala Ala Pro Ala Pro Ser Ala Pro Ala Ala Ser
        435                 440                 445

Pro Ala Ala Pro Ala Pro Ala Ser Pro Ala Ala Pro Ala Pro Ser Ala
    450                 455                 460

Pro Ala Ala Ser Pro Ala Ala Pro Ala Pro Ala Ser Pro Ala Ala Pro
465                 470                 475                 480

Ala Pro Ser Ala Pro Ala Ala Ser Pro Ala Ala Pro Ala Pro Ala Ser
                485                 490                 495

Pro Ala Ala Pro Ala Pro Ser Ala Pro Ala Ala Ser Pro Ala Ala Pro
            500                 505                 510

Ala Pro Ala Ser Pro Ala Ala Pro Ala Pro Ser Ala Pro Ala Ala Ser
        515                 520                 525

Pro Ala Ala Pro Ala Pro Ala Ser Pro Ala Ala Pro Ala Pro Ser Ala
    530                 535                 540

Pro Ala Ala Ser Pro Ala Ala Pro Ala Pro Ala Ser Pro Ala Ala Pro
545                 550                 555                 560

Ala Pro Ser Ala Pro Ala Ala Ser Pro Ala Ala Pro Ala Pro Ala Ser
                565                 570                 575

Pro Ala Ala Pro Ala Pro Ser Ala Pro Ala Ala Ser Pro Ala Ala Pro
            580                 585                 590

Ala Pro Ala Ser Pro Ala Ala Pro Ala Pro Ser Ala Pro Ala Ala Ser
        595                 600                 605

Pro Ala Ala Pro Ala Pro Ala Ser Pro Ala Ala Pro Ala Pro Ser Ala
    610                 615                 620

Pro Ala Ala Ser Pro Ala Ala Pro Ala Pro Ala Ser Pro Ala Ala Pro
625                 630                 635                 640

Ala Pro Ser Ala Pro Ala Ala Ser Pro Ala Ala Pro Ala Pro Ala Ser
                645                 650                 655

Pro Ala Ala Pro Ala Pro Ser Ala Pro Ala Ala Ser Pro Ala Ala Pro
            660                 665                 670

Ala Pro Ala Ser Pro Ala Ala Pro Ala Pro Ser Ala Pro Ala Ala Ser
        675                 680                 685

Pro Ala Ala Pro Ala Pro Ala Ser Pro Ala Ala Pro Ala Pro Ser Ala
```

-continued

```
    690                 695                 700

Pro Ala Ala Ser Pro Ala Ala Pro Ala Pro Ala Ser Pro Ala Ala Pro
705                 710                 715                 720

Ala Pro Ser Ala Pro Ala Ala Ser Pro Ala Ala Pro Ala Pro Ala Ser
                725                 730                 735

Pro Ala Ala Pro Ala Pro Ser Ala Pro Ala Ala Ser Pro Ala Ala Pro
            740                 745                 750

Ala Pro Ala Ser Pro Ala Ala Pro Ala Pro Ser Ala Pro Ala Ala Ser
        755                 760                 765

Pro Ala Ala Pro Ala Pro Ala Ser Pro Ala Ala Pro Ala Pro Ser Ala
    770                 775                 780

Pro Ala Ala Ser Pro Ala Ala Pro Ala Pro Ala Ser Pro Ala Ala Pro
785                 790                 795                 800

Ala Pro Ser Ala Pro Ala Ala Ser Pro Ala Ala Pro Ala Pro Ala Ser
                805                 810                 815

Pro Ala Ala Pro Ala Pro Ser Ala Pro Ala Ala Ser Pro Ala Ala Pro
            820                 825                 830

Ala Pro Ala Ser Pro Ala Ala Pro Ala Pro Ser Ala Pro Ala Ala Gly
        835                 840                 845

Gly Gly Gly Ser Gly Gly Gly Gly Ser Gly Gly Gly Gly Ser Gln Leu
    850                 855                 860

Ser Leu Pro Ser Ile Leu Pro Asn Glu Asn Glu Lys Val Val Gln Leu
865                 870                 875                 880

Asn Ser Ser Phe Ser Leu Arg Cys Phe Gly Glu Ser Glu Val Ser Trp
                885                 890                 895

Gln Tyr Pro Met Ser Glu Glu Glu Ser Ser Asp Val Glu Ile Arg Asn
            900                 905                 910

Glu Glu Asn Asn Ser Gly Leu Phe Val Thr Val Leu Glu Val Ser Ser
        915                 920                 925

Ala Ser Ala Ala His Thr Gly Leu Tyr Thr Cys Tyr Tyr Asn His Thr
    930                 935                 940

Gln Thr Glu Glu Asn Glu Leu Glu Gly Arg His Ile Tyr Ile Tyr Val
945                 950                 955                 960

Pro Asp Pro Asp Val Ala Phe Val Pro Leu Gly Met Thr Asp Tyr Leu
                965                 970                 975

Val Ile Val Glu Asp Asp Asp Ser Ala Ile Ile Pro Cys Arg Thr Thr
            980                 985                 990

Asp Pro Glu Thr Pro Val Thr Leu  His Asn Ser Glu Gly  Val Val Pro
        995                 1000                1005

Ala Ser  Tyr Asp Ser Arg Gln  Gly Phe Asn Gly Thr  Phe Thr Val
    1010                1015                1020

Gly Pro  Tyr Ile Cys Glu Ala  Thr Val Lys Gly Lys  Lys Phe Gln
    1025                1030                1035

Thr Ile  Pro Phe Asn Val Tyr  Ala Leu Lys Ala Thr  Ser Glu Leu
    1040                1045                1050

Asp Leu  Glu Met Glu Ala Leu  Lys Thr Val Tyr Lys  Ser Gly Glu
    1055                1060                1065

Thr Ile  Val Val Thr Cys Ala  Val Phe Asn Asn Glu  Val Val Asp
    1070                1075                1080

Leu Gln  Trp Thr Tyr Pro Gly  Glu Val Lys Gly Lys  Gly Ile Thr
    1085                1090                1095

Met Leu  Glu Glu Ile Lys Val  Pro Ser Ile Lys Leu  Val Tyr Thr
    1100                1105                1110
```

```
Leu Thr  Val Pro Glu Ala Thr  Val Lys Asp Ser Gly  Asp Tyr Glu
    1115                 1120                 1125

Cys Ala  Ala Arg Gln Ala Thr  Arg Glu Val Lys Glu  Met Lys Lys
    1130                 1135                 1140

Val Thr  Ile Ser Val His Glu  Lys Gly His His His  His His His
    1145                 1150                 1155
```

<210> SEQ ID NO 43
<211> LENGTH: 2772
<212> TYPE: DNA
<213> ORGANISM: Artificial Sequence
<220> FEATURE:
<223> OTHER INFORMATION: Sequence encoding EPS1116P

<400> SEQUENCE: 43

```
atggggacct ctcatcctgc cttcctggtg ctggggtgcc tgctgaccgg cctgtctctg     60

attctgtgcc agctgagcct gccaagcatc ctgcctaacg aaaatgagaa ggtggtccag    120

ctgaacagct ccttcagtct gagatgcttt ggcgaatcag aggtgagctg gcagtaccca    180

atgtcagagg aagagtctag tgacgtggaa attaggaatg aagagaacaa ttcaggactg    240

ttcgtgaccg tcctggaggt gtcaagcgcc agcgccgctc acaccggact gtacacatgt    300

tactataacc atactcagac cgaagagaat gaactggagg ggaggcacat ctccatccac    360

gtgcccgatc ctgacgtggc ctttgcccca ctgggaatga cagattacct ggtcatcgtc    420

gaggacgatg actctgccat cattccctgc cgcacctcag actccgaaac tcctgtgacc    480

ctgcataaca gtgagggcgt ggtccccgcc tcctacgatt ctcgacaggg attcaatggc    540

accttcaccg tcggacccta tatctgtgag gccactgtga agggcaagaa attccagacc    600

attcctttta acgtgtacgc actgaaagcc acatccgaac tggacctgga aatggaggcc    660

ctgaagactg tctataaatc tggagagact atcgtggtca cctgcgccgt gttcaacaat    720

gaagtggtcg atgcgcagtg gacttacccc ggcgaggtca agggcaaagg gattaccatg    780

gacgaagaga tcaaggtgcc tagccagaag ctggtgtaca ccctgacagt cccagaagcc    840

accgtgaagg attccgggga ctatgagtgt gcagcccggc aggcctccag agaagtgaag    900

gagatgaaga aagtgacaat cagtgtccac gagaaaggag caagccccgc cgctccagcc    960

cccgcaagcc cagccgcacc agcaccttcc gcaccagccg cctccccagc agcacccgca   1020

cccgcttccc ctgccgcccc cgcccctagc gcccccgccg cctcccctgc cgccccagcc   1080

cccgcctctc cagccgcccc tgccccatct gccccagccg ccagcccagc cgcccccgcc   1140

cctgccagcc ccgccgcccc agccccctcc gcccctgctg cttcccctgc cgcccctgcc   1200

ccagccagcc cagctgctcc tgctccaagc gcccctgctg caagcccagc tgctccagcc   1260

cccgcctctc ccgctgctcc agctccttct gcccctgctg cttccccagc tgctcccgcc   1320

cctgcctctc ctgctgctcc tgctccctcc gcccctgctg catcccccgc tgctcctgcc   1380

ccagcttccc cagctgcacc tgctccaagc gccccagctg caagcccagc tgcacctgca   1440

cctgcttccc ccgctgcccc tgccccaagc gcccccgccg catcccccgc cgcaccagcc   1500

cccgcctcac ccgcagcacc agccccatca gcaccagccg cctcaccagc cgcccccgca   1560

cccgcaagtc cagcagcacc cgcaccatcc gcccccgccg caagcccagc cgcccccgct   1620

ccagcatccc ctgccgcccc cgcccccagc gcccccgccg cctcccctgc cgccccagcc   1680

cccgcctctc cagccgcccc tgccccatct gccccagccg ccagccccgc cgcccccgcc   1740

cctgccagcc ccgccgcccc agccccctcc gcccctgctg cttcccccgc cgcccctgcc   1800
```

```
ccagccagcc cagctgctcc cgctccaagc gcccccgctg caagcccagc tgctccagcc   1860

cccgcctctc ccgctgctcc agctccttct gcccctgctg cttcccccgc tgctcccgcc   1920

cccgcctctc ctgctgctcc cgctccctcc gcccctgctg catcccccgc tgctcctgcc   1980

ccagcttccc cagctgcacc tgctcccagc gccccagctg caagccccgc tgcacctgca   2040

cctgcttccc ccgctgcccc tgccccaagc gcccccgccg cctcacccgc agcccccgct   2100

ccagccagcc ccgcagcacc agcaccctca gccccagcct cagataccgg ccggcctttt   2160

gtggagatgt actccgaaat ccccgagatc attcacatga ccgaagggcg agagctggtc   2220

atcccatgcc gggtgacaag ccccaacatt actgtgaccc tgaagaaatt ccctctggat   2280

actctgatcc cagacgggaa gaggatcatt tgggacagcc gcaaaggctt catcatttcc   2340

aatgccacat ataaggaaat tggcctgctg acatgcgagg ccactgtgaa cgggcacctg   2400

tacaaaacca attatctgac acatcggcag acaaacacta tcattgatgt ggtcctgagc   2460

ccttcccatg ggatcgaact gagcgtcgga gagaagctgg tgctgaattg tacagccaga   2520

actgaactga acgtgggcat tgacttcaat tgggagtacc cctcctctaa gcaccagcat   2580

aagaaactgg tgaataggga tctgaaaacc cagtctggga gtgagatgaa gaaatttctg   2640

tctaccctga caatcgatgg cgtgacacgc agtgaccagg ggctgtatac ttgtgcagcc   2700

agttcaggcc tgatgaccaa gaagaacagc acatttgtcc gagtccacga aaagcaccac   2760

caccaccatc ac                                                       2772
```

```
<210> SEQ ID NO 44
<211> LENGTH: 924
<212> TYPE: PRT
<213> ORGANISM: Artificial Sequence
<220> FEATURE:
<223> OTHER INFORMATION: Sequence of EPS1116P

<400> SEQUENCE: 44

Met Gly Thr Ser His Pro Ala Phe Leu Val Leu Gly Cys Leu Leu Thr
1               5                   10                  15

Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45

Cys Phe Gly Glu Ser Glu Val Ser Trp Gln Tyr Pro Met Ser Glu Glu
    50                  55                  60

Glu Ser Ser Asp Val Glu Ile Arg Asn Glu Glu Asn Asn Ser Gly Leu
65                  70                  75                  80

Phe Val Thr Val Leu Glu Val Ser Ser Ala Ser Ala Ala His Thr Gly
                85                  90                  95

Leu Tyr Thr Cys Tyr Tyr Asn His Thr Gln Thr Glu Glu Asn Glu Leu
            100                 105                 110

Glu Gly Arg His Ile Ser Ile His Val Pro Asp Pro Asp Val Ala Phe
        115                 120                 125

Ala Pro Leu Gly Met Thr Asp Tyr Leu Val Ile Val Glu Asp Asp Asp
    130                 135                 140

Ser Ala Ile Ile Pro Cys Arg Thr Ser Asp Ser Glu Thr Pro Val Thr
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
```

```
            180                 185                 190

Val Lys Gly Lys Lys Phe Gln Thr Ile Pro Phe Asn Val Tyr Ala Leu
        195                 200                 205

Lys Ala Thr Ser Glu Leu Asp Leu Glu Met Glu Ala Leu Lys Thr Val
    210                 215                 220

Tyr Lys Ser Gly Glu Thr Ile Val Val Thr Cys Ala Val Phe Asn Asn
225                 230                 235                 240

Glu Val Val Asp Ala Gln Trp Thr Tyr Pro Gly Glu Val Lys Gly Lys
                245                 250                 255

Gly Ile Thr Met Asp Glu Glu Ile Lys Val Pro Ser Gln Lys Leu Val
            260                 265                 270

Tyr Thr Leu Thr Val Pro Glu Ala Thr Val Lys Asp Ser Gly Asp Tyr
        275                 280                 285

Glu Cys Ala Ala Arg Gln Ala Ser Arg Glu Val Lys Glu Met Lys Lys
    290                 295                 300

Val Thr Ile Ser Val His Glu Lys Gly Ala Ser Pro Ala Ala Pro Ala
305                 310                 315                 320

Pro Ala Ser Pro Ala Ala Pro Ala Pro Ser Ala Pro Ala Ala Ser Pro
                325                 330                 335

Ala Ala Pro Ala Pro Ala Ser Pro Ala Ala Pro Ala Pro Ser Ala Pro
            340                 345                 350

Ala Ala Ser Pro Ala Ala Pro Ala Pro Ala Ser Pro Ala Ala Pro Ala
        355                 360                 365

Pro Ser Ala Pro Ala Ala Ser Pro Ala Ala Pro Ala Pro Ala Ser Pro
    370                 375                 380

Ala Ala Pro Ala Pro Ser Ala Pro Ala Ala Ser Pro Ala Ala Pro Ala
385                 390                 395                 400

Pro Ala Ser Pro Ala Ala Pro Ala Pro Ser Ala Pro Ala Ala Ser Pro
                405                 410                 415

Ala Ala Pro Ala Pro Ala Ser Pro Ala Ala Pro Ala Pro Ser Ala Pro
            420                 425                 430

Ala Ala Ser Pro Ala Ala Pro Ala Pro Ala Ser Pro Ala Ala Pro Ala
        435                 440                 445

Pro Ser Ala Pro Ala Ala Ser Pro Ala Ala Pro Ala Pro Ala Ser Pro
    450                 455                 460

Ala Ala Pro Ala Pro Ser Ala Pro Ala Ala Ser Pro Ala Ala Pro Ala
465                 470                 475                 480

Pro Ala Ser Pro Ala Ala Pro Ala Pro Ser Ala Pro Ala Ala Ser Pro
                485                 490                 495

Ala Ala Pro Ala Pro Ala Ser Pro Ala Ala Pro Ala Pro Ser Ala Pro
            500                 505                 510

Ala Ala Ser Pro Ala Ala Pro Ala Pro Ala Ser Pro Ala Ala Pro Ala
        515                 520                 525

Pro Ser Ala Pro Ala Ala Ser Pro Ala Ala Pro Ala Pro Ala Ser Pro
    530                 535                 540

Ala Ala Pro Ala Pro Ser Ala Pro Ala Ala Ser Pro Ala Ala Pro Ala
545                 550                 555                 560

Pro Ala Ser Pro Ala Ala Pro Ala Pro Ser Ala Pro Ala Ala Ser Pro
                565                 570                 575

Ala Ala Pro Ala Pro Ala Ser Pro Ala Ala Pro Ala Pro Ser Ala Pro
            580                 585                 590

Ala Ala Ser Pro Ala Ala Pro Ala Pro Ala Ser Pro Ala Ala Pro Ala
        595                 600                 605
```

```
Pro Ser Ala Pro Ala Ala Ser Pro Ala Ala Pro Ala Pro Ala Ser Pro
    610                 615                 620

Ala Ala Pro Ala Pro Ser Ala Pro Ala Ala Ser Pro Ala Ala Pro Ala
625                 630                 635                 640

Pro Ala Ser Pro Ala Ala Pro Ala Pro Ser Ala Pro Ala Ala Ser Pro
                645                 650                 655

Ala Ala Pro Ala Pro Ala Ser Pro Ala Ala Pro Ala Pro Ser Ala Pro
            660                 665                 670

Ala Ala Ser Pro Ala Ala Pro Ala Pro Ala Ser Pro Ala Ala Pro Ala
        675                 680                 685

Pro Ser Ala Pro Ala Ala Ser Pro Ala Ala Pro Ala Pro Ala Ser Pro
    690                 695                 700

Ala Ala Pro Ala Pro Ser Ala Pro Ala Ser Asp Thr Gly Arg Pro Phe
705                 710                 715                 720

Val Glu Met Tyr Ser Glu Ile Pro Glu Ile Ile His Met Thr Glu Gly
                725                 730                 735

Arg Glu Leu Val Ile Pro Cys Arg Val Thr Ser Pro Asn Ile Thr Val
            740                 745                 750

Thr Leu Lys Lys Phe Pro Leu Asp Thr Leu Ile Pro Asp Gly Lys Arg
        755                 760                 765

Ile Ile Trp Asp Ser Arg Lys Gly Phe Ile Ile Ser Asn Ala Thr Tyr
    770                 775                 780

Lys Glu Ile Gly Leu Leu Thr Cys Glu Ala Thr Val Asn Gly His Leu
785                 790                 795                 800

Tyr Lys Thr Asn Tyr Leu Thr His Arg Gln Thr Asn Thr Ile Ile Asp
                805                 810                 815

Val Val Leu Ser Pro Ser His Gly Ile Glu Leu Ser Val Gly Glu Lys
            820                 825                 830

Leu Val Leu Asn Cys Thr Ala Arg Thr Glu Leu Asn Val Gly Ile Asp
        835                 840                 845

Phe Asn Trp Glu Tyr Pro Ser Ser Lys His Gln His Lys Lys Leu Val
    850                 855                 860

Asn Arg Asp Leu Lys Thr Gln Ser Gly Ser Glu Met Lys Lys Phe Leu
865                 870                 875                 880

Ser Thr Leu Thr Ile Asp Gly Val Thr Arg Ser Asp Gln Gly Leu Tyr
                885                 890                 895

Thr Cys Ala Ala Ser Ser Gly Leu Met Thr Lys Lys Asn Ser Thr Phe
            900                 905                 910

Val Arg Val His Glu Lys His His His His His His
        915                 920
```

<210> SEQ ID NO 45
<211> LENGTH: 2385
<212> TYPE: DNA
<213> ORGANISM: Artificial Sequence
<220> FEATURE:
<223> OTHER INFORMATION: Sequence encoding EPS1103P, excluding signal
      peptide and purification tag

<400> SEQUENCE: 45

```
cagctgagcc tgccttcaat cctgcccaac gagaatgaga aggtggtgca gctgaactcc      60

agcttcagcc tgagatgctt tggcgagtct gaggtgtcct ggcagtaccc tatgtctgag     120

gaggagtctt ccgacgtgga gatccgcaat gaggagaaca attccggcct gttcgtgacc     180

gtgctggagg tgagctctgc cagcgccgct cacaccggcc tgtacacatg ttactataac     240
```

```
cataccccaga cagaggagaa tgagctggag ggcagacaca tctacatcta tgtgcccgat    300
cctgacgtgg cctttgtgcc actgggcatg accgattacc tggtcatcgt ggaggacgat    360
gactctgcca tcatcccctg caggaccaca gacccagaga cacccgtgac actgcataac    420
tccgagggag tggtgccagc tagctacgat tctcggcagg gcttcaatgg cacctttaca    480
gtgggcccct atatctgtga ggccaccgtg aagggcaaga agttccagac aatccctttt    540
aacgtgtacg ccctgaaggc tacctctgag ctggacctgg agatggaggc cctgaagaca    600
gtgtataagt ccggcgagac aatcgtggtg acatgcgccg tgttcaacaa tgaggtggtg    660
gatctgcagt ggacctaccc tggcgaggtg aagggcaagg gcatcacaat gctggaggag    720
atcaaggtgc cttccatcaa gctggtgtac accctgacag tgccagaggc caccgtgaag    780
gatagcggcg actatgagtg tgctgctagg caggctacca gggaggtgaa ggagatgaag    840
aaggtgacaa tctccgtgca cgagaaggga gctagcccag ctgctccagc tccagctagc    900
cccgccgctc ctgctccatc tgctcctgct gcttccccag ctgctcccgc ccctgcttct    960
cctgctgctc cagctccatc cgccccagct gcttctcctg ccgctcctgc cccagcttcc   1020
ccagccgctc ccgccccttc cgctccagcc gcctctcccg ccgcccctgc tccagctagc   1080
ccagcagccc cagccccttc tgctccagcc gcctctccag ccgcccctgc tcccgcatcc   1140
cccgccgccc ccgccccttc cgcccctgcc gcctccccag ctgccccagc tcctgcctct   1200
cctgctgccc ctgctccatc cgctccagcc gccagtcccg ccgcccccgc tccagctagc   1260
ccagccgcac cagccccttc tgctcccgcc gcctctcccg ccgcacctgc tccagcatcc   1320
cccgccgccc cagccccttc cgcccctgca gcctccccag ctgcccccgc tcctgcctct   1380
cctgcagccc ctgctccttc cgctccagcc gcatctcccg ccgccccagc cccagctagc   1440
ccagcagcac cagccccctc tgctccagcc gccagccctg ccgcccctgc tcccgcttcc   1500
cccgccgccc cagcaccttc cgcccctgcc gcatccccag cagcccccgc tcctgccagc   1560
cctgctgccc ctgcaccttc cgctccagcc gcttctcccg ccgccccagc acccgctagc   1620
ccagctgccc ctgccccttc tgctccagca gcctctcctg ccgcccctgc tcctgcatcc   1680
cccgccgcac ccgccccttc cgcccccgcc gcctccccag ctgcaccagc tccagcctct   1740
ccagctgctc cagctccttc cgccccagct agcgataccg gccgcccttt tgtggagatg   1800
tacagcgaga tccccgagat catccacatg accgagggca gggagctggt catcccatgc   1860
cgggtgacat ctcccaacat caccgtgaca ctgaagaagt tccctctgga taccctgatc   1920
ccagacggca agagaatcat ctgggactct cgcaagggct ttatcatctc caatgccaca   1980
tataaggaga tcggcctgct gacctgcgag gctacagtga acggccacct gtacaagacc   2040
aattatctga cacataggca gaccaacaca atcatcgatg tggtgctgag cccatctcat   2100
ggcatcgagc tgagcgtggg cgagaagctg gtgctgaatt gtaccgcccg gacagagctg   2160
aacgtgggca tcgacttcaa ttgggagtac ccttccagca agcaccagca taagaagctg   2220
gtgaacagag atctgaagac ccagtccggc agcgagatga agaagtttct gagcaccctg   2280
acaatcgatg gcgtgacccg ctctgaccag ggcctgtata catgtgccgc ttcttccggc   2340
ctgatgacta agaaaaactc cacctttgtg cgggtccacg aaaaa                    2385
```

<210> SEQ ID NO 46
<211> LENGTH: 795
<212> TYPE: PRT
<213> ORGANISM: Artificial Sequence
<220> FEATURE:

<223> OTHER INFORMATION: Sequence of EPS1103P, excluding signal peptide
      and purification tag

<400> SEQUENCE: 46

```
Gln Leu Ser Leu Pro Ser Ile Leu Pro Asn Glu Asn Glu Lys Val Val
1               5                   10                  15

Gln Leu Asn Ser Ser Phe Ser Leu Arg Cys Phe Gly Glu Ser Glu Val
            20                  25                  30

Ser Trp Gln Tyr Pro Met Ser Glu Glu Glu Ser Ser Asp Val Glu Ile
        35                  40                  45

Arg Asn Glu Glu Asn Asn Ser Gly Leu Phe Val Thr Val Leu Glu Val
    50                  55                  60

Ser Ser Ala Ser Ala Ala His Thr Gly Leu Tyr Thr Cys Tyr Tyr Asn
65                  70                  75                  80

His Thr Gln Thr Glu Glu Asn Glu Leu Glu Gly Arg His Ile Tyr Ile
                85                  90                  95

Tyr Val Pro Asp Pro Asp Val Ala Phe Val Pro Leu Gly Met Thr Asp
            100                 105                 110

Tyr Leu Val Ile Val Glu Asp Asp Asp Ser Ala Ile Ile Pro Cys Arg
        115                 120                 125

Thr Thr Asp Pro Glu Thr Pro Val Thr Leu His Asn Ser Glu Gly Val
    130                 135                 140

Val Pro Ala Ser Tyr Asp Ser Arg Gln Gly Phe Asn Gly Thr Phe Thr
145                 150                 155                 160

Val Gly Pro Tyr Ile Cys Glu Ala Thr Val Lys Gly Lys Lys Phe Gln
                165                 170                 175

Thr Ile Pro Phe Asn Val Tyr Ala Leu Lys Ala Thr Ser Glu Leu Asp
            180                 185                 190

Leu Glu Met Glu Ala Leu Lys Thr Val Tyr Lys Ser Gly Glu Thr Ile
        195                 200                 205

Val Val Thr Cys Ala Val Phe Asn Asn Glu Val Val Asp Leu Gln Trp
    210                 215                 220

Thr Tyr Pro Gly Glu Val Lys Gly Lys Gly Ile Thr Met Leu Glu Glu
225                 230                 235                 240

Ile Lys Val Pro Ser Ile Lys Leu Val Tyr Thr Leu Thr Val Pro Glu
                245                 250                 255

Ala Thr Val Lys Asp Ser Gly Asp Tyr Glu Cys Ala Ala Arg Gln Ala
            260                 265                 270

Thr Arg Glu Val Lys Glu Met Lys Lys Val Thr Ile Ser Val His Glu
        275                 280                 285

Lys Gly Ala Ser Pro Ala Ala Pro Ala Pro Ala Ser Pro Ala Ala Pro
    290                 295                 300

Ala Pro Ser Ala Pro Ala Ala Ser Pro Ala Ala Pro Ala Pro Ala Ser
305                 310                 315                 320

Pro Ala Ala Pro Ala Pro Ser Ala Pro Ala Ala Ser Pro Ala Ala Pro
                325                 330                 335

Ala Pro Ala Ser Pro Ala Ala Pro Ala Pro Ser Ala Pro Ala Ala Ser
            340                 345                 350

Pro Ala Ala Pro Ala Pro Ala Ser Pro Ala Ala Pro Ala Pro Ser Ala
        355                 360                 365

Pro Ala Ala Ser Pro Ala Ala Pro Ala Pro Ala Ser Pro Ala Ala Pro
    370                 375                 380

Ala Pro Ser Ala Pro Ala Ala Ser Pro Ala Ala Pro Ala Pro Ala Ser
385                 390                 395                 400
```

```
Pro Ala Ala Pro Ala Pro Ser Ala Pro Ala Ala Ser Pro Ala Ala Pro
                405                 410                 415

Ala Pro Ala Ser Pro Ala Ala Pro Ala Pro Ser Ala Pro Ala Ala Ser
            420                 425                 430

Pro Ala Ala Pro Ala Pro Ala Ser Pro Ala Ala Pro Ala Pro Ser Ala
        435                 440                 445

Pro Ala Ala Ser Pro Ala Ala Pro Ala Pro Ala Ser Pro Ala Ala Pro
    450                 455                 460

Ala Pro Ser Ala Pro Ala Ala Ser Pro Ala Ala Pro Ala Pro Ala Ser
465                 470                 475                 480

Pro Ala Ala Pro Ala Pro Ser Ala Pro Ala Ala Ser Pro Ala Ala Pro
                485                 490                 495

Ala Pro Ala Ser Pro Ala Ala Pro Ala Pro Ser Ala Pro Ala Ala Ser
            500                 505                 510

Pro Ala Ala Pro Ala Pro Ala Ser Pro Ala Ala Pro Ala Pro Ser Ala
        515                 520                 525

Pro Ala Ala Ser Pro Ala Ala Pro Ala Pro Ala Ser Pro Ala Ala Pro
    530                 535                 540

Ala Pro Ser Ala Pro Ala Ala Ser Pro Ala Ala Pro Ala Pro Ala Ser
545                 550                 555                 560

Pro Ala Ala Pro Ala Pro Ser Ala Pro Ala Ala Ser Pro Ala Ala Pro
                565                 570                 575

Ala Pro Ala Ser Pro Ala Ala Pro Ala Pro Ser Ala Pro Ala Ser Asp
            580                 585                 590

Thr Gly Arg Pro Phe Val Glu Met Tyr Ser Glu Ile Pro Glu Ile Ile
        595                 600                 605

His Met Thr Glu Gly Arg Glu Leu Val Ile Pro Cys Arg Val Thr Ser
    610                 615                 620

Pro Asn Ile Thr Val Thr Leu Lys Lys Phe Pro Leu Asp Thr Leu Ile
625                 630                 635                 640

Pro Asp Gly Lys Arg Ile Ile Trp Asp Ser Arg Lys Gly Phe Ile Ile
                645                 650                 655

Ser Asn Ala Thr Tyr Lys Glu Ile Gly Leu Leu Thr Cys Glu Ala Thr
            660                 665                 670

Val Asn Gly His Leu Tyr Lys Thr Asn Tyr Leu Thr His Arg Gln Thr
        675                 680                 685

Asn Thr Ile Ile Asp Val Val Leu Ser Pro Ser His Gly Ile Glu Leu
    690                 695                 700

Ser Val Gly Glu Lys Leu Val Leu Asn Cys Thr Ala Arg Thr Glu Leu
705                 710                 715                 720

Asn Val Gly Ile Asp Phe Asn Trp Glu Tyr Pro Ser Ser Lys His Gln
                725                 730                 735

His Lys Lys Leu Val Asn Arg Asp Leu Lys Thr Gln Ser Gly Ser Glu
            740                 745                 750

Met Lys Lys Phe Leu Ser Thr Leu Thr Ile Asp Gly Val Thr Arg Ser
        755                 760                 765

Asp Gln Gly Leu Tyr Thr Cys Ala Ala Ser Ser Gly Leu Met Thr Lys
    770                 775                 780

Lys Asn Ser Thr Phe Val Arg Val His Glu Lys
785                 790                 795
```

<210> SEQ ID NO 47
<211> LENGTH: 2685

```
<212> TYPE: DNA
<213> ORGANISM: Artificial Sequence
<220> FEATURE:
<223> OTHER INFORMATION: Sequence encoding EPS1104P, excluding signal
      peptide and purification tag

<400> SEQUENCE: 47

cagctgagcc tgccctccat cctgcctaac gagaatgaga aggtggtgca gctgaactcc     60

agcttctccc tgagatgctt tggcgagtct gaggtgtcct ggcagtaccc aatgagcgag    120

gaggagtctt ccgacgtgga gatccgcaat gaggagaaca attctggcct gttcgtgacc    180

gtgctggagg tgagctctgc ctccgccgct cacaccggcc tgtacacatg ttactataac    240

catacccaga cagaggagaa tgagctggag ggcagacaca tctacatcta tgtgcccgat    300

cctgacgtgg cctttgtgcc actgggcatg accgattacc tggtcatcgt ggaggacgat    360

gacagcgcca tcatcccctg caggaccaca gaccccgaga cacctgtgac actgcataac    420

tctgagggcg tggtgccagc cagctacgat tctcggcagg gcttcaatgg cacctttaca    480

gtgggcccct atatctgtga ggccaccgtg aagggcaaga agttccagac aatccctttt    540

aacgtgtacg ccctgaaggc taccagcgag ctggacctgg agatggaggc cctgaagaca    600

gtgtataagt ctggcgagac aatcgtggtg acatgcgccg tgttcaacaa tgaggtggtg    660

gatctgcagt ggacctaccc cggcgaggtg aagggcaagg gcatcacaat gctggaggag    720

atcaaggtgc cttctatcaa gctggtgtac accctgacag tgccagaggc caccgtgaag    780

gattccggcg actatgagtg tgccgctagg caggctaccc gggaggtgaa ggagatgaag    840

aaggtgacaa tctctgtgca cgagaaggga gcttccccag ctgctccagc tccagcttcc    900

cccgccgctc ctgccccatc tgctccagct gcctctccag ctgctccagc tcctgctagc    960

cctgccgctc cagccccctc cgcccctgcc gcttctccag ccgctcctgc cccagctagc   1020

cctgctgctc cagctccttc cgctccagcc gcctctccag ccgctccagc ccccgcctct   1080

cctgctgccc cagctccttc tgctccagct gccagccccg ccgcccctgc ccccgcctct   1140

cccgctgccc ctgctccttc cgccccagct gcctcccctg ctgctcctgc cccagcttca   1200

cctgccgccc ctgccccttc cgctccagcc gcatctcccg ccgctccagc ccccgcaagc   1260

cctgcagccc cagctccctc tgctccagct gcctcacccg ccgcccctgc ccctgcctct   1320

cccgctgccc ccgctccttc cgccccagca gcctcccctg cagctcctgc cccagcttct   1380

ccagccgctc ccgccccttc cgctcccgcc gcctctcctg ctgcaccagc cccegcttcc   1440

ccagctgctc ctgctccatc cgccccagct gcttccccag ctgctccagc tccagcttcc   1500

cccgccgctc ctgccccatc tgctccagct gcctctccag ctgctccagc tcctgctagc   1560

cctgccgctc cagccccctc cgcccctgcc gcttctccag ccgctcctgc cccagctagc   1620

cctgctgctc cagctccttc cgctccagcc gcctctccag ccgctccagc ccccgcctct   1680

cctgctgccc cagctccttc tgctccagct gccagccccg ccgcccctgc ccccgcctct   1740

cccgctgccc ctgctccttc cgccccagct gcctcccctg ctgctcctgc cccagcttca   1800

cctgccgccc ctgccccttc cgctccagcc gcatctcccg ccgctccagc ccccgcaagc   1860

cctgcagccc cagctccctc tgctccagct gcctcacccg ccgcccctgc ccctgcctct   1920

cccgctgccc ccgctccttc cgccccagca gcctcccctg cagctcctgc cccagcttct   1980

ccagccgctc ccgccccttc cgctcccgcc gcctctcctg ctgcaccagc ccccgcttcc   2040

ccagctgctc ctgctccatc cgccccagct agcgataccg gccgcccttt tgtggagatg   2100

tacagcgaga tccctgagat catccacatg accgagggca gggagctggt catcccatgc   2160
```

```
cgggtgacat ctcccaacat caccgtgaca ctgaagaagt tccctctgga taccctgatc   2220

ccagacggca agagaatcat ctgggacagc cgcaagggct ttatcatctc taatgccaca   2280

tataaggaga tcggcctgct gacctgcgag gctacagtga acggccacct gtacaagacc   2340

aattatctga cacataggca gaccaacaca atcatcgatg tggtgctgag cccctctcat   2400

ggcatcgagc tgtccgtggg cgagaagctg gtgctgaatt gtaccgcccg gacagagctg   2460

aacgtgggca tcgacttcaa ttgggagtac ccttccagca agcaccagca taagaagctg   2520

gtgaacagag atctgaagac ccagtccggc agcgagatga agaagtttct gtccaccctg   2580

acaatcgatg gagtgacccg cagcgaccag ggcctgtata catgtgccgc ttcttccggc   2640

ctgatgacta agaaaaatag cacctttgtg agggtccacg aaaaa                   2685
```

<210> SEQ ID NO 48
<211> LENGTH: 895
<212> TYPE: PRT
<213> ORGANISM: Artificial Sequence
<220> FEATURE:
<223> OTHER INFORMATION: Sequence of EPS1104P, excluding signal peptide and purification tag

<400> SEQUENCE: 48

```
Gln Leu Ser Leu Pro Ser Ile Leu Pro Asn Glu Asn Glu Lys Val Val
1               5                   10                  15

Gln Leu Asn Ser Ser Phe Ser Leu Arg Cys Phe Gly Glu Ser Glu Val
            20                  25                  30

Ser Trp Gln Tyr Pro Met Ser Glu Glu Glu Ser Ser Asp Val Glu Ile
        35                  40                  45

Arg Asn Glu Glu Asn Asn Ser Gly Leu Phe Val Thr Val Leu Glu Val
    50                  55                  60

Ser Ser Ala Ser Ala Ala His Thr Gly Leu Tyr Thr Cys Tyr Tyr Asn
65                  70                  75                  80

His Thr Gln Thr Glu Glu Asn Glu Leu Glu Gly Arg His Ile Tyr Ile
                85                  90                  95

Tyr Val Pro Asp Pro Asp Val Ala Phe Val Pro Leu Gly Met Thr Asp
            100                 105                 110

Tyr Leu Val Ile Val Glu Asp Asp Asp Ser Ala Ile Ile Pro Cys Arg
        115                 120                 125

Thr Thr Asp Pro Glu Thr Pro Val Thr Leu His Asn Ser Glu Gly Val
    130                 135                 140

Val Pro Ala Ser Tyr Asp Ser Arg Gln Gly Phe Asn Gly Thr Phe Thr
145                 150                 155                 160

Val Gly Pro Tyr Ile Cys Glu Ala Thr Val Lys Gly Lys Lys Phe Gln
                165                 170                 175

Thr Ile Pro Phe Asn Val Tyr Ala Leu Lys Ala Thr Ser Glu Leu Asp
            180                 185                 190

Leu Glu Met Glu Ala Leu Lys Thr Val Tyr Lys Ser Gly Glu Thr Ile
        195                 200                 205

Val Val Thr Cys Ala Val Phe Asn Asn Glu Val Val Asp Leu Gln Trp
    210                 215                 220

Thr Tyr Pro Gly Glu Val Lys Gly Lys Gly Ile Thr Met Leu Glu Glu
225                 230                 235                 240

Ile Lys Val Pro Ser Ile Lys Leu Val Tyr Thr Leu Thr Val Pro Glu
                245                 250                 255

Ala Thr Val Lys Asp Ser Gly Asp Tyr Glu Cys Ala Ala Arg Gln Ala
```

-continued

```
            260                 265                 270

Thr Arg Glu Val Lys Glu Met Lys Lys Val Thr Ile Ser Val His Glu
        275                 280                 285

Lys Gly Ala Ser Pro Ala Ala Pro Ala Pro Ala Ser Pro Ala Ala Pro
    290                 295                 300

Ala Pro Ser Ala Pro Ala Ala Ser Pro Ala Ala Pro Ala Pro Ala Ser
305                 310                 315                 320

Pro Ala Ala Pro Ala Pro Ser Ala Pro Ala Ala Ser Pro Ala Ala Pro
                325                 330                 335

Ala Pro Ala Ser Pro Ala Ala Pro Ala Pro Ser Ala Pro Ala Ala Ser
            340                 345                 350

Pro Ala Ala Pro Ala Pro Ala Ser Pro Ala Ala Pro Ala Pro Ser Ala
        355                 360                 365

Pro Ala Ala Ser Pro Ala Ala Pro Ala Pro Ala Ser Pro Ala Ala Pro
    370                 375                 380

Ala Pro Ser Ala Pro Ala Ala Ser Pro Ala Ala Pro Ala Pro Ala Ser
385                 390                 395                 400

Pro Ala Ala Pro Ala Pro Ser Ala Pro Ala Ala Ser Pro Ala Ala Pro
                405                 410                 415

Ala Pro Ala Ser Pro Ala Ala Pro Ala Pro Ser Ala Pro Ala Ala Ser
            420                 425                 430

Pro Ala Ala Pro Ala Pro Ala Ser Pro Ala Ala Pro Ala Pro Ser Ala
        435                 440                 445

Pro Ala Ala Ser Pro Ala Ala Pro Ala Pro Ala Ser Pro Ala Ala Pro
    450                 455                 460

Ala Pro Ser Ala Pro Ala Ala Ser Pro Ala Ala Pro Ala Pro Ala Ser
465                 470                 475                 480

Pro Ala Ala Pro Ala Pro Ser Ala Pro Ala Ala Ser Pro Ala Ala Pro
                485                 490                 495

Ala Pro Ala Ser Pro Ala Ala Pro Ala Pro Ser Ala Pro Ala Ala Ser
            500                 505                 510

Pro Ala Ala Pro Ala Pro Ala Ser Pro Ala Ala Pro Ala Pro Ser Ala
        515                 520                 525

Pro Ala Ala Ser Pro Ala Ala Pro Ala Pro Ala Ser Pro Ala Ala Pro
    530                 535                 540

Ala Pro Ser Ala Pro Ala Ala Ser Pro Ala Ala Pro Ala Pro Ala Ser
545                 550                 555                 560

Pro Ala Ala Pro Ala Pro Ser Ala Pro Ala Ala Ser Pro Ala Ala Pro
                565                 570                 575

Ala Pro Ala Ser Pro Ala Ala Pro Ala Pro Ser Ala Pro Ala Ala Ser
            580                 585                 590

Pro Ala Ala Pro Ala Pro Ala Ser Pro Ala Ala Pro Ala Pro Ser Ala
        595                 600                 605

Pro Ala Ala Ser Pro Ala Ala Pro Ala Pro Ala Ser Pro Ala Ala Pro
    610                 615                 620

Ala Pro Ser Ala Pro Ala Ala Ser Pro Ala Ala Pro Ala Pro Ala Ser
625                 630                 635                 640

Pro Ala Ala Pro Ala Pro Ser Ala Pro Ala Ala Ser Pro Ala Ala Pro
                645                 650                 655

Ala Pro Ala Ser Pro Ala Ala Pro Ala Pro Ser Ala Pro Ala Ala Ser
            660                 665                 670

Pro Ala Ala Pro Ala Pro Ala Ser Pro Ala Ala Pro Ala Pro Ser Ala
        675                 680                 685
```

```
Pro Ala Ser Asp Thr Gly Arg Pro Phe Val Glu Met Tyr Ser Glu Ile
    690                 695                 700

Pro Glu Ile Ile His Met Thr Glu Gly Arg Glu Leu Val Ile Pro Cys
705                 710                 715                 720

Arg Val Thr Ser Pro Asn Ile Thr Val Thr Leu Lys Lys Phe Pro Leu
                725                 730                 735

Asp Thr Leu Ile Pro Asp Gly Lys Arg Ile Ile Trp Asp Ser Arg Lys
            740                 745                 750

Gly Phe Ile Ile Ser Asn Ala Thr Tyr Lys Glu Ile Gly Leu Leu Thr
        755                 760                 765

Cys Glu Ala Thr Val Asn Gly His Leu Tyr Lys Thr Asn Tyr Leu Thr
    770                 775                 780

His Arg Gln Thr Asn Thr Ile Ile Asp Val Val Leu Ser Pro Ser His
785                 790                 795                 800

Gly Ile Glu Leu Ser Val Gly Glu Lys Leu Val Leu Asn Cys Thr Ala
                805                 810                 815

Arg Thr Glu Leu Asn Val Gly Ile Asp Phe Asn Trp Glu Tyr Pro Ser
            820                 825                 830

Ser Lys His Gln His Lys Lys Leu Val Asn Arg Asp Leu Lys Thr Gln
        835                 840                 845

Ser Gly Ser Glu Met Lys Lys Phe Leu Ser Thr Leu Thr Ile Asp Gly
    850                 855                 860

Val Thr Arg Ser Asp Gln Gly Leu Tyr Thr Cys Ala Ala Ser Ser Gly
865                 870                 875                 880

Leu Met Thr Lys Lys Asn Ser Thr Phe Val Arg Val His Glu Lys
                885                 890                 895
```

```
<210> SEQ ID NO 49
<211> LENGTH: 2085
<212> TYPE: DNA
<213> ORGANISM: Artificial Sequence
<220> FEATURE:
<223> OTHER INFORMATION: Sequence encoding EPS1105P, excluding signal
      peptide and purification tag

<400> SEQUENCE: 49

agcgataccg gccgcccctt cgtggagatg tacagcgaga tccctgagat catccacatg      60

accgagggca gggagctggt catcccttgc cgggtgacat ctccaaacat caccgtgaca     120

ctgaagaagt tcccccctgga taccctgatc cctgacggca agagaatcat ctgggactct     180

cgcaagggct ttatcatctc caatgccacc tataaggaga tcggcctgct gacctgcgag     240

gctacagtga acggccacct gtacaagacc aattatctga cacatcggca gaccaacaca     300

atcatcgatg tggtgctgag cccttctcat ggcatcgagc tgtccgtggg cgagaagctg     360

gtgctgaatt gtaccgccag aacagagctg aacgtgggca tcgatttcaa ttgggagtac     420

ccatccagca agcaccagca taagaagctg gtgaacaggg acctgaagac ccagtccggc     480

agcgagatga agaagtttct gtctaccctg acaatcgatg gagtgacccg ctccgaccag     540

ggcctgtata catgtgccgc ttcttccggc ctgatgacca agaagaatag cacatttgtg     600

agggtgcacg agaaggcctc cccagctgct ccagctcctg ctagcccagc cgctccagcc     660

ccctctgctc cagccgcttc ccccgccgct cctgccccag cttctccagc cgctcccgcc     720

ccttccgccc ctgccgcttc tcctgctgct ccagcccctg cctctcctgc cgctcctgcc     780

ccatccgctc ccgccgctag ccctgccgct cccgcccctg ctagccctgc tgcccctgct     840
```

```
ccttctgctc ctgctgcctc tccagctgcc ccagctcctg cctcccctgc tgcccctgca    900
ccatccgccc cagccgcttc tcctgcagct ccagcccctg ccagccctgc tgccccagct    960
ccttccgctc ctgctgccag tccagctgcc cctgctcctg ctagccctgc tgcacctgct   1020
ccttctgctc ccgctgcctc tccagctgca ccagctcctg cctcccccgc tgcccctgct   1080
ccatccgccc ccgccgcttc tcctgccgcc ccagcccctg cctctccagc tgctccagct   1140
ccctccgctc ctgctgccag cccagctgcc cctgcacctg ctagccctgc tgctcctgcc   1200
ccctctgccc cagctcagct gtctctgcca tccatcctgc ccaacgagaa tgagaaggtg   1260
gtgcagctga acagctcttt ctctctgcgg tgctttggcg agagcgaggt gtcttggcag   1320
taccccatgt ccgaggagga gtccagcgac gtggagatca gaaatgagga gaacaatagc   1380
ggcctgttcg tgaccgtgct ggaggtgtct tccgcctctg ccgctcacac cggcctgtac   1440
acatgttact ataaccatac ccagacagag gagaatgagc tggagggccg gcacatctac   1500
atctatgtgc ctgatccaga cgtggccttt gtgcccctgg gcatgaccga ttacctggtc   1560
atcgtggagg acgatgactc cgccatcatc ccttgccgca ccacagaccc cgagacacct   1620
gtgacactgc ataacagcga gggagtggtg ccagcttcct acgatagcag gcagggcttc   1680
aatggcacct ttacagtggg cccttatatc tgtgaggcca ccgtgaaggg caagaagttc   1740
cagacaatcc ccttcaacgt gtacgccctg aaggctacct ccgagctgga cctggagatg   1800
gaggccctga agacagtgta taagagcggc gagacaatcg tggtgacatg cgccgtgttc   1860
aacaatgagg tggtggatct gcagtggacc taccctggcg aggtgaaggg caagggcatc   1920
acaatgctgg aggagatcaa ggtgccaagc atcaagctgg tgtacaccct gacagtgccc   1980
gaggccaccg tgaaggattc tggcgactat gagtgtgccg ctaggcaggc tacacgggag   2040
gtgaaagaaa tgaagaaggt cacaatcagc gtccacgaaa agggg                   2085
```

```
<210> SEQ ID NO 50
<211> LENGTH: 695
<212> TYPE: PRT
<213> ORGANISM: Artificial Sequence
<220> FEATURE:
<223> OTHER INFORMATION: Sequence of EPS1105P, excluding signal peptide
      and purification tag

<400> SEQUENCE: 50

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140
```

-continued

```
His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Ala Ser Pro
        195                 200                 205

Ala Ala Pro Ala Pro Ala Ser Pro Ala Ala Pro Ala Pro Ser Ala Pro
    210                 215                 220

Ala Ala Ser Pro Ala Ala Pro Ala Pro Ala Ser Pro Ala Ala Pro Ala
225                 230                 235                 240

Pro Ser Ala Pro Ala Ala Ser Pro Ala Ala Pro Ala Pro Ala Ser Pro
                245                 250                 255

Ala Ala Pro Ala Pro Ser Ala Pro Ala Ala Ser Pro Ala Ala Pro Ala
            260                 265                 270

Pro Ala Ser Pro Ala Ala Pro Ala Pro Ser Ala Pro Ala Ala Ser Pro
        275                 280                 285

Ala Ala Pro Ala Pro Ala Ser Pro Ala Ala Pro Ala Pro Ser Ala Pro
    290                 295                 300

Ala Ala Ser Pro Ala Ala Pro Ala Pro Ala Ser Pro Ala Ala Pro Ala
305                 310                 315                 320

Pro Ser Ala Pro Ala Ala Ser Pro Ala Ala Pro Ala Pro Ala Ser Pro
                325                 330                 335

Ala Ala Pro Ala Pro Ser Ala Pro Ala Ala Ser Pro Ala Ala Pro Ala
            340                 345                 350

Pro Ala Ser Pro Ala Ala Pro Ala Pro Ser Ala Pro Ala Ala Ser Pro
        355                 360                 365

Ala Ala Pro Ala Pro Ala Ser Pro Ala Ala Pro Ala Pro Ser Ala Pro
    370                 375                 380

Ala Ala Ser Pro Ala Ala Pro Ala Pro Ala Ser Pro Ala Ala Pro Ala
385                 390                 395                 400

Pro Ser Ala Pro Ala Gln Leu Ser Leu Pro Ser Ile Leu Pro Asn Glu
                405                 410                 415

Asn Glu Lys Val Val Gln Leu Asn Ser Ser Phe Ser Leu Arg Cys Phe
            420                 425                 430

Gly Glu Ser Glu Val Ser Trp Gln Tyr Pro Met Ser Glu Glu Glu Ser
        435                 440                 445

Ser Asp Val Glu Ile Arg Asn Glu Glu Asn Asn Ser Gly Leu Phe Val
    450                 455                 460

Thr Val Leu Glu Val Ser Ser Ala Ser Ala Ala His Thr Gly Leu Tyr
465                 470                 475                 480

Thr Cys Tyr Tyr Asn His Thr Gln Thr Glu Glu Asn Glu Leu Glu Gly
                485                 490                 495

Arg His Ile Tyr Ile Tyr Val Pro Asp Pro Asp Val Ala Phe Val Pro
            500                 505                 510

Leu Gly Met Thr Asp Tyr Leu Val Ile Val Glu Asp Asp Asp Ser Ala
        515                 520                 525

Ile Ile Pro Cys Arg Thr Thr Asp Pro Glu Thr Pro Val Thr Leu His
    530                 535                 540

Asn Ser Glu Gly Val Val Pro Ala Ser Tyr Asp Ser Arg Gln Gly Phe
545                 550                 555                 560
```

-continued

```
Asn Gly Thr Phe Thr Val Gly Pro Tyr Ile Cys Glu Ala Thr Val Lys
                565                 570                 575

Gly Lys Lys Phe Gln Thr Ile Pro Phe Asn Val Tyr Ala Leu Lys Ala
            580                 585                 590

Thr Ser Glu Leu Asp Leu Glu Met Glu Ala Leu Lys Thr Val Tyr Lys
        595                 600                 605

Ser Gly Glu Thr Ile Val Val Thr Cys Ala Val Phe Asn Asn Glu Val
    610                 615                 620

Val Asp Leu Gln Trp Thr Tyr Pro Gly Glu Val Lys Gly Lys Gly Ile
625                 630                 635                 640

Thr Met Leu Glu Glu Ile Lys Val Pro Ser Ile Lys Leu Val Tyr Thr
                645                 650                 655

Leu Thr Val Pro Glu Ala Thr Val Lys Asp Ser Gly Asp Tyr Glu Cys
            660                 665                 670

Ala Ala Arg Gln Ala Thr Arg Glu Val Lys Glu Met Lys Lys Val Thr
        675                 680                 685

Ile Ser Val His Glu Lys Gly
    690                 695
```

<210> SEQ ID NO 51
<211> LENGTH: 2175
<212> TYPE: DNA
<213> ORGANISM: Artificial Sequence
<220> FEATURE:
<223> OTHER INFORMATION: Sequence encoding EPS1106P, excluding signal
      peptide and purification tag

<400> SEQUENCE: 51

```
cagctgtccc tgccttccat cctgcctaac gagaacgaga aggtggtgca gctgaactcc      60

tccttctctc tgcggtgctt cggcgagtcc gaagtgtctt ggcagtaccc catgtccgaa     120

gaggaatcct ccgacgtgga aatccggaac gaggaaaaca actccggcct gttcgtgacc     180

gtgctggaag tgtcctctgc ctctgctgct cacaccggac tgtacacctg ttactacaat     240

cacacccaga ccgaagagaa cgagctggaa ggccggcaca tctacatcta cgtgcccgat     300

cctgacgtgg cctttgtgcc tctgggcatg accgactacc tggtcatcgt ggaagatgac     360

gactccgcta tcatcccctg ccggaccaca gatcctgaga cacctgtgac actgcacaac     420

tccgaaggcg tggtgcctgc ctcctacgat tctagacagg gcttcaacgg caccttcacc     480

gtgggacctt acatctgcga ggctaccgtg aagggcaaga agttccagac aatccccttc     540

aacgtgtacg ccctgaaggc cacctctgag ctggacctgg aaatggaagc cctgaaaacc     600

gtgtacaaga gcggcgagac aatcgtcgtg acctgcgccg tgttcaacaa cgaggtggtg     660

gacctgcagt ggacctatcc tggcgaagtg aaaggcaagg gcatcaccat gctggaagag     720

atcaaggtgc cctccatcaa gctggtgtat accctgaccg tgcctgaggc cacagtgaag     780

gactctggcg actacgagtg tgccgctaga caggccacca gagaagtcaa agagatgaag     840

aaagtcacca tctccgtgca cgagaaaggc ggcggaggcg gaagcggtgg cggaggaagc     900

ggaggcggcg gatctgcttc tcctgctgct ccagctccag cttctccagc agctcctgca     960

ccttctgcac cagctgcaag tcctgcagca cccgcaccag ctagtcctgc cgctcctgct    1020

cctagtgctc ctgccgcaag tccagctgct cccgctcctg catcaccagc cgcaccagca    1080

ccaagtgctc cagctgcctc tccagcagca ccagctccag caagccctgc tgcaccagca    1140

ccttcagctc cagcagcatc acccgctgca cccgctccag catctcccgc tgctccagca    1200

ccaagcgcac ccgctgctag cccagccgct ccagctcctg ccagtcctgc tgctcctgca    1260
```

```
ccatctgctc ccgcagcttc accagctgct cccgcaccag ctagcccagc agcaccagca   1320

ccatctgcac ccgccgcatc tcccgccgca ccagctccag ctagtcccgc agctcccgct   1380

ccatctgctc cagccgctag tcccgctgct cctgctccag ctagtcctgc tgcacccgct   1440

cctagcgcac cagctgcttc acccgcagct ccagctccag cttcacccgc tgcaccagct   1500

ccatctgctc cagctggtgg cggaggatct ggcggaggcg gatctggcgg cggtggttct   1560

tctgataccg gcagaccctt cgtggaaatg tacagcgaga tccccgagat catccacatg   1620

accgagggca gagagctggt catcccttgc agagtgacct ctcctaacat cacagtgacc   1680

ctgaagaagt ttcccctgga cacactgatc cccgacggca agagaatcat ctgggactcc   1740

cggaagggct tcatcatctc caacgccacc tacaaagaga tcggactgct gacctgcgaa   1800

gccactgtga acggccacct gtacaagacc aactatctga cccacagaca gaccaacacc   1860

atcatcgacg tggtgctgag cccctctcat ggcatcgagc tgtccgtggg agagaaactg   1920

gtgctgaact gcaccgccag aaccgagctg aacgtgggca tcgacttcaa ctgggagtac   1980

cccagctcca aacaccagca caagaagctg gtcaaccggg atctgaaaac ccagtccggc   2040

tccgaaatga agaaattcct gagcaccctg accatcgacg gcgtgaccag atctgaccag   2100

ggcctgtata cctgtgccgc ctcttctggc ctgatgacca agaaaaactc caccttcgtg   2160

cgggtccacg agaag                                                    2175
```

```
<210> SEQ ID NO 52
<211> LENGTH: 725
<212> TYPE: PRT
<213> ORGANISM: Artificial Sequence
<220> FEATURE:
<223> OTHER INFORMATION: Sequence of EPS1106P, excluding signal peptide
      and purification tag

<400> SEQUENCE: 52

Gln Leu Ser Leu Pro Ser Ile Leu Pro Asn Glu Asn Glu Lys Val Val
1               5                   10                  15

Gln Leu Asn Ser Ser Phe Ser Leu Arg Cys Phe Gly Glu Ser Glu Val
            20                  25                  30

Ser Trp Gln Tyr Pro Met Ser Glu Glu Glu Ser Ser Asp Val Glu Ile
        35                  40                  45

Arg Asn Glu Glu Asn Asn Ser Gly Leu Phe Val Thr Val Leu Glu Val
    50                  55                  60

Ser Ser Ala Ser Ala Ala His Thr Gly Leu Tyr Thr Cys Tyr Tyr Asn
65                  70                  75                  80

His Thr Gln Thr Glu Glu Asn Glu Leu Glu Gly Arg His Ile Tyr Ile
                85                  90                  95

Tyr Val Pro Asp Pro Asp Val Ala Phe Val Pro Leu Gly Met Thr Asp
            100                 105                 110

Tyr Leu Val Ile Val Glu Asp Asp Asp Ser Ala Ile Ile Pro Cys Arg
        115                 120                 125

Thr Thr Asp Pro Glu Thr Pro Val Thr Leu His Asn Ser Glu Gly Val
    130                 135                 140

Val Pro Ala Ser Tyr Asp Ser Arg Gln Gly Phe Asn Gly Thr Phe Thr
145                 150                 155                 160

Val Gly Pro Tyr Ile Cys Glu Ala Thr Val Lys Gly Lys Lys Phe Gln
                165                 170                 175

Thr Ile Pro Phe Asn Val Tyr Ala Leu Lys Ala Thr Ser Glu Leu Asp
            180                 185                 190
```

-continued

```
Leu Glu Met Glu Ala Leu Lys Thr Val Tyr Lys Ser Gly Glu Thr Ile
        195                 200                 205

Val Val Thr Cys Ala Val Phe Asn Asn Glu Val Val Asp Leu Gln Trp
    210                 215                 220

Thr Tyr Pro Gly Glu Val Lys Gly Lys Gly Ile Thr Met Leu Glu Glu
225                 230                 235                 240

Ile Lys Val Pro Ser Ile Lys Leu Val Tyr Thr Leu Thr Val Pro Glu
                245                 250                 255

Ala Thr Val Lys Asp Ser Gly Asp Tyr Glu Cys Ala Ala Arg Gln Ala
            260                 265                 270

Thr Arg Glu Val Lys Glu Met Lys Lys Val Thr Ile Ser Val His Glu
        275                 280                 285

Lys Gly Gly Gly Gly Gly Ser Gly Gly Gly Gly Ser Gly Gly Gly Gly
    290                 295                 300

Ser Ala Ser Pro Ala Ala Pro Ala Pro Ala Ser Pro Ala Ala Pro Ala
305                 310                 315                 320

Pro Ser Ala Pro Ala Ala Ser Pro Ala Ala Pro Ala Pro Ala Ser Pro
                325                 330                 335

Ala Ala Pro Ala Pro Ser Ala Pro Ala Ala Ser Pro Ala Ala Pro Ala
            340                 345                 350

Pro Ala Ser Pro Ala Ala Pro Ala Pro Ser Ala Pro Ala Ala Ser Pro
        355                 360                 365

Ala Ala Pro Ala Pro Ala Ser Pro Ala Ala Pro Ala Pro Ser Ala Pro
    370                 375                 380

Ala Ala Ser Pro Ala Ala Pro Ala Pro Ala Ser Pro Ala Ala Pro Ala
385                 390                 395                 400

Pro Ser Ala Pro Ala Ala Ser Pro Ala Ala Pro Ala Pro Ala Ser Pro
                405                 410                 415

Ala Ala Pro Ala Pro Ser Ala Pro Ala Ala Ser Pro Ala Ala Pro Ala
            420                 425                 430

Pro Ala Ser Pro Ala Ala Pro Ala Pro Ser Ala Pro Ala Ala Ser Pro
        435                 440                 445

Ala Ala Pro Ala Pro Ala Ser Pro Ala Ala Pro Ala Pro Ser Ala Pro
    450                 455                 460

Ala Ala Ser Pro Ala Ala Pro Ala Pro Ala Ser Pro Ala Ala Pro Ala
465                 470                 475                 480

Pro Ser Ala Pro Ala Ala Ser Pro Ala Ala Pro Ala Pro Ala Ser Pro
                485                 490                 495

Ala Ala Pro Ala Pro Ser Ala Pro Ala Gly Gly Gly Gly Ser Gly Gly
            500                 505                 510

Gly Gly Ser Gly Gly Gly Gly Ser Ser Asp Thr Gly Arg Pro Phe Val
        515                 520                 525

Glu Met Tyr Ser Glu Ile Pro Glu Ile Ile His Met Thr Glu Gly Arg
    530                 535                 540

Glu Leu Val Ile Pro Cys Arg Val Thr Ser Pro Asn Ile Thr Val Thr
545                 550                 555                 560

Leu Lys Lys Phe Pro Leu Asp Thr Leu Ile Pro Asp Gly Lys Arg Ile
                565                 570                 575

Ile Trp Asp Ser Arg Lys Gly Phe Ile Ile Ser Asn Ala Thr Tyr Lys
            580                 585                 590

Glu Ile Gly Leu Leu Thr Cys Glu Ala Thr Val Asn Gly His Leu Tyr
        595                 600                 605
```

```
Lys Thr Asn Tyr Leu Thr His Arg Gln Thr Asn Thr Ile Ile Asp Val
    610                 615                 620

Val Leu Ser Pro Ser His Gly Ile Glu Leu Ser Val Gly Glu Lys Leu
625                 630                 635                 640

Val Leu Asn Cys Thr Ala Arg Thr Glu Leu Asn Val Gly Ile Asp Phe
                645                 650                 655

Asn Trp Glu Tyr Pro Ser Ser Lys His Gln His Lys Lys Leu Val Asn
            660                 665                 670

Arg Asp Leu Lys Thr Gln Ser Gly Ser Glu Met Lys Lys Phe Leu Ser
        675                 680                 685

Thr Leu Thr Ile Asp Gly Val Thr Arg Ser Asp Gln Gly Leu Tyr Thr
    690                 695                 700

Cys Ala Ala Ser Ser Gly Leu Met Thr Lys Lys Asn Ser Thr Phe Val
705                 710                 715                 720

Arg Val His Glu Lys
                725


<210> SEQ ID NO 53
<211> LENGTH: 2175
<212> TYPE: DNA
<213> ORGANISM: Artificial Sequence
<220> FEATURE:
<223> OTHER INFORMATION: Sequence encoding EPS1107P, excluding signal
      peptide and purification tag

<400> SEQUENCE: 53

tctgataccg gcagaccctt cgtggaaatg tacagcgaga tccccgagat catccacatg      60

accgagggca gagagctggt catcccctgc agagtgacct ctcctaacat caccgtgact     120

ctgaagaagt tccctctgga cacactgatc cccgacggca agagaatcat ctgggactcc     180

cggaagggct tcatcatctc caacgccacc tacaaagaga tcggcctgct gacctgcgag     240

gccaccgtta atggccacct gtacaagacc aactatctga cccacagaca gaccaacacc     300

atcatcgacg tggtgctgag cccctctcat ggcatcgagc tgtccgtggg agaaaagctg     360

gtgctgaact gcaccgccag aaccgagctg aacgtgggca tcgacttcaa ctgggagtac     420

ccctccagca agcaccagca caagaagctg gtcaaccggg acctgaaaac ccagtccggc     480

tccgagatga agaaattcct gagcaccctg accatcgacg gcgtgaccag atctgaccag     540

ggcctgtata cctgcgccgc ttcctctggc ctgatgacca agaaaaactc caccttcgtg     600

cgggtgcacg agaaaggtgg cggaggatct ggcggaggcg gctctggcgg cggtggatct     660

gcttctcctg ctgctccagc tccagcttct ccagcagctc ctgcaccttc tgcaccagct     720

gcaagtcctg cagcacccgc accagctagt cctgccgctc ctgctcctag tgctcctgcc     780

gcaagtccag ctgctcccgc tcctgcaagc ccagctgcac cagcaccaag tgctccagct     840

gcctcaccag ccgcaccagc tccagcaagc cctgcagctc ccgctccttc agctcctgct     900

gcttctcccg cagcacccgc tccagcatca ccagccgctc cagcaccatc agctccagca     960

gcatctcctg cagctccagc tcctgctagt cccgctgctc ccgcacctag tgcaccagcc    1020

gcttctcccg ccgctcctgc tcctgcatct cctgctgcac ccgctccatc tgctcccgcc    1080

gcatcacccg cagctcccgc accagcctct ccagctgcac cagctcctag cgcaccagca    1140

gctagcccag ctgctcctgc accagctagc cccgcagctc cagctccaag cgctcctgct    1200

gcatccccag ctgctccagc tcctgcctca ccagctgctc cagcaccttc tgctcccgct    1260

ggcggtggcg gaagcggagg tggtggtagt ggcggcggag gttctcagct gtccctgcct    1320
```

```
tctatcctgc ctaacgagaa cgagaaggtg gtccagctga actcctcctt ctctctgcgg   1380

tgcttcggcg agtccgaagt gtcttggcag taccccatgt ccgaagagga atcctccgac   1440

gtggaaatcc ggaacgagga aaacaactcc ggcctgttcg tgaccgtgct ggaagtgtcc   1500

tctgcctctg ctgctcacac cggcctgtac acatgctact acaatcacac ccagaccgaa   1560

gagaacgagc tggaaggccg gcacatctac atctacgtgc ccgatcctga cgtggccttt   1620

gtgcctctgg gcatgaccga ctacctggtc atcgtggaag atgacgactc cgctatcatc   1680

ccttgccgga ccaccgatcc agagacacct gtgacactgc acaactccga aggcgtggtg   1740

cctgcctcct acgattctag acagggcttc aacggcacct tcaccgtggg accttacatc   1800

tgcgaggcta cagtgaaggg caagaagttt cagacaatcc ccttcaacgt gtacgccctg   1860

aaggccacct ctgagctgga cctggaaatg gaagctctga aaaccgtgta caagtccggc   1920

gagacaatcg tcgtgacctg tgccgtgttc aacaacgaag tggtggacct gcagtggacc   1980

tatcctggcg aagtgaaagg caagggcatc accatgctgg aagagatcaa ggtgccctcc   2040

atcaagctgg tgtataccct gaccgtgcct gaggccactg tgaaggactc tggcgactac   2100

gagtgtgccg ctagacaggc caccagagaa gtcaaagaaa tgaagaaagt gaccatctcc   2160

gtccacgaga agggc                                                    2175
```

```
<210> SEQ ID NO 54
<211> LENGTH: 725
<212> TYPE: PRT
<213> ORGANISM: Artificial Sequence
<220> FEATURE:
<223> OTHER INFORMATION: Sequence of EPS1107P, excluding signal peptide
      and purification tag

<400> SEQUENCE: 54

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Gly Gly Gly
        195                 200                 205
```

```
Gly Ser Gly Gly Gly Gly Ser Gly Gly Gly Gly Ser Ala Ser Pro Ala
    210                 215                 220

Ala Pro Ala Pro Ala Ser Pro Ala Ala Pro Ala Pro Ser Ala Pro Ala
225                 230                 235                 240

Ala Ser Pro Ala Ala Pro Ala Pro Ala Ser Pro Ala Ala Pro Ala Pro
                245                 250                 255

Ser Ala Pro Ala Ala Ser Pro Ala Ala Pro Ala Pro Ala Ser Pro Ala
            260                 265                 270

Ala Pro Ala Pro Ser Ala Pro Ala Ala Ser Pro Ala Ala Pro Ala Pro
        275                 280                 285

Ala Ser Pro Ala Ala Pro Ala Pro Ser Ala Pro Ala Ala Ser Pro Ala
    290                 295                 300

Ala Pro Ala Pro Ala Ser Pro Ala Ala Pro Ala Pro Ser Ala Pro Ala
305                 310                 315                 320

Ala Ser Pro Ala Ala Pro Ala Pro Ala Ser Pro Ala Ala Pro Ala Pro
                325                 330                 335

Ser Ala Pro Ala Ala Ser Pro Ala Ala Pro Ala Pro Ala Ser Pro Ala
            340                 345                 350

Ala Pro Ala Pro Ser Ala Pro Ala Ala Ser Pro Ala Ala Pro Ala Pro
        355                 360                 365

Ala Ser Pro Ala Ala Pro Ala Pro Ser Ala Pro Ala Ala Ser Pro Ala
    370                 375                 380

Ala Pro Ala Pro Ala Ser Pro Ala Ala Pro Ala Pro Ser Ala Pro Ala
385                 390                 395                 400

Ala Ser Pro Ala Ala Pro Ala Pro Ala Ser Pro Ala Ala Pro Ala Pro
                405                 410                 415

Ser Ala Pro Ala Gly Gly Gly Gly Ser Gly Gly Gly Gly Ser Gly Gly
            420                 425                 430

Gly Gly Ser Gln Leu Ser Leu Pro Ser Ile Leu Pro Asn Glu Asn Glu
        435                 440                 445

Lys Val Val Gln Leu Asn Ser Ser Phe Ser Leu Arg Cys Phe Gly Glu
    450                 455                 460

Ser Glu Val Ser Trp Gln Tyr Pro Met Ser Glu Glu Glu Ser Ser Asp
465                 470                 475                 480

Val Glu Ile Arg Asn Glu Glu Asn Asn Ser Gly Leu Phe Val Thr Val
                485                 490                 495

Leu Glu Val Ser Ser Ala Ser Ala Ala His Thr Gly Leu Tyr Thr Cys
            500                 505                 510

Tyr Tyr Asn His Thr Gln Thr Glu Glu Asn Glu Leu Glu Gly Arg His
        515                 520                 525

Ile Tyr Ile Tyr Val Pro Asp Pro Asp Val Ala Phe Val Pro Leu Gly
    530                 535                 540

Met Thr Asp Tyr Leu Val Ile Val Glu Asp Asp Asp Ser Ala Ile Ile
545                 550                 555                 560

Pro Cys Arg Thr Thr Asp Pro Glu Thr Pro Val Thr Leu His Asn Ser
                565                 570                 575

Glu Gly Val Val Pro Ala Ser Tyr Asp Ser Arg Gln Gly Phe Asn Gly
            580                 585                 590

Thr Phe Thr Val Gly Pro Tyr Ile Cys Glu Ala Thr Val Lys Gly Lys
        595                 600                 605

Lys Phe Gln Thr Ile Pro Phe Asn Val Tyr Ala Leu Lys Ala Thr Ser
    610                 615                 620
```

-continued

```
Glu Leu Asp Leu Glu Met Glu Ala Leu Lys Thr Val Tyr Lys Ser Gly
625                 630                 635                 640

Glu Thr Ile Val Val Thr Cys Ala Val Phe Asn Asn Glu Val Val Asp
                645                 650                 655

Leu Gln Trp Thr Tyr Pro Gly Glu Val Lys Gly Lys Gly Ile Thr Met
            660                 665                 670

Leu Glu Glu Ile Lys Val Pro Ser Ile Lys Leu Val Tyr Thr Leu Thr
        675                 680                 685

Val Pro Glu Ala Thr Val Lys Asp Ser Gly Asp Tyr Glu Cys Ala Ala
    690                 695                 700

Arg Gln Ala Thr Arg Glu Val Lys Glu Met Lys Lys Val Thr Ile Ser
705                 710                 715                 720

Val His Glu Lys Gly
                725


<210> SEQ ID NO 55
<211> LENGTH: 2085
<212> TYPE: DNA
<213> ORGANISM: Artificial Sequence
<220> FEATURE:
<223> OTHER INFORMATION: Sequence encoding EPS1109P, excluding signal
      peptide and purification tag

<400> SEQUENCE: 55

gcttctccag ccgctccagc tcctgcttct cctgctgcac cagcaccatc tgctccagct      60

gcaagtccag ctgctcccgc accagcaagt cctgcagcac ccgctcctag tgctccagca     120

gcatctcccg cagcaccagc tccagcttca ccagcagctc ccgctccatc agcaccagcc     180

gcatcacccg ctgctccagc accagcttct cccgccgctc ctgcaccttc tgcacccgca     240

gctagccctg ctgctcctgc tccagcatct ccagctgcac ccgctccaag cgcacccgct     300

gctagtccag cagcaccagc accagctagt cccgctgctc cagctccttc tgctccagca     360

gcttcaccag ccgctccagc accagctagc ccagccgcac cagcacctag tgctcccgcc     420

gctagtcctg cagctccagc tcctgctagc ccagctgctc ccgctcctag cgctcctgcc     480

gcttcaccag ctgcaccagc tccagcaagt ccagccgctc ctgctccaag tgcaccagct     540

gcctctccag ctgctcctgc tcctgcaagt cccgcagctc cagcacctag cgcaccagca     600

tctgataccg gcagaccctt cgtggaaatg tacagcgaga tccccgagat catccacatg     660

accgagggca gagagctggt catcccctgc agagtgacct ctcctaacat caccgtgact     720

ctgaagaagt tccctctgga cacactgatc cccgacggca agagaatcat ctgggactcc     780

cggaagggct tcatcatctc caacgccacc tacaaagaga tcggcctgct gacctgcgag     840

gccaccgtta atggccacct gtacaagacc aactatctga cccacagaca gaccaacacc     900

atcatcgacg tggtgctgag cccctctcat ggcatcgagc tgtccgtggg agaaaagctc     960

gtgctgaact gcaccgccag aaccgagctg aacgtgggca tcgacttcaa ctgggagtac    1020

cccagctcca aacaccagca caagaaactg gtcaaccggg acctgaaaac ccagtccggc    1080

tccgagatga agaaattcct gagcaccctg accatcgacg gcgtgaccag atctgaccag    1140

ggcctgtata cctgcgccgc ttcttctggc ctgatgacca agaaaaactc caccttcgtg    1200

cgcgtgcacg agaagcagct gtccctgcct tctatcctgc ctaacgagaa cgagaaggtg    1260

gtccagctga actcctcctt ctctctgcgg tgcttcggcg agtccgaagt gtcttggcag    1320

taccccatgt ccgaagagga atcctccgac gtggaaatcc ggaacgagga aaacaactcc    1380

ggcctgttcg tgaccgtgct ggaagtgtcc tctgcctctg ctgctcacac cggcctgtac    1440
```

```
acatgctact acaatcacac ccagaccgaa gagaacgagc tggaaggccg gcacatctac   1500

atctacgtgc ccgatcctga cgtggccttt gtgcctctgg gcatgaccga ctacctggtc   1560

atcgtggaag atgacgactc cgctatcatc ccttgccgga ccaccgatcc agagacacct   1620

gtgacactgc acaactccga aggcgtggtg cctgcctcct acgattctag acagggcttc   1680

aacggcacct tcaccgtggg accttacatc tgcgaggcta cagtgaaggg caagaagttt   1740

cagacaatcc ccttcaacgt gtacgccctg aaggccacct ctgagctgga cctggaaatg   1800

gaagctctga aaaccgtgta caagtccggc gagacaatcg tcgtgacctg tgccgtgttc   1860

aacaacgagg tggtggacct gcagtggacc tatcctggcg aagtgaaagg caagggcatc   1920

accatgctgg aagagatcaa ggtgccctcc atcaagctgg tgtataccct gaccgtgcct   1980

gaggccactg tgaaggactc tggcgactac gagtgtgccg ctagacaggc caccagagaa   2040

gtcaaagaaa tgaagaaagt gaccatctcc gtccacgaga agggc                  2085
```

```
<210> SEQ ID NO 56
<211> LENGTH: 695
<212> TYPE: PRT
<213> ORGANISM: Artificial Sequence
<220> FEATURE:
<223> OTHER INFORMATION: Sequence of EPS1109P, excluding signal peptide
      and purification tag

<400> SEQUENCE: 56

Ala Ser Pro Ala Ala Pro Ala Pro Ala Ser Pro Ala Ala Pro Ala Pro
1               5                   10                  15

Ser Ala Pro Ala Ala Ser Pro Ala Ala Pro Ala Pro Ala Ser Pro Ala
            20                  25                  30

Ala Pro Ala Pro Ser Ala Pro Ala Ala Ser Pro Ala Ala Pro Ala Pro
        35                  40                  45

Ala Ser Pro Ala Ala Pro Ala Pro Ser Ala Pro Ala Ala Ser Pro Ala
    50                  55                  60

Ala Pro Ala Pro Ala Ser Pro Ala Ala Pro Ala Pro Ser Ala Pro Ala
65                  70                  75                  80

Ala Ser Pro Ala Ala Pro Ala Pro Ala Ser Pro Ala Ala Pro Ala Pro
                85                  90                  95

Ser Ala Pro Ala Ala Ser Pro Ala Ala Pro Ala Pro Ala Ser Pro Ala
            100                 105                 110

Ala Pro Ala Pro Ser Ala Pro Ala Ala Ser Pro Ala Ala Pro Ala Pro
        115                 120                 125

Ala Ser Pro Ala Ala Pro Ala Pro Ser Ala Pro Ala Ala Ser Pro Ala
    130                 135                 140

Ala Pro Ala Pro Ala Ser Pro Ala Ala Pro Ala Pro Ser Ala Pro Ala
145                 150                 155                 160

Ala Ser Pro Ala Ala Pro Ala Pro Ala Ser Pro Ala Ala Pro Ala Pro
                165                 170                 175

Ser Ala Pro Ala Ala Ser Pro Ala Ala Pro Ala Pro Ala Ser Pro Ala
            180                 185                 190

Ala Pro Ala Pro Ser Ala Pro Ala Ser Asp Thr Gly Arg Pro Phe Val
        195                 200                 205

Glu Met Tyr Ser Glu Ile Pro Glu Ile Ile His Met Thr Glu Gly Arg
    210                 215                 220

Glu Leu Val Ile Pro Cys Arg Val Thr Ser Pro Asn Ile Thr Val Thr
225                 230                 235                 240
```

```
Leu Lys Lys Phe Pro Leu Asp Thr Leu Ile Pro Asp Gly Lys Arg Ile
                245                 250                 255

Ile Trp Asp Ser Arg Lys Gly Phe Ile Ile Ser Asn Ala Thr Tyr Lys
            260                 265                 270

Glu Ile Gly Leu Leu Thr Cys Glu Ala Thr Val Asn Gly His Leu Tyr
        275                 280                 285

Lys Thr Asn Tyr Leu Thr His Arg Gln Thr Asn Thr Ile Ile Asp Val
    290                 295                 300

Val Leu Ser Pro Ser His Gly Ile Glu Leu Ser Val Gly Glu Lys Leu
305                 310                 315                 320

Val Leu Asn Cys Thr Ala Arg Thr Glu Leu Asn Val Gly Ile Asp Phe
                325                 330                 335

Asn Trp Glu Tyr Pro Ser Ser Lys His Gln His Lys Lys Leu Val Asn
            340                 345                 350

Arg Asp Leu Lys Thr Gln Ser Gly Ser Glu Met Lys Lys Phe Leu Ser
        355                 360                 365

Thr Leu Thr Ile Asp Gly Val Thr Arg Ser Asp Gln Gly Leu Tyr Thr
    370                 375                 380

Cys Ala Ala Ser Ser Gly Leu Met Thr Lys Lys Asn Ser Thr Phe Val
385                 390                 395                 400

Arg Val His Glu Lys Gln Leu Ser Leu Pro Ser Ile Leu Pro Asn Glu
                405                 410                 415

Asn Glu Lys Val Val Gln Leu Asn Ser Ser Phe Ser Leu Arg Cys Phe
            420                 425                 430

Gly Glu Ser Glu Val Ser Trp Gln Tyr Pro Met Ser Glu Glu Glu Ser
        435                 440                 445

Ser Asp Val Glu Ile Arg Asn Glu Glu Asn Asn Ser Gly Leu Phe Val
    450                 455                 460

Thr Val Leu Glu Val Ser Ser Ala Ser Ala Ala His Thr Gly Leu Tyr
465                 470                 475                 480

Thr Cys Tyr Tyr Asn His Thr Gln Thr Glu Glu Asn Glu Leu Glu Gly
                485                 490                 495

Arg His Ile Tyr Ile Tyr Val Pro Asp Pro Asp Val Ala Phe Val Pro
            500                 505                 510

Leu Gly Met Thr Asp Tyr Leu Val Ile Val Glu Asp Asp Asp Ser Ala
        515                 520                 525

Ile Ile Pro Cys Arg Thr Thr Asp Pro Glu Thr Pro Val Thr Leu His
    530                 535                 540

Asn Ser Glu Gly Val Val Pro Ala Ser Tyr Asp Ser Arg Gln Gly Phe
545                 550                 555                 560

Asn Gly Thr Phe Thr Val Gly Pro Tyr Ile Cys Glu Ala Thr Val Lys
                565                 570                 575

Gly Lys Lys Phe Gln Thr Ile Pro Phe Asn Val Tyr Ala Leu Lys Ala
            580                 585                 590

Thr Ser Glu Leu Asp Leu Glu Met Glu Ala Leu Lys Thr Val Tyr Lys
        595                 600                 605

Ser Gly Glu Thr Ile Val Val Thr Cys Ala Val Phe Asn Asn Glu Val
    610                 615                 620

Val Asp Leu Gln Trp Thr Tyr Pro Gly Glu Val Lys Gly Lys Gly Ile
625                 630                 635                 640

Thr Met Leu Glu Glu Ile Lys Val Pro Ser Ile Lys Leu Val Tyr Thr
                645                 650                 655

Leu Thr Val Pro Glu Ala Thr Val Lys Asp Ser Gly Asp Tyr Glu Cys
```

```
            660                 665                 670

Ala Ala Arg Gln Ala Thr Arg Glu Val Lys Glu Met Lys Lys Val Thr
        675                 680                 685

Ile Ser Val His Glu Lys Gly
    690                 695


<210> SEQ ID NO 57
<211> LENGTH: 2085
<212> TYPE: DNA
<213> ORGANISM: Artificial Sequence
<220> FEATURE:
<223> OTHER INFORMATION: Sequence encoding EPS1110P, excluding signal
      peptide and purification tag

<400> SEQUENCE: 57

gcttctccag ccgctccagc tcctgcttct cctgctgcac cagcaccatc tgctccagct     60

gcaagtccag ctgctcccgc accagcaagt cctgcagcac ccgctcctag tgctccagca    120

gcatctcccg cagcaccagc tccagcttca ccagcagctc ccgctccatc agcaccagcc    180

gcatcacccg ctgctccagc accagcttct cccgccgctc ctgcaccttc tgcacccgca    240

gctagccctg ctgctcctgc tccagcatct ccagctgcac ccgctccaag cgcacccgct    300

gctagtccag cagcaccagc accagctagt cccgctgctc cagctccttc tgctccagca    360

gcttcaccag ccgctccagc accagctagc ccagccgcac cagcacctag tgctcccgcc    420

gctagtcctg cagctccagc tcctgctagc ccagctgctc ccgctcctag cgctcctgcc    480

gcttcaccag ctgcaccagc tccagcaagt ccagccgctc ctgctccaag tgcaccagct    540

gcctctccag ctgctcctgc tcctgcaagt cccgcagctc cagcacctag cgcaccagct    600

caactgtccc tgccttccat cctgcctaac gagaacgaga aggtggtcca gctgaactcc    660

tccttctctc tgcggtgctt cggcgagtcc gaagtgtctt ggcagtaccc catgtccgaa    720

gaggaatcct ccgacgtgga aatccggaac gaggaaaaca actccggcct gttcgtgacc    780

gtgctggaag tgtcctctgc ctctgctgct cacaccggcc tgtacacctg ttactacaat    840

cacacccaga ccgaagagaa cgagctggaa ggccggcaca tctacatcta cgtgcccgat    900

cctgacgtgg cctttgtgcc tctgggcatg accgactacc tggtcatcgt ggaagatgac    960

gactccgcta tcatcccctg ccggaccaca gatcctgaga cacctgtgac actgcacaac   1020

tccgaaggcg tggtgcctgc ctcctacgat tctagacagg gcttcaacgg caccttcacc   1080

gtgggacctt acatctgcga ggctaccgtg aagggcaaga agttccagac aatccccttc   1140

aacgtgtacg ccctgaaggc cacctctgag ctggacctgg aaatggaagc cctgaaaacc   1200

gtgtacaagt ccggcgagac aatcgtcgtg acctgcgccg tgttcaacaa cgaggtggtg   1260

gacctgcagt ggacctatcc tggcgaagtg aaaggcaagg gcatcaccat gctggaagag   1320

atcaaggtgc cctccatcaa gctggtgtat accctgaccg tgcctgaggc cacagtgaag   1380

gactctggcg actacgagtg tgccgctaga caggccacca gagaagtcaa agagatgaag   1440

aaagtcacca tctccgtgca cgagaagggc tccgataccg gcagaccctt cgtggaaatg   1500

tacagcgaga tccccgagat catccacatg accgagggca gagagctggt catccccttgc   1560

agagtgacct ctcctaacat cacagtgacc ctgaagaagt ttcccctgga cacactgatc   1620

cccgacggca agagaatcat ctgggactcc cggaagggct tcatcatctc caacgccacc   1680

tacaaagaga tcggcctgct gacctgtgaa gccaccgtga atggccacct gtacaagacc   1740

aactatctga cccacagaca gaccaacacc atcatcgacg tggtgctgtc cccaagccat   1800
```

ggcatcgagc tgtccgtggg agaaaagctc gtgctgaact gcaccgccag aaccgagctg 1860
aacgtgggca tcgacttcaa ctgggagtac cccagctcca aacaccagca caagaaactg 1920
gtcaaccggg acctcaagac ccagtccggc tccgaaatga agaaattcct gagcaccctg 1980
accatcgacg gcgtgaccag atctgaccag ggactgtata cctgtgccgc ctcctctggc 2040
ctgatgacca agaaaaactc caccttcgtg cgggtccacg agaag 2085

<210> SEQ ID NO 58
<211> LENGTH: 695
<212> TYPE: PRT
<213> ORGANISM: Artificial Sequence
<220> FEATURE:
<223> OTHER INFORMATION: Sequence of EPS1110P, excluding signal peptide and purification tag

<400> SEQUENCE: 58

Ala Ser Pro Ala Ala Pro Ala Pro Ala Ser Pro Ala Ala Pro Ala Pro
1 5 10 15

Ser Ala Pro Ala Ala Ser Pro Ala Ala Pro Ala Pro Ala Ser Pro Ala
20 25 30

Ala Pro Ala Pro Ser Ala Pro Ala Ala Ser Pro Ala Ala Pro Ala Pro
35 40 45

Ala Ser Pro Ala Ala Pro Ala Pro Ser Ala Pro Ala Ala Ser Pro Ala
50 55 60

Ala Pro Ala Pro Ala Ser Pro Ala Ala Pro Ala Pro Ser Ala Pro Ala
65 70 75 80

Ala Ser Pro Ala Ala Pro Ala Pro Ala Ser Pro Ala Ala Pro Ala Pro
85 90 95

Ser Ala Pro Ala Ala Ser Pro Ala Ala Pro Ala Pro Ala Ser Pro Ala
100 105 110

Ala Pro Ala Pro Ser Ala Pro Ala Ala Ser Pro Ala Ala Pro Ala Pro
115 120 125

Ala Ser Pro Ala Ala Pro Ala Pro Ser Ala Pro Ala Ala Ser Pro Ala
130 135 140

Ala Pro Ala Pro Ala Ser Pro Ala Ala Pro Ala Pro Ser Ala Pro Ala
145 150 155 160

Ala Ser Pro Ala Ala Pro Ala Pro Ala Ser Pro Ala Ala Pro Ala Pro
165 170 175

Ser Ala Pro Ala Ala Ser Pro Ala Ala Pro Ala Pro Ala Ser Pro Ala
180 185 190

Ala Pro Ala Pro Ser Ala Pro Ala Gln Leu Ser Leu Pro Ser Ile Leu
195 200 205

Pro Asn Glu Asn Glu Lys Val Val Gln Leu Asn Ser Ser Phe Ser Leu
210 215 220

Arg Cys Phe Gly Glu Ser Glu Val Ser Trp Gln Tyr Pro Met Ser Glu
225 230 235 240

Glu Glu Ser Ser Asp Val Glu Ile Arg Asn Glu Glu Asn Asn Ser Gly
245 250 255

Leu Phe Val Thr Val Leu Glu Val Ser Ser Ala Ser Ala Ala His Thr
260 265 270

Gly Leu Tyr Thr Cys Tyr Tyr Asn His Thr Gln Thr Glu Glu Asn Glu
275 280 285

Leu Glu Gly Arg His Ile Tyr Ile Tyr Val Pro Asp Pro Asp Val Ala
290 295 300

Phe Val Pro Leu Gly Met Thr Asp Tyr Leu Val Ile Val Glu Asp Asp

```
305                 310                 315                 320

Asp Ser Ala Ile Ile Pro Cys Arg Thr Thr Asp Pro Glu Thr Pro Val
                325                 330                 335

Thr Leu His Asn Ser Glu Gly Val Val Pro Ala Ser Tyr Asp Ser Arg
            340                 345                 350

Gln Gly Phe Asn Gly Thr Phe Thr Val Gly Pro Tyr Ile Cys Glu Ala
        355                 360                 365

Thr Val Lys Gly Lys Lys Phe Gln Thr Ile Pro Phe Asn Val Tyr Ala
    370                 375                 380

Leu Lys Ala Thr Ser Glu Leu Asp Leu Glu Met Glu Ala Leu Lys Thr
385                 390                 395                 400

Val Tyr Lys Ser Gly Glu Thr Ile Val Val Thr Cys Ala Val Phe Asn
                405                 410                 415

Asn Glu Val Val Asp Leu Gln Trp Thr Tyr Pro Gly Glu Val Lys Gly
            420                 425                 430

Lys Gly Ile Thr Met Leu Glu Glu Ile Lys Val Pro Ser Ile Lys Leu
        435                 440                 445

Val Tyr Thr Leu Thr Val Pro Glu Ala Thr Val Lys Asp Ser Gly Asp
    450                 455                 460

Tyr Glu Cys Ala Ala Arg Gln Ala Thr Arg Glu Val Lys Glu Met Lys
465                 470                 475                 480

Lys Val Thr Ile Ser Val His Glu Lys Gly Ser Asp Thr Gly Arg Pro
                485                 490                 495

Phe Val Glu Met Tyr Ser Glu Ile Pro Glu Ile Ile His Met Thr Glu
            500                 505                 510

Gly Arg Glu Leu Val Ile Pro Cys Arg Val Thr Ser Pro Asn Ile Thr
        515                 520                 525

Val Thr Leu Lys Lys Phe Pro Leu Asp Thr Leu Ile Pro Asp Gly Lys
    530                 535                 540

Arg Ile Ile Trp Asp Ser Arg Lys Gly Phe Ile Ile Ser Asn Ala Thr
545                 550                 555                 560

Tyr Lys Glu Ile Gly Leu Leu Thr Cys Glu Ala Thr Val Asn Gly His
                565                 570                 575

Leu Tyr Lys Thr Asn Tyr Leu Thr His Arg Gln Thr Asn Thr Ile Ile
            580                 585                 590

Asp Val Val Leu Ser Pro Ser His Gly Ile Glu Leu Ser Val Gly Glu
        595                 600                 605

Lys Leu Val Leu Asn Cys Thr Ala Arg Thr Glu Leu Asn Val Gly Ile
    610                 615                 620

Asp Phe Asn Trp Glu Tyr Pro Ser Ser Lys His Gln His Lys Lys Leu
625                 630                 635                 640

Val Asn Arg Asp Leu Lys Thr Gln Ser Gly Ser Glu Met Lys Lys Phe
                645                 650                 655

Leu Ser Thr Leu Thr Ile Asp Gly Val Thr Arg Ser Asp Gln Gly Leu
            660                 665                 670

Tyr Thr Cys Ala Ala Ser Ser Gly Leu Met Thr Lys Lys Asn Ser Thr
        675                 680                 685

Phe Val Arg Val His Glu Lys
    690                 695
```

<210> SEQ ID NO 59
<211> LENGTH: 1818
<212> TYPE: DNA
<213> ORGANISM: Artificial Sequence
<220> FEATURE:
<223> OTHER INFORMATION: Sequence encoding EPS1111P, excluding signal peptide and purification tag

<400> SEQUENCE: 59

```
gcttctccag ccgctccagc tcctgcttct cctgctgcac cagcaccatc tgctccagct     60
gcaagtccag ctgctcccgc accagcaagt cctgcagcac ccgctcctag tgctccagca    120
gcatctcccg cagcaccagc tccagcttca ccagcagctc ccgctccatc agcaccagcc    180
gcatcacccg ctgctccagc accagcttct cccgccgctc ctgcaccttc tgcacccgca    240
gctagccctg ctgctcctgc tccagcatct ccagctgcac ccgctccaag cgcacccgct    300
gctagtccag cagcaccagc accagctagt cccgctgctc cagctccttc tgctccagca    360
gcttcaccag ccgctccagc accagctagc ccagccgcac cagcacctag tgctcccgcc    420
gctagtcctg cagctccagc tcctgctagc ccagctgctc ccgctcctag cgctcctgcc    480
gcttcaccag ctgcaccagc tccagcaagt ccagccgctc ctgctccaag tgcaccagct    540
gcctctccag ctgctcctgc tcctgcaagt cccgcagctc cagcacctag cgcaccagca    600
tctgataccg gcagaccctt cgtggaaatg tacagcgaga tccccgagat catccacatg    660
accgagggca gagagctggt catcccctgc agagtgacct ctcctaacat caccgtgact    720
ctgaagaagt tccctctgga cacactgatc cccgacggca agagaatcat ctgggactcc    780
cggaagggct tcatcatctc caacgccacc tacaaagaga tcggcctgct gacctgcgag    840
gccaccgtta atggccacct gtacaagacc aactatctga cccacagaca gaccaacacc    900
atcatcgacg tggtgctgag cccctctcat ggcatcgagc tgtccgtggg agaaaagctc    960
gtgctgaact gcaccgccag aaccgagctg aacgtgggca tcgacttcaa ctgggagtac   1020
cccagctcca aacaccagca caagaaactg gtcaaccggg acctgaaaac ccagtccggc   1080
tccgagatga agaaattcct gagcaccctg accatcgacg gcgtgaccag atctgaccag   1140
ggcctgtata cctgcgccgc ttcttctggc ctgatgacca agaaaaactc caccttcgtg   1200
cgcgtgcacg agaagaacga tgccgaggaa ctgttcatct tcctgaccga gattaccgag   1260
atcacaatcc cctgccgcgt gacagatcct cagctggtgg ttaccctgca tgagaagaaa   1320
ggcgacgtgg ccctgcctgt gccttacgat catcagagag gcttctccgg catcttcgag   1380
gaccggtctt acatctgcaa gaccaccatc ggcgacagag aggtggactc cgacgcctac   1440
tacgtgtaca gactccaggt gtcctccatc aacgtgtccg tgaatgccgt gcagacagtt   1500
gtgcggcagg gcgagaatat caccctgatg tgcatcgtga tcggcaacga ggtggtcaac   1560
ttcgagtgga cctatcctcg gaaagaatct ggccggctgg tggaacctgt gaccgacttc   1620
ctgctggaca tgccctacca catccggtct atcctgcaca tcccttccgc cgagctggaa   1680
gattccggca cctacacctg taacgtgacc gagtccgtga acgaccacca ggacgagaag   1740
gccatcaata tcaccgtggt ggaatccggc tacgtgcggc tgttgggaga agtgggcaca   1800
ctgcagtttg ctgagctg                                                 1818
```

<210> SEQ ID NO 60
<211> LENGTH: 606
<212> TYPE: PRT
<213> ORGANISM: Artificial Sequence
<220> FEATURE:
<223> OTHER INFORMATION: Sequence of EPS1111P, excluding signal peptide and purification tag

<400> SEQUENCE: 60

```
Ala Ser Pro Ala Ala Pro Ala Pro Ala Ser Pro Ala Ala Pro Ala Pro
1               5                   10                  15

Ser Ala Pro Ala Ala Ser Pro Ala Ala Pro Ala Pro Ala Ser Pro Ala
            20                  25                  30

Ala Pro Ala Pro Ser Ala Pro Ala Ala Ser Pro Ala Ala Pro Ala Pro
        35                  40                  45

Ala Ser Pro Ala Ala Pro Ala Pro Ser Ala Pro Ala Ala Ser Pro Ala
    50                  55                  60

Ala Pro Ala Pro Ala Ser Pro Ala Ala Pro Ala Pro Ser Ala Pro Ala
65                  70                  75                  80

Ala Ser Pro Ala Ala Pro Ala Pro Ala Ser Pro Ala Ala Pro Ala Pro
                85                  90                  95

Ser Ala Pro Ala Ala Ser Pro Ala Ala Pro Ala Pro Ala Ser Pro Ala
            100                 105                 110

Ala Pro Ala Pro Ser Ala Pro Ala Ala Ser Pro Ala Ala Pro Ala Pro
        115                 120                 125

Ala Ser Pro Ala Ala Pro Ala Pro Ser Ala Pro Ala Ala Ser Pro Ala
    130                 135                 140

Ala Pro Ala Pro Ala Ser Pro Ala Ala Pro Ala Pro Ser Ala Pro Ala
145                 150                 155                 160

Ala Ser Pro Ala Ala Pro Ala Pro Ala Ser Pro Ala Ala Pro Ala Pro
                165                 170                 175

Ser Ala Pro Ala Ala Ser Pro Ala Ala Pro Ala Pro Ala Ser Pro Ala
            180                 185                 190

Ala Pro Ala Pro Ser Ala Pro Ala Ser Asp Thr Gly Arg Pro Phe Val
        195                 200                 205

Glu Met Tyr Ser Glu Ile Pro Glu Ile Ile His Met Thr Glu Gly Arg
    210                 215                 220

Glu Leu Val Ile Pro Cys Arg Val Thr Ser Pro Asn Ile Thr Val Thr
225                 230                 235                 240

Leu Lys Lys Phe Pro Leu Asp Thr Leu Ile Pro Asp Gly Lys Arg Ile
                245                 250                 255

Ile Trp Asp Ser Arg Lys Gly Phe Ile Ile Ser Asn Ala Thr Tyr Lys
            260                 265                 270

Glu Ile Gly Leu Leu Thr Cys Glu Ala Thr Val Asn Gly His Leu Tyr
        275                 280                 285

Lys Thr Asn Tyr Leu Thr His Arg Gln Thr Asn Thr Ile Ile Asp Val
    290                 295                 300

Val Leu Ser Pro Ser His Gly Ile Glu Leu Ser Val Gly Glu Lys Leu
305                 310                 315                 320

Val Leu Asn Cys Thr Ala Arg Thr Glu Leu Asn Val Gly Ile Asp Phe
                325                 330                 335

Asn Trp Glu Tyr Pro Ser Ser Lys His Gln His Lys Lys Leu Val Asn
            340                 345                 350

Arg Asp Leu Lys Thr Gln Ser Gly Ser Glu Met Lys Lys Phe Leu Ser
        355                 360                 365

Thr Leu Thr Ile Asp Gly Val Thr Arg Ser Asp Gln Gly Leu Tyr Thr
    370                 375                 380

Cys Ala Ala Ser Ser Gly Leu Met Thr Lys Lys Asn Ser Thr Phe Val
385                 390                 395                 400

Arg Val His Glu Lys Asn Asp Ala Glu Glu Leu Phe Ile Phe Leu Thr
                405                 410                 415

Glu Ile Thr Glu Ile Thr Ile Pro Cys Arg Val Thr Asp Pro Gln Leu
```

```
            420                 425                 430

Val Val Thr Leu His Glu Lys Lys Gly Asp Val Ala Leu Pro Val Pro
        435                 440                 445

Tyr Asp His Gln Arg Gly Phe Ser Gly Ile Phe Glu Asp Arg Ser Tyr
    450                 455                 460

Ile Cys Lys Thr Thr Ile Gly Asp Arg Glu Val Asp Ser Asp Ala Tyr
465                 470                 475                 480

Tyr Val Tyr Arg Leu Gln Val Ser Ser Ile Asn Val Ser Val Asn Ala
                485                 490                 495

Val Gln Thr Val Val Arg Gln Gly Glu Asn Ile Thr Leu Met Cys Ile
            500                 505                 510

Val Ile Gly Asn Glu Val Val Asn Phe Glu Trp Thr Tyr Pro Arg Lys
        515                 520                 525

Glu Ser Gly Arg Leu Val Glu Pro Val Thr Asp Phe Leu Leu Asp Met
    530                 535                 540

Pro Tyr His Ile Arg Ser Ile Leu His Ile Pro Ser Ala Glu Leu Glu
545                 550                 555                 560

Asp Ser Gly Thr Tyr Thr Cys Asn Val Thr Glu Ser Val Asn Asp His
                565                 570                 575

Gln Asp Glu Lys Ala Ile Asn Ile Thr Val Val Glu Ser Gly Tyr Val
            580                 585                 590

Arg Leu Leu Gly Glu Val Gly Thr Leu Gln Phe Ala Glu Leu
        595                 600                 605
```

```
<210> SEQ ID NO 61
<211> LENGTH: 3288
<212> TYPE: DNA
<213> ORGANISM: Artificial Sequence
<220> FEATURE:
<223> OTHER INFORMATION: Sequence encoding EPS1113P, excluding signal
      peptide and purification tag

<400> SEQUENCE: 61

cagctgtccc tgccttctat cctgcctaac gagaacgaga aggtggtgca gctgaactcc      60

tccttctctc tgcggtgctt cggcgagtcc gaagtgtctt ggcagtaccc catgtccgaa     120

gaggaatcct ccgacgtgga aatccggaac gaggaaaaca actccggcct gttcgtgacc     180

gtgctggaag tgtcctctgc ctctgctgct cacaccggcc tgtacacctg ttactacaat     240

cacacccaga ccgaagagaa cgagctggaa ggccggcaca tctacatcta cgtgcccgat     300

cctgacgtgg cctttgtgcc tctgggcatg accgactacc tggtcatcgt ggaagatgac     360

gactccgcta tcatcccctg ccggaccaca gatcctgaga cacctgtgac actgcacaac     420

tccgaaggcg tggtgcctgc ctcctacgat tctagacagg gcttcaacgg caccttcacc     480

gtgggacctt acatctgcga ggctaccgtg aagggcaaga agttccagac aatccccttc     540

aacgtgtacg ccctgaaggc cacctctgag ctggacctgg aaatggaagc cctgaaaacc     600

gtgtacaagt ccggcgagac aatcgtcgtg acctgcgccg tgttcaacaa cgaggtggtg     660

gacctgcagt ggacctatcc tggcgaagtg aaaggcaagg gcatcaccat gctggaagag     720

atcaaggtgc cctccatcaa gctggtgtat accctgaccg tgcctgaggc cacagtgaag     780

gactctggcg actacgagtg tgccgctaga caggccacca gagaagtcaa agagatgaag     840

aaagtcacca tctccgtgca cgagaagggc gcctctccag ctgctcctgc tccagctagt     900

cctgcagctc cagctccatc tgcaccagct gcttctccag cagcacccgc accagcttct     960

cccgccgctc ctgcacctag tgcaccagca gctagccctg ctgcaccagc accagcaagt    1020
```

```
ccagccgcac cagctcctag tgctccagct gcatcccctg ctgctcccgc tcctgcttca   1080
ccagccgctc cagcaccatc agctcccgca gcatctccag cagctccagc tcctgcttct   1140
cctgctgcac ccgctccatc tgctcccgct gcaagtcctg ctgctcctgc accagcatca   1200
cccgcagctc ccgcaccaag cgctccagcc gcttcacccg cagcaccagc tccagcctca   1260
ccagcagcac cagcaccttc cgctccagct gctagtccag ccgctcctgc tcctgcaagc   1320
cccgctgctc cagctcctag cgcacccgct gctagccccg cagctcccgc tccagcaagc   1380
ccagcagctc ctgctccttc tgctccagca gcatctcctg ccgcaccagc tccagctagc   1440
ccagctgctc ccgcaccatc cgcaccagca gcaagtcccg cagctccagc accagctagt   1500
cccgcagcac ccgcaccttc agcaccagcc gcatcaccag ctgctccagc tccagcatct   1560
cccgctgcac cagcaccaag tgctcccgct gcttctcctg cagctcctgc tccagcctct   1620
ccagctgctc ccgcaccttc tgctccagct gcctctccag ctgctccagc accagcttca   1680
ccagctgctc ccgctcctag tgctcctgcc gctagtccag cagctcccgc accagctagc   1740
cctgccgctc ctgctccaag tgctccagcc gcaagtcccg ctgcacccgc tccagcttct   1800
ccagcagctc ccgctccaag cgcacccgca gcttctcccg ctgctcccgc accagcaagt   1860
cctgctgctc cagctccttc agctcctgcc gcttctcctg ctgctccagc tcctgcaagt   1920
ccagctgctc cagcaccaag tgcaccagca gcaagtccag ctgctcctgc tcctgcctct   1980
ccagcagcac cagctcctag cgcaccagcc gccagtcctg cagcaccagc tccagcttct   2040
cccgctgctc ctgctccttc agcaccagct gctagtcctg ctgctcctgc tccagcttct   2100
cctgccgctc cagcaccaag cgctccagct gcatctcccg cagctcccgc tccagcatct   2160
cctgcagcac ccgcaccatc agctccagct gcttccccag ccgctcctgc accagctagc   2220
ccagcagctc ctgcacctag cgctcccgct gcttcaccag cagctccagc accagccagt   2280
ccagctgctc ctgcaccatc tgcacccgct gctagtcccg ctgctccagc tcctgctagc   2340
cctgcagcac cagctccaag tgcacccgcc gcatcacccg ccgcaccagc accagcaagc   2400
cctgcagcac ccgctccaag cgctccagct gctagcccag cagcaccagc accagcatca   2460
ccagccgctc cagcaccttc tgcaccagca gcttcacccg ctgcacccgc tccagcatca   2520
cccgccgctc cagctcctag cgctcctgca gcctctcctg cagctccagc accagcaagc   2580
cccgctgcac cagcaccatc tgctccagca gctagccctg cagctcccgc tcctgcatct   2640
cccgccgcac cagctccatc tgcacccgca gcatctgata ccggcagacc cttcgtggaa   2700
atgtacagcg agatccccga gatcatccac atgaccgagg gcagagagct ggtcatccct   2760
tgcagagtga cctctcctaa catcacagtg accctgaaga agtttcccct ggacacactg   2820
atccccgacg gcaagagaat catctgggac tcccggaagg gcttcatcat ctccaacgcc   2880
acctacaaag agatcggcct gctgacctgt gaagccaccg tgaatggcca cctgtacaag   2940
accaactatc tgacccacag acagaccaac accatcatcg acgtggtgct gagcccctct   3000
catggcatcg agctgtccgt gggagagaag ctcgtgctga actgtaccgc cagaaccgag   3060
ctgaacgtgg gcatcgactt caactgggag taccctagct ccaaacacca gcacaagaaa   3120
ctggtcaacc gggacctcaa gacccagtcc ggctccgaaa tgaagaaatt cctgtccaca   3180
ctgaccatcg acggcgtgac cagatctgac cagggactgt atacctgtgc cgcctcctct   3240
ggcctgatga ccaagaaaaa ctccaccttc gtgcgggtcc acgagaag                3288
```

<210> SEQ ID NO 62

<211> LENGTH: 1096
<212> TYPE: PRT
<213> ORGANISM: Artificial Sequence
<220> FEATURE:
<223> OTHER INFORMATION: Sequence of EPS1113P, excluding signal peptide and purification tag

<400> SEQUENCE: 62

Gln Leu Ser Leu Pro Ser Ile Leu Pro Asn Glu Asn Glu Lys Val Val
1 5 10 15

Gln Leu Asn Ser Ser Phe Ser Leu Arg Cys Phe Gly Glu Ser Glu Val
20 25 30

Ser Trp Gln Tyr Pro Met Ser Glu Glu Glu Ser Ser Asp Val Glu Ile
35 40 45

Arg Asn Glu Glu Asn Asn Ser Gly Leu Phe Val Thr Val Leu Glu Val
50 55 60

Ser Ser Ala Ser Ala Ala His Thr Gly Leu Tyr Thr Cys Tyr Tyr Asn
65 70 75 80

His Thr Gln Thr Glu Glu Asn Glu Leu Glu Gly Arg His Ile Tyr Ile
85 90 95

Tyr Val Pro Asp Pro Asp Val Ala Phe Val Pro Leu Gly Met Thr Asp
100 105 110

Tyr Leu Val Ile Val Glu Asp Asp Asp Ser Ala Ile Ile Pro Cys Arg
115 120 125

Thr Thr Asp Pro Glu Thr Pro Val Thr Leu His Asn Ser Glu Gly Val
130 135 140

Val Pro Ala Ser Tyr Asp Ser Arg Gln Gly Phe Asn Gly Thr Phe Thr
145 150 155 160

Val Gly Pro Tyr Ile Cys Glu Ala Thr Val Lys Gly Lys Lys Phe Gln
165 170 175

Thr Ile Pro Phe Asn Val Tyr Ala Leu Lys Ala Thr Ser Glu Leu Asp
180 185 190

Leu Glu Met Glu Ala Leu Lys Thr Val Tyr Lys Ser Gly Glu Thr Ile
195 200 205

Val Val Thr Cys Ala Val Phe Asn Asn Glu Val Val Asp Leu Gln Trp
210 215 220

Thr Tyr Pro Gly Glu Val Lys Gly Lys Gly Ile Thr Met Leu Glu Glu
225 230 235 240

Ile Lys Val Pro Ser Ile Lys Leu Val Tyr Thr Leu Thr Val Pro Glu
245 250 255

Ala Thr Val Lys Asp Ser Gly Asp Tyr Glu Cys Ala Ala Arg Gln Ala
260 265 270

Thr Arg Glu Val Lys Glu Met Lys Lys Val Thr Ile Ser Val His Glu
275 280 285

Lys Gly Ala Ser Pro Ala Ala Pro Ala Pro Ala Ser Pro Ala Ala Pro
290 295 300

Ala Pro Ser Ala Pro Ala Ala Ser Pro Ala Ala Pro Ala Pro Ala Ser
305 310 315 320

Pro Ala Ala Pro Ala Pro Ser Ala Pro Ala Ala Ser Pro Ala Ala Pro
325 330 335

Ala Pro Ala Ser Pro Ala Ala Pro Ala Pro Ser Ala Pro Ala Ala Ser
340 345 350

Pro Ala Ala Pro Ala Pro Ala Ser Pro Ala Ala Pro Ala Pro Ser Ala
355 360 365

Pro Ala Ala Ser Pro Ala Ala Pro Ala Pro Ala Ser Pro Ala Ala Pro

-continued

```
    370                 375                 380

Ala Pro Ser Ala Pro Ala Ala Ser Pro Ala Ala Pro Ala Pro Ala Ser
385                 390                 395                 400

Pro Ala Ala Pro Ala Pro Ser Ala Pro Ala Ala Ser Pro Ala Ala Pro
                405                 410                 415

Ala Pro Ala Ser Pro Ala Ala Pro Ala Pro Ser Ala Pro Ala Ala Ser
            420                 425                 430

Pro Ala Ala Pro Ala Pro Ala Ser Pro Ala Ala Pro Ala Pro Ser Ala
        435                 440                 445

Pro Ala Ala Ser Pro Ala Ala Pro Ala Pro Ala Ser Pro Ala Ala Pro
    450                 455                 460

Ala Pro Ser Ala Pro Ala Ala Ser Pro Ala Ala Pro Ala Pro Ala Ser
465                 470                 475                 480

Pro Ala Ala Pro Ala Pro Ser Ala Pro Ala Ala Ser Pro Ala Ala Pro
                485                 490                 495

Ala Pro Ala Ser Pro Ala Ala Pro Ala Pro Ser Ala Pro Ala Ala Ser
            500                 505                 510

Pro Ala Ala Pro Ala Pro Ala Ser Pro Ala Ala Pro Ala Pro Ser Ala
        515                 520                 525

Pro Ala Ala Ser Pro Ala Ala Pro Ala Pro Ala Ser Pro Ala Ala Pro
    530                 535                 540

Ala Pro Ser Ala Pro Ala Ala Ser Pro Ala Ala Pro Ala Pro Ala Ser
545                 550                 555                 560

Pro Ala Ala Pro Ala Pro Ser Ala Pro Ala Ala Ser Pro Ala Ala Pro
                565                 570                 575

Ala Pro Ala Ser Pro Ala Ala Pro Ala Pro Ser Ala Pro Ala Ala Ser
            580                 585                 590

Pro Ala Ala Pro Ala Pro Ala Ser Pro Ala Ala Pro Ala Pro Ser Ala
        595                 600                 605

Pro Ala Ala Ser Pro Ala Ala Pro Ala Pro Ala Ser Pro Ala Ala Pro
    610                 615                 620

Ala Pro Ser Ala Pro Ala Ala Ser Pro Ala Ala Pro Ala Pro Ala Ser
625                 630                 635                 640

Pro Ala Ala Pro Ala Pro Ser Ala Pro Ala Ala Ser Pro Ala Ala Pro
                645                 650                 655

Ala Pro Ala Ser Pro Ala Ala Pro Ala Pro Ser Ala Pro Ala Ala Ser
            660                 665                 670

Pro Ala Ala Pro Ala Pro Ala Ser Pro Ala Ala Pro Ala Pro Ser Ala
        675                 680                 685

Pro Ala Ala Ser Pro Ala Ala Pro Ala Pro Ala Ser Pro Ala Ala Pro
    690                 695                 700

Ala Pro Ser Ala Pro Ala Ala Ser Pro Ala Ala Pro Ala Pro Ala Ser
705                 710                 715                 720

Pro Ala Ala Pro Ala Pro Ser Ala Pro Ala Ala Ser Pro Ala Ala Pro
                725                 730                 735

Ala Pro Ala Ser Pro Ala Ala Pro Ala Pro Ser Ala Pro Ala Ala Ser
            740                 745                 750

Pro Ala Ala Pro Ala Pro Ala Ser Pro Ala Ala Pro Ala Pro Ser Ala
        755                 760                 765

Pro Ala Ala Ser Pro Ala Ala Pro Ala Pro Ala Ser Pro Ala Ala Pro
    770                 775                 780

Ala Pro Ser Ala Pro Ala Ala Ser Pro Ala Ala Pro Ala Pro Ala Ser
785                 790                 795                 800
```

```
Pro Ala Ala Pro Ala Pro Ser Ala Pro Ala Ala Ser Pro Ala Ala Pro
                805                 810                 815

Ala Pro Ala Ser Pro Ala Ala Pro Ala Pro Ser Ala Pro Ala Ala Ser
            820                 825                 830

Pro Ala Ala Pro Ala Pro Ala Ser Pro Ala Ala Pro Ala Pro Ser Ala
        835                 840                 845

Pro Ala Ala Ser Pro Ala Ala Pro Ala Pro Ala Ser Pro Ala Ala Pro
    850                 855                 860

Ala Pro Ser Ala Pro Ala Ala Ser Pro Ala Ala Pro Ala Pro Ala Ser
865                 870                 875                 880

Pro Ala Ala Pro Ala Pro Ser Ala Pro Ala Ala Ser Asp Thr Gly Arg
                885                 890                 895

Pro Phe Val Glu Met Tyr Ser Glu Ile Pro Glu Ile Ile His Met Thr
            900                 905                 910

Glu Gly Arg Glu Leu Val Ile Pro Cys Arg Val Thr Ser Pro Asn Ile
        915                 920                 925

Thr Val Thr Leu Lys Lys Phe Pro Leu Asp Thr Leu Ile Pro Asp Gly
    930                 935                 940

Lys Arg Ile Ile Trp Asp Ser Arg Lys Gly Phe Ile Ile Ser Asn Ala
945                 950                 955                 960

Thr Tyr Lys Glu Ile Gly Leu Leu Thr Cys Glu Ala Thr Val Asn Gly
                965                 970                 975

His Leu Tyr Lys Thr Asn Tyr Leu Thr His Arg Gln Thr Asn Thr Ile
            980                 985                 990

Ile Asp Val Val Leu Ser Pro Ser  His Gly Ile Glu Leu  Ser Val Gly
        995                 1000                1005

Glu Lys  Leu Val Leu Asn Cys  Thr Ala Arg Thr Glu  Leu Asn Val
    1010                 1015                 1020

Gly Ile  Asp Phe Asn Trp Glu  Tyr Pro Ser Ser Lys  His Gln His
    1025                 1030                 1035

Lys Lys  Leu Val Asn Arg Asp  Leu Lys Thr Gln Ser  Gly Ser Glu
    1040                 1045                 1050

Met Lys  Lys Phe Leu Ser Thr  Leu Thr Ile Asp Gly  Val Thr Arg
    1055                 1060                 1065

Ser Asp  Gln Gly Leu Tyr Thr  Cys Ala Ala Ser Ser  Gly Leu Met
    1070                 1075                 1080

Thr Lys  Lys Asn Ser Thr Phe  Val Arg Val His Glu  Lys
    1085                 1090                 1095
```

<210> SEQ ID NO 63
<211> LENGTH: 3378
<212> TYPE: DNA
<213> ORGANISM: Artificial Sequence
<220> FEATURE:
<223> OTHER INFORMATION: Sequence encoding EPS1114P, excluding signal peptide and purification tag

<400> SEQUENCE: 63

```
cagctgtccc tgccttccat cctgcctaac gagaacgaga aggtggtgca gctgaactcc     60

tccttctctc tgcggtgctt cggcgagtcc gaagtgtctt ggcagtaccc catgtccgaa    120

gaggaatcct ccgacgtgga aatccggaac gaggaaaaca actccggcct gttcgtgacc    180

gtgctggaag tgtcctctgc ctctgctgct cacaccggac tgtacacctg ttactacaat    240

cacacccaga ccgaagagaa cgagctggaa ggccggcaca tctacatcta cgtgcccgat    300
```

```
cctgacgtgg cctttgtgcc tctgggcatg accgactacc tggtcatcgt ggaagatgac    360
gactccgcta tcatcccctg ccggaccaca gatcctgaga cacctgtgac actgcacaac    420
tccgaaggcg tggtgcctgc ctcctacgat tctagacagg gcttcaacgg caccttcacc    480
gtgggacctt acatctgcga ggctaccgtg aagggcaaga agttccagac aatccccttc    540
aacgtgtacg ccctgaaggc cacctctgag ctggacctgg aaatggaagc cctgaaaacc    600
gtgtacaaga gcggcgagac aatcgtcgtg acctgcgccg tgttcaacaa cgaggtggtg    660
gacctgcagt ggacctatcc tggcgaagtg aaaggcaagg gcatcaccat gctggaagag    720
atcaaggtgc cctccatcaa gctggtgtat accctgaccg tgcctgaggc cacagtgaag    780
gactctggcg actacgagtg tgccgctaga caggccacca gagaagtcaa agagatgaag    840
aaagtcacca tctccgtgca cgagaaaggc ggcggaggcg gaagcggtgg cggaggaagc    900
ggaggcggcg gatctgcttc tcctgctgct cctgctccag ctagtcctgc tgcaccagca    960
ccttcagctc cagctgcttc tccagcagca cccgcaccag catcaccagc cgctccagca   1020
ccaagtgcac cagctgctag cccagctgct cccgctcctg catctcctgc agcaccagct   1080
ccatctgcac cagcagcaag tccagcagct ccagctcctg cttcacccgc tgctcccgca   1140
ccatctgctc cagccgcatc acccgctgca ccagctccag cttctcccgc cgctccagct   1200
ccttctgctc ctgcagcatc tcctgctgct ccagcaccag caagcccagc cgctcctgct   1260
ccatcagcac ccgctgcctc tccagctgct cctgcaccag cctctccagc tgcacccgct   1320
cctagtgctc cagctgcaag tcccgccgca ccagcaccag ctagtcctgc agctcctgca   1380
ccaagcgctc cagcagcttc ccctgcagct cctgctcctg cctctcctgc cgctcctgct   1440
cctagtgcac cagccgcatc tcccgcagct cccgctcctg ctagtccagc agctcccgca   1500
ccttctgcac cagcagcttc cccagccgca ccagctccag caagccccgc tgctccagca   1560
cctagtgctc ccgctgcctc accagcagct cccgctccag caagccctgc tgcacccgct   1620
ccaagcgcac cagcagcatc accagctgca cccgcaccag ctagcccagc agcaccagct   1680
cctagcgctc ccgcagctag ccctgctgct cccgcaccag cttcacccgc agcacccgct   1740
ccatcagctc ccgccgctag tcccgctgct cctgctcctg caagccctgc tgctcctgct   1800
ccttctgctc cagctgctag tcctgccgct cctgctccag cttctccagc agctcctgca   1860
cctagcgcac ccgccgctag tccagcagca ccagcaccag cttctccagc tgcaccagca   1920
ccatcagcac ccgcagcttc accagcagct ccagcaccag catctcccgc agctccagca   1980
ccatcagctc cagcagcaag cccagctgca ccagctccag catcaccagc tgctcccgct   2040
ccaagcgctc ctgctgcttc tcctgccgca ccagctccag ccagtccagc agcacccgct   2100
ccaagtgcac ccgccgcttc tccagctgct ccagctcctg ctagccccgc agctccagct   2160
ccaagtgctc cagccgccag tcctgcagct cccgcaccag ctagccccgc tgctcctgca   2220
ccatccgcac cagctgctag tcccgcagca ccagctccag ctagcccagc cgcaccagca   2280
ccatctgctc ccgctgctag ccctgcagca cccgctccag ccagtcctgc tgctccagct   2340
ccatctgctc ccgccgcttc tcctgcagct cctgcaccag cttctcccgc tgctcctgct   2400
cctagcgctc cagcagcctc tccagcagca ccagctccag caagtcctgc agcaccagca   2460
cctagtgcac cagcagcttc acccgctgct cccgctccag catctccagc tgctccagca   2520
ccttctgctc cagctgcaag ccccgcagct cctgcaccag caagtcctgc cgctccagct   2580
cctagcgctc ctgctgcaag tccagctgct cccgctccag cttcaccagc cgcaccagca   2640
ccttccgcac cagcagctag tccagctgct cctgctccag ctagcccagc tgctccagct   2700
```

```
ccttcagcac cagcagccgg tggcggagga tctggcggag gcggatctgg cggcggtggt   2760

tcttctgata ccggcagacc cttcgtggaa atgtacagcg agatccccga gatcatccac   2820

atgaccgagg gcagagagct ggtcatccct tgcagagtga cctctcctaa catcacagtg   2880

accctgaaga agtttcccct ggacacactg atccccgacg gcaagagaat catctgggac   2940

tcccggaagg gcttcatcat ctccaacgcc acctacaaag agatcggact gctgacctgc   3000

gaagccactg tgaacggcca cctgtacaag accaactatc tgacccacag acagaccaac   3060

accatcatcg acgtggtgct gagcccctct catggcatcg agctgtccgt gggagagaaa   3120

ctggtgctga actgcaccgc cagaaccgag ctgaacgtgg gcatcgactt caactgggag   3180

taccccagct ccaaacacca gcacaagaag ctggtcaacc gggatctgaa aacccagtcc   3240

ggctccgaaa tgaagaaatt cctgagcacc ctgaccatcg acggcgtgac cagatctgac   3300

cagggcctgt atacctgtgc cgcctcttct ggcctgatga ccaagaaaaa ctccaccttc   3360

gtgcgggtcc acgagaag                                                  3378
```

<210> SEQ ID NO 64
<211> LENGTH: 1126
<212> TYPE: PRT
<213> ORGANISM: Artificial Sequence
<220> FEATURE:
<223> OTHER INFORMATION: Sequence of EPS1114P, excluding signal peptide and purification tag

<400> SEQUENCE: 64

```
Gln Leu Ser Leu Pro Ser Ile Leu Pro Asn Glu Asn Glu Lys Val Val
1               5                   10                  15

Gln Leu Asn Ser Ser Phe Ser Leu Arg Cys Phe Gly Glu Ser Glu Val
            20                  25                  30

Ser Trp Gln Tyr Pro Met Ser Glu Glu Glu Ser Ser Asp Val Glu Ile
        35                  40                  45

Arg Asn Glu Glu Asn Asn Ser Gly Leu Phe Val Thr Val Leu Glu Val
    50                  55                  60

Ser Ser Ala Ser Ala Ala His Thr Gly Leu Tyr Thr Cys Tyr Tyr Asn
65                  70                  75                  80

His Thr Gln Thr Glu Glu Asn Glu Leu Glu Gly Arg His Ile Tyr Ile
                85                  90                  95

Tyr Val Pro Asp Pro Asp Val Ala Phe Val Pro Leu Gly Met Thr Asp
            100                 105                 110

Tyr Leu Val Ile Val Glu Asp Asp Asp Ser Ala Ile Ile Pro Cys Arg
        115                 120                 125

Thr Thr Asp Pro Glu Thr Pro Val Thr Leu His Asn Ser Glu Gly Val
    130                 135                 140

Val Pro Ala Ser Tyr Asp Ser Arg Gln Gly Phe Asn Gly Thr Phe Thr
145                 150                 155                 160

Val Gly Pro Tyr Ile Cys Glu Ala Thr Val Lys Gly Lys Lys Phe Gln
                165                 170                 175

Thr Ile Pro Phe Asn Val Tyr Ala Leu Lys Ala Thr Ser Glu Leu Asp
            180                 185                 190

Leu Glu Met Glu Ala Leu Lys Thr Val Tyr Lys Ser Gly Glu Thr Ile
        195                 200                 205

Val Val Thr Cys Ala Val Phe Asn Asn Glu Val Val Asp Leu Gln Trp
    210                 215                 220

Thr Tyr Pro Gly Glu Val Lys Gly Lys Gly Ile Thr Met Leu Glu Glu
```

-continued

```
225                 230                 235                 240

Ile Lys Val Pro Ser Ile Lys Leu Val Tyr Thr Leu Thr Val Pro Glu
                245                 250                 255

Ala Thr Val Lys Asp Ser Gly Asp Tyr Glu Cys Ala Ala Arg Gln Ala
            260                 265                 270

Thr Arg Glu Val Lys Glu Met Lys Lys Val Thr Ile Ser Val His Glu
        275                 280                 285

Lys Gly Gly Gly Gly Gly Ser Gly Gly Gly Gly Ser Gly Gly Gly Gly
    290                 295                 300

Ser Ala Ser Pro Ala Ala Pro Ala Pro Ala Ser Pro Ala Ala Pro Ala
305                 310                 315                 320

Pro Ser Ala Pro Ala Ala Ser Pro Ala Ala Pro Ala Pro Ala Ser Pro
                325                 330                 335

Ala Ala Pro Ala Pro Ser Ala Pro Ala Ala Ser Pro Ala Ala Pro Ala
            340                 345                 350

Pro Ala Ser Pro Ala Ala Pro Ala Pro Ser Ala Pro Ala Ala Ser Pro
        355                 360                 365

Ala Ala Pro Ala Pro Ala Ser Pro Ala Ala Pro Ala Pro Ser Ala Pro
    370                 375                 380

Ala Ala Ser Pro Ala Ala Pro Ala Pro Ala Ser Pro Ala Ala Pro Ala
385                 390                 395                 400

Pro Ser Ala Pro Ala Ala Ser Pro Ala Ala Pro Ala Pro Ala Ser Pro
                405                 410                 415

Ala Ala Pro Ala Pro Ser Ala Pro Ala Ala Ser Pro Ala Ala Pro Ala
            420                 425                 430

Pro Ala Ser Pro Ala Ala Pro Ala Pro Ser Ala Pro Ala Ala Ser Pro
        435                 440                 445

Ala Ala Pro Ala Pro Ala Ser Pro Ala Ala Pro Ala Pro Ser Ala Pro
    450                 455                 460

Ala Ala Ser Pro Ala Ala Pro Ala Pro Ala Ser Pro Ala Ala Pro Ala
465                 470                 475                 480

Pro Ser Ala Pro Ala Ala Ser Pro Ala Ala Pro Ala Pro Ala Ser Pro
                485                 490                 495

Ala Ala Pro Ala Pro Ser Ala Pro Ala Ala Ser Pro Ala Ala Pro Ala
            500                 505                 510

Pro Ala Ser Pro Ala Ala Pro Ala Pro Ser Ala Pro Ala Ala Ser Pro
        515                 520                 525

Ala Ala Pro Ala Pro Ala Ser Pro Ala Ala Pro Ala Pro Ser Ala Pro
    530                 535                 540

Ala Ala Ser Pro Ala Ala Pro Ala Pro Ala Ser Pro Ala Ala Pro Ala
545                 550                 555                 560

Pro Ser Ala Pro Ala Ala Ser Pro Ala Ala Pro Ala Pro Ala Ser Pro
                565                 570                 575

Ala Ala Pro Ala Pro Ser Ala Pro Ala Ala Ser Pro Ala Ala Pro Ala
            580                 585                 590

Pro Ala Ser Pro Ala Ala Pro Ala Pro Ser Ala Pro Ala Ala Ser Pro
        595                 600                 605

Ala Ala Pro Ala Pro Ala Ser Pro Ala Ala Pro Ala Pro Ser Ala Pro
    610                 615                 620

Ala Ala Ser Pro Ala Ala Pro Ala Pro Ala Ser Pro Ala Ala Pro Ala
625                 630                 635                 640

Pro Ser Ala Pro Ala Ala Ser Pro Ala Ala Pro Ala Pro Ala Ser Pro
                645                 650                 655
```

-continued

```
Ala Ala Pro Ala Pro Ser Ala Pro Ala Ala Ser Pro Ala Ala Pro Ala
            660                 665                 670

Pro Ala Ser Pro Ala Ala Pro Ala Pro Ser Ala Pro Ala Ala Ser Pro
        675                 680                 685

Ala Ala Pro Ala Pro Ala Ser Pro Ala Ala Pro Ala Pro Ser Ala Pro
    690                 695                 700

Ala Ala Ser Pro Ala Ala Pro Ala Pro Ala Ser Pro Ala Ala Pro Ala
705                 710                 715                 720

Pro Ser Ala Pro Ala Ala Ser Pro Ala Ala Pro Ala Pro Ala Ser Pro
                725                 730                 735

Ala Ala Pro Ala Pro Ser Ala Pro Ala Ala Ser Pro Ala Ala Pro Ala
            740                 745                 750

Pro Ala Ser Pro Ala Ala Pro Ala Pro Ser Ala Pro Ala Ala Ser Pro
        755                 760                 765

Ala Ala Pro Ala Pro Ala Ser Pro Ala Ala Pro Ala Pro Ser Ala Pro
    770                 775                 780

Ala Ala Ser Pro Ala Ala Pro Ala Pro Ala Ser Pro Ala Ala Pro Ala
785                 790                 795                 800

Pro Ser Ala Pro Ala Ala Ser Pro Ala Ala Pro Ala Pro Ala Ser Pro
                805                 810                 815

Ala Ala Pro Ala Pro Ser Ala Pro Ala Ala Ser Pro Ala Ala Pro Ala
            820                 825                 830

Pro Ala Ser Pro Ala Ala Pro Ala Pro Ser Ala Pro Ala Ala Ser Pro
        835                 840                 845

Ala Ala Pro Ala Pro Ala Ser Pro Ala Ala Pro Ala Pro Ser Ala Pro
    850                 855                 860

Ala Ala Ser Pro Ala Ala Pro Ala Pro Ala Ser Pro Ala Ala Pro Ala
865                 870                 875                 880

Pro Ser Ala Pro Ala Ala Ser Pro Ala Ala Pro Ala Pro Ala Ser Pro
                885                 890                 895

Ala Ala Pro Ala Pro Ser Ala Pro Ala Ala Gly Gly Gly Gly Ser Gly
            900                 905                 910

Gly Gly Gly Ser Gly Gly Gly Gly Ser Ser Asp Thr Gly Arg Pro Phe
        915                 920                 925

Val Glu Met Tyr Ser Glu Ile Pro Glu Ile Ile His Met Thr Glu Gly
    930                 935                 940

Arg Glu Leu Val Ile Pro Cys Arg Val Thr Ser Pro Asn Ile Thr Val
945                 950                 955                 960

Thr Leu Lys Lys Phe Pro Leu Asp Thr Leu Ile Pro Asp Gly Lys Arg
                965                 970                 975

Ile Ile Trp Asp Ser Arg Lys Gly Phe Ile Ile Ser Asn Ala Thr Tyr
            980                 985                 990

Lys Glu Ile Gly Leu Leu Thr Cys  Glu Ala Thr Val Asn  Gly His Leu
        995                 1000                 1005

Tyr Lys  Thr Asn Tyr Leu Thr  His Arg Gln Thr Asn  Thr Ile Ile
    1010                 1015                 1020

Asp Val  Val Leu Ser Pro Ser  His Gly Ile Glu Leu  Ser Val Gly
    1025                 1030                 1035

Glu Lys  Leu Val Leu Asn Cys  Thr Ala Arg Thr Glu  Leu Asn Val
    1040                 1045                 1050

Gly Ile  Asp Phe Asn Trp Glu  Tyr Pro Ser Ser Lys  His Gln His
    1055                 1060                 1065
```

```
Lys Lys Leu Val Asn Arg Asp Leu Lys Thr Gln Ser Gly Ser Glu
    1070                1075                1080

Met Lys Lys Phe Leu Ser Thr Leu Thr Ile Asp Gly Val Thr Arg
    1085                1090                1095

Ser Asp Gln Gly Leu Tyr Thr Cys Ala Ala Ser Ser Gly Leu Met
    1100                1105                1110

Thr Lys Lys Asn Ser Thr Phe Val Arg Val His Glu Lys
    1115                1120                1125


<210> SEQ ID NO 65
<211> LENGTH: 3378
<212> TYPE: DNA
<213> ORGANISM: Artificial Sequence
<220> FEATURE:
<223> OTHER INFORMATION: Sequence encoding EPS1115P, excluding signal
      peptide and purification tag

<400> SEQUENCE: 65

tctgataccg gcagaccctt cgtggaaatg tacagcgaga tccccgagat catccacatg     60

accgagggca gagagctggt catcccctgc agagtgacct ctcctaacat caccgtgact    120

ctgaagaagt tccctctgga cacactgatc cccgacggca agagaatcat ctgggactcc    180

cggaagggct tcatcatctc caacgccacc tacaaagaga tcggcctgct gacctgcgag    240

gccaccgtta atggccacct gtacaagacc aactatctga cccacagaca gaccaacacc    300

atcatcgacg tggtgctgag cccctctcat ggcatcgagc tgtccgtggg agaaaagctg    360

gtgctgaact gcaccgccag aaccgagctg aacgtgggca tcgacttcaa ctgggagtac    420

ccctccagca agcaccagca caagaagctg gtcaaccggg acctgaaaac ccagtccggc    480

tccgagatga agaaattcct gagcaccctg accatcgacg gcgtgaccag atctgaccag    540

ggcctgtata cctgcgccgc ttcctctggc ctgatgacca agaaaaactc caccttcgtg    600

cgggtgcacg agaaaggtgg cggaggatct ggcggaggcg gctctggcgg cggtggatct    660

gcttctcctg ctgctccagc tccagcttct ccagcagctc ctgcaccttc tgcaccagct    720

gcaagtcctg cagcacccgc accagctagt cctgccgctc ctgctcctag tgctcctgcc    780

gcaagtccag ctgctcccgc tcctgcaagc ccagctgcac cagcaccaag tgctccagct    840

gcctcaccag ccgcaccagc tccagcaagc cctgcagctc ccgctccttc agctcctgct    900

gcttctcccg cagcacccgc tccagcatca ccagccgctc cagcaccatc agctccagca    960

gcatctcctg cagctccagc tcctgctagt cccgctgctc ccgcacctag tgcaccagcc   1020

gcttctcccg ccgctcctgc tcctgcatct cctgctgcac ccgctccatc tgctcccgcc   1080

gcatcacccg cagctcccgc accagcctct ccagctgcac cagctcctag cgcaccagca   1140

gctagcccag ctgctcctgc accagctagc cccgcagctc cagctccaag cgctcctgct   1200

gcatccccag ctgctccagc tcctgcctca ccagctgctc cagcaccttc tgctcccgcc   1260

gcttctcctg ccgcaccagc tccagctagt ccagccgcac cagcaccatc tgcacccgct   1320

gctagccctg ctgcaccagc tccagcatca cccgctgcac cagctccatc cgcaccagct   1380

gcttcaccag cagctcccgc tccagcttca cccgctgctc ccgctcctag cgctcccgca   1440

gcttcaccag ctgcacccgc tccagccagt ccagctgctc ccgcaccatc cgcaccagca   1500

gcaagtcccg ccgctccagc tccagctagc ccagctgctc cagctccatc tgcaccagcc   1560

gcatctccag ctgctccagc tccagctagt cctgctgcac ccgctcctag cgctccagct   1620

gcaagtcctg ccgctcctgc tccagcctct cctgccgctc cagcacctag cgctcccgct   1680
```

gccagtccag cagctccagc tcctgcatct cccgccgcac cagcaccaag cgcacccgca 1740
gcatctcccg ctgctcccgc tccagcaagc cctgccgctc ctgcaccaag tgcaccagca 1800
gcatccccag cagctcccgc tccagcatct ccagcagctc cagctccaag tgctccagca 1860
gctagtcctg ctgctccagc tcctgctagc cctgcagctc ctgcaccatc tgctcccgca 1920
gccagtcctg cagctcctgc accagcaagt ccagctgctc ctgcacctag cgctccagct 1980
gcatctcccg ctgcaccagc tccagcaagt cccgctgctc ctgctccttc tgctccagca 2040
gcttcccctg ctgctcctgc tcctgcttca cccgccgctc cagctccatc tgctcccgct 2100
gcctctccag ccgctcctgc accagcatca ccagctgctc ccgcaccaag cgcacccgct 2160
gcaagcccag ccgctcctgc tcctgctagt ccagccgctc ctgcaccttc agcacccgca 2220
gcttccccag ctgctccagc tccagcaagt ccagcagctc cagctccttc cgctccagct 2280
gcaagccccg cagctccagc tcctgcttct cctgctgctc ctgcaccatc agctccagct 2340
gctagtccag cagctcctgc accagccagt cctgccgcac cagcaccttc agctccagct 2400
gcttcacccg ctgctcccgc accagctagt ccagccgctc cagcaccaag tgctcccgcc 2460
gctggtggtg gtggatctgg tggtggcgga agcggaggtg gtggttctca gctgtccctg 2520
ccttccatcc tgcctaacga gaacgagaag gtggtccagc tgaactcctc cttctctctg 2580
cggtgcttcg gcgagtccga agtgtcttgg cagtacccca tgtccgaaga ggaatcctcc 2640
gacgtggaaa tccggaacga ggaaaacaac tccggcctgt tcgtgaccgt gctggaagtg 2700
tcctctgcct ctgctgctca caccggcctg tacacatgct actacaatca cacccagacc 2760
gaagagaacg agctggaagg ccggcacatc tacatctacg tgcccgatcc tgacgtggcc 2820
tttgtgcctc tgggcatgac cgactacctg gtcatcgtgg aagatgacga ctccgctatc 2880
atcccttgcc ggaccaccga tccagagaca cctgtgacac tgcacaactc cgaaggcgtg 2940
gtgcctgcct cctacgattc tagacagggc ttcaacggca ccttcaccgt gggaccttac 3000
atctgcgagg ctacagtgaa gggcaagaag tttcagacaa tccccttcaa cgtgtacgcc 3060
ctgaaggcca cctctgagct ggacctggaa atggaagctc tgaaaaccgt gtacaagtcc 3120
ggcgagacaa tcgtcgtgac ctgtgccgtg ttcaacaacg aagtggtgga cctgcagtgg 3180
acctatcctg gcgaagtgaa aggcaagggc atcacaatgc tggaagagat caaggtgccc 3240
tccatcaagc tggtgtatac cctgaccgtg cctgaggcca ctgtgaagga ctctggcgac 3300
tacgagtgtg ccgctagaca ggccaccaga gaagtcaaag aaatgaagaa agtgaccatc 3360
tccgtccacg agaagggc 3378

<210> SEQ ID NO 66
<211> LENGTH: 1126
<212> TYPE: PRT
<213> ORGANISM: Artificial Sequence
<220> FEATURE:
<223> OTHER INFORMATION: Sequence of EPS1115P, excluding signal peptide
and purification tag

<400> SEQUENCE: 66

Ser Asp Thr Gly Arg Pro Phe Val Glu Met Tyr Ser Glu Ile Pro Glu
1 5 10 15

Ile Ile His Met Thr Glu Gly Arg Glu Leu Val Ile Pro Cys Arg Val
20 25 30

Thr Ser Pro Asn Ile Thr Val Thr Leu Lys Lys Phe Pro Leu Asp Thr
35 40 45

Leu Ile Pro Asp Gly Lys Arg Ile Ile Trp Asp Ser Arg Lys Gly Phe

```
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Gly Gly Gly
        195                 200                 205

Gly Ser Gly Gly Gly Gly Ser Gly Gly Gly Gly Ser Ala Ser Pro Ala
    210                 215                 220

Ala Pro Ala Pro Ala Ser Pro Ala Ala Pro Ala Pro Ser Ala Pro Ala
225                 230                 235                 240

Ala Ser Pro Ala Ala Pro Ala Pro Ala Ser Pro Ala Ala Pro Ala Pro
                245                 250                 255

Ser Ala Pro Ala Ala Ser Pro Ala Ala Pro Ala Pro Ala Ser Pro Ala
            260                 265                 270

Ala Pro Ala Pro Ser Ala Pro Ala Ala Ser Pro Ala Ala Pro Ala Pro
        275                 280                 285

Ala Ser Pro Ala Ala Pro Ala Pro Ser Ala Pro Ala Ala Ser Pro Ala
    290                 295                 300

Ala Pro Ala Pro Ala Ser Pro Ala Ala Pro Ala Pro Ser Ala Pro Ala
305                 310                 315                 320

Ala Ser Pro Ala Ala Pro Ala Pro Ala Ser Pro Ala Ala Pro Ala Pro
                325                 330                 335

Ser Ala Pro Ala Ala Ser Pro Ala Ala Pro Ala Pro Ala Ser Pro Ala
            340                 345                 350

Ala Pro Ala Pro Ser Ala Pro Ala Ala Ser Pro Ala Ala Pro Ala Pro
        355                 360                 365

Ala Ser Pro Ala Ala Pro Ala Pro Ser Ala Pro Ala Ala Ser Pro Ala
    370                 375                 380

Ala Pro Ala Pro Ala Ser Pro Ala Ala Pro Ala Pro Ser Ala Pro Ala
385                 390                 395                 400

Ala Ser Pro Ala Ala Pro Ala Pro Ala Ser Pro Ala Ala Pro Ala Pro
                405                 410                 415

Ser Ala Pro Ala Ala Ser Pro Ala Ala Pro Ala Pro Ala Ser Pro Ala
            420                 425                 430

Ala Pro Ala Pro Ser Ala Pro Ala Ala Ser Pro Ala Ala Pro Ala Pro
        435                 440                 445

Ala Ser Pro Ala Ala Pro Ala Pro Ser Ala Pro Ala Ala Ser Pro Ala
    450                 455                 460

Ala Pro Ala Pro Ala Ser Pro Ala Ala Pro Ala Pro Ser Ala Pro Ala
465                 470                 475                 480
```

-continued

```
Ala Ser Pro Ala Ala Pro Ala Pro Ala Ser Pro Ala Ala Pro Ala Pro
                485                 490                 495

Ser Ala Pro Ala Ala Ser Pro Ala Ala Pro Ala Pro Ala Ser Pro Ala
            500                 505                 510

Ala Pro Ala Pro Ser Ala Pro Ala Ala Ser Pro Ala Ala Pro Ala Pro
        515                 520                 525

Ala Ser Pro Ala Ala Pro Ala Pro Ser Ala Pro Ala Ala Ser Pro Ala
    530                 535                 540

Ala Pro Ala Pro Ala Ser Pro Ala Ala Pro Ala Pro Ser Ala Pro Ala
545                 550                 555                 560

Ala Ser Pro Ala Ala Pro Ala Pro Ala Ser Pro Ala Ala Pro Ala Pro
                565                 570                 575

Ser Ala Pro Ala Ala Ser Pro Ala Ala Pro Ala Pro Ala Ser Pro Ala
            580                 585                 590

Ala Pro Ala Pro Ser Ala Pro Ala Ala Ser Pro Ala Ala Pro Ala Pro
        595                 600                 605

Ala Ser Pro Ala Ala Pro Ala Pro Ser Ala Pro Ala Ala Ser Pro Ala
    610                 615                 620

Ala Pro Ala Pro Ala Ser Pro Ala Ala Pro Ala Pro Ser Ala Pro Ala
625                 630                 635                 640

Ala Ser Pro Ala Ala Pro Ala Pro Ala Ser Pro Ala Ala Pro Ala Pro
                645                 650                 655

Ser Ala Pro Ala Ala Ser Pro Ala Ala Pro Ala Pro Ala Ser Pro Ala
            660                 665                 670

Ala Pro Ala Pro Ser Ala Pro Ala Ala Ser Pro Ala Ala Pro Ala Pro
        675                 680                 685

Ala Ser Pro Ala Ala Pro Ala Pro Ser Ala Pro Ala Ala Ser Pro Ala
    690                 695                 700

Ala Pro Ala Pro Ala Ser Pro Ala Ala Pro Ala Pro Ser Ala Pro Ala
705                 710                 715                 720

Ala Ser Pro Ala Ala Pro Ala Pro Ala Ser Pro Ala Ala Pro Ala Pro
                725                 730                 735

Ser Ala Pro Ala Ala Ser Pro Ala Ala Pro Ala Pro Ala Ser Pro Ala
            740                 745                 750

Ala Pro Ala Pro Ser Ala Pro Ala Ala Ser Pro Ala Ala Pro Ala Pro
        755                 760                 765

Ala Ser Pro Ala Ala Pro Ala Pro Ser Ala Pro Ala Ala Ser Pro Ala
    770                 775                 780

Ala Pro Ala Pro Ala Ser Pro Ala Ala Pro Ala Pro Ser Ala Pro Ala
785                 790                 795                 800

Ala Ser Pro Ala Ala Pro Ala Pro Ala Ser Pro Ala Ala Pro Ala Pro
                805                 810                 815

Ser Ala Pro Ala Ala Gly Gly Gly Gly Ser Gly Gly Gly Gly Ser Gly
            820                 825                 830

Gly Gly Gly Ser Gln Leu Ser Leu Pro Ser Ile Leu Pro Asn Glu Asn
        835                 840                 845

Glu Lys Val Val Gln Leu Asn Ser Ser Phe Ser Leu Arg Cys Phe Gly
    850                 855                 860

Glu Ser Glu Val Ser Trp Gln Tyr Pro Met Ser Glu Glu Glu Ser Ser
865                 870                 875                 880

Asp Val Glu Ile Arg Asn Glu Glu Asn Asn Ser Gly Leu Phe Val Thr
                885                 890                 895
```

```
Val Leu Glu Val Ser Ser Ala Ser Ala Ala His Thr Gly Leu Tyr Thr
            900                 905                 910

Cys Tyr Tyr Asn His Thr Gln Thr Glu Glu Asn Glu Leu Glu Gly Arg
        915                 920                 925

His Ile Tyr Ile Tyr Val Pro Asp Pro Asp Val Ala Phe Val Pro Leu
    930                 935                 940

Gly Met Thr Asp Tyr Leu Val Ile Val Glu Asp Asp Asp Ser Ala Ile
945                 950                 955                 960

Ile Pro Cys Arg Thr Thr Asp Pro Glu Thr Pro Val Thr Leu His Asn
                965                 970                 975

Ser Glu Gly Val Val Pro Ala Ser Tyr Asp Ser Arg Gln Gly Phe Asn
            980                 985                 990

Gly Thr Phe Thr Val Gly Pro Tyr  Ile Cys Glu Ala Thr  Val Lys Gly
        995                 1000                1005

Lys Lys  Phe Gln Thr Ile Pro  Phe Asn Val Tyr Ala  Leu Lys Ala
    1010                1015                1020

Thr Ser  Glu Leu Asp Leu Glu  Met Glu Ala Leu Lys  Thr Val Tyr
    1025                1030                1035

Lys Ser  Gly Glu Thr Ile Val  Val Thr Cys Ala Val  Phe Asn Asn
    1040                1045                1050

Glu Val  Val Asp Leu Gln Trp  Thr Tyr Pro Gly Glu  Val Lys Gly
    1055                1060                1065

Lys Gly  Ile Thr Met Leu Glu  Glu Ile Lys Val Pro  Ser Ile Lys
    1070                1075                1080

Leu Val  Tyr Thr Leu Thr Val  Pro Glu Ala Thr Val  Lys Asp Ser
    1085                1090                1095

Gly Asp  Tyr Glu Cys Ala Ala  Arg Gln Ala Thr Arg  Glu Val Lys
    1100                1105                1110

Glu Met  Lys Lys Val Thr Ile  Ser Val His Glu Lys  Gly
    1115                1120                1125
```

<210> SEQ ID NO 67
<211> LENGTH: 2685
<212> TYPE: DNA
<213> ORGANISM: Artificial Sequence
<220> FEATURE:
<223> OTHER INFORMATION: Sequence encoding EPS1116P, excluding signal peptide and purification tag

<400> SEQUENCE: 67

```
cagctgagcc tgccaagcat cctgcctaac gaaaatgaga aggtggtcca gctgaacagc     60

tccttcagtc tgagatgctt tggcgaatca gaggtgagct ggcagtaccc aatgtcagag    120

gaagagtcta gtgacgtgga aattaggaat gaagagaaca attcaggact gttcgtgacc    180

gtcctggagg tgtcaagcgc cagcgccgct cacaccggac tgtacacatg ttactataac    240

catactcaga ccgaagagaa tgaactggag gggaggcaca tctccatcca cgtgcccgat    300

cctgacgtgg cctttgcccc actgggaatg acagattacc tggtcatcgt cgaggacgat    360

gactctgcca tcattccctg ccgcacctca gactccgaaa ctcctgtgac cctgcataac    420

agtgagggcg tggtccccgc ctcctacgat tctcgacagg gattcaatgg caccttcacc    480

gtcggaccct atatctgtga ggccactgtg aagggcaaga aattccagac cattcctttt    540

aacgtgtacg cactgaaagc cacatccgaa ctggacctgg aaatggaggc cctgaagact    600

gtctataaat ctggagagac tatcgtggtc acctgcgccg tgttcaacaa tgaagtggtc    660

gatgcgcagt ggacttaccc cggcgaggtc aagggcaaag ggattaccat ggacgaagag    720
```

```
atcaaggtgc ctagccagaa gctggtgtac accctgacag tcccagaagc caccgtgaag    780
gattccgggg actatgagtg tgcagcccgg caggcctcca gagaagtgaa ggagatgaag    840
aaagtgacaa tcagtgtcca cgagaaagga gcaagccccg ccgctccagc ccccgcaagc    900
ccagccgcac cagcaccttc cgcaccagcc gcctccccag cagcacccgc acccgcttcc    960
cctgccgccc ccgcccctag cgcccccgcc gcctcccctg ccgccccagc ccccgcctct   1020
ccagccgccc ctgccccatc tgccccagcc gccagcccag ccgcccccgc ccctgccagc   1080
cccgccgccc cagccccctc cgcccctgct gcttcccctg ccgcccctgc cccagccagc   1140
ccagctgctc ctgctccaag cgcccctgct gcaagcccag ctgctccagc ccccgcctct   1200
cccgctgctc cagctccttc tgcccctgct gcttccccag ctgctcccgc ccctgcctct   1260
cctgctgctc ctgctccctc cgcccctgct gcatcccccg ctgctcctgc cccagcttcc   1320
ccagctgcac ctgctccaag cgccccagct gcaagcccag ctgcacctgc acctgcttcc   1380
cccgctgccc ctgccccaag cgcccccgcc gcatcccccg ccgcaccagc ccccgcctca   1440
cccgcagcac cagccccatc agcaccagcc gcctcaccag ccgcccccgc acccgcaagt   1500
ccagcagcac ccgcaccatc cgcccccgcc gcaagcccag ccgcccccgc tccagcatcc   1560
cctgccgccc ccgcccccag cgcccccgcc gcctcccctg ccgccccagc ccccgcctct   1620
ccagccgccc ctgccccatc tgccccagcc gccagccccg ccgcccccgc ccctgccagc   1680
cccgccgccc cagccccctc cgcccctgct gcttcccccg ccgcccctgc cccagccagc   1740
ccagctgctc ccgctccaag cgcccccgct gcaagcccag ctgctccagc ccccgcctct   1800
cccgctgctc cagctccttc tgcccctgct gcttcccccg ctgctcccgc ccccgcctct   1860
cctgctgctc ccgctccctc cgcccctgct gcatcccccg ctgctcctgc cccagcttcc   1920
ccagctgcac ctgctcccag cgccccagct gcaagccccg ctgcacctgc acctgcttcc   1980
cccgctgccc ctgccccaag cgcccccgcc gcctcacccg cagcccccgc tccagccagc   2040
cccgcagcac cagcaccctc agccccagcc tcagataccg gccggccttt tgtggagatg   2100
tactccgaaa tccccgagat cattcacatg accgaagggc gagagctggt catcccatgc   2160
cgggtgacaa gccccaacat tactgtgacc ctgaagaaat tccctctgga tactctgatc   2220
ccagacggga agaggatcat ttgggacagc cgcaaaggct tcatcatttc caatgccaca   2280
tataaggaaa ttggcctgct gacatgcgag gccactgtga acgggcacct gtacaaaacc   2340
aattatctga cacatcggca gacaaacact atcattgatg tggtcctgag cccttcccat   2400
gggatcgaac tgagcgtcgg agagaagctg gtgctgaatt gtacagccag aactgaactg   2460
aacgtgggca ttgacttcaa ttgggagtac ccctcctcta agcaccagca taagaaactg   2520
gtgaataggg atctgaaaac ccagtctggg agtgagatga agaaatttct gtctaccctg   2580
acaatcgatg gcgtgacacg cagtgaccag gggctgtata cttgtgcagc cagttcaggc   2640
ctgatgacca agaagaacag cacatttgtc cgagtccacg aaaag                   2685
```

<210> SEQ ID NO 68
<211> LENGTH: 895
<212> TYPE: PRT
<213> ORGANISM: Artificial Sequence
<220> FEATURE:
<223> OTHER INFORMATION: Sequence of EPS1116P, excluding signal peptide
and purification tag

<400> SEQUENCE: 68

Gln Leu Ser Leu Pro Ser Ile Leu Pro Asn Glu Asn Glu Lys Val Val

-continued

```
1               5                   10                  15

Gln Leu Asn Ser Ser Phe Ser Leu Arg Cys Phe Gly Glu Ser Glu Val
            20                  25                  30

Ser Trp Gln Tyr Pro Met Ser Glu Glu Glu Ser Ser Asp Val Glu Ile
        35                  40                  45

Arg Asn Glu Glu Asn Asn Ser Gly Leu Phe Val Thr Val Leu Glu Val
    50                  55                  60

Ser Ser Ala Ser Ala Ala His Thr Gly Leu Tyr Thr Cys Tyr Tyr Asn
65                  70                  75                  80

His Thr Gln Thr Glu Glu Asn Glu Leu Glu Gly Arg His Ile Ser Ile
                85                  90                  95

His Val Pro Asp Pro Asp Val Ala Phe Ala Pro Leu Gly Met Thr Asp
            100                 105                 110

Tyr Leu Val Ile Val Glu Asp Asp Asp Ser Ala Ile Ile Pro Cys Arg
        115                 120                 125

Thr Ser Asp Ser Glu Thr Pro Val Thr Leu His Asn Ser Glu Gly Val
    130                 135                 140

Val Pro Ala Ser Tyr Asp Ser Arg Gln Gly Phe Asn Gly Thr Phe Thr
145                 150                 155                 160

Val Gly Pro Tyr Ile Cys Glu Ala Thr Val Lys Gly Lys Lys Phe Gln
                165                 170                 175

Thr Ile Pro Phe Asn Val Tyr Ala Leu Lys Ala Thr Ser Glu Leu Asp
            180                 185                 190

Leu Glu Met Glu Ala Leu Lys Thr Val Tyr Lys Ser Gly Glu Thr Ile
        195                 200                 205

Val Val Thr Cys Ala Val Phe Asn Asn Glu Val Val Asp Ala Gln Trp
    210                 215                 220

Thr Tyr Pro Gly Glu Val Lys Gly Lys Gly Ile Thr Met Asp Glu Glu
225                 230                 235                 240

Ile Lys Val Pro Ser Gln Lys Leu Val Tyr Thr Leu Thr Val Pro Glu
                245                 250                 255

Ala Thr Val Lys Asp Ser Gly Asp Tyr Glu Cys Ala Ala Arg Gln Ala
            260                 265                 270

Ser Arg Glu Val Lys Glu Met Lys Lys Val Thr Ile Ser Val His Glu
        275                 280                 285

Lys Gly Ala Ser Pro Ala Ala Pro Ala Pro Ala Ser Pro Ala Ala Pro
    290                 295                 300

Ala Pro Ser Ala Pro Ala Ala Ser Pro Ala Ala Pro Ala Pro Ala Ser
305                 310                 315                 320

Pro Ala Ala Pro Ala Pro Ser Ala Pro Ala Ala Ser Pro Ala Ala Pro
                325                 330                 335

Ala Pro Ala Ser Pro Ala Ala Pro Ala Pro Ser Ala Pro Ala Ala Ser
            340                 345                 350

Pro Ala Ala Pro Ala Pro Ala Ser Pro Ala Ala Pro Ala Pro Ser Ala
        355                 360                 365

Pro Ala Ala Ser Pro Ala Ala Pro Ala Pro Ala Ser Pro Ala Ala Pro
    370                 375                 380

Ala Pro Ser Ala Pro Ala Ala Ser Pro Ala Ala Pro Ala Pro Ala Ser
385                 390                 395                 400

Pro Ala Ala Pro Ala Pro Ser Ala Pro Ala Ala Ser Pro Ala Ala Pro
                405                 410                 415

Ala Pro Ala Ser Pro Ala Ala Pro Ala Pro Ser Ala Pro Ala Ala Ser
            420                 425                 430
```

```
Pro Ala Ala Pro Ala Pro Ala Ser Pro Ala Ala Pro Ala Pro Ser Ala
        435                 440                 445

Pro Ala Ala Ser Pro Ala Ala Pro Ala Pro Ala Ser Pro Ala Ala Pro
    450                 455                 460

Ala Pro Ser Ala Pro Ala Ala Ser Pro Ala Ala Pro Ala Pro Ala Ser
465                 470                 475                 480

Pro Ala Ala Pro Ala Pro Ser Ala Pro Ala Ala Ser Pro Ala Ala Pro
                485                 490                 495

Ala Pro Ala Ser Pro Ala Ala Pro Ala Pro Ser Ala Pro Ala Ala Ser
            500                 505                 510

Pro Ala Ala Pro Ala Pro Ala Ser Pro Ala Ala Pro Ala Pro Ser Ala
        515                 520                 525

Pro Ala Ala Ser Pro Ala Ala Pro Ala Pro Ala Ser Pro Ala Ala Pro
    530                 535                 540

Ala Pro Ser Ala Pro Ala Ala Ser Pro Ala Ala Pro Ala Pro Ala Ser
545                 550                 555                 560

Pro Ala Ala Pro Ala Pro Ser Ala Pro Ala Ala Ser Pro Ala Ala Pro
                565                 570                 575

Ala Pro Ala Ser Pro Ala Ala Pro Ala Pro Ser Ala Pro Ala Ala Ser
            580                 585                 590

Pro Ala Ala Pro Ala Pro Ala Ser Pro Ala Ala Pro Ala Pro Ser Ala
        595                 600                 605

Pro Ala Ala Ser Pro Ala Ala Pro Ala Pro Ala Ser Pro Ala Ala Pro
    610                 615                 620

Ala Pro Ser Ala Pro Ala Ala Ser Pro Ala Ala Pro Ala Pro Ala Ser
625                 630                 635                 640

Pro Ala Ala Pro Ala Pro Ser Ala Pro Ala Ala Ser Pro Ala Ala Pro
                645                 650                 655

Ala Pro Ala Ser Pro Ala Ala Pro Ala Pro Ser Ala Pro Ala Ala Ser
            660                 665                 670

Pro Ala Ala Pro Ala Pro Ala Ser Pro Ala Ala Pro Ala Pro Ser Ala
        675                 680                 685

Pro Ala Ser Asp Thr Gly Arg Pro Phe Val Glu Met Tyr Ser Glu Ile
    690                 695                 700

Pro Glu Ile Ile His Met Thr Glu Gly Arg Glu Leu Val Ile Pro Cys
705                 710                 715                 720

Arg Val Thr Ser Pro Asn Ile Thr Val Thr Leu Lys Lys Phe Pro Leu
                725                 730                 735

Asp Thr Leu Ile Pro Asp Gly Lys Arg Ile Ile Trp Asp Ser Arg Lys
            740                 745                 750

Gly Phe Ile Ile Ser Asn Ala Thr Tyr Lys Glu Ile Gly Leu Leu Thr
        755                 760                 765

Cys Glu Ala Thr Val Asn Gly His Leu Tyr Lys Thr Asn Tyr Leu Thr
    770                 775                 780

His Arg Gln Thr Asn Thr Ile Ile Asp Val Val Leu Ser Pro Ser His
785                 790                 795                 800

Gly Ile Glu Leu Ser Val Gly Glu Lys Leu Val Leu Asn Cys Thr Ala
                805                 810                 815

Arg Thr Glu Leu Asn Val Gly Ile Asp Phe Asn Trp Glu Tyr Pro Ser
            820                 825                 830

Ser Lys His Gln His Lys Lys Leu Val Asn Arg Asp Leu Lys Thr Gln
        835                 840                 845
```

```
Ser Gly Ser Glu Met Lys Lys Phe Leu Ser Thr Leu Thr Ile Asp Gly
    850                 855                 860

Val Thr Arg Ser Asp Gln Gly Leu Tyr Thr Cys Ala Ala Ser Ser Gly
865                 870                 875                 880

Leu Met Thr Lys Lys Asn Ser Thr Phe Val Arg Val His Glu Lys
                885                 890                 895


<210> SEQ ID NO 69
<211> LENGTH: 600
<212> TYPE: DNA
<213> ORGANISM: Artificial Sequence
<220> FEATURE:
<223> OTHER INFORMATION: Sequence encoding PA polypeptide/linker

<400> SEQUENCE: 69

gccgctcctg ctgctccagc tcctgctgcc ccagcagccc ctgccccagc tgctcctgca     60

gcagctcccg cagccccagc acccgccgca ccagcagctc cagcccctgc agcaccagct    120

gctgcccctg ccgcccctgc tccagccgca cccgctgcac ccgcaccagc tgccccagcc    180

gccgcacccg cagctccagc tcccgctgct cctgctgcac cagcccctgc cgctccagca    240

gccgcaccag cagcaccagc cccagctgct cccgctgctc cagcacccgc agcccccgca    300

gcagcaccag ccgctcctgc tcctgccgcc ccagcagctc ctgctccagc agcccctgct    360

gctgctccag cagcaccagc accagctgct ccagctgccc cagctcctgc agcacccgcc    420

gctgctcccg cagctcctgc ccctgctgca cccgcagcac ccgctccagc agcacctgca    480

gctgcaccag ctgctcccgc acctgccgct cccgcagctc ccgctcctgc agctccagcc    540

gcagctcctg ctgctcctgc accagcagct cccgccgcac cagctccagc tgcccctgct    600


<210> SEQ ID NO 70
<211> LENGTH: 200
<212> TYPE: PRT
<213> ORGANISM: Artificial Sequence
<220> FEATURE:
<223> OTHER INFORMATION: Sequence of PA polypeptide/linker

<400> SEQUENCE: 70

Ala Ala Pro Ala Ala Pro Ala Pro Ala Ala Pro Ala Ala Pro Ala Pro
1               5                   10                  15

Ala Ala Pro Ala Ala Ala Pro Ala Ala Pro Ala Pro Ala Ala Pro Ala
            20                  25                  30

Ala Pro Ala Pro Ala Ala Pro Ala Ala Ala Pro Ala Ala Pro Ala Pro
        35                  40                  45

Ala Ala Pro Ala Ala Pro Ala Pro Ala Ala Pro Ala Ala Ala Pro Ala
    50                  55                  60

Ala Pro Ala Pro Ala Ala Pro Ala Ala Pro Ala Pro Ala Ala Pro Ala
65                  70                  75                  80

Ala Ala Pro Ala Ala Pro Ala Pro Ala Ala Pro Ala Ala Pro Ala Pro
                85                  90                  95

Ala Ala Pro Ala Ala Ala Pro Ala Ala Pro Ala Pro Ala Ala Pro Ala
            100                 105                 110

Ala Pro Ala Pro Ala Ala Pro Ala Ala Ala Pro Ala Ala Pro Ala Pro
        115                 120                 125

Ala Ala Pro Ala Ala Pro Ala Pro Ala Ala Pro Ala Ala Ala Pro Ala
    130                 135                 140

Ala Pro Ala Pro Ala Ala Pro Ala Ala Pro Ala Pro Ala Ala Pro Ala
145                 150                 155                 160
```

-continued

```
Ala Ala Pro Ala Ala Pro Ala Pro Ala Ala Pro Ala Ala Pro Ala Pro
                165                 170                 175

Ala Ala Pro Ala Ala Ala Pro Ala Ala Pro Ala Pro Ala Ala Pro Ala
            180                 185                 190

Ala Pro Ala Pro Ala Ala Pro Ala
        195                 200


<210> SEQ ID NO 71
<211> LENGTH: 20
<212> TYPE: PRT
<213> ORGANISM: Artificial Sequence
<220> FEATURE:
<223> OTHER INFORMATION: Sequence of PA polypeptide/linker

<400> SEQUENCE: 71

Ala Ser Pro Ala Ala Pro Ala Pro Ala Ser Pro Ala Ala Pro Ala Pro
1               5                   10                  15

Ser Ala Pro Ala
            20


<210> SEQ ID NO 72
<211> LENGTH: 18
<212> TYPE: PRT
<213> ORGANISM: Artificial Sequence
<220> FEATURE:
<223> OTHER INFORMATION: Sequence of PA polypeptide/linker

<400> SEQUENCE: 72

Ala Ala Pro Ala Ala Pro Ala Pro Ala Ala Pro Ala Ala Pro Ala Ala
                5                   10                  15

Pro Ala

<210> SEQ ID NO 73
<211> LENGTH: 5
<212> TYPE: PRT
<213> ORGANISM: Artificial Sequence
<220> FEATURE:
<223> OTHER INFORMATION: Sequence of GS polypeptide/linker

<400> SEQUENCE: 73

Gly Gly Gly Gly Ser
                5
```